US012485136B2

(12) United States Patent
Bermingham et al.

(10) Patent No.: US 12,485,136 B2
(45) Date of Patent: Dec. 2, 2025

(54) METHODS FOR THE TREATMENT OF TRINUCLEOTIDE REPEAT EXPANSION DISORDERS ASSOCIATED WITH MLH3 ACTIVITY

(71) Applicant: TAKEDA PHARMACEUTICALS U.S.A., INC., Cambridge, MA (US)

(72) Inventors: Nessan Anthony Bermingham, Cambridge, MA (US); Brian R. Bettencourt, Cambridge, MA (US); Peter Edward Bialek, Cambridge, MA (US)

(73) Assignee: Takeda Pharmaceuticals U.S.A., Inc., Cambridge, MA (US)

( * ) Notice: Subject to any disclaimer, the term of this patent is extended or adjusted under 35 U.S.C. 154(b) by 212 days.

(21) Appl. No.: 17/299,277

(22) PCT Filed: Dec. 2, 2019

(86) PCT No.: PCT/US2019/064059
§ 371 (c)(1),
(2) Date: Jun. 2, 2021

(87) PCT Pub. No.: WO2020/117706
PCT Pub. Date: Jun. 11, 2020

(65) Prior Publication Data

US 2023/0042436 A1 Feb. 9, 2023

Related U.S. Application Data

(60) Provisional application No. 62/877,104, filed on Jul. 22, 2019, provisional application No. 62/774,777, filed on Dec. 3, 2018.

(51) Int. Cl.
*A61K 31/7125* (2006.01)
*A61P 25/28* (2006.01)
*C12N 15/113* (2010.01)

(52) U.S. Cl.
CPC .......... *A61K 31/7125* (2013.01); *A61P 25/28* (2018.01); *C12N 15/113* (2013.01)

(58) Field of Classification Search
CPC .............. C12N 15/113; C12N 2310/11; C12N 2310/322; C12N 2310/3525; A61K 31/7125; A61K 31/7088; A61P 25/28
See application file for complete search history.

(56) References Cited

U.S. PATENT DOCUMENTS 3,687,808 A 8/1972 Merigan, Jr. et al.
4,469,863 A 9/1984 Ts'o et al.
4,476,301 A 10/1984 Imbach et al.
4,587,044 A 5/1986 Miller et al.
4,605,735 A 8/1986 Miyoshi et al.
4,667,025 A 5/1987 Miyoshi et al.
4,683,202 A 7/1987 Mullis
4,762,779 A 8/1988 Snitman
4,789,737 A 12/1988 Miyoshi et al.
4,824,941 A 4/1989 Gordon et al.
4,828,979 A 5/1989 Klevan et al.
4,835,263 A 5/1989 Nguyen et al.
4,837,028 A 6/1989 Allen
4,845,205 A 7/1989 Dinh et al.
4,876,335 A 10/1989 Yamane et al.
4,897,355 A 1/1990 Eppstein et al.
4,904,582 A 2/1990 Tullis
4,948,882 A 8/1990 Ruth
4,958,013 A 9/1990 Letsinger
4,981,957 A 1/1991 Lebleu et al.
5,023,243 A 6/1991 Tullis
5,034,506 A 7/1991 Summerton et al.
5,082,830 A 1/1992 Brakel et al.
5,109,124 A 4/1992 Ramachandran et al.
5,112,963 A 5/1992 Pieles et al.
5,118,800 A 6/1992 Smith et al.
5,118,802 A 6/1992 Smith et al.
5,130,302 A 7/1992 Spiel et al.
5,134,066 A 7/1992 Rogers et al.
5,138,045 A 8/1992 Cook et al.
5,166,315 A 11/1992 Summerton et al.
5,171,678 A 12/1992 Behr et al.
5,175,273 A 12/1992 Bischofberger et al.
5,177,195 A 1/1993 Gregory et al.
(Continued)

FOREIGN PATENT DOCUMENTS

WO WO-8804924 A1 7/1988
WO WO-9116024 A1 10/1991
(Continued)

OTHER PUBLICATIONS

Halabi et al., Feb. 26, 2018, "GAA•TTC repeat expansion in human cells is mediated by mismatch repair complex MutLy and depends upon the endonuclease domain in MLH3 isoform one" Nucleic Acids Research, 46(8), p. 4022-4032 (Year: 2018).*
(Continued)

*Primary Examiner* — Soren Harward
*Assistant Examiner* — Jenna L Persons
(74) *Attorney, Agent, or Firm* — Sterne, Kessler, Goldstein & Fox P.L.L.C.

(57) ABSTRACT

The present disclosure features useful compositions and methods to treat repeat expansion disorders, e.g., in a subject in need thereof. In some aspects, the compositions and methods described herein are useful in the treatment of disorders associated with MLH3 activity.

9 Claims, 2 Drawing Sheets

Specification includes a Sequence Listing.

(56) References Cited

U.S. PATENT DOCUMENTS

| | | | |
|---|---|---|---|
| 5,185,444 | A | 2/1993 | Summerton et al. |
| 5,188,897 | A | 2/1993 | Suhadolnik et al. |
| 5,214,134 | A | 5/1993 | Weis et al. |
| 5,214,136 | A | 5/1993 | Lin et al. |
| 5,216,141 | A | 6/1993 | Benner |
| 5,218,105 | A | 6/1993 | Cook et al. |
| 5,235,033 | A | 8/1993 | Summerton et al. |
| 5,245,022 | A | 9/1993 | Weis et al. |
| 5,254,469 | A | 10/1993 | Warren, III et al. |
| 5,258,506 | A | 11/1993 | Urdea et al. |
| 5,262,536 | A | 11/1993 | Hobbs, Jr. |
| 5,264,423 | A | 11/1993 | Cohen et al. |
| 5,264,562 | A | 11/1993 | Matteucci |
| 5,264,564 | A | 11/1993 | Matteucci |
| 5,272,250 | A | 12/1993 | Spiel et al. |
| 5,276,019 | A | 1/1994 | Cohen et al. |
| 5,278,302 | A | 1/1994 | Caruthers et al. |
| 5,283,185 | A | 2/1994 | Epand et al. |
| 5,286,717 | A | 2/1994 | Cohen et al. |
| 5,292,873 | A | 3/1994 | Rokita et al. |
| 5,317,098 | A | 5/1994 | Shizuya et al. |
| 5,319,080 | A | 6/1994 | Leumann |
| 5,321,131 | A | 6/1994 | Agrawal et al. |
| 5,359,044 | A | 10/1994 | Cook et al. |
| 5,367,066 | A | 11/1994 | Urdea et al. |
| 5,371,241 | A | 12/1994 | Brush |
| 5,391,723 | A | 2/1995 | Priest |
| 5,393,878 | A | 2/1995 | Leumann |
| 5,399,676 | A | 3/1995 | Froehler |
| 5,405,938 | A | 4/1995 | Summerton et al. |
| 5,405,939 | A | 4/1995 | Suhadolnik et al. |
| 5,414,077 | A | 5/1995 | Lin et al. |
| 5,416,203 | A | 5/1995 | Letsinger |
| 5,432,272 | A | 7/1995 | Benner |
| 5,434,257 | A | 7/1995 | Matteucci et al. |
| 5,445,934 | A | 8/1995 | Fodor et al. |
| 5,446,137 | A | 8/1995 | Maag et al. |
| 5,451,463 | A | 9/1995 | Nelson et al. |
| 5,453,496 | A | 9/1995 | Caruthers et al. |
| 5,455,233 | A | 10/1995 | Spiel et al. |
| 5,457,187 | A | 10/1995 | Gmeiner et al. |
| 5,459,255 | A | 10/1995 | Cook et al. |
| 5,466,677 | A | 11/1995 | Baxter et al. |
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,486,603 | A | 1/1996 | Buhr |
| 5,489,677 | A | 2/1996 | Sanghvi et al. |
| 5,502,177 | A | 3/1996 | Matteucci et al. |
| 5,510,475 | A | 4/1996 | Agrawal et al. |
| 5,512,439 | A | 4/1996 | Hornes et al. |
| 5,512,667 | A | 4/1996 | Reed et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,465 | A | 6/1996 | Haralambidis et al. |
| 5,525,711 | A | 6/1996 | Hawkins et al. |
| 5,536,821 | A | 7/1996 | Agrawal et al. |
| 5,539,082 | A | 7/1996 | Nielsen et al. |
| 5,541,307 | A | 7/1996 | Cook et al. |
| 5,541,313 | A | 7/1996 | Ruth |
| 5,541,316 | A | 7/1996 | Engelskirchen et al. |
| 5,543,152 | A | 8/1996 | Webb et al. |
| 5,545,730 | A | 8/1996 | Urdea et al. |
| 5,550,111 | A | 8/1996 | Suhadolnik et al. |
| 5,552,538 | A | 9/1996 | Urdea et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,552 | A | 10/1996 | Magda et al. |
| 5,567,810 | A | 10/1996 | Weis et al. |
| 5,567,811 | A | 10/1996 | Misiura et al. |
| 5,571,799 | A | 11/1996 | Tkachuk et al. |
| 5,574,142 | A | 11/1996 | Meyer, Jr. et al. |
| 5,576,427 | A | 11/1996 | Cook et al. |
| 5,578,717 | A | 11/1996 | Urdea et al. |
| 5,578,718 | A | 11/1996 | Cook et al. |
| 5,580,731 | A | 12/1996 | Chang et al. |
| 5,585,481 | A | 12/1996 | Arnold, Jr. et al. |
| 5,587,361 | A | 12/1996 | Cook et al. |
| 5,587,371 | A | 12/1996 | Sessler et al. |
| 5,587,469 | A | 12/1996 | Cook et al. |
| 5,591,584 | A | 1/1997 | Chang et al. |
| 5,591,722 | A | 1/1997 | Montgomery et al. |
| 5,594,121 | A | 1/1997 | Froehler et al. |
| 5,595,726 | A | 1/1997 | Magda et al. |
| 5,596,086 | A | 1/1997 | Matteucci et al. |
| 5,596,091 | A | 1/1997 | Switzer |
| 5,597,696 | A | 1/1997 | Linn et al. |
| 5,597,909 | A | 1/1997 | Urdea et al. |
| 5,599,923 | A | 2/1997 | Sessler et al. |
| 5,599,928 | A | 2/1997 | Hemmi et al. |
| 5,602,240 | A | 2/1997 | De et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,646,265 | A | 7/1997 | McGee |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,677,195 | A | 10/1997 | Winkler et al. |
| 5,677,437 | A | 10/1997 | Teng et al. |
| 5,677,439 | A | 10/1997 | Weis et al. |
| 5,681,941 | A | 10/1997 | Cook et al. |
| 5,688,941 | A | 11/1997 | Cook et al. |
| 5,700,920 | A | 12/1997 | Altmann et al. |
| 5,714,331 | A | 2/1998 | Buchardt et al. |
| 5,719,262 | A | 2/1998 | Buchardt et al. |
| 5,744,305 | A | 4/1998 | Fodor et al. |
| 5,750,692 | A | 5/1998 | Cook et al. |
| 5,770,722 | A | 6/1998 | Lockhart et al. |
| 5,854,033 | A | 12/1998 | Lizardi |
| 5,874,219 | A | 2/1999 | Rava et al. |
| 5,976,567 | A | 11/1999 | Wheeler et al. |
| 5,981,501 | A | 11/1999 | Wheeler et al. |
| 6,015,886 | A | 1/2000 | Dale et al. |
| 6,028,188 | A | 2/2000 | Arnold, Jr. et al. |
| 6,124,445 | A | 9/2000 | Imbach et al. |
| 6,147,200 | A | 11/2000 | Manoharan et al. |
| 6,160,109 | A | 12/2000 | Just et al. |
| 6,166,197 | A | 12/2000 | Cook et al. |
| 6,169,170 | B1 | 1/2001 | Gryaznov et al. |
| 6,172,209 | B1 | 1/2001 | Manoharan et al. |
| 6,222,025 | B1 | 4/2001 | Cook et al. |
| 6,235,887 | B1 | 5/2001 | Froehler et al. |
| 6,239,265 | B1 | 5/2001 | Cook |
| 6,268,490 | B1 | 7/2001 | Imanishi et al. |
| 6,277,603 | B1 | 8/2001 | Cook |
| 6,294,664 | B1 | 9/2001 | Ravikumar et al. |
| 6,320,017 | B1 | 11/2001 | Ansell |
| 6,326,199 | B1 | 12/2001 | Cook et al. |
| 6,346,614 | B1 | 2/2002 | Metelev et al. |
| 6,380,368 | B1 | 4/2002 | Froehler et al. |
| 6,444,423 | B1 | 9/2002 | Meade et al. |
| 6,525,191 | B1 | 2/2003 | Ramasamy |
| 6,528,640 | B1 | 3/2003 | Beigelman et al. |
| 6,531,590 | B1 | 3/2003 | Manoharan et al. |
| 6,534,484 | B1 | 3/2003 | Wheeler et al. |
| 6,534,639 | B1 | 3/2003 | Manoharan et al. |
| 6,576,752 | B1 | 6/2003 | Manoharan et al. |
| 6,586,410 | B1 | 7/2003 | Wheeler et al. |
| 6,608,035 | B1 | 8/2003 | Agrawal et al. |
| 6,617,438 | B1 | 9/2003 | Beigelman et al. |
| 6,639,062 | B2 | 10/2003 | Manoharan et al. |
| 6,670,461 | B1 | 12/2003 | Wengel et al. |
| 6,683,167 | B2 | 1/2004 | Metelev et al. |

(56) References Cited

U.S. PATENT DOCUMENTS

| | | | |
|---|---|---|---|
| 6,770,748 | B2 | 8/2004 | Imanishi et al. |
| 6,783,931 | B1 | 8/2004 | Cook et al. |
| 6,794,499 | B2 | 9/2004 | Wengel et al. |
| 6,815,432 | B2 | 11/2004 | Wheeler et al. |
| 6,858,225 | B2 | 2/2005 | Semple et al. |
| 6,858,715 | B2 | 2/2005 | Ravikumar et al. |
| 6,867,294 | B1 | 3/2005 | Sanghvi et al. |
| 6,878,805 | B2 | 4/2005 | Manoharan et al. |
| 6,900,297 | B1 | 5/2005 | Cook et al. |
| 6,998,484 | B2 | 2/2006 | Koch et al. |
| 7,015,315 | B1 | 3/2006 | Cook et al. |
| 7,034,133 | B2 | 4/2006 | Wengel et al. |
| 7,037,646 | B1 | 5/2006 | Cook et al. |
| 7,041,816 | B2 | 5/2006 | Ravikumar et al. |
| 7,045,610 | B2 | 5/2006 | Dempcy et al. |
| 7,053,207 | B2 | 5/2006 | Wengel |
| 7,084,125 | B2 | 8/2006 | Wengel |
| RE39,464 | E | 1/2007 | Cook et al. |
| 7,273,933 | B1 | 9/2007 | Krotz et al. |
| 7,321,029 | B2 | 1/2008 | Gryaznov et al. |
| 7,399,845 | B2 | 7/2008 | Swayze et al. |
| 7,427,605 | B2 | 9/2008 | Davis et al. |
| 7,427,672 | B2 | 9/2008 | Imanishi et al. |
| 7,495,088 | B1 | 2/2009 | Brakel et al. |
| 7,569,686 | B1 | 8/2009 | Bhat et al. |
| 7,741,457 | B2 | 6/2010 | Seth et al. |
| 8,022,193 | B2 | 9/2011 | Seth et al. |
| 8,030,467 | B2 | 10/2011 | Seth et al. |
| 8,058,069 | B2 | 11/2011 | Yaworski et al. |
| 8,106,022 | B2 | 1/2012 | Manoharan et al. |
| 8,278,283 | B2 | 10/2012 | Seth et al. |
| 8,278,425 | B2 | 10/2012 | Prakash et al. |
| 8,278,426 | B2 | 10/2012 | Seth et al. |
| 8,314,227 | B2 | 11/2012 | Wengel |
| 9,006,198 | B2 | 4/2015 | Bennett et al. |
| 2002/0068709 | A1 | 6/2002 | Orum et al. |
| 2004/0171570 | A1 | 9/2004 | Allerson et al. |
| 2006/0058255 | A1 | 3/2006 | Chen et al. |
| 2008/0039618 | A1 | 2/2008 | Allerson et al. |
| 2009/0012281 | A1 | 1/2009 | Swayze et al. |
| 2010/0324120 | A1 | 12/2010 | Chen et al. |
| 2011/0313020 | A1 | 12/2011 | Templin et al. |
| 2012/0157511 | A1 | 6/2012 | Manoharan et al. |
| 2013/0011922 | A1 | 1/2013 | Quay et al. |
| 2013/0096289 | A1 | 4/2013 | Wengel |
| 2013/0190383 | A1 | 7/2013 | Vaish et al. |
| 2013/0317086 | A1 | 11/2013 | Guire et al. |
| 2014/0135376 | A1 | 5/2014 | Engbersen et al. |
| 2014/0342003 | A1 | 11/2014 | Saltzman et al. |
| 2015/0174549 | A1 | 6/2015 | Lim et al. |
| 2015/0307554 | A1 | 10/2015 | Castillo Rodriguez |
| 2015/0335764 | A1 | 11/2015 | Martinez Fong |
| 2016/0230189 | A1 | 8/2016 | Kotha et al. |
| 2016/0251478 | A1 | 9/2016 | Saltzman et al. |
| 2016/0279256 | A1 | 9/2016 | Wang et al. |
| 2016/0369269 | A1 | 12/2016 | Shen et al. |
| 2017/0044539 | A1 | 2/2017 | Oestergaard et al. |
| 2017/0121454 | A1 | 5/2017 | Saltzman et al. |
| 2017/0182082 | A1* | 6/2017 | Swayze .............. A61K 31/7125 |
| 2017/0183655 | A1* | 6/2017 | Grabczyk ............ C12N 15/113 |
| 2018/0009866 | A1 | 1/2018 | Hoge et al. |
| 2018/0216108 | A1 | 8/2018 | Vargeese et al. |
| 2018/0305689 | A1 | 10/2018 | Saetrom et al. |

FOREIGN PATENT DOCUMENTS

| | | | |
|---|---|---|---|
| WO | WO-9324640 | A2 | 12/1993 |
| WO | WO-9400569 | A1 | 1/1994 |
| WO | WO-9402595 | A1 | 2/1994 |
| WO | WO-9637194 | A1 | 11/1996 |
| WO | WO-9640964 | A2 | 12/1996 |
| WO | WO-9713499 | A1 | 4/1997 |
| WO | WO-9839359 | A1 | 9/1998 |
| WO | WO-9914226 | A2 | 3/1999 |
| WO | WO-0003683 | A2 | 1/2000 |
| WO | WO-0123613 | A1 | 4/2001 |
| WO | WO-2004094636 | A1 | 11/2004 |
| WO | WO-2008042973 | A2 | 4/2008 |
| WO | WO-2008157747 | A1 | 12/2008 |
| WO | WO-2011005861 | A1 | 1/2011 |
| WO | WO-2012177906 | A1 | 12/2012 |
| WO | WO-2013036868 | A1 | 3/2013 |
| WO | WO-2014076195 | A1 | 5/2014 |
| WO | WO-2014179620 | A1 | 11/2014 |
| WO | WO-2014179627 | A2 | 11/2014 |
| WO | WO-2016161380 | A1 | 10/2016 |
| WO | WO-2016170348 | A2 | 10/2016 |
| WO | WO-2017192679 | A1 | 11/2017 |
| WO | WO-2018195165 | A1 | 10/2018 |
| WO | WO-2020117706 | A1 | 6/2020 |

OTHER PUBLICATIONS

GPP Web Portal, shRNA clone IDs: TRCN0000038737, TRCN0000038736, TRCN0000038738, and TRCN0000038735, accessed Jul. 26, 2024 (Year: 2018).*

Aartsma-Rus, 2009, "Guidelines for Antisense Oligonucleotide Design and Insight Into Splice-modulating Mechanisms" The American Society of Gene Therapy, 17(3), p. 548-553 (Year: 2009).*

Reference Sequence NM_001040108.1; *Homo sapiens* mutL homolog 3 (MLH3), transcript variant 1, mRNA, Feb. 5, 2018, accessed Jul. 26, 2024 (Year: 2018).*

Pinto et al., Oct. 2013, "Mismatch Repair Genes Mlh1 and Mlh3 Modify CAG Instability in Huntington's Disease Mice: Genome-Wide and Candidate Approaches" PLOS Genetics, 9(10), e1003930 (Year: 2013).*

Vickers et al., 2001, "Fully modified 2' MOE oligonucleotides redirect polyadenylation", Nucleic Acids Research, vol. 29, No. 6, p. 1293-1299 (Year: 2001).*

Zamaratski et al., 2001, "A critical survey of the structure-function of the antisense oligorRNA heteroduplex as substrate for RNase H", J. Biochem. Biophys. Methods, 48 (2001), p. 189-208 (Year: 2001).*

Lima et al., 2007, Molecular Pharmacology, vol. 71, No. 1 p. 83-91 (Year: 2007).*

Monia et al., 1993, The Journal of Biological Chemistry, vol. 268, No. 19, p. 14514-14522 (Year: 1993).*

Akhtar, S., and Juliano, R. L., "Cellular uptake and intracellular fate of antisense oligonucleotides," Trends in Cell Biology 2(5):139-144, Elsevier Science Publishers Ltd., United Kingdom (May 1992).

Allen, T. M., and Chonn, A., "Large unilamellar liposomes with low uptake into the reticuloendothelial system," FEBS Letters 223(1):42-46, John Wiley & Sons Ltd., United Kingdom (Oct. 1987).

Al-Mahdawi, S., et al., "GAA repeat expansion mutation mouse models of Friedreich ataxia exhibit oxidative stress leading to progressive neuronal and cardiac pathology," Genomics 88(5):580-590, Academic Press, United States (Nov. 2006).

Arnold, A. S., et al., "Specific betal-adrenergic receptor silencing with small interfering RNA lowers high blood pressure and improves cardiac function in myocardial ischemia," Journal of Hypertension 25(1):197-205, Lippincott Williams & Wilkins, United Kingdom (Jan. 2007).

Bangham, A. D., et al., "Diffusion of univalent ions across the lamellae of swollen phospholipids," Journal of Molecular Biology 13(1):238-252, Elsevier, Netherlands (1965).

Barany, F., "Genetic disease detection and DNA amplification using cloned thermostable ligase," Proc Natl Acad Sci USA 88(1):189-193, National Academy of Sciences, United States (Jan. 1991).

Berge, S. M., et al., "Pharmaceutical salts," Journal of Pharmaceutical Sciences 66(1):1-19, John Wiley & Sons, United States (Jan. 1977).

Bergstrom, D. E., "Unnatural nucleosides with unusual base pairing properties," Current Protocols in Nucleic Acid Chemistry 37(1):1.4.1-1.4.32, Wiley Interscience, United States (Jun. 2009).

Bettencourt, C., et al., "DNA repair pathways underlie a common genetic mechanism modulating onset in polyglutamine diseases," Annals of Neurology 79(6):983-990, Wiley Periodicals, United States (Jun. 2016).

(56) References Cited

OTHER PUBLICATIONS

Black, R. D., and Sang, C. N., "Advances and limitations in the evaluation of analgesic combination therapy," Neurology 65(12 Suppl 4): S3-S6, Lippincott Williams & Wilkins, United States (Dec. 2005).
Bonnet, M. E., et al., "Systemic delivery of DNA or siRNA mediated by linear polyethylenimine (L-PEI) does not induce an inflammatory response," Pharmaceutical Research 25(12):2972-2982, Kluwer Academic/Plenum Publishers, United States (Dec. 2008).
Bourn, R. L., et al., "Pms2 suppresses large expansions of the (GAA•TTC)$_n$ sequence in neuronal tissues," PLoS One 7(10):e47085, Public Library of Science, United States (2012).
Carroll, J. B., et al., "Potent and selective antisense oligonucleotides targeting single-nucleotide polymorphisms in the Huntington disease gene / allele-specific silencing of mutant huntingtin," Molecular Therapy 19(12):2178-2185, Cell Press, United States (Dec. 2011).
Chatterjee, N., et al., "Mismatch repair enhances convergent transcription-induced cell death at trinucleotide repeats by activating ATR," DNA Repair 42:26-32, Elsevier, Netherlands. (Jun. 2016).
Chien, P., et al., "Novel cationic cardiolipin analogue-based liposome for efficient DNA and small interfering RNA delivery in vitro and in vivo," Cancer Gene Therapy 12(3):321-328, Nature Publishing Group, United Kingdom (Mar. 2005).
Coppede, F., et al., "The hOGGl Ser326Cys polymorphism and Huntington's disease," Toxicology 278(2):199-203, Elsevier, Ireland (Dec. 2010).
Crooke, S. T., et al., "Pharmacokinetic properties of several novel oligonucleotide analogs in mice," The Journal of Pharmacology and Experimental Therapeutics 277(2):923-937, American Society for Pharmacology and Experimental Therapeutics, United States (May 1996).
Drouet, V., et al., "Allele-specific silencing of mutant huntingtin in rodent brain and human stem cells," PLoS One 9(6):e99341, Public Library of Science, United States (Jun. 2014).
Du Plessis, J., et al., "Topical delivery of liposomally encapsulated gamma-interferon," Antiviral Research 18(3-4):259-265, Elsevier, Netherlands (Jun. 1992).
Englisch, U., and Gauss, D. H., "Chemically Modified Oligonucleotides as Probes and Inhibitors," Angewandte Chemie International Edition 30(6):613-629, Germany Chemical Society, Germany (1991).
Feigner, J. H., et al., "Enhanced gene delivery and mechanism studies with a novel series of cationic lipid formulations," The Journal of Biological Chemistry 269(4):2550-2561, Elsevier Inc., United States (Jan. 1994).
Feigner, P. L., et al., "Lipofection: a highly efficient, lipid-mediated DNA-transfection procedure," Proc Natl Acad Sci USA 84(21):7413-7417, National Academy of Sciences, United States (Nov. 1987).
Fluiter, K., et al., "Filling the gap in LNA antisense oligo gapmers: the effects of unlocked nucleic acid (UNA) and 4'-C-hydroxymethyl-DNA modifications on RNase H recruitment and efficacy of an LNA gapmer," Molecular BioSystems 5(8):838-843, Royal Society of Chemistry, United Kingdom (Aug. 2009).
Fukunaga, M., et al., "Liposome entrapment enhances the hypocalcemic action of parenterally administered calcitonin, " Endocrinology 115(2):757-761, Oxford University Press, United Kingdom (Aug. 1984).
Gabizon, A., and Papahadjopoulos, D., "Liposome formulations with prolonged circulation time in blood and enhanced uptake by tumors," Proc Natl Acad Sci USA 85(18):6949-6953, National Academy of Sciences, United States (Sep. 1988).
Gao, X., and Huang, L., "A novel cationic liposome reagent for efficient transfection of mammalian cells," Biochemical and Biophysical Research Communications 179(1):280-285, Elsevier, United States (Aug. 1991).
Geary, R. S., et al., "Absolute bioavailability of 2'-O-(2-methoxyethyl)-modified antisense oligonucleotides following intraduodenal instillation in rats," Journal of Pharmacology and Experimental Therapeutics 296(3):898-904, American Society for Pharmacology and Experimental Therapeutics, United States (Mar. 2001).
Genbank, "*Homo sapiens* mutL homolog 3 (MLH3), transcript variant 1, mRNA," Accession No. NM_001040108.1, accessed at URL:[https://www.ncbi.nlm.nih.gov/nuccore/NM_001040108.1] on Dec. 18, 2024, 6 pages.
Genbank, "Mus musculus mutL homolog 3 (Mlh3), transcript variant 1, mRNA," Accession No. NM_175337.2, accessed at URL:[https://www.ncbi.nlm.nih.gov/nuccore/NM_175337.2] on Dec. 18, 2024, 5 pages.
Genbank, "Predicted: Macaca fascicularis mutL homolog 3 (MLH3), transcript variant X1, mRNA," Accession No. XM_005561790.2, accessed at URL:[https://www.ncbi.nlm.nih.gov/nuccore/XM_005561790.2] on Dec. 18, 2024, 3 pages.
Genbank, "Rattus norvegicus mutL homolog 3 (Mlh3), mRNA," Accession No. NM_001108043.1, accessed at URL:[https://www.ncbi.nlm.nih.gov/nuccore/NM_001108043.1] on Dec. 18, 4 pages.
Genpept, "DNA mismatch repair protein Mlh3 isoform 1 [*Homo sapiens*]," Accession No. NP_001035197.1, accessed at URL:[https://www.ncbi.nlm.nih.gov/protein/NP_001035197.1] on Dec. 18, 2024, 4 pages.
Genetic Modifiers of Huntington's Disease (GeM-HD) Consortium, "Identification of genetic factors that modify clinical onset of Huntington's disease," Cell 162(3):516-526, Cell Press, United States (Jul. 2015).
Gershon, H., et al., "Mode of formation and structural features of DNA-cationic liposome complexes used for transfection," Biochemistry 32(28):7143-7151, American Chemical Society, United States (Jul. 1993).
Gomes-Pereira, M., and Monckton, D. G., "Ethidium bromide modifies the agarose electrophoretic mobility of CAG.CTG alternative DNA structures generated by PCR," Frontiers in Cellular Neuroscience 11:153, Frontiers Research Foundation, Switzerland (May 2017).
Goold, R., et al., "FAN1 modifies Huntington's disease progression by stabilizing the expanded HTT CAG repeat," Human Molecular Genetics 28(4):650-661, Oxford University Press, United Kingdom (Feb. 2019).
Grunweller, A., et al., "Comparison of different antisense strategies in mammalian cells using locked nucleic acids, 2'-O-methyl RNA, phosphorothioates and small interfering RNA," Nucleic Acids Research 31(12):3185-3193, Oxford University Press, United Kingdom (Jun. 2003).
Guatelli, J. C., et al., "Isothermal, in vitro amplification of nucleic acids by a multienzyme reaction modeled after retroviral replication," Proc Natl Acad Sci USA 87(5):1874-1878, National Academy of Sciences, United States (Mar. 1990).
Halabi, A., et al., "DNA mismatch repair complex MutSB promotes GAA•TTC repeat expansion in human cells," The Journal of Biological Chemistry 287(35):29958-29967, Elsevier Inc., United States (Aug. 2012).
Hirao, I., et al., "Natural versus artificial creation of base pairs in DNA: origin of nucleobases from the perspectives of unnatural base pair studies," Accounts of Chemical Research 45(12):2055-2065, American Chemical Society, United States (Dec. 2012).
Hu, Z., et al., "Topical delivery of Ciclosporin—A from nonionic liposomal systems: an in vivo/in vitro correlation study using hairless mouse skin," STP Pharma Sci 4(6):466-469, Société Française des Sciences et Techniques Pharmaceutiques, France (1994).
Halabi, A., et al., "GAA+TTC Repeat ExpansionIn Human Cells is Mediated By Mismatch Repair Complex MutLy and Depends Upon the Endonuclease Domain in MLH3 Isoform One," Nucleic Acid Research 46(8):4022-4032, Oxford Academic, United Kingdom (2018).
International Search Report and Written Opinion for International Application No. PCT/US2019/064059, ISA/US, Commissioner for Patents, Virginia, mailed on Mar. 3, 2020, 10 pages.
Itani, T., et al., "A simple and efficient liposome method for transfection of DNA into mammalian cells grown in suspension," Gene 56(2-3):267-276, Elsevier, Netherlands (1987).

(56) References Cited

OTHER PUBLICATIONS

Jensen, T. B., et al., "Unlocked nucleic acid (UNA) and UNA derivatives: thermal denaturation studies," Nucleic Acids Symposium Series No. 52:133-134, 2008 Oxford University Press, United Kingdom (Sep. 2008).
Kabanov, A. V., et al., "A new class of antivirals: antisense oligonucleotides combined with a hydrophobic substituent effectively inhibit influenza virus reproduction and synthesis of virus-specific proteins in MDCK cells," FEBS letters 259(2):327-330, John Wiley & Sons Ltd, United Kingdom (1990).
Kalota, A., et al., "2'-deoxy-2'-fluoro-beta-D-arabinonucleic acid (2'F-ANA) modified oligonucleotides (ON) effect highly efficient, and persistent, gene silencing," Nucleic Acids Research 34(2):451-461, Oxford University Press, United Kingdom (Jan. 2006).
Kim, S., et al., "Preparation of multivesicular liposomes," Biochimica Et Biophysica Acta 728(3):339-348, Elsevier, Netherlands (Mar. 1983).
Kovtun, I. V., et al., "OGGI initiates age-dependent CAG trinucleotide expansion in somatic cells," Nature 447(7143):447-452, Nature Publishing Group, United Kingdom (May 2007).
Kubo, T., et al., "Chemically modified symmetric and asymmetric duplex RNAs: an enhanced stability to nuclease degradation and gene silencing effect," Biochemical and Biophysical Research Communications 365(1):54-61, Elsevier, United States (Jan. 2008).
Kwoh, D. Y., et al., "Transcription-based amplification system and detection of amplified human immunodeficiency virus type 1 with a bead-based sandwich hybridization format," Proc Natl Acad Sci USA 86(4):1173-1177, National Academy of Sciences, United States (1989).
Lam, K. S., et al., "A new type of synthetic peptide library for identifying ligand-binding activity," Nature 354:82-84, Nature Publishing Group, United States (1991).
Larson, E., et al., "Age-, tissue- and length-dependent bidirectional somatic CAG•CTG repeat instability in an allelic series of R6/2 Huntington disease mice," Neurobiology of Disease 76:98-111, Academic Press, United States (Apr. 2015).
Lee, J. M., et al., "A novel approach to investigate tissue-specific trinucleotide repeat instability," BMC Systems Biology 4:29, BioMed Central, United Kingdom (Mar. 2010).
Letsinger, R. L., et al., "Cholesteryl-conjugated oligonucleotides: synthesis, properties, and activity as inhibitors of replication of human immunodeficiency virus in cell culture," Proc Natl Acad Sci USA 86(17):6553-6556, National Academy of Science, United States (Sep. 1989).
Li, Y., et al., "Establishment and maintenance of primary fibroblast repositories for rare diseases-friedreich's ataxia example," Biopreservation and Biobanking 14(4):324-329, Mary Ann Liebert Inc., United States (Aug. 2016).
Liu, S., "Radiolabeled multimeric cyclic RGD peptides as integrin alpha,beta3 targeted radiotracers for tumor imaging," Molecular Pharmaceutics 3(5):472-487, American Chemical Society, United States (Sep.-Oct. 2006).
Lizardi, P. M., et al., "Exponential amplification of recombinant—RNA hybridization probes," Nature Biotechnology 6:1197-1202, Nature Publishing Group, United Kingdom (Oct. 1988).
Long, J. D., et al., "Genetic modification of Huntington disease acts early in the prediagnosis phase," American Journal of Human Genetics 103(3):349-357, 9 pages, Elsevier, Netherlands (Sep. 2018).
Mangiarini, L., et al., "Exon 1 of the HD gene with an expanded CAG repeat is sufficient to cause a progressive neurological phenotype in transgenic mice," Cell 87(3):493-506, Cell Press, United States (Nov. 1996).
Mangiarini, L., et al., "Instability of highly expanded CAG repeats in mice transgenic for the Huntington's disease mutation," Nature Genetics 15(2):197-200, Nature Publishing Group, United Kingdom (Feb. 1997).
Mannino R. J., and Gould-Fogerite, S., "Liposome mediated gene transfer," BioTechniques, 6(7):682-690, Future Science, United Kingdom (Jul.-Aug. 1988).
Manoharan, M., et al., "Chemical modifications to improve uptake and bioavailability of antisense oligonucleotides," Annals of the New York Academy of Sciences 660:306-309, Blackwell, United States (Oct. 1992).
Manoharan, M., et al., "Cholic acid oligonucliotide conjugates for antisense applications," Bioorganic & Medicinal Chemistry Letters 4(8):1053-1060, Elsevier, United States (1994).
Manoharan, M., et al., "Introduction of a lipophilic thioether tether in the minor groove of nucleic acids for antisense applications," Bioorganic & Medicinal Chemistry Letters 3(12):2765-2770, Elsevier, United States (Dec. 1993).
Manoharan, M., et al., "Oligonucleotide conjugates: alteration of the pharmacokinetic properties of antisense agents," Nucleosides and Nucleotides 14:969-973, M. Dekker, United States (1995).
Manoharan, M., et al., "Lipidic nucleic acids," Tetrahedron Letters 36:3651-3654, Elsevier, United Kingdom (1995).
Martin, P., "A new access to 2'-O-alkylated ribonucleosides and properties of 2'-O-alkylated oligoribonucleotides," Helvetica Chimica Acta 78(2):486-504, John Wiley & Sons, Switzerland (Jan. 1995).
Mayer, L. D., et al., "Vesicles of variable sizes produced by a rapid extrusion procedure," Biochim Biophys Acta 858(1):161-168, Elsevier, Netherlands (Jun. 1986).
Mayhew, E., et al., "Characterization of liposomes prepared using a microemulsifier," Biochim Biophys Acta 775(2):169-174, Elsevier, Netherlands (Aug. 1984).
Min, K-L., et al., "Oligonucleotides comprised of alternating 2'-deoxy-2'-fluoro-beta-D-arabinonucleosides and D-2'-deoxyribonucleosides (2'F-ANA/DNA 'altimers') induce efficient RNA cleavage mediated by RNase H," Bioorganic & Medicinal Chemistry Letters 12(18):2651-2654, Elsevier Science Ltd., United Kingdom (Sep. 2002).
Mishra, R. K., et al., "Improved leishmanicidal effect of phosphorotioate antisense oligonucleotides by LDL-mediated delivery," Biochimica et Biophysica Acta 1264(2):229-237, Elsevier, Netherlands (1995).
Morales, F., et al., "A polymorphism in the MSH3 mismatch repair gene is associated with the levels of somatic instability of the expanded CTG repeat in the blood DNA of myotonic dystrophy type 1 patients," DNA Repair 40:57-66, Elsevier, Netherlands (Apr. 2016).
Mullis, K. B., and Faloona, F. A., "Specific synthesis of DNA in vitro via a polymerase- catalyzed chain reaction," Methods in Enzymology, 155:335-350, Academic Press, United States (1987).
Nabel, E. G., et al., "Gene transfer in vivo with DNA-liposome complexes: lack of autoimmunity and gonadal localization," Human Gene Therapy 3(6):649-656, Mary Ann Liebert Inc., United States (Dec. 1992).
Nabel, G. J., et al., "Direct gene transfer with DNA-liposome complexes in melanoma: expression, biologic activity, and lack of toxicity in humans," Proc Natl Acad Sci USA 90(23):11307-11311, National Academy of Sciences, United States (Dec. 1993).
Nicolau, C., et al., "Liposomes as carriers for in vivo gene transfer and expression," Methods in Enzymology 149:157-176, Academic Press, United States (1987).
Nielsen, P. E., et al., "Sequence-selective recognition of DNA by strand displacement with a thymine-substituted polyamide," Science 254(5037):1497-1500, American Association for the Advancement of Science, United States (Dec. 1991).
Oberhauser, B., and Wagner, E., "Effective incorporation of 2'-O-methyl-oligoribonucleotides into liposomes and enhanced cell association through modification with thiocholesterol," Nucleic Acids Research 20(3):533-538, Oxford University Press, United Kingdom (1992).
Olson, F., et al., "Preparation of liposomes of defined size distribution by extrusion through polycarbonate membranes," Biochimica Et Biophysica Acta 557(1):9-23, Elsevier, Netherlands (Oct. 1979).
Pal, A., et al., "Systemic delivery of RafsiRNA using cationic cardiolipin liposomes silences Raf-1 expression and inhibits tumor growth in xenograft model of human prostate cancer," International Journal of Oncology 26(4):1087-1091, Spandidos, Greece (Apr. 2005).
Pandey, S.K., et al., "Identification and characterization of modified antisense oligonucleotides targeting DMPK in mice and nonhuman primates for the treatment of myotonic dystrophy type 1," J Phar-

(56) References Cited

OTHER PUBLICATIONS macology and Experimental Therapeutics 355(2):329-340, American Society for Pharmacology and Experimental Therapeutics, United States (Nov. 2015).
Papahadjopoulos, D and Gabizon, A., "Targeting of liposomes to tumor cells in vivo," Annals of the New York Academy of Sciences 507:64-74, Blackwell, United States (1987).
Pinto, R. M., et al., "Mismatch repair genes Mlh1 and Mlh3 modify CAG instability in Huntington's disease mice: genome-wide and candidate approaches," PLoS Genetics 9(10):e1003930, Public Library of Science, United States (Oct. 2013).
Pouladi, M.A., et al., "Choosing an animal model for the study of Huntington's disease," Nature Reviews. Neuroscience 14(10):708-721, Nature Publishing Group, United Kingdom (Oct. 2013).
Saison-Behmoaras, T., et al., "Short modified antisense oligonucleotides directed against Ha-ras point mutation induce selective cleavage of the mRNA and inhibit T24 cells proliferation," The EMBO Journal 10(5):1111-1118, Wiley Blackwell, United Kingdom (1991).
Shea, R. G., et al., "Synthesis, hybridization properties and antiviral activity of lipid-oligodeoxynucleotide conjugates," Nucleic Acids Research 18(13):3777-3783, Oxford University Press, United Kingdom (1990).
Simeoni, F., et al., "Insight into the mechanism of the peptide-based gene delivery system MPG: implications for delivery of siRNA into mammalian cells," Nucleic Acids Research 31(11):2717-2724, Oxford University Press, United Kingdom (Jun. 2003).
Skotte, N. H., et al., "Allele-specific suppression of mutant huntingtin using antisense oligonucleotides: providing a therapeutic option for all Huntington disease patients," PLoS One 9(9):e107434, Public Library of Science, United States (Sep. 2014).
Sorensen, D. R., et al., "Gene silencing by systemic delivery of synthetic siRNAs in adult mice," Journal of Molecular Biology 327(4):761-766, Elsevier, United Kingdom (Apr. 2003).
Straubinger, R. M., and Papahadjopoulos, D., "Liposomes as carriers for intracellular delivery of nucleic acids," Methods in Enzymology 101:512-527, Academic Press, United States (1983).
Strauss, W. M., and Jaenisch, R., "Molecular complementation of a collagen mutation in mammalian cells using yeast artificial chromosomes," The EMBO Journal 11(2):417-422, Wiley Blackwell, United Kingdom (Feb. 1992).
Summerton, J., et al., "Morpholino and phosphorothioate antisense oligomers compared in cell-free and in-cell systems," Antisense and Nucleic Acid Drug Development 7(2):63-70, Mary Ann Liebert Inc., United States (Apr. 1997).
Svinarchuk, F. P., et al., "Inhibition of HIV proliferation in MT-4 cells by antisense oligonucleotide conjugated to lipophilic groups," Biochimie 75(1-2):49-54, Elsevier, France (1993).
Szoka Jr., F. S., and Papahadjopoulos, D., "Procedure for preparation of liposomes with large internal aqueous space and high capture by reverse-phase evaporation," Proc Natl Acad Sci USA 75(9):4194-4198, National Academy of Sciences, United States (Sep. 1978).
Tomalia, D. A., et al., "Dendrimers as multi-purpose nanodevices for oncology drug delivery and diagnostic imaging," Biochemical Society Transactions 35(Pt 1):61-67, Portland Press, United Kingdom (Feb. 2007).
Tome, S., et al., "MSH2 ATPase domain mutation affects CTG*CAG repeat instability in transgenic mice," PLoS Genetics 5(5):e1000482, Public Library of Science, United States (May 2009).
Verma, U. N., et al., "Small interfering RNAs directed against beta-catenin inhibit the in vitro and in vivo growth of colon cancer cells," Clinical Cancer Research 9(4):1291-1300, American Association for Cancer Research, United States (Apr. 2003).
Wang, C. Y., and Huang, L., "Plasmid DNA adsorbed to pH-sensitive liposomes efficiently transforms the target cells," Biochemical and Biophysical Research Communications 147(3):980-985, Elsevier, United States (Sep. 1987).
Wang, C. Y., and Huang, L., "pH-sensitive immunoliposomes mediate target-cell-specific delivery and controlled expression of a foreign gene in mouse," Proc Natl Acad Sci USA 84(22):7851-7855, National Academy of Sciences, United States (Nov. 1987).
Warby, S. C., et al., "CAG expansion in the Huntington disease gene is associated with a specific and targetable predisposing haplogroup," American Journal of Human Genetics 84(3):351-366, Cell Press, United States (Mar. 2009).
Weiner, N., et al., "Liposomes: a novel topical delivery system for pharmaceutical and cosmetic applications," Journal of Drug Targeting 2(5):405-410, Harwood Academic Publishers GmbH, United States (1994).
Wheeler, V. C., et al., "Length-dependent gametic CAG repeat instability in the Huntington's disease knock-in mouse," Human Molecular Genetics 8(1):115-122, Oxford University Press, United Kingdom (Jan. 1999).
Wheeler, V. C., et al., "Long glutamine tracts cause nuclear localization of a novel form of huntingtin in medium spiny striatal neurons in $Hdh^{Q92}$ and $Hdh^{Q111}$ knock-in mice," Human Molecular Genetics 9(4):503-513, Oxford University Press, United Kingdom (Mar. 2000).
Wu, N. Z., et al., "Increased microvascular permeability contributes to preferential accumulation of Stealth liposomes in tumor tissue," Cancer Research 53(16):3765-3670, American Association for Cancer Research, United States (Aug. 1993).
Xu, Z. Z., and Mathews, D. H., "Secondary Structure Prediction of Single Sequences Using RNAstructure," Methods in Molecular Biology 1490:15-34, Humana Press, United States (2016).
Yoo, H., et al., "PAMAM dendrimers as delivery agents for antisense oligonucleotides," Pharmaceutical Research 16(12):1799-1804, Kluwer Academic/Plenum Publishers, United States (Dec. 1999).
Zhang, W., et al., "Treatment of type 1 myotonic dystrophy by engineering site-specific RNA endonucleases that target (CUG)(n) repeats," Molecular Therapy 22(2):312-320, Cell Press, United States (Feb. 2014).
Zhou, X., et al., "Lipophilic polylysines mediate efficient DNA transfection in mammalian cells," Biochim Biophys Acta 1065(1):8-14, Elsevier, Netherlands (May 1991).
Zhou, X., and Huang, L., "Targeted delivery of DNA by liposomes and polymers," Journal of Controlled Release 19:269-274, Elsevier Science Publishers, United States (1992).
Zhou, C., et al., "Fine tuning of electrostatics around the internucleotidic phosphate through incorporation of modified 2',4'-carbocyclic-LNAs and -ENAs leads to significant modulation of antisense properties," The Journal of Organic Chemistry 74(1):118-134, American Chemical Society, United States (Jan. 2009).
Zimmermann, T. S., et al., "RNAi-mediated gene silencing in non-human primates," Nature 441(7089):111-114, Nature Publishing Group, United Kingdom (Mar. 2006).
Aigner, A., "Delivery Systems for the Direct Application of siRNAs toInduce RNA Interference (RNAi) In Vivo," Journal of Biomedicine and Biotechnology, 2006, 71659, pp. 1-15, Hindawi Publishing Corp. (2006).
Chauhan, D., et al., "Antisense Inhibition of Hmlh1 is Not Sufficient For Loss of DNA Mismatch Repair Function in the HCT116+ Chromosome 3 Cell Line," Clinical Cancer Research 6:3827-3831, American Cancer Research, United States (2000).
Tome, S., et al., "MSH3 Polymorphisms and Protein Levels Affect CAG Repeat Instability in Huntington's Disease Mice," Plos Genetics 9(2):e1003280, Public Library of Science, United States (2013).
Sanghvi, Y. S., Crooke, S. T., and Lebleu, B., "Chapter 15—Heterocyclic Base Modifications in Nucleic acids and their Applications in Antisense Oligonucleotides," in *Antisense Research and Applications*, pp. 273-288, CRC Press, United States (1993).
Seznec, H., et al., "Transgenic Mice Carrying Large Human Genomic Sequences With Expanded CTG Repeat Mimic Closely the DM CTG Repeat Intergenerational and Somatic Instability," Human Molecular Genetics 9(8):1185-1194, Oxford, United Kingdom (May 2000).

* cited by examiner

METHODS FOR THE TREATMENT OF TRINUCLEOTIDE REPEAT EXPANSION DISORDERS ASSOCIATED WITH MLH3 ACTIVITY

INCORPORATION BY REFERENCE OF SEQUENCE LISTING

The contents of the text file named "2024-06-07-4398_0060003_Seqlisting_ST25 txt" which was created on May 30, 2024 and is 993,791 bytes in size, is hereby incorporated by reference in its entirety.

BACKGROUND

Trinucleotide repeat expansion disorders are genetic disorders caused by trinucleotide repeat expansions. Trinucleotide repeat expansions are a type of genetic mutation where nucleotide repeats in certain genes or introns exceed the normal, stable threshold for that gene. The trinucleotide repeats can result in defective or toxic gene products, impair RNA transcription, and/or cause toxic effects by forming toxic mRNA transcripts.

Trinucleotide repeat expansion disorders are generally categorized by the type of repeat expansion. For example, Type 1 disorders such as Huntington's disease are caused by CAG repeats which result in a series of glutamine residues known as a polyglutamine tract, Type 2 disorders are caused by heterogeneous expansions that are generally small in magnitude, and Type 3 disorders such as fragile X syndrome are characterized by large repeat expansions that are generally located outside of the protein coding region of the genes. Triucleotide repeat expansion disorders are characterized by a wide variety of symptoms such as progressive degeneration of nerve cells that is common in the Type 1 disorders.

Subjects with a trinucleotide repeat expansion disorder or those who are considered at risk for developing a trinucleotide repeat expansion disorder have a constitutive nucleotide expansion in a gene associated with disease (i e., the trinucleotide repeat expansion is present in the gene during embryogenesis). Constitutive trinucleotide repeat expansions can undergo expansion after embryogenesis (i.e., somatic trinucleotide repeat expansion). Both constitutive trinucleotide repeat expansion and somatic trinucleotide repeat expansion can be associated with presence of disease, age at onset of disease, and/or rate of progression of disease.

SUMMARY OF THE DISCLOSURE

The present invention features useful compositions and methods to treat trinucleotide repeat expansion disorders, e.g., in a subject in need thereof. In some aspects, the compositions and methods described herein are useful in the treatment of disorders associated with MLH3 activity.

Ollgonucleoddes

Some aspects of this disclosure are directed to a single-stranded oligonucleotide of 10-30 linked nucleosides in length, wherein the oligonucleotide comprises a region of at least 10 contiguous nucleobases having at least 80% complementary to an MLH3 gene. In some aspects, the oligonucleotide comprises: (a) a DNA core sequence comprising linked deoxyribonucleosides; (b) a 5' flanking sequence comprising linked nucleosides; and (c) a 3' flanking sequence comprising linked nucleosides; wherein the DNA core comprises a region of at least 10 contiguous nucleobases having at least 80% complementarity to an MLH3 gene and is positioned between the 5' flanking sequence and the 3' flanking sequence; wherein the 5' flanking sequence and the 3' flanking sequence each comprises at least two linked nucleosides; and wherein at least one nucleoside of each flanking sequence comprises an alternative nucleoside.

In some aspects, the disclosure is directed to a single-stranded oligonucleotide of 10-30 linked nucleosides in length for inhibiting expression of a human MLH3 gene in a cell, wherein the oligonucleotide comprises a region of at least 10 contiguous nucleobases having at least 80% complementarity to an MLH3 gene. In some aspects, the oligonucleotide comprises: (a) a DNA core comprising linked deoxyribonucleosides; (b) a 5' flanking sequence comprising linked nucleosides; and (c) a 3' flanking sequence comprising linked nucleosides; wherein the DNA core comprises a region of at least 10 contiguous nucleobases having at least 80% complementarity to an MLH3 gene and is positioned between the 5' flanking sequence and the 3' flanking sequence, wherein the 5' flanking sequence and the 3' flanking sequence each comprises at least two linked nucleosides; and wherein at least one nucleoside of each flanking sequence comprises an alternative nucleoside. In some aspects, the region of at least 10 nucleobases has at least 90% complementary to an MLH3 gene. In some aspects, the region of at least 10 nucleobases has at least 95% complementary to an MLH3 gene.

In some aspects, the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1536-1598, 1623-1660, 1739-1764, 1782-1823, 1847-1908, 2026-2051, 2063-2094, 2115-2146, 2256-2290, 2387-2414, 2421-2592, 2727-2788, 2826-2937, 3005-3043, 3078-3107, 3159-3185, 3214-3239, 3244-3272, 3282-3308, 3426-3483, 3561-3587, 3642-3769, 3804-3839, 3950-3977, 4004-4040, 4052-4115, 4139-4199, 4241-4301, 4328-4365, 4420-4448, 4472-4536, 4669-4708, or 4784-4810 of the MLH3 gene. In some aspects, the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1568-1598, 1623-1660, 1782-1823, 1870-1904, 2063-2094, 2115-2146, 2256-2287, 2387-2414, 2422-2592, 2727-2788, 2826-2937, 3009-3043, 3078-3107, 3159-3185, 3214-3272, 3282-3307, 3426-3483, 3561-3587, 3642-3767, 3804-3839, 3950-3977, 4004-4039, 4052-4115, 4139-4199, 4241-4301, 4329-4365, 4420-4448, 4472-4536, 4680-4708, or 4784-4810 of the MLH3 gene. In some aspects, the region of at least 10 nucleobases is complementary to an MLH3 gene corresponding to a sequence of reference mRNA NM_001040108.1 at one or more of positions 221-293, 321-506, 534-635, 681-740, 842-875, 953-1024, 1129-1158, 1179-1264, 1287-1316,1351-1378, 1568-1598,1623-1659, 1782-1823, 1870-1904, 2064-2091, 2115-2146, 2256-2287, 2387-2414, 2422-2592, 2727-2788,2829-2937, 3010-3043, 3079-3107, 3159-3185, 3246-3271, 3282-3307, 3426-3474, 3561-3587, 3642-3707, 3804-3839, 3950-3977, 4004-4039, 4052-4114, 4139-4164, 4174-4199, 4241-4288, 4329-4365, 4421-4448, 4472-4536, 4680-4708, or 4784-4810 of the MLH3 gene. In some aspects, the region of at least 10 nucleobases is complementary to an MLH3 gene corresponding to a sequence of reference mRNA NM_001040108.1 at one or more of positions 331-362, 393-438, 479-505, 534-574, 587-612, 681-740, 847-873, 991-1024, 1210-1262, 1351-1378, 1571-1597, 1623-1648, 1874-1902, 2066-2091, 2256-2281, 2388-2414, 2470-2515, 2732-2788, 2853-2878, 2901-2927, 3282-3307, 3562-3587, 4056-4083, 4241-4266, or 4506-4531 of the MLH3 gene. In some aspects, the region of at least 10 nucleobases is complementary to an MLH3 gene corresponding to a sequence of reference mRNA NM_001040108.1 at one or more of positions 335-449, 587-612, 682-736, 848-873, 991-1016, 1179-1204, 1233-1260, 1351-1378, 1626-1651, 1874-1903, 2066-2091, 2115-2146, 2256-2287, 2389-2414, 2471-2499, 2762-2787, 2853-2878, 2911-2936, 3562-3587, 3814-3839, 4006-4031, 4056-4083, or 4244-4269 of the MLH3 gene. In some aspects, the region of at least 10 nucleobases is complementary to an MLH3 gene corresponding to a sequence of reference mRNA NM_001040108.1 at one or more of positions 355-393, 952-984, 1177-1205, 2026-2052, 2066-2094, 2470-2498, 3159-3185, 3458-3485, or 4259-4292 of the MLH3 gene.

In some aspects, the oligonucleotide comprises the nucleobase sequence of any one of SEQ ID NOs: 6-4710. In some aspects, the oligonucleotide comprises the nucleobase sequence of any one of SEQ ID NOs: 89, 92, 102, 107-108, 110-111, 115-116, 150, 154, 160-161, 163-164, 166, 168, 175-176, 178, 180, 182-183, 185-189, 201, 211-212, 229-231, 234-238, 241, 248-250, 254, 265-269, 282-283, 285-288, 294, 296, 319-322, 328-329, 366-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086, 1110-1111, 1126, 1149, 1172, 1176-1181, 1185, 1260, 1271-1274,1276-1277, 1297, 1302, 1387-1390, 1392-1393, 1396, 1461-1463, 1473-1474, 1482, 1490-1491, 1495, 1498-1502, 1505, 1508, 1510-1514, 1516-1518, 1525-1526, 1529-1530, 1546-1547, 1572, 1596-1597, 1721-1722, 1724-1727, 1744-1746, 1797, 1800-1802, 1824-1826, 1832, 1835-1836, 1859, 1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-2785, 2789, 2791-2792, 2794-2795, 2797, 2848-2852, or 2917-2918. In some aspects, the oligonucleotide comprises the nucleobase sequence of any one of SEQ ID NOs: 89, 92, 102, 107-108, 111, 116, 150, 154, 160-161, 163-164, 166, 168, 175-176, 178, 180, 182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-1111, 1126, 1172, 1176-1181, 1271-1274, 1276-1277, 1297, 1302, 1387, 1390, 1392-1393, 1461-1463, 1474, 1482, 1490-1491, 1498-1502, 1505, 1508, 1510-1512, 1514, 1516-1518, 1525-1526, 1529-1530, 1546-1547, 1572, 1597, 1721-1722, 1724-1727, 1744-1746, 1797, 1800-1801, 1824-1826, 1832, 1835-1836, 1859, 1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, or 2917-2918. In some aspects, the oligonucleotide comprises the nucleobase sequence of any one of SEQ ID NOs: 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368, 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, or 2917-2918. In some aspects, the oligonucleotide comprises the nucleobase sequence of any one of SEQ ID NOs: 160-161, 163-164, 166, 211-212, 230-231, 267-268, 282, 294, 322, 366-367, 391-394, 399, 514-515, 594, 602, 728, 750, 752-753, 755, 828, 830, 975-976, 1002, 1176-1179, 1274, 1387, 1462-1463, 1510, 1514, 1529-1530, 1726-1727, 1745-1746, 1824, 1871-1872, 2090, 2256, 2528-2530, 2644, or 2792. In some aspects, the oligonucleotide comprises the nucleobase sequence of any one of SEQ ID NOs: 164, 186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, or 2646. In some aspects, the oligonucleotide comprises the nucleobase sequence of any one of SEQ ID NOs. 174-176,178,180-187, 566-569, 573, 701-704, 1260-1261, 1274-1277, 1510-1513, 2000-2001, 2194, 2196, 2661-2664, or 2666.

In some aspects, the nucleobase sequence of the oligonucleotide consists of any one of SEQ ID NOs: 6-4710. In some aspects, the oligonuclectide consists of the nucleobase sequence of any one of SEQ ID NOs: 89, 92, 102, 107-108, 110-111, 115-116, 150, 154, 160-161, 163-164, 166, 168, 175-176,178,180,182-183, 185-189, 201, 211-212, 229-231, 234-238, 241, 248-250, 254, 265-269, 282-283, 285-288, 294, 296, 319-322, 328-329, 366-367-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086, 1110-1111, 1126, 1149, 1172, 1176-1181, 1185, 1260, 1271-1274, 1276-1277, 1297, 1302, 1387-1390, 1392-1393, 1396, 1461-1463, 1473-1474, 1482, 1490-1491, 1495, 1498-1502, 1505, 1508, 1510-1514, 1516-1518, 1525-1526, 1529-1530, 1546-1547, 1572, 1596-1597, 1721-1722, 1724-1725-1726-1727, 1744-1746, 1797, 1800-1802, 1824-1826, 1832, 1835-1836, 1859, 1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-

2785, 2789, 2791-2792, 2794-2795, 2797, 2848-2852, or 2917-2918. In some aspects, the oligonucleotide consists of the nucleobase sequence of any one of SEQ ID NOs. 89, 92, 102, 107-108, 111, 116, 150, 154, 160-161, 163-164, 166, 168, 175-176,178,180,182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-1111, 1126, 1172, 1176-1181, 1271-1274,1276-1277, 1297, 1302, 1387, 1390, 1392-1393, 1461-1462-1463, 1474, 1482, 1490-1491, 1498-1502, 1505, 1508, 1510-1512, 1514, 1516-1518, 1525-1526, 1529-1530, 1546-1547,1572,1597,1721-1722, 1724-1727, 1744-1746, 1797, 1800-1801, 1824-1826, 1832, 1835-1836, 1859, 1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, or 2917-2918 In some aspects, the oligonucleotide consists of the nucleobase sequence of any one of SEQ ID NOs: 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368, 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, or 2917-2918. In some aspects, the oligonucleotide consists of the nucleobase sequence of any one of SEQ ID NOs: 160-161, 163-164, 166, 211-212, 230-231, 267-268, 282, 294, 322, 366-367, 391-394, 399, 514-515, 594, 602, 728, 750, 752-753, 755, 828, 830, 975-976, 1002, 1176-1179, 1274, 1387, 1462-1463, 1510, 1514, 1529-1530, 1726-1727, 1745-1746, 1824, 1871-1872, 2090, 2256, 2528-2530, 2644, or 2792. In some aspects, the oligonucleotide consists of the nucleobase sequence of any one of SEQ ID NOs: 164, 186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, or 2646 In some aspects, the oligonucleotide consists of the nucleobase sequence of any one of SEQ ID NOs: 174-176, 178, 180-187, 566-569, 573, 701-704, 1260-1261, 1274-1277, 1510-1513, 2000-2001, 2194, 2196, 2661-2664, or 2666

In some aspects, the oligonucleotide exhibits at least 50% mRNA inhibition at 20 nM oligonucleotide concentration when determined using a cell assay when compared with a control cell. In some aspects, the oligonucleotide exhibits at least 60% mRNA inhibition at a 20 nM oligonucleotide concentration when determined using a cell assay when compared with a control cell. In some aspects, the oligonucleotide exhibits at least 70% mRNA inhibition at a 20 nM oligonucleotide concentration when determined using a cell assay when compared with a control cell. In some aspects, the oligonucleotide exhibits at least 85% mRNA inhibition at a 20 nM oligonucleotide concentration when determined using a cell assay when compared with a control cell. In some aspects, the oligonucleotide exhibits at least 50% mRNA inhibition at a 2 nM oligonucleotide concentration when determined using a cell assay when compared with a control cell. In some aspects, the oligonucleotide exhibits at least 60% mRNA inhibition at a 2 nM oligonucleotide concentration when determined using a cell assay when compared with a control cell. In some aspects, the oligonucleotide exhibits at least 70% mRNA inhibition at a 2 nM oligonucleotide concentration when determined using a cell assay when compared with a control cell. In some aspects, the oligonucleotide exhibits at least 85% mRNA inhibition at a 2 nM oligonucleotide concentration when determined using a cell assay when compared with a control cell. The cell assay can comprise transfecting a mammalian cell, such as HEK293, NIH3T3, or HeLa, with oligonucleotides using LIPOFECTAMINE™ 2000 (Invitrogen) and measuring mRNA levels compared to a mammalian cell transfected with a mock oligonucleotide. In some aspects, the oligonucleotide comprises at least one alternative internucleoside linkage. In some aspects, the at least one alternative internucleoside linkage is a phosphorothioate internucleoside linkage. In some aspects, the at least one alternative internucleoside linkage is a 2'-alkoxy internucleoside linkage. In some aspects, the at least one alternative internucleoside linkage is an alkyl phosphate intemudeoside linkage.

In some aspects, the oligonucleotide comprises at least one alternative nucleobase. In some aspects, the alternative nucleobase is 5-methylcytosine, pseudouridine, or 5-methoxyuridine.

In some aspects, the oligonucleotide comprises at least one alternative sugar moiety. In some aspects, the alternative sugar moiety is 2-OMe or a bicyclic nucleic acid.

In some aspects, the oligonucleotide further comprises a ligand conjugated to the 5' end or the 3' end of the oligonucleotide through a monovalent or branched bivalent or trivalent linker.

In some aspects, the oligonucleotide comprises a region complementary to at least 17 contiguous nucleotides of a MLH3 gene. In some aspects, the oligonucleotide comprises a region complementary to at least 19 contiguous nucleotides of a MLH3 gene. In some aspects, the oligonucleotide comprises a region complementary to 19 to 23 contiguous nucleotides of a MLH3 gene. In some aspects, the oligonucleotide comprises a region complementary to 19 contiguous nucleotides of a MLH3 gene. In some aspects, the oligonucleotide comprises a region complementary to 20 contiguous nucleotides of a MLH3 gene. In some aspects, the oligonucleotide is from about 15 to 25 nucleosides in length. In some aspects, the oligonucleotide is 20 nucleosides in length.

Pharmaceutical Compositions and Methods of Treatment Using the Same

In some aspects, the application is directed to a pharmaceutical composition comprising one or more of the oligonucleotides described herein and a pharmaceutically acceptable carrier or excipient.

In some aspects, the application is directed to a composition comprising one or more of the oligonucleotides described herein and a lipid nanoparticle, a polyplex nanoparticle, a lipoplex nanoparticle, or a liposome.

In some aspects, the application is directed to a method of inhibiting transcription of MLH3 in a cell, the method comprising contacting the cell with one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome; for a time sufficient to obtain degradation of an mRNA transcript of a MLH3 gene, inhibiting expression of the MLH3 gene in the cell.

In some aspects, the application is directed to a method of treating, preventing, or delaying the progression a trinucleotide repeat expansion disorder in a subject in need thereof, the method comprising contacting the cell with one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome; for a time sufficient to obtain degradation of an mRNA transcript of a MLH3 gene, inhibiting expression of the MLH3 gene in the cell.

In some aspects, the application is directed to a method of reducing the level and/or activity of MLH3 in a cell of a subject identified as having a trinucleotide repeat expansion disorder, the method comprising contacting the cell with one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome, for a time sufficient to obtain degradation of an mRNA transcript of a MLH3 gene, inhibiting expression of the MLH3 gene in the cell.

In some aspects, the application is directed to a method for inhibiting expression of an MLH3 gene in a cell comprising contacting the cell with one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome; for a time sufficient to obtain degradation of an mRNA transcript of a MLH3 gene, inhibiting expression of the MLH3 gene in the cell, and maintaining the cell for a time sufficient to obtain degradation of a mRNA transcript of an MLH3 gene, thereby inhibiting expression of the MLH3 gene in the cell.

In some aspects, the application is directed to a method of decreasing trinucleotide repeat expansion in a cell, the method comprising contacting the cell with one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome; for a time sufficient to obtain degradation of an mRNA transcript of a MLH3 gene, inhibiting expression of the MLH3 gene in the cell.

In some aspects, the cell is in a subject. In some aspects, the subject is a human. In some aspects, the cell is a cell of the central nervous system or a muscle cell.

In some aspects, the subject is identified as having a trinucleotide repeat expansion disorder. In some aspects, the trinucleotide repeat expansion disorder is a polyglutamine disease. In some aspects, the polyglutamine disease is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, and Huntington's disease-like 2. In some aspects, the trinucleotide repeat expansion disorder is Huntington's disease.

In some aspects, the trinucleotide repeat expansion disorder is a non-polyglutamine disease. In some aspects, the non-polyglutamine disease is selected from the group consisting of fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy. In some aspects, the trinucleotide repeat expansion disorder is Friedreich's ataxia. In some aspects, the trinucleotide repeat expansion disorder is myotonic dystrophy type 1.

In some aspects, the application is directed one or more of the oligonucleotides described herein, a pharmaceutical composition of one or more of the oligonucleotides described herein, or the composition of one or more oligonucleotides described herein and a lipid nanoparticle, a polyplex nanoparticle, a lipoplex nanoparticle, or a liposome, for use in the prevention or treatment of a trinucleotide repeat expansion disorder.

In some aspects, the one or more of the oligonucleotides described herein, the pharmaceutical composition of one or more of the oligonucleotides described herein, or the composition of one or more oligonucleotides described herein and a lipid nanoparticle, a polyplex nanoparticle, a lipoplex nanoparticle, or a liposome is administered intrathecally.

In some aspects, the one or more of the oligonucleotides described herein, the pharmaceutical composition of one or more of the oligonucleotides described herein, or the composition of one or more oligonucleotides described herein and a lipid nanoparticle, a polyplex nanoparticle, a lipoplex nanoparticle, or a liposome is administered intraventricularly.

In some aspects, the one or more of the oligonucleotides described herein, the pharmaceutical composition of one or more of the oligonucleotides described herein, or the composition of one or more oligonucleotides described herein and a lipid nanoparticle, a polyplex nanoparticle, a lipoplex nanoparticle, or a liposome is administered intramuscularly.

In some aspects, the application is directed to a method of treating, preventing, or delaying progression a disorder in a subject in need thereof wherein the subject is suffering from trinucleotide repeat expansion disorder, comprising administering to said subject one or more of the oligonucleotides described herein, the pharmaceutical composition of one or more of the oligonucleotides described herein, or the composition of one or more oligonucleotides described herein and a lipid nanoparticle, a polyplex nanoparticle, a lipoplex nanoparticle, or a liposome.

In some aspects, the method of treating, preventing, or delaying progression of a disorder in a subject further comprises administering an additional therapeutic agent. In some aspects, the additional therapeutic agent is another oligonucleotide that hybridizes to an mRNA encoding the Huntingtin gene.

In some aspects, the method of treating, preventing, or delaying progression of a disorder in a subject progression delays progression of the trinucleotide repeat expansion disorder by at least 120 days, for example, at least 6 months, at least 12 months, at least 2 years, at least 3 years, at least 4 years, at least 5 years, at least 10 years or more, when compared with a predicted progression.

In some aspects, the application is directed to one or more of the oligonucleotides described herein, the pharmaceutical composition of one or more of the oligonucleotides described herein, or the composition of one or more oligonucleotides described herein and a lipid nanoparticle, a polyplex nanoparticle, a lipoplex nanoparticle, or a liposome for use in preventing or delaying progression of a trinucleotide repeat expansion disorder in a subject

Definitions

For convenience, the meaning of some terms and phrases used in the specification, examples, and appended claims are provided below. Unless stated otherwise, or implicit from context, the following terms and phrases include the meanings provided below. The definitions are provided to aid in describing particular aspects, and are not intended to limit the claimed technology, because the scope of the technology is limited only by the claims. Unless otherwise defined, all technical and scientific terms used herein have the same meaning as commonly understood by one of ordinary skill in the art to which this technology belongs. If there is an apparent discrepancy between the usage of a term in the art and its definition provided herein, the definition provided within the specification shall prevail.

In this application, unless otherwise clear from context, (i) the term 'a' can be understood to mean 'at least one'; (ii) the term 'or' can be understood to mean "and/or"; and (iii) the terms 'including' and 'comprising' can be understood to encompass itemized components or steps whether presented by themselves or together with one or more additional components or steps.

As used herein, the terms 'about' and "approximately" refer to a value that is within 10% above or below the value being described. For example, the term "about 5 nM" indicates a range of from 4.5 to 5.5 nM.

The term 'at least' prior to a number or series of numbers is understood to include the number adjacent to the term "at least", and all subsequent numbers or integers that could logically be included, as clear from context. For example, the number of nucleotides in a nucleic acid molecule must be an integer. For example, "at least 18 nucleotides of a 21-nucleotide nucleic acid molecule" means that 18, 19, 20, or 21 nucleotides have the indicated property. When at least is present before a series of numbers or a range, it is understood that "at least" can modify each of the numbers in the series or range. "At least" is also not limited to integers (e.g., "at least 5%" includes 5.0%, 5.1%, 5.18% without consideration of the number of significant figures. As used herein, "no more than" or "less than" is understood as the value adjacent to the phrase and logical lower values or integers, as logical from context, to zero. For example, an oligonucleotide with "no more than 3 mismatches to a target sequence" has 3, 2, 1, or 0 mismatches to a target sequence. When "no more than" is present before a series of numbers or a range, it is understood that "no more than" can modify each of the numbers in the series or range. As used herein, the term "administration" refers to the administration of a composition (e.g., a compound or a preparation that includes a compound as described herein) to a subject or system. Administration to an animal subject (e.g., to a human) can be by any appropriate route, such as one described herein.

As used herein, a "combination therapy" or"administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some aspects, the delivery of the two or more agents is simultaneous or concurrent and the agents can be co-formulated. In some aspects, the two or more agents are not co-formulated and are administered in a sequential manner as part of a prescribed regimen. In some aspects, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, one therapeutic agent of the combination can be administered by intravenous injection while another therapeutic agent of the combination can be administered orally.

As used herein, the term "MLH3" refers to mutL homolog 3, a DNA mismatch repair protein, having an amino acid sequence from any vertebrate or mammalian source, including, but not limited to, human, bovine, chicken, rodent, mouse, rat, porcine, ovine, primate, monkey, and guinea pig, unless specified otherwise. The term also refers to fragments and variants of native MLH3 that maintain at least one in vivo or in vitro activity of a native MLH3. The term encompasses full-length unprocessed precursor forms of MLH3 as well as mature forms resulting from post-translational cleavage of the signal peptide. MLH3 is encoded by the MLH3 gene. The nucleic acid sequence of an exemplary *Homo sapiens* (human) MLH3 gene is set forth in NCBI Reference No. NM_001040108.1 or in SEQ ID NO: 1. The term "MLH3" also refers to natural variants of the wild-type MLH3 protein, such as proteins having at least 85% identity (e.g., 85%, 86%, 87%, 88%, 89%, 90%, 91%, 92%, 93%, 94%, 95%, 96%, 97%, 98%, 99%, 99.9% identity, or more) to the amino acid sequence of wild-type human MLH3, which is set forth in NCBI Reference No. NP_001035197.1 or in SEQ ID NO: 2. The nucleic acid sequence of an exemplary *Mus musculus* (mouse) MLH3 gene is set forth in NCBI Reference No. NM_175337.2 or in SEQ ID NO: 3. The nucleic acid sequence of an exemplary *Rattus norvegicus* (rat) MLH3 gene is set forth in NCBI Reference No. NM_001108043.1 or in SEQ ID NO: 4. The nucleic acid sequence of an exemplary *Macaca fascicularis* (cyno) MLH3 gene is set forth in NCBI Reference XM_005561790.2 or in SEQ ID NO: 5. The term "MLH3" as used herein, also refers to a particular polypeptide expressed in a cell by naturally occurring DNA sequence variations of the MLH3 gene, such as a single nucleotide polymorphism in the MLH3 gene. Numerous SNPs within the MLH3 gene have been identified and can be found at, for example, NCBI dbSNP (see, e.g., www.ncbi.nlm.nih.gov/snp). Non-limiting examples of SNPs within the MLH3 gene can be found at, NCBI dbSNP Accession Nos.: rs28757011; rs28756991; rs28756990; rs28756982;

rs28756981; rs17782839; rs7156586; rs175081; rs175080; rs175057; rs175049; rs108621; rs13712; and rs7303.

As used herein, "target sequence" refers to a contiguous portion of the nucleotide sequence of an mRNA molecule formed during the transcription of an MLH3 gene, including mRNA that is a product of RNA processing of a primary transcription product. In one aspect, the target portion of the sequence will be at least long enough to serve as a substrate for oligonucleotide-directed (e.g., antisense oligonucleotide (ASO)-directed) cleavage at or near that portion of the nucleotide sequence of an mRNA molecule formed during the transcription of a MLH3 gene. The target sequence can be, for example, from about 9-36 nucleotides in length, e.g., about 15-30 nucleotides in length. For example, the target sequence can be 15, 16, 17, 18, 19, 20, 21, 22, 23, 24, 25, 26, 27, 28, 29, or 30 or from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be.

"G," "C," "A," "T," and "U" each generally stand for a naturally-occurring nucleotide that contains guanine, cytosine, adenine, thymidine, and uracil as a base, respectively. However, it will be understood that the term "nucleotide" can refer to an alternative nucleotide, as further detailed below, or a surrogate replacement moiety. The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of oligonucleotides described herein by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods described herein.

The terms "nucleobase" and "base" include the purine (e.g. adenine and guanine) and pyrimidine (e.g. uracil, thymine, and cytosine) moiety present in nucleosides and nucleotides which form hydrogen bonds in nucleic acid hybridization. The term nucleobase also encompasses alternative nucleobases which can differ from naturally-occurring nucleobases, but are functional during nucleic acid hybridization. In this context "nucleobase" refers to both naturally occurring nucleobases such as adenine, guanine, cytosine, thymidine, uracil, xanthine, and hypoxanthine, as well as alternative nucleobases. Such variants are for example described in Hirao et al (2012) Accounts of Chemical Research vol 45 page 2055 and Bergstrom (2009) Current Protocols in Nucleic Acid Chemistry Suppl 37.1.4.1.

The term "nucleoside" refers to a monomeric unit of an oligonucleotide or a polynucleotide having a nucleobase and a sugar moiety A nucleoside can include those that are naturally-occurring as well as alternative nucleosides, such as those described herein. The nucleobase of a nucleoside can be a naturally-occurring nucleobase or an alternative nucleobase. Similarly, the sugar moiety of a nucleoside can be a naturally-occurring sugar or an alternative sugar.

The term "alternative nucleoside" refers to a nucleoside having an alternative sugar or an alternative nucleobase, such as those described herein.

In some aspects, the nucleobase moiety is modified by changing the purine or pyrimidine into a modified punne or pyrimidine, such as substituted purine or substituted pyrimidine, such as an "alternative nucleobase" selected from isocytosine, pseudoisocytosine, 5-methyl cytosine, 5-thiozolo-cytosine, 5-propynyl-cytosine, 5-propynyl-uridine, 5-bromouridine 5-thiazolo-uridine, 2-thio-uridine, pseudouridine, 1-methylpseudouridine, 5-methoxyuridine, 2'-thio-thymine, inosine, diaminopurine, 6-aminopurine, 2-aminopurine, 2,6-diaminopurine, and 2-chloro-6-aminopurine. The nucleobase moieties can be indicated by the letter code for each corresponding nucleobase, e.g. A, T, G, C, or U, wherein each letter can include alternative nucleobases of equivalent function. In some aspects, e.g., for gapmers, 5-methyl cytosine LNA nucleosides can be used.

A "sugar" or "sugar moiety," includes naturally occurring sugars having a furanose ring. A sugar also includes an "alternative sugar," defined as a structure that is capable of replacing the furanose ring of a nucleoside. In some aspects, alternative sugars are non-furanose (or 4'-substituted furanose) rings or ring systems or open systems Such structures include simple changes relative to the natural furanose ring, such as a six-membered ring, or can be more complicated as is the case with the non-ring system used in peptide nucleic acid. Alternative sugars can include sugar surrogates wherein the furanose ring has been replaced with another ring system such as, for example, a morpholino or hexitol ring system. Sugar moieties useful in the preparation of oligonucleotides having motifs include, without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic alternative sugars (such as the 2'-O-$CH_2$-4' or 2'-O—($CH_2$)2-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. In most nucleosides having an alternative sugar moiety, the heterocyclic nucleobase is generally maintained to permit hybridization.

A "nucleotide," as used herein, refers to a monomeric unit of an oligonucleotide or polynucleotide that comprises a nucleoside and an internucleosidic linkage. The intemucleosidic linkage can include a phosphate linkage. Similarly, "linked nucleosides" can be linked by phosphate linkages. Many "alternative intemucleosidic linkages' are known in the art, including, but not limited to, phosphate, phosphorothioate, and boronophosphate linkages Alternative nucleosides include bicyclic nucleosides (BNAs) (e.g., locked nucleosides (LNAs) and constrained ethyl (cEt) nucleosides), peptide nucleosides (PNAs), phosphotriesters, phosphorothionates, phosphoramidates, and other variants of the phosphate backbone of native nucleoside, including those described herein.

An "alternative nucleotide," as used herein, refers to a nucleotide having an alternative nucleoside or an alternative sugar, and an internucleoside linkage, which can include alternative nucleoside linkages.

The terms "oligonucleotide" and "polynucleotide," as used herein, are defined as it is generally understood by the skilled person as a molecule comprising two or more covalently linked nucleosides. Such covalently bound nucleosides can be referred to as nucleic acid molecules or oligomers. Oligonucleotides are commonly made in the laboratory by solid-phase chemical synthesis followed by purification. When referring to a sequence of the oligonucleotide, reference is made to the sequence or order of nucleobase moieties, or modifications thereof, of the covalently linked nucleotides or nucleosides. The oligonucleotide can be man-made. For example, the oligonucleotide can be chemically synthesized, and be purified or isolated. Oligonucleotide is also intended to include (i) compounds that have one or more furanose moieties that are replaced by furanose derivatives or by any structure, cyclic or acyclic, that can be used as a point of covalent attachment for the base moiety, (ii) compounds that have one or more phosphodiester linkages that are either modified, as in the case of phosphoramidate or phosphorothioate linkages, or completely replaced by a suitable linking moiety as in the case of formacetal or riboacetal linkages, and/or (iii) compounds that have one or more linked furanose-phosphodiester linkage moieties replaced by any structure, cyclic or acyclic, that can be used as a point of covalent attachment for the base moiety. The oligonucleotide can comprise one or more alternative nucleosides or nucleotides (e.g., including those described herein). It is also understood that oligonucleotide includes compositions lacking a sugar moiety or nucleobase but is still capable of forming a pairing with or hybridizing to a target sequence.

"Oligonucleotide" refers to a short polynucleotide (e.g., of 100 or fewer linked nucleosides).

"Chimeric" oligonucleotides or "chimeras," as used herein, are oligonucleotides which contain two or more chemically distinct regions, each made up of at least one monomer unit, i.e., a nucleotide or nucleoside in the case of an oligonucleotide. Chimeric oligonucleotides also include "gapmers."

The oligonucleotide can be of any length that permits specific degradation of a desired target RNA through an RNase H-mediated pathway, and can range from about 10-30 nucleosides in length, e.g., about 15-30 nucleosides in length or about 18-20 nucleosides in length, for example, about 10, 11, 12, 13, 14, 15, 16, 17, 18, 19, 20, 21, 22, 23, 24, 25, 26, 27, 28, 29, or 30 nucleosides in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 nucleosides in length. Ranges and lengths intermediate to the above recited ranges and lengths are also contemplated.

As used herein, the term "oligonucleotide comprising a nucleobase sequence" refers to an oligonucleotide comprising a chain of nucleotides or nucleosides that is described by the sequence referred to using the standard nucleotide nomenclature.

The term "contiguous nucleobase region" refers to the region of the oligonucleotide which is complementary to the target nucleic acid. The term can be used interchangeably herein with the term "contiguous nucleotide sequence" or "contiguous nucleobase sequence." In some aspects, all the nucleotides of the oligonucleotide are present in the contiguous nucleotide or nucleoside region. In some aspects, the oligonucleotide comprises the contiguous nucleotide region and can comprise further nucleotide(s) or nucleoside(s), for example a nucleotide linker region which can be used to attach a functional group to the contiguous nucleotide sequence. The nucleotide linker region can be complementary to the target nucleic acid. In some aspects, the internucleoside linkages present between the nucleotides of the contiguous nucleotide region are all phosphorothioate internucleoside linkages. In some aspects, the contiguous nucleotide region comprises one or more sugar-modified nucleosides.

The term "gapmer," as used herein, refers to an oligonucleotide which comprises a region of RNase H recruiting oligonucleotides (gap or DNA core) which is flanked 5' and 3' by regions which comprise one or more affinity enhancing alternative nucleosides (wings or flanking sequence). Various gapmer designs are described herein. Headmers and tailmers are oligonucleotides capable of recruiting RNase H where one of the flanks is missing, i.e. only one of the ends of the oligonucleotide comprises affinity enhancing alternative nucleosides. For headmers the 3' flanking sequence is missing (i.e. the 5' flanking sequence comprises affinity enhancing alternative nucleosides) and for tailmers the 5' flanking sequence is missing (i.e. the 3' flanking sequence comprises affinity enhancing alternative nucleosides) A "mixed flanking sequence gapmer" refers to a gapmer wherein the flanking sequences comprise at least one alternative nucleoside, such as at least one DNA nucleoside or at least one 2' substituted alternative nucleoside, such as, for example, 7-O-alkyl-RNA, 7-O-methyl-RNA, 7-alkoxy-RNA, 2'-O-methoxyethyl-RNA (MOE), 7-amino-DNA, 2'-Fluoro-RNA, 7-F-ANA nucleoside(s), or bicyclic nucleosides (e.g., locked nucleosides or constrained ethyl (cEt) nucleosides). In some aspects, the mixed flanking sequence gapmer has one flanking sequence which comprises alternative nucleosides (e.g. 5' or 3') and the other flanking sequence (3' or 5' respectfully) comprises 2' substituted alternative nucleoside(s).

A "linker" or "linking group" is a connection between two atoms that links one chemical group or segment of interest to another chemical group or segment of interest via one or more covalent bonds. Conjugate moieties can be attached to the oligonucleotide directly or through a linking moiety (e g linker or tether). Linkers serve to covalently connect a third region, e.g. a conjugate moiety to an oligonucleotide (e.g. the termini of region A or C). In some aspects, the conjugate or oligonucleotide conjugate can comprise a linker region which is positioned between the oligonucleotide and the conjugate moiety. In some aspects, the linker between the conjugate and oligonucleotide is biocleavable. Phosphodiester containing biocleavable linkers are described in more detail in WO 2014/076195 (herein incorporated by reference).

As used herein, and unless otherwise indicated, the term "complementary," when used to describe a first nucleotide or nucleoside sequence in relation to a second nucleotide or nucleoside sequence, refers to the ability of an oligonucleotide or polynucleotide comprising the first nucleotide or nucleoside sequence to hybridize and form a duplex structure under certain conditions with an oligonucleotide or polynucleotide comprising the second nucleotide sequence, as will be understood by the skilled person Such conditions can, for example, be stringent conditions, where stringent conditions can include: 400 mM NaCl, 40 mM PIPES pH 6.4, 1 mM EDTA, 50° C., or 70° C., for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can be used. The skilled person will be able to determine the set of conditions most appropriate for a test of complementarity of two sequences in accordance with the ultimate application of the hybridized nucleotides or nucleosides.

"Complementary" sequences, as used herein, can include, or be formed entirely from, non-Watson-Crick base pairs and/or base pairs formed from non-natural and alternative nucleotides or nucleosides, in so far as the above requirements with respect to their ability to hybridize are fulfilled. Such non-Watson-Crick base pairs include, but are not limited to, G:U Wobble or Hoogstein base pairing. Complementary sequences between an oligonucleotide and a target sequence as described herein, include base-pairing of the oligonucleotide or polynucleotide comprising a first nucleotide or nucleoside sequence to an oligonucleotide or polynucleotide comprising a second nucleotide or nucleoside sequence over the entire length of one or both nucleotide or nucleoside sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via an RNase H-mediated pathway. "Substantially complementary" can refer to a polynucleotide that is substantially complementary to a contiguous portion of the mRNA of interest (e.g., an mRNA encoding MLH3). For example, a polynucleotide is complementary to at least a part of a MLH3 mRNA if the sequence is substantially complementary to a non-interrupted portion of an mRNA encoding MLH3.

As used herein, the term "region of complementarity" refers to the region on the oligonucleotide that is substantially complementary to all or a portion of a gene, primary transcript, a sequence (e.g., a target sequence, e.g., an MLH3 nucleotide sequence), or processed mRNA, so as to interfere with expression of the endogenous gene (e.g., MLH3). Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

As used herein, an "agent that reduces the level and/or activity of MLH3" refers to any polynucleotide agent (e.g., an oligonucleotide, e.g., an ASO) that reduces the level of or inhibits expression of MLH3 in a cell or subject. The phrase "inhibiting expression of MLH3," as used herein, includes inhibition of expression of any MLH3 gene (such as, e.g., a mouse MLH3 gene, a rat MLH3 gene, a monkey MLH3 gene, or a human MLH3 gene) as well as variants or mutants of a MLH3 gene that encode a MLH3 protein. Thus, the MLH3 gene can be a wild-type MLH3 gene, a mutant MLH3 gene, or a transgenic MLH3 gene in the context of a genetically manipulated cell, group of cells, or organism.

By "reducing the activity of MLH3," is meant decreasing the level of an activity related to MLH3 (e.g., by reducing the amount of trinucleotide repeats in a gene associated with a trinucleotide repeat expansion disorder that is related to MLH3 activity). The activity level of MLH3 can be measured using any method known in the art (e.g., by directly sequencing a gene associated with a trinucleotide repeat expansion disorder to measure the levels of trinucleotide repeats).

By "reducing the level of MLH3," is meant decreasing the level of MLH3 in a cell or subject, e.g., by administering an oligonucleotide to the cell or subject. The level of MLH3 can be measured using any method known in the art (e.g., by measuring the levels of MLH3 mRNA or levels of MLH3 protein in a cell or a subject).

By "modulating the activity of a MutLγ heterodimer comprising MLH3," is meant altering the level of an activity related to a MutLγ heterodimer (e.g., e.g., by altering the amount of trinucleotide repeats in a gene associated with a trinucleotide repeat expansion disorder that is related to a MutLγ heterodimer. The activity level of a MutLγ heterodimer can be measured using any method known in the art (e.g., by directly sequencing a gene associated with a trinucleotide repeat expansion disorder to measure the levels of trinucleotide repeats).

As used herein, the term "inhibitor" refers to any agent which reduces the level and/or activity of a protein (e.g., MLH3). Non-limiting examples of inhibitors include polynucleotides (e.g., oligonucleotide, e.g., ASOs). The term "inhibiting," as used herein, is used interchangeably with "reducing," "silencing," "downregulating," "suppressing," and other similar terms, and includes any level of inhibition.

As used herein, the term "selective for MLH3 over MLH1" refers to a compound which inhibits the level and/or activity of MLH3 at least 5% (e.g., at least 10%, at least 25%, at least 50%, at least 75%, or at least 100%) greater than the compound inhibits the level and/or activity of MLH1.

The phrase "contacting a cell with an oligonucleotide," such as an oligonucleotide, as used herein, includes contacting a cell by any possible means. Contacting a cell with an oligonucleotide includes contacting a cell in vitro with the oligonucleotide or contacting a cell in vivo with the oligonucleotide. The contacting can be done directly or indirectly Thus, for example, the oligonucleotide can be put into physical contact with the cell by the individual performing the method, or alternatively, the oligonucleotide agent can be put into a situation that will permit or cause it to subsequently come into contact with the cell.

Contacting a cell in vitro can be done, for example, by incubating the cell with the oligonucleotide. Contacting a cell in vivo can be done, for example, by injecting the oligonucleotide into or near the tissue where the cell is located, or by injecting the oligonucleotide agent into another area, e.g., the bloodstream or the subcutaneous space, such that the agent will subsequently reach the tissue where the cell to be contacted is located. For example, the oligonucleotide can contain and/or be coupled to a ligand, e.g., GalNAc3, that directs the oligonucleotide to a site of interest, e.g., the liver. Combinations of in vitro and in vivo methods of contacting are also possible. For example, a cell can be contacted in vitro with an oligonucleotide and subsequently transplanted into a subject.

In one aspect, contacting a cell with an oligonucleotide includes "introducing" or "delivering the oligonucleotide into the cell" by facilitating or effecting uptake or absorption into the cell. Absorption or uptake of an ASO can occur through unaided diffusive or active cellular processes, or by auxiliary agents or devices. Introducing an oligonucleotide into a cell can be in vitro and/or in vivo. For example, for in vivo introduction, oligonucleotides can be injected into a tissue site or administered systemically. In vitro introduction into a cell includes methods known in the art such as electroporation and lipofection. Further approaches are described herein below and/or are known in the art.

As used herein, "lipid nanoparticle" or "LNP" is a vesicle comprising a lipid layer encapsulating a pharmaceutically active molecule, such as a nucleic acid molecule, e.g., an oligonucleotide. LNP refers to a stable nucleic acid-lipid particle. LNPs typically contain a cationic lipid, a non-cationic lipid, and a lipid that prevents aggregation of the particle (e.g., a PEG-lipid conjugate). LNPs are described in, for example, U.S. Pat. Nos. 6,858,225; 6,815,432; 8,158,601; and 8,058,069, the entire contents of which are hereby incorporated herein by reference.

As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the oligonucleotide composition. The lipophilic material isolates the aqueous interior from an aqueous exterior, which typically does not include the oligonucleotide composition, although in some examples, it can. Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

The term "antisense," as used herein, refers to a nucleic acid comprising an oligonucleotide or polynucleotide that is sufficiently complementary to all or a portion of a gene, primary transcript, or processed mRNA, so as to interfere with expression of the endogenous gene (e.g., MLH3). "Complementary" polynucleotides are those that are capable of base pairing according to the standard Watson-Crick complementarity rules Specifically, purines will base pair with pyrimidines to form a combination of guanine paired with cytosine (G:C) and adenine paired with either thymine (A:T) in the case of DNA, or adenine paired with uracil (AU) in the case of RNA. It is understood that two polynucleotides can hybridize to each other even if they are not completely complementary to each other, provided that each has at least one region that is substantially complementary to the other.

As used herein, the terms "effective amount", "therapeutically effective amount," and "a "sufficient amount" of an agent that reduces the level and/or activity of MLH3 (e.g., in a cell or a subject) described herein refer to a quantity sufficient to, when administered to the subject, including a human, effect beneficial or desired results, including clinical results, and, as such, an "effective amount" or synonym thereto depends on the context in which it is being applied. For example, in the context of treating a trinucleotide repeat expansion disorder, it is an amount of the agent that reduces the level and/or activity of MLH3 sufficient to achieve a treatment response as compared to the response obtained without administration of the agent that reduces the level and/or activity of MLH3. The amount of a given agent that reduces the level and/or activity of MLH3 described herein that will correspond to such an amount will vary depending upon various factors, such as the given agent, the pharmaceutical formulation, the route of administration, the type of disease or disorder, the identity of the subject (e.g., age, sex, and/or weight) or host being treated, and the like, but can nevertheless be routinely determined by one of skill in the art. Also, as used herein, a "therapeutically effective amount" of an agent that reduces the level and/or activity of MLH3 of the present disclosure is an amount which results in a beneficial or desired result in a subject as compared to a control. As defined herein, a therapeutically effective amount of an agent that reduces the level and/or activity of MLH3 of the present disclosure can be readily determined by one of ordinary skill by routine methods known in the art. Dosage regimen can be adjusted to provide the optimum therapeutic response.

"Prophylactically effective amount," as used herein, is intended to include the amount of an oligonucleotide that, when administered to a subject having or predisposed to have a trinucleotide repeat expansion disorder, is sufficient to prevent or ameliorate the disease or one or more symptoms of the disease. Ameliorating the disease includes slowing the course of the disease or reducing the severity of later-developing disease. The "prophylactically effective amount" can vary depending on the oligonucleotide, how the agent is administered, the degree of risk of disease, and the history, age, weight, family history, genetic makeup, the types of preceding or concomitant treatments, if any, and other individual characteristics of the patient to be treated. A prophylactically effective amount can refer to, for example, an amount of the agent that reduces the level and/or activity of MLH3 (e.g., in a cell or a subject) described herein or can refer to a quantity sufficient to, when administered to the subject, including a human, delay the onset of one or more of the trinucleotide repeat disorders described herein by at least 120 days, for example, at least 6 months, at least 12 months, at least 2 years, at least 3 years, at least 4 years, at least 5 years, at least 10 years or more, when compared with the predicted onset.

A "therapeutically-effective amount" or "prophylactically effective amount" also includes an amount (either administered in a single or in multiple doses) of an oligonucleotide that produces some desired local or systemic effect at a reasonable benefit/risk ratio applicable to any treatment. Oligonucleotides employed in the methods described herein can be administered in a sufficient amount to produce a reasonable benefit/risk ratio applicable to such treatment.

As used herein, the term "region of complementarity" refers to the region on the oligonucleotide that is substantially complementary to all or a portion of a gene, primary transcript, a sequence (e.g., a target sequence, e.g., an MLH3 nucleotide sequence), or processed mRNA, so as to interfere with expression of the endogenous gene (e.g., MLH3). Where the region of complementanty is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the oligonucleotide.

An "amount effective to reduce trinucleotide repeat expansion" of a particular gene refers to an amount of the agent that reduces the level and/or activity of MLH3 (e.g., in a cell or a subject) described herein, or to a quantity sufficient to, when administered to the subject, including a human, to reduce the trinucleotide repeat expansion of a particular gene (e.g., a gene associated with a trinucleotide repeat expansion disorder described herein).

As used herein, the term "a subject identified as having a trinucleotide repeat expansion disorder" refers to a subject identified as having a molecular or pathological state, disease or condition of or associated with a trinucleotide repeat expansion disorder, such as the identification of a trinucleotide repeat expansion disorder or symptoms thereof, or to identification of a subject having or suspected of having a trinucleotide repeat expansion disorder who can benefit from a particular treatment regimen.

As used herein, "trinucleotide repeat expansion disorder" refers to a class of genetic diseases or disorders characterized by excessive trinucleotide repeats (e.g., trinucleotide repeats such as CAG) in a gene or intron in the subject which exceed the normal, stable threshold, for the gene or intron. Nucleotide repeats are common in the human genome and are not normally associated with disease. In some cases, however, the number of repeats expands beyond a stable threshold and can lead to disease, with the severity of symptoms generally correlated with the number of repeats. Trinucleotide repeat expansion disorders include 'polyglutamine' and "non-polyglutamine" disorders.

By "determining the level of a protein" is meant the detection of a protein, or an mRNA encoding the protein, by methods known in the art either directly or indirectly. "Directly determining" means performing a process (e.g., performing an assay or test on a sample or analyzing a sample"as that term is defined herein) to obtain the physical entity or value. "Indirectly determining" refers to receiving the physical entity or value from another party or source (e.g., a third-party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure mRNA levels are known in the art.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps (DNA core sequences), if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values can be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

$$100 \text{ multiplied by (the fraction } X/Y)$$

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

By 'level' is meant a level or activity of a protein, or mRNA encoding the protein (e.g., MLH3), optionally as compared to a reference. The reference can be any useful reference, as defined herein. By a "decreased level" or an "increased level" of a protein is meant a decrease or increase in protein level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein can be expressed in mass/vol (e.g., g/dL, mg/mL, μg/mL, or ng/mL) or percentage relative to total protein or mRNA in a sample.

The term "pharmaceutical composition," as used herein, represents a composition containing a compound described herein formulated with a pharmaceutically acceptable excipient, and can be manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup), for topical administration (e.g., as a cream, gel, lotion, or ointment); for intravenous administration (e.g., as a sterile solution free of particulate emboli and in a solvent system suitable for intravenous use); for intrathecal injection; for intracerebroventricular injections; for intraparenchymal injection; or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients can include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citnc acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of any of the compounds described herein. For example, pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C G. Wermuth), Wiley-VCH, 2008. The salts can be prepared in situ during the final isolation and purification of the compounds described herein or separately by reacting a free base group with a suitable organic acid.

The compounds described herein can have ionizable groups so as to be capable of preparation as pharmaceutically acceptable salts. These salts can be acid addition salts involving inorganic or organic acids or the salts can, in the case of acidic forms of the compounds described herein, be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts can be prepared from pharmaceutically acceptable non-toxic acids and bases including inorganic and organic acids and bases. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

By a "reference" is meant any useful reference used to compare protein or mRNA levels or activity. The reference can be any sample, standard, standard curve, or level that is used for comparison purposes. The reference can be a normal reference sample or a reference standard or level. A "reference sample" can be, for example, a control, e.g., a predetermined negative control value such as a "normal control" or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound described herein; a sample from a subject that has been treated by a compound described herein; or a sample of a purified protein (e.g., any described herein) at a known normal concentration. By "reference standard or level" is meant a value or number derived from a reference sample. A "normal control value" is a pre-determined value indicative of non-disease state, e.g., a value expected in a healthy control subject. Typically, a normal control value is expressed as a range ("between X and Y"), a high threshold ("no higher than X"), or a low threshold ("no lower than X"). A subject having a measured value within the normal control value for a particular biomarker is typically referred to as "within normal limits" for that biomarker. A normal reference standard or level can be a value or number derived from a normal subject not having a disease or disorder (e.g., a trinucleotide repeat expansion disorder); a subject that has been treated with a compound described herein. In some aspects, the reference sample, standard, or level is matched to the sample subject sample by at least one of the following criteria, age, weight, sex, disease stage, and overall health. A standard curve of levels of a purified protein, e.g., any described herein, within the normal reference range can be used as a reference.

As used herein, the term "subject" refers to any organism to which a composition can be administered, e.g., for experimental, diagnostic, prophylactic, and/or therapeutic purposes Typical subjects include any animal (e.g., mammals such as mice, rats, rabbits, non-human primates, and humans) A subject can seek or be in need of treatment, require treatment, be receiving treatment, be receiving treatment in the future, or be a human or animal who is under care by a trained professional for a particular disease or condition.

As used herein, the terms "treat," "treated," and "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects Treatment also includes prolonging survival as compared to expected survival if not receiving treatment.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein can retain or improve upon the biological activity of the original material.

The details of one or more aspects are set forth in the description below. Other features, objects, and advantages will be apparent from the description and from the claims.

DETAILED DESCRIPTION

Figure 1:
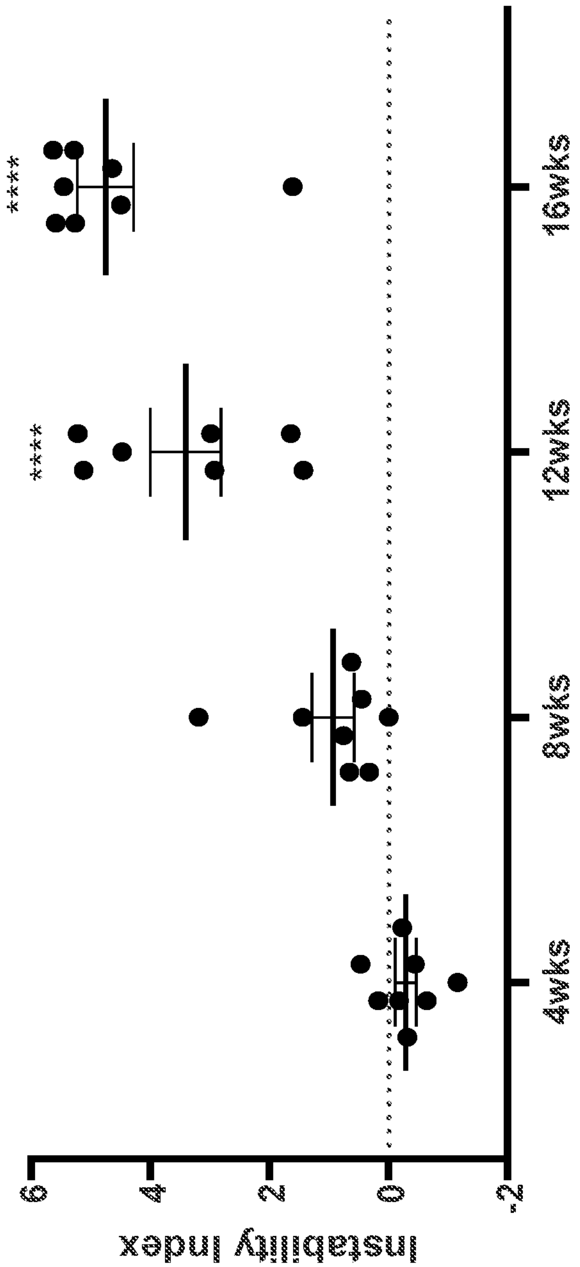
FIG. 1 is a distribution plot showing the somatic expansion of a human HTT transgene in the striatum as measured by the instability index in R6/2 mice at 4, 8, 12, and 16 weeks of age (4 male and 4 female per age group).The bars are mean values and error bars indicate standard deviation.

The present inventors have found that inhibition or depletion of MLH3 level and/or activity in a cell is effective in the treatment of a trinucleotide repeat expansion disorder. Accordingly, useful compositions and methods to treat triucleotide repeat expansion disorders, e.g., in a subject in need thereof are provided herein.

I. Trinuleotide Repeat Expansion Disorders.

Trinucleotide repeat expansion disorders are a family of genetic disorders characterized by the pathogenic expansion of a repeat region within a genomic region. In such disorders, the number of repeats exceeds that of a gene's normal, stable threshold, expanding into a diseased range.

Trinucleotide repeat expansion disorders generally can be categorized as "polyglutamine" or "non-polyglutamine." Polyglutamine disorders, including Huntington's disease (HD) and several spinocerebellar ataxias, are caused by a CAG (glutamine) repeats in the protein-coding regions of specific genes. Non-polyglutamine disorders are more heterogeneous and can be caused by CAG trinucleotide repeat expansions in non-coding regions, as in Myotonic dystrophy, or by the expansion of trinucleotide repeats other than CAG that can be in coding or non-coding regions such as the CGG repeat expansion responsible for Fragile X Syndrome.

Trinucleotide repeat expansion disorders are dynamic in the sense that the number of repeats can vary from generation-to-generation, or even from cell-to-cell in the same individual. Repeat expansion is believed to be caused by polymerase "slipping" during DNA replication. Tandem repeats in the DNA sequence can "loop out" while maintaining complementary base pairing between the parent strand and daughter strands. If the loop structure is formed from the daughter strand, the number of repeats will increase.

Conversely, if the loop structure is formed from the parent strand, the number of repeats will decrease. It appears that expansion is more common than reduction. In general, the length of repeat expansion is negatively correlated with prognosis longer repeats are correlated with an earlier age of onset and worsened disease severity. Thus, trinucleotide repeat expansion disorders are subject to .anticipation," meaning the severity of symptoms and/or age of onset worsen through successive generations of affected families due to the expansion of these repeats from one generation to the next.

Trinucleotide repeat expansion disorders are well known in the art. Exemplary trinucleotide repeat expansion disorders and the trinucleotide repeats of the genes commonly associated with them are included in Table 1.

TABLE 1

Exemplary Trinucleotide Repeat Expansion Disorders

| Disease | Gene | Nucleotide Repeat |
|---|---|---|
| ARX-nonsyndromic X-linked mental retardation (XLMR) | ARX | GCG |
| Baratela-Scott Syndrome | XYLT1 | GGC |
| Blepharophimosis/Ptosis/Epicanthus inversus syndrome type II | FOXL2 | GCG |
| Cleidocranial dysplasia (CCD) | RUNX2 | GCG |
| Congenital central hypoventilation | PHOX-2B | GCG |
| Congenital central hypoventilation syndrome (CCHS) | PHOX2B | GCG |
| Creutzfeldt-Jakob disease | PRNP | |
| Dentatorubral-pallidoluysian atrophy (DRPLA)/Haw River syndrome | ATN1 | CAG |
| Early infantile epileptic encephalopathy (Ohtahara syndrome) | ARX | GCG |
| FRA2A syndrome | AFF3 | CGC |
| FRA7A syndrome | ZNF713 | CGG |
| Fragile X mental retardation (FRAX-E) | AFF2/FMR2 | GCC |
| Fragile X Syndrome (FXS) | FMR1 | CGG |
| Fragile X-associated Primary Ovarian Insufficiency (FXPOI) | FMR1 | CGG |
| Fragile X-associated Tremor Ataxia Syndrome (FXTAS) | FMR1 | CGG |
| Friedreich ataxia (FRDA) | FXN | GAA |
| Fuchs' Corneal Endothelial Dystrophy (FECD) | TCF4 | CTG |
| Hand-foot genital syndrome (HFGS) | HOXA13 | GCG |
| Holoprosencephaly disorder (HPE) | ZIC2 | GCG |
| Huntington disease-like 2 (HDL2) | JPH3 | CTG |
| Huntington's Disease (HD) | HTT | CAG |
| Infantile spasm syndrome/West syndrome (ISS) | ARX | GCG |
| Jacobsen syndrome | | |
| KCNN3-associated (e.g., schizophrenia) | KCNN3 | CAG |
| Multiple Skeletal dysplasias | COMP | GAC |
| Myotonic Dystrophy type 1 (DM1) | DMPK | CTG |
| Myotonic Dystrophy type 2 (DM2) | CNBP | CCTG |
| NCOA3-associated (e.g., increased risk of prostate cancer) | NCOA3 | CAG |

TABLE 1-continued

Exemplary Trinucleotide Repeat Expansion Disorders

| Disease | Gene | Nucleotide Repeat |
|---|---|---|
| Neuronal intranuclear inclusion disease (NIID) | NOTCH2NLC | GGC |
| Oculopharyngeal Muscular Dystrophy (OPMD) | PABPN1 | GCG |
| Spastic ataxia - Charlevoix-Saguenay | | |
| Spinal Muscular Bulbar Atrophy (SMBA) | AR | CAG |
| Spinocerebellar ataxia type 1 (SCA1) | ATXN1 | CAG |
| Spinocerebellar ataxia type 10 (SCA10) | ATXN10 | ATTCT |
| Spinocerebellar ataxia type 12 (SCA12) | PPP2R2B | CAG |
| Spinocerebellar ataxia type 17 (SCA17) | TBP/ATXN17 | CAG |
| Spinocerebellar ataxia type 2 (SCA2) | ATXN2 | CAG |
| Spinocerebellar ataxia type 3 (SCA3)/Machado-Joseph Disease | ATXN3 | CAG |
| Spinocerebellar ataxia type 45 (SCA45) | FAT2 | CAG |
| Spinocerebellar ataxia type 6 (SCA6) | CACNA1A | CAG |
| Spinocerebellar ataxia type 7 (SCA7) | ATXN7 | CAG |
| Spinocerebellar ataxia type 8 (SCA8) | ATXN8 | CTG |
| Syndromic neurodevelopmental disorder with cerebellar, ocular, craniofacial, and genital features (COFG syndrome) | MAB21L1 | CAG |
| Synpolydactyly (SPD I) | HOXD13 | GCG |
| Synpolydactyly (SPD II) | HOXD12 | GCG |

The proteins associated With trinucleotide repeat expansion disorders are typically selected based on an experimental association of the protein associated with a trinucleotide repeat expansion disorder to a trinucleotide repeat expansion disorder. For example, the production rate or circulating concentration of a protein associated with a trinucleotide repeat expansion disorder can be elevated or depressed in a population having at ninucleotide repeat expansion disorder relative to a population lacking the trinucleotide repeat expansion disorder. Differences in protein levels can be assessed using proteomic techniques including but not limited to Western blot, immunohistochemical staining, enzyme linked immunosorbent assay (ELISA), and mass spectrometry. Alternatively, the proteins associated with trinucleotide repeat expansion disorders can be identified by obtaining gene expression profiles of the genes encoding the proteins using genomic techniques including, but not limited to, DNA microarray analysis, serial analysis of gene expression (SAGE), and quantitative real-time polymerase chain reaction (qPCR).

II. Evidence tor the Involvement of Mismatch Repair Pathway in Trinucleotide Repeat Expansion There is growing evidence that DNA repair pathways, particularly mismatch repair (MMR), are involved in the expansion of trinucleotide repeats. A recent genome-wide association (GWA) analysis led to the identification of loci harboring genetic variations that alter the age at neurological onset of Huntington's disease (HD) (GEM-HD Consortium, Cell. 2015 Jul. 30; 162(3):516-26) The study identified MLH1, the human homolog of the *E. coli* DNA mismatch repair gene mutL A subsequent GWA study in polyglutamine disease patients found significant association of age at onset when grouping all polyglutamine diseases (HD and SCAs) with DNA repair genes as a group, as well as significant associations for specific SNPs in FAN1 and PMS2 with the diseases (Bettencourt et al., (2016) Ann. Neurol., 79: 983-990). These results were consistent with those from an earlier study comparing differences in repeat expansion in two different mouse models of Huntington's Disease, which identified Mlh1 and Mlh3 as novel critical modifiers of CAG instability (Pinto et al., (2013) Mismatch Repair Genes Mih1 and Mlh3 Modify CAG Instability in Huntington's Disease Mice: Genome-Wide and Candidate Approaches. PLoS Genet 9(10). e1003930). Another member of the mismatch repair pathway, 8-oxo-guanine glycosylase (OGG1) has also been implicated in expansion, as somatic expansion was found to be reduced in transgenic mice lacking OGG1 (Kovtun 1. V. et al. (2007) Nature 447, 447-452). However, another study found that human subjects containing a Ser326Cys polymorphism in hOGG1, which results in reduced OGG1 activity, results in increased mutant huntingtin (Coppede et al., (2009) Toxicol., 278: 199-203). Likewise, complete inactivation of Fan1, another component of the DNA repair pathway, in a mouse HD model produces somatic CAG expansions (Long et al. (2018) J. Hum Genet., 103: 1-9). MSH3, another component of the mismatch repair pathway, has been reported to be linked to somatic expansion: polymorphisms in Msh3 was associated with somatic instability of the expanded CTG trinucleotide repeat in myotonic dystrophy type 1 (DM1) patients (Morales et al., (2016) DNA Repair 40: 57-66). Furthermore, natural polymorphisms in Msh3 and Mih1 have been revealed as mediators of mouse strain specific differences in CTG•CAG repeat instability (Pinto et al. (2013) ibid; Tome et al., (2013) PLoS Genet 9 e1003280). Further evidence of Msh2 and Msh3's involvement in expansion repeats was reported in a study in which short hairpin RNA (shRNA) knockdown of either MSH2 or MSH3 slowed, and ectopic expression of either MSH2 or MSH3 induced GAA trinucleotide repeat expansion of the Friedreich Ataxia (FRDA) gene in fibroblasts derived from FRDA patients (Halabi et al., (2012) J. Biol Chem. 287, 29958-29967). In spite of some inconsistent results provided above, there is strong evidence that the MMR pathway plays some role in the expansion of trinucleotide repeats in various disorders. Moreover, they are the first to recognize that the inhibition of the MMR pathway provides for the treatment or prevention of these repeat expansion disorders; however, no therapy is currently available or in development which modulates MMR for purposes of treating or preventing these repeat expansion disorders.

III. Olgonucleotde Agents

Agents described herein that reduce the level and/or activity of MLH3 in a cell can be, for example, a polynucleotide, e.g., an oligonucleotide. These agents reduce the level of an activity related to MLH3, or a related downstream effect, or reduce the level of MLH3 in a cell or subject.

In some aspects, the agent that reduces the level and/or activity of MLH3 is a polynucleotide. In some aspects, the polynucleotide is a single-stranded oligonucleotide, e.g., that acts by way of an RNase H-mediated pathway. Oligonucleotides include DNA and DNA/RNA chimeric molecules, typically about 10 to 30 nucleotides in length, which recognize polynucleotide target sequences or sequence portions through hydrogen bonding interactions with the nucleotide bases of the target sequence (e.g., MLH3). An oligonucleotide molecule can decrease the expression level (e.g., protein level or mRNA level) of MLH3. For example, an oligonucleotide includes oligonucleotides that targets full-length MLH3. In some aspects, the oligonucleotide molecule recruits an RNase H enzyme, leading to target mRNA degradation.

In some aspects, the oligonucleotide decreases the level and/or activity of a positive regulator of function. In other aspects, the oligonucleotide increases the level and/or activity of an inhibitor of a positive regulator of function. In some aspects, the oligonucleotide increases the level and/or activity of a negative regulator of function.

In some aspects, the oligonucleotide decreases the level and/or activity or function of MLH3. In some aspects, the oligonucleotide inhibits expression of MLH3. In other aspects, the oligonucleotide increases degradation of MLH3 and/or decreases the stability (i.e., half-life) of MLH3. The oligonucleotide can be chemically synthesized.

The oligonucleotide includes an oligonucleotide having a region of complementarity (e.g., a contiguous nucleobase region) which is complementary to at least a part of an mRNA formed in the expression of a MLH3 gene. The region of complementarity can be about 30 nucleotides or less in length (e.g., about 30, 29, 28, 27, 26, 25, 24, 23, 22, 21, 20, 19, or 18 nucleotides or less in length). Upon contact with a cell expressing the MLH3 gene, the oligonucleotide can inhibit the expression of the MLH3 gene (e.g., a human, a primate, a non-primate, or a bird MLH3 gene) by at least about 10% as assayed by, for example, a PCR or branched DNA (bDNA)-based method, or by a protein-based method, such as by immunofluorescence analysis, using, for example, Western Blotting or flowcytometric techniques.

Similarly, the region of complementarity to the target sequence can be between 10 and 30 linked nucleosides in length, e.g., 10, 11, 12, 13, 14, 15, 16, 17, 18, 19, 20, 21, 22, 23, 24, 25, 26, 27, 28, 29, or 30 or between 10-29, 10-28, 10-27, 10-26, 10-25, 10-24, 10-23, 10-22, 10-21, 10-20, 10-19, 10-18,10-17, 10-16, 10-15, 10-14,10-13, 10-12, 15-29, 15-28, 15-27, 15-26,15-25, 15-24, 15-23, 15-22, 15-21, 15-20,15-19, 15-18, 15-17, 18-30, 18-29, 18-28, 18-27, 18-26, 18-25,18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24,20-23, 20-22, 20-21, 21-30, 21-29, 21-28, 21-27, 21-26, 21-25, 21-24, 21-23, or 21-22 linked nucleosides in length. Ranges and lengths intermediate to the above recited ranges and lengths are also contemplated.

An oligonucleotide can be synthesized by standard methods known in the art as further discussed below, e.g., by use of an automated DNA synthesizer, such as are commercially available from, for example, Biosearch, Applied Biosystems, Inc.

The oligonucleotide compound can be prepared using solution-phase or solid-phase organic synthesis or both. Organic synthesis offers the advantage that the oligonucleotide comprising unnatural or alternative nucleotides can be easily prepared. Single-stranded oligonucleotides can be prepared using solution-phase or solid-phase organic synthesis or both.

In one aspect, an oligonucleotide described herein includes a region of at least 10 contiguous nucleobases having at least 80% (e.g., at least 85%, at least 90%, at least 95%, or at least 99%) complementary to at least 10 contiguous nucleotides of a MLH3 gene. In some aspects, the oligonucleotide comprises a sequence complementary to at least 17 contiguous nucleotides, 19-23 contiguous nucleotides, 19 contiguous nucleotides, or 20 contiguous nucleotides of a MLH3 gene. The oligonucleotide sequence can be selected from the group of sequences provided in any one of SEQ ID NOs. 6-4710.

In one aspect, the sequence is substantially complementary to a sequence of an mRNA generated in the expression of a MLH3 gene. In some aspects, the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1536-1598, 1623-1660, 1739-1764, 1782-1823, 1847-1908, 2026-2051, 2063-2094, 2115-2146, 2256-2290, 2387-2414, 2421-2592, 2727-2788, 2826-2937, 3005-3043, 3078-3107, 3159-3185, 3214-3239, 3244-3272, 3282-3308, 3426-3483, 3561-3587, 3642-3769, 3804-3839, 3950-3977, 4004-4040, 4052-4115, 4139-4199, 4241-4301, 4328-4365, 4420-4448, 4472-4536, 4669-4708, and 4784-4810 of the MLH3 gene. In some aspects, the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1568-1598,1623-1660, 1782-1823,1870-1904, 2063-2094, 2115-2146, 2256-2287, 2387-2414, 2422-2592, 2727-2788, 2826-2937, 3009-3043, 3078-3107, 3159-3185, 3214-3272, 3282-3307, 3426-3483, 3561-3587, 3642-3767, 3804-3839, 3950-3977, 4004-4039, 4052-4115, 4139-4199, 4241-4301, 4329-4365, 4420-4448, 4472-4536, 4680-4708, and 4784-4810 of the MLH3 gene. In some aspects, the region of at least 10 nucleobases is complementary to an MLH3 gene corresponding to a sequence of reference mRNA NM_001040108.1 at one or more of positions 221-293, 321-506, 534-635, 681-740, 842-875, 953-1024, 1129-1158, 1179-1264, 1287-1316, 1351-1378, 1568-1598, 1623-1659, 1782-1823, 1870-1904, 2064-2091, 2115-2146, 2256-2287, 2387-2414, 2422-2592, 2727-2788, 2829-2937, 3010-3043, 3079-3107, 3159-3185, 3246-3271, 3282-3307, 3426-3474, 3561-3587, 3642-3707, 3804-3839, 3950-3977, 4004-4039, 4052-4114, 4139-4164, 4174-4199, 4241-4288, 4329-4365, 4421-4448, 4472-4536, 4680-4708, and 4784-4810 of the MLH3 gene. In some aspects, the region of at least 10 nucleobases is complementary to an MLH3 gene corresponding to a sequence of reference mRNA NM_001040108.1 at one or more of positions 331-362, 393-438, 479-505, 534-574, 587-612, 681-740, 847-873, 991-1024, 1210-1262, 1351-1378, 1571-1597, 1623-1648, 1874-1902, 2066-2091, 2256-2281, 2388-2414, 2470-2515, 2732-2788, 2853-2878, 2901-2927, 3282-3307, 3562-3587, 4056-4083, 4241-4266, and 4506-4531 of the MLH3 gene. In some aspects, the region of at least 10 nucleobases is complementary to an MLH3 gene corresponding to a sequence of reference mRNA NM_001040108.1 at one or more of positions 335-449, 587-612, 682-736, 848-873, 991-1016, 1179-1204, 1233-1260, 1351-1378, 1626-1651, 1874-1903, 2066-2091, 2115-2146, 2256-2287, 2389-2414, 2471-2499, 2762-2787, 2853-2878, 2911-2936, 3562-3587, 3814-3839, 4006-4031, 4056-4083, and 4244-4269 of the MLH3 gene. In some aspects, the region of at least 10 nucleobases is complementary to an MLH3 gene corresponding to a sequence of reference mRNA NM_001040108.1 at one or more of positions 355-393, 952-984, 1177-1205, 2026-2052, 2066-2094, 2470-2498, 3159-3185, 3458-3485, and 4259-4292 of the MLH3 gene.

In some aspects, the oligonucleotide comprises the nucleobase sequence of any one of SEQ ID NOs: 6-4710. In some aspects, the oligonucleotide comprises the nucleobase sequence of any one of SEQ ID NOs: 89, 92, 102, 107-108, 110-111, 115-116, 150, 154, 160-161, 163-164, 166, 168, 175-176, 178, 180, 182-183, 185-189, 201, 211-212, 229-231, 234-238, 241, 248-250, 254, 265-269, 282-283, 285-288, 294, 296, 319-322, 328-329, 366-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086, 1110-1111, 1126, 1149, 1172, 1176-1181, 1185, 1260, 1271-1274, 1276-1277, 1297, 1302, 1387-1390, 1392-1393, 1396, 1461-1463, 1473-1474, 1482, 1490-1491, 1495, 1498-1502, 1505, 1508, 1510-1514, 1516-1518, 1525-1526, 1529-1530, 1546-1547, 1572, 1596-1597, 1721-1722, 1724-1727, 1744-1746, 1797, 1800-1802, 1824-1826, 1832, 1835-1836, 1859, 1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-2785, 2789, 2791-2792, 2794-2795, 2797, 2848-2852, and 2917-2918. In some aspects, the oligonucleotide comprises the nucleobase sequence of any one of SEQ ID NOs: 89, 92, 102, 107-108, 111, 116, 150, 154, 160-161, 163-164, 166, 168, 175-176, 178, 180, 182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-1111, 1126, 1172, 1176-1181, 1271-1274, 1276-1277, 1297, 1302, 1387, 1390, 1392-1393, 1461-1463, 1474, 1482, 1490-1491, 1498-1502, 1505, 1508, 1510-1512, 1514, 1516-1518,1525-1526, 1529-1530, 1546-1547, 1572, 1597, 1721-1722, 1724-1727, 1744-1746, 1797, 1800-1801, 1824-1826, 1832, 1835-1836, 1859, 1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, and 2917-2918. In some aspects, the oligonucleotide comprises the nucleobase sequence of any one of SEQ ID NOs: 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368, 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, and 2917-2918. In some aspects, the oligonucleotide comprises the nucleobase sequence of any one of SEQ ID NOs: 160-161, 163-164, 166, 211-212, 230-231, 267-268, 282, 294, 322, 366-367, 391-394, 399, 514-515, 594, 602, 728, 750, 752-753, 755, 828, 830, 975-976, 1002, 1176-1179, 1274, 1387, 1462-1463, 1510, 1514, 1529-1530, 1726-1727, 1745-1746, 1824, 1871-1872, 2090, 2256, 2528-2530, 2644, and 2792 In some aspects, the oligonucleotide comprises the nucleobase sequence of any one of SEQ ID NOs: 164, 186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, and 2646. In some aspects, the oligonucleotide comprises the nucleobase sequence of any one of SEQ ID NOs: 174-176, 178, 180-187, 566-569, 573, 701-704, 1260-1261, 1274-1277, 1510-1513, 2000-2001, 2194, 2196, 2661-2664, and 2666.

In some aspects, the nucleobase sequence of the oligonucleotide consists of any one of SEQ ID NOs: 6-4710. In some aspects, the oligonucleotide consists of the nucleobase sequence of any one of SEQ ID NOs: 89, 92, 102, 107-108, 110-111, 115-116, 150, 154, 160-161, 163-164, 166, 168, 175-176, 178, 180, 182-183, 185-189, 201, 211-212, 229-231, 234-238, 241, 248-250, 254, 265-269, 282-283, 285-288, 294, 296, 319-322, 328-329, 366-367-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086, 1110-1111, 1126, 1149, 1172, 1176-1181, 1185, 1260, 1271-1274, 1276-1277, 1297, 1302, 1387-1390, 1392-1393, 1396, 1461-1463, 1473-1474, 1482, 1490-1491, 1495, 1498-1502, 1505, 1508, 1510-1514, 1516-1518, 1525-1526, 1529-1530, 1546-1547, 1572, 1596-1597, 1721-1722, 1724-1725-1726-1727, 1744-1746, 1797, 1800-1802, 1824-1826, 1832, 1835-1836, 1859, 1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-2785, 2789, 2791-2792, 2794-2795, 2797, 2848-2852, and 2917-2918. In some aspects, the oligonucleotide consists of the nucleobase sequence of any one of SEQ ID NOs: 89, 92, 102, 107-108, 111, 116, 150, 154, 160-161, 163-164, 166, 168, 175-176, 178, 180, 182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-

1111, 1126, 1172, 1176-1181, 1271-1274, 1276-1277, 1297, 1302, 1387, 1390, 1392-1393, 1461-1462-1463, 1474, 1482, 1490-1491, 1498-1502, 1505, 1508, 1510-1512, 1514, 1516-1518, 1525-1526,1529-1530, 1546-1547, 1572, 1597, 1721-1722, 1724-1727, 1744-1746, 1797, 1800-1801, 1824-1826, 1832, 1835-1836, 1859, 1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, and 2917-2918. In some aspects, the oligonucleotide consists of the nucleobase sequence of any one of SEQ ID NOs: 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368, 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, and 2917-2918. In some aspects, the oligonucleotide consists of the nucleobase sequence of any one of SEQ ID NOs. 160-161, 163-164, 166, 211-212, 230-231, 267-268, 282, 294, 322, 366-367, 391-394, 399, 514-515, 594, 602, 728, 750, 752-753, 755, 828, 830, 975-976, 1002, 1176-1179, 1274, 1387, 1462-1463, 1510, 1514, 1529-1530, 1726-1727, 1745-1746, 1824, 1871-1872, 2090, 2256, 2528-2530, 2644, and 2792. In some aspects, the oligonucleotide consists of the nucleobase sequence of any one of SEQ ID NOs: 164,186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, and 2646. In some aspects, the oligonucleotide consists of the nucleobase sequence of any one of SEQ ID NOs: 174-176, 178, 180-187, 566-569, 573, 701-704, 1260-1261, 1274-1277,1510-1513, 2000-2001, 2194, 2196, 2661-2664, and 2666. In some aspects. In some aspects, the oligonucleotide exhibits at least 50% mRNA inhibition at 20 nM oligonucleotide concentration when determined using a cell assay when compared with a control cell.

In some aspects, the oligonucleotide exhibits at least 60% mRNA inhibition at a 20 nM oligonucleotide concentration when determined using a cell assay when compared with a control cell. In some aspects, the oligonucleotide exhibits at least 70% mRNA inhibition at a 20 nM oligonucleotide concentration when determined using a cell assay when compared with a control cell. In some aspects, the oligonucleotide exhibits at least 85% mRNA inhibition at a 20 nM oligonucleotide concentration when determined using a cell assay when compared with a control cell. In some aspects, the oligonucleotide exhibits at least 50% mRNA inhibition at a 2 nM oligonucleotide concentration when determined using a cell assay when compared with a control cell. In some aspects, the oligonucleotide exhibits at least 60% mRNA inhibition at a 20 nM oligonucleotide concentration when determined using a cell assay when compared with a control cell. In some aspects, the oligonucleotide exhibits at least 70% mRNA inhibition at a 2 nM oligonucleotide concentration when determined using a cell assay when compared with a control cell. In some aspects, the oligonucleotide exhibits at least 85% mRNA inhibition at a 2 nM oligonucleotide concentration when determined using a cell assay when compared with a control cell.

The cell assay can comprise transfecting mammalian cells, such as HEK293, NIH3T3, or HeLa cells, with the desired concentration of oligonucleotide (e.g., 2 nM or 20 nM) using LIPOFECTAMINE™ 2000 (Invitrogen) and comparing MLH3 mRNA levels of transfected cells to MLH3 levels of control cells. Control cells can be transfected with oligonucleotides not specific to MLH3 or mock transfected mRNA levels can be determined using RT-qPCR and MLH3 mRNA levels can be normalized to GAPDH mRNA levels. The percent inhibition can be calculated as the percent of MLH3 mRNA concentration relative to the MLH3 concentration of the control cells.

In some aspects, the oligonucleotide or contiguous nucleotide region thereof, has a gapmer design or structure also referred herein merely as gapmer." In a gapmer structure the oligonucleotide comprises at least three distinct structural regions a 5'-flanking sequence (also known as a 5'-wing), a DNA core sequence (also known as a gap) and a 3'-flanking sequence (also known as a 3'-wing), in "5->3' orientation. In this design, the 5' and 3' flanking sequences comprise at least one alternative nucleoside which is adjacent to a DNA core sequence, and can in some aspects comprise a contiguous stretch of 2-7 alternative nucleosides, or a contiguous stretch of alternative and DNA nucleosides (mixed flanking sequences comprising both alternative and DNA nucleosides).

The length of the 5'-flanking sequence region can be at least two nucleosides in length (e.g., at least at least 2, at least 3, at least 4, at least 5, or more nucleosides in length). The length of the 3'-flanking sequence region can be at least two nucleosides in length (e.g., at least 2, at least 3, at least at least 4, at least 5, or more nucleosides in length) The 5' and 3' flanking sequences can be symmetrical or asymmetrical with respect to the number of nucleosides they comprise. In some aspects, the DNA core sequence comprises about 10 nucleosides flanked by a 5' and a 3' flanking sequence each comprising about 5 nucleosides, also referred to as a 5-10-5 gapmer.

Consequently, the nucleosides of the 5' flanking sequence and the 3' flanking sequence which are adjacent to the DNA core sequence are alternative nucleosides, such as 2' alternative nucleosides. The DNA core sequence comprises a contiguous stretch of nucleotides which are capable of recruiting RNase H, when the oligonucleotide is in duplex with the MLH3 target nucleic acid. In some aspects, the DNA core sequence comprises a contiguous stretch of 5-16 DNA nucleosides. In other aspects, the DNA core sequence comprises a region of at least 10 contiguous nucleobases having at least 80% (e.g., at least 85%, at least 90%, at least 95%, or at least 99%) complementarity to a MLH3 gene. In some aspects, the gapmer comprises a region complementary to at least 17 contiguous nucleotides, 19-23 contiguous nucleotides, or 19 contiguous nucleotides of a MLH3 gene.

The gapmer is complementary to the MLH3 target nucleic acid, and can therefore be the contiguous nucleoside region of the oligonucleotide.

The 5' and 3' flanking sequences, flanking the 5' and 3' ends of the DNA core sequence, can comprise one or more affinity enhancing alternative nucleosides. In some aspects, the 5' and/or 3' flanking sequence comprises at least one 2'-O-methoxyethyl (MOE) nucleoside. In some aspects, the 5' and/or 3' flanking sequences, contain at least tv MOE nucleosides. In some aspects, the 5' flanking sequence comprises at least one MOE nucleoside. In some aspects, both the 5' and 3' flanking sequence comprise a MOE nucleoside. In some aspects, all the nucleosides in the flanking sequences are MOE nucleosides. In other aspects, the flanking sequence can comprise both MOE nucleosides and other nucleosides (mixed flanking sequence), such as DNA nucleosides and/or non-MOE alternative nucleosides, such as bicyclic nucleosides (BNAs) (e.g., LNA nucleosides or cET nucleosides), or other 2' substituted nucleosides. In this case the DNA core sequence is defined as a contiguous sequence of at least 5 RNase H recruiting nucleosides (such as 5-16 DNA nucleosides) flanked at the 5' and 3' end by an affinity enhancing alternative nucleoside, such as an MOE nucleoside.

In other aspects, the 5' and/or 3' flanking sequence comprises at least one BNA (e.g., at least one LNA nucleoside or cET nucleoside). In some aspects, 5' and/or 3' flanking sequence comprises at least 2 bicyclic nucleosides. In some aspects, the 5' flanking sequence comprises at least one BNA. In some aspects, both the 5' and 3' flanking sequence comprise a BNA. In some aspects, all the nucleosides in the flanking sequences are BNAs. In other aspects, the flanking sequence can comprise both BNAs and other nucleosides (mixed flanking sequences), such as DNA nucleosides and/or non-BNA alternative nucleosides, such as 2' substituted nucleosides. In this case the DNA core sequence is defined as a contiguous sequence of at least five RNase H recruiting nucleosides (such as 5-16 DNA nucleosides) flanked at the 5' and 3' end by an affinity enhancing alternative nucleoside, such as a BNA, such as an LNA, such as beta-D-oxy-LNA.

The 5' flank attached to the 5' end of the DNA core sequence comprises, contains, or consists of at least one alternative sugar moiety (e.g., at least three, at least four, at least five, at least six, at least seven, or more alternative sugar moieties). In some aspects, the flanking sequence comprises or consists of from 1 to 7 alternative nucleobases, such as from 2 to 6 alternative nucleobases, such as from 2 to 5 alternative nucleobases, such as from 2 to 4 alternative nucleobases, such as from 1 to 3 alternative nucleobases, such as one, two, three or four alternative nucleobases. In some aspects, the flanking sequence comprises or consists of at least one alternative internucleoside linkage (e.g., at least three, at least four, at least five, at least six, at least seven, or more alternative internucleoside linkages).

The 3' flank attached to the 3' end of the DNA core sequence comprises, contains, or consists of at least one alternative sugar moiety (e.g., at least three, at least four, at least five, at least six, at least seven, or more alternative sugar moieties). In some aspects, the flanking sequence comprises or consists of from 1 to 7 alternative nucleobases, such as from 2 to 6 alternative nucleobases, such as from 2 to 5 alternative nucleobases, such as from 2 to 4 alternative nucleobases, such as from 1 to 3 alternative nucleobases, such as one, two, three, or four alternative nucleobases. In some aspects, the flanking sequence comprises or consists of at least one alternative internucleoside linkage (e.g., at least three, at least four, at least five, at least six, at least seven, or more alternative internucleoside linkages).

In an aspect, one or more or all of the alternative sugar moieties in the flanking sequence are 2' alternative sugar moieties.

In a further aspect, one or more of the 2' alternative sugar moieties in the wing regions are selected from 2'-O-alkyl-sugar moieties, 7-O-methyl-sugar moieties, 2'-amino-sugar moieties, 7-fluoro-sugar moieties, 2'-alkoxy-sugar moieties, MOE sugar moieties, LNA sugar moieties, arabino nucleic acid (ANA) sugar moieties, and 2'-fluoro-ANA sugar moieties.

In one aspect, all the alternative nucleosides in the flanking sequences are bicyclic nucleosides. In a further aspect, the bicyclic nucleosides in the flanking sequences are independently selected from the group consisting of oxy-LNA, thio-LNA, amino-LNA, cET, and/or ENA, in either the beta-D or alpha-L configurations or combinations thereof.

In some aspects, the one or more alternative internucleoside linkages in the flanking sequences are phosphorothioate internucleoside linkages. In some aspects, the phosphorothioate linkages are stereochemically pure phosphorothioate linkages. In some aspects, the phosphorothioate linkages are Sp phosphorothioate linkages. In other aspects, the phosphorothioate linkages are Rp phosphorothioate linkages. In some aspects, the alternative internucleoside linkages are 2'-alkoxy internucleoside linkages. In other aspects, the alternative internucleoside linkages are alkyl phosphate internucleoside linkages.

The DNA core sequence can comprise, contain, or consist of at least 5-16 consecutive DNA nucleosides capable of recruiting RNase H. In some aspects, all of the nucleosides of the DNA core sequence are DNA units. In further aspects, the DNA core region can consist of a mixture of DNA and other nucleosides capable of mediating RNase H cleavage. In some aspects, at least 50% of the nucleosides of the DNA core sequence are DNA, such as at least 60%, at least 70% or at least 80%, or at least 90% DNA. In some aspects, all of the nucelosides of the DNA core sequence are RNA units.

The oligonucleotide comprises a contiguous region which is complementary to the target nucleic acid. In some aspects, the oligonucleotide can further comprise additional linked nucleosides positioned 5' and/or 3' to either the 5' and 3' flanking sequences. These additional linked nucleosides can be attached to the 5' end of the 5' flanking sequence or the 3' end of the 3' flanking sequence, respectively. The additional nucleosides can, in some aspects, form part of the contiguous sequence which is complementary to the target nucleic acid, or in other aspects, can be non-complementary to the target nucleic acid.

The inclusion of the additional nucleosides at either, or both of the 5' and 3' flanking sequences can independently comprise one, two, three, four, or five additional nucleotides, which can be complementary or non-complementary to the target nucleic acid. In this respect, the oligonucleotide can, in some aspects, comprise a contiguous sequence capable of modulating the target which is flanked at the 5' and/or 3' end by additional nucleotides. Such additional nucleosides can serve as a nuclease susceptible biocleavable linker, and can therefore be used to attach a functional group such as a conjugate moiety to the oligonucleotide. In some aspects, the additional 5' and/or 3' end nucleosides are linked with phosphodiester linkages, and can be DNA or RNA. In another aspect, the additional 5' and/or 3' end nucleosides are alternative nucleosides which can for example be included to enhance nuclease stability or for ease of synthesis.

In other aspects, the oligonucleotides utilize "altimer" design and comprise alternating 2'-fluoro-ANA and DNA regions that are alternated every three nucleosides. Altimer oligonucleotides are discussed in more detail in Min, et al, Bioorganic & Medicinal Chemistry Letters, 2002, 12(18): 2651-2654 and Kalota, et al., Nuc Acid Res. 2006, 34(2): 451-61 (herein incorporated by reference).

In other aspects, the oligonucleotides utilize "hemimer" design and comprise a single 2'-modified flanking sequence adjacent to (on either side of the 5' or the 3' side of) a DNA core sequence. Hemimer oligonucleotides are discussed in more detail in Geary et al., 2001, J. Pharm. Exp. Therap., 296: 898-904 (herein incorporated by reference).

In some aspects, an oligonucleotide has a nucleic acid sequence with at least 50% (e.g., at least 50%, at least 60%, at least 70%, at least 80%, at least 85%, at least 90%, at least 95%, at least 96%, at least 97%, at least 98%, at least 99%, or 100%) sequence identity to the nucleic acid sequence of any one of SEQ ID NOs: 6-4710. In some aspects, an oligonucleotide has a nucleic acid sequence with at least 85% sequence identity to the nucleic acid sequence of any one of SEQ ID NOs: 6-4710.

It will be understood that, although the sequences in SEQ ID NOs: 6-4710 are described as unmodified and/or unconjugated sequences, the nucleosides of the oligonucleotide can comprise any one of the sequences set forth in any one of SEQ ID NOs. 6-4710 that is an alternative nucleoside and/or conjugated as described in detail below.

The skilled person is well aware that oligonucleotides having a structure of between about 18-base pairs can be particularly effective in inducing RNase H-mediated degradation. However, one can appreciate that shorter or longer oligonucleotides can be effective. In the aspects described above, by virtue of the nature of the oligonucleotide sequences provided herein, oligonucleotides described herein can include shorter or longer oligonucleotide sequences. It can be reasonably expected that shorter oligonucleotides minus only a few linked nucleosides on one or both ends can be similarly effective as compared to the oligonucleotides described above. Hence, oligonucleotides having a sequence of at least 8, 9, 10, 11, 12, 13, 14, 15, 16, 17, 18, 19, 20, or more contiguous linked nucleosides derived from one of the sequences provided herein, and differing in their ability to inhibit the expression of a MLH3 gene by not more than about 5, 10, 15, 20, 25, or 30% inhibition from an oligonucleotide comprising the full sequence, are contemplated to be within the scope.

The oligonucleotides described herein can function via nuclease mediated degradation of the target nucleic acid, where the oligonucleotides are capable of recruiting a nuclease, such as an endonuclease like endoribonuclease (RNase) (e.g., RNase H). Examples of oligonucleotide designs which operate via nuclease mediated mechanisms are oligonucleotides which typically comprise a region of at least 5 or 6 DNA nucleosides and are flanked on one side or both sides by affinity enhancing alternative nucleosides, for example gapmers, headmers, and tailmers.

The RNase H activity of an oligonucleotide refers to its ability to recruit RNase H when in a duplex with a complementary RNA molecule. WO01/23613 provides in vitro methods for determining RNase H activity, which can be used to determine the ability to recruit RNase H. Typically an oligonucleotide is deemed capable of recruiting RNase H if it, when provided with a complementary target nucleic acid sequence, has an initial rate, as measured in pmol/N/min, of at least 5%, such as at least 10% or more than 20% of the of the initial rate determined when using an oligonucleotide having the same base sequence as the modified oligonucleotide being tested, but containing only DNA monomers, with phosphorothioate linkages between all monomers in the oligonucleotide, and using the methodology provided by Example 91-95 of WO01/23613 (hereby incorporated by reference).

Furthermore, the oligonucleotides described herein identify a site(s) in a MLH3 transcript that is susceptible to RNase H-mediated cleavage. As used herein, an oligonucleotide is said to target within a particular site of an RNA transcript if the oligonucleotide promotes cleavage of the transcript anywhere within that particular site. Such an oligonucleotide will generally include at least about 5-10 contiguous linked nucleosides from one of the sequences provided herein coupled to additional linked nucleoside sequences taken from the region contiguous to the selected sequence in a MLH3 gene.

Inhibitory oligonucleotides can be designed by methods well known in the art. While a target sequence is generally about 10-30 linked nucleosides in length, there is wide variation in the suitability of particular sequences in this range for directing cleavage of any given target RNA.

Oligonucleotides with homology sufficient to provide sequence specificity required to uniquely degrade any RNA can be designed using programs known in the art.

Systematic testing of several designed species for optimization of the inhibitory oligonucleotide sequence can be undertaken in accordance with the teachings provided herein. Considerations when designing interfering oligonucleotides include, but are not limited to, biophysical, thermodynamic, and structural considerations, base preferences at specific positions, and homology. The making and use of inhibitory therapeutic agents based on non-coding oligonucleotides are also known in the art.

Various software packages and the guidelines set out herein provide guidance for the identification of optimal target sequences for any given gene target, but an empirical approach can be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an oligonucleotide agent, mediate the best inhibition of target gene expression Thus, while the sequences identified herein represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified herein, further optimization could be achieved by systematically either adding or removing linked nucleosides to generate longer or shorter sequences and testing those sequences generated by walking a window of the longer or shorter size up or down the target RNA from that point. Again, coupling this approach to generating new candidate targets with testing for effectiveness of oligonucleotides based on those target sequences in an inhibition assay as known in the art and/or as described herein can lead to further improvements in the efficiency of inhibition.

Further still, such optimized sequences can be adjusted by, e.g., the introduction of alternative nucleosides, alternative sugar moieties, and/or alternative internudeosidic linkages as described herein or as known in the art, including alternative nucleosides, alternative sugar moieties, and/or alternative internucleosidic linkages as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor. An oligonucleotide agent as described herein can contain one or more mismatches to the target sequence. In one aspect, an oligonucleotide as described herein contains no more than 3 mismatches. If the oligonucleotide contains mismatches to a target sequence, in some aspects, the area of mismatch is not located in the center of the region of complementarity. If the oligonucleotide contains mismatches to the target sequence, in some aspects, the mismatch should be restricted to be within the last 5 nucleotides from either the 5'- or 3-end of the region of complementarity. For example, for a 30-linked nucleoside oligonucleotide agent, the contiguous nucleobase region which is complementary to a region of a MLH3 gene, generally does not contain any mismatch within the central 5-10 linked nucleosides. The methods described herein or methods known in the art can be used to determine whether an oligonucleotide containing a mismatch to a target sequence is effective in inhibiting the expression of a MLH3 gene. Consideration of the efficacy of oligonucleotides with mismatches in inhibiting expression of a MLH3 gene is important, especially if the particular region of complementarity in a MLH3 gene is known to have polymorphic sequence variation within the population.

Construction of vectors for expression of polynucleotides for use can be accomplished using conventional techniques which do not require detailed explanation to one of ordinary skill in the art. For generation of efficient expression vectors, it is necessary to have regulatory sequences that control the expression of the polynucleotide. These regulatory sequences include promoter and enhancer sequences and are influenced by specific cellular factors that interact with these sequences, and are well known in the art.

A. Alternative Oligonucleosides.

In one aspect, one or more of the linked nucleosides or intemucleosidic linkages of the oligonucleotide, is naturally occurring, and does not comprise, e.g., chemical modifications and/or conjugations known in the art and described herein. In another aspect, one or more of the linked nucleosides or internucleosidic linkages of an oligonucleotide described herein, is chemically modified to enhance stability or other beneficial characteristics. Without being bound by theory, it is believed that certain modifications can increase nuclease resistance and/or serum stability, or decrease immunogenicity. For example, oligonucleotides can contain nucleotides found to occur naturally in DNA or RNA (e.g., adenine, thymidine, guanosine, cytidine, undine, or inosine) or can contain alternative nucleosides or internudeosidic linkages which have one or more chemical modifications to one or more components of the nucleotide (e.g., the nucleobase, sugar, or phospho-linker moiety). Oligonucleotides can be linked to one another through naturally occurring phosphodiester bonds, or can contain alternative linkages (e.g., covalently linked through phosphorothioate (e.g., Sp phosphorothioate or Rp phosphorothioate), 3'-methylenephosphonate, 5'-methylenephosphonate, 3'-phosphoamidate, 2'-5' phosphodiester, guanidinium, S-methylthiourea, 2'-alkoxy, alkyl phosphate, or peptide bonds).

In some aspects, substantially all of the nucleosides or internucleosidic linkages of an oligonucleotide are alternative nucleosides. In other aspects, all of the nudeosides or internucleosidic linkages of an oligonucleotide described herein are alternative nucleosides. Oligonucleotides in which "substantially all of the nucleosides are alternative nucleosides" are largely but not wholly modified and can include not more than five, four, three, two, or one naturally-occurring nucleosides. In still other aspects, oligonucleotides can include not more than five, four, three, two, or one alternative nucleosides.

The nucleic acids can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Alternative nucleotides and nucleosides include those with modifications including, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. The nucleobase can be an isonucleoside in which the nucleobase is moved from the C1 position of the sugar moiety to a different position (e.g. C2, C3, C4, or C5). Specific examples of oligonucleotide compounds useful in the aspects described herein include, but are not limited to alternative nucleosides containing modified backbones or no natural internucleoside linkages. Nucleotides and nucleosides having modified backbones include, among others, those that do not have a phosphorus atom in the backbone. For the purposes of this specification, and as sometimes referenced in the art, alternative RNAs that do not have a phosphorus atom in their internucleoside backbone can be considered to be oligonucleosides. In some aspects, an oligonucleotide will have a phosphorus atom in its internucleoside backbone.

Alternative internucleoside linkages include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boronophosphates having normal 3'-5' linkages, 2'-5'-linked analogs of these, and those having inverted polarity wherein the adjacent pairs of nucleoside units are linked 3'-5' to 5'-3' or 7-5' to 5'-2'. Various salts, mixed salts, and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677, 5,476,925; 5,519,126; 5,536,821; 5,541,316; 5,550,111; 5,563,253; 5,571,799; 5,587,361, 5,625,050; 6,028,188, 6,124,445; 6,160, 109, 6,169,170; 6,172,209, 6,239,265; 6,277,603, 6,326, 199; 6.346,614, 6,444,423; 6,531,590; 6,534,639; 6,608, 035, 6,683,167; 6,858,715, 6,867,294; 6,878,805; 7,015, 315; 7,041,816, 7,273,933; 7,321,029, and U.S. Pat. RE39464, the entire contents of each of which are hereby incorporated herein by reference.

Alternative internucleoside linkages that do not include a phosphorus atom therein have backbones that are formed by short chain alkyl or cycloalkyl intemudeoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones, methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S, and $CH_2$ component parts.

Representative U.S. patents that teach the preparation of the above oligonudeosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other aspects, suitable oligonucleotides include those in which both the sugar and the internucleoside linkage, i.e., the backbone, of the nucleotide units are replaced. The base units are maintained for hybridization with an appropriate nucleic acid target compound. One such oligomeric compound, a mimetic that has been shown to have excellent hybridization properties, is referred to as a peptide nucleic acid (PNA). In PNA compounds, the sugar of a nucleoside is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the oligonucleotides are described in, for example, in Nielsen et al., Science, 1991, 254, 1497-1500.

Some aspects include oligonucleotides with phosphorothioate backbones and oligonucleotides with heteroatom backbones, and in particular —CH—NH—$CH_2$—, —$CH_2$—N($CH_3$)—O—$CH_2$-[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240 In some aspects, the oligonucleotides featured herein have morpholino backbone structures of the above-referenced U.S. Pat. No. 5,034,506. In other aspects, the oligonucleotides described herein include phosphorodiamidate morpholino oligomers (PMO), in which the deoxyribose moiety is replaced by a morpholine ring, and the charged phosphodiester inter-subunit linkage is replaced by an uncharged phophorodiamidate linkage, as described in Summerton, et al., Antisense Nucleic Acid Drug Dev. 1997, 7.63-70.

Alternative nucleosides and nucleotides can contain one or more substituted sugar moieties. The oligonucleotides, e.g., oligonucleotides, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include —O[$(CH_2)_n$O]$_m$$CH_3$, —O$(CH_2)_n$O$CH_3$, —O$(CH_2)_n$—$NH_2$, —O$(CH_2)_n$$CH_3$, —O$(CH_2)_n$—ONH2, and —O$(CH_2)_n$—ON[$(CH_2)_n$$CH_3$]2, where n and m are from 1 to about 10. In other aspects, oligonucleotides include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In some aspects, the modification includes a 2'-methoxyethoxy (2'-O—$CH_2CH_2OCH_3$, also known as 2-O-(2-methoxyethyl) or 2'-MOE) (Martin et al., Helv. Chin. Acta, 1995, 78-486-504) i.e., an alkoxy-alkoxy group. MOE nucleosides confer several beneficial properties to oligonucleotides including, but not limited to, increased nuclease resistance, improved pharmacokinetics properties, reduced non-specific protein binding, reduced toxicity, reduced immunostimulatory properties, and enhanced target affinity as compared to unmodified oligonucleotides.

Another exemplary alternative contains 2'-dimethylaminooxyethoxy, i.e., a —O($CH_2$)2ON($CH_3$)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$(CH_2)_2$—O—$(CH_2)_2$—N$(CH_3)_2$. Further exemplary alternatives include: 5-Me-2'-F nucleotides, 5-Me-2'-OMe nucleotides, 5-Me-2'-deoxynucleotides, (both R and S isomers in these three families); 2'-alkoxyalkyl; and 2'-NMA (N-methylacetamide).

Other alternatives include 2'-methoxy (2-$OCH_3$), 2'-aminopropoxy (2'-$OCH_2CH_2CH_2NH_2$) and 2'-fluoro (2'-F). Similar modifications can also be made at other positions on the nucleosides and nucleotides of an oligonucleotide, particularly the 3' position of the sugar on the 3' terminal nucleotide or in 2'-5' linked oligonucleotides and the 5' position of 5' terminal nucleotide. Oligonucleotides can have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An oligonucleotide can include nucleobase (often referred to in the art simply as "base") alternatives (e.g., modifications or substitutions). Unmodified or natural nucleobases include the purine bases adenine (A) and guanine (G), and the pyrimidine bases thymine (T), cytosine (C) and uracil (U). Alternative nucleobases include other synthetic and natural nucleobases such as 5-methylcytidine, 5-hydroxymethylcytidine, 5-formylcytidine, 5-carboxycytidine, pyrrolocytidine, dideoxycytidine, undine, 5-methoxyuridine, 5-hydroxydeoxyuridine, dihydroundine, 4-thiourdine, pseudouridine, 1-methyl-pseudouridine, deoxyundine, 5-hydroxybutynl-2'-deoxyuridine, xanthine, hypoxanthine, 7-deaza-xanthine, thienoguanine, 8-aza-7-deazaguanosine, 7-methylguanosine, 7-deazaguanosine, 6-aminomethyl-7-deazaguanosine, 8-aminoguanine, 2,2,7-tnmethylguanosine, 8-methyladenine, 8-azidoadenine, 7-methyladenine, 7-deazaadenine, 3-deazaadenine, 2,6-diaminopurine, 2-aminopurine, 7-deaza-8-aza-adenine, 8-amino-adenine, thymine, dideoxythymine, 5-nitroindole, 2-aminoadenine, 6-methyl and other alkyl derivatives of adenine and guanine, 2-propyl and other alkyl derivatives of adenine and guanine, 2-thiouridine, 2thiothymine and 2-thiocytosine, 5-halouracil and cytosine, 5-propynyl uridine and cytidine, 6-azo uridine, cytidine and thymine, 4-thiouridine, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uridines and cytidines, 8-azaguanine and 8-azaadenine, and 3-deazaguanine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in. The Concise Encyclopedia Of Polymer Science And Engineering, pages 858-859, Kroschwitz, J. L, ed. John Wiley & Sons, 1990, these disclosed by Englisch et al., (1991) Angewandte Chemie, International Edition, 30:613, and those disclosed by Sanghvi, Y S., Chapter 15, Antisense Research and Applications, pages 289-302, Crooke, S. T. and Lebleu, B., Ed., CRC Press, 1993. Certain of these nucleobases are particularly useful for increasing the binding affinity of the oligonucleotides. These include 5-substituted pyrimidines, 6-azapyrimidines, and N-2, N-6 and 0-6 substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., Antisense Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted alternative nucleobases as well as other alternative nucleobases include, but are not limited to, the above noted U.S. Pat. Nos. 3,687,808, 4,845,205; 5,130, 30; 5,134,066; 5,175,273; 5,367,066; 5,432,272; 5,457,187, 5,459,255; 5,484,908, 5,502,177; 5,525,711, 5,552,540; 5,587,469, 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In other aspects, the sugar moiety in the nucleotide can be a ribose molecule, optionally having a 2'-O-methyl, 2'-O-MOE, 2'-F, 2'-amino, 2'-O-propyl, 2'-aminopropyl, or 2'-OH modification.

An oligonucleotide can include one or more bicyclic sugar moieties. A "bicyclic sugar" is a furanosyl ring modified by the bridging of two atoms A "bicyclic nucleoside" ("BNA") is a nudeoside having a sugar moiety comprising a bridge connecting two carbon atoms of the sugar ring, thereby forming a bicyclic ring system. In some aspects, the bridge connects the 4'-carbon and the 2'-carbon of the sugar ring. Thus, in some aspects, an oligonucleotide can include one or more locked nucleosides. A locked nucleoside is a nucleoside having a modified ribose moiety in which the ribose moiety comprises an extra bridge connecting the 2' and 4' carbons. In other words, a locked nucleoside is a nucleoside comprising a bicyclic sugar moiety comprising a 4'—$CH_2$—O-2' bridge. This structure effectively "locks" the ribose in the 3'-endo structural conformation. The addition of locked nucleosides to oligonucleotides has been shown to increase oligonucleotide stability in serum, and to reduce off-target effects (Grunweller, A. et al., (2003) Nucleic Acids Research 31(12):3185-3193). Examples of bicyclic nucleosides for use in the polynucleotides include without limitation nucleosides comprising a bridge between the 4' and the 2' ribosyl ring atoms. In some aspects, the polynucleotide agents include one or more bicyclic nucleosides comprising a 4' to 2' bridge. Examples of such 4' to 2' bridged bicyclic nucleosides, include but are not limited to 4'-($CH_2$)—O-2 (LNA); 4'-($CH_2$)—S-2'; 4'—(CH:)2-O-2' (ENA); 4'—CH($CH_3$)—O-2' (also referred to as "constrained ethyl" or "cEt") and 4'-CH($CH_2OCH_3$)—O-2' (and analogs thereof; see, e.g., U.S. Pat. No. 7,399,845). 4'-C($CH_3$)(CHs)—O-2' (and analogs thereof, see e.g., U.S. Pat. No. 8,278,283); 4'—$CH_2$—N($OCH_3$)-2' (and analogs thereof, see e.g., U.S. Pat. No. 8,278,425); 4'—$CH_2$—O—N($CH_3$)2-2' (see, e.g., U.S. Patent Publication No. 2004/0171570); 4'—$CH_2$—N(R)—O-2', wherein R is H, C1-C12 alkyl, or a protecting group (see, e.g., U.S. Pat. No. 7,427,672); 4'—$CH_2$—C(H)($CH_3$)-2' (see, e.g., Chattopadhyaya et al., J. Org. Chem., 2009, 74, 118-134); and 4'—$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748, 6,794,499; 6,998,484, 7,053,207; 7,034,133, 7,084,125; 7,399,845; 7,427,672; 7,569,686, 7,741,457; 8,022,193, 8,030,467; 8,278,425, 8,278,426; 8,278,283. US 2008/0039618; and US 2009/0012281, the entire contents of each of which are hereby incorporated herein by reference Any of the foregoing bicyclic nucleosides can be prepared having one or more stereochemical sugar configurations including for example α-L-ribofuranose and β-D-ribofuranose (see WO 99/14226).

An oligonucleotide can be modified to include one or more constrained ethyl nucleosides. As used herein, a "constrained ethyl nucleoside" or "cEt" is a locked nucleoside comprising a bicyclic sugar moiety comprising a 4'—CH($CH_3$)—O-2' bridge. In one aspect, a constrained ethyl nucleoside is in the S conformation referred to herein as "S-cEt."

An oligonucleotide can include one or more "conformationally restricted nucleosides" ("CRN") CRN are nucleoside analogs with a linker connecting the C2' and C4' carbons of ribose or the C3 and —C5' carbons of ribose CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

In some aspects, an oligonucleotide comprises one or more monomers that are UNA (unlocked nucleoside) nucleosides. UNA is unlocked acyclic nucleoside, wherein any of the bonds of the sugar has been removed, forming an unlocked "sugar" residue. In one example, UNA also encompasses monomer with bonds between C1'—C4' have been removed (i.e. the covalent carbon-oxygen-carbon bond between the C1' and C4' carbons). In another example, the C2'—C3' bond (i.e. the covalent carbon-carbon bond between the C2' and C3' carbons) of the sugar has been removed (see Nuc. Acids Symp. Series, 52, 133-134 (2008) and Fluiter et al., Mol. Biosyst., 2009, 10, 1039 hereby incorporated by reference).

Representative U.S. publications that teach the preparation of UNA include, but are not limited to, U.S. Pat. No. 8,314,227; and US Patent Publication Nos. 2013/0096289; 2013/0011922. and 2011/0313020, the entire contents of each of which are hereby incorporated herein by reference.

The ribose molecule can be modified with a cyclopropane ring to produce a tricyclodeoxynucleic acid (tricyclo DNA) The ribose moiety can be substituted for another sugar such as 1,5,-anhydrohexitol, threose to produce a threose nucleoside (TNA), or arabinose to produce an arabino nucleoside. The ribose molecule can be replaced with non-sugars such as cyclohexene to produce cyclohexene nucleoside or glycol to produce glycol nucleosides.

Potentially stabilizing modifications to the ends of nucleoside molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other alternatives chemistries of an oligonucleotide include a 5' phosphate or 5' phosphate mimic, e.g., a 5'-terminal phosphate or phosphate mimic of an oligonucleotide. Suitable phosphate mimics are disclosed in, for example US Patent Publication No 2012/0157511, the entire contents of which are incorporated herein by reference.

Exemplary oligonucleotides comprise nucleosides with alternative sugar moieties and can comprise DNA or RNA nucleosides. In some aspects, the oligonucleotide comprises nucleosides comprising alternative sugar moieties and DNA nucleosides. Incorporation of alternative nucleosides into the oligonucleotide can enhance the affinity of the oligonucleotide for the target nucleic acid. In that case, the alternative nucleosides can be referred to as affinity enhancing alternative nucleotides.

In some aspects, the oligonucleotide comprises at least 1 alternative nucleoside, such as at least 2, at least 3, at least 4, at least 5, at least 6, at least 7, at least 8, at least 9, at least 10, at least 11, at least 12, at least 13, at least 14, at least 15 or at least 16 alternative nucleosides. In other aspects, the oligonucleotides comprise from 1 to 10 alternative nucleosides, such as from 2 to 9 alternative nucleosides, such as from 3 to 8 alternative nucleosides, such as from 4 to 7 alternative nucleosides, such as 6 or 7 alternative nucleosides. In an aspect, the oligonucleotide can comprise alternatives, which are independently selected from these three types of alternatives (alternative sugar moiety, alternative nucleobase, and alternative internucleoside linkage), or a combination thereof. In one aspect, the oligonucleotide comprises one or more nucleosides comprising alternative sugar moieties, e.g., 2' sugar alternative nucleosides. In some aspects, the oligonucleotide comprises the one or more 2 sugar alternative nucleoside independently selected from the group consisting of 2'-O-alkyl-RNA, 2'-O-methyl-RNA, 2'-alkoxy-RNA, 2'-O-methoxyethyl-RNA, 2'-amino-DNA, 2'-fluoro-DNA, arabino nucleic acid (ANA), 2'-fluoro-ANA, and BNA (e.g., LNA) nucleosides. In some aspects, the one or more alternative nucleoside is a BNA.

In some aspects, at least 1 of the alternative nucleosides is a BNA (e.g., an LNA), such as at least 2, such as at least 3, at least 4, at least 5, at least 6, at least 7, or at least 8 of the alternative nucleosides are BNAs. In a still further aspect, all the alternative nucleosides are BNAs.

In a further aspect the oligonucleotide comprises at least one alternative internucleoside linkage. In some aspects, the internucleoside linkages within the contiguous nucleotide sequence are phosphorothioate or boronophosphate internucleoside linkages. In some aspects, all the internucleotide linkages in the contiguous sequence of the oligonucleotide are phosphorothioate linkages. In some aspects, the phosphorothioate linkages are stereochemically pure phosphorothioate linkages. In some aspects, the phosphorothioate linkages are Sp phosphorothioate linkages. In other aspects, the phosphorothioate linkages are Rp phosphorothioate linkages.

In some aspects, the oligonucleotide comprises at least one alternative nucleoside which is a 2'-MOE-RNA, such as 2, 3, 4, 5, 6, 7, 8, 9, or 10.2'-MOE-RNA nucleoside units. In some aspects, the 2'-MOE-RNA nucleoside units are connected by phosphorothioate linkages. In some aspects, at least one of said alternative nucleoside is 2'-fluoro DNA, such as 2, 3, 4, 5, 6, 7, 8, 9, or 10.2'-fluoro-DNA nucleoside units. In some aspects, the oligonucleotide comprises at least one BNA unit and at least one 2' substituted modified nucleoside. In some aspects, the oligonucleotide comprises both 2' sugar modified nucleosides and DNA units. In some aspects, the oligonucleotide or contiguous nucleotide region thereof is a gapmer oligonucleotide.

B. Oligonucleotides Conjugated to Ligands

Oligonucleotides can be chemically linked to one or more ligands, moieties, or conjugates that enhance the activity, cellular distribution, or cellular uptake of the oligonucleotide. Such moieties include but are not limited to lipid moieties such as a cholesterol moiety (Letsinger et al., (1989) Proc. Natl. Acid. Sci. USA, 86: 6553-6556), cholic acid (Manoharan et al., (1994) Biorg. Med. Chem. Let., 4:1053-1060). a thioether, e.g., beryl-S-tritylthiol (Manoharan et al., (1992) Ann. N.Y. Acad. Sci., 660:306-309, Manoharan et al., (1993) Biorg. Med. Chem. Let., 3:2765-2770). a thiocholesterol (Oberhauser et al., (1992) Nucd. Acids Res., 20:533-538), an aliphatic chain, e.g., dodecandiol or undecyl residues (Saison-Behmoaras et al., (1991) EMBO J, 10:1111-1118; Kabanov et al, (1990) FEBS Lett, 259:327-330; Svinarchuk et al., (1993) Biochimie, 75:49-54), a phospholipid, e.g., di-hexadecyl-rac-glycerol or triethyl-ammonium 1,2-di-O-hexadecyl-rac-glycero-3-phosphonate (Manoharan et al., (1995) Tetrahedron Left, 36:3651-3654; Shea et al., (1990) Nucd. Acids Res., 18-3777-3783), a polyamine or a polyethylene glycol chain (Manoharan et al., (1995) Nucleosides & Nucleotides, 14-969-973), or adamantane acetic acid (Manoharan et al., (1995) Tetrahedron Lett., 36:3651-3654), a palmityl moiety (Mishra et al., (1995) Biochim. Biophys. Acta, 1264:229-237), or an octadecylamine or hexylamino-carbonyloxycholesterol moiety (Crooke et al., (1996) J. Pharmacol. Exp. Ther., 277:923-937).

In one aspect, a ligand alters the distribution, targeting, or lifetime of an oligonucleotide agent into which it is incorporated. In some aspects, a ligand provides an enhanced affinity for a selected target, e.g., molecule, cell or cell type, compartment, e.g., a cellular or organ compartment, tissue, organ, or region of the body, as, e.g., compared to a species absent such a ligand.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylglucosamine, N-acetylgalactosamine, or hyaluronic acid); or a lipid. The ligand can be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly (2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e g acridines), cross-linkers (e g psoralen, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, $[MPEG]_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can include hormones and hormone receptors. They can include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose.

The ligand can be a substance, e.g., a drug, which can increase the uptake of the oligonucleotide agent into the cell, for example, by disrupting the cell's cytoskeleton, e.g., by disrupting the cell's microtubules, microfilaments, and/or intermediate filaments. The drug can be, for example, taxon, vincrstine, vinblastine, cytochalasin, nocodazole, japlakinolide, latrunculin A, phalloidin, swinholide A, indanocine, or myoservin.

In some aspects, a ligand attached to an oligonucleotide as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycendes, diacylglycende, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases, or 20 bases, comprising multiple of phosphorothioate linkages in the backbone are also amenable as ligands (e.g. as PK modulating ligands). In addition, aptamers that bind serum components (e g serum proteins) are also suitable for use as PK modulating ligands in the aspects described herein.

Ligand-conjugated oligonucleotides can be synthesized by the use of an oligonucleotide that bears a pendant reactive functionality, such as that derived from the attachment of a linking molecule onto the oligonucleotide (described below). This reactive oligonucleotide can be reacted directly with commercially-available ligands, ligands that are synthesized bearing any of a variety of protecting groups, or ligands that have a linking moiety attached thereto.

The oligonucleotides used in the conjugates can be conveniently and routinely made through the well-known technique of solid-phase synthesis. Equipment for such synthesis is sold by several vendors including, for example, Applied Biosystems (Foster City, Calif.). Any other means for such synthesis known in the art can additionally or alternatively be employed. It is also known to use similar techniques to prepare other oligonucleotides, such as the phosphorothioates and alkylated derivatives.

In the ligand-conjugated oligonucleotides, such as the ligand-molecule bearing sequence-specific linked nucleosides, the oligonucleotides and oligonucleosides can be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using conjugate precursors that already bear a linking moiety, the synthesis of the sequence-specific linked nucleosides is typically completed, and the ligand molecule is then reacted with the linking moiety to form the ligand-conjugated oligonucleotide. In some aspects, the oligonucleotides or linked nucleosides are synthesized by an automated synthesizer using phosphoramidites derived from ligand-nucleoside conjugates in addition to the standard phosphoramidites and non-standard phosphoramidites that are commercially available and routinely used in oligonucleotide synthesis.

i. Lipid Conjugates

In one aspect, the ligand or conjugate is a lipid or lipid-based molecule. Such a lipid or lipid-based molecule can bind a serum protein, e.g., human serum albumin (HSA). An HSA binding ligand allows for distribution of the conjugate to a target tissue, e.g., a non-kidney target tissue of the body. A lipid or lipid-based ligand can (a) increase resistance to degradation of the conjugate, (b) increase targeting or transport into a target cell or cell membrane, and/or (c) can be used to adjust binding to a serum protein, e.g., HSA.

In another aspect, the ligand is a moiety, e.g., a vitamin, which is taken up by a target cell, e.g., a proliferating cell. Exemplary vitamins include vitamin A, E, and K.

ii. Cell Permeation Agents

In another aspect, the ligand is a cell-permeation agent, such a helical cell-permeation agent. In one aspect, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. In some aspects, the helical agent is an alpha-helical agent, which can have a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to oligonucleotide agents can affect pharmacokinetic distribution of the oligonucleotide, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp, or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO. 4711). An RFGF analogue (e.g., amino acid sequence AALLPVLLAAP (SEQ ID NO. 4712) containing a hydrophobic MTS can be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 4713)) and the *Drosophila* Antennapedia protein (RQIKIWFQNRRMKWKK (SEQ ID NO: 4714)) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to an oligonucleotide agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods can be linear or cyclic, and can be modified, e.g., glycosylated or methylated, to facilitate targeting to a specific tissue(s). RGD-containing peptides and peptidiomimemtics can include D-amino acids, as well as synthetic RGD mimics. In addition to RGD, one can use other moieties that target the integnn ligand. Some conjugates of this ligand target PECAM-1 or VEGF.

A cell permeation peptide is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin, or bactenecin), or a peptide containing only one or two dominating amino acids (e.g., PR-39 or indolicidin). A cell permeation peptide can include a nuclear localization signal (NLS). For example, a cell permeation peptide can be a bipartite amphipathic peptide, such as MPG. which is derived from the fusion peptide domain of HIV-1 gp41 and the NLS of SV40 large T antigen (Simeoni et al, Nucl Acids Res. 31:2717-2724, 2003).

iii. Carbohydrate Conjugates

In some aspects of the compositions and methods described herein, an oligonucleotide further comprises a carbohydrate. The carbohydrate conjugated oligonucleotides are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include C5 and above (e.g., C5, C6, C7, or C8) sugars. di- and trisaccharides include sugars having two or three monosaccharide units (e.g., C5, C6, C7, or C8).

In one aspect, a carbohydrate conjugate for use in the compositions and methods described herein is a monosaccharide.

In some aspects, the carbohydrate conjugate further comprises one or more additional ligands as described above, such as, but not limited to, a PK modulator and/or a cell permeation peptide.

Additional carbohydrate conjugates (and linkers) suitable for use include those described in PCT Publication Nos. WO 2014/179620 and WO 2014/179627, the entire contents of each of which are incorporated herein by reference.

iv. Linkers

In some aspects, the conjugate or ligand described herein can be attached to an oligonucleotide with various linkers that can be cleavable or non-cleavable.

Linkers typically comprise a direct bond or an atom such as oxygen or sulfur, a unit such as $NR^8$, C(O), C(O)NH, SO, $SO_2$, $SO_2NH$ or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocydylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynyl-heteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocydylalkyl, alkynylheterocyclylalkenyl, alkynylheterocydylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, $N(R^8)$, C(O), substituted or unsubstituted aryl, substituted or unsubstituted heteroaryl, substituted or unsubstituted heterocyclic; where $R^8$ is hydrogen, acyl, aliphatic or substituted aliphatic. In one aspect, the linker is between about 1-24, 2-24, 3-24, 4-24, 5-24, 6-24, 6-18, 7-18, 8-18, 7-17, 8-17, 6-16, 7-17, 8-16 or 1, 2, 3, 4, 5, 6, 7, 8, 9, 10, 11, 12, 13, 14, 15, 16, 17, 18, 19, 20, 21, 21, 22, 23, or 24 atoms.

A cleavable linking group is one which is sufficiently stable outside the cell, but which upon entry into a target cell is cleaved to release the two parts the linker is holding together. In some aspects, the cleavable linking group is cleaved at least about 10 times, 20, times, 30 times, 40 times, 50 times, 60 times, 70 times, 80 times, 90 times, or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential, or the presence of degradative molecules. Generally, cleavage agents are more prevalent or found at higher levels or activities inside cells than in serum or blood. Examples of such degradative agents include: redox agents which are selective for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7 3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to test the candidate cleavable linking group for the ability to resist cleavage in the blood or when in contact with other non-target tissue. Thus, one can determine the relative susceptibility to cleavage between at least two conditions, where at least one condition is selected to be indicative of cleavage in a target cell and another conditions is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In some aspects, useful candidate compounds are cleaved at least about 2, 4, 10, 20, 30, 40, 50, 60, 70, 80, 90, or 100 times faster in the cell (or under in vitro conditions selected to mimic intracellular conditions) as compared to blood or serum (or under in vitro conditions selected to mimic extracellular conditions).

a Redox Cleavable Linking Groups

In one aspect, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular oligonucleotide moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can be evaluated under conditions which are selected to mimic blood or serum conditions. In one aspect, candidate compounds are cleaved by at most about 10% in the blood. In other aspects, useful candidate compounds are degraded at least about 2, 4, 10, 20, 30, 40, 50, 60, 70, 80, 90, or 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

b. Phosphate-Based Cleavable Linking Groups

In another aspect, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are $—O—P(O)OR^k)—O—$, $—O—P(S)(OR^k)—O—$, $—O—P(S)(SR^k)—O—$, $—S—P(O)(OR^k)—S—$, $—O—P(O)(OR^k)—S—$, $—S—P(O)(OR^k)—S—O—P(S)(OR^k)—S—$, $—S—P(S)(OR^k)—O—$, $—O—P(O)(R^k)—O—$, $—O—P(S)(R^k)—O—$, $—S—P(O)(R^k)—O—$, $—S—P(S)(R^k)—O—$, $—S—P(OXR^k)—S—$, $—O—P(S)R^k)—S—$. These candidates can be evaluated using methods analogous to those described above.

c. Acid Cleavable Linking Groups

In another aspect, a cleavable linker comprises an acid cleavable linking group. An acid cleavable linking group is a linking group that is cleaved under acidic conditions. In some aspects, acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C═NN—, C(O)O, or —OC(O). In one aspect, the carbon is attached to the oxygen of the ester (the alkoxy group) is an aryl group, substituted alkyl group, or tertiary alkyl group such as dimethyl pentyl or t-butyl. These candidates can be evaluated using methods analogous to those described above.

d. Ester-Based Linking Groups

In another aspect, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)— These candidates can be evaluated using methods analogous to those described above.

e. Peptide-Based Cleaving Groups

In yet another aspect, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene, or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and R$^B$ are the R groups of the two adjacent amino acids. These candidates can be evaluated using methods analogous to those described above.

In one aspect, an oligonucleotide is conjugated to a carbohydrate through a linker. Linkers include bivalent and trivalent branched linker groups. Linkers for oligonucleotide carbohydrate conjugates include, but are not limited to, those described in formulas 24-35 of PCT Publication No WO 2018/195165.

Representative U.S. patents that teach the preparation of oligonucleotide conjugates include, but are not limited to, U.S. Pat. Nos. 4,828,979; 4,948,882; 5,218,105; 5,525,465; 5,541,313; 5,545,730; 5,552,538, 5,578,717, 5,580,731, 5,591,584; 5,109,124, 5,118,802; 5,138,045, 5,414,077; 5,486,603, 5,512,439; 5,578,718, 5,608,046; 4,587,044; 4,605,735; 4,667,025, 4,762,779; 4,789,737, 4,824,941; 4,835,263, 4,876,335; 4,904,582, 4,958,013; 5,082,830, 5,112,963; 5,214,136, 5,082,830; 5,112,963; 5,214,136; 5,245,022, 5,254,469; 5,258,506; 5,262,536; 5,272,250; 5,292,873; 5,317,098, 5,371,241, 5,391,723; 5,416,203, 5,451,463; 5,510,475; 5,512,667; 5,514,785; 5,565,552; 5,567,810; 5,574,142; 5,585,481; 5,587,371. 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an oligonucleotide. Oligonucleotide compounds that are chimeric compounds are also contemplated. Chimeric oligonucleotides typically contain at least one region wherein the RNA is modified so as to confer upon the oligonucleotide increased resistance to nuclease degradation, increased cellular uptake, and/or increased binding affinity for the target nucleic acid. An additional region of the oligonucleotide can serve as a substrate for enzymes capable of cleaving RNA:DNA By way of example, RNase H is a cellular endonuclease which cleaves the RNA strand of an RNA-DNA duplex Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxy oligonucleotides hybridizing to the same target region. Cleavage of the RNA target can be routinely detected by gel electrophoresis and, if necessary, associated nucleic acid hybridization techniques known in the art.

In certain instances, the nucleotides of an oligonucleotide can be modified by a non-ligand group. A number of non-ligand molecules have been conjugated to oligonucleotides in order to enhance the activity, cellular distribution, or cellular uptake of the oligonucleotide, and procedures for performing such conjugations are available in the scientific literature Such non-ligand moieties have included lipid moieties, such as cholesterol (Kubo, T. et al., Biochem. Biophys. Res Comm, 2007, 365(1):54-61; Letsinger et al., Proc. Nati. Acad Sci. USA, 1989, 86:6553), cholic acid (Manoharan et al., Bioorg. Med. Chem. Lett., 1994, 4-1053), a thioether, e.g., hexyl-S-tritylthiol (Manoharan et al., Ann. N Y. Acad. Sci., 1992, 660-306: Manoharan et al., Bioorg. Med Chem. Let, 1993, 3:2765), a thiocholesterol (Oberhauser et al., Nucl. Acids Res., 1992, 20.533), an aliphatic chain, e.g., dodecandiol or undecyl residues (Saison-Behmoaras et al., EMBO J., 1991, 10:111; Kabanov et al., FEBS Lett, 1990, 259:327, Svinarchuk et al., Biochimie, 1993, 75:49), a phospholipid, e.g., di-hexadecyl-rac-glycerol ortriethylammonium 1,2-di-O-hexadecyl-rac-glycero-3-H-phosphonate (Manoharan et al., Tetrahedron Lett., 1995, 36:3651; Shea et al., Nucl. Acids Res., 1990, 18:3777), a polyamine or a polyethylene glycol chain (Manoharan et al., Nucleosides & Nuclectides, 1995, 14:969), or adamantane acetic acid (Manoharan et al., Tetrahedron Lett., 1995, 36:3651), a palmityl moiety (Mishra et al., Biochim. Biophys Acta, 1995, 1264:229), or an octadecylamine or hexylamino-carbonyl-oxycholesterol moiety (Crooke et al., J. Pharmacol. Exp. Ther., 1996, 277:923). Representative United States patents that teach the preparation of such oligonucleotide conjugates have been listed above. Typical conjugation protocols involve the synthesis of an oligonucleotide bearing an aminolinker at one or more positions of the sequence. The amino group is then reacted with the molecule being conjugated using appropriate coupling or activating reagents. The conjugation reaction can be performed either with the oligonucleotide still bound to the solid support or following cleavage of the oligonucleotide, in solution phase. Purification of the oligonucleotide conjugate by HPLC typically affords the pure conjugate.

IV. Pharmaceutical Uses

The oligonucleotide compositions described herein are useful in the methods described herein, and, while not bound by theory, are believed to exert their desirable effects through their ability to modulate the level, status, and/or activity of a MutLγ heterodimer comprising MLH3, e.g., by inhibiting the activity or level of the MLH3 protein in a cell in a mammal.

An aspect relates to methods of treating disorders related to DNA mismatch repair such as trinucleotide repeat expansion disorders in a subject in need thereof. Another aspect includes reducing the level of MLH3 in a cell of a subject identified as having a trinucleotide repeat expansion disorder. Still another aspect includes a method of inhibiting expression of MLH3 in a cell in a subject. Further aspects include methods of decreasing trinucleotide repeat expansion in a cell. The methods include contacting a cell with an oligonucleotide, in an amount effective to inhibit expression of MLH3 in the cell, thereby inhibiting expression of MLH3 in the cell.

Based on the above methods, an oligonucleotide described herein, or a composition comprising such an oligonucleotide, for use in therapy, or for use as a medicament, or for use in treating disorders related to DNA mismatch repair such as trinucleotide repeat expansion disorders in a subject in need thereof, or for use in reducing the level of MLH3 in a cell of a subject identified as having a trinucleotide repeat expansion disorder, or for use in inhibiting expression of MLH3 in a cell in a subject, or for use in decreasing trinucleotide repeat expansion in a cell is contemplated. The uses include the contacting of a cell with the oligonucleotide, in an amount effective to inhibit expression of MLH3 in the cell, thereby inhibiting expression of MLH3 in the cell Aspects described below in relation to the methods described herein are also applicable to these further aspects.

Contacting of a cell with an oligonucleotide can be done in vitro or in vivo. Contacting a cell in vivo with the oligonucleotide includes contacting a cell or group of cells within a subject, e.g., a human subject, with the oligonucleotide. Combinations of in vitro and in vivo methods of contacting a cell are also possible. Contacting a cell can be direct or indirect, as discussed above. Furthermore, contacting a cell can be accomplished via a targeting ligand, including any ligand described herein or known in the art. In some aspects, the targeting ligand is a carbohydrate moiety, e.g., a GalNAc3 ligand, or any other ligand that directs the oligonucleotide to a site of interest. Cells can include those of the central nervous system, or muscle cells.

Inhibiting expression of a MLH3 gene includes any level of inhibition of a MLH3 gene, e.g., at least partial suppression of the expression of a MLH3 gene, such as an inhibition by at least about 20%. In some aspects, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of a MLH3 gene can be assessed based on the level of any variable associated with MLH3 gene expression, e.g., MLH3 mRNA level or MLH3 protein level.

Inhibition can be assessed by a decrease in an absolute or relative level of one or more of these variables compared with a control level. The control level can be any type of control level that is utilized in the art, e.g., a pre-dose baseline level, or a level determined from a similar subject, cell, or sample that is untreated or treated with a control (such as, e.g., buffer only control or inactive agent control).

In some aspects, surrogate markers can be used to detect inhibition of MLH3. For example, effective treatment of a trinucleotide repeat expansion disorder, as demonstrated by acceptable diagnostic and monitoring criteria with an agent to reduce MLH3 expression can be understood to demonstrate a clinically relevant reduction in MLH3.

In some aspects of the methods described herein, expression of a MLH3 gene is inhibited by at least 20%, 25%, 30%, 35%, 40%, 45%, 50%, 55%, 60%, 65%, 70%, 75%, 80%, 85%, 90%, or 95%, or to below the level of detection of the assay. In some aspects, the methods include a clinically relevant inhibition of expression of MLH3, e.g., as demonstrated by a clinically relevant outcome after treatment of a subject with an agent to reduce the expression of MLH3.

Inhibition of the expression of a MLH3 gene can be manifested by a reduction of the amount of mRNA expressed by a first cell or group of cells (such cells can be present, for example, in a sample derived from a subject) in which a MLH3 gene is transcribed and which has or have been treated (e.g., by contacting the cell or cells with an oligonucleotide, or by administering an oligonucleotide to a subject in which the cells are or were present) such that the expression of a MLH3 gene is inhibited, as compared to a second cell or group of cells substantially identical to the first cell or group of cells but which has not or have not been so treated (control cell(s) not treated with an oligonucleotide or not treated with an oligonucleotide targeted to the gene of interest). The degree of inhibition can be expressed in terms of:

$$\frac{(\text{mRNA in control cells}) - (\text{mRNA in treated cells})}{(\text{mRNA in control cells})} \times 100\%$$

In other aspects, inhibition of the expression of a MLH3 gene can be assessed in terms of a reduction of a parameter that is functionally linked to MLH3 gene expression, e.g., MLH3 protein expression or MLH3 signaling pathways. MLH3 gene silencing can be determined in any cell expressing MLH3, either endogenous or heterologous from an expression construct, and by any assay known in the art.

Inhibition of the expression of a MLH3 protein can be manifested by a reduction in the level of the MLH3 protein that is expressed by a cell or group of cells (e.g., the level of protein expressed in a sample derived from a subject) As explained above, for the assessment of mRNA suppression, the inhibition of protein expression levels in a treated cell or group of cells can similarly be expressed as a percentage of the level of protein in a control cell or group of cells.

A control cell or group of cells that can be used to assess the inhibition of the expression of a MLH3 gene includes a cell or group of cells that has not yet been contacted with an oligonucleotide described herein. For example, the control cell or group of cells can be derived from an individual subject (e.g., a human or animal subject) prior to treatment of the subject with an oligonucleotide.

The level of MLH3 mRNA that is expressed by a cell or group of cells can be determined using any method known in the art for assessing mRNA expression. In one aspect, the level of expression of MLH3 in a sample is determined by detecting a transcribed polynucleotide, or portion thereof, e.g., mRNA of the MLH3 gene RNA can be extracted from cells using RNA extraction techniques including, for example, using acid phenol/guanidine isothiocyanate extraction (RNAzoI B; Biogenesis), RNEASY™ RNA preparation kits (Qiagen) or PAXgene (PreAnalytix, Switzerland). Typical assay formats utilizing ribonucleic acid hybridization include nuclear run-on assays, RT-PCR, RNase protection assays, northern blotting, in situ hybridization, and microarray analysis. Circulating MLH3 mRNA can be detected using methods the described in PCT Publication WO2012/177906, the entire contents of which are hereby incorporated herein by reference. In some aspects, the level of expression of MLH3 is determined using a nucleic acid probe. The term "probe," as used herein, refers to any molecule that is capable of selectively binding to a specific MLH3 sequence, e.g. to an mRNA or polypeptide. Probes can be synthesized by one of skill in the art, or derived from appropriate biological preparations. Probes can be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or northern analyses, polymerase chain reaction (PCR) analyses, and probe arrays. One method for the determination of mRNA levels involves contacting the isolated mRNA with a nucleic acid molecule (probe) that can hybridize to MLH3 mRNA. In one aspect, the mRNA is immobilized on a solid surface and contacted with a probe, for example by running the isolated mRNA on an agarose gel and transferring the mRNA from the gel to a membrane, such as nitrocellulose. In an alternative aspect, the probe(s) are immobilized on a solid surface and the mRNA is contacted with the probe(s), for example, in an AFFYMETRIX gene chip array A skilled artisan can readily adapt known mRNA detection methods for use in determining the level of MLH3 mRNA.

An alternative method for determining the level of expression of MLH3 in a sample involves the process of nucleic acid amplification and/or reverse transcriptase (to prepare cDNA) of for example mRNA in the sample, e.g., by RT-PCR (the experimental aspect set forth in Mullis, 1987, U.S. Pat. No. 4,683,202), ligase chain reaction (Barany (1991) Proc. Natl. Acad. Sci. USA 88:189-193), self-sustained sequence replication (Guatelli et al. (1990) Proc. Natl Acad Sci. USA 87:1874-1878), transcriptional amplification system (Kwoh et al. (1989) Proc Nati. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In some aspects, the level of expression of MLH3 is determined by quantitative fluorogenic RT-PCR (i e., the TAQMAN™ System) or the DUAL-GLO® Luciferase assay.

The expression levels of MLH3 mRNA can be monitored using a membrane blot (such as used in hybridization analysis such as northern, Southern, dot, and the like), or microwells, sample tubes, gels, beads or fibers (or any solid support comprising bound nucleic acids). See U.S. Pat. Nos. 5,770,722; 5,874,219; 5,744,305, 5,677,195; and 5,445,934, which are incorporated herein by reference. The determination of MLH3 expression level can comprise using nucleic acid probes in solution.

In some aspects, the level of mRNA expression is assessed using branched DNA (bDNA) assays or real time PCR (qPCR). The use of this PCR method is described and exemplified in the Examples presented herein. Such methods can be used for the detection of MLH3 nucleic acids.

The level of MLH3 protein expression can be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoeledrophoresis, western blotting, radioimmunoassay (RIA), enzyme-linked immunosorbent assays (ELISAs), immunofluorescent assays, electrochemiluminescence assays, and the like. Such assays can be used for the detection of proteins indicative of the presence or replication of MLH3 proteins.

In some aspects of the methods described herein, the oligonucleotide is administered to a subject such that the oligonucleotide is delivered to a specific site within the subject. The inhibition of expression of MLH3 can be assessed using measurements of the level or change in the level of MLH3 mRNA or MLH3 protein in a sample derived from a specific site within the subject. In some aspects, the methods include a clinically relevant inhibition of expression of MLH3, e.g., as demonstrated by a clinically relevant outcome after treatment of a subject with an agent to reduce the expression of MLH3.

In other aspects, the oligonucleotide is administered in an amount and for a time effective to result in one of (or more, e.g., two or more, three or more, four or more of): (a) decrease the number of trinucleotide repeats, (b) decrease the level of polyglutamine, (c) decreased cell death (e.g., CNS cell death and/or muscle cell death), (d) delayed onset of the disorder, (e) increased survival of subject, and (f) increased progression free survival of a subject.

Treating trinucleotide repeat expansion disorders can result in an increase in average survival time of an individual or a population of subjects treated with an oligonucleotide described herein in comparison to a population of untreated subjects. For example, the survival time of an individual or average survival time of a population is increased by more than 30 days (more than 60 days, 90 days, or 120 days). An increase in survival time of an individual or in average survival time of a population can be measured by any reproducible means. An increase in survival time of an individual can be measured, for example, by calculating for an individual the length of survival time following the initiation of treatment with the compound described herein. An increase in average survival time of a population can be measured, for example, by calculating for the average length of survival time following initiation of treatment with the compound described herein. An increase in survival time of an individual can be measured, for example, by calculating for an individual length of survival time following completion of a first round of treatment with a compound or pharmaceutically acceptable salt of a compound described herein. An increase in average survival time of a population can be measured, for example, by calculating for a population the average length of survival time following completion of a first round of treatment with a compound or pharmaceutically acceptable salt of a compound described herein.

Treating trinucleotide repeat expansion disorders can result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects can be measured by any reproducible means, for example, by calculating for a population the average number of disease-related deaths per unit time following initiation of treatment with a compound or pharmaceutically acceptable salt of a compound described herein. A decrease in the mortality rate of a population can be measured, for example, by calculating for a population the average number of disease-related deaths per unit time following completion of a first round of treatment with a compound or pharmaceutically acceptable salt of a compound described herein.

A. Delivery of Anti-MLH3 Agents

The delivery of an oligonucleotide to a cell e.g., a cell within a subject, such as a human subject e.g., a subject in need thereof, such as a subject having a trinucleotide repeat expansion disorder can be achieved in a number of different ways. For example, delivery can be performed by contacting a cell with an oligonucleotide described herein either in vitro or in vivo. In vivo delivery can be performed directly by administering a composition comprising an oligonucleotide to a subject. These alternatives are discussed further below.

In general, any method of delivering a nucleic acid molecule (in vitro or in vivo) can be adapted for use with an oligonucleotide (see e.g., Akhtar S and Julian R L, (1992) Trends Cell. Biol. 2(5):139-144 and WO94/02595, which are incorporated herein by reference in their entireties). For in vivo delivery, factors to consider in order to deliver an oligonucleotide molecule include, for example, biological stability of the delivered molecule, prevention of non-specific effects, and accumulation of the delivered molecule in the target tissue. The non-specific effects of an oligonucleotide can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the oligonucleotide to be administered.

For administering an oligonucleotide systemically for the treatment of a disease, the oligonucleotide can include alternative nucleobases, alternative sugar moieties, and/or alternative internucleoside linkages, or alternatively delivered using a drug delivery system; both methods act to prevent the rapid degradation of the oligonucleotide by endo- and exo-nucleases in vivo. Modification of the oligonucleotide or the pharmaceutical carrier can permit targeting of the oligonucleotide composition to the target tissue and avoid undesirable off-target effects. Oligonucleotide molecules can be modified by chemical conjugation to lipophilic groups such as cholesterol to enhance cellular uptake and prevent degradation. In an alternative aspect, the oligonucleotide can be delivered using drug delivery systems such as a nanoparticle, a lipid nanoparticle, a polyplex nanoparticle, a lipoplex nanoparticle, a dendrimer, a polymer, liposomes, or a cationic delivery system. Positively charged cationic delivery systems facilitate binding of an oligonucleotide molecule (negatively charged) and also enhance interactions at the negatively charged cell membrane to permit efficient uptake of an oligonucleotide by the cell. Cationic lipids, dendrimers, or polymers can either be bound to an oligonucleotide, or induced to form a vesicle or micelle that encases an oligonucleotide. The formation of vesicles or micelles further prevents degradation of the oligonucleotide when administered systemically. In general, any methods of delivery of nucleic acids known in the art can be adaptable to the delivery of the oligonucleotides described herein. Methods for making and administering cationic oligonucleotide complexes are well within the abilities of one skilled in the art (see e.g., Sorensen, D R., et al. (2003) J. Mol. Biol 327:761-766; Verma, U N. et al., (2003) Clin. Cancer Res. 9:1291-1300; Arnold, A S et al., (2007) J. Hypertens. 25:197-205, which are incorporated herein by reference in their entirety). Some non-limiting examples of drug delivery systems useful for systemic delivery of oligonucleotides include DOTAP (Sorensen, D R., et al (2003), supra; Verma, U N. et al., (2003), supra), Oligofectamine, "solid nucleic acid lipid particles" (Zimmermann, T S. et al., (2006) Nature 441:111-114), cardiolipin (Chien, P Y. et al., (2005) Cancer Gene Ther. 12:321-328. Pal, A. et al., (2005) Int J. Oncol. 26:1087-1091), polyethyleneimine (Bonnet M E. et al., (2008) Pharm. Res. August 16 Epub ahead of print; Aigner, A (2006) J. Biomed. Biotechnol. 71659), Arg-Gly-Asp (RGD) peptides (Liu, S. (2006) Mol. Pharm 3:472-487), and polyamidoamines (Tomalia, D A. et al., (2007) Biochem. Soc. Trans. 35:61-67; Yoo, H. et al., (1999) Pharm. Res. 16:1799-1804). In some aspects, an oligonucleotide forms a complex with cydodextrin for systemic administration Methods for administration and pharmaceutical compositions of oligonucleotides and cyclodextrins can be found in U.S. Pat. No. 7,427,605, which is herein incorporated by reference in its entirety. In some aspects, the oligonucleotides described herein are delivered by polyplex or lipoplex nanoparticles. Methods for administration and pharmaceutical compositions of oligonucleotides and polyplex nanopartides and lipoplex nanoparticles can be found in U.S. Patent Application Nos. 2017/0121454; 2016/0369269; 2016/0279256, 2016/0251478; 2016/0230189; 2015/0335764, 2015/0307554; 2015/0174549; 2014/0342003; 2014/0135376; and 2013/0317086, which are herein incorporated by reference in their entirety.

i. Membranous Molecular Assembly Delivery Methods

The oligonucleotides can be delivered using a variety of membranous molecular assembly delivery methods including polymeric, biodegradable microparticle, or microcapsule delivery devices known in the art. For example, a colloidal dispersion system can be used for targeted delivery of an oligonucleotide agent described herein Colloidal dispersion systems include macromolecule complexes, nanocapsules, microspheres, beads, and lipid-based systems including oil-in-water emulsions, micelles, mixed micelles, and liposomes. Liposomes are artificial membrane vesicles that are useful as delivery vehicles in vitro and in vivo. It has been shown that large unilamellar vesicles (LUV), which range in size from 0.2-4.0 μm can encapsulate a substantial percentage of an aqueous buffer containing large macromolecules. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the oligonucleotide are delivered into the cell where the oligonucleotide can specifically bind to a target RNA and can mediate RNase H-mediated gene silencing. In some cases, the liposomes are also specifically targeted, e.g., to direct the oligonucleotide to particular cell types. The composition of the liposome is usually a combination of phospholipids, usually in combination with steroids, especially cholesterol. Other phospholipids or other lipids can be used. The physical characteristics of liposomes depend on pH, ionic strength, and the presence of divalent cations.

A liposome containing an oligonucleotide can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and can be nonionic Exemplary detergents include cholate, CHAPS, octylglucoside, deoxycholate, and lauroyl sarcosine. The oligonucleotide preparation is then added to the micelles that include the lipid component. The cationic groups on the lipid interact with the oligonucleotide and condense around the oligonucleotide to form a liposome. After condensation, the detergent is removed, e.g., by dialysis, to yield a liposomal preparation of oligonucleotide.

If necessary, a carrier compound that assists in condensation can be added during the condensation reaction, e.g., by controlled addition. For example, the carrier compound can be a polymer other than a nucleic acid (e.g., spermine or spermidine). The pH can be adjusted to favor condensation.

Methods for producing stable polynucleotide delivery vehicles, which incorporate a polynucleotide/cationic lipid complex as a structural component of the delivery vehicle, are further described in, e.g., WO 96/37194, the entire contents of which are incorporated herein by reference. Liposome formation can include one or more aspects of exemplary methods described in Feigner, P. L et al., (1987) Proc. Natl. Acad. Sci. USA 8:7413-7417; U.S. Pat. No. 4,897,355. U.S. Pat. No. 5,171,678; Bangham et al., (1965) M. Mol. Biol. 23:238, Olson et al., (1979) Biochim. Biophys. Acta 557:9; Szoka et al., (1978) Proc. Natl. Acad. Sci. 75: 4194, Mayhew et al., (1984) Biochim. Biophys. Acta 775:169; Kim et al., (1983) Biochim. Biophys. Acta 728: 339; and Fukunaga et al., (1984) Endocrinol. 115:757. Commonly used techniques for preparing lipid aggregates of appropriate size for use as delivery vehicles include sonication and freeze-thaw plus extrusion (see, e.g., Mayer et al., (1986) Biochim. Biophys. Acta 858:161. Microfluidization can be used when consistently small (50 to 200 nm) and relatively uniform aggregates are desired (Mayhew et al., (1984) Biochim. Biophys. Acta 775:169). These methods are readily adapted to packaging oligonucleotide preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al. (1987) Biochem. Biophys. Res. Commun., 147:980-985).

Liposomes, which are pH-sensitive or negatively charged, entrap nucleic acids rather than complex with them. Since both the nucleic acid and the lipid are similarly charged, repulsion rather than complex formation occurs. Nevertheless, some nucleic acid is entrapped within the aqueous interior of these liposomes. pH sensitive liposomes have been used to deliver nucleic acids encoding the thymidine kinase gene to cell monolayers in culture. Expression of the exogenous gene was detected in the target cells (Zhou et al. (1992) Journal of Controlled Release, 19:269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Feigner, (1994) J Biol Chem. 269:2550; Nabel, (1993) Proc. Natl. Acad. Sci. 90:11307; Nabel, (1992) Human Gene Ther 3:649; Gershon, (1993) Biochem. 32:7143; and Strauss, (1992) EMBO J. 11:417.

Non-ionic liposomal systems have also been examined to determine their utility in the delivery of drugs to the skin, in particular systems comprising non-ionic surfactant and cholesterol. Non-ionic liposomal formulations comprising NOVASOME™ I (glyceryl dilaurate/cholesteroVpolyoxyethylene-10-stearyl ether) and NOVASOME™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cydosporine A into different layers of the skin (Hu et al., (1994) S.T.P.Pharma. Sci., 4(6):466).

Liposomes can be sterically stabilized liposomes, comprising one or more specialized lipids that result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., (1987) FEBS Letters, 223:42; Wu et al., (1993) Cancer Research, 53:3765).

Various liposomes comprising one or more glycolipids are known in the art. Papahadjopoulos et al. (Ann. N.Y. Acad. Sci., (1987), 507:64) reported the ability of monosialoganglioside $G^{M1}$, galactocerebroside sulfate, and phosphatidylinositol to improve blood half-lives of liposomes. These findings were expounded upon by Gabizon et al. (Proc. Natl. Acad. Sci. U.S.A., (1988), 85:6949). U.S. Pat. No. 4,837,028 and WO 88/04924, both to Allen et al, disclose liposomes comprising (1) sphingomyelin and (2) the ganglioside GM1 or a galactocerebroside sulfate ester U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al)

In one aspect, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver oligonucleotides to macrophages.

Further advantages of liposomes include, liposomes obtained from natural phospholipids are biocompatible and biodegradable; liposomes can incorporate a wide range of water and lipid soluble drugs; liposomes can protect encapsulated oligonucleotides in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of oligonucleotide (see, e.g., Feigner, P. L et al., (1987) Proc Natl. Acad. Sci. USA 8:7413-7417, and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. LIPOFECTIN$^{T}$M Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis (oleoyloxy)-3,3-(trimethylammonia)propane ("DOTAP") (Boehnnger Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (TRANSFECTAM™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chor") which has been formulated into liposomes in combination with DOPE (See, Gao, X. and Huang, L, (1991) Biochim. Biophys. Res. Commun. 179.280). Lipopolylysine, made by conjugating polylysine to DOPE, has been reported to be effective for transfection in the presence of serum (Zhou, X et al., (1991) Biochim Biophys Acta 1065-8). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine® (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer oligonucleotide into the skin. In some implementations, liposomes are used for delivering oligonucleotide to epidermal cells and also to enhance the penetration of oligonucleotide into dermal tissues, e.g., into skin. For example, the liposomes can be applied topically. Topical delivery of drugs formulated as liposomes to the skin has been documented (see, e.g., Weiner et al., (1992) Journal of Drug Targeting, vol. 2,405-410 and du Plessis et al., (1992) Antiviral Research, 18:259-265; Mannino, R. J. and Fould-Fogerite, S., (1998) Biotechniques 6:682-690; Itani, T. et al., (1987) Gene 56:267-276; Nicolau, C. et al. (1987) Meth. Enzymol. 149:157-176; Straubinger, R. M. and Papahadjopoulos, D. (1983) Meth. Enzymol. 101:512-527; Wang, C. Y. and Huang, L., (1987) Proc. Natl. Acad. Sci USA 84:7851-7855).

Non-ionic liposomal systems have also been examined to determine their utility in the delivery of drugs to the skin, in particular systems comprising non-ionic surfactant and cholesterol. Non-ionic liposomal formulations comprising NOVASOME I (glyceryl dilaurate/cholesterol/polyoxyethylene-10-stearyl ether) and NOVASOME II (glyceryl distearate/cholesterol/polyoxyethylene-10-stearyl ether) were used to deliver a drug into the dermis of mouse skin. Such formulations with oligonucleotides are useful for treating a dermatological disorder.

The targeting of liposomes is also possible based on, for example, organ-specificity, cell-specificity, and organelle-specificity and is known in the art. In the case of a liposomal targeted delivery system, lipid groups can be incorporated into the lipid bilayer of the liposome to maintain the targeting ligand in stable association with the liposomal bilayer Various linking groups can be used for joining the lipid chains to the targeting ligand. Additional methods are known in the art and are described, for example in U.S. Patent Application Publication No. 20060058255, the linking groups of which are herein incorporated by reference.

Liposomes that include oligonucleotides can be made highly deformable Such deformability can enable the liposomes to penetrate through pore that are smaller than the average radius of the liposome. For example, transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes can be made by adding surface edge activators, usually surfactants, to a standard liposomal composition. Transfersomes that include oligonucleotides can be delivered, for example, subcutaneously by infection to deliver oligonucleotides to keratinocytes in the skin. To cross intact mammalian skin, lipid vesicles must pass through a series of fine pores, each with a diameter less than 50 nm, under the influence of a suitable transdermal gradient. In addition, due to the lipid properties, these transfersomes can be self-optimizing (adaptive to the shape of pores, e.g., in the skin), self-repairing, and can frequently reach their targets without fragmenting, and often self-loading. Transfersomes have been used to deliver serum albumin to the skin. The transfersome-mediated delivery of serum albumin has been shown to be as effective as subcutaneous injection of a solution containing serum albumin.

Other suitable formulations are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application No. PCT/US2007/080331, filed Oct. 3, 2007 also describes suitable formulations.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categonzing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general, their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines, and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The oligonucleotides for use in the methods can be provided as micellar formulations. Micelles are a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic ii. Lipid Nanoparticle-Based Delivery Methods Oligonucleotides can be fully encapsulated in a lipid formulation, e.g., a lipid nanoparticle (LNP), or other nucleic acid-lipid particle. LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No WO 00/03683. The particles typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one aspect, the lipid to drug ratio (mass/mass ratio) (e.g., lipid to oligonucleotide ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated.

Non-limiting examples of cationic lipids include N,N-dioleyl-N,N-dimethylammonium chloride (DODAC), N,N-distearyl-N,N-dimethylammonium bromide (DDAB), N—(I-(2,3-dioleoyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyetetrahydro-3aH-cyclopenta[d][1,3]dioxol-5-amine (ALN100), (6Z,9Z,28Z,31Z)-heptatriaconta-6,9,28,31-tetraen-19-yl4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yeethylazanediyedidodecan-2-ol (Tech G1), or a mixture thereof. The cationic lipid can comprise, for example, from about 20 mol % to about 50 mol % or about 40 mol % of the total lipid present in the particle.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be, for example, from about 5 mol % to about 90 mol %, about 10 mol %, or about 60 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide ($C_{16}$), or a mixture thereof. The PEG-DAA conjugate can be, for example, a PEG-dilaurylaxypropyl ($C_{12}$), a PEG-dimyristylaxypropyl ($C_{14}$), a PEG-dpalmityloxypropyl ($C_{16}$), or a PEG-distearyloxypropyl ($C_{18}$). The conjugated lipid that prevents aggregation of particles can be, for example, from 0 mol % to about 20 mol % or about 2 mol % of the total lipid present in the particle.

In some aspects, the nucleic acid-lipid particle further includes cholesterol at, e.g., about 10 mol % to about 60 mol % or about 50 mol % of the total lipid present in the particle B. Combination Therapies An oligonucleotide can be used alone or in combination with at least one additional therapeutic agent, e.g., other agents that treat trinucleotide repeat expansion disorders or symptoms associated therewith, or in combination with other types of therapies to treat trinucleotide repeat expansion disorders. In combination treatments, the dosages of one or more of the therapeutic compounds can be reduced from standard dosages when administered alone. For example, doses can be determined empirically from drug combinations and permutations or can be deduced by isobolographic analysis (e.g., Black et al., Neurology 65:S3-S6 (2005)) In this case, dosages of the compounds when combined should provide a therapeutic effect.

In some aspects, the oligonucleotide agents described herein can be used in combination with at least one additional therapeutic agent to treat a trinucleotide repeat expansion disorder associated with gene having a trinucleotide repeat (e.g., any of the trinucleotide repeat expansion disorders and associated genes having a trinucleotide repeat listed in Table 1). In some aspects, at least one of the additional therapeutic agents can be an oligonucleotide (e.g., an ASO) that hybridizes with the mRNA of gene associated with a trinucleotide repeat expansion disorder (e.g., any of the genes listed in Table 1). In some aspects, the trinucleotide repeat expansion disorder is Huntington's disease (HD) In some aspects, the gene associated with a trinucleotide repeat expansion disorder is Huntingtin (HTT). Several allelic variants of the Huntingtin gene have been implicated in the etiology of Huntington's disease. In some cases, these variants are identified on the basis of having unique HD-associated single nucleotide polymorphisms (SNPs). In some aspects, the oligonucleotide hybridizes to an mRNA of the Huntingtin gene containing any of the HD-associated SNPs known in the art (e.g., any of the HD-associated SNPs described in Skotte et al., PLoS One 2014, 9(9): e107434, Carroll et al., Mol. Ther. 2011, 19(12): 2178-85, Warby et al., Am. J. Hum. Gen. 2009, 84(3). 351-66 (herein incorporated by reference)). In some aspects, the oligonucleotide that is an additional therapeutic agent hybridizes to an mRNA of the Huntingtin gene lacking any of the HD-associated SNPs. In some of the aspects, the oligonucleotide hybridizes to an mRNA of the Huntingtin gene having any of the SNPs selected from the group of rs362307 and rs365331. In some aspects, the oligonucleotide that is an additional therapeutic agent can be a modified oligonucleotide (e.g., an oligonucleotide including any of the modifications described herein). In some aspects, the modified oligonucleotide that is an additional therapeutic agent comprises one or more phosphorothioate internucleoside linkages. In some aspects, the modified oligonucleotide that is an additional therapeutic agent comprises one or more 2'-MOE moieties. In some aspects, the oligonucleotide that is an additional therapeutic agent hybridizes to the mRNA of the Huntingtin gene has a sequence selected from the SEQ ID NOs. 6-285 of U.S. Pat. No. 9,006,198; SEQ ID NOs. 6-8 of US Patent Application Publication No. 2017/0044539; SEQ ID NOs. 1-1565 of US Patent Application Publication 2018/0216108; and SEQ ID NOs 1-2432 of PCT Publication WO 2017/192679, the sequences of which are hereby incorporated by reference.

In some aspects, at least one of the additional therapeutic agent is a chemotherapeutic agent (e.g., a cytotoxic agent or other chemical compound useful in the treatment of a trinucleotide repeat expansion disorder).

In some aspects, at least one of the additional therapeutic agents can be a therapeutic agent which is a non-drug treatment. For example, at least one of the additional therapeutic agents is physical therapy.

In any of the combination aspects described herein, the two or more therapeutic agents can be administered simultaneously or sequentially, in either order. For example a first therapeutic agent can be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to hours, up to 21 hours, up to 22 hours, up to 23 hours up to 24 hours or up to 1-7, 1-14, 1-21 or 1-30 days before or after one or more of the additional therapeutic agents.

V. Pharmaceutical Compositions

The oligonucleotides described herein can be formulated into pharmaceutical compositions for administration to human subjects in a biologically compatible form suitable for administration in vivo.

The compounds described herein can be used in the form of the free base, in the form of salts, solvates, and as prodrugs. All forms are within the methods described herein. In accordance with the methods described herein, the described oligonucleotides or salts, solvates, or prodrugs thereof can be administered to a patient in a variety of forms depending on the selected route of administration, as will be understood by those skilled in the art. The compounds described herein can be administered, for example, by oral, parenteral, intrathecal, intracerebroventricular, intraparenchymal, buccal, sublingual, nasal, rectal, patch, pump, ortransdermal administration and the pharmaceutical compositions formulated accordingly. Parenteral administration includes intravenous, intraperitoneal, subcutaneous, intramuscular, transepithelial, nasal, intrapulmonary, intrathecal, intracerebroventricular, intraparenchymal, rectal, and topical modes of administration. Parenteral administration can be by continuous infusion over a selected period of time.

A compound described herein can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, a compound described herein can be incorporated with an excipient and used in the form of ingestible tablets, buccal tablets, troches, capsules, elixirs, suspensions, syrups, and wafers. A compound described herein can be administered parenterally. Solutions of a compound described herein can be prepared in water suitably mixed with a surfactant, such as hydroxypropylcellulose. Dispersions can be prepared in glycerol, liquid polyethylene glycols, DMSO, and mixtures thereof with or without alcohol, and in oils. Under ordinary conditions of storage and use, these preparations can contain a preservative to prevent the growth of microorganisms. Conventional procedures and ingredients for the selection and preparation of suitable formulations are described, for example, in Remington's Pharmaceutical Sciences (2012, 22nd ed.) and in. The United States Pharmacopeia: The National Formulary (USP 41 NF 36), published in 2018. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that can be easily administered via syringe. Compositions for nasal administration can conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container can be a unitary dispensing device, such as a single dose nasal inhaler or an aerosol dispenser fitted with a metering valve which is intended for disposal after use. Where the dosage form includes an aerosol dispenser, it will contain a propellant, which can be a compressed gas, such as compressed air or an organic propellant, such as fluorochlorohydrocarbon. The aerosol dosage forms can take the form of a pump-atomizer Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter The compounds described herein can be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

VI. Dosages

The dosage of the compositions (e.g., a composition including an oligonucleotide) described herein, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. The compositions described herein can be administered initially in a suitable dosage that can be adjusted as required, depending on the clinical response. In some aspects, the dosage of a composition (e.g., a composition including an oligonucleotide) is a prophylactically or a therapeutically effective amount VII. Kits Kits including (a) a pharmaceutical composition including an oligonucleotide agent that reduces the level and/or activity of MLH3 in a cell or subject described herein, and (b) a package insert with instructions to perform any of the methods described herein are contemplated. In some aspects, the kit includes (a) a pharmaceutical composition including an oligonucleotide agent that reduces the level and/or activity of MLH3 in a cell or subject described herein, (b) an additional therapeutic agent, and (c) a package insert with instructions to perform any of the methods described herein.

EXAMPLES

Example 1. Design and Selection of Antisense Oligonucleotides

Identification and selection of target transcripts: Target transcript selection and off-target scoring (below) utilized NCBI RefSeq sequences, downloaded from NCBI 21 Nov. 2018. Experimentally validated "NM" transcript models were used except for cynomolgus monkey, which only has "XM" predicted models for the large majority of genes. The longest human, mouse, rat, and cynomolgus monkey MLH3 transcript that contained all mapped internal exons was selected (SEQ IDs 1, 3, 4, and 5 for human, mouse, rat, and cynomolgus monkey, respectively, SEQ ID NO:2 is the protein sequence).

Selection of 20mer oligonucleotide sequences: All antisense 20mer sub-sequences per transcript were generated Candidate antisense oligonucleotides ('ASOs') were selected that met the following thermodynamic and physical characteristics determined by the inventors: predicted melting temperature of ASO:target duplex ("$T_m$") of 30-65° C., predicted melting temperature of hairpins ("$T_{hairpin}$")<35° C., predicted melting temperature of homopolymer formation ("$T_{homo}$")<25° C., GC content of 20-60%, no G homopolymers 4 or longer, and no A, T, or C homopolymers of 6 or longer. These selected or 'preferred' oligonucleotides were further evaluated for specificity (off-target scoring, below).

Off-target scoring: The specificity of the preferred ASOs was evaluated via alignment to all unspliced RefSeq transcripts ("NM" models for human, mouse, and rat; "NM' and'XM" models for cynomolgus monkey), using the FASTA algorithm with an E value cutoff of 1000. The number of mismatches between each ASO and each transcript (per species) was tallied. An "off-target score" for each ASO in each species was calculated as the lowest number of mismatches to any transcript other than those encoded by the MLH3 gene Selection of ASOs for screening: A set of 480 preferred ASOs was selected for screening according to both specificity and ASO:mRNA (target) hybridization energy maximization information as follows. All candidate ASOs were evaluated for delta G of hybridization with the predicted target mRNA secondary structure ($\Delta G_{overall}$) according to Xu and Mathews (*Methods Mol Biol.* 1490:15-34 (2016)). Next, two subsets of ASOs were chosen: First, 40 ASOs that matched human, cyno, and mouse target transcripts, had off-target scores of at least 1 in three species, and negative $\Delta G^{overall}$; second, 440 ASOs that matched human and cyno target transcripts, had off-target scores of at least 2 in both species, and $\Delta G^{overall}$ less than −9.5 degrees Celsius.

The sequences, positions in human transcript, conservation in other species and species-specific off-target scores of each ASO are given in Table 2. Wherever indicated as "NC", the ASO does not match the MLH3 gene in that species, and therefore off-target scores were not generated.

ASOs were synthesized as 5-10-5 "flanking sequence-DNA core sequence-flanking sequence" antisense oligonucleotides, with riboniucleotides at positions 1-5 and 16-20 and deoxyribonucleotides at positions 6-15. and with the following generic structure:

5-NmsNmsNmsNmsNms NsNsNsNsNs NsNsNsNsNs NmsNmsNmsNmsNm-3'

Wherein:

Nm: 2'-MOE residues (including 5methyl-2'-MOE-C and 5methyl-2'-MOE-U)

N: DNA/RNA residues s: phosphorothioate (the backbone is fully phosphorothioate-modified)

All "C" within the DNA core (positions 6-15) are 5-Methyl-2'-MOE-dC

All "T" in positions 1-5 or 16-20 are 5-methyl-2'-MOE-U.

For primary screens at 2 nM and 20 nM, desalted oligonucleotides were used. For detailed characterization of a subset of oligonucleotides, oligonucleotides were further purified by HPLC.

TABLE 2

Exemplary Oligonucleotides

| SEQ ID NO | Position | Sequence | Off-target Score Human | Cyno | Mouse | Rat |
|---|---|---|---|---|---|---|
| 6 | 75 | CTTGGATCTTGAGGCTCGTG | 3 | NC | NC | NC |
| 7 | 76 | CCTTGGATCTTGAGGCTCGT | 2 | NC | NC | NC |
| 8 | 77 | ACCTTGGATCTTGAGGCTCG | 3 | NC | NC | NC |
| 9 | 78 | CACCTTGGATCTTGAGGCTC | 2 | NC | NC | NC |
| 10 | 79 | GCACCTTGGATCTTGAGGCT | 2 | NC | NC | NC |
| 11 | 116 | AATTCTCCGACACCAACCGC | 3 | NC | NC | NC |
| 12 | 117 | AAATTCTCCGACACCAACCG | 3 | NC | NC | NC |
| 13 | 118 | CAAATTCTCCGACACCAACC | 2 | NC | NC | NC |
| 14 | 119 | ACAAATTCTCCGACACCAAC | 2 | NC | NC | NC |
| 15 | 120 | AACAAATTCTCCGACACCAA | 2 | NC | NC | NC |
| 16 | 121 | TAACAAATTCTCCGACACCA | 2 | NC | NC | NC |
| 17 | 122 | TTAACAAATTCTCCGACACC | 2 | NC | NC | NC |
| 18 | 123 | CTTAACAAATTCTCCGACAC | 3 | NC | NC | NC |
| 19 | 124 | GCTTAACAAATTCTCCGACA | 2 | NC | NC | NC |
| 20 | 125 | CGCTTAACAAATTCTCCGAC | 3 | NC | NC | NC |
| 21 | 126 | CCGCTTAACAAATTCTCCGA | 3 | NC | NC | NC |
| 22 | 127 | CCCGCTTAACAAATTCTCCG | 2 | NC | NC | NC |
| 23 | 128 | TCCCGCTTAACAAATTCTCC | 2 | NC | NC | NC |
| 24 | 129 | GTCCCGCTTAACAAATTCTC | 2 | NC | NC | NC |
| 25 | 130 | AGTCCCGCTTAACAAATTCT | 3 | NC | NC | NC |
| 26 | 131 | GAGTCCCGCTTAACAAATTC | 2 | NC | NC | NC |
| 27 | 132 | GGAGTCCCGCTTAACAAATT | 2 | NC | NC | NC |
| 28 | 133 | TGGAGTCCCGCTTAACAAAT | 3 | NC | NC | NC |
| 29 | 134 | CTGGAGTCCCGCTTAACAAA | 2 | NC | NC | NC |
| 30 | 135 | CCTGGAGTCCCGCTTAACAA | 3 | NC | NC | NC |
| 31 | 138 | TTGCCTGGAGTCCCGCTTAA | 3 | NC | NC | NC |
| 32 | 139 | ATTGCCTGGAGTCCCGCTTA | 3 | NC | NC | NC |
| 33 | 140 | AATTGCCTGGAGTCCCGCTT | 3 | NC | NC | NC |
| 34 | 141 | TAATTGCCTGGAGTCCCGCT | 3 | NC | NC | NC |
| 35 | 142 | ATAATTGCCTGGAGTCCCGC | 2 | NC | NC | NC |
| 36 | 143 | AATAATTGCCTGGAGTCCCG | 2 | NC | NC | NC |
| 37 | 144 | AAATAATTGCCTGGAGTCCC | 2 | NC | NC | NC |
| 38 | 145 | GAAATAATTGCCTGGAGTCC | 2 | NC | NC | NC |
| 39 | 146 | GGAAATAATTGCCTGGAGTC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 40 | 147 | TGGAAATAATTGCCTGGAGT | 1 | NC | NC | NC |
| 41 | 148 | CTGGAAATAATTGCCTGGAG | 2 | NC | NC | NC |
| 42 | 149 | ACTGGAAATAATTGCCTGGA | 2 | NC | NC | NC |
| 43 | 150 | GACTGGAAATAATTGCCTGG | 1 | NC | NC | NC |
| 44 | 151 | TGACTGGAAATAATTGCCTG | 2 | NC | NC | NC |
| 45 | 152 | CTGACTGGAAATAATTGCCT | 1 | NC | NC | NC |
| 46 | 153 | TCTGACTGGAAATAATTGCC | 2 | NC | NC | NC |
| 47 | 154 | CTCTGACTGGAAATAATTGC | 2 | NC | NC | NC |
| 48 | 155 | TCTCTGACTGGAAATAATTG | 2 | NC | NC | NC |
| 49 | 156 | TTCTCTGACTGGAAATAATT | 2 | NC | NC | NC |
| 50 | 157 | CTTCTCTGACTGGAAATAAT | 2 | NC | NC | NC |
| 51 | 158 | CCTTCTCTGACTGGAAATAA | 2 | NC | NC | NC |
| 52 | 159 | TCCTTCTCTGACTGGAAATA | 1 | NC | NC | NC |
| 53 | 160 | TTCCTTCTCTGACTGGAAAT | 1 | NC | NC | NC |
| 54 | 162 | GTTTCCTTCTCTGACTGGAA | 0 | NC | NC | NC |
| 55 | 163 | GGTTTCCTTCTCTGACTGGA | 1 | NC | NC | NC |
| 56 | 164 | TGGTTTCCTTCTCTGACTGG | 2 | NC | NC | NC |
| 57 | 165 | CTGGTTTCCTTCTCTGACTG | 2 | NC | NC | NC |
| 58 | 166 | ACTGGTTTCCTTCTCTGACT | 2 | NC | NC | NC |
| 59 | 167 | CACTGGTTTCCTTCTCTGAC | 2 | NC | NC | NC |
| 60 | 168 | GCACTGGTTTCCTTCTCTGA | 2 | NC | NC | NC |
| 61 | 169 | GGCACTGGTTTCCTTCTCTG | 1 | NC | NC | NC |
| 62 | 170 | AGGCACTGGTTTCCTTCTCT | 1 | NC | NC | NC |
| 63 | 186 | AGATGGTGAGAATGCCAGGC | 2 | NC | NC | NC |
| 64 | 187 | AAGATGGTGAGAATGCCAGG | 2 | NC | NC | NC |
| 65 | 188 | AAAGATGGTGAGAATGCCAG | 1 | NC | NC | NC |
| 66 | 190 | AGAAAGATGGTGAGAATGCC | 1 | 1 | NC | NC |
| 67 | 191 | TAGAAAGATGGTGAGAATGC | 2 | 1 | NC | NC |
| 68 | 192 | GTAGAAAGATGGTGAGAATG | 2 | 1 | NC | NC |
| 69 | 193 | GGTAGAAAGATGGTGAGAAT | 2 | 2 | NC | NC |
| 70 | 194 | AGGTAGAAAGATGGTGAGAA | 2 | 1 | NC | NC |
| 71 | 195 | TAGGTAGAAAGATGGTGAGA | 2 | 2 | NC | NC |
| 72 | 196 | GTAGGTAGAAAGATGGTGAG | 2 | 2 | NC | NC |
| 73 | 197 | GGTAGGTAGAAAGATGGTGA | 2 | 2 | NC | NC |
| 74 | 198 | TGGTAGGTAGAAAGATGGTG | 2 | 2 | NC | NC |
| 75 | 199 | ATGGTAGGTAGAAAGATGGT | 2 | 2 | NC | NC |
| 76 | 200 | CATGGTAGGTAGAAAGATGG | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 77 | 201 | TCATGGTAGGTAGAAAGATG | 2 | 2 | NC | NC |
| 78 | 202 | ATCATGGTAGGTAGAAAGAT | 1 | 2 | NC | NC |
| 79 | 203 | GATCATGGTAGGTAGAAAGA | 2 | 2 | NC | NC |
| 80 | 204 | TGATCATGGTAGGTAGAAAG | 2 | 2 | NC | NC |
| 81 | 205 | TTGATCATGGTAGGTAGAAA | 2 | 2 | NC | NC |
| 82 | 206 | CTTGATCATGGTAGGTAGAA | 2 | 2 | NC | NC |
| 83 | 207 | ACTTGATCATGGTAGGTAGA | 2 | 2 | NC | NC |
| 84 | 208 | CACTTGATCATGGTAGGTAG | 2 | 2 | NC | NC |
| 85 | 209 | GCACTTGATCATGGTAGGTA | 2 | 2 | NC | NC |
| 86 | 210 | AGCACTTGATCATGGTAGGT | 2 | 2 | NC | NC |
| 87 | 211 | AAGCACTTGATCATGGTAGG | 2 | 2 | NC | NC |
| 88 | 223 | ACTTCAACTGACAAGCACTT | 2 | 2 | NC | NC |
| 89 | 224 | TACTTCAACTGACAAGCACT | 2 | 2 | NC | NC |
| 90 | 225 | GTACTTCAACTGACAAGCAC | 2 | 2 | NC | NC |
| 91 | 226 | TGTACTTCAACTGACAAGCA | 1 | 2 | NC | NC |
| 92 | 227 | TTGTACTTCAACTGACAAGC | 2 | 2 | NC | NC |
| 93 | 229 | GCTTGTACTTCAACTGACAA | 2 | 2 | NC | NC |
| 94 | 230 | GGCTTGTACTTCAACTGACA | 2 | 2 | NC | NC |
| 95 | 231 | TGGCTTGTACTTCAACTGAC | 2 | 2 | NC | NC |
| 96 | 232 | TTGGCTTGTACTTCAACTGA | 2 | 2 | NC | NC |
| 97 | 233 | TTTGGCTTGTACTTCAACTG | 2 | 2 | NC | NC |
| 98 | 234 | ATTTGGCTTGTACTTCAACT | 2 | 2 | NC | NC |
| 99 | 235 | AATTTGGCTTGTACTTCAAC | 2 | 2 | NC | NC |
| 100 | 236 | CAATTTGGCTTGTACTTCAA | 2 | 2 | NC | NC |
| 101 | 237 | GCAATTTGGCTTGTACTTCA | 2 | 2 | NC | NC |
| 102 | 238 | CGCAATTTGGCTTGTACTTC | 2 | 3 | NC | NC |
| 103 | 239 | ACGCAATTTGGCTTGTACTT | 2 | 3 | NC | NC |
| 104 | 240 | AACGCAATTTGGCTTGTACT | 2 | 3 | NC | NC |
| 105 | 241 | GAACGCAATTTGGCTTGTAC | 2 | 2 | NC | NC |
| 106 | 242 | AGAACGCAATTTGGCTTGTA | 2 | 2 | NC | NC |
| 107 | 243 | CAGAACGCAATTTGGCTTGT | 3 | 2 | NC | NC |
| 108 | 244 | CCAGAACGCAATTTGGCTTG | 3 | 3 | NC | NC |
| 109 | 245 | ACCAGAACGCAATTTGGCTT | 3 | 2 | NC | NC |
| 110 | 246 | AACCAGAACGCAATTTGGCT | 2 | 2 | NC | NC |
| 111 | 247 | AAACCAGAACGCAATTTGGC | 2 | 2 | NC | NC |
| 112 | 249 | CCAAACCAGAACGCAATTTG | 2 | 3 | NC | NC |
| 113 | 250 | GCCAAACCAGAACGCAATTT | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 114 | 269 | TTGGCCCAAGGAGCTTATGG | 1 | 2 | NC | NC |
| 115 | 270 | ATTGGCCCAAGGAGCTTATG | 2 | 2 | NC | NC |
| 116 | 271 | CATTGGCCCAAGGAGCTTAT | 2 | 3 | NC | NC |
| 117 | 272 | ACATTGGCCCAAGGAGCTTA | 2 | 3 | NC | NC |
| 118 | 273 | CACATTGGCCCAAGGAGCTT | 2 | 3 | NC | NC |
| 119 | 274 | ACACATTGGCCCAAGGAGCT | 1 | 2 | NC | NC |
| 120 | 275 | AACACATTGGCCCAAGGAGC | 2 | 2 | NC | NC |
| 121 | 276 | CAACACATTGGCCCAAGGAG | 2 | 2 | NC | NC |
| 122 | 277 | TCAACACATTGGCCCAAGGA | 2 | 2 | NC | NC |
| 123 | 278 | CTCAACACATTGGCCCAAGG | 2 | 2 | NC | NC |
| 124 | 279 | CCTCAACACATTGGCCCAAG | 2 | 2 | NC | NC |
| 125 | 280 | TCCTCAACACATTGGCCCAA | 1 | 1 | NC | NC |
| 126 | 281 | TTCCTCAACACATTGGCCCA | 1 | 1 | NC | NC |
| 127 | 282 | GTTCCTCAACACATTGGCCC | 2 | 2 | NC | NC |
| 128 | 283 | AGTTCCTCAACACATTGGCC | 2 | 1 | NC | NC |
| 129 | 284 | AAGTTCCTCAACACATTGGC | 2 | 2 | NC | NC |
| 130 | 285 | CAAGTTCCTCAACACATTGG | 2 | 2 | NC | NC |
| 131 | 286 | GCAAGTTCCTCAACACATTG | 2 | 2 | NC | NC |
| 132 | 287 | GGCAAGTTCCTCAACACATT | 2 | 2 | NC | NC |
| 133 | 288 | GGGCAAGTTCCTCAACACAT | 2 | 2 | NC | NC |
| 134 | 289 | AGGGCAAGTTCCTCAACACA | 2 | 2 | NC | NC |
| 135 | 296 | ACTGTTGAGGGCAAGTTCCT | 2 | 2 | NC | NC |
| 136 | 297 | TACTGTTGAGGGCAAGTTCC | 2 | 2 | NC | NC |
| 137 | 298 | ATACTGTTGAGGGCAAGTTC | 2 | 2 | NC | NC |
| 138 | 299 | AATACTGTTGAGGGCAAGTT | 2 | 1 | NC | NC |
| 139 | 300 | CAATACTGTTGAGGGCAAGT | 2 | 2 | NC | NC |
| 140 | 301 | TCAATACTGTTGAGGGCAAG | 2 | 2 | NC | NC |
| 141 | 302 | ATCAATACTGTTGAGGGCAA | 1 | 1 | NC | NC |
| 142 | 303 | CATCAATACTGTTGAGGGCA | 2 | 2 | NC | NC |
| 143 | 304 | GCATCAATACTGTTGAGGGC | 2 | 2 | NC | NC |
| 144 | 305 | AGCATCAATACTGTTGAGGG | 2 | 2 | NC | NC |
| 145 | 306 | CAGCATCAATACTGTTGAGG | 2 | 2 | NC | NC |
| 146 | 307 | TCAGCATCAATACTGTTGAG | 2 | 2 | NC | NC |
| 147 | 308 | TTCAGCATCAATACTGTTGA | 2 | 2 | NC | NC |
| 148 | 309 | CTTCAGCATCAATACTGTTG | 2 | 2 | NC | NC |
| 149 | 323 | AGCCACACATTTTGCTTCAG | 1 | 2 | NC | NC |
| 150 | 324 | CAGCCACACATTTTGCTTCA | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 151 | 325 | ACAGCCACACATTTTGCTTC | 2 | 2 | NC | NC |
| 152 | 326 | GACAGCCACACATTTTGCTT | 2 | 2 | NC | NC |
| 153 | 327 | TGACAGCCACACATTTTGCT | 1 | 2 | NC | NC |
| 154 | 328 | CTGACAGCCACACATTTTGC | 2 | 2 | NC | NC |
| 155 | 329 | CCTGACAGCCACACATTTTG | 1 | 1 | NC | NC |
| 156 | 330 | CCCTGACAGCCACACATTTT | 1 | 2 | NC | NC |
| 157 | 331 | ACCCTGACAGCCACACATTT | 1 | 1 | NC | NC |
| 158 | 332 | CACCCTGACAGCCACACATT | 1 | 1 | NC | NC |
| 159 | 333 | TCACCCTGACAGCCACACAT | 1 | 1 | NC | NC |
| 160 | 334 | TTCACCCTGACAGCCACACA | 2 | 1 | NC | NC |
| 161 | 335 | ATTCACCCTGACAGCCACAC | 2 | 2 | NC | NC |
| 162 | 336 | TATTCACCCTGACAGCCACA | 2 | 2 | NC | NC |
| 163 | 337 | ATATTCACCCTGACAGCCAC | 2 | 2 | NC | NC |
| 164 | 338 | CATATTCACCCTGACAGCCA | 2 | 2 | NC | NC |
| 165 | 339 | CCATATTCACCCTGACAGCC | 1 | 2 | NC | NC |
| 166 | 340 | TCCATATTCACCCTGACAGC | 2 | 2 | NC | NC |
| 167 | 341 | TTCCATATTCACCCTGACAG | 2 | 2 | NC | NC |
| 168 | 342 | TTTCCATATTCACCCTGACA | 2 | 2 | NC | NC |
| 169 | 343 | GTTTCCATATTCACCCTGAC | 2 | 2 | NC | NC |
| 170 | 344 | GGTTTCCATATTCACCCTGA | 2 | 2 | NC | NC |
| 171 | 345 | AGGTTTCCATATTCACCCTG | 2 | 2 | NC | NC |
| 172 | 346 | AAGGTTTCCATATTCACCCT | 2 | 2 | NC | NC |
| 173 | 347 | GAAGGTTTCCATATTCACCC | 2 | 2 | NC | NC |
| 174 | 358 | ACTTGAACTTGGAAGGTTTC | 2 | 2 | 2 | 2 |
| 175 | 359 | CACTTGAACTTGGAAGGTTT | 2 | 2 | 2 | 1 |
| 176 | 360 | TCACTTGAACTTGGAAGGTT | 1 | 1 | 1 | 2 |
| 177 | 361 | ATCACTTGAACTTGGAAGGT | 0 | 0 | 1 | 2 |
| 178 | 362 | TATCACTTGAACTTGGAAGG | 1 | 1 | 2 | 3 |
| 179 | 363 | CTATCACTTGAACTTGGAAG | 2 | 2 | 1 | 2 |
| 180 | 364 | TCTATCACTTGAACTTGGAA | 2 | 1 | 1 | 2 |
| 181 | 365 | GTCTATCACTTGAACTTGGA | 2 | 1 | 1 | 2 |
| 182 | 366 | TGTCTATCACTTGAACTTGG | 2 | 2 | 1 | 1 |
| 183 | 367 | TTGTCTATCACTTGAACTTG | 2 | 2 | 2 | 2 |
| 184 | 368 | ATTGTCTATCACTTGAACTT | 2 | 2 | 2 | NC |
| 185 | 369 | CATTGTCTATCACTTGAACT | 2 | 2 | 2 | NC |
| 186 | 370 | CCATTGTCTATCACTTGAAC | 2 | 2 | 2 | NC |
| 187 | 371 | TCCATTGTCTATCACTTGAA | 2 | 2 | 2 | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 188 | 372 | ATCCATTGTCTATCACTTGA | 2 | 2 | NC | NC |
| 189 | 373 | AATCCATTGTCTATCACTTG | 2 | 2 | NC | NC |
| 190 | 374 | AAATCCATTGTCTATCACTT | 1 | 1 | NC | NC |
| 191 | 375 | CAAATCCATTGTCTATCACT | 2 | 2 | NC | NC |
| 192 | 376 | CCAAATCCATTGTCTATCAC | 2 | 2 | NC | NC |
| 193 | 377 | CCCAAATCCATTGTCTATCA | 2 | 2 | NC | NC |
| 194 | 378 | TCCCAAATCCATTGTCTATC | 2 | 2 | NC | NC |
| 195 | 379 | ATCCCAAATCCATTGTCTAT | 2 | 2 | NC | NC |
| 196 | 380 | CATCCCAAATCCATTGTCTA | 2 | 2 | NC | NC |
| 197 | 381 | CCATCCCAAATCCATTGTCT | 1 | 1 | NC | NC |
| 198 | 382 | CCCATCCCAAATCCATTGTC | 1 | 1 | NC | NC |
| 199 | 383 | CCCCATCCCAAATCCATTGT | 1 | 2 | NC | NC |
| 200 | 385 | CTCCCCATCCCAAATCCATT | 1 | 1 | NC | NC |
| 201 | 386 | ACTCCCCATCCCAAATCCAT | 2 | 2 | NC | NC |
| 202 | 387 | CACTCCCCATCCCAAATCCA | 1 | 2 | NC | NC |
| 203 | 388 | TCACTCCCCATCCCAAATCC | 1 | 2 | NC | NC |
| 204 | 389 | ATCACTCCCCATCCCAAATC | 1 | 1 | NC | NC |
| 205 | 390 | CATCACTCCCCATCCCAAAT | 2 | 2 | NC | NC |
| 206 | 391 | TCATCACTCCCCATCCCAAA | 2 | 2 | NC | NC |
| 207 | 392 | ATCATCACTCCCCATCCCAA | 2 | 2 | NC | NC |
| 208 | 393 | CATCATCACTCCCCATCCCA | 2 | 2 | NC | NC |
| 209 | 394 | ACATCATCACTCCCCATCCC | 1 | 2 | NC | NC |
| 210 | 395 | TACATCATCACTCCCCATCC | 1 | 2 | NC | NC |
| 211 | 396 | CTACATCATCACTCCCCATC | 2 | 2 | NC | NC |
| 212 | 397 | TCTACATCATCACTCCCCAT | 2 | 2 | NC | NC |
| 213 | 398 | CTCTACATCATCACTCCCCA | 2 | 1 | NC | NC |
| 214 | 399 | TCTCTACATCATCACTCCCC | 2 | 1 | NC | NC |
| 215 | 400 | TTCTCTACATCATCACTCCC | 2 | 1 | NC | NC |
| 216 | 401 | TTTCTCTACATCATCACTCC | 2 | 2 | NC | NC |
| 217 | 402 | CTTTCTCTACATCATCACTC | 2 | 2 | NC | NC |
| 218 | 403 | ACTTTCTCTACATCATCACT | 2 | 1 | NC | NC |
| 219 | 404 | CACTTTCTCTACATCATCAC | 1 | 1 | NC | NC |
| 220 | 405 | CCACTTTCTCTACATCATCA | 1 | 1 | NC | NC |
| 221 | 406 | CCCACTTTCTCTACATCATC | 1 | 2 | NC | NC |
| 222 | 407 | TCCCACTTTCTCTACATCAT | 1 | 2 | NC | NC |
| 223 | 408 | TTCCCACTTTCTCTACATCA | 2 | 2 | NC | NC |
| 224 | 409 | TTTCCCACTTTCTCTACATC | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 225 | 410 | ATTTCCCACTTTCTCTACAT | 1 | 1 | NC | NC |
| 226 | 411 | GATTTCCCACTTTCTCTACA | 1 | 2 | NC | NC |
| 227 | 412 | CGATTTCCCACTTTCTCTAC | 2 | 2 | NC | NC |
| 228 | 413 | ACGATTTCCCACTTTCTCTA | 2 | 2 | NC | NC |
| 229 | 414 | AACGATTTCCCACTTTCTCT | 2 | 2 | NC | NC |
| 230 | 415 | TAACGATTTCCCACTTTCTC | 2 | 2 | NC | NC |
| 231 | 416 | ATAACGATTTCCCACTTTCT | 2 | 2 | NC | NC |
| 232 | 417 | AATAACGATTTCCCACTTTC | 2 | 2 | NC | NC |
| 233 | 418 | AAATAACGATTTCCCACTTT | 2 | 2 | NC | NC |
| 234 | 426 | TACTGGTGAAATAACGATTT | 2 | 3 | NC | NC |
| 235 | 427 | TTACTGGTGAAATAACGATT | 2 | 2 | NC | NC |
| 236 | 428 | TTTACTGGTGAAATAACGAT | 2 | 2 | NC | NC |
| 237 | 429 | ATTTACTGGTGAAATAACGA | 2 | 2 | NC | NC |
| 238 | 430 | CATTTACTGGTGAAATAACG | 2 | 2 | NC | NC |
| 239 | 431 | GCATTTACTGGTGAAATAAC | 1 | 2 | NC | NC |
| 240 | 432 | GGCATTTACTGGTGAAATAA | 2 | 2 | NC | NC |
| 241 | 433 | TGGCATTTACTGGTGAAATA | 2 | 2 | NC | NC |
| 242 | 434 | GTGGCATTTACTGGTGAAAT | 2 | 1 | NC | NC |
| 243 | 435 | AGTGGCATTTACTGGTGAAA | 2 | 2 | NC | NC |
| 244 | 436 | GAGTGGCATTTACTGGTGAA | 2 | 2 | NC | NC |
| 245 | 437 | CGAGTGGCATTTACTGGTGA | 2 | 2 | NC | NC |
| 246 | 438 | CCGAGTGGCATTTACTGGTG | 3 | 3 | NC | NC |
| 247 | 451 | TCCAAGTCCTGTACCGAGTG | 2 | 2 | NC | NC |
| 248 | 452 | CTCCAAGTCCTGTACCGAGT | 3 | 3 | NC | NC |
| 249 | 453 | TCTCCAAGTCCTGTACCGAG | 3 | 3 | NC | NC |
| 250 | 454 | TTCTCCAAGTCCTGTACCGA | 2 | 3 | NC | NC |
| 251 | 455 | ATTCTCCAAGTCCTGTACCG | 2 | 3 | NC | NC |
| 252 | 456 | GATTCTCCAAGTCCTGTACC | 2 | 2 | NC | NC |
| 253 | 457 | GGATTCTCCAAGTCCTGTAC | 1 | 2 | NC | NC |
| 254 | 468 | CATAAAACCTTGGATTCTCC | 2 | 1 | NC | NC |
| 255 | 469 | CCATAAAACCTTGGATTCTC | 2 | 2 | NC | NC |
| 256 | 470 | ACCATAAAACCTTGGATTCT | 1 | 2 | NC | NC |
| 257 | 471 | AACCATAAAACCTTGGATTC | 2 | 2 | NC | NC |
| 258 | 472 | AAACCATAAAACCTTGGATT | 2 | 2 | NC | NC |
| 259 | 473 | GAAACCATAAAACCTTGGAT | 2 | 2 | NC | NC |
| 260 | 474 | GGAAACCATAAAACCTTGGA | 2 | 2 | NC | NC |
| 261 | 476 | TCGGAAACCATAAAACCTTG | 2 | 3 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 262 | 477 | CTCGGAAACCATAAAACCTT | 3 | 3 | NC | NC |
| 263 | 478 | CCTCGGAAACCATAAAACCT | 2 | 2 | NC | NC |
| 264 | 479 | TCCTCGGAAACCATAAAACC | 2 | 2 | NC | NC |
| 265 | 480 | CTCCTCGGAAACCATAAAAC | 2 | 2 | NC | NC |
| 266 | 481 | TCTCCTCGGAAACCATAAAA | 2 | 2 | NC | NC |
| 267 | 482 | CTCTCCTCGGAAACCATAAA | 2 | 2 | NC | NC |
| 268 | 483 | CCTCTCCTCGGAAACCATAA | 2 | 2 | NC | NC |
| 269 | 484 | GCCTCTCCTCGGAAACCATA | 2 | 1 | NC | NC |
| 270 | 509 | GGCCATGTCAGCAATATTTG | 2 | NC | NC | NC |
| 271 | 510 | TGGCCATGTCAGCAATATTT | 1 | NC | NC | NC |
| 272 | 511 | CTGGCCATGTCAGCAATATT | 2 | NC | NC | NC |
| 273 | 512 | ACTGGCCATGTCAGCAATAT | 2 | NC | NC | NC |
| 274 | 513 | CACTGGCCATGTCAGCAATA | 2 | NC | NC | NC |
| 275 | 514 | GCACTGGCCATGTCAGCAAT | 2 | NC | NC | NC |
| 276 | 515 | AGCACTGGCCATGTCAGCAA | 1 | NC | NC | NC |
| 277 | 527 | CGAAATTTCCACAGCACTGG | 2 | NC | NC | NC |
| 278 | 528 | ACGAAATTTCCACAGCACTG | 2 | NC | NC | NC |
| 279 | 529 | GACGAAATTTCCACAGCACT | 2 | NC | NC | NC |
| 280 | 530 | GGACGAAATTTCCACAGCAC | 2 | NC | NC | NC |
| 281 | 531 | TGGACGAAATTTCCACAGCA | 2 | NC | NC | NC |
| 282 | 537 | TTTTCTTGGACGAAATTTCC | 2 | 2 | NC | NC |
| 283 | 538 | TTTTTCTTGGACGAAATTTC | 2 | 1 | NC | NC |
| 284 | 539 | GTTTTTCTTGGACGAAATTT | 2 | 2 | NC | NC |
| 285 | 540 | TGTTTTTCTTGGACGAAATT | 2 | 2 | NC | NC |
| 286 | 541 | CTGTTTTTCTTGGACGAAAT | 2 | 2 | NC | NC |
| 287 | 542 | CCTGTTTTTCTTGGACGAAA | 3 | 1 | NC | NC |
| 288 | 543 | TCCTGTTTTTCTTGGACGAA | 2 | 2 | NC | NC |
| 289 | 547 | ATTGTCCTGTTTTTCTTGGA | 1 | 2 | NC | NC |
| 290 | 548 | CATTGTCCTGTTTTTCTTGG | 1 | 2 | NC | NC |
| 291 | 549 | TCATTGTCCTGTTTTTCTTG | 1 | 1 | NC | NC |
| 292 | 550 | TTCATTGTCCTGTTTTTCTT | 0 | 2 | NC | NC |
| 293 | 551 | TTTCATTGTCCTGTTTTTCT | 1 | 1 | NC | NC |
| 294 | 552 | TTTTCATTGTCCTGTTTTTC | 2 | 1 | NC | NC |
| 295 | 553 | GTTTTCATTGTCCTGTTTTT | 1 | 2 | NC | NC |
| 296 | 554 | AGTTTTCATTGTCCTGTTTT | 2 | 1 | NC | NC |
| 297 | 555 | AAGTTTTCATTGTCCTGTTT | 2 | 1 | NC | NC |
| 298 | 556 | AAAGTTTTCATTGTCCTGTT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 299 | 557 | AAAAGTTTTCATTGTCCTGT | 2 | 2 | NC | NC |
| 300 | 558 | CAAAAGTTTTCATTGTCCTG | 2 | 2 | NC | NC |
| 301 | 559 | ACAAAAGTTTTCATTGTCCT | 2 | 2 | NC | NC |
| 302 | 560 | CACAAAAGTTTTCATTGTCC | 2 | 2 | NC | NC |
| 303 | 561 | TCACAAAAGTTTTCATTGTC | 1 | 1 | NC | NC |
| 304 | 562 | TTCACAAAAGTTTTCATTGT | 1 | 1 | NC | NC |
| 305 | 563 | TTTCACAAAAGTTTTCATTG | 2 | 1 | NC | NC |
| 306 | 564 | GTTTCACAAAAGTTTTCATT | 2 | 2 | NC | NC |
| 307 | 565 | AGTTTCACAAAAGTTTTCAT | 1 | 2 | NC | NC |
| 308 | 566 | CAGTTTCACAAAAGTTTTCA | 1 | 1 | NC | NC |
| 309 | 567 | ACAGTTTCACAAAAGTTTTC | 2 | 2 | NC | NC |
| 310 | 568 | AACAGTTTCACAAAAGTTTT | 1 | 1 | NC | NC |
| 311 | 569 | AAACAGTTTCACAAAAGTTT | 2 | 2 | NC | NC |
| 312 | 580 | TTTCCACTCTGAAACAGTTT | 1 | 2 | NC | NC |
| 313 | 581 | TTTTCCACTCTGAAACAGTT | 1 | 2 | NC | NC |
| 314 | 582 | CTTTTCCACTCTGAAACAGT | 2 | 2 | NC | NC |
| 315 | 583 | GCTTTTCCACTCTGAAACAG | 2 | 2 | NC | NC |
| 316 | 584 | GGCTTTTCCACTCTGAAACA | 2 | 1 | NC | NC |
| 317 | 585 | GGGCTTTTCCACTCTGAAAC | 2 | 2 | NC | NC |
| 318 | 586 | AGGGCTTTTCCACTCTGAAA | 2 | 2 | NC | NC |
| 319 | 587 | CAGGGCTTTTCCACTCTGAA | 2 | 2 | NC | NC |
| 320 | 588 | TCAGGGCTTTTCCACTCTGA | 2 | 2 | NC | NC |
| 321 | 589 | TTCAGGGCTTTTCCACTCTG | 2 | 2 | NC | NC |
| 322 | 590 | TTTCAGGGCTTTTCCACTCT | 2 | 1 | NC | NC |
| 323 | 591 | CTTTCAGGGCTTTTCCACTC | 1 | 1 | NC | NC |
| 324 | 592 | GCTTTCAGGGCTTTTCCACT | 1 | 1 | NC | NC |
| 325 | 593 | AGCTTTCAGGGCTTTTCCAC | 1 | 2 | NC | NC |
| 326 | 611 | AGTCACATCAGCTTCACAAG | 2 | 2 | NC | NC |
| 327 | 612 | TAGTCACATCAGCTTCACAA | 2 | 2 | NC | NC |
| 328 | 613 | CTAGTCACATCAGCTTCACA | 3 | 3 | NC | NC |
| 329 | 614 | TCTAGTCACATCAGCTTCAC | 2 | 2 | NC | NC |
| 330 | 615 | CTCTAGTCACATCAGCTTCA | 2 | NC | NC | NC |
| 331 | 616 | GCTCTAGTCACATCAGCTTC | 2 | NC | NC | NC |
| 332 | 617 | TGCTCTAGTCACATCAGCTT | 2 | NC | NC | NC |
| 333 | 618 | TTGCTCTAGTCACATCAGCT | 2 | NC | NC | NC |
| 334 | 619 | CTTGCTCTAGTCACATCAGC | 2 | NC | NC | NC |
| 335 | 620 | GCTTGCTCTAGTCACATCAG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 336 | 621 | CGCTTGCTCTAGTCACATCA | 2 | NC | NC | NC |
| 337 | 622 | GCGCTTGCTCTAGTCACATC | 2 | NC | NC | NC |
| 338 | 635 | TACAGTAGTCCCAGCGCTTG | 2 | NC | NC | NC |
| 339 | 636 | TTACAGTAGTCCCAGCGCTT | 2 | NC | NC | NC |
| 340 | 637 | GTTACAGTAGTCCCAGCGCT | 3 | NC | NC | NC |
| 341 | 638 | TGTTACAGTAGTCCCAGCGC | 2 | NC | NC | NC |
| 342 | 639 | CTGTTACAGTAGTCCCAGCG | 2 | NC | NC | NC |
| 343 | 651 | ATAGGTTATACACTGTTACA | 1 | 2 | NC | NC |
| 344 | 652 | AATAGGTTATACACTGTTAC | 2 | 2 | NC | NC |
| 345 | 653 | AAATAGGTTATACACTGTTA | 1 | 1 | NC | NC |
| 346 | 654 | AAAATAGGTTATACACTGTT | 2 | 1 | NC | NC |
| 347 | 655 | TAAAATAGGTTATACACTGT | 1 | 1 | NC | NC |
| 348 | 656 | GTAAAATAGGTTATACACTG | 2 | 2 | NC | NC |
| 349 | 657 | GGTAAAATAGGTTATACACT | 1 | 1 | NC | NC |
| 350 | 658 | TGGTAAAATAGGTTATACAC | 2 | 2 | NC | NC |
| 351 | 659 | CTGGTAAAATAGGTTATACA | 2 | 2 | NC | NC |
| 352 | 660 | GCTGGTAAAATAGGTTATAC | 2 | 2 | NC | NC |
| 353 | 661 | AGCTGGTAAAATAGGTTATA | 2 | 2 | NC | NC |
| 354 | 662 | AAGCTGGTAAAATAGGTTAT | 1 | NC | NC | NC |
| 355 | 663 | GAAGCTGGTAAAATAGGTTA | 1 | NC | NC | NC |
| 356 | 664 | GGAAGCTGGTAAAATAGGTT | 1 | NC | NC | NC |
| 357 | 665 | AGGAAGCTGGTAAAATAGGT | 1 | NC | NC | NC |
| 358 | 666 | CAGGAAGCTGGTAAAATAGG | 1 | NC | NC | NC |
| 359 | 667 | ACAGGAAGCTGGTAAAATAG | 2 | NC | NC | NC |
| 360 | 668 | TACAGGAAGCTGGTAAAATA | 2 | NC | NC | NC |
| 361 | 669 | TTACAGGAAGCTGGTAAAAT | 2 | NC | NC | NC |
| 362 | 670 | CTTACAGGAAGCTGGTAAAA | 2 | NC | NC | NC |
| 363 | 671 | CCTTACAGGAAGCTGGTAAA | 2 | NC | NC | NC |
| 364 | 682 | ATGCATTTCCTCCTTACAGG | 2 | 2 | NC | NC |
| 365 | 683 | CATGCATTTCCTCCTTACAG | 2 | 2 | NC | NC |
| 366 | 684 | CCATGCATTTCCTCCTTACA | 2 | 2 | NC | NC |
| 367 | 685 | TCCATGCATTTCCTCCTTAC | 2 | 2 | NC | NC |
| 368 | 686 | GTCCATGCATTTCCTCCTTA | 2 | 2 | NC | NC |
| 369 | 687 | GGTCCATGCATTTCCTCCTT | 1 | 1 | NC | NC |
| 370 | 688 | GGGTCCATGCATTTCCTCCT | 2 | 2 | NC | NC |
| 371 | 689 | AGGGTCCATGCATTTCCTCC | 1 | 1 | NC | NC |
| 372 | 690 | TAGGGTCCATGCATTTCCTC | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 373 | 691 | CTAGGGTCCATGCATTTCCT | 3 | 3 | NC | NC |
| 374 | 692 | TCTAGGGTCCATGCATTTCC | 2 | 2 | NC | NC |
| 375 | 693 | GTCTAGGGTCCATGCATTTC | 2 | 3 | NC | NC |
| 376 | 694 | AGTCTAGGGTCCATGCATTT | 2 | 2 | NC | NC |
| 377 | 695 | CAGTCTAGGGTCCATGCATT | 2 | 3 | NC | NC |
| 378 | 696 | CCAGTCTAGGGTCCATGCAT | 2 | 2 | NC | NC |
| 379 | 697 | TCCAGTCTAGGGTCCATGCA | 2 | 2 | NC | NC |
| 380 | 699 | ACTCCAGTCTAGGGTCCATG | 1 | 2 | NC | NC |
| 381 | 700 | AACTCCAGTCTAGGGTCCAT | 2 | 2 | NC | NC |
| 382 | 701 | AAACTCCAGTCTAGGGTCCA | 2 | 2 | NC | NC |
| 383 | 702 | CAAACTCCAGTCTAGGGTCC | 2 | 2 | NC | NC |
| 384 | 703 | TCAAACTCCAGTCTAGGGTC | 2 | 2 | NC | NC |
| 385 | 704 | CTCAAACTCCAGTCTAGGGT | 2 | 2 | NC | NC |
| 386 | 705 | TCTCAAACTCCAGTCTAGGG | 2 | 2 | NC | NC |
| 387 | 706 | TTCTCAAACTCCAGTCTAGG | 2 | 2 | NC | NC |
| 388 | 707 | CTTCTCAAACTCCAGTCTAG | 2 | 2 | NC | NC |
| 389 | 708 | CCTTCTCAAACTCCAGTCTA | 2 | 2 | NC | NC |
| 390 | 709 | ACCTTCTCAAACTCCAGTCT | 2 | 2 | NC | NC |
| 391 | 710 | AACCTTCTCAAACTCCAGTC | 2 | 2 | NC | NC |
| 392 | 711 | TAACCTTCTCAAACTCCAGT | 2 | 1 | NC | NC |
| 393 | 712 | CTAACCTTCTCAAACTCCAG | 2 | 2 | NC | NC |
| 394 | 713 | CCTAACCTTCTCAAACTCCA | 2 | 1 | NC | NC |
| 395 | 714 | GCCTAACCTTCTCAAACTCC | 2 | 2 | NC | NC |
| 396 | 715 | TGCCTAACCTTCTCAAACTC | 2 | 2 | NC | NC |
| 397 | 716 | CTGCCTAACCTTCTCAAACT | 2 | 1 | NC | NC |
| 398 | 717 | TCTGCCTAACCTTCTCAAAC | 2 | 1 | NC | NC |
| 399 | 718 | CTCTGCCTAACCTTCTCAAA | 2 | 2 | NC | NC |
| 400 | 719 | TCTCTGCCTAACCTTCTCAA | 2 | NC | NC | NC |
| 401 | 720 | TTCTCTGCCTAACCTTCTCA | 2 | NC | NC | NC |
| 402 | 721 | ATTCTCTGCCTAACCTTCTC | 2 | NC | NC | NC |
| 403 | 722 | TATTCTCTGCCTAACCTTCT | 2 | NC | NC | NC |
| 404 | 723 | CTATTCTCTGCCTAACCTTC | 2 | NC | NC | NC |
| 405 | 724 | TCTATTCTCTGCCTAACCTT | 2 | NC | NC | NC |
| 406 | 725 | TTCTATTCTCTGCCTAACCT | 2 | NC | NC | NC |
| 407 | 726 | CTTCTATTCTCTGCCTAACC | 2 | NC | NC | NC |
| 408 | 727 | GCTTCTATTCTCTGCCTAAC | 1 | NC | NC | NC |
| 409 | 728 | AGCTTCTATTCTCTGCCTAA | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 410 | 729 | GAGCTTCTATTCTCTGCCTA | 2 | NC | NC | NC |
| 411 | 730 | AGAGCTTCTATTCTCTGCCT | 1 | NC | NC | NC |
| 412 | 731 | GAGAGCTTCTATTCTCTGCC | 2 | NC | NC | NC |
| 413 | 736 | AGTGAGAGAGCTTCTATTCT | 2 | NC | NC | NC |
| 414 | 737 | GAGTGAGAGAGCTTCTATTC | 2 | NC | NC | NC |
| 415 | 738 | TGAGTGAGAGAGCTTCTATT | 2 | NC | NC | NC |
| 416 | 739 | ATGAGTGAGAGAGCTTCTAT | 2 | NC | NC | NC |
| 417 | 740 | CATGAGTGAGAGAGCTTCTA | 2 | NC | NC | NC |
| 418 | 742 | TGCATGAGTGAGAGAGCTTC | 2 | NC | NC | NC |
| 419 | 743 | GTGCATGAGTGAGAGAGCTT | 1 | NC | NC | NC |
| 420 | 744 | GGTGCATGAGTGAGAGAGCT | 1 | NC | NC | NC |
| 421 | 746 | AGGGTGCATGAGTGAGAGAG | 2 | NC | NC | NC |
| 422 | 747 | AAGGGTGCATGAGTGAGAGA | 1 | NC | NC | NC |
| 423 | 748 | GAAGGGTGCATGAGTGAGAG | 1 | NC | NC | NC |
| 424 | 749 | GGAAGGGTGCATGAGTGAGA | 1 | NC | NC | NC |
| 425 | 750 | TGGAAGGGTGCATGAGTGAG | 2 | NC | NC | NC |
| 426 | 751 | ATGGAAGGGTGCATGAGTGA | 2 | NC | NC | NC |
| 427 | 752 | AATGGAAGGGTGCATGAGTG | 2 | NC | NC | NC |
| 428 | 753 | AAATGGAAGGGTGCATGAGT | 2 | NC | NC | NC |
| 429 | 754 | GAAATGGAAGGGTGCATGAG | 1 | NC | NC | NC |
| 430 | 755 | AGAAATGGAAGGGTGCATGA | 2 | NC | NC | NC |
| 431 | 756 | AAGAAATGGAAGGGTGCATG | 2 | NC | NC | NC |
| 432 | 757 | AAAGAAATGGAAGGGTGCAT | 2 | NC | NC | NC |
| 433 | 758 | GAAAGAAATGGAAGGGTGCA | 2 | NC | NC | NC |
| 434 | 759 | AGAAAGAAATGGAAGGGTGC | 2 | NC | NC | NC |
| 435 | 760 | GAGAAAGAAATGGAAGGGTG | 1 | NC | NC | NC |
| 436 | 761 | AGAGAAAGAAATGGAAGGGT | 1 | NC | NC | NC |
| 437 | 762 | AAGAGAAAGAAATGGAAGGG | 1 | NC | NC | NC |
| 438 | 763 | AAAGAGAAAGAAATGGAAGG | 0 | NC | NC | NC |
| 439 | 764 | CAAAGAGAAAGAAATGGAAG | 1 | NC | NC | NC |
| 440 | 765 | TCAAAGAGAAAGAAATGGAA | 1 | NC | NC | NC |
| 441 | 766 | CTCAAAGAGAAAGAAATGGA | 1 | NC | NC | NC |
| 442 | 767 | TCTCAAAGAGAAAGAAATGG | 2 | NC | NC | NC |
| 443 | 776 | AACATCATTTCTCAAAGAGA | 1 | 2 | NC | NC |
| 444 | 777 | AAACATCATTTCTCAAAGAG | 2 | 2 | NC | NC |
| 445 | 778 | GAAACATCATTTCTCAAAGA | 1 | 2 | NC | NC |
| 446 | 779 | AGAAACATCATTTCTCAAAG | 1 | 1 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 447 | 780 | CAGAAACATCATTTCTCAAA | 0 | 1 | NC | NC |
| 448 | 781 | CCAGAAACATCATTTCTCAA | 0 | 1 | NC | NC |
| 449 | 782 | ACCAGAAACATCATTTCTCA | 1 | 0 | NC | NC |
| 450 | 783 | AACCAGAAACATCATTTCTC | 1 | 1 | NC | NC |
| 451 | 785 | GGAACCAGAAACATCATTTC | 1 | 1 | NC | NC |
| 452 | 786 | TGGAACCAGAAACATCATTT | 1 | 1 | NC | NC |
| 453 | 787 | ATGGAACCAGAAACATCATT | 2 | 1 | NC | NC |
| 454 | 788 | CATGGAACCAGAAACATCAT | 2 | 2 | NC | NC |
| 455 | 789 | CCATGGAACCAGAAACATCA | 2 | 2 | NC | NC |
| 456 | 790 | ACCATGGAACCAGAAACATC | 2 | 2 | NC | NC |
| 457 | 791 | AACCATGGAACCAGAAACAT | 2 | 2 | NC | NC |
| 458 | 792 | GAACCATGGAACCAGAAACA | 1 | 2 | NC | NC |
| 459 | 793 | AGAACCATGGAACCAGAAAC | 2 | 2 | NC | NC |
| 460 | 794 | AAGAACCATGGAACCAGAAA | 2 | 1 | NC | NC |
| 461 | 795 | GAAGAACCATGGAACCAGAA | 2 | 2 | NC | NC |
| 462 | 796 | TGAAGAACCATGGAACCAGA | 1 | 1 | NC | NC |
| 463 | 797 | CTGAAGAACCATGGAACCAG | 2 | NC | NC | NC |
| 464 | 798 | GCTGAAGAACCATGGAACCA | 2 | NC | NC | NC |
| 465 | 799 | AGCTGAAGAACCATGGAACC | 2 | NC | NC | NC |
| 466 | 800 | GAGCTGAAGAACCATGGAAC | 2 | NC | NC | NC |
| 467 | 801 | GGAGCTGAAGAACCATGGAA | 2 | NC | NC | NC |
| 468 | 802 | GGGAGCTGAAGAACCATGGA | 2 | NC | NC | NC |
| 469 | 803 | AGGGAGCTGAAGAACCATGG | 2 | NC | NC | NC |
| 470 | 804 | TAGGGAGCTGAAGAACCATG | 2 | NC | NC | NC |
| 471 | 805 | TTAGGGAGCTGAAGAACCAT | 2 | NC | NC | NC |
| 472 | 806 | TTTAGGGAGCTGAAGAACCA | 2 | NC | NC | NC |
| 473 | 807 | TTTTAGGGAGCTGAAGAACC | 2 | NC | NC | NC |
| 474 | 808 | GTTTTAGGGAGCTGAAGAAC | 2 | NC | NC | NC |
| 475 | 809 | GGTTTTAGGGAGCTGAAGAA | 2 | NC | NC | NC |
| 476 | 810 | TGGTTTTAGGGAGCTGAAGA | 2 | NC | NC | NC |
| 477 | 811 | TTGGTTTTAGGGAGCTGAAG | 2 | NC | NC | NC |
| 478 | 812 | TTTGGTTTTAGGGAGCTGAA | 2 | NC | NC | NC |
| 479 | 813 | CTTTGGTTTTAGGGAGCTGA | 2 | NC | NC | NC |
| 480 | 814 | TCTTTGGTTTTAGGGAGCTG | 1 | NC | NC | NC |
| 481 | 815 | GTCTTTGGTTTTAGGGAGCT | 2 | NC | NC | NC |
| 482 | 816 | CGTCTTTGGTTTTAGGGAGC | 2 | NC | NC | NC |
| 483 | 817 | ACGTCTTTGGTTTTAGGGAG | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 484 | 818 | TACGTCTTTGGTTTTAGGGA | 2 | 2 | NC | NC |
| 485 | 819 | ATACGTCTTTGGTTTTAGGG | 2 | 2 | NC | NC |
| 486 | 820 | CATACGTCTTTGGTTTTAGG | 2 | 2 | NC | NC |
| 487 | 821 | ACATACGTCTTTGGTTTTAG | 2 | 2 | NC | NC |
| 488 | 822 | AACATACGTCTTTGGTTTTA | 2 | 2 | NC | NC |
| 489 | 823 | GAACATACGTCTTTGGTTTT | 2 | 2 | NC | NC |
| 490 | 824 | GGAACATACGTCTTTGGTTT | 3 | 3 | NC | NC |
| 491 | 825 | GGGAACATACGTCTTTGGTT | 2 | 3 | NC | NC |
| 492 | 826 | CGGGAACATACGTCTTTGGT | 3 | 3 | NC | NC |
| 493 | 827 | TCGGGAACATACGTCTTTGG | 3 | 3 | NC | NC |
| 494 | 828 | ATCGGGAACATACGTCTTTG | 3 | 2 | NC | NC |
| 495 | 829 | AATCGGGAACATACGTCTTT | 2 | 2 | NC | NC |
| 496 | 830 | AAATCGGGAACATACGTCTT | 2 | 2 | NC | NC |
| 497 | 831 | AAAATCGGGAACATACGTCT | 3 | 2 | NC | NC |
| 498 | 832 | CAAAATCGGGAACATACGTC | 3 | 3 | NC | NC |
| 499 | 833 | ACAAAATCGGGAACATACGT | 3 | 3 | NC | NC |
| 500 | 834 | GACAAAATCGGGAACATACG | 3 | 3 | NC | NC |
| 501 | 835 | TGACAAAATCGGGAACATAC | 2 | 2 | NC | NC |
| 502 | 836 | TTGACAAAATCGGGAACATA | 2 | 2 | NC | NC |
| 503 | 837 | TTTGACAAAATCGGGAACAT | 2 | 2 | NC | NC |
| 504 | 838 | ATTTGACAAAATCGGGAACA | 2 | 2 | NC | NC |
| 505 | 839 | AATTTGACAAAATCGGGAAC | 2 | 2 | NC | NC |
| 506 | 840 | AAATTTGACAAAATCGGGAA | 2 | 2 | NC | NC |
| 507 | 841 | TAAATTTGACAAAATCGGGA | 2 | 2 | NC | NC |
| 508 | 842 | ATAAATTTGACAAAATCGGG | 2 | 2 | NC | NC |
| 509 | 843 | CATAAATTTGACAAAATCGG | 2 | 2 | NC | NC |
| 510 | 844 | CCATAAATTTGACAAAATCG | 2 | 2 | NC | NC |
| 511 | 845 | TCCATAAATTTGACAAAATC | 2 | 1 | NC | NC |
| 512 | 848 | CAATCCATAAATTTGACAAA | 1 | 2 | NC | NC |
| 513 | 849 | CCAATCCATAAATTTGACAA | 2 | 2 | NC | NC |
| 514 | 850 | CCCAATCCATAAATTTGACA | 2 | 2 | NC | NC |
| 515 | 851 | TCCCAATCCATAAATTTGAC | 2 | 2 | NC | NC |
| 516 | 852 | TTCCCAATCCATAAATTTGA | 2 | 1 | NC | NC |
| 517 | 853 | TTTCCCAATCCATAAATTTG | 2 | 1 | NC | NC |
| 518 | 854 | CTTTCCCAATCCATAAATTT | 1 | 1 | NC | NC |
| 519 | 855 | ACTTTCCCAATCCATAAATT | 1 | 2 | NC | NC |
| 520 | 856 | GACTTTCCCAATCCATAAAT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 521 | 857 | GGACTTTCCCAATCCATAAA | 2 | 2 | NC | NC |
| 522 | 868 | CTTAGCTTTTGGGACTTTCC | 2 | NC | NC | NC |
| 523 | 869 | TCTTAGCTTTTGGGACTTTC | 2 | NC | NC | NC |
| 524 | 870 | CTCTTAGCTTTTGGGACTTT | 2 | NC | NC | NC |
| 525 | 871 | TCTCTTAGCTTTTGGGACTT | 2 | NC | NC | NC |
| 526 | 872 | TTCTCTTAGCTTTTGGGACT | 2 | NC | NC | NC |
| 527 | 873 | TTTCTCTTAGCTTTTGGGAC | 2 | NC | NC | NC |
| 528 | 874 | ATTTCTCTTAGCTTTTGGGA | 2 | NC | NC | NC |
| 529 | 875 | TATTTCTCTTAGCTTTTGGG | 2 | NC | NC | NC |
| 530 | 876 | TTATTTCTCTTAGCTTTTGG | 2 | NC | NC | NC |
| 531 | 877 | CTTATTTCTCTTAGCTTTTG | 2 | NC | NC | NC |
| 532 | 878 | ACTTATTTCTCTTAGCTTTT | 2 | NC | NC | NC |
| 533 | 879 | AACTTATTTCTCTTAGCTTT | 1 | NC | NC | NC |
| 534 | 880 | AAACTTATTTCTCTTAGCTT | 1 | NC | NC | NC |
| 535 | 881 | AAAACTTATTTCTCTTAGCT | 2 | NC | NC | NC |
| 536 | 882 | TAAAACTTATTTCTCTTAGC | 2 | NC | NC | NC |
| 537 | 900 | GCTCAAACTCTTTATATTTA | 2 | NC | NC | NC |
| 538 | 901 | AGCTCAAACTCTTTATATTT | 1 | NC | NC | NC |
| 539 | 902 | AAGCTCAAACTCTTTATATT | 2 | NC | NC | NC |
| 540 | 903 | TAAGCTCAAACTCTTTATAT | 1 | NC | NC | NC |
| 541 | 904 | CTAAGCTCAAACTCTTTATA | 1 | NC | NC | NC |
| 542 | 905 | ACTAAGCTCAAACTCTTTAT | 2 | NC | NC | NC |
| 543 | 906 | CACTAAGCTCAAACTCTTTA | 2 | NC | NC | NC |
| 544 | 907 | CCACTAAGCTCAAACTCTTT | 2 | NC | NC | NC |
| 545 | 908 | GCCACTAAGCTCAAACTCTT | 2 | NC | NC | NC |
| 546 | 909 | AGCCACTAAGCTCAAACTCT | 2 | NC | NC | NC |
| 547 | 936 | TGTTGTAATGTGCTTCAGAG | 2 | NC | NC | NC |
| 548 | 937 | TTGTTGTAATGTGCTTCAGA | 2 | NC | NC | NC |
| 549 | 938 | CTTGTTGTAATGTGCTTCAG | 2 | NC | NC | NC |
| 550 | 939 | TCTTGTTGTAATGTGCTTCA | 2 | NC | NC | NC |
| 551 | 940 | TTCTTGTTGTAATGTGCTTC | 2 | NC | NC | NC |
| 552 | 941 | ATTCTTGTTGTAATGTGCTT | 2 | NC | NC | NC |
| 553 | 942 | TATTCTTGTTGTAATGTGCT | 2 | NC | NC | NC |
| 554 | 943 | ATATTCTTGTTGTAATGTGC | 1 | NC | NC | NC |
| 555 | 944 | CATATTCTTGTTGTAATGTG | 1 | NC | NC | NC |
| 556 | 945 | GCATATTCTTGTTGTAATGT | 1 | NC | NC | NC |
| 557 | 946 | TGCATATTCTTGTTGTAATG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 558 | 947 | CTGCATATTCTTGTTGTAAT | 2 | NC | NC | NC |
| 559 | 948 | ACTGCATATTCTTGTTGTAA | 2 | NC | NC | NC |
| 560 | 949 | AACTGCATATTCTTGTTGTA | 2 | NC | NC | NC |
| 561 | 950 | AAACTGCATATTCTTGTTGT | 2 | NC | NC | NC |
| 562 | 951 | AAAACTGCATATTCTTGTTG | 2 | NC | NC | NC |
| 563 | 952 | AAAAACTGCATATTCTTGTT | 2 | NC | NC | NC |
| 564 | 953 | CAAAAACTGCATATTCTTGT | 1 | NC | NC | NC |
| 565 | 954 | ACAAAAACTGCATATTCTTG | 2 | NC | NC | NC |
| 566 | 955 | AACAAAAACTGCATATTCTT | 1 | 2 | 1 | 2 |
| 567 | 956 | AAACAAAAACTGCATATTCT | 1 | 1 | 1 | 2 |
| 568 | 957 | CAAACAAAAACTGCATATTC | 2 | 2 | 2 | 1 |
| 569 | 958 | ACAAACAAAAACTGCATATT | 1 | 1 | 1 | 2 |
| 570 | 959 | CACAAACAAAAACTGCATAT | 1 | 1 | 2 | 2 |
| 571 | 960 | TCACAAACAAAAACTGCATA | 0 | 1 | 2 | 2 |
| 572 | 961 | TTCACAAACAAAAACTGCAT | 0 | 2 | 2 | 2 |
| 573 | 962 | GTTCACAAACAAAAACTGCA | 1 | 2 | 1 | 2 |
| 574 | 974 | AACTAGTCTTTTGTTCACAA | 1 | NC | NC | NC |
| 575 | 975 | AAACTAGTCTTTTGTTCACA | 1 | NC | NC | NC |
| 576 | 976 | AAAACTAGTCTTTTGTTCAC | 1 | NC | NC | NC |
| 577 | 977 | TAAAACTAGTCTTTTGTTCA | 1 | NC | NC | NC |
| 578 | 978 | TTAAAACTAGTCTTTTGTTC | 1 | NC | NC | NC |
| 579 | 979 | CTTAAAACTAGTCTTTTGTT | 1 | NC | NC | NC |
| 580 | 980 | CCTTAAAACTAGTCTTTTGT | 2 | NC | NC | NC |
| 581 | 981 | TCCTTAAAACTAGTCTTTTG | 2 | NC | NC | NC |
| 582 | 982 | GTCCTTAAAACTAGTCTTTT | 2 | NC | NC | NC |
| 583 | 983 | TGTCCTTAAAACTAGTCTTT | 2 | NC | NC | NC |
| 584 | 984 | TTGTCCTTAAAACTAGTCTT | 2 | NC | NC | NC |
| 585 | 985 | TTTGTCCTTAAAACTAGTCT | 1 | NC | NC | NC |
| 586 | 986 | CTTTGTCCTTAAAACTAGTC | 2 | NC | NC | NC |
| 587 | 987 | GCTTTGTCCTTAAAACTAGT | 1 | NC | NC | NC |
| 588 | 988 | AGCTTTGTCCTTAAAACTAG | 2 | NC | NC | NC |
| 589 | 989 | TAGCTTTGTCCTTAAAACTA | 2 | NC | NC | NC |
| 590 | 990 | GTAGCTTTGTCCTTAAAACT | 2 | NC | NC | NC |
| 591 | 991 | TGTAGCTTTGTCCTTAAAAC | 2 | 2 | NC | NC |
| 592 | 992 | ATGTAGCTTTGTCCTTAAAA | 1 | 2 | NC | NC |
| 593 | 993 | TATGTAGCTTTGTCCTTAAA | 2 | 2 | NC | NC |
| 594 | 994 | TTATGTAGCTTTGTCCTTAA | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 595 | 995 | TTTATGTAGCTTTGTCCTTA | 1 | 2 | NC | NC |
| 596 | 996 | GTTTATGTAGCTTTGTCCTT | 2 | 2 | NC | NC |
| 597 | 997 | AGTTTATGTAGCTTTGTCCT | 3 | 2 | NC | NC |
| 598 | 998 | GAGTTTATGTAGCTTTGTCC | 2 | 2 | NC | NC |
| 599 | 999 | TGAGTTTATGTAGCTTTGTC | 2 | 2 | NC | NC |
| 600 | 1000 | ATGAGTTTATGTAGCTTTGT | 2 | 1 | NC | NC |
| 601 | 1001 | AATGAGTTTATGTAGCTTTG | 1 | 1 | NC | NC |
| 602 | 1002 | CAATGAGTTTATGTAGCTTT | 2 | 2 | NC | NC |
| 603 | 1003 | TCAATGAGTTTATGTAGCTT | 1 | 1 | NC | NC |
| 604 | 1004 | GTCAATGAGTTTATGTAGCT | 2 | 2 | NC | NC |
| 605 | 1005 | AGTCAATGAGTTTATGTAGC | 2 | 2 | NC | NC |
| 606 | 1006 | AAGTCAATGAGTTTATGTAG | 2 | 2 | NC | NC |
| 607 | 1007 | AAAGTCAATGAGTTTATGTA | 2 | 2 | NC | NC |
| 608 | 1008 | AAAAGTCAATGAGTTTATGT | 2 | 2 | NC | NC |
| 609 | 1009 | AAAAAGTCAATGAGTTTATG | 1 | 2 | NC | NC |
| 610 | 1015 | CTTAATAAAAAGTCAATGAG | 2 | 1 | NC | NC |
| 611 | 1016 | CCTTAATAAAAAGTCAATGA | 1 | 2 | NC | NC |
| 612 | 1017 | TCCTTAATAAAAAGTCAATG | 2 | 2 | NC | NC |
| 613 | 1020 | CTTTCCTTAATAAAAAGTCA | 1 | 2 | NC | NC |
| 614 | 1021 | TCTTTCCTTAATAAAAAGTC | 0 | 2 | NC | NC |
| 615 | 1033 | CATATAATACTTTCTTTCCT | 1 | NC | NC | NC |
| 616 | 1034 | GCATATAATACTTTCTTTCC | 1 | NC | NC | NC |
| 617 | 1035 | TGCATATAATACTTTCTTTC | 2 | NC | NC | NC |
| 618 | 1037 | CTTGCATATAATACTTTCTT | 2 | NC | NC | NC |
| 619 | 1038 | GCTTGCATATAATACTTTCT | 2 | NC | NC | NC |
| 620 | 1039 | GGCTTGCATATAATACTTTC | 3 | NC | NC | NC |
| 621 | 1040 | TGGCTTGCATATAATACTTT | 3 | NC | NC | NC |
| 622 | 1041 | TTGGCTTGCATATAATACTT | 2 | NC | NC | NC |
| 623 | 1042 | TTTGGCTTGCATATAATACT | 1 | 1 | NC | NC |
| 624 | 1043 | CTTTGGCTTGCATATAATAC | 2 | 2 | NC | NC |
| 625 | 1044 | TCTTTGGCTTGCATATAATA | 2 | 2 | NC | NC |
| 626 | 1045 | TTCTTTGGCTTGCATATAAT | 1 | 2 | NC | NC |
| 627 | 1046 | ATTCTTTGGCTTGCATATAA | 1 | NC | NC | NC |
| 628 | 1047 | CATTCTTTGGCTTGCATATA | 2 | NC | NC | NC |
| 629 | 1048 | CCATTCTTTGGCTTGCATAT | 1 | NC | NC | NC |
| 630 | 1067 | CATTTGCCTACTGGTGGGAC | 2 | NC | NC | NC |
| 631 | 1068 | TCATTTGCCTACTGGTGGGA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 632 | 1069 | TTCATTTGCCTACTGGTGGG | 2 | NC | NC | NC |
| 633 | 1070 | ATTCATTTGCCTACTGGTGG | 1 | NC | NC | NC |
| 634 | 1071 | AATTCATTTGCCTACTGGTG | 2 | NC | NC | NC |
| 635 | 1072 | GAATTCATTTGCCTACTGGT | 2 | NC | NC | NC |
| 636 | 1073 | TGAATTCATTTGCCTACTGG | 2 | NC | NC | NC |
| 637 | 1074 | TTGAATTCATTTGCCTACTG | 1 | NC | NC | NC |
| 638 | 1075 | CTTGAATTCATTTGCCTACT | 1 | NC | NC | NC |
| 639 | 1076 | ACTTGAATTCATTTGCCTAC | 2 | NC | NC | NC |
| 640 | 1077 | GACTTGAATTCATTTGCCTA | 1 | NC | NC | NC |
| 641 | 1078 | AGACTTGAATTCATTTGCCT | 2 | NC | NC | NC |
| 642 | 1079 | AAGACTTGAATTCATTTGCC | 1 | NC | NC | NC |
| 643 | 1080 | GAAGACTTGAATTCATTTGC | 2 | NC | NC | NC |
| 644 | 1081 | CGAAGACTTGAATTCATTTG | 2 | NC | NC | NC |
| 645 | 1082 | CCGAAGACTTGAATTCATTT | 2 | NC | NC | NC |
| 646 | 1083 | GCCGAAGACTTGAATTCATT | 3 | NC | NC | NC |
| 647 | 1084 | TGCCGAAGACTTGAATTCAT | 2 | NC | NC | NC |
| 648 | 1085 | GTGCCGAAGACTTGAATTCA | 2 | NC | NC | NC |
| 649 | 1086 | GGTGCCGAAGACTTGAATTC | 2 | NC | NC | NC |
| 650 | 1113 | ATATGCCATAGAGTTCTGGG | 2 | 2 | NC | NC |
| 651 | 1114 | TATATGCCATAGAGTTCTGG | 2 | 2 | NC | NC |
| 652 | 1115 | ATATATGCCATAGAGTTCTG | 2 | 2 | NC | NC |
| 653 | 1116 | CATATATGCCATAGAGTTCT | 2 | 2 | NC | NC |
| 654 | 1117 | ACATATATGCCATAGAGTTC | 2 | 2 | NC | NC |
| 655 | 1118 | TACATATATGCCATAGAGTT | 2 | 2 | NC | NC |
| 656 | 1119 | TTACATATATGCCATAGAGT | 1 | 2 | NC | NC |
| 657 | 1120 | ATTACATATATGCCATAGAG | 2 | 2 | NC | NC |
| 658 | 1121 | AATTACATATATGCCATAGA | 1 | 2 | NC | NC |
| 659 | 1122 | TAATTACATATATGCCATAG | 2 | 2 | NC | NC |
| 660 | 1125 | CATTAATTACATATATGCCA | 2 | 2 | NC | NC |
| 661 | 1126 | ACATTAATTACATATATGCC | 2 | 2 | NC | NC |
| 662 | 1127 | CACATTAATTACATATATGC | 2 | 1 | NC | NC |
| 663 | 1128 | GCACATTAATTACATATATG | 1 | 2 | NC | NC |
| 664 | 1130 | CTGCACATTAATTACATATA | 1 | 1 | NC | NC |
| 665 | 1131 | ACTGCACATTAATTACATAT | 1 | 2 | NC | NC |
| 666 | 1132 | CACTGCACATTAATTACATA | 2 | 2 | NC | NC |
| 667 | 1133 | GCACTGCACATTAATTACAT | 2 | 1 | NC | NC |
| 668 | 1134 | GGCACTGCACATTAATTACA | 1 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 669 | 1135 | TGGCACTGCACATTAATTAC | 2 | 2 | NC | NC |
| 670 | 1136 | TTGGCACTGCACATTAATTA | 2 | 2 | NC | NC |
| 671 | 1137 | ATTGGCACTGCACATTAATT | 2 | 2 | NC | NC |
| 672 | 1138 | AATTGGCACTGCACATTAAT | 2 | 2 | NC | NC |
| 673 | 1139 | GAATTGGCACTGCACATTAA | 2 | 2 | NC | NC |
| 674 | 1140 | AGAATTGGCACTGCACATTA | 2 | 2 | NC | NC |
| 675 | 1141 | CAGAATTGGCACTGCACATT | 2 | 2 | NC | NC |
| 676 | 1142 | ACAGAATTGGCACTGCACAT | 2 | 2 | NC | NC |
| 677 | 1143 | CACAGAATTGGCACTGCACA | 2 | 2 | NC | NC |
| 678 | 1144 | TCACAGAATTGGCACTGCAC | 1 | 2 | NC | NC |
| 679 | 1145 | CTCACAGAATTGGCACTGCA | 2 | 2 | NC | NC |
| 680 | 1146 | ACTCACAGAATTGGCACTGC | 2 | 2 | NC | NC |
| 681 | 1148 | ATACTCACAGAATTGGCACT | 2 | 2 | NC | NC |
| 682 | 1149 | CATACTCACAGAATTGGCAC | 2 | 2 | NC | NC |
| 683 | 1150 | TCATACTCACAGAATTGGCA | 2 | 2 | NC | NC |
| 684 | 1151 | ATCATACTCACAGAATTGGC | 2 | 3 | NC | NC |
| 685 | 1152 | CATCATACTCACAGAATTGG | 2 | 2 | NC | NC |
| 686 | 1153 | ACATCATACTCACAGAATTG | 2 | 2 | NC | NC |
| 687 | 1154 | CACATCATACTCACAGAATT | 1 | 2 | NC | NC |
| 688 | 1155 | ACACATCATACTCACAGAAT | 2 | 2 | NC | NC |
| 689 | 1156 | CACACATCATACTCACAGAA | 1 | 2 | NC | NC |
| 690 | 1157 | GCACACATCATACTCACAGA | 2 | 2 | NC | NC |
| 691 | 1158 | TGCACACATCATACTCACAG | 2 | 1 | NC | NC |
| 692 | 1159 | ATGCACACATCATACTCACA | 1 | 2 | NC | NC |
| 693 | 1160 | CATGCACACATCATACTCAC | 2 | 2 | NC | NC |
| 694 | 1161 | CCATGCACACATCATACTCA | 2 | 2 | NC | NC |
| 695 | 1162 | TCCATGCACACATCATACTC | 1 | 2 | NC | NC |
| 696 | 1163 | CTCCATGCACACATCATACT | 1 | 1 | NC | NC |
| 697 | 1176 | GAGTTTTGGCTGGCTCCATG | 2 | 2 | NC | NC |
| 698 | 1177 | AGAGTTTTGGCTGGCTCCAT | 2 | 2 | NC | NC |
| 699 | 1178 | CAGAGTTTTGGCTGGCTCCA | 2 | 2 | NC | NC |
| 700 | 1179 | TCAGAGTTTTGGCTGGCTCC | 2 | 2 | NC | NC |
| 701 | 1180 | ATCAGAGTTTTGGCTGGCTC | 2 | 2 | 2 | 2 |
| 702 | 1181 | AATCAGAGTTTTGGCTGGCT | 2 | 2 | 2 | 2 |
| 703 | 1182 | CAATCAGAGTTTTGGCTGGC | 2 | 2 | 2 | 2 |
| 704 | 1183 | TCAATCAGAGTTTTGGCTGG | 2 | 2 | 2 | 2 |
| 705 | 1184 | TTCAATCAGAGTTTTGGCTG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 706 | 1185 | ATTCAATCAGAGTTTTGGCT | 2 | NC | NC | NC |
| 707 | 1186 | AATTCAATCAGAGTTTTGGC | 2 | NC | NC | NC |
| 708 | 1187 | AAATTCAATCAGAGTTTTGG | 2 | NC | NC | NC |
| 709 | 1188 | GAAATTCAATCAGAGTTTTG | 2 | NC | NC | NC |
| 710 | 1189 | TGAAATTCAATCAGAGTTTT | 1 | NC | NC | NC |
| 711 | 1196 | CCAGTTCTGAAATTCAATCA | 1 | NC | NC | NC |
| 712 | 1197 | CCCAGTTCTGAAATTCAATC | 2 | NC | NC | NC |
| 713 | 1198 | TCCCAGTTCTGAAATTCAAT | 2 | NC | NC | NC |
| 714 | 1199 | GTCCCAGTTCTGAAATTCAA | 2 | NC | NC | NC |
| 715 | 1200 | TGTCCCAGTTCTGAAATTCA | 2 | NC | NC | NC |
| 716 | 1201 | GTGTCCCAGTTCTGAAATTC | 1 | NC | NC | NC |
| 717 | 1202 | AGTGTCCCAGTTCTGAAATT | 1 | NC | NC | NC |
| 718 | 1203 | GAGTGTCCCAGTTCTGAAAT | 2 | NC | NC | NC |
| 719 | 1204 | AGAGTGTCCCAGTTCTGAAA | 2 | 2 | NC | NC |
| 720 | 1205 | GAGAGTGTCCCAGTTCTGAA | 2 | 2 | NC | NC |
| 721 | 1206 | AGAGAGTGTCCCAGTTCTGA | 2 | 2 | NC | NC |
| 722 | 1207 | AAGAGAGTGTCCCAGTTCTG | 2 | 2 | NC | NC |
| 723 | 1208 | CAAGAGAGTGTCCCAGTTCT | 1 | 2 | NC | NC |
| 724 | 1209 | ACAAGAGAGTGTCCCAGTTC | 2 | 2 | NC | NC |
| 725 | 1210 | AACAAGAGAGTGTCCCAGTT | 1 | 2 | NC | NC |
| 726 | 1211 | AAACAAGAGAGTGTCCCAGT | 2 | 2 | NC | NC |
| 727 | 1212 | AAAACAAGAGAGTGTCCCAG | 2 | 1 | NC | NC |
| 728 | 1213 | CAAAACAAGAGAGTGTCCCA | 2 | 1 | NC | NC |
| 729 | 1214 | GCAAAACAAGAGAGTGTCCC | 2 | NC | NC | NC |
| 730 | 1215 | TGCAAAACAAGAGAGTGTCC | 2 | NC | NC | NC |
| 731 | 1216 | ATGCAAAACAAGAGAGTGTC | 1 | NC | NC | NC |
| 732 | 1217 | AATGCAAAACAAGAGAGTGT | 2 | NC | NC | NC |
| 733 | 1218 | GAATGCAAAACAAGAGAGTG | 1 | NC | NC | NC |
| 734 | 1219 | TGAATGCAAAACAAGAGAGT | 1 | NC | NC | NC |
| 735 | 1220 | CTGAATGCAAAACAAGAGAG | 1 | NC | NC | NC |
| 736 | 1221 | CCTGAATGCAAAACAAGAGA | 2 | NC | NC | NC |
| 737 | 1222 | TCCTGAATGCAAAACAAGAG | 2 | NC | NC | NC |
| 738 | 1223 | TTCCTGAATGCAAAACAAGA | 1 | NC | NC | NC |
| 739 | 1224 | CTTCCTGAATGCAAAACAAG | 1 | NC | NC | NC |
| 740 | 1225 | CCTTCCTGAATGCAAAACAA | 2 | NC | NC | NC |
| 741 | 1226 | TCCTTCCTGAATGCAAAACA | 1 | NC | NC | NC |
| 742 | 1227 | CTCCTTCCTGAATGCAAAAC | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 743 | 1228 | ACTCCTTCCTGAATGCAAAA | 2 | NC | NC | NC |
| 744 | 1229 | CACTCCTTCCTGAATGCAAA | 2 | NC | NC | NC |
| 745 | 1230 | TCACTCCTTCCTGAATGCAA | 1 | NC | NC | NC |
| 746 | 1231 | TTCACTCCTTCCTGAATGCA | 1 | NC | NC | NC |
| 747 | 1232 | TTTCACTCCTTCCTGAATGC | 1 | NC | NC | NC |
| 748 | 1233 | TTTTCACTCCTTCCTGAATG | 2 | NC | NC | NC |
| 749 | 1234 | ATTTTCACTCCTTCCTGAAT | 2 | 1 | NC | NC |
| 750 | 1235 | CATTTTCACTCCTTCCTGAA | 2 | 2 | NC | NC |
| 751 | 1236 | ACATTTTCACTCCTTCCTGA | 2 | 2 | NC | NC |
| 752 | 1237 | AACATTTTCACTCCTTCCTG | 2 | 2 | NC | NC |
| 753 | 1238 | AAACATTTTCACTCCTTCCT | 2 | 2 | NC | NC |
| 754 | 1239 | AAAACATTTTCACTCCTTCC | 1 | 1 | NC | NC |
| 755 | 1240 | AAAAACATTTTCACTCCTTC | 2 | 1 | NC | NC |
| 756 | 1241 | TAAAAACATTTTCACTCCTT | 1 | 0 | NC | NC |
| 757 | 1242 | TTAAAAACATTTTCACTCCT | 2 | 1 | NC | NC |
| 758 | 1243 | TTTAAAAACATTTTCACTCC | 2 | 2 | NC | NC |
| 759 | 1244 | CTTTAAAAACATTTTCACTC | 1 | 1 | NC | NC |
| 760 | 1245 | GCTTTAAAAACATTTTCACT | 1 | 1 | NC | NC |
| 761 | 1246 | TGCTTTAAAAACATTTTCAC | 0 | 1 | NC | NC |
| 762 | 1248 | CTTGCTTTAAAAACATTTTC | 1 | 1 | NC | NC |
| 763 | 1262 | CACAAATAATTTTTCTTGCT | 0 | 1 | NC | NC |
| 764 | 1263 | CCACAAATAATTTTTCTTGC | 1 | 2 | NC | NC |
| 765 | 1264 | TCCACAAATAATTTTTCTTG | 1 | 2 | NC | NC |
| 766 | 1272 | CTGATAATTCCACAAATAAT | 2 | 2 | NC | NC |
| 767 | 1273 | CCTGATAATTCCACAAATAA | 2 | 2 | NC | NC |
| 768 | 1274 | ACCTGATAATTCCACAAATA | 2 | 2 | NC | NC |
| 769 | 1275 | CACCTGATAATTCCACAAAT | 2 | 2 | NC | NC |
| 770 | 1276 | TCACCTGATAATTCCACAAA | 2 | 2 | NC | NC |
| 771 | 1277 | CTCACCTGATAATTCCACAA | 2 | 1 | NC | NC |
| 772 | 1278 | CCTCACCTGATAATTCCACA | 2 | 2 | NC | NC |
| 773 | 1279 | TCCTCACCTGATAATTCCAC | 2 | 2 | NC | NC |
| 774 | 1280 | ATCCTCACCTGATAATTCCA | 2 | 2 | NC | NC |
| 775 | 1281 | TATCCTCACCTGATAATTCC | 2 | 2 | NC | NC |
| 776 | 1282 | ATATCCTCACCTGATAATTC | 2 | 2 | NC | NC |
| 777 | 1283 | AATATCCTCACCTGATAATT | 2 | 2 | NC | NC |
| 778 | 1284 | TAATATCCTCACCTGATAAT | 2 | 2 | NC | NC |
| 779 | 1285 | TTAATATCCTCACCTGATAA | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 780 | 1286 | CTTAATATCCTCACCTGATA | 2 | 2 | NC | NC |
| 781 | 1287 | CCTTAATATCCTCACCTGAT | 2 | 2 | NC | NC |
| 782 | 1288 | TCCTTAATATCCTCACCTGA | 2 | 2 | NC | NC |
| 783 | 1289 | TTCCTTAATATCCTCACCTG | 2 | 2 | NC | NC |
| 784 | 1290 | ATTCCTTAATATCCTCACCT | 2 | 2 | NC | NC |
| 785 | 1291 | AATTCCTTAATATCCTCACC | 1 | 1 | NC | NC |
| 786 | 1292 | AAATTCCTTAATATCCTCAC | 2 | 2 | NC | NC |
| 787 | 1293 | TAAATTCCTTAATATCCTCA | 2 | 2 | NC | NC |
| 788 | 1294 | CTAAATTCCTTAATATCCTC | 2 | 2 | NC | NC |
| 789 | 1295 | ACTAAATTCCTTAATATCCT | 2 | 2 | NC | NC |
| 790 | 1296 | CACTAAATTCCTTAATATCC | 2 | 2 | NC | NC |
| 791 | 1297 | TCACTAAATTCCTTAATATC | 1 | 1 | NC | NC |
| 792 | 1299 | CTTCACTAAATTCCTTAATA | 1 | 1 | NC | NC |
| 793 | 1300 | TCTTCACTAAATTCCTTAAT | 2 | 1 | NC | NC |
| 794 | 1301 | ATCTTCACTAAATTCCTTAA | 2 | 2 | NC | NC |
| 795 | 1302 | TATCTTCACTAAATTCCTTA | 2 | 2 | NC | NC |
| 796 | 1303 | TTATCTTCACTAAATTCCTT | 1 | 1 | NC | NC |
| 797 | 1304 | ATTATCTTCACTAAATTCCT | 2 | 2 | NC | NC |
| 798 | 1305 | CATTATCTTCACTAAATTCC | 2 | 2 | NC | NC |
| 799 | 1306 | CCATTATCTTCACTAAATTC | 2 | 2 | NC | NC |
| 800 | 1307 | ACCATTATCTTCACTAAATT | 2 | 2 | NC | NC |
| 801 | 1308 | AACCATTATCTTCACTAAAT | 2 | 2 | NC | NC |
| 802 | 1309 | AAACCATTATCTTCACTAAA | 1 | 2 | NC | NC |
| 803 | 1310 | AAAACCATTATCTTCACTAA | 2 | 2 | NC | NC |
| 804 | 1311 | TAAAACCATTATCTTCACTA | 1 | 1 | NC | NC |
| 805 | 1312 | CTAAAACCATTATCTTCACT | 1 | NC | NC | NC |
| 806 | 1313 | ACTAAAACCATTATCTTCAC | 2 | NC | NC | NC |
| 807 | 1314 | AACTAAAACCATTATCTTCA | 2 | NC | NC | NC |
| 808 | 1315 | AAACTAAAACCATTATCTTC | 2 | NC | NC | NC |
| 809 | 1323 | CATCAAATAAACTAAAACCA | 2 | NC | NC | NC |
| 810 | 1324 | GCATCAAATAAACTAAAACC | 2 | NC | NC | NC |
| 811 | 1325 | AGCATCAAATAAACTAAAAC | 2 | NC | NC | NC |
| 812 | 1327 | GTAGCATCAAATAAACTAAA | 2 | NC | NC | NC |
| 813 | 1328 | AGTAGCATCAAATAAACTAA | 2 | NC | NC | NC |
| 814 | 1329 | GAGTAGCATCAAATAAACTA | 2 | NC | NC | NC |
| 815 | 1330 | AGAGTAGCATCAAATAAACT | 2 | NC | NC | NC |
| 816 | 1331 | AAGAGTAGCATCAAATAAAC | 1 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 817 | 1332 | GAAGAGTAGCATCAAATAAA | 1 | 2 | NC | NC |
| 818 | 1333 | TGAAGAGTAGCATCAAATAA | 2 | 2 | NC | NC |
| 819 | 1334 | CTGAAGAGTAGCATCAAATA | 2 | 2 | NC | NC |
| 820 | 1335 | TCTGAAGAGTAGCATCAAAT | 2 | 1 | NC | NC |
| 821 | 1336 | TTCTGAAGAGTAGCATCAAA | 2 | 2 | NC | NC |
| 822 | 1337 | CTTCTGAAGAGTAGCATCAA | 2 | 2 | NC | NC |
| 823 | 1342 | ACACGCTTCTGAAGAGTAGC | 2 | 2 | NC | NC |
| 824 | 1343 | CACACGCTTCTGAAGAGTAG | 2 | 2 | NC | NC |
| 825 | 1344 | TCACACGCTTCTGAAGAGTA | 2 | 2 | NC | NC |
| 826 | 1346 | AGTCACACGCTTCTGAAGAG | 3 | 2 | NC | NC |
| 827 | 1347 | AAGTCACACGCTTCTGAAGA | 2 | 2 | NC | NC |
| 828 | 1354 | TCATCGGAAGTCACACGCTT | 2 | 3 | NC | NC |
| 829 | 1355 | CTCATCGGAAGTCACACGCT | 2 | 2 | NC | NC |
| 830 | 1356 | TCTCATCGGAAGTCACACGC | 2 | 2 | NC | NC |
| 831 | 1357 | CTCTCATCGGAAGTCACACG | 2 | 2 | NC | NC |
| 832 | 1358 | CCTCTCATCGGAAGTCACAC | 2 | 2 | NC | NC |
| 833 | 1359 | TCCTCTCATCGGAAGTCACA | 2 | 2 | NC | NC |
| 834 | 1360 | CTCCTCTCATCGGAAGTCAC | 2 | 2 | NC | NC |
| 835 | 1361 | GCTCCTCTCATCGGAAGTCA | 3 | NC | NC | NC |
| 836 | 1362 | TGCTCCTCTCATCGGAAGTC | 2 | NC | NC | NC |
| 837 | 1363 | TTGCTCCTCTCATCGGAAGT | 3 | NC | NC | NC |
| 838 | 1364 | ATTGCTCCTCTCATCGGAAG | 2 | NC | NC | NC |
| 839 | 1365 | AATTGCTCCTCTCATCGGAA | 3 | NC | NC | NC |
| 840 | 1366 | AAATTGCTCCTCTCATCGGA | 3 | NC | NC | NC |
| 841 | 1367 | GAAATTGCTCCTCTCATCGG | 2 | NC | NC | NC |
| 842 | 1368 | GGAAATTGCTCCTCTCATCG | 2 | NC | NC | NC |
| 843 | 1369 | TGGAAATTGCTCCTCTCATC | 2 | NC | NC | NC |
| 844 | 1370 | CTGGAAATTGCTCCTCTCAT | 2 | NC | NC | NC |
| 845 | 1371 | CCTGGAAATTGCTCCTCTCA | 1 | NC | NC | NC |
| 846 | 1372 | TCCTGGAAATTGCTCCTCTC | 1 | NC | NC | NC |
| 847 | 1373 | TTCCTGGAAATTGCTCCTCT | 2 | NC | NC | NC |
| 848 | 1374 | CTTCCTGGAAATTGCTCCTC | 1 | NC | NC | NC |
| 849 | 1375 | GCTTCCTGGAAATTGCTCCT | 2 | NC | NC | NC |
| 850 | 1376 | TGCTTCCTGGAAATTGCTCC | 2 | NC | NC | NC |
| 851 | 1377 | ATGCTTCCTGGAAATTGCTC | 2 | NC | NC | NC |
| 852 | 1378 | CATGCTTCCTGGAAATTGCT | 1 | NC | NC | NC |
| 853 | 1379 | ACATGCTTCCTGGAAATTGC | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 854 | 1380 | TACATGCTTCCTGGAAATTG | 1 | NC | NC | NC |
| 855 | 1381 | TTACATGCTTCCTGGAAATT | 2 | NC | NC | NC |
| 856 | 1382 | ATTACATGCTTCCTGGAAAT | 2 | NC | NC | NC |
| 857 | 1383 | TATTACATGCTTCCTGGAAA | 2 | 2 | NC | NC |
| 858 | 1384 | TTATTACATGCTTCCTGGAA | 2 | 2 | NC | NC |
| 859 | 1385 | ATTATTACATGCTTCCTGGA | 2 | 2 | NC | NC |
| 860 | 1386 | TATTATTACATGCTTCCTGG | 1 | 2 | NC | NC |
| 861 | 1387 | ATATTATTACATGCTTCCTG | 2 | 2 | NC | NC |
| 862 | 1388 | AATATTATTACATGCTTCCT | 2 | 2 | NC | NC |
| 863 | 1389 | AAATATTATTACATGCTTCC | 2 | 1 | NC | NC |
| 864 | 1403 | CTCATAGGAATCTAAAATAT | 2 | 2 | NC | NC |
| 865 | 1404 | TCTCATAGGAATCTAAAATA | 2 | 2 | NC | NC |
| 866 | 1405 | ATCTCATAGGAATCTAAAAT | 2 | 2 | NC | NC |
| 867 | 1406 | CATCTCATAGGAATCTAAAA | 2 | 2 | NC | NC |
| 868 | 1407 | ACATCTCATAGGAATCTAAA | 2 | 2 | NC | NC |
| 869 | 1408 | AACATCTCATAGGAATCTAA | 2 | 2 | NC | NC |
| 870 | 1409 | AAACATCTCATAGGAATCTA | 2 | 2 | NC | NC |
| 871 | 1410 | TAAACATCTCATAGGAATCT | 2 | 2 | NC | NC |
| 872 | 1411 | TTAAACATCTCATAGGAATC | 2 | 2 | NC | NC |
| 873 | 1412 | ATTAAACATCTCATAGGAAT | 2 | 2 | NC | NC |
| 874 | 1413 | AATTAAACATCTCATAGGAA | 1 | 1 | NC | NC |
| 875 | 1414 | AAATTAAACATCTCATAGGA | 1 | 2 | NC | NC |
| 876 | 1415 | CAAATTAAACATCTCATAGG | 2 | 2 | NC | NC |
| 877 | 1416 | GCAAATTAAACATCTCATAG | 1 | 2 | NC | NC |
| 878 | 1417 | TGCAAATTAAACATCTCATA | 1 | 1 | NC | NC |
| 879 | 1418 | CTGCAAATTAAACATCTCAT | 2 | NC | NC | NC |
| 880 | 1419 | ACTGCAAATTAAACATCTCA | 2 | NC | NC | NC |
| 881 | 1420 | GACTGCAAATTAAACATCTC | 2 | NC | NC | NC |
| 882 | 1421 | TGACTGCAAATTAAACATCT | 1 | NC | NC | NC |
| 883 | 1422 | TTGACTGCAAATTAAACATC | 2 | NC | NC | NC |
| 884 | 1423 | TTTGACTGCAAATTAAACAT | 2 | NC | NC | NC |
| 885 | 1436 | TCTTTTCACAGCTTTTGACT | 1 | NC | NC | NC |
| 886 | 1437 | TTCTTTTCACAGCTTTTGAC | 1 | NC | NC | NC |
| 887 | 1438 | TTTCTTTTCACAGCTTTTGA | 1 | NC | NC | NC |
| 888 | 1439 | TTTTCTTTTCACAGCTTTTG | 1 | NC | NC | NC |
| 889 | 1440 | TTTTTCTTTTCACAGCTTTT | 1 | NC | NC | NC |
| 890 | 1441 | GTTTTTCTTTTCACAGCTTT | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 891 | 1442 | AGTTTTTCTTTTCACAGCTT | 1 | NC | NC | NC |
| 892 | 1443 | TAGTTTTTCTTTTCACAGCT | 1 | NC | NC | NC |
| 893 | 1444 | GTAGTTTTTCTTTTCACAGC | 0 | NC | NC | NC |
| 894 | 1445 | AGTAGTTTTTCTTTTCACAG | 1 | NC | NC | NC |
| 895 | 1446 | CAGTAGTTTTTCTTTTCACA | 2 | NC | NC | NC |
| 896 | 1447 | GCAGTAGTTTTTCTTTTCAC | 1 | NC | NC | NC |
| 897 | 1448 | TGCAGTAGTTTTTCTTTTCA | 1 | NC | NC | NC |
| 898 | 1449 | CTGCAGTAGTTTTTCTTTTC | 2 | NC | NC | NC |
| 899 | 1450 | TCTGCAGTAGTTTTTCTTTT | 1 | NC | NC | NC |
| 900 | 1451 | TTCTGCAGTAGTTTTTCTTT | 1 | NC | NC | NC |
| 901 | 1452 | TTTCTGCAGTAGTTTTTCTT | 1 | NC | NC | NC |
| 902 | 1453 | TTTTCTGCAGTAGTTTTTCT | 1 | NC | NC | NC |
| 903 | 1454 | GTTTTCTGCAGTAGTTTTTC | 2 | NC | NC | NC |
| 904 | 1455 | CGTTTTCTGCAGTAGTTTTT | 2 | NC | NC | NC |
| 905 | 1456 | ACGTTTTCTGCAGTAGTTTT | 2 | NC | NC | NC |
| 906 | 1457 | TACGTTTTCTGCAGTAGTTT | 2 | NC | NC | NC |
| 907 | 1458 | TTACGTTTTCTGCAGTAGTT | 2 | NC | NC | NC |
| 908 | 1459 | TTTACGTTTTCTGCAGTAGT | 2 | NC | NC | NC |
| 909 | 1460 | GTTTACGTTTTCTGCAGTAG | 3 | NC | NC | NC |
| 910 | 1461 | TGTTTACGTTTTCTGCAGTA | 2 | NC | NC | NC |
| 911 | 1462 | GTGTTTACGTTTTCTGCAGT | 3 | NC | NC | NC |
| 912 | 1463 | TGTGTTTACGTTTTCTGCAG | 2 | NC | NC | NC |
| 913 | 1464 | GTGTGTTTACGTTTTCTGCA | 2 | NC | NC | NC |
| 914 | 1465 | TGTGTGTTTACGTTTTCTGC | 2 | NC | NC | NC |
| 915 | 1466 | CTGTGTGTTTACGTTTTCTG | 2 | NC | NC | NC |
| 916 | 1467 | TCTGTGTGTTTACGTTTTCT | 1 | NC | NC | NC |
| 917 | 1468 | CTCTGTGTGTTTACGTTTTC | 1 | NC | NC | NC |
| 918 | 1469 | ACTCTGTGTGTTTACGTTTT | 2 | NC | NC | NC |
| 919 | 1470 | AACTCTGTGTGTTTACGTTT | 2 | NC | NC | NC |
| 920 | 1471 | GAACTCTGTGTGTTTACGTT | 1 | NC | NC | NC |
| 921 | 1472 | AGAACTCTGTGTGTTTACGT | 2 | NC | NC | NC |
| 922 | 1473 | TAGAACTCTGTGTGTTTACG | 3 | NC | NC | NC |
| 923 | 1474 | CTAGAACTCTGTGTGTTTAC | 2 | NC | NC | NC |
| 924 | 1475 | CCTAGAACTCTGTGTGTTTA | 2 | NC | NC | NC |
| 925 | 1476 | CCCTAGAACTCTGTGTGTTT | 2 | NC | NC | NC |
| 926 | 1477 | TCCCTAGAACTCTGTGTGTT | 2 | NC | NC | NC |
| 927 | 1478 | ATCCCTAGAACTCTGTGTGT | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 928 | 1479 | AATCCCTAGAACTCTGTGTG | 2 | NC | NC | NC |
| 929 | 1480 | GAATCCCTAGAACTCTGTGT | 2 | NC | NC | NC |
| 930 | 1481 | TGAATCCCTAGAACTCTGTG | 2 | NC | NC | NC |
| 931 | 1482 | CTGAATCCCTAGAACTCTGT | 2 | NC | NC | NC |
| 932 | 1483 | TCTGAATCCCTAGAACTCTG | 2 | NC | NC | NC |
| 933 | 1484 | TTCTGAATCCCTAGAACTCT | 2 | NC | NC | NC |
| 934 | 1485 | CTTCTGAATCCCTAGAACTC | 2 | NC | NC | NC |
| 935 | 1486 | GCTTCTGAATCCCTAGAACT | 2 | NC | NC | NC |
| 936 | 1487 | AGCTTCTGAATCCCTAGAAC | 2 | NC | NC | NC |
| 937 | 1488 | TAGCTTCTGAATCCCTAGAA | 2 | NC | NC | NC |
| 938 | 1489 | GTAGCTTCTGAATCCCTAGA | 2 | NC | NC | NC |
| 939 | 1490 | GGTAGCTTCTGAATCCCTAG | 2 | NC | NC | NC |
| 940 | 1491 | TGGTAGCTTCTGAATCCCTA | 2 | NC | NC | NC |
| 941 | 1492 | CTGGTAGCTTCTGAATCCCT | 2 | NC | NC | NC |
| 942 | 1493 | TCTGGTAGCTTCTGAATCCC | 2 | NC | NC | NC |
| 943 | 1494 | TTCTGGTAGCTTCTGAATCC | 2 | NC | NC | NC |
| 944 | 1495 | TTTCTGGTAGCTTCTGAATC | 2 | NC | NC | NC |
| 945 | 1496 | TTTTCTGGTAGCTTCTGAAT | 2 | NC | NC | NC |
| 946 | 1497 | TTTTTCTGGTAGCTTCTGAA | 2 | NC | NC | NC |
| 947 | 1522 | ATGTACAAAAATGCATCATT | 1 | NC | NC | NC |
| 948 | 1523 | AATGTACAAAAATGCATCAT | 1 | NC | NC | NC |
| 949 | 1524 | AAATGTACAAAAATGCATCA | 1 | NC | NC | NC |
| 950 | 1525 | TAAATGTACAAAAATGCATC | 1 | NC | NC | NC |
| 951 | 1527 | CATAAATGTACAAAAATGCA | 1 | NC | NC | NC |
| 952 | 1528 | TCATAAATGTACAAAAATGC | 1 | NC | NC | NC |
| 953 | 1533 | CTGATTCATAAATGTACAAA | 2 | NC | NC | NC |
| 954 | 1534 | CCTGATTCATAAATGTACAA | 2 | NC | NC | NC |
| 955 | 1535 | ACCTGATTCATAAATGTACA | 2 | NC | NC | NC |
| 956 | 1536 | CACCTGATTCATAAATGTAC | 2 | NC | NC | NC |
| 957 | 1537 | CCACCTGATTCATAAATGTA | 2 | NC | NC | NC |
| 958 | 1538 | ACCACCTGATTCATAAATGT | 2 | NC | NC | NC |
| 959 | 1539 | GACCACCTGATTCATAAATG | 2 | 2 | NC | NC |
| 960 | 1540 | GGACCACCTGATTCATAAAT | 2 | 2 | NC | NC |
| 961 | 1542 | CTGGACCACCTGATTCATAA | 2 | 2 | NC | NC |
| 962 | 1543 | CCTGGACCACCTGATTCATA | 1 | 1 | NC | NC |
| 963 | 1544 | GCCTGGACCACCTGATTCAT | 1 | 1 | NC | NC |
| 964 | 1563 | GCTCTGTCATTTTGCTATGG | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 965 | 1564 | GGCTCTGTCATTTTGCTATG | 2 | 2 | NC | NC |
| 966 | 1565 | TGGCTCTGTCATTTTGCTAT | 1 | 2 | NC | NC |
| 967 | 1566 | ATGGCTCTGTCATTTTGCTA | 2 | 2 | NC | NC |
| 968 | 1567 | GATGGCTCTGTCATTTTGCT | 2 | 2 | NC | NC |
| 969 | 1568 | AGATGGCTCTGTCATTTTGC | 1 | 2 | NC | NC |
| 970 | 1569 | AAGATGGCTCTGTCATTTTG | 2 | 2 | NC | NC |
| 971 | 1570 | AAAGATGGCTCTGTCATTTT | 2 | 2 | NC | NC |
| 972 | 1571 | TAAAGATGGCTCTGTCATTT | 2 | 2 | NC | NC |
| 973 | 1572 | GTAAAGATGGCTCTGTCATT | 2 | 2 | NC | NC |
| 974 | 1573 | TGTAAAGATGGCTCTGTCAT | 2 | 2 | NC | NC |
| 975 | 1574 | TTGTAAAGATGGCTCTGTCA | 2 | 2 | NC | NC |
| 976 | 1575 | TTTGTAAAGATGGCTCTGTC | 2 | 2 | NC | NC |
| 977 | 1576 | TTTTGTAAAGATGGCTCTGT | 2 | 2 | NC | NC |
| 978 | 1577 | GTTTTGTAAAGATGGCTCTG | 1 | 2 | NC | NC |
| 979 | 1578 | TGTTTTGTAAAGATGGCTCT | 1 | 2 | NC | NC |
| 980 | 1579 | TTGTTTTGTAAAGATGGCTC | 2 | 2 | NC | NC |
| 981 | 1580 | TTTGTTTTGTAAAGATGGCT | 2 | 2 | NC | NC |
| 982 | 1581 | CTTTGTTTTGTAAAGATGGC | 1 | 2 | NC | NC |
| 983 | 1582 | TCTTTGTTTTGTAAAGATGG | 1 | 1 | NC | NC |
| 984 | 1586 | GCTGTCTTTGTTTTGTAAAG | 2 | 1 | NC | NC |
| 985 | 1587 | AGCTGTCTTTGTTTTGTAAA | 2 | 1 | NC | NC |
| 986 | 1588 | GAGCTGTCTTTGTTTTGTAA | 2 | 2 | NC | NC |
| 987 | 1589 | AGAGCTGTCTTTGTTTTGTA | 2 | 2 | NC | NC |
| 988 | 1590 | AAGAGCTGTCTTTGTTTTGT | 1 | 1 | NC | NC |
| 989 | 1604 | CTTTGATTCTGAGCAAGAGC | 2 | NC | NC | NC |
| 990 | 1605 | TCTTTGATTCTGAGCAAGAG | 2 | NC | NC | NC |
| 991 | 1606 | ATCTTTGATTCTGAGCAAGA | 2 | NC | NC | NC |
| 992 | 1607 | CATCTTTGATTCTGAGCAAG | 2 | NC | NC | NC |
| 993 | 1608 | ACATCTTTGATTCTGAGCAA | 2 | NC | NC | NC |
| 994 | 1609 | AACATCTTTGATTCTGAGCA | 2 | NC | NC | NC |
| 995 | 1610 | TAACATCTTTGATTCTGAGC | 2 | NC | NC | NC |
| 996 | 1611 | CTAACATCTTTGATTCTGAG | 2 | NC | NC | NC |
| 997 | 1612 | TCTAACATCTTTGATTCTGA | 2 | NC | NC | NC |
| 998 | 1613 | TTCTAACATCTTTGATTCTG | 2 | NC | NC | NC |
| 999 | 1614 | GTTCTAACATCTTTGATTCT | 2 | NC | NC | NC |
| 1000 | 1615 | TGTTCTAACATCTTTGATTC | 2 | NC | NC | NC |
| 1001 | 1625 | AATTGTCTCTTGTTCTAACA | 1 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1002 | 1626 | CAATTGTCTCTTGTTCTAAC | 2 | 2 | NC | NC |
| 1003 | 1627 | ACAATTGTCTCTTGTTCTAA | 2 | 1 | NC | NC |
| 1004 | 1628 | TACAATTGTCTCTTGTTCTA | 2 | 2 | NC | NC |
| 1005 | 1629 | CTACAATTGTCTCTTGTTCT | 2 | 2 | NC | NC |
| 1006 | 1630 | GCTACAATTGTCTCTTGTTC | 2 | 2 | NC | NC |
| 1007 | 1631 | TGCTACAATTGTCTCTTGTT | 2 | 2 | NC | NC |
| 1008 | 1633 | GATGCTACAATTGTCTCTTG | 2 | 2 | NC | NC |
| 1009 | 1634 | TGATGCTACAATTGTCTCTT | 2 | 2 | NC | NC |
| 1010 | 1635 | CTGATGCTACAATTGTCTCT | 2 | 2 | NC | NC |
| 1011 | 1636 | TCTGATGCTACAATTGTCTC | 2 | 1 | NC | NC |
| 1012 | 1637 | TTCTGATGCTACAATTGTCT | 2 | 1 | NC | NC |
| 1013 | 1638 | CTTCTGATGCTACAATTGTC | 2 | 2 | NC | NC |
| 1014 | 1639 | GCTTCTGATGCTACAATTGT | 2 | 2 | NC | NC |
| 1015 | 1641 | CAGCTTCTGATGCTACAATT | 2 | NC | NC | NC |
| 1016 | 1642 | CCAGCTTCTGATGCTACAAT | 2 | NC | NC | NC |
| 1017 | 1643 | TCCAGCTTCTGATGCTACAA | 2 | NC | NC | NC |
| 1018 | 1644 | CTCCAGCTTCTGATGCTACA | 2 | NC | NC | NC |
| 1019 | 1645 | TCTCCAGCTTCTGATGCTAC | 2 | NC | NC | NC |
| 1020 | 1646 | TTCTCCAGCTTCTGATGCTA | 2 | NC | NC | NC |
| 1021 | 1648 | TTTTCTCCAGCTTCTGATGC | 2 | NC | NC | NC |
| 1022 | 1649 | ATTTTCTCCAGCTTCTGATG | 2 | NC | NC | NC |
| 1023 | 1650 | CATTTTCTCCAGCTTCTGAT | 2 | NC | NC | NC |
| 1024 | 1651 | TCATTTTCTCCAGCTTCTGA | 1 | NC | NC | NC |
| 1025 | 1652 | CTCATTTTCTCCAGCTTCTG | 1 | NC | NC | NC |
| 1026 | 1653 | TCTCATTTTCTCCAGCTTCT | 2 | NC | NC | NC |
| 1027 | 1654 | TTCTCATTTTCTCCAGCTTC | 1 | NC | NC | NC |
| 1028 | 1655 | TTTCTCATTTTCTCCAGCTT | 1 | NC | NC | NC |
| 1029 | 1656 | GTTTCTCATTTTCTCCAGCT | 2 | NC | NC | NC |
| 1030 | 1657 | TGTTTCTCATTTTCTCCAGC | 2 | NC | NC | NC |
| 1031 | 1658 | ATGTTTCTCATTTTCTCCAG | 1 | NC | NC | NC |
| 1032 | 1659 | TATGTTTCTCATTTTCTCCA | 1 | NC | NC | NC |
| 1033 | 1660 | TTATGTTTCTCATTTTCTCC | 1 | 1 | NC | NC |
| 1034 | 1661 | TTTATGTTTCTCATTTTCTC | 1 | 1 | NC | NC |
| 1035 | 1679 | ATGTTCCAGGAAAGATTTTT | 1 | NC | NC | NC |
| 1036 | 1680 | TATGTTCCAGGAAAGATTTT | 2 | NC | NC | NC |
| 1037 | 1681 | CTATGTTCCAGGAAAGATTT | 2 | NC | NC | NC |
| 1038 | 1682 | GCTATGTTCCAGGAAAGATT | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1039 | 1683 | AGCTATGTTCCAGGAAAGAT | 2 | NC | NC | NC |
| 1040 | 1684 | GAGCTATGTTCCAGGAAAGA | 1 | NC | NC | NC |
| 1041 | 1685 | AGAGCTATGTTCCAGGAAAG | 2 | NC | NC | NC |
| 1042 | 1686 | AAGAGCTATGTTCCAGGAAA | 2 | NC | NC | NC |
| 1043 | 1687 | AAAGAGCTATGTTCCAGGAA | 2 | NC | NC | NC |
| 1044 | 1688 | TAAAGAGCTATGTTCCAGGA | 2 | NC | NC | NC |
| 1045 | 1689 | CTAAAGAGCTATGTTCCAGG | 2 | 2 | NC | NC |
| 1046 | 1690 | TCTAAAGAGCTATGTTCCAG | 1 | 2 | NC | NC |
| 1047 | 1691 | TTCTAAAGAGCTATGTTCCA | 2 | 2 | NC | NC |
| 1048 | 1692 | TTTCTAAAGAGCTATGTTCC | 2 | 2 | NC | NC |
| 1049 | 1693 | TTTTCTAAAGAGCTATGTTC | 1 | 1 | NC | NC |
| 1050 | 1694 | ATTTTCTAAAGAGCTATGTT | 1 | NC | NC | NC |
| 1051 | 1695 | GATTTTCTAAAGAGCTATGT | 2 | NC | NC | NC |
| 1052 | 1696 | GGATTTTCTAAAGAGCTATG | 2 | NC | NC | NC |
| 1053 | 1697 | CGGATTTTCTAAAGAGCTAT | 2 | NC | NC | NC |
| 1054 | 1698 | ACGGATTTTCTAAAGAGCTA | 2 | NC | NC | NC |
| 1055 | 1699 | CACGGATTTTCTAAAGAGCT | 2 | NC | NC | NC |
| 1056 | 1700 | ACACGGATTTTCTAAAGAGC | 2 | NC | NC | NC |
| 1057 | 1701 | CACACGGATTTTCTAAAGAG | 2 | NC | NC | NC |
| 1058 | 1702 | CCACACGGATTTTCTAAAGA | 2 | NC | NC | NC |
| 1059 | 1703 | TCCACACGGATTTTCTAAAG | 2 | NC | NC | NC |
| 1060 | 1714 | TCTAAACTGGTTCCACACGG | 2 | NC | NC | NC |
| 1061 | 1715 | TTCTAAACTGGTTCCACACG | 1 | NC | NC | NC |
| 1062 | 1716 | TTTCTAAACTGGTTCCACAC | 1 | NC | NC | NC |
| 1063 | 1717 | ATTTCTAAACTGGTTCCACA | 2 | NC | NC | NC |
| 1064 | 1718 | CATTTCTAAACTGGTTCCAC | 2 | NC | NC | NC |
| 1065 | 1719 | ACATTTCTAAACTGGTTCCA | 2 | NC | NC | NC |
| 1066 | 1720 | AACATTTCTAAACTGGTTCC | 1 | NC | NC | NC |
| 1067 | 1721 | AAACATTTCTAAACTGGTTC | 2 | NC | NC | NC |
| 1068 | 1722 | AAAACATTTCTAAACTGGTT | 1 | NC | NC | NC |
| 1069 | 1723 | AAAAACATTTCTAAACTGGT | 1 | NC | NC | NC |
| 1070 | 1724 | TAAAAACATTTCTAAACTGG | 1 | NC | NC | NC |
| 1071 | 1727 | GCTTAAAAACATTTCTAAAC | 2 | NC | NC | NC |
| 1072 | 1728 | GGCTTAAAAACATTTCTAAA | 2 | NC | NC | NC |
| 1073 | 1729 | GGGCTTAAAAACATTTCTAA | 2 | NC | NC | NC |
| 1074 | 1730 | AGGGCTTAAAAACATTTCTA | 1 | NC | NC | NC |
| 1075 | 1731 | AAGGGCTTAAAAACATTTCT | 1 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1076 | 1732 | AAAGGGCTTAAAAACATTTC | 1 | 1 | NC | NC |
| 1077 | 1733 | AAAAGGGCTTAAAAACATTT | 1 | 1 | NC | NC |
| 1078 | 1734 | GAAAAGGGCTTAAAAACATT | 1 | 2 | NC | NC |
| 1079 | 1735 | TGAAAAGGGCTTAAAAACAT | 1 | 1 | NC | NC |
| 1080 | 1736 | CTGAAAAGGGCTTAAAAACA | 2 | 1 | NC | NC |
| 1081 | 1737 | TCTGAAAAGGGCTTAAAAAC | 1 | 1 | NC | NC |
| 1082 | 1738 | GTCTGAAAAGGGCTTAAAAA | 2 | 2 | NC | NC |
| 1083 | 1739 | TGTCTGAAAAGGGCTTAAAA | 1 | 1 | NC | NC |
| 1084 | 1740 | GTGTCTGAAAAGGGCTTAAA | 2 | 2 | NC | NC |
| 1085 | 1741 | GGTGTCTGAAAAGGGCTTAA | 2 | 2 | NC | NC |
| 1086 | 1742 | TGGTGTCTGAAAAGGGCTTA | 2 | 2 | NC | NC |
| 1087 | 1743 | ATGGTGTCTGAAAAGGGCTT | 1 | 1 | NC | NC |
| 1088 | 1744 | CATGGTGTCTGAAAAGGGCT | 2 | 2 | NC | NC |
| 1089 | 1745 | ACATGGTGTCTGAAAAGGGC | 2 | 2 | NC | NC |
| 1090 | 1756 | TCCTCAAAGTGACATGGTGT | 1 | NC | NC | NC |
| 1091 | 1757 | CTCCTCAAAGTGACATGGTG | 2 | NC | NC | NC |
| 1092 | 1758 | TCTCCTCAAAGTGACATGGT | 2 | NC | NC | NC |
| 1093 | 1759 | CTCTCCTCAAAGTGACATGG | 3 | NC | NC | NC |
| 1094 | 1760 | ACTCTCCTCAAAGTGACATG | 2 | NC | NC | NC |
| 1095 | 1766 | CTGCCCACTCTCCTCAAAGT | 1 | NC | NC | NC |
| 1096 | 1768 | TCCTGCCCACTCTCCTCAAA | 2 | NC | NC | NC |
| 1097 | 1769 | ATCCTGCCCACTCTCCTCAA | 2 | NC | NC | NC |
| 1098 | 1772 | TAGATCCTGCCCACTCTCCT | 2 | NC | NC | NC |
| 1099 | 1774 | TCTAGATCCTGCCCACTCTC | 2 | NC | NC | NC |
| 1100 | 1775 | TTCTAGATCCTGCCCACTCT | 2 | NC | NC | NC |
| 1101 | 1776 | TTTCTAGATCCTGCCCACTC | 2 | NC | NC | NC |
| 1102 | 1777 | ATTTCTAGATCCTGCCCACT | 2 | NC | NC | NC |
| 1103 | 1778 | TATTTCTAGATCCTGCCCAC | 2 | NC | NC | NC |
| 1104 | 1779 | ATATTTCTAGATCCTGCCCA | 2 | NC | NC | NC |
| 1105 | 1780 | CATATTTCTAGATCCTGCCC | 2 | NC | NC | NC |
| 1106 | 1781 | CCATATTTCTAGATCCTGCC | 2 | NC | NC | NC |
| 1107 | 1782 | TCCATATTTCTAGATCCTGC | 2 | NC | NC | NC |
| 1108 | 1783 | TTCCATATTTCTAGATCCTG | 2 | NC | NC | NC |
| 1109 | 1784 | TTTCCATATTTCTAGATCCT | 1 | 1 | NC | NC |
| 1110 | 1785 | CTTTCCATATTTCTAGATCC | 2 | 2 | NC | NC |
| 1111 | 1786 | TCTTTCCATATTTCTAGATC | 2 | 2 | NC | NC |
| 1112 | 1787 | TTCTTTCCATATTTCTAGAT | 1 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1113 | 1788 | TTTCTTTCCATATTTCTAGA | 1 | 1 | NC | NC |
| 1114 | 1789 | CTTTCTTTCCATATTTCTAG | 1 | 1 | NC | NC |
| 1115 | 1790 | ACTTTCTTTCCATATTTCTA | 2 | 2 | NC | NC |
| 1116 | 1791 | TACTTTCTTTCCATATTTCT | 1 | 2 | NC | NC |
| 1117 | 1792 | GTACTTTCTTTCCATATTTC | 2 | 2 | NC | NC |
| 1118 | 1793 | AGTACTTTCTTTCCATATTT | 2 | 1 | NC | NC |
| 1119 | 1794 | TAGTACTTTCTTTCCATATT | 1 | 2 | NC | NC |
| 1120 | 1795 | GTAGTACTTTCTTTCCATAT | 1 | 2 | NC | NC |
| 1121 | 1796 | AGTAGTACTTTCTTTCCATA | 2 | 2 | NC | NC |
| 1122 | 1797 | CAGTAGTACTTTCTTTCCAT | 1 | 2 | NC | NC |
| 1123 | 1798 | ACAGTAGTACTTTCTTTCCA | 1 | 2 | NC | NC |
| 1124 | 1799 | AACAGTAGTACTTTCTTTCC | 1 | 2 | NC | NC |
| 1125 | 1800 | TAACAGTAGTACTTTCTTTC | 2 | 2 | NC | NC |
| 1126 | 1801 | TTAACAGTAGTACTTTCTTT | 2 | 2 | NC | NC |
| 1127 | 1802 | ATTAACAGTAGTACTTTCTT | 2 | 2 | NC | NC |
| 1128 | 1803 | CATTAACAGTAGTACTTTCT | 2 | 2 | NC | NC |
| 1129 | 1804 | CCATTAACAGTAGTACTTTC | 2 | NC | NC | NC |
| 1130 | 1805 | GCCATTAACAGTAGTACTTT | 2 | NC | NC | NC |
| 1131 | 1806 | TGCCATTAACAGTAGTACTT | 2 | NC | NC | NC |
| 1132 | 1807 | ATGCCATTAACAGTAGTACT | 2 | NC | NC | NC |
| 1133 | 1808 | CATGCCATTAACAGTAGTAC | 1 | NC | NC | NC |
| 1134 | 1809 | CCATGCCATTAACAGTAGTA | 2 | NC | NC | NC |
| 1135 | 1810 | GCCATGCCATTAACAGTAGT | 2 | NC | NC | NC |
| 1136 | 1811 | AGCCATGCCATTAACAGTAG | 2 | NC | NC | NC |
| 1137 | 1812 | CAGCCATGCCATTAACAGTA | 2 | NC | NC | NC |
| 1138 | 1824 | TCAAGATGTTGGCAGCCATG | 1 | NC | NC | NC |
| 1139 | 1825 | TTCAAGATGTTGGCAGCCAT | 2 | NC | NC | NC |
| 1140 | 1826 | TTTCAAGATGTTGGCAGCCA | 2 | NC | NC | NC |
| 1141 | 1827 | TTTTCAAGATGTTGGCAGCC | 2 | NC | NC | NC |
| 1142 | 1828 | TTTTTCAAGATGTTGGCAGC | 1 | NC | NC | NC |
| 1143 | 1829 | ATTTTTCAAGATGTTGGCAG | 1 | NC | NC | NC |
| 1144 | 1830 | TATTTTTCAAGATGTTGGCA | 2 | NC | NC | NC |
| 1145 | 1831 | TTATTTTTCAAGATGTTGGC | 2 | NC | NC | NC |
| 1146 | 1832 | ATTATTTTTCAAGATGTTGG | 2 | NC | NC | NC |
| 1147 | 1848 | GTTGATTCTGAATTCTATTA | 2 | 2 | NC | NC |
| 1148 | 1849 | GGTTGATTCTGAATTCTATT | 2 | 2 | NC | NC |
| 1149 | 1850 | TGGTTGATTCTGAATTCTAT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1150 | 1851 | TTGGTTGATTCTGAATTCTA | 2 | NC | NC | NC |
| 1151 | 1852 | TTTGGTTGATTCTGAATTCT | 2 | NC | NC | NC |
| 1152 | 1853 | CTTTGGTTGATTCTGAATTC | 2 | NC | NC | NC |
| 1153 | 1854 | TCTTTGGTTGATTCTGAATT | 2 | NC | NC | NC |
| 1154 | 1855 | CTCTTTGGTTGATTCTGAAT | 2 | NC | NC | NC |
| 1155 | 1856 | TCTCTTTGGTTGATTCTGAA | 2 | NC | NC | NC |
| 1156 | 1857 | ATCTCTTTGGTTGATTCTGA | 2 | NC | NC | NC |
| 1157 | 1858 | AATCTCTTTGGTTGATTCTG | 2 | NC | NC | NC |
| 1158 | 1859 | AAATCTCTTTGGTTGATTCT | 2 | NC | NC | NC |
| 1159 | 1860 | TAAATCTCTTTGGTTGATTC | 2 | NC | NC | NC |
| 1160 | 1861 | TTAAATCTCTTTGGTTGATT | 2 | NC | NC | NC |
| 1161 | 1862 | TTTAAATCTCTTTGGTTGAT | 2 | NC | NC | NC |
| 1162 | 1863 | CTTTAAATCTCTTTGGTTGA | 2 | NC | NC | NC |
| 1163 | 1864 | TCTTTAAATCTCTTTGGTTG | 2 | NC | NC | NC |
| 1164 | 1865 | ATCTTTAAATCTCTTTGGTT | 2 | NC | NC | NC |
| 1165 | 1866 | CATCTTTAAATCTCTTTGGT | 2 | NC | NC | NC |
| 1166 | 1867 | GCATCTTTAAATCTCTTTGG | 2 | NC | NC | NC |
| 1167 | 1868 | AGCATCTTTAAATCTCTTTG | 2 | NC | NC | NC |
| 1168 | 1869 | TAGCATCTTTAAATCTCTTT | 1 | NC | NC | NC |
| 1169 | 1870 | GTAGCATCTTTAAATCTCTT | 2 | NC | NC | NC |
| 1170 | 1871 | AGTAGCATCTTTAAATCTCT | 1 | 1 | NC | NC |
| 1171 | 1872 | CAGTAGCATCTTTAAATCTC | 1 | 1 | NC | NC |
| 1172 | 1873 | TCAGTAGCATCTTTAAATCT | 2 | 1 | NC | NC |
| 1173 | 1874 | TTCAGTAGCATCTTTAAATC | 1 | 1 | NC | NC |
| 1174 | 1875 | CTTCAGTAGCATCTTTAAAT | 1 | 1 | NC | NC |
| 1175 | 1876 | ACTTCAGTAGCATCTTTAAA | 2 | 2 | NC | NC |
| 1176 | 1877 | CACTTCAGTAGCATCTTTAA | 2 | 1 | NC | NC |
| 1177 | 1878 | CCACTTCAGTAGCATCTTTA | 2 | 2 | NC | NC |
| 1178 | 1879 | CCCACTTCAGTAGCATCTTT | 2 | 2 | NC | NC |
| 1179 | 1880 | TCCCACTTCAGTAGCATCTT | 2 | 2 | NC | NC |
| 1180 | 1881 | ATCCCACTTCAGTAGCATCT | 2 | 2 | NC | NC |
| 1181 | 1882 | CATCCCACTTCAGTAGCATC | 2 | 2 | NC | NC |
| 1182 | 1883 | GCATCCCACTTCAGTAGCAT | 2 | 2 | NC | NC |
| 1183 | 1884 | GGCATCCCACTTCAGTAGCA | 2 | 2 | NC | NC |
| 1184 | 1885 | TGGCATCCCACTTCAGTAGC | 2 | 2 | NC | NC |
| 1185 | 1886 | CTGGCATCCCACTTCAGTAG | 2 | 2 | NC | NC |
| 1186 | 1887 | GCTGGCATCCCACTTCAGTA | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1187 | 1912 | CATAATGTTGTTGCAAAAGG | 2 | NC | NC | NC |
| 1188 | 1913 | CCATAATGTTGTTGCAAAAG | 2 | NC | NC | NC |
| 1189 | 1914 | CCCATAATGTTGTTGCAAAA | 2 | NC | NC | NC |
| 1190 | 1915 | CCCCATAATGTTGTTGCAAA | 2 | NC | NC | NC |
| 1191 | 1916 | TCCCCATAATGTTGTTGCAA | 1 | NC | NC | NC |
| 1192 | 1917 | CTCCCCATAATGTTGTTGCA | 2 | NC | NC | NC |
| 1193 | 1918 | ACTCCCCATAATGTTGTTGC | 1 | NC | NC | NC |
| 1194 | 1919 | TACTCCCCATAATGTTGTTG | 2 | NC | NC | NC |
| 1195 | 1920 | GTACTCCCCATAATGTTGTT | 2 | NC | NC | NC |
| 1196 | 1921 | TGTACTCCCCATAATGTTGT | 2 | NC | NC | NC |
| 1197 | 1922 | ATGTACTCCCCATAATGTTG | 2 | NC | NC | NC |
| 1198 | 1923 | TATGTACTCCCCATAATGTT | 2 | NC | NC | NC |
| 1199 | 1924 | CTATGTACTCCCCATAATGT | 2 | NC | NC | NC |
| 1200 | 1925 | ACTATGTACTCCCCATAATG | 2 | NC | NC | NC |
| 1201 | 1926 | CACTATGTACTCCCCATAAT | 2 | NC | NC | NC |
| 1202 | 1927 | GCACTATGTACTCCCCATAA | 2 | NC | NC | NC |
| 1203 | 1928 | AGCACTATGTACTCCCCATA | 2 | NC | NC | NC |
| 1204 | 1929 | GAGCACTATGTACTCCCCAT | 3 | NC | NC | NC |
| 1205 | 1930 | TGAGCACTATGTACTCCCCA | 1 | NC | NC | NC |
| 1206 | 1931 | CTGAGCACTATGTACTCCCC | 3 | NC | NC | NC |
| 1207 | 1932 | TCTGAGCACTATGTACTCCC | 2 | NC | NC | NC |
| 1208 | 1933 | GTCTGAGCACTATGTACTCC | 3 | NC | NC | NC |
| 1209 | 1934 | TGTCTGAGCACTATGTACTC | 3 | NC | NC | NC |
| 1210 | 1935 | CTGTCTGAGCACTATGTACT | 2 | NC | NC | NC |
| 1211 | 1936 | TCTGTCTGAGCACTATGTAC | 2 | NC | NC | NC |
| 1212 | 1937 | CTCTGTCTGAGCACTATGTA | 2 | NC | NC | NC |
| 1213 | 1947 | TTTTCTCTTTCTCTGTCTGA | 1 | NC | NC | NC |
| 1214 | 1948 | TTTTTCTCTTTCTCTGTCTG | 1 | NC | NC | NC |
| 1215 | 1967 | ACAATTGCTAGATTCTTTTT | 2 | NC | NC | NC |
| 1216 | 1968 | CACAATTGCTAGATTCTTTT | 2 | NC | NC | NC |
| 1217 | 1969 | CCACAATTGCTAGATTCTTT | 2 | NC | NC | NC |
| 1218 | 1970 | TCCACAATTGCTAGATTCTT | 2 | NC | NC | NC |
| 1219 | 1971 | TTCCACAATTGCTAGATTCT | 2 | NC | NC | NC |
| 1220 | 1972 | CTTCCACAATTGCTAGATTC | 2 | NC | NC | NC |
| 1221 | 1973 | TCTTCCACAATTGCTAGATT | 2 | NC | NC | NC |
| 1222 | 1974 | TTCTTCCACAATTGCTAGAT | 2 | NC | NC | NC |
| 1223 | 1975 | CTTCTTCCACAATTGCTAGA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1224 | 1976 | TCTTCTTCCACAATTGCTAG | 2 | NC | NC | NC |
| 1225 | 1977 | TTCTTCTTCCACAATTGCTA | 2 | NC | NC | NC |
| 1226 | 1978 | TTTCTTCTTCCACAATTGCT | 1 | NC | NC | NC |
| 1227 | 1979 | ATTTCTTCTTCCACAATTGC | 2 | NC | NC | NC |
| 1228 | 1980 | CATTTCTTCTTCCACAATTG | 2 | NC | NC | NC |
| 1229 | 1981 | ACATTTCTTCTTCCACAATT | 2 | NC | NC | NC |
| 1230 | 1982 | AACATTTCTTCTTCCACAAT | 1 | NC | NC | NC |
| 1231 | 1983 | AAACATTTCTTCTTCCACAA | 1 | NC | NC | NC |
| 1232 | 1984 | AAAACATTTCTTCTTCCACA | 1 | NC | NC | NC |
| 1233 | 1985 | AAAAACATTTCTTCTTCCAC | 1 | NC | NC | NC |
| 1234 | 1986 | TAAAAACATTTCTTCTTCCA | 1 | NC | NC | NC |
| 1235 | 1987 | CTAAAAACATTTCTTCTTCC | 2 | NC | NC | NC |
| 1236 | 1988 | ACTAAAAACATTTCTTCTTC | 1 | NC | NC | NC |
| 1237 | 1993 | CCATAACTAAAAACATTTCT | 2 | NC | NC | NC |
| 1238 | 1994 | CCCATAACTAAAAACATTTC | 2 | NC | NC | NC |
| 1239 | 1995 | GCCCATAACTAAAAACATTT | 2 | NC | NC | NC |
| 1240 | 1996 | CGCCCATAACTAAAAACATT | 3 | NC | NC | NC |
| 1241 | 1997 | TCGCCCATAACTAAAAACAT | 2 | NC | NC | NC |
| 1242 | 1998 | CTCGCCCATAACTAAAAACA | 2 | NC | NC | NC |
| 1243 | 1999 | ACTCGCCCATAACTAAAAAC | 3 | NC | NC | NC |
| 1244 | 2000 | AACTCGCCCATAACTAAAAA | 2 | NC | NC | NC |
| 1245 | 2001 | TAACTCGCCCATAACTAAAA | 2 | NC | NC | NC |
| 1246 | 2002 | TTAACTCGCCCATAACTAAA | 3 | NC | NC | NC |
| 1247 | 2003 | TTTAACTCGCCCATAACTAA | 3 | NC | NC | NC |
| 1248 | 2004 | ATTTAACTCGCCCATAACTA | 3 | NC | NC | NC |
| 1249 | 2005 | AATTTAACTCGCCCATAACT | 3 | NC | NC | NC |
| 1250 | 2006 | TAATTTAACTCGCCCATAAC | 2 | NC | NC | NC |
| 1251 | 2007 | ATAATTTAACTCGCCCATAA | 2 | NC | NC | NC |
| 1252 | 2008 | CATAATTTAACTCGCCCATA | 3 | NC | NC | NC |
| 1253 | 2009 | ACATAATTTAACTCGCCCAT | 3 | NC | NC | NC |
| 1254 | 2010 | AACATAATTTAACTCGCCCA | 3 | NC | NC | NC |
| 1255 | 2011 | GAACATAATTTAACTCGCCC | 3 | NC | NC | NC |
| 1256 | 2012 | GGAACATAATTTAACTCGCC | 2 | NC | NC | NC |
| 1257 | 2013 | TGGAACATAATTTAACTCGC | 2 | NC | NC | NC |
| 1258 | 2027 | AGTTATAAAGCCAGTGGAAC | 2 | 2 | NC | NC |
| 1259 | 2028 | GAGTTATAAAGCCAGTGGAA | 2 | 2 | NC | NC |
| 1260 | 2029 | TGAGTTATAAAGCCAGTGGA | 2 | 1 | 2 | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1261 | 2030 | ATGAGTTATAAAGCCAGTGG | 2 | 2 | 2 | NC |
| 1262 | 2031 | CATGAGTTATAAAGCCAGTG | 2 | NC | NC | NC |
| 1263 | 2032 | ACATGAGTTATAAAGCCAGT | 2 | NC | NC | NC |
| 1264 | 2033 | TACATGAGTTATAAAGCCAG | 2 | NC | NC | NC |
| 1265 | 2034 | CTACATGAGTTATAAAGCCA | 2 | NC | NC | NC |
| 1266 | 2035 | ACTACATGAGTTATAAAGCC | 2 | NC | NC | NC |
| 1267 | 2045 | TTCATTTTGTACTACATGAG | 2 | NC | NC | NC |
| 1268 | 2046 | TTTCATTTTGTACTACATGA | 1 | NC | NC | NC |
| 1269 | 2047 | TTTTCATTTTGTACTACATG | 1 | NC | NC | NC |
| 1270 | 2065 | GTTTCAGTTGATTTAGTTTT | 2 | 2 | NC | NC |
| 1271 | 2066 | TGTTTCAGTTGATTTAGTTT | 2 | 1 | NC | NC |
| 1272 | 2067 | CTGTTTCAGTTGATTTAGTT | 2 | 2 | NC | NC |
| 1273 | 2068 | TCTGTTTCAGTTGATTTAGT | 2 | 2 | NC | NC |
| 1274 | 2069 | TTCTGTTTCAGTTGATTTAG | 2 | 1 | 2 | NC |
| 1275 | 2070 | GTTCTGTTTCAGTTGATTTA | 2 | 2 | 2 | NC |
| 1276 | 2071 | TGTTCTGTTTCAGTTGATTT | 1 | 1 | 1 | NC |
| 1277 | 2072 | ATGTTCTGTTTCAGTTGATT | 1 | 1 | 2 | NC |
| 1278 | 2073 | AATGTTCTGTTTCAGTTGAT | 1 | NC | NC | NC |
| 1279 | 2074 | GAATGTTCTGTTTCAGTTGA | 2 | NC | NC | NC |
| 1280 | 2075 | TGAATGTTCTGTTTCAGTTG | 2 | NC | NC | NC |
| 1281 | 2076 | ATGAATGTTCTGTTTCAGTT | 2 | NC | NC | NC |
| 1282 | 2077 | AATGAATGTTCTGTTTCAGT | 2 | NC | NC | NC |
| 1283 | 2078 | AAATGAATGTTCTGTTTCAG | 2 | NC | NC | NC |
| 1284 | 2079 | TAAATGAATGTTCTGTTTCA | 1 | NC | NC | NC |
| 1285 | 2080 | TTAAATGAATGTTCTGTTTC | 1 | NC | NC | NC |
| 1286 | 2097 | CAGGTCTAACATAATTTTTA | 1 | 1 | NC | NC |
| 1287 | 2098 | CCAGGTCTAACATAATTTTT | 2 | 1 | NC | NC |
| 1288 | 2099 | ACCAGGTCTAACATAATTTT | 2 | 1 | NC | NC |
| 1289 | 2100 | GACCAGGTCTAACATAATTT | 3 | 2 | NC | NC |
| 1290 | 2101 | GGACCAGGTCTAACATAATT | 3 | 2 | NC | NC |
| 1291 | 2102 | GGGACCAGGTCTAACATAAT | 3 | 2 | NC | NC |
| 1292 | 2103 | TGGGACCAGGTCTAACATAA | 3 | 2 | NC | NC |
| 1293 | 2104 | GTGGGACCAGGTCTAACATA | 3 | 3 | NC | NC |
| 1294 | 2105 | TGTGGGACCAGGTCTAACAT | 2 | 2 | NC | NC |
| 1295 | 2106 | GTGTGGGACCAGGTCTAACA | 2 | 3 | NC | NC |
| 1296 | 2108 | ACGTGTGGGACCAGGTCTAA | 2 | 2 | NC | NC |
| 1297 | 2118 | TTTCTTGGGCACGTGTGGGA | 2 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1298 | 2120 | TGTTTCTTGGGCACGTGTGG | 2 | 3 | NC | NC |
| 1299 | 2121 | ATGTTTCTTGGGCACGTGTG | 2 | 2 | NC | NC |
| 1300 | 2122 | AATGTTTCTTGGGCACGTGT | 2 | 2 | NC | NC |
| 1301 | 2123 | AAATGTTTCTTGGGCACGTG | 2 | 2 | NC | NC |
| 1302 | 2124 | CAAATGTTTCTTGGGCACGT | 2 | 2 | NC | NC |
| 1303 | 2131 | CTATTTCCAAATGTTTCTTG | 1 | 2 | NC | NC |
| 1304 | 2132 | TCTATTTCCAAATGTTTCTT | 1 | 2 | NC | NC |
| 1305 | 2133 | TTCTATTTCCAAATGTTTCT | 1 | 1 | NC | NC |
| 1306 | 2134 | GTTCTATTTCCAAATGTTTC | 2 | 2 | NC | NC |
| 1307 | 2135 | TGTTCTATTTCCAAATGTTT | 1 | 1 | NC | NC |
| 1308 | 2136 | GTGTTCTATTTCCAAATGTT | 2 | 1 | NC | NC |
| 1309 | 2137 | CGTGTTCTATTTCCAAATGT | 2 | 2 | NC | NC |
| 1310 | 2138 | ACGTGTTCTATTTCCAAATG | 2 | 2 | NC | NC |
| 1311 | 2139 | GACGTGTTCTATTTCCAAAT | 2 | 2 | NC | NC |
| 1312 | 2140 | TGACGTGTTCTATTTCCAAA | 2 | 2 | NC | NC |
| 1313 | 2141 | ATGACGTGTTCTATTTCCAA | 2 | 2 | NC | NC |
| 1314 | 2142 | AATGACGTGTTCTATTTCCA | 2 | 2 | NC | NC |
| 1315 | 2143 | GAATGACGTGTTCTATTTCC | 2 | 2 | NC | NC |
| 1316 | 2144 | TGAATGACGTGTTCTATTTC | 2 | 2 | NC | NC |
| 1317 | 2145 | CTGAATGACGTGTTCTATTT | 2 | 2 | NC | NC |
| 1318 | 2146 | ACTGAATGACGTGTTCTATT | 2 | 2 | NC | NC |
| 1319 | 2147 | AACTGAATGACGTGTTCTAT | 2 | 2 | NC | NC |
| 1320 | 2148 | CAACTGAATGACGTGTTCTA | 2 | 2 | NC | NC |
| 1321 | 2149 | TCAACTGAATGACGTGTTCT | 2 | 3 | NC | NC |
| 1322 | 2150 | TTCAACTGAATGACGTGTTC | 3 | 3 | NC | NC |
| 1323 | 2151 | TTTCAACTGAATGACGTGTT | 2 | 2 | NC | NC |
| 1324 | 2152 | GTTTCAACTGAATGACGTGT | 3 | 2 | NC | NC |
| 1325 | 2153 | AGTTTCAACTGAATGACGTG | 2 | 3 | NC | NC |
| 1326 | 2164 | TTGATGTCTGGAGTTTCAAC | 2 | NC | NC | NC |
| 1327 | 2165 | TTTGATGTCTGGAGTTTCAA | 2 | NC | NC | NC |
| 1328 | 2166 | CTTTGATGTCTGGAGTTTCA | 1 | NC | NC | NC |
| 1329 | 2167 | TCTTTGATGTCTGGAGTTTC | 2 | NC | NC | NC |
| 1330 | 2168 | ATCTTTGATGTCTGGAGTTT | 2 | NC | NC | NC |
| 1331 | 2169 | AATCTTTGATGTCTGGAGTT | 2 | NC | NC | NC |
| 1332 | 2170 | AAATCTTTGATGTCTGGAGT | 2 | NC | NC | NC |
| 1333 | 2171 | TAAATCTTTGATGTCTGGAG | 2 | NC | NC | NC |
| 1334 | 2172 | CTAAATCTTTGATGTCTGGA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1335 | 2173 | GCTAAATCTTTGATGTCTGG | 2 | NC | NC | NC |
| 1336 | 2174 | GGCTAAATCTTTGATGTCTG | 2 | NC | NC | NC |
| 1337 | 2175 | TGGCTAAATCTTTGATGTCT | 2 | NC | NC | NC |
| 1338 | 2176 | CTGGCTAAATCTTTGATGTC | 2 | NC | NC | NC |
| 1339 | 2177 | GCTGGCTAAATCTTTGATGT | 2 | NC | NC | NC |
| 1340 | 2178 | TGCTGGCTAAATCTTTGATG | 2 | NC | NC | NC |
| 1341 | 2179 | GTGCTGGCTAAATCTTTGAT | 2 | NC | NC | NC |
| 1342 | 2180 | AGTGCTGGCTAAATCTTTGA | 2 | NC | NC | NC |
| 1343 | 2181 | AAGTGCTGGCTAAATCTTTG | 2 | NC | NC | NC |
| 1344 | 2182 | AAAGTGCTGGCTAAATCTTT | 2 | NC | NC | NC |
| 1345 | 2183 | TAAAGTGCTGGCTAAATCTT | 2 | NC | NC | NC |
| 1346 | 2184 | TTAAAGTGCTGGCTAAATCT | 2 | NC | NC | NC |
| 1347 | 2185 | CTTAAAGTGCTGGCTAAATC | 2 | NC | NC | NC |
| 1348 | 2186 | ACTTAAAGTGCTGGCTAAAT | 2 | NC | NC | NC |
| 1349 | 2187 | TACTTAAAGTGCTGGCTAAA | 2 | NC | NC | NC |
| 1350 | 2188 | TTACTTAAAGTGCTGGCTAA | 2 | NC | NC | NC |
| 1351 | 2189 | TTTACTTAAAGTGCTGGCTA | 2 | NC | NC | NC |
| 1352 | 2190 | CTTTACTTAAAGTGCTGGCT | 2 | NC | NC | NC |
| 1353 | 2199 | GACCAGATTCTTTACTTAAA | 2 | NC | NC | NC |
| 1354 | 2200 | TGACCAGATTCTTTACTTAA | 1 | NC | NC | NC |
| 1355 | 2201 | TTGACCAGATTCTTTACTTA | 1 | NC | NC | NC |
| 1356 | 2202 | ATTGACCAGATTCTTTACTT | 1 | NC | NC | NC |
| 1357 | 2203 | AATTGACCAGATTCTTTACT | 2 | NC | NC | NC |
| 1358 | 2204 | CAATTGACCAGATTCTTTAC | 2 | NC | NC | NC |
| 1359 | 2205 | GCAATTGACCAGATTCTTTA | 2 | NC | NC | NC |
| 1360 | 2206 | GGCAATTGACCAGATTCTTT | 1 | NC | NC | NC |
| 1361 | 2233 | ATATTCGTTCTGCAATTTTT | 2 | NC | NC | NC |
| 1362 | 2234 | TATATTCGTTCTGCAATTTT | 2 | NC | NC | NC |
| 1363 | 2235 | TTATATTCGTTCTGCAATTT | 2 | NC | NC | NC |
| 1364 | 2236 | CTTATATTCGTTCTGCAATT | 2 | NC | NC | NC |
| 1365 | 2237 | ACTTATATTCGTTCTGCAAT | 2 | NC | NC | NC |
| 1366 | 2238 | AACTTATATTCGTTCTGCAA | 2 | NC | NC | NC |
| 1367 | 2239 | TAACTTATATTCGTTCTGCA | 2 | NC | NC | NC |
| 1368 | 2240 | ATAACTTATATTCGTTCTGC | 2 | NC | NC | NC |
| 1369 | 2241 | CATAACTTATATTCGTTCTG | 2 | NC | NC | NC |
| 1370 | 2242 | CCATAACTTATATTCGTTCT | 2 | NC | NC | NC |
| 1371 | 2243 | CCCATAACTTATATTCGTTC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1372 | 2244 | GCCCATAACTTATATTCGTT | 3 | NC | NC | NC |
| 1373 | 2245 | AGCCCATAACTTATATTCGT | 2 | NC | NC | NC |
| 1374 | 2246 | TAGCCCATAACTTATATTCG | 3 | NC | NC | NC |
| 1375 | 2247 | CTAGCCCATAACTTATATTC | 2 | NC | NC | NC |
| 1376 | 2248 | TCTAGCCCATAACTTATATT | 2 | NC | NC | NC |
| 1377 | 2249 | CTCTAGCCCATAACTTATAT | 2 | NC | NC | NC |
| 1378 | 2250 | TCTCTAGCCCATAACTTATA | 2 | NC | NC | NC |
| 1379 | 2251 | TTCTCTAGCCCATAACTTAT | 2 | NC | NC | NC |
| 1380 | 2252 | ATTCTCTAGCCCATAACTTA | 2 | NC | NC | NC |
| 1381 | 2253 | CATTCTCTAGCCCATAACTT | 1 | NC | NC | NC |
| 1382 | 2254 | TCATTCTCTAGCCCATAACT | 2 | NC | NC | NC |
| 1383 | 2255 | TTCATTCTCTAGCCCATAAC | 2 | NC | NC | NC |
| 1384 | 2256 | GTTCATTCTCTAGCCCATAA | 2 | NC | NC | NC |
| 1385 | 2257 | GGTTCATTCTCTAGCCCATA | 2 | NC | NC | NC |
| 1386 | 2258 | AGGTTCATTCTCTAGCCCAT | 2 | NC | NC | NC |
| 1387 | 2259 | TAGGTTCATTCTCTAGCCCA | 2 | 2 | NC | NC |
| 1388 | 2260 | GTAGGTTCATTCTCTAGCCC | 2 | 2 | NC | NC |
| 1389 | 2261 | TGTAGGTTCATTCTCTAGCC | 2 | 2 | NC | NC |
| 1390 | 2262 | CTGTAGGTTCATTCTCTAGC | 2 | 2 | NC | NC |
| 1391 | 2263 | GCTGTAGGTTCATTCTCTAG | 2 | 2 | NC | NC |
| 1392 | 2264 | TGCTGTAGGTTCATTCTCTA | 2 | 2 | NC | NC |
| 1393 | 2265 | TTGCTGTAGGTTCATTCTCT | 2 | 2 | NC | NC |
| 1394 | 2266 | GTTGCTGTAGGTTCATTCTC | 2 | 2 | NC | NC |
| 1395 | 2267 | AGTTGCTGTAGGTTCATTCT | 2 | 2 | NC | NC |
| 1396 | 2268 | AAGTTGCTGTAGGTTCATTC | 2 | 2 | NC | NC |
| 1397 | 2269 | TAAGTTGCTGTAGGTTCATT | 2 | 2 | NC | NC |
| 1398 | 2270 | ATAAGTTGCTGTAGGTTCAT | 2 | 2 | NC | NC |
| 1399 | 2271 | TATAAGTTGCTGTAGGTTCA | 2 | NC | NC | NC |
| 1400 | 2272 | GTATAAGTTGCTGTAGGTTC | 1 | NC | NC | NC |
| 1401 | 2273 | TGTATAAGTTGCTGTAGGTT | 2 | NC | NC | NC |
| 1402 | 2274 | TTGTATAAGTTGCTGTAGGT | 2 | NC | NC | NC |
| 1403 | 2275 | ATTGTATAAGTTGCTGTAGG | 2 | NC | NC | NC |
| 1404 | 2276 | CATTGTATAAGTTGCTGTAG | 2 | NC | NC | NC |
| 1405 | 2277 | ACATTGTATAAGTTGCTGTA | 1 | NC | NC | NC |
| 1406 | 2278 | AACATTGTATAAGTTGCTGT | 2 | NC | NC | NC |
| 1407 | 2279 | AAACATTGTATAAGTTGCTG | 2 | NC | NC | NC |
| 1408 | 2280 | AAAACATTGTATAAGTTGCT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1409 | 2281 | GAAAACATTGTATAAGTTGC | 2 | NC | NC | NC |
| 1410 | 2282 | AGAAAACATTGTATAAGTTG | 1 | NC | NC | NC |
| 1411 | 2283 | CAGAAAACATTGTATAAGTT | 2 | NC | NC | NC |
| 1412 | 2284 | GCAGAAAACATTGTATAAGT | 2 | NC | NC | NC |
| 1413 | 2285 | AGCAGAAAACATTGTATAAG | 2 | NC | NC | NC |
| 1414 | 2286 | AAGCAGAAAACATTGTATAA | 1 | NC | NC | NC |
| 1415 | 2287 | AAAGCAGAAAACATTGTATA | 1 | NC | NC | NC |
| 1416 | 2288 | AAAAGCAGAAAACATTGTAT | 2 | NC | NC | NC |
| 1417 | 2289 | GAAAAGCAGAAAACATTGTA | 1 | NC | NC | NC |
| 1418 | 2290 | TGAAAAGCAGAAAACATTGT | 2 | NC | NC | NC |
| 1419 | 2301 | TGCTACCTTCCTGAAAAGCA | 2 | NC | NC | NC |
| 1420 | 2302 | TTGCTACCTTCCTGAAAAGC | 2 | NC | NC | NC |
| 1421 | 2303 | TTTGCTACCTTCCTGAAAAG | 2 | NC | NC | NC |
| 1422 | 2304 | TTTTGCTACCTTCCTGAAAA | 1 | NC | NC | NC |
| 1423 | 2305 | TTTTTGCTACCTTCCTGAAA | 1 | NC | NC | NC |
| 1424 | 2321 | GCAATCTGTTTGTGATTTTT | 2 | NC | NC | NC |
| 1425 | 2322 | TGCAATCTGTTTGTGATTTT | 2 | NC | NC | NC |
| 1426 | 2323 | ATGCAATCTGTTTGTGATTT | 2 | NC | NC | NC |
| 1427 | 2324 | TATGCAATCTGTTTGTGATT | 2 | NC | NC | NC |
| 1428 | 2325 | ATATGCAATCTGTTTGTGAT | 2 | NC | NC | NC |
| 1429 | 2326 | AATATGCAATCTGTTTGTGA | 2 | NC | NC | NC |
| 1430 | 2327 | TAATATGCAATCTGTTTGTG | 2 | NC | NC | NC |
| 1431 | 2328 | ATAATATGCAATCTGTTTGT | 2 | NC | NC | NC |
| 1432 | 2330 | AGATAATATGCAATCTGTTT | 1 | NC | NC | NC |
| 1433 | 2334 | TATCAGATAATATGCAATCT | 2 | NC | NC | NC |
| 1434 | 2335 | GTATCAGATAATATGCAATC | 2 | NC | NC | NC |
| 1435 | 2336 | TGTATCAGATAATATGCAAT | 1 | NC | NC | NC |
| 1436 | 2337 | ATGTATCAGATAATATGCAA | 1 | 1 | NC | NC |
| 1437 | 2338 | GATGTATCAGATAATATGCA | 2 | 2 | NC | NC |
| 1438 | 2339 | GGATGTATCAGATAATATGC | 2 | 2 | NC | NC |
| 1439 | 2340 | GGGATGTATCAGATAATATG | 2 | 2 | NC | NC |
| 1440 | 2368 | GAAACGTGTCTATACCAGGG | 2 | 2 | NC | NC |
| 1441 | 2369 | GGAAACGTGTCTATACCAGG | 3 | NC | NC | NC |
| 1442 | 2370 | TGGAAACGTGTCTATACCAG | 2 | NC | NC | NC |
| 1443 | 2371 | TTGGAAACGTGTCTATACCA | 2 | NC | NC | NC |
| 1444 | 2372 | ATTGGAAACGTGTCTATACC | 3 | NC | NC | NC |
| 1445 | 2373 | CATTGGAAACGTGTCTATAC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1446 | 2374 | TCATTGGAAACGTGTCTATA | 3 | NC | NC | NC |
| 1447 | 2375 | ATCATTGGAAACGTGTCTAT | 2 | NC | NC | NC |
| 1448 | 2376 | TATCATTGGAAACGTGTCTA | 2 | NC | NC | NC |
| 1449 | 2377 | CTATCATTGGAAACGTGTCT | 2 | NC | NC | NC |
| 1450 | 2378 | ACTATCATTGGAAACGTGTC | 2 | NC | NC | NC |
| 1451 | 2379 | TACTATCATTGGAAACGTGT | 3 | NC | NC | NC |
| 1452 | 2380 | CTACTATCATTGGAAACGTG | 3 | NC | NC | NC |
| 1453 | 2381 | CCTACTATCATTGGAAACGT | 3 | NC | NC | NC |
| 1454 | 2382 | TCCTACTATCATTGGAAACG | 3 | NC | NC | NC |
| 1455 | 2383 | TTCCTACTATCATTGGAAAC | 2 | NC | NC | NC |
| 1456 | 2385 | TTTTCCTACTATCATTGGAA | 1 | NC | NC | NC |
| 1457 | 2386 | GTTTTCCTACTATCATTGGA | 2 | NC | NC | NC |
| 1458 | 2387 | TGTTTTCCTACTATCATTGG | 2 | NC | NC | NC |
| 1459 | 2388 | CTGTTTTCCTACTATCATTG | 1 | NC | NC | NC |
| 1460 | 2389 | TCTGTTTTCCTACTATCATT | 1 | 2 | NC | NC |
| 1461 | 2390 | ATCTGTTTTCCTACTATCAT | 2 | 2 | NC | NC |
| 1462 | 2391 | TATCTGTTTTCCTACTATCA | 2 | 2 | NC | NC |
| 1463 | 2392 | TTATCTGTTTTCCTACTATC | 2 | 2 | NC | NC |
| 1464 | 2393 | TTTATCTGTTTTCCTACTAT | 1 | 2 | NC | NC |
| 1465 | 2394 | ATTTATCTGTTTTCCTACTA | 1 | 1 | NC | NC |
| 1466 | 2395 | AATTTATCTGTTTTCCTACT | 1 | 1 | NC | NC |
| 1467 | 2396 | TAATTTATCTGTTTTCCTAC | 1 | 2 | NC | NC |
| 1468 | 2405 | GAAACCAATTAATTTATCTG | 2 | NC | NC | NC |
| 1469 | 2407 | GAGAAACCAATTAATTTATC | 1 | NC | NC | NC |
| 1470 | 2421 | GGACGATTGGTTTGGAGAAA | 1 | NC | NC | NC |
| 1471 | 2422 | CGGACGATTGGTTTGGAGAA | 2 | NC | NC | NC |
| 1472 | 2423 | ACGGACGATTGGTTTGGAGA | 3 | NC | NC | NC |
| 1473 | 2424 | TACGGACGATTGGTTTGGAG | 2 | 3 | NC | NC |
| 1474 | 2425 | TTACGGACGATTGGTTTGGA | 3 | 3 | NC | NC |
| 1475 | 2426 | CTTACGGACGATTGGTTTGG | 3 | 3 | NC | NC |
| 1476 | 2427 | TCTTACGGACGATTGGTTTG | 3 | 3 | NC | NC |
| 1477 | 2428 | TTCTTACGGACGATTGGTTT | 2 | 3 | NC | NC |
| 1478 | 2429 | CTTCTTACGGACGATTGGTT | 2 | 3 | NC | NC |
| 1479 | 2430 | GCTTCTTACGGACGATTGGT | 2 | 3 | NC | NC |
| 1480 | 2431 | AGCTTCTTACGGACGATTGG | 3 | 3 | NC | NC |
| 1481 | 2432 | TAGCTTCTTACGGACGATTG | 3 | 3 | NC | NC |
| 1482 | 2433 | TTAGCTTCTTACGGACGATT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1483 | 2434 | CTTAGCTTCTTACGGACGAT | 2 | 2 | NC | NC |
| 1484 | 2435 | GCTTAGCTTCTTACGGACGA | 3 | 3 | NC | NC |
| 1485 | 2436 | AGCTTAGCTTCTTACGGACG | 2 | 3 | NC | NC |
| 1486 | 2448 | GCTGTGAACTCAAGCTTAGC | 3 | 3 | NC | NC |
| 1487 | 2449 | AGCTGTGAACTCAAGCTTAG | 2 | 2 | NC | NC |
| 1488 | 2450 | TAGCTGTGAACTCAAGCTTA | 1 | 1 | NC | NC |
| 1489 | 2451 | CTAGCTGTGAACTCAAGCTT | 1 | 2 | NC | NC |
| 1490 | 2453 | TCCTAGCTGTGAACTCAAGC | 2 | 2 | NC | NC |
| 1491 | 2454 | ATCCTAGCTGTGAACTCAAG | 2 | 2 | NC | NC |
| 1492 | 2455 | GATCCTAGCTGTGAACTCAA | 2 | 2 | NC | NC |
| 1493 | 2456 | AGATCCTAGCTGTGAACTCA | 2 | 2 | NC | NC |
| 1494 | 2457 | AAGATCCTAGCTGTGAACTC | 2 | 2 | NC | NC |
| 1495 | 2458 | AAAGATCCTAGCTGTGAACT | 2 | 2 | NC | NC |
| 1496 | 2459 | TAAAGATCCTAGCTGTGAAC | 2 | 2 | NC | NC |
| 1497 | 2460 | CTAAAGATCCTAGCTGTGAA | 2 | 2 | NC | NC |
| 1498 | 2461 | TCTAAAGATCCTAGCTGTGA | 2 | 2 | NC | NC |
| 1499 | 2462 | CTCTAAAGATCCTAGCTGTG | 2 | 2 | NC | NC |
| 1500 | 2463 | TCTCTAAAGATCCTAGCTGT | 2 | 2 | NC | NC |
| 1501 | 2464 | TTCTCTAAAGATCCTAGCTG | 2 | 2 | NC | NC |
| 1502 | 2465 | CTTCTCTAAAGATCCTAGCT | 2 | 2 | NC | NC |
| 1503 | 2466 | ACTTCTCTAAAGATCCTAGC | 2 | 2 | NC | NC |
| 1504 | 2467 | AACTTCTCTAAAGATCCTAG | 2 | 2 | NC | NC |
| 1505 | 2468 | AAACTTCTCTAAAGATCCTA | 2 | 2 | NC | NC |
| 1506 | 2469 | TAAACTTCTCTAAAGATCCT | 2 | 2 | NC | NC |
| 1507 | 2470 | TTAAACTTCTCTAAAGATCC | 2 | 2 | NC | NC |
| 1508 | 2471 | CTTAAACTTCTCTAAAGATC | 2 | 2 | NC | NC |
| 1509 | 2472 | TCTTAAACTTCTCTAAAGAT | 1 | 1 | NC | NC |
| 1510 | 2473 | CTCTTAAACTTCTCTAAAGA | 2 | 1 | 1 | 2 |
| 1511 | 2474 | CCTCTTAAACTTCTCTAAAG | 1 | 1 | 2 | 2 |
| 1512 | 2475 | GCCTCTTAAACTTCTCTAAA | 2 | 1 | 2 | 2 |
| 1513 | 2476 | TGCCTCTTAAACTTCTCTAA | 2 | 1 | 1 | 2 |
| 1514 | 2477 | TTGCCTCTTAAACTTCTCTA | 2 | 1 | NC | NC |
| 1515 | 2478 | ATTGCCTCTTAAACTTCTCT | 1 | 1 | NC | NC |
| 1516 | 2479 | TATTGCCTCTTAAACTTCTC | 2 | 2 | NC | NC |
| 1517 | 2480 | ATATTGCCTCTTAAACTTCT | 2 | 2 | NC | NC |
| 1518 | 2481 | CATATTGCCTCTTAAACTTC | 2 | 2 | NC | NC |
| 1519 | 2482 | CCATATTGCCTCTTAAACTT | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1520 | 2483 | CCCATATTGCCTCTTAAACT | 2 | 2 | NC | NC |
| 1521 | 2484 | TCCCATATTGCCTCTTAAAC | 2 | 2 | NC | NC |
| 1522 | 2485 | TTCCCATATTGCCTCTTAAA | 2 | 2 | NC | NC |
| 1523 | 2486 | CTTCCCATATTGCCTCTTAA | 2 | 2 | NC | NC |
| 1524 | 2487 | CCTTCCCATATTGCCTCTTA | 2 | 2 | NC | NC |
| 1525 | 2488 | ACCTTCCCATATTGCCTCTT | 2 | 2 | NC | NC |
| 1526 | 2489 | AACCTTCCCATATTGCCTCT | 2 | 2 | NC | NC |
| 1527 | 2490 | CAACCTTCCCATATTGCCTC | 2 | 2 | NC | NC |
| 1528 | 2491 | TCAACCTTCCCATATTGCCT | 2 | 2 | NC | NC |
| 1529 | 2492 | TTCAACCTTCCCATATTGCC | 2 | 2 | NC | NC |
| 1530 | 2493 | TTTCAACCTTCCCATATTGC | 2 | 2 | NC | NC |
| 1531 | 2494 | TTTTCAACCTTCCCATATTG | 2 | 2 | NC | NC |
| 1532 | 2495 | ATTTTCAACCTTCCCATATT | 1 | 1 | NC | NC |
| 1533 | 2496 | GATTTTCAACCTTCCCATAT | 2 | 2 | NC | NC |
| 1534 | 2497 | GGATTTTCAACCTTCCCATA | 1 | 2 | NC | NC |
| 1535 | 2498 | AGGATTTTCAACCTTCCCAT | 2 | 2 | NC | NC |
| 1536 | 2499 | GAGGATTTTCAACCTTCCCA | 1 | 2 | NC | NC |
| 1537 | 2500 | AGAGGATTTTCAACCTTCCC | 1 | 1 | NC | NC |
| 1538 | 2501 | CAGAGGATTTTCAACCTTCC | 2 | 2 | NC | NC |
| 1539 | 2502 | CCAGAGGATTTTCAACCTTC | 1 | 2 | NC | NC |
| 1540 | 2503 | TCCAGAGGATTTTCAACCTT | 1 | 1 | NC | NC |
| 1541 | 2504 | ATCCAGAGGATTTTCAACCT | 1 | 1 | NC | NC |
| 1542 | 2505 | TATCCAGAGGATTTTCAACC | 2 | 2 | NC | NC |
| 1543 | 2506 | GTATCCAGAGGATTTTCAAC | 2 | 2 | NC | NC |
| 1544 | 2507 | TGTATCCAGAGGATTTTCAA | 1 | 1 | NC | NC |
| 1545 | 2508 | CTGTATCCAGAGGATTTTCA | 2 | 2 | NC | NC |
| 1546 | 2519 | TTCCTCTACTTCTGTATCCA | 2 | 2 | NC | NC |
| 1547 | 2520 | TTTCCTCTACTTCTGTATCC | 2 | 2 | NC | NC |
| 1548 | 2521 | CTTTCCTCTACTTCTGTATC | 2 | 2 | NC | NC |
| 1549 | 2522 | ACTTTCCTCTACTTCTGTAT | 2 | 1 | NC | NC |
| 1550 | 2523 | TACTTTCCTCTACTTCTGTA | 1 | 1 | NC | NC |
| 1551 | 2524 | TTACTTTCCTCTACTTCTGT | 2 | 2 | NC | NC |
| 1552 | 2525 | ATTACTTTCCTCTACTTCTG | 2 | NC | NC | NC |
| 1553 | 2526 | CATTACTTTCCTCTACTTCT | 1 | NC | NC | NC |
| 1554 | 2527 | CCATTACTTTCCTCTACTTC | 1 | NC | NC | NC |
| 1555 | 2528 | TCCATTACTTTCCTCTACTT | 0 | NC | NC | NC |
| 1556 | 2529 | CTCCATTACTTTCCTCTACT | 0 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1557 | 2530 | ACTCCATTACTTTCCTCTAC | 0 | NC | NC | NC |
| 1558 | 2531 | GACTCCATTACTTTCCTCTA | 1 | NC | NC | NC |
| 1559 | 2532 | TGACTCCATTACTTTCCTCT | 1 | NC | NC | NC |
| 1560 | 2533 | GTGACTCCATTACTTTCCTC | 1 | NC | NC | NC |
| 1561 | 2534 | AGTGACTCCATTACTTTCCT | 2 | NC | NC | NC |
| 1562 | 2535 | TAGTGACTCCATTACTTTCC | 2 | NC | NC | NC |
| 1563 | 2536 | GTAGTGACTCCATTACTTTC | 2 | NC | NC | NC |
| 1564 | 2537 | GGTAGTGACTCCATTACTTT | 2 | NC | NC | NC |
| 1565 | 2538 | TGGTAGTGACTCCATTACTT | 3 | NC | NC | NC |
| 1566 | 2539 | TTGGTAGTGACTCCATTACT | 2 | NC | NC | NC |
| 1567 | 2540 | ATTGGTAGTGACTCCATTAC | 2 | NC | NC | NC |
| 1568 | 2541 | GATTGGTAGTGACTCCATTA | 3 | NC | NC | NC |
| 1569 | 2542 | AGATTGGTAGTGACTCCATT | 1 | NC | NC | NC |
| 1570 | 2543 | GAGATTGGTAGTGACTCCAT | 2 | NC | NC | NC |
| 1571 | 2544 | TGAGATTGGTAGTGACTCCA | 2 | NC | NC | NC |
| 1572 | 2545 | CTGAGATTGGTAGTGACTCC | 2 | 3 | NC | NC |
| 1573 | 2546 | ACTGAGATTGGTAGTGACTC | 2 | 3 | NC | NC |
| 1574 | 2547 | GACTGAGATTGGTAGTGACT | 2 | 2 | NC | NC |
| 1575 | 2548 | AGACTGAGATTGGTAGTGAC | 2 | NC | NC | NC |
| 1576 | 2549 | AAGACTGAGATTGGTAGTGA | 2 | NC | NC | NC |
| 1577 | 2550 | GAAGACTGAGATTGGTAGTG | 2 | NC | NC | NC |
| 1578 | 2551 | TGAAGACTGAGATTGGTAGT | 2 | NC | NC | NC |
| 1579 | 2552 | TTGAAGACTGAGATTGGTAG | 2 | NC | NC | NC |
| 1580 | 2553 | CTTGAAGACTGAGATTGGTA | 1 | NC | NC | NC |
| 1581 | 2554 | ACTTGAAGACTGAGATTGGT | 2 | NC | NC | NC |
| 1582 | 2555 | AACTTGAAGACTGAGATTGG | 2 | NC | NC | NC |
| 1583 | 2556 | CAACTTGAAGACTGAGATTG | 2 | NC | NC | NC |
| 1584 | 2557 | TCAACTTGAAGACTGAGATT | 1 | NC | NC | NC |
| 1585 | 2558 | TTCAACTTGAAGACTGAGAT | 2 | NC | NC | NC |
| 1586 | 2559 | GTTCAACTTGAAGACTGAGA | 2 | NC | NC | NC |
| 1587 | 2560 | GGTTCAACTTGAAGACTGAG | 2 | NC | NC | NC |
| 1588 | 2561 | AGGTTCAACTTGAAGACTGA | 2 | NC | NC | NC |
| 1589 | 2562 | CAGGTTCAACTTGAAGACTG | 2 | NC | NC | NC |
| 1590 | 2563 | TCAGGTTCAACTTGAAGACT | 2 | NC | NC | NC |
| 1591 | 2564 | GTCAGGTTCAACTTGAAGAC | 2 | NC | NC | NC |
| 1592 | 2565 | TGTCAGGTTCAACTTGAAGA | 2 | NC | NC | NC |
| 1593 | 2566 | ATGTCAGGTTCAACTTGAAG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1594 | 2567 | AATGTCAGGTTCAACTTGAA | 2 | NC | NC | NC |
| 1595 | 2568 | GAATGTCAGGTTCAACTTGA | 2 | 2 | NC | NC |
| 1596 | 2569 | AGAATGTCAGGTTCAACTTG | 2 | 2 | NC | NC |
| 1597 | 2570 | CAGAATGTCAGGTTCAACTT | 2 | 2 | NC | NC |
| 1598 | 2584 | TTCTTGTCCTTCAGCAGAAT | 2 | NC | NC | NC |
| 1599 | 2585 | GTTCTTGTCCTTCAGCAGAA | 1 | NC | NC | NC |
| 1600 | 2586 | GGTTCTTGTCCTTCAGCAGA | 2 | NC | NC | NC |
| 1601 | 2587 | CGGTTCTTGTCCTTCAGCAG | 2 | NC | NC | NC |
| 1602 | 2588 | GCGGTTCTTGTCCTTCAGCA | 2 | NC | NC | NC |
| 1603 | 2589 | AGCGGTTCTTGTCCTTCAGC | 1 | NC | NC | NC |
| 1604 | 2590 | AAGCGGTTCTTGTCCTTCAG | 1 | NC | NC | NC |
| 1605 | 2591 | TAAGCGGTTCTTGTCCTTCA | 2 | NC | NC | NC |
| 1606 | 2592 | CTAAGCGGTTCTTGTCCTTC | 2 | NC | NC | NC |
| 1607 | 2593 | TCTAAGCGGTTCTTGTCCTT | 3 | NC | NC | NC |
| 1608 | 2594 | CTCTAAGCGGTTCTTGTCCT | 3 | NC | NC | NC |
| 1609 | 2595 | TCTCTAAGCGGTTCTTGTCC | 2 | NC | NC | NC |
| 1610 | 2596 | TTCTCTAAGCGGTTCTTGTC | 2 | NC | NC | NC |
| 1611 | 2597 | GTTCTCTAAGCGGTTCTTGT | 2 | NC | NC | NC |
| 1612 | 2598 | AGTTCTCTAAGCGGTTCTTG | 2 | NC | NC | NC |
| 1613 | 2600 | AGAGTTCTCTAAGCGGTTCT | 2 | NC | NC | NC |
| 1614 | 2601 | CAGAGTTCTCTAAGCGGTTC | 3 | NC | NC | NC |
| 1615 | 2602 | TCAGAGTTCTCTAAGCGGTT | 3 | NC | NC | NC |
| 1616 | 2603 | ATCAGAGTTCTCTAAGCGGT | 3 | NC | NC | NC |
| 1617 | 2604 | CATCAGAGTTCTCTAAGCGG | 3 | NC | NC | NC |
| 1618 | 2605 | ACATCAGAGTTCTCTAAGCG | 2 | NC | NC | NC |
| 1619 | 2606 | AACATCAGAGTTCTCTAAGC | 1 | NC | NC | NC |
| 1620 | 2607 | AAACATCAGAGTTCTCTAAG | 1 | NC | NC | NC |
| 1621 | 2608 | CAAACATCAGAGTTCTCTAA | 1 | NC | NC | NC |
| 1622 | 2609 | ACAAACATCAGAGTTCTCTA | 1 | NC | NC | NC |
| 1623 | 2610 | TACAAACATCAGAGTTCTCT | 2 | NC | NC | NC |
| 1624 | 2611 | TTACAAACATCAGAGTTCTC | 2 | NC | NC | NC |
| 1625 | 2612 | TTTACAAACATCAGAGTTCT | 2 | NC | NC | NC |
| 1626 | 2613 | TTTTACAAACATCAGAGTTC | 2 | NC | NC | NC |
| 1627 | 2614 | ATTTTACAAACATCAGAGTT | 2 | 2 | NC | NC |
| 1628 | 2615 | GATTTTACAAACATCAGAGT | 2 | 1 | NC | NC |
| 1629 | 2616 | TGATTTTACAAACATCAGAG | 2 | 2 | NC | NC |
| 1630 | 2617 | GTGATTTTACAAACATCAGA | 1 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1631 | 2618 | AGTGATTTTACAAACATCAG | 2 | 1 | NC | NC |
| 1632 | 2619 | TAGTGATTTTACAAACATCA | 2 | 1 | NC | NC |
| 1633 | 2620 | GTAGTGATTTTACAAACATC | 2 | 2 | NC | NC |
| 1634 | 2621 | AGTAGTGATTTTACAAACAT | 2 | 2 | NC | NC |
| 1635 | 2622 | TAGTAGTGATTTTACAAACA | 1 | 2 | NC | NC |
| 1636 | 2623 | ATAGTAGTGATTTTACAAAC | 2 | 2 | NC | NC |
| 1637 | 2624 | CATAGTAGTGATTTTACAAA | 2 | 1 | NC | NC |
| 1638 | 2625 | CCATAGTAGTGATTTTACAA | 2 | NC | NC | NC |
| 1639 | 2626 | TCCATAGTAGTGATTTTACA | 2 | NC | NC | NC |
| 1640 | 2627 | CTCCATAGTAGTGATTTTAC | 2 | NC | NC | NC |
| 1641 | 2628 | GCTCCATAGTAGTGATTTTA | 2 | NC | NC | NC |
| 1642 | 2629 | TGCTCCATAGTAGTGATTTT | 2 | NC | NC | NC |
| 1643 | 2630 | ATGCTCCATAGTAGTGATTT | 2 | NC | NC | NC |
| 1644 | 2631 | TATGCTCCATAGTAGTGATT | 3 | NC | NC | NC |
| 1645 | 2632 | CTATGCTCCATAGTAGTGAT | 3 | NC | NC | NC |
| 1646 | 2640 | CTGAATCACTATGCTCCATA | 2 | NC | NC | NC |
| 1647 | 2641 | TCTGAATCACTATGCTCCAT | 2 | NC | NC | NC |
| 1648 | 2642 | ATCTGAATCACTATGCTCCA | 2 | NC | NC | NC |
| 1649 | 2643 | TATCTGAATCACTATGCTCC | 2 | NC | NC | NC |
| 1650 | 2644 | CTATCTGAATCACTATGCTC | 2 | NC | NC | NC |
| 1651 | 2645 | ACTATCTGAATCACTATGCT | 2 | NC | NC | NC |
| 1652 | 2646 | TACTATCTGAATCACTATGC | 2 | NC | NC | NC |
| 1653 | 2647 | CTACTATCTGAATCACTATG | 2 | NC | NC | NC |
| 1654 | 2648 | ACTACTATCTGAATCACTAT | 2 | NC | NC | NC |
| 1655 | 2649 | AACTACTATCTGAATCACTA | 2 | NC | NC | NC |
| 1656 | 2650 | CAACTACTATCTGAATCACT | 1 | NC | NC | NC |
| 1657 | 2651 | ACAACTACTATCTGAATCAC | 1 | NC | NC | NC |
| 1658 | 2652 | GACAACTACTATCTGAATCA | 2 | NC | NC | NC |
| 1659 | 2653 | TGACAACTACTATCTGAATC | 2 | NC | NC | NC |
| 1660 | 2654 | TTGACAACTACTATCTGAAT | 1 | NC | NC | NC |
| 1661 | 2655 | GTTGACAACTACTATCTGAA | 2 | NC | NC | NC |
| 1662 | 2656 | GGTTGACAACTACTATCTGA | 2 | NC | NC | NC |
| 1663 | 2657 | TGGTTGACAACTACTATCTG | 2 | NC | NC | NC |
| 1664 | 2658 | CTGGTTGACAACTACTATCT | 1 | NC | NC | NC |
| 1665 | 2659 | GCTGGTTGACAACTACTATC | 2 | NC | NC | NC |
| 1666 | 2660 | TGCTGGTTGACAACTACTAT | 2 | NC | NC | NC |
| 1667 | 2661 | TTGCTGGTTGACAACTACTA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1668 | 2662 | CTTGCTGGTTGACAACTACT | 2 | NC | NC | NC |
| 1669 | 2663 | GCTTGCTGGTTGACAACTAC | 2 | NC | NC | NC |
| 1670 | 2664 | GGCTTGCTGGTTGACAACTA | 2 | NC | NC | NC |
| 1671 | 2665 | TGGCTTGCTGGTTGACAACT | 2 | NC | NC | NC |
| 1672 | 2666 | GTGGCTTGCTGGTTGACAAC | 2 | NC | NC | NC |
| 1673 | 2667 | TGTGGCTTGCTGGTTGACAA | 2 | NC | NC | NC |
| 1674 | 2668 | ATGTGGCTTGCTGGTTGACA | 2 | NC | NC | NC |
| 1675 | 2669 | GATGTGGCTTGCTGGTTGAC | 2 | NC | NC | NC |
| 1676 | 2670 | GGATGTGGCTTGCTGGTTGA | 2 | NC | NC | NC |
| 1677 | 2671 | AGGATGTGGCTTGCTGGTTG | 2 | NC | NC | NC |
| 1678 | 2672 | AAGGATGTGGCTTGCTGGTT | 2 | NC | NC | NC |
| 1679 | 2673 | TAAGGATGTGGCTTGCTGGT | 2 | NC | NC | NC |
| 1680 | 2674 | TTAAGGATGTGGCTTGCTGG | 2 | NC | NC | NC |
| 1681 | 2675 | GTTAAGGATGTGGCTTGCTG | 2 | NC | NC | NC |
| 1682 | 2676 | AGTTAAGGATGTGGCTTGCT | 2 | NC | NC | NC |
| 1683 | 2677 | GAGTTAAGGATGTGGCTTGC | 2 | NC | NC | NC |
| 1684 | 2678 | TGAGTTAAGGATGTGGCTTG | 2 | NC | NC | NC |
| 1685 | 2679 | CTGAGTTAAGGATGTGGCTT | 2 | NC | NC | NC |
| 1686 | 2680 | TCTGAGTTAAGGATGTGGCT | 2 | NC | NC | NC |
| 1687 | 2681 | CTCTGAGTTAAGGATGTGGC | 2 | NC | NC | NC |
| 1688 | 2682 | TCTCTGAGTTAAGGATGTGG | 2 | NC | NC | NC |
| 1689 | 2683 | TTCTCTGAGTTAAGGATGTG | 2 | NC | NC | NC |
| 1690 | 2684 | CTTCTCTGAGTTAAGGATGT | 2 | NC | NC | NC |
| 1691 | 2685 | ACTTCTCTGAGTTAAGGATG | 2 | NC | NC | NC |
| 1692 | 2686 | AACTTCTCTGAGTTAAGGAT | 2 | NC | NC | NC |
| 1693 | 2687 | AAACTTCTCTGAGTTAAGGA | 2 | NC | NC | NC |
| 1694 | 2688 | GAAACTTCTCTGAGTTAAGG | 2 | NC | NC | NC |
| 1695 | 2689 | GGAAACTTCTCTGAGTTAAG | 2 | NC | NC | NC |
| 1696 | 2690 | TGGAAACTTCTCTGAGTTAA | 2 | NC | NC | NC |
| 1697 | 2691 | ATGGAAACTTCTCTGAGTTA | 2 | NC | NC | NC |
| 1698 | 2693 | GAATGGAAACTTCTCTGAGT | 2 | NC | NC | NC |
| 1699 | 2694 | AGAATGGAAACTTCTCTGAG | 2 | NC | NC | NC |
| 1700 | 2699 | CTTGGAGAATGGAAACTTCT | 1 | NC | NC | NC |
| 1701 | 2700 | CCTTGGAGAATGGAAACTTC | 2 | NC | NC | NC |
| 1702 | 2701 | TCCTTGGAGAATGGAAACTT | 1 | NC | NC | NC |
| 1703 | 2702 | ATCCTTGGAGAATGGAAACT | 2 | NC | NC | NC |
| 1704 | 2703 | CATCCTTGGAGAATGGAAAC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1705 | 2704 | TCATCCTTGGAGAATGGAAA | 1 | NC | NC | NC |
| 1706 | 2705 | TTCATCCTTGGAGAATGGAA | 2 | 2 | NC | NC |
| 1707 | 2706 | CTTCATCCTTGGAGAATGGA | 2 | 2 | NC | NC |
| 1708 | 2707 | TCTTCATCCTTGGAGAATGG | 2 | 2 | NC | NC |
| 1709 | 2708 | ATCTTCATCCTTGGAGAATG | 2 | 2 | NC | NC |
| 1710 | 2709 | AATCTTCATCCTTGGAGAAT | 2 | 2 | NC | NC |
| 1711 | 2710 | CAATCTTCATCCTTGGAGAA | 1 | 2 | NC | NC |
| 1712 | 2712 | AACAATCTTCATCCTTGGAG | 2 | 2 | NC | NC |
| 1713 | 2713 | AAACAATCTTCATCCTTGGA | 2 | 2 | NC | NC |
| 1714 | 2714 | TAAACAATCTTCATCCTTGG | 2 | 2 | NC | NC |
| 1715 | 2715 | CTAAACAATCTTCATCCTTG | 2 | 2 | NC | NC |
| 1716 | 2716 | TCTAAACAATCTTCATCCTT | 2 | 2 | NC | NC |
| 1717 | 2717 | TTCTAAACAATCTTCATCCT | 2 | 2 | NC | NC |
| 1718 | 2718 | GTTCTAAACAATCTTCATCC | 2 | 2 | NC | NC |
| 1719 | 2719 | TGTTCTAAACAATCTTCATC | 2 | 2 | NC | NC |
| 1720 | 2729 | AGGCATCTGTTGTTCTAAAC | 2 | 1 | NC | NC |
| 1721 | 2730 | TAGGCATCTGTTGTTCTAAA | 2 | 2 | NC | NC |
| 1722 | 2731 | CTAGGCATCTGTTGTTCTAA | 2 | 2 | NC | NC |
| 1723 | 2732 | ACTAGGCATCTGTTGTTCTA | 2 | 3 | NC | NC |
| 1724 | 2733 | AACTAGGCATCTGTTGTTCT | 2 | 2 | NC | NC |
| 1725 | 2734 | AAACTAGGCATCTGTTGTTC | 2 | 2 | NC | NC |
| 1726 | 2735 | CAAACTAGGCATCTGTTGTT | 2 | 1 | NC | NC |
| 1727 | 2736 | TCAAACTAGGCATCTGTTGT | 2 | 2 | NC | NC |
| 1728 | 2737 | CTCAAACTAGGCATCTGTTG | 2 | 3 | NC | NC |
| 1729 | 2738 | TCTCAAACTAGGCATCTGTT | 2 | 2 | NC | NC |
| 1730 | 2739 | CTCTCAAACTAGGCATCTGT | 1 | 2 | NC | NC |
| 1731 | 2740 | TCTCTCAAACTAGGCATCTG | 1 | 2 | NC | NC |
| 1732 | 2741 | TTCTCTCAAACTAGGCATCT | 1 | 2 | NC | NC |
| 1733 | 2742 | TTTCTCTCAAACTAGGCATC | 2 | 2 | NC | NC |
| 1734 | 2743 | CTTTCTCTCAAACTAGGCAT | 2 | 2 | NC | NC |
| 1735 | 2744 | ACTTTCTCTCAAACTAGGCA | 2 | NC | NC | NC |
| 1736 | 2745 | GACTTTCTCTCAAACTAGGC | 2 | NC | NC | NC |
| 1737 | 2746 | GGACTTTCTCTCAAACTAGG | 2 | NC | NC | NC |
| 1738 | 2747 | AGGACTTTCTCTCAAACTAG | 1 | NC | NC | NC |
| 1739 | 2748 | TAGGACTTTCTCTCAAACTA | 2 | NC | NC | NC |
| 1740 | 2749 | ATAGGACTTTCTCTCAAACT | 2 | NC | NC | NC |
| 1741 | 2750 | CATAGGACTTTCTCTCAAAC | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1742 | 2751 | TCATAGGACTTTCTCTCAAA | 2 | NC | NC | NC |
| 1743 | 2763 | ACTCCTTCAGGGTCATAGGA | 2 | NC | NC | NC |
| 1744 | 2764 | AACTCCTTCAGGGTCATAGG | 2 | 2 | NC | NC |
| 1745 | 2765 | TAACTCCTTCAGGGTCATAG | 2 | 2 | NC | NC |
| 1746 | 2766 | ATAACTCCTTCAGGGTCATA | 2 | 2 | NC | NC |
| 1747 | 2767 | GATAACTCCTTCAGGGTCAT | 2 | 2 | NC | NC |
| 1748 | 2768 | AGATAACTCCTTCAGGGTCA | 2 | 2 | NC | NC |
| 1749 | 2769 | GAGATAACTCCTTCAGGGTC | 2 | 2 | NC | NC |
| 1750 | 2780 | TCTATTAAAGAGAGATAACT | 1 | 1 | NC | NC |
| 1751 | 2781 | TTCTATTAAAGAGAGATAAC | 2 | 2 | NC | NC |
| 1752 | 2784 | GTTTTCTATTAAAGAGAGAT | 1 | 0 | NC | NC |
| 1753 | 2785 | GGTTTTCTATTAAAGAGAGA | 2 | 1 | NC | NC |
| 1754 | 2786 | AGGTTTTCTATTAAAGAGAG | 2 | 2 | NC | NC |
| 1755 | 2787 | AAGGTTTTCTATTAAAGAGA | 2 | 2 | NC | NC |
| 1756 | 2788 | AAAGGTTTTCTATTAAAGAG | 1 | 2 | NC | NC |
| 1757 | 2789 | CAAAGGTTTTCTATTAAAGA | 1 | 1 | NC | NC |
| 1758 | 2790 | CCAAAGGTTTTCTATTAAAG | 1 | 2 | NC | NC |
| 1759 | 2791 | TCCAAAGGTTTTCTATTAAA | 1 | 1 | NC | NC |
| 1760 | 2792 | GTCCAAAGGTTTTCTATTAA | 2 | 1 | NC | NC |
| 1761 | 2793 | GGTCCAAAGGTTTTCTATTA | 2 | 2 | NC | NC |
| 1762 | 2794 | AGGTCCAAAGGTTTTCTATT | 2 | 2 | NC | NC |
| 1763 | 2795 | AAGGTCCAAAGGTTTTCTAT | 2 | 2 | NC | NC |
| 1764 | 2796 | CAAGGTCCAAAGGTTTTCTA | 2 | 2 | NC | NC |
| 1765 | 2797 | TCAAGGTCCAAAGGTTTTCT | 2 | 2 | NC | NC |
| 1766 | 2798 | CTCAAGGTCCAAAGGTTTTC | 2 | 2 | NC | NC |
| 1767 | 2799 | TCTCAAGGTCCAAAGGTTTT | 2 | 1 | NC | NC |
| 1768 | 2800 | TTCTCAAGGTCCAAAGGTTT | 2 | 2 | NC | NC |
| 1769 | 2801 | CTTCTCAAGGTCCAAAGGTT | 2 | 2 | NC | NC |
| 1770 | 2802 | ACTTCTCAAGGTCCAAAGGT | 2 | 2 | NC | NC |
| 1771 | 2803 | GACTTCTCAAGGTCCAAAGG | 2 | 1 | NC | NC |
| 1772 | 2804 | TGACTTCTCAAGGTCCAAAG | 1 | 1 | NC | NC |
| 1773 | 2805 | ATGACTTCTCAAGGTCCAAA | 1 | 1 | NC | NC |
| 1774 | 2806 | GATGACTTCTCAAGGTCCAA | 1 | 2 | NC | NC |
| 1775 | 2807 | AGATGACTTCTCAAGGTCCA | 1 | 2 | NC | NC |
| 1776 | 2808 | CAGATGACTTCTCAAGGTCC | 1 | 2 | NC | NC |
| 1777 | 2809 | TCAGATGACTTCTCAAGGTC | 2 | 2 | NC | NC |
| 1778 | 2810 | TTCAGATGACTTCTCAAGGT | 1 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1779 | 2811 | ATTCAGATGACTTCTCAAGG | 1 | 2 | NC | NC |
| 1780 | 2812 | GATTCAGATGACTTCTCAAG | 2 | 2 | NC | NC |
| 1781 | 2813 | TGATTCAGATGACTTCTCAA | 2 | 2 | NC | NC |
| 1782 | 2814 | GTGATTCAGATGACTTCTCA | 2 | 2 | NC | NC |
| 1783 | 2815 | AGTGATTCAGATGACTTCTC | 2 | 2 | NC | NC |
| 1784 | 2816 | TAGTGATTCAGATGACTTCT | 2 | 2 | NC | NC |
| 1785 | 2817 | CTAGTGATTCAGATGACTTC | 2 | 2 | NC | NC |
| 1786 | 2818 | GCTAGTGATTCAGATGACTT | 2 | 2 | NC | NC |
| 1787 | 2819 | GGCTAGTGATTCAGATGACT | 3 | 2 | NC | NC |
| 1788 | 2820 | AGGCTAGTGATTCAGATGAC | 3 | 2 | NC | NC |
| 1789 | 2821 | GAGGCTAGTGATTCAGATGA | 3 | 2 | NC | NC |
| 1790 | 2822 | AGAGGCTAGTGATTCAGATG | 2 | 2 | NC | NC |
| 1791 | 2823 | TAGAGGCTAGTGATTCAGAT | 2 | 2 | NC | NC |
| 1792 | 2824 | TTAGAGGCTAGTGATTCAGA | 2 | 1 | NC | NC |
| 1793 | 2825 | TTTAGAGGCTAGTGATTCAG | 3 | 1 | NC | NC |
| 1794 | 2826 | ATTTAGAGGCTAGTGATTCA | 2 | 2 | NC | NC |
| 1795 | 2827 | AATTTAGAGGCTAGTGATTC | 2 | 2 | NC | NC |
| 1796 | 2828 | TAATTTAGAGGCTAGTGATT | 2 | 2 | NC | NC |
| 1797 | 2829 | ATAATTTAGAGGCTAGTGAT | 2 | 2 | NC | NC |
| 1798 | 2830 | GATAATTTAGAGGCTAGTGA | 2 | 2 | NC | NC |
| 1799 | 2831 | GGATAATTTAGAGGCTAGTG | 2 | 2 | NC | NC |
| 1800 | 2832 | TGGATAATTTAGAGGCTAGT | 3 | 3 | NC | NC |
| 1801 | 2833 | CTGGATAATTTAGAGGCTAG | 2 | 2 | NC | NC |
| 1802 | 2834 | TCTGGATAATTTAGAGGCTA | 2 | 2 | NC | NC |
| 1803 | 2835 | GTCTGGATAATTTAGAGGCT | 2 | 2 | NC | NC |
| 1804 | 2836 | AGTCTGGATAATTTAGAGGC | 2 | NC | NC | NC |
| 1805 | 2837 | CAGTCTGGATAATTTAGAGG | 2 | NC | NC | NC |
| 1806 | 2838 | TCAGTCTGGATAATTTAGAG | 2 | NC | NC | NC |
| 1807 | 2839 | TTCAGTCTGGATAATTTAGA | 2 | NC | NC | NC |
| 1808 | 2840 | CTTCAGTCTGGATAATTTAG | 2 | NC | NC | NC |
| 1809 | 2841 | CCTTCAGTCTGGATAATTTA | 2 | NC | NC | NC |
| 1810 | 2842 | CCCTTCAGTCTGGATAATTT | 2 | NC | NC | NC |
| 1811 | 2843 | ACCCTTCAGTCTGGATAATT | 2 | NC | NC | NC |
| 1812 | 2844 | AACCCTTCAGTCTGGATAAT | 2 | NC | NC | NC |
| 1813 | 2845 | GAACCCTTCAGTCTGGATAA | 2 | NC | NC | NC |
| 1814 | 2846 | GGAACCCTTCAGTCTGGATA | 3 | NC | NC | NC |
| 1815 | 2847 | CGGAACCCTTCAGTCTGGAT | 3 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1816 | 2848 | TCGGAACCCTTCAGTCTGGA | 3 | NC | NC | NC |
| 1817 | 2849 | TTCGGAACCCTTCAGTCTGG | 3 | NC | NC | NC |
| 1818 | 2850 | TTTCGGAACCCTTCAGTCTG | 2 | NC | NC | NC |
| 1819 | 2851 | CTTTCGGAACCCTTCAGTCT | 2 | NC | NC | NC |
| 1820 | 2852 | TCTTTCGGAACCCTTCAGTC | 3 | NC | NC | NC |
| 1821 | 2853 | CTCTTTCGGAACCCTTCAGT | 3 | NC | NC | NC |
| 1822 | 2854 | TCTCTTTCGGAACCCTTCAG | 2 | NC | NC | NC |
| 1823 | 2855 | TTCTCTTTCGGAACCCTTCA | 2 | NC | NC | NC |
| 1824 | 2856 | TTTCTCTTTCGGAACCCTTC | 3 | 2 | NC | NC |
| 1825 | 2857 | GTTTCTCTTTCGGAACCCTT | 2 | 2 | NC | NC |
| 1826 | 2858 | AGTTTCTCTTTCGGAACCCT | 2 | 2 | NC | NC |
| 1827 | 2859 | GAGTTTCTCTTTCGGAACCC | 3 | 2 | NC | NC |
| 1828 | 2860 | TGAGTTTCTCTTTCGGAACC | 1 | 2 | NC | NC |
| 1829 | 2861 | TTGAGTTTCTCTTTCGGAAC | 2 | 2 | NC | NC |
| 1830 | 2862 | TTTGAGTTTCTCTTTCGGAA | 1 | 1 | NC | NC |
| 1831 | 2863 | GTTTGAGTTTCTCTTTCGGA | 2 | 2 | NC | NC |
| 1832 | 2864 | TGTTTGAGTTTCTCTTTCGG | 2 | 2 | NC | NC |
| 1833 | 2865 | TTGTTTGAGTTTCTCTTTCG | 1 | 2 | NC | NC |
| 1834 | 2866 | ATTGTTTGAGTTTCTCTTTC | 1 | 1 | NC | NC |
| 1835 | 2867 | CATTGTTTGAGTTTCTCTTT | 2 | 2 | NC | NC |
| 1836 | 2868 | CCATTGTTTGAGTTTCTCTT | 2 | 2 | NC | NC |
| 1837 | 2869 | CCCATTGTTTGAGTTTCTCT | 2 | NC | NC | NC |
| 1838 | 2870 | CCCCATTGTTTGAGTTTCTC | 2 | NC | NC | NC |
| 1839 | 2871 | TCCCCATTGTTTGAGTTTCT | 1 | NC | NC | NC |
| 1840 | 2872 | ATCCCCATTGTTTGAGTTTC | 2 | NC | NC | NC |
| 1841 | 2873 | CATCCCCATTGTTTGAGTTT | 2 | NC | NC | NC |
| 1842 | 2874 | TCATCCCCATTGTTTGAGTT | 1 | NC | NC | NC |
| 1843 | 2875 | ATCATCCCCATTGTTTGAGT | 2 | NC | NC | NC |
| 1844 | 2876 | CATCATCCCCATTGTTTGAG | 1 | NC | NC | NC |
| 1845 | 2877 | TCATCATCCCCATTGTTTGA | 2 | NC | NC | NC |
| 1846 | 2878 | CTCATCATCCCCATTGTTTG | 2 | NC | NC | NC |
| 1847 | 2879 | ACTCATCATCCCCATTGTTT | 2 | NC | NC | NC |
| 1848 | 2880 | GACTCATCATCCCCATTGTT | 2 | NC | NC | NC |
| 1849 | 2881 | CGACTCATCATCCCCATTGT | 2 | NC | NC | NC |
| 1850 | 2882 | ACGACTCATCATCCCCATTG | 1 | NC | NC | NC |
| 1851 | 2883 | AACGACTCATCATCCCCATT | 2 | NC | NC | NC |
| 1852 | 2884 | AAACGACTCATCATCCCCAT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1853 | 2885 | AAAACGACTCATCATCCCCA | 2 | NC | NC | NC |
| 1854 | 2886 | TAAAACGACTCATCATCCCC | 2 | NC | NC | NC |
| 1855 | 2887 | TTAAAACGACTCATCATCCC | 1 | NC | NC | NC |
| 1856 | 2888 | ATTAAAACGACTCATCATCC | 0 | NC | NC | NC |
| 1857 | 2889 | CATTAAAACGACTCATCATC | 0 | 2 | NC | NC |
| 1858 | 2890 | TCATTAAAACGACTCATCAT | 1 | 2 | NC | NC |
| 1859 | 2891 | TTCATTAAAACGACTCATCA | 2 | 2 | NC | NC |
| 1860 | 2892 | GTTCATTAAAACGACTCATC | 2 | 2 | NC | NC |
| 1861 | 2893 | AGTTCATTAAAACGACTCAT | 2 | 2 | NC | NC |
| 1862 | 2894 | AAGTTCATTAAAACGACTCA | 2 | 2 | NC | NC |
| 1863 | 2895 | GAAGTTCATTAAAACGACTC | 2 | 3 | NC | NC |
| 1864 | 2896 | GGAAGTTCATTAAAACGACT | 2 | 2 | NC | NC |
| 1865 | 2897 | TGGAAGTTCATTAAAACGAC | 3 | 3 | NC | NC |
| 1866 | 2898 | TTGGAAGTTCATTAAAACGA | 2 | 2 | NC | NC |
| 1867 | 2899 | TTTGGAAGTTCATTAAAACG | 1 | 2 | NC | NC |
| 1868 | 2900 | ATTTGGAAGTTCATTAAAAC | 1 | 2 | NC | NC |
| 1869 | 2902 | GAATTTGGAAGTTCATTAAA | 2 | 2 | NC | NC |
| 1870 | 2903 | TGAATTTGGAAGTTCATTAA | 2 | 2 | NC | NC |
| 1871 | 2904 | CTGAATTTGGAAGTTCATTA | 2 | 2 | NC | NC |
| 1872 | 2905 | TCTGAATTTGGAAGTTCATT | 2 | 1 | NC | NC |
| 1873 | 2906 | ATCTGAATTTGGAAGTTCAT | 2 | 2 | NC | NC |
| 1874 | 2907 | AATCTGAATTTGGAAGTTCA | 2 | 2 | NC | NC |
| 1875 | 2908 | GAATCTGAATTTGGAAGTTC | 2 | 2 | NC | NC |
| 1876 | 2909 | GGAATCTGAATTTGGAAGTT | 2 | 2 | NC | NC |
| 1877 | 2910 | TGGAATCTGAATTTGGAAGT | 1 | 1 | NC | NC |
| 1878 | 2911 | CTGGAATCTGAATTTGGAAG | 2 | 2 | NC | NC |
| 1879 | 2912 | ACTGGAATCTGAATTTGGAA | 2 | 2 | NC | NC |
| 1880 | 2913 | TACTGGAATCTGAATTTGGA | 2 | 2 | NC | NC |
| 1881 | 2914 | CTACTGGAATCTGAATTTGG | 2 | 2 | NC | NC |
| 1882 | 2915 | CCTACTGGAATCTGAATTTG | 2 | 2 | NC | NC |
| 1883 | 2927 | CTTGCTGTCTTTCCTACTGG | 2 | NC | NC | NC |
| 1884 | 2928 | ACTTGCTGTCTTTCCTACTG | 2 | NC | NC | NC |
| 1885 | 2929 | AACTTGCTGTCTTTCCTACT | 2 | NC | NC | NC |
| 1886 | 2930 | CAACTTGCTGTCTTTCCTAC | 1 | NC | NC | NC |
| 1887 | 2931 | ACAACTTGCTGTCTTTCCTA | 1 | NC | NC | NC |
| 1888 | 2932 | CACAACTTGCTGTCTTTCCT | 2 | NC | NC | NC |
| 1889 | 2943 | TTAACACACTGCACAACTTG | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 1890 | 2944 | GTTAACACACTGCACAACTT | 1 | 2 | NC | NC |
| 1891 | 2945 | TGTTAACACACTGCACAACT | 1 | 2 | NC | NC |
| 1892 | 2957 | ACAAAAATCTTGTGTTAACA | 2 | 2 | NC | NC |
| 1893 | 2958 | TACAAAAATCTTGTGTTAAC | 2 | 2 | NC | NC |
| 1894 | 2960 | CATACAAAAATCTTGTGTTA | 2 | 1 | NC | NC |
| 1895 | 2961 | ACATACAAAAATCTTGTGTT | 2 | 1 | NC | NC |
| 1896 | 2962 | AACATACAAAAATCTTGTGT | 2 | 1 | NC | NC |
| 1897 | 2963 | TAACATACAAAAATCTTGTG | 1 | 2 | NC | NC |
| 1898 | 2980 | TCATGCTTGTTGTTAAATAA | 2 | NC | NC | NC |
| 1899 | 2981 | TTCATGCTTGTTGTTAAATA | 2 | NC | NC | NC |
| 1900 | 2982 | TTTCATGCTTGTTGTTAAAT | 1 | NC | NC | NC |
| 1901 | 2983 | TTTTCATGCTTGTTGTTAAA | 1 | NC | NC | NC |
| 1902 | 2984 | TTTTTCATGCTTGTTGTTAA | 1 | NC | NC | NC |
| 1903 | 3000 | TGACACCATTCTCTGTTTTT | 2 | 2 | NC | NC |
| 1904 | 3001 | ATGACACCATTCTCTGTTTT | 2 | 2 | NC | NC |
| 1905 | 3002 | GATGACACCATTCTCTGTTT | 2 | 2 | NC | NC |
| 1906 | 3003 | GGATGACACCATTCTCTGTT | 2 | 3 | NC | NC |
| 1907 | 3004 | GGGATGACACCATTCTCTGT | 2 | 2 | NC | NC |
| 1908 | 3005 | TGGGATGACACCATTCTCTG | 2 | 2 | NC | NC |
| 1909 | 3006 | TTGGGATGACACCATTCTCT | 1 | 1 | NC | NC |
| 1910 | 3007 | GTTGGGATGACACCATTCTC | 2 | 2 | NC | NC |
| 1911 | 3008 | TGTTGGGATGACACCATTCT | 2 | 2 | NC | NC |
| 1912 | 3009 | ATGTTGGGATGACACCATTC | 2 | 2 | NC | NC |
| 1913 | 3010 | GATGTTGGGATGACACCATT | 2 | 3 | NC | NC |
| 1914 | 3011 | TGATGTTGGGATGACACCAT | 2 | 2 | NC | NC |
| 1915 | 3012 | CTGATGTTGGGATGACACCA | 2 | 2 | NC | NC |
| 1916 | 3013 | TCTGATGTTGGGATGACACC | 2 | 2 | NC | NC |
| 1917 | 3014 | ATCTGATGTTGGGATGACAC | 2 | 2 | NC | NC |
| 1918 | 3015 | AATCTGATGTTGGGATGACA | 2 | 2 | NC | NC |
| 1919 | 3016 | GAATCTGATGTTGGGATGAC | 2 | 2 | NC | NC |
| 1920 | 3017 | AGAATCTGATGTTGGGATGA | 2 | 2 | NC | NC |
| 1921 | 3018 | CAGAATCTGATGTTGGGATG | 2 | 2 | NC | NC |
| 1922 | 3019 | GCAGAATCTGATGTTGGGAT | 2 | 2 | NC | NC |
| 1923 | 3020 | GGCAGAATCTGATGTTGGGA | 2 | 2 | NC | NC |
| 1924 | 3021 | TGGCAGAATCTGATGTTGGG | 2 | 1 | NC | NC |
| 1925 | 3022 | GTGGCAGAATCTGATGTTGG | 2 | 2 | NC | NC |
| 1926 | 3023 | TGTGGCAGAATCTGATGTTG | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1927 | 3024 | GTGTGGCAGAATCTGATGTT | 2 | 2 | NC | NC |
| 1928 | 3025 | TGTGTGGCAGAATCTGATGT | 2 | 1 | NC | NC |
| 1929 | 3065 | GTTAGAATGTGTTTTACTAT | 1 | 1 | NC | NC |
| 1930 | 3066 | TGTTAGAATGTGTTTTACTA | 2 | 2 | NC | NC |
| 1931 | 3067 | CTGTTAGAATGTGTTTTACT | 2 | 2 | NC | NC |
| 1932 | 3068 | GCTGTTAGAATGTGTTTTAC | 2 | 2 | NC | NC |
| 1933 | 3069 | TGCTGTTAGAATGTGTTTTA | 2 | 1 | NC | NC |
| 1934 | 3070 | TTGCTGTTAGAATGTGTTTT | 2 | 2 | NC | NC |
| 1935 | 3071 | ATTGCTGTTAGAATGTGTTT | 2 | 2 | NC | NC |
| 1936 | 3072 | TATTGCTGTTAGAATGTGTT | 2 | 2 | NC | NC |
| 1937 | 3073 | GTATTGCTGTTAGAATGTGT | 2 | 2 | NC | NC |
| 1938 | 3074 | TGTATTGCTGTTAGAATGTG | 2 | 2 | NC | NC |
| 1939 | 3075 | TTGTATTGCTGTTAGAATGT | 2 | 2 | NC | NC |
| 1940 | 3076 | GTTGTATTGCTGTTAGAATG | 2 | 2 | NC | NC |
| 1941 | 3077 | TGTTGTATTGCTGTTAGAAT | 2 | 2 | NC | NC |
| 1942 | 3078 | CTGTTGTATTGCTGTTAGAA | 2 | 2 | NC | NC |
| 1943 | 3079 | TCTGTTGTATTGCTGTTAGA | 2 | 2 | NC | NC |
| 1944 | 3080 | CTCTGTTGTATTGCTGTTAG | 2 | 2 | NC | NC |
| 1945 | 3081 | TCTCTGTTGTATTGCTGTTA | 2 | 2 | NC | NC |
| 1946 | 3082 | TTCTCTGTTGTATTGCTGTT | 2 | 2 | NC | NC |
| 1947 | 3083 | GTTCTCTGTTGTATTGCTGT | 2 | 2 | NC | NC |
| 1948 | 3084 | AGTTCTCTGTTGTATTGCTG | 2 | 1 | NC | NC |
| 1949 | 3085 | CAGTTCTCTGTTGTATTGCT | 2 | 2 | NC | NC |
| 1950 | 3096 | CTGATATCACACAGTTCTCT | 2 | 2 | NC | NC |
| 1951 | 3097 | TCTGATATCACACAGTTCTC | 2 | 2 | NC | NC |
| 1952 | 3098 | TTCTGATATCACACAGTTCT | 2 | 1 | NC | NC |
| 1953 | 3099 | TTTCTGATATCACACAGTTC | 2 | 2 | NC | NC |
| 1954 | 3100 | GTTTCTGATATCACACAGTT | 2 | 2 | NC | NC |
| 1955 | 3101 | AGTTTCTGATATCACACAGT | 2 | 2 | NC | NC |
| 1956 | 3102 | GAGTTTCTGATATCACACAG | 2 | 2 | NC | NC |
| 1957 | 3103 | GGAGTTTCTGATATCACACA | 2 | 2 | NC | NC |
| 1958 | 3104 | AGGAGTTTCTGATATCACAC | 2 | 2 | NC | NC |
| 1959 | 3105 | AAGGAGTTTCTGATATCACA | 2 | 2 | NC | NC |
| 1960 | 3106 | AAAGGAGTTTCTGATATCAC | 2 | 2 | NC | NC |
| 1961 | 3107 | CAAAGGAGTTTCTGATATCA | 1 | 2 | NC | NC |
| 1962 | 3108 | CCAAAGGAGTTTCTGATATC | 1 | 2 | NC | NC |
| 1963 | 3109 | ACCAAAGGAGTTTCTGATAT | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 1964 | 3110 | TACCAAAGGAGTTTCTGATA | 2 | 2 | NC | NC |
| 1965 | 3111 | ATACCAAAGGAGTTTCTGAT | 2 | 2 | NC | NC |
| 1966 | 3112 | AATACCAAAGGAGTTTCTGA | 1 | 1 | NC | NC |
| 1967 | 3113 | CAATACCAAAGGAGTTTCTG | 1 | 1 | NC | NC |
| 1968 | 3114 | GCAATACCAAAGGAGTTTCT | 2 | 2 | NC | NC |
| 1969 | 3127 | GAATTATTATAGGGCAATAC | 2 | NC | NC | NC |
| 1970 | 3128 | AGAATTATTATAGGGCAATA | 2 | NC | NC | NC |
| 1971 | 3129 | TAGAATTATTATAGGGCAAT | 1 | NC | NC | NC |
| 1972 | 3130 | TTAGAATTATTATAGGGCAA | 1 | NC | NC | NC |
| 1973 | 3131 | TTTAGAATTATTATAGGGCA | 2 | NC | NC | NC |
| 1974 | 3132 | CTTTAGAATTATTATAGGGC | 2 | NC | NC | NC |
| 1975 | 3133 | ACTTTAGAATTATTATAGGG | 2 | NC | NC | NC |
| 1976 | 3138 | CGGTAACTTTAGAATTATTA | 2 | NC | NC | NC |
| 1977 | 3139 | CCGGTAACTTTAGAATTATT | 2 | NC | NC | NC |
| 1978 | 3140 | ACCGGTAACTTTAGAATTAT | 2 | NC | NC | NC |
| 1979 | 3141 | TACCGGTAACTTTAGAATTA | 2 | NC | NC | NC |
| 1980 | 3142 | TTACCGGTAACTTTAGAATT | 1 | NC | NC | NC |
| 1981 | 3143 | TTTACCGGTAACTTTAGAAT | 2 | NC | NC | NC |
| 1982 | 3144 | CTTTACCGGTAACTTTAGAA | 3 | NC | NC | NC |
| 1983 | 3145 | TCTTTACCGGTAACTTTAGA | 2 | NC | NC | NC |
| 1984 | 3146 | ATCTTTACCGGTAACTTTAG | 2 | NC | NC | NC |
| 1985 | 3147 | AATCTTTACCGGTAACTTTA | 2 | NC | NC | NC |
| 1986 | 3148 | GAATCTTTACCGGTAACTTT | 3 | NC | NC | NC |
| 1987 | 3149 | TGAATCTTTACCGGTAACTT | 2 | NC | NC | NC |
| 1988 | 3150 | CTGAATCTTTACCGGTAACT | 3 | NC | NC | NC |
| 1989 | 3151 | TCTGAATCTTTACCGGTAAC | 2 | NC | NC | NC |
| 1990 | 3152 | ATCTGAATCTTTACCGGTAA | 3 | NC | NC | NC |
| 1991 | 3153 | CATCTGAATCTTTACCGGTA | 3 | NC | NC | NC |
| 1992 | 3154 | ACATCTGAATCTTTACCGGT | 3 | NC | NC | NC |
| 1993 | 3155 | AACATCTGAATCTTTACCGG | 2 | NC | NC | NC |
| 1994 | 3156 | GAACATCTGAATCTTTACCG | 2 | NC | NC | NC |
| 1995 | 3157 | AGAACATCTGAATCTTTACC | 2 | NC | NC | NC |
| 1996 | 3158 | AAGAACATCTGAATCTTTAC | 2 | 2 | NC | NC |
| 1997 | 3159 | TAAGAACATCTGAATCTTTA | 2 | 2 | NC | NC |
| 1998 | 3160 | ATAAGAACATCTGAATCTTT | 1 | 2 | NC | NC |
| 1999 | 3161 | GATAAGAACATCTGAATCTT | 2 | 2 | NC | NC |
| 2000 | 3162 | TGATAAGAACATCTGAATCT | 1 | 2 | 2 | 1 |

TABLE 2-continued

Exemplary Oligonucleotides

| SEQ ID NO | Position | Sequence | Off-target Score Human | Cyno | Mouse | Rat |
|---|---|---|---|---|---|---|
| 2001 | 3163 | CTGATAAGAACATCTGAATC | 2 | 2 | 1 | 2 |
| 2002 | 3164 | TCTGATAAGAACATCTGAAT | 2 | 2 | 1 | 2 |
| 2003 | 3165 | CTCTGATAAGAACATCTGAA | 1 | 2 | NC | NC |
| 2004 | 3166 | GCTCTGATAAGAACATCTGA | 2 | 2 | NC | NC |
| 2005 | 3167 | GGCTCTGATAAGAACATCTG | 2 | NC | NC | NC |
| 2006 | 3168 | AGGCTCTGATAAGAACATCT | 2 | NC | NC | NC |
| 2007 | 3169 | GAGGCTCTGATAAGAACATC | 1 | NC | NC | NC |
| 2008 | 3170 | TGAGGCTCTGATAAGAACAT | 1 | NC | NC | NC |
| 2009 | 3171 | CTGAGGCTCTGATAAGAACA | 2 | NC | NC | NC |
| 2010 | 3172 | TCTGAGGCTCTGATAAGAAC | 2 | NC | NC | NC |
| 2011 | 3173 | TTCTGAGGCTCTGATAAGAA | 2 | NC | NC | NC |
| 2012 | 3174 | GTTCTGAGGCTCTGATAAGA | 1 | NC | NC | NC |
| 2013 | 3175 | TGTTCTGAGGCTCTGATAAG | 1 | NC | NC | NC |
| 2014 | 3176 | TTGTTCTGAGGCTCTGATAA | 1 | NC | NC | NC |
| 2015 | 3177 | GTTGTTCTGAGGCTCTGATA | 1 | NC | NC | NC |
| 2016 | 3178 | TGTTGTTCTGAGGCTCTGAT | 2 | NC | NC | NC |
| 2017 | 3179 | CTGTTGTTCTGAGGCTCTGA | 2 | NC | NC | NC |
| 2018 | 3180 | TCTGTTGTTCTGAGGCTCTG | 2 | NC | NC | NC |
| 2019 | 3181 | ATCTGTTGTTCTGAGGCTCT | 2 | NC | NC | NC |
| 2020 | 3182 | TATCTGTTGTTCTGAGGCTC | 1 | NC | NC | NC |
| 2021 | 3183 | CTATCTGTTGTTCTGAGGCT | 1 | NC | NC | NC |
| 2022 | 3184 | CCTATCTGTTGTTCTGAGGC | 2 | NC | NC | NC |
| 2023 | 3185 | TCCTATCTGTTGTTCTGAGG | 2 | NC | NC | NC |
| 2024 | 3186 | TTCCTATCTGTTGTTCTGAG | 1 | NC | NC | NC |
| 2025 | 3187 | CTTCCTATCTGTTGTTCTGA | 2 | NC | NC | NC |
| 2026 | 3188 | ACTTCCTATCTGTTGTTCTG | 2 | NC | NC | NC |
| 2027 | 3189 | GACTTCCTATCTGTTGTTCT | 2 | NC | NC | NC |
| 2028 | 3190 | AGACTTCCTATCTGTTGTTC | 2 | NC | NC | NC |
| 2029 | 3191 | AAGACTTCCTATCTGTTGTT | 2 | NC | NC | NC |
| 2030 | 3192 | CAAGACTTCCTATCTGTTGT | 2 | NC | NC | NC |
| 2031 | 3193 | TCAAGACTTCCTATCTGTTG | 2 | NC | NC | NC |
| 2032 | 3194 | GTCAAGACTTCCTATCTGTT | 2 | NC | NC | NC |
| 2033 | 3195 | AGTCAAGACTTCCTATCTGT | 2 | NC | NC | NC |
| 2034 | 3206 | TCCACTGGGAGAGTCAAGAC | 2 | NC | NC | NC |
| 2035 | 3217 | TTCATTAACATTCCACTGGG | 2 | 2 | NC | NC |
| 2036 | 3218 | ATTCATTAACATTCCACTGG | 1 | 2 | NC | NC |
| 2037 | 3219 | GATTCATTAACATTCCACTG | 1 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2038 | 3220 | GGATTCATTAACATTCCACT | 2 | NC | NC | NC |
| 2039 | 3221 | CGGATTCATTAACATTCCAC | 2 | NC | NC | NC |
| 2040 | 3222 | CCGGATTCATTAACATTCCA | 3 | NC | NC | NC |
| 2041 | 3223 | ACCGGATTCATTAACATTCC | 2 | NC | NC | NC |
| 2042 | 3224 | TACCGGATTCATTAACATTC | 3 | NC | NC | NC |
| 2043 | 3225 | CTACCGGATTCATTAACATT | 3 | NC | NC | NC |
| 2044 | 3226 | TCTACCGGATTCATTAACAT | 3 | NC | NC | NC |
| 2045 | 3227 | TTCTACCGGATTCATTAACA | 2 | NC | NC | NC |
| 2046 | 3228 | CTTCTACCGGATTCATTAAC | 3 | NC | NC | NC |
| 2047 | 3229 | TCTTCTACCGGATTCATTAA | 2 | NC | NC | NC |
| 2048 | 3230 | ATCTTCTACCGGATTCATTA | 2 | NC | NC | NC |
| 2049 | 3231 | CATCTTCTACCGGATTCATT | 2 | NC | NC | NC |
| 2050 | 3232 | GCATCTTCTACCGGATTCAT | 2 | NC | NC | NC |
| 2051 | 3233 | GGCATCTTCTACCGGATTCA | 2 | NC | NC | NC |
| 2052 | 3234 | TGGCATCTTCTACCGGATTC | 2 | NC | NC | NC |
| 2053 | 3235 | GTGGCATCTTCTACCGGATT | 2 | NC | NC | NC |
| 2054 | 3236 | TGTGGCATCTTCTACCGGAT | 2 | NC | NC | NC |
| 2055 | 3237 | CTGTGGCATCTTCTACCGGA | 2 | NC | NC | NC |
| 2056 | 3239 | ACCTGTGGCATCTTCTACCG | 2 | NC | NC | NC |
| 2057 | 3240 | CACCTGTGGCATCTTCTACC | 2 | NC | NC | NC |
| 2058 | 3241 | TCACCTGTGGCATCTTCTAC | 2 | NC | NC | NC |
| 2059 | 3242 | GTCACCTGTGGCATCTTCTA | 2 | NC | NC | NC |
| 2060 | 3243 | GGTCACCTGTGGCATCTTCT | 1 | NC | NC | NC |
| 2061 | 3244 | TGGTCACCTGTGGCATCTTC | 1 | NC | NC | NC |
| 2062 | 3245 | TTGGTCACCTGTGGCATCTT | 2 | NC | NC | NC |
| 2063 | 3246 | TTTGGTCACCTGTGGCATCT | 2 | NC | NC | NC |
| 2064 | 3247 | TTTTGGTCACCTGTGGCATC | 2 | 2 | NC | NC |
| 2065 | 3248 | ATTTTGGTCACCTGTGGCAT | 2 | 2 | NC | NC |
| 2066 | 3249 | CATTTTGGTCACCTGTGGCA | 2 | 2 | NC | NC |
| 2067 | 3250 | CCATTTTGGTCACCTGTGGC | 2 | 3 | NC | NC |
| 2068 | 3263 | CTGAAAACAAATTCCATTTT | 1 | NC | NC | NC |
| 2069 | 3264 | TCTGAAAACAAATTCCATTT | 1 | NC | NC | NC |
| 2070 | 3265 | CTCTGAAAACAAATTCCATT | 1 | NC | NC | NC |
| 2071 | 3266 | ACTCTGAAAACAAATTCCAT | 2 | NC | NC | NC |
| 2072 | 3267 | CACTCTGAAAACAAATTCCA | 1 | NC | NC | NC |
| 2073 | 3268 | TCACTCTGAAAACAAATTCC | 2 | NC | NC | NC |
| 2074 | 3269 | CTCACTCTGAAAACAAATTC | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2075 | 3270 | CCTCACTCTGAAAACAAATT | 2 | NC | NC | NC |
| 2076 | 3271 | TCCTCACTCTGAAAACAAAT | 2 | NC | NC | NC |
| 2077 | 3272 | TTCCTCACTCTGAAAACAAA | 2 | NC | NC | NC |
| 2078 | 3273 | ATTCCTCACTCTGAAAACAA | 2 | NC | NC | NC |
| 2079 | 3274 | GATTCCTCACTCTGAAAACA | 2 | NC | NC | NC |
| 2080 | 3275 | AGATTCCTCACTCTGAAAAC | 2 | NC | NC | NC |
| 2081 | 3276 | TAGATTCCTCACTCTGAAAA | 2 | NC | NC | NC |
| 2082 | 3277 | TTAGATTCCTCACTCTGAAA | 2 | NC | NC | NC |
| 2083 | 3278 | TTTAGATTCCTCACTCTGAA | 2 | NC | NC | NC |
| 2084 | 3279 | CTTTAGATTCCTCACTCTGA | 2 | NC | NC | NC |
| 2085 | 3280 | GCTTTAGATTCCTCACTCTG | 1 | NC | NC | NC |
| 2086 | 3281 | TGCTTTAGATTCCTCACTCT | 2 | NC | NC | NC |
| 2087 | 3282 | TTGCTTTAGATTCCTCACTC | 2 | NC | NC | NC |
| 2088 | 3283 | CTTGCTTTAGATTCCTCACT | 1 | 2 | NC | NC |
| 2089 | 3284 | TCTTGCTTTAGATTCCTCAC | 1 | 2 | NC | NC |
| 2090 | 3285 | CTCTTGCTTTAGATTCCTCA | 2 | 1 | NC | NC |
| 2091 | 3286 | GCTCTTGCTTTAGATTCCTC | 2 | 2 | NC | NC |
| 2092 | 3300 | CAGTTTCAGAACAAGCTCTT | 2 | 2 | NC | NC |
| 2093 | 3301 | TCAGTTTCAGAACAAGCTCT | 2 | 1 | NC | NC |
| 2094 | 3302 | TTCAGTTTCAGAACAAGCTC | 2 | 2 | NC | NC |
| 2095 | 3303 | CTTCAGTTTCAGAACAAGCT | 2 | 2 | NC | NC |
| 2096 | 3304 | TCTTCAGTTTCAGAACAAGC | 1 | 2 | NC | NC |
| 2097 | 3305 | CTCTTCAGTTTCAGAACAAG | 1 | 1 | NC | NC |
| 2098 | 3306 | ACTCTTCAGTTTCAGAACAA | 2 | 2 | NC | NC |
| 2099 | 3307 | GACTCTTCAGTTTCAGAACA | 2 | 2 | NC | NC |
| 2100 | 3308 | TGACTCTTCAGTTTCAGAAC | 2 | 2 | NC | NC |
| 2101 | 3309 | TTGACTCTTCAGTTTCAGAA | 2 | 2 | NC | NC |
| 2102 | 3310 | TTTGACTCTTCAGTTTCAGA | 2 | 2 | NC | NC |
| 2103 | 3311 | GTTTGACTCTTCAGTTTCAG | 2 | 2 | NC | NC |
| 2104 | 3312 | TGTTTGACTCTTCAGTTTCA | 2 | 2 | NC | NC |
| 2105 | 3313 | GTGTTTGACTCTTCAGTTTC | 2 | 2 | NC | NC |
| 2106 | 3314 | CGTGTTTGACTCTTCAGTTT | 2 | 2 | NC | NC |
| 2107 | 3315 | ACGTGTTTGACTCTTCAGTT | 2 | 2 | NC | NC |
| 2108 | 3316 | CACGTGTTTGACTCTTCAGT | 2 | 2 | NC | NC |
| 2109 | 3317 | ACACGTGTTTGACTCTTCAG | 2 | 2 | NC | NC |
| 2110 | 3318 | AACACGTGTTTGACTCTTCA | 3 | 2 | NC | NC |
| 2111 | 3330 | GCCAATCTGAACAACACGTG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2112 | 3331 | TGCCAATCTGAACAACACGT | 2 | NC | NC | NC |
| 2113 | 3332 | CTGCCAATCTGAACAACACG | 2 | NC | NC | NC |
| 2114 | 3333 | GCTGCCAATCTGAACAACAC | 1 | NC | NC | NC |
| 2115 | 3334 | CGCTGCCAATCTGAACAACA | 2 | NC | NC | NC |
| 2116 | 3335 | CCGCTGCCAATCTGAACAAC | 2 | NC | NC | NC |
| 2117 | 3336 | GCCGCTGCCAATCTGAACAA | 2 | NC | NC | NC |
| 2118 | 3337 | TGCCGCTGCCAATCTGAACA | 2 | NC | NC | NC |
| 2119 | 3338 | ATGCCGCTGCCAATCTGAAC | 2 | NC | NC | NC |
| 2120 | 3339 | AATGCCGCTGCCAATCTGAA | 1 | NC | NC | NC |
| 2121 | 3340 | AAATGCCGCTGCCAATCTGA | 1 | NC | NC | NC |
| 2122 | 3341 | GAAATGCCGCTGCCAATCTG | 2 | NC | NC | NC |
| 2123 | 3342 | CGAAATGCCGCTGCCAATCT | 2 | NC | NC | NC |
| 2124 | 3343 | TCGAAATGCCGCTGCCAATC | 2 | NC | NC | NC |
| 2125 | 3344 | ATCGAAATGCCGCTGCCAAT | 2 | NC | NC | NC |
| 2126 | 3345 | CATCGAAATGCCGCTGCCAA | 3 | NC | NC | NC |
| 2127 | 3346 | ACATCGAAATGCCGCTGCCA | 2 | NC | NC | NC |
| 2128 | 3347 | TACATCGAAATGCCGCTGCC | 3 | NC | NC | NC |
| 2129 | 3348 | CTACATCGAAATGCCGCTGC | 3 | NC | NC | NC |
| 2130 | 3349 | GCTACATCGAAATGCCGCTG | 3 | NC | NC | NC |
| 2131 | 3350 | GGCTACATCGAAATGCCGCT | 3 | NC | NC | NC |
| 2132 | 3354 | CCAGGGCTACATCGAAATGC | 3 | 2 | NC | NC |
| 2133 | 3356 | TCCCAGGGCTACATCGAAAT | 3 | NC | NC | NC |
| 2134 | 3357 | TTCCCAGGGCTACATCGAAA | 2 | NC | NC | NC |
| 2135 | 3358 | CTTCCCAGGGCTACATCGAA | 2 | NC | NC | NC |
| 2136 | 3359 | TCTTCCCAGGGCTACATCGA | 2 | NC | NC | NC |
| 2137 | 3360 | TTCTTCCCAGGGCTACATCG | 2 | NC | NC | NC |
| 2138 | 3361 | ATTCTTCCCAGGGCTACATC | 2 | NC | NC | NC |
| 2139 | 3362 | CATTCTTCCCAGGGCTACAT | 1 | NC | NC | NC |
| 2140 | 3363 | CCATTCTTCCCAGGGCTACA | 1 | NC | NC | NC |
| 2141 | 3364 | ACCATTCTTCCCAGGGCTAC | 1 | NC | NC | NC |
| 2142 | 3365 | AACCATTCTTCCCAGGGCTA | 2 | NC | NC | NC |
| 2143 | 3366 | AAACCATTCTTCCCAGGGCT | 2 | NC | NC | NC |
| 2144 | 3367 | TAAACCATTCTTCCCAGGGC | 2 | NC | NC | NC |
| 2145 | 3368 | ATAAACCATTCTTCCCAGGG | 2 | NC | NC | NC |
| 2146 | 3369 | CATAAACCATTCTTCCCAGG | 2 | NC | NC | NC |
| 2147 | 3370 | ACATAAACCATTCTTCCCAG | 2 | NC | NC | NC |
| 2148 | 3371 | GACATAAACCATTCTTCCCA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2149 | 3372 | TGACATAAACCATTCTTCCC | 2 | NC | NC | NC |
| 2150 | 3373 | TTGACATAAACCATTCTTCC | 2 | NC | NC | NC |
| 2151 | 3374 | GTTGACATAAACCATTCTTC | 2 | NC | NC | NC |
| 2152 | 3375 | TGTTGACATAAACCATTCTT | 2 | NC | NC | NC |
| 2153 | 3376 | TTGTTGACATAAACCATTCT | 2 | 2 | NC | NC |
| 2154 | 3377 | TTTGTTGACATAAACCATTC | 2 | 2 | NC | NC |
| 2155 | 3378 | TTTTGTTGACATAAACCATT | 2 | 2 | NC | NC |
| 2156 | 3379 | ATTTTGTTGACATAAACCAT | 2 | 2 | NC | NC |
| 2157 | 3380 | CATTTTGTTGACATAAACCA | 2 | 2 | NC | NC |
| 2158 | 3381 | TCATTTTGTTGACATAAACC | 2 | 2 | NC | NC |
| 2159 | 3389 | GAGTCCAGTCATTTTGTTGA | 2 | 2 | NC | NC |
| 2160 | 3390 | TGAGTCCAGTCATTTTGTTG | 2 | 3 | NC | NC |
| 2161 | 3391 | CTGAGTCCAGTCATTTTGTT | 1 | 2 | NC | NC |
| 2162 | 3402 | CAATGAATGTGCTGAGTCCA | 2 | 2 | NC | NC |
| 2163 | 3429 | AAGCAGCCTGAATGTCCTCA | 2 | 2 | NC | NC |
| 2164 | 3430 | CAAGCAGCCTGAATGTCCTC | 1 | 1 | NC | NC |
| 2165 | 3431 | ACAAGCAGCCTGAATGTCCT | 2 | 2 | NC | NC |
| 2166 | 3432 | TACAAGCAGCCTGAATGTCC | 2 | 1 | NC | NC |
| 2167 | 3433 | GTACAAGCAGCCTGAATGTC | 2 | 2 | NC | NC |
| 2168 | 3434 | AGTACAAGCAGCCTGAATGT | 2 | 2 | NC | NC |
| 2169 | 3435 | TAGTACAAGCAGCCTGAATG | 3 | 2 | NC | NC |
| 2170 | 3436 | TTAGTACAAGCAGCCTGAAT | 2 | 2 | NC | NC |
| 2171 | 3437 | TTTAGTACAAGCAGCCTGAA | 2 | 2 | NC | NC |
| 2172 | 3438 | CTTTAGTACAAGCAGCCTGA | 2 | 3 | NC | NC |
| 2173 | 3439 | TCTTTAGTACAAGCAGCCTG | 2 | 2 | NC | NC |
| 2174 | 3440 | GTCTTTAGTACAAGCAGCCT | 2 | 2 | NC | NC |
| 2175 | 3441 | GGTCTTTAGTACAAGCAGCC | 3 | 2 | NC | NC |
| 2176 | 3442 | AGGTCTTTAGTACAAGCAGC | 3 | 2 | NC | NC |
| 2177 | 3443 | CAGGTCTTTAGTACAAGCAG | 2 | 2 | NC | NC |
| 2178 | 3444 | TCAGGTCTTTAGTACAAGCA | 3 | 2 | NC | NC |
| 2179 | 3445 | GTCAGGTCTTTAGTACAAGC | 2 | 2 | NC | NC |
| 2180 | 3446 | TGTCAGGTCTTTAGTACAAG | 1 | 2 | NC | NC |
| 2181 | 3447 | TTGTCAGGTCTTTAGTACAA | 2 | 2 | NC | NC |
| 2182 | 3448 | GTTGTCAGGTCTTTAGTACA | 1 | 3 | NC | NC |
| 2183 | 3449 | AGTTGTCAGGTCTTTAGTAC | 2 | 3 | NC | NC |
| 2184 | 3450 | CAGTTGTCAGGTCTTTAGTA | 2 | 2 | NC | NC |
| 2185 | 3451 | ACAGTTGTCAGGTCTTTAGT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2186 | 3452 | CACAGTTGTCAGGTCTTTAG | 2 | 2 | NC | NC |
| 2187 | 3453 | CCACAGTTGTCAGGTCTTTA | 2 | 3 | NC | NC |
| 2188 | 3454 | GCCACAGTTGTCAGGTCTTT | 2 | 2 | NC | NC |
| 2189 | 3455 | AGCCACAGTTGTCAGGTCTT | 2 | 2 | NC | NC |
| 2190 | 3456 | CAGCCACAGTTGTCAGGTCT | 2 | 2 | NC | NC |
| 2191 | 3457 | ACAGCCACAGTTGTCAGGTC | 2 | 2 | NC | NC |
| 2192 | 3458 | CACAGCCACAGTTGTCAGGT | 2 | 2 | NC | NC |
| 2193 | 3460 | TCCACAGCCACAGTTGTCAG | 2 | 1 | 2 | NC |
| 2194 | 3461 | ATCCACAGCCACAGTTGTCA | 2 | 1 | 1 | NC |
| 2195 | 3462 | CATCCACAGCCACAGTTGTC | 2 | 1 | 2 | NC |
| 2196 | 3463 | ACATCCACAGCCACAGTTGT | 2 | 2 | 1 | NC |
| 2197 | 3464 | AACATCCACAGCCACAGTTG | 1 | NC | NC | NC |
| 2198 | 3465 | CAACATCCACAGCCACAGTT | 2 | NC | NC | NC |
| 2199 | 3466 | ACAACATCCACAGCCACAGT | 2 | NC | NC | NC |
| 2200 | 3467 | TACAACATCCACAGCCACAG | 2 | NC | NC | NC |
| 2201 | 3468 | GTACAACATCCACAGCCACA | 2 | NC | NC | NC |
| 2202 | 3469 | AGTACAACATCCACAGCCAC | 2 | NC | NC | NC |
| 2203 | 3470 | AAGTACAACATCCACAGCCA | 2 | NC | NC | NC |
| 2204 | 3471 | CAAGTACAACATCCACAGCC | 2 | NC | NC | NC |
| 2205 | 3472 | TCAAGTACAACATCCACAGC | 1 | NC | NC | NC |
| 2206 | 3473 | CTCAAGTACAACATCCACAG | 2 | NC | NC | NC |
| 2207 | 3474 | TCTCAAGTACAACATCCACA | 2 | NC | NC | NC |
| 2208 | 3475 | TTCTCAAGTACAACATCCAC | 2 | NC | NC | NC |
| 2209 | 3476 | ATTCTCAAGTACAACATCCA | 2 | NC | NC | NC |
| 2210 | 3477 | CATTCTCAAGTACAACATCC | 2 | NC | NC | NC |
| 2211 | 3478 | CCATTCTCAAGTACAACATC | 2 | NC | NC | NC |
| 2212 | 3479 | CCCATTCTCAAGTACAACAT | 2 | NC | NC | NC |
| 2213 | 3480 | ACCCATTCTCAAGTACAACA | 2 | NC | NC | NC |
| 2214 | 3481 | GACCCATTCTCAAGTACAAC | 2 | NC | NC | NC |
| 2215 | 3482 | AGACCCATTCTCAAGTACAA | 2 | NC | NC | NC |
| 2216 | 3491 | CCTGTACTGAGACCCATTCT | 2 | 2 | NC | NC |
| 2217 | 3492 | ACCTGTACTGAGACCCATTC | 2 | 2 | NC | NC |
| 2218 | 3493 | CACCTGTACTGAGACCCATT | 3 | 2 | NC | NC |
| 2219 | 3494 | ACACCTGTACTGAGACCCAT | 2 | 3 | NC | NC |
| 2220 | 3495 | GACACCTGTACTGAGACCCA | 2 | 2 | NC | NC |
| 2221 | 3496 | TGACACCTGTACTGAGACCC | 2 | 2 | NC | NC |
| 2222 | 3497 | TTGACACCTGTACTGAGACC | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2223 | 3498 | GTTGACACCTGTACTGAGAC | 2 | NC | NC | NC |
| 2224 | 3510 | CGCTTCTAAAAGGTTGACAC | 3 | NC | NC | NC |
| 2225 | 3511 | TCGCTTCTAAAAGGTTGACA | 2 | NC | NC | NC |
| 2226 | 3512 | GTCGCTTCTAAAAGGTTGAC | 3 | NC | NC | NC |
| 2227 | 3513 | GGTCGCTTCTAAAAGGTTGA | 3 | NC | NC | NC |
| 2228 | 3514 | AGGTCGCTTCTAAAAGGTTG | 2 | NC | NC | NC |
| 2229 | 3515 | AAGGTCGCTTCTAAAAGGTT | 2 | NC | NC | NC |
| 2230 | 3516 | CAAGGTCGCTTCTAAAAGGT | 2 | NC | NC | NC |
| 2231 | 3517 | ACAAGGTCGCTTCTAAAAGG | 3 | 3 | NC | NC |
| 2232 | 3518 | AACAAGGTCGCTTCTAAAAG | 2 | 2 | NC | NC |
| 2233 | 3519 | GAACAAGGTCGCTTCTAAAA | 2 | 1 | NC | NC |
| 2234 | 3520 | AGAACAAGGTCGCTTCTAAA | 2 | 2 | NC | NC |
| 2235 | 3521 | AAGAACAAGGTCGCTTCTAA | 2 | 2 | NC | NC |
| 2236 | 3522 | GAAGAACAAGGTCGCTTCTA | 2 | 3 | NC | NC |
| 2237 | 3523 | GGAAGAACAAGGTCGCTTCT | 2 | 2 | NC | NC |
| 2238 | 3524 | AGGAAGAACAAGGTCGCTTC | 2 | 2 | NC | NC |
| 2239 | 3525 | AAGGAAGAACAAGGTCGCTT | 2 | 2 | NC | NC |
| 2240 | 3526 | AAAGGAAGAACAAGGTCGCT | 2 | 2 | NC | NC |
| 2241 | 3527 | GAAAGGAAGAACAAGGTCGC | 2 | 2 | NC | NC |
| 2242 | 3528 | GGAAAGGAAGAACAAGGTCG | 2 | 2 | NC | NC |
| 2243 | 3529 | AGGAAAGGAAGAACAAGGTC | 2 | 2 | NC | NC |
| 2244 | 3530 | AAGGAAAGGAAGAACAAGGT | 1 | 2 | NC | NC |
| 2245 | 3531 | GAAGGAAAGGAAGAACAAGG | 1 | 1 | NC | NC |
| 2246 | 3532 | GGAAGGAAAGGAAGAACAAG | 1 | 1 | NC | NC |
| 2247 | 3533 | CGGAAGGAAAGGAAGAACAA | 2 | 1 | NC | NC |
| 2248 | 3534 | TCGGAAGGAAAGGAAGAACA | 2 | 2 | NC | NC |
| 2249 | 3535 | CTCGGAAGGAAAGGAAGAAC | 2 | 1 | NC | NC |
| 2250 | 3536 | TCTCGGAAGGAAAGGAAGAA | 2 | 1 | NC | NC |
| 2251 | 3537 | CTCTCGGAAGGAAAGGAAGA | 2 | 2 | NC | NC |
| 2252 | 3538 | GCTCTCGGAAGGAAAGGAAG | 2 | 2 | NC | NC |
| 2253 | 3539 | AGCTCTCGGAAGGAAAGGAA | 1 | 2 | NC | NC |
| 2254 | 3540 | GAGCTCTCGGAAGGAAAGGA | 1 | 2 | NC | NC |
| 2255 | 3564 | GTCTCATCACAGTCCTCTCT | 2 | 2 | NC | NC |
| 2256 | 3565 | TGTCTCATCACAGTCCTCTC | 2 | 2 | NC | NC |
| 2257 | 3573 | TGTTATCCTGTCTCATCACA | 2 | 2 | NC | NC |
| 2258 | 3574 | CTGTTATCCTGTCTCATCAC | 1 | 2 | NC | NC |
| 2259 | 3575 | TCTGTTATCCTGTCTCATCA | 1 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2260 | 3576 | CTCTGTTATCCTGTCTCATC | 2 | 2 | NC | NC |
| 2261 | 3577 | TCTCTGTTATCCTGTCTCAT | 2 | 2 | NC | NC |
| 2262 | 3578 | ATCTCTGTTATCCTGTCTCA | 1 | 2 | NC | NC |
| 2263 | 3579 | TATCTCTGTTATCCTGTCTC | 1 | 1 | NC | NC |
| 2264 | 3580 | GTATCTCTGTTATCCTGTCT | 1 | 1 | NC | NC |
| 2265 | 3581 | AGTATCTCTGTTATCCTGTC | 2 | 2 | NC | NC |
| 2266 | 3592 | GTATCATCCACAGTATCTCT | 2 | 2 | NC | NC |
| 2267 | 3593 | AGTATCATCCACAGTATCTC | 2 | NC | NC | NC |
| 2268 | 3594 | CAGTATCATCCACAGTATCT | 1 | NC | NC | NC |
| 2269 | 3595 | ACAGTATCATCCACAGTATC | 1 | NC | NC | NC |
| 2270 | 3596 | AACAGTATCATCCACAGTAT | 2 | NC | NC | NC |
| 2271 | 3597 | TAACAGTATCATCCACAGTA | 2 | NC | NC | NC |
| 2272 | 3598 | CTAACAGTATCATCCACAGT | 2 | NC | NC | NC |
| 2273 | 3599 | ACTAACAGTATCATCCACAG | 2 | NC | NC | NC |
| 2274 | 3600 | TACTAACAGTATCATCCACA | 2 | NC | NC | NC |
| 2275 | 3601 | CTACTAACAGTATCATCCAC | 2 | NC | NC | NC |
| 2276 | 3602 | GCTACTAACAGTATCATCCA | 2 | NC | NC | NC |
| 2277 | 3603 | CGCTACTAACAGTATCATCC | 3 | NC | NC | NC |
| 2278 | 3604 | TCGCTACTAACAGTATCATC | 2 | NC | NC | NC |
| 2279 | 3605 | TTCGCTACTAACAGTATCAT | 2 | NC | NC | NC |
| 2280 | 3606 | ATTCGCTACTAACAGTATCA | 3 | NC | NC | NC |
| 2281 | 3607 | GATTCGCTACTAACAGTATC | 3 | NC | NC | NC |
| 2282 | 3608 | CGATTCGCTACTAACAGTAT | 3 | NC | NC | NC |
| 2283 | 3621 | ACAAAGACTGAAGCGATTCG | 3 | NC | NC | NC |
| 2284 | 3622 | AACAAAGACTGAAGCGATTC | 2 | NC | NC | NC |
| 2285 | 3623 | GAACAAAGACTGAAGCGATT | 3 | NC | NC | NC |
| 2286 | 3624 | AGAACAAAGACTGAAGCGAT | 2 | NC | NC | NC |
| 2287 | 3625 | GAGAACAAAGACTGAAGCGA | 2 | NC | NC | NC |
| 2288 | 3626 | TGAGAACAAAGACTGAAGCG | 1 | NC | NC | NC |
| 2289 | 3627 | CTGAGAACAAAGACTGAAGC | 0 | 0 | NC | NC |
| 2290 | 3628 | TCTGAGAACAAAGACTGAAG | 1 | 1 | NC | NC |
| 2291 | 3629 | TTCTGAGAACAAAGACTGAA | 1 | 1 | NC | NC |
| 2292 | 3630 | ATTCTGAGAACAAAGACTGA | 2 | 2 | NC | NC |
| 2293 | 3631 | CATTCTGAGAACAAAGACTG | 2 | 2 | NC | NC |
| 2294 | 3632 | CCATTCTGAGAACAAAGACT | 2 | 2 | NC | NC |
| 2295 | 3633 | CCCATTCTGAGAACAAAGAC | 1 | 1 | NC | NC |
| 2296 | 3634 | TCCCATTCTGAGAACAAAGA | 1 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2297 | 3635 | GTCCCATTCTGAGAACAAAG | 2 | 1 | NC | NC |
| 2298 | 3636 | TGTCCCATTCTGAGAACAAA | 2 | 1 | NC | NC |
| 2299 | 3637 | TTGTCCCATTCTGAGAACAA | 2 | 1 | NC | NC |
| 2300 | 3638 | ATTGTCCCATTCTGAGAACA | 2 | 2 | NC | NC |
| 2301 | 3639 | GATTGTCCCATTCTGAGAAC | 3 | 2 | NC | NC |
| 2302 | 3640 | GGATTGTCCCATTCTGAGAA | 2 | 2 | NC | NC |
| 2303 | 3641 | TGGATTGTCCCATTCTGAGA | 2 | 2 | NC | NC |
| 2304 | 3642 | CTGGATTGTCCCATTCTGAG | 2 | 2 | NC | NC |
| 2305 | 3643 | ACTGGATTGTCCCATTCTGA | 2 | 2 | NC | NC |
| 2306 | 3644 | TACTGGATTGTCCCATTCTG | 2 | 2 | NC | NC |
| 2307 | 3645 | ATACTGGATTGTCCCATTCT | 2 | 2 | NC | NC |
| 2308 | 3646 | AATACTGGATTGTCCCATTC | 2 | 2 | NC | NC |
| 2309 | 3647 | AAATACTGGATTGTCCCATT | 1 | 2 | NC | NC |
| 2310 | 3648 | CAAATACTGGATTGTCCCAT | 2 | 2 | NC | NC |
| 2311 | 3649 | GCAAATACTGGATTGTCCCA | 2 | 2 | NC | NC |
| 2312 | 3650 | GGCAAATACTGGATTGTCCC | 2 | 2 | NC | NC |
| 2313 | 3652 | CGGGCAAATACTGGATTGTC | 3 | 3 | NC | NC |
| 2314 | 3653 | ACGGGCAAATACTGGATTGT | 2 | 2 | NC | NC |
| 2315 | 3654 | AACGGGCAAATACTGGATTG | 2 | 2 | NC | NC |
| 2316 | 3655 | TAACGGGCAAATACTGGATT | 3 | 2 | NC | NC |
| 2317 | 3656 | ATAACGGGCAAATACTGGAT | 2 | 2 | NC | NC |
| 2318 | 3657 | GATAACGGGCAAATACTGGA | 2 | 3 | NC | NC |
| 2319 | 3658 | GGATAACGGGCAAATACTGG | 3 | 3 | NC | NC |
| 2320 | 3659 | TGGATAACGGGCAAATACTG | 2 | 2 | NC | NC |
| 2321 | 3660 | CTGGATAACGGGCAAATACT | 3 | 2 | NC | NC |
| 2322 | 3661 | TCTGGATAACGGGCAAATAC | 2 | 3 | NC | NC |
| 2323 | 3662 | CTCTGGATAACGGGCAAATA | 3 | 2 | NC | NC |
| 2324 | 3663 | CCTCTGGATAACGGGCAAAT | 2 | 3 | NC | NC |
| 2325 | 3664 | ACCTCTGGATAACGGGCAAA | 3 | 2 | NC | NC |
| 2326 | 3665 | AACCTCTGGATAACGGGCAA | 2 | 3 | NC | NC |
| 2327 | 3666 | CAACCTCTGGATAACGGGCA | 2 | 2 | NC | NC |
| 2328 | 3668 | AGCAACCTCTGGATAACGGG | 2 | 2 | NC | NC |
| 2329 | 3669 | CAGCAACCTCTGGATAACGG | 2 | 2 | NC | NC |
| 2330 | 3678 | TTACATCAACAGCAACCTCT | 2 | 2 | NC | NC |
| 2331 | 3679 | CTTACATCAACAGCAACCTC | 2 | 2 | NC | NC |
| 2332 | 3680 | GCTTACATCAACAGCAACCT | 2 | 2 | NC | NC |
| 2333 | 3685 | CCACTGCTTACATCAACAGC | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2334 | 3686 | GCCACTGCTTACATCAACAG | 2 | 2 | NC | NC |
| 2335 | 3710 | TTTAACTGCTAAGCTCTCAG | 2 | 2 | NC | NC |
| 2336 | 3711 | TTTTAACTGCTAAGCTCTCA | 2 | 2 | NC | NC |
| 2337 | 3712 | ATTTTAACTGCTAAGCTCTC | 2 | 2 | NC | NC |
| 2338 | 3713 | AATTTTAACTGCTAAGCTCT | 2 | 2 | NC | NC |
| 2339 | 3714 | GAATTTTAACTGCTAAGCTC | 2 | 2 | NC | NC |
| 2340 | 3715 | TGAATTTTAACTGCTAAGCT | 2 | 2 | NC | NC |
| 2341 | 3716 | GTGAATTTTAACTGCTAAGC | 1 | 1 | NC | NC |
| 2342 | 3717 | TGTGAATTTTAACTGCTAAG | 2 | 1 | NC | NC |
| 2343 | 3718 | TTGTGAATTTTAACTGCTAA | 2 | 1 | NC | NC |
| 2344 | 3719 | GTTGTGAATTTTAACTGCTA | 2 | 2 | NC | NC |
| 2345 | 3720 | TGTTGTGAATTTTAACTGCT | 2 | 1 | NC | NC |
| 2346 | 3721 | ATGTTGTGAATTTTAACTGC | 2 | 2 | NC | NC |
| 2347 | 3722 | GATGTTGTGAATTTTAACTG | 2 | 2 | NC | NC |
| 2348 | 3723 | AGATGTTGTGAATTTTAACT | 2 | 1 | NC | NC |
| 2349 | 3724 | AAGATGTTGTGAATTTTAAC | 2 | 1 | NC | NC |
| 2350 | 3725 | CAAGATGTTGTGAATTTTAA | 1 | 1 | NC | NC |
| 2351 | 3743 | GGTGAAACGATAGGGATACA | 2 | 3 | NC | NC |
| 2352 | 3744 | TGGTGAAACGATAGGGATAC | 3 | 3 | NC | NC |
| 2353 | 3745 | TTGGTGAAACGATAGGGATA | 3 | 2 | NC | NC |
| 2354 | 3746 | TTTGGTGAAACGATAGGGAT | 3 | 2 | NC | NC |
| 2355 | 3747 | CTTTGGTGAAACGATAGGGA | 3 | 2 | NC | NC |
| 2356 | 3748 | CCTTTGGTGAAACGATAGGG | 2 | NC | NC | NC |
| 2357 | 3750 | TTCCTTTGGTGAAACGATAG | 1 | NC | NC | NC |
| 2358 | 3751 | ATTCCTTTGGTGAAACGATA | 2 | NC | NC | NC |
| 2359 | 3752 | CATTCCTTTGGTGAAACGAT | 2 | NC | NC | NC |
| 2360 | 3753 | TCATTCCTTTGGTGAAACGA | 2 | NC | NC | NC |
| 2361 | 3754 | ATCATTCCTTTGGTGAAACG | 3 | NC | NC | NC |
| 2362 | 3755 | AATCATTCCTTTGGTGAAAC | 2 | NC | NC | NC |
| 2363 | 3756 | GAATCATTCCTTTGGTGAAA | 2 | NC | NC | NC |
| 2364 | 3757 | TGAATCATTCCTTTGGTGAA | 2 | NC | NC | NC |
| 2365 | 3758 | ATGAATCATTCCTTTGGTGA | 2 | NC | NC | NC |
| 2366 | 3759 | AATGAATCATTCCTTTGGTG | 2 | NC | NC | NC |
| 2367 | 3768 | CCTGCATTGAATGAATCATT | 1 | 2 | NC | NC |
| 2368 | 3769 | ACCTGCATTGAATGAATCAT | 2 | 2 | NC | NC |
| 2369 | 3770 | AACCTGCATTGAATGAATCA | 1 | 2 | NC | NC |
| 2370 | 3771 | GAACCTGCATTGAATGAATC | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2371 | 3772 | AGAACCTGCATTGAATGAAT | 2 | 2 | NC | NC |
| 2372 | 3773 | GAGAACCTGCATTGAATGAA | 2 | 2 | NC | NC |
| 2373 | 3774 | GGAGAACCTGCATTGAATGA | 2 | 2 | NC | NC |
| 2374 | 3786 | TATCTACTTGCTGGAGAACC | 2 | NC | NC | NC |
| 2375 | 3787 | TTATCTACTTGCTGGAGAAC | 2 | NC | NC | NC |
| 2376 | 3788 | GTTATCTACTTGCTGGAGAA | 2 | NC | NC | NC |
| 2377 | 3789 | TGTTATCTACTTGCTGGAGA | 2 | NC | NC | NC |
| 2378 | 3790 | TTGTTATCTACTTGCTGGAG | 2 | NC | NC | NC |
| 2379 | 3791 | CTTGTTATCTACTTGCTGGA | 2 | NC | NC | NC |
| 2380 | 3792 | ACTTGTTATCTACTTGCTGG | 2 | NC | NC | NC |
| 2381 | 3793 | AACTTGTTATCTACTTGCTG | 2 | NC | NC | NC |
| 2382 | 3794 | AAACTTGTTATCTACTTGCT | 2 | NC | NC | NC |
| 2383 | 3795 | TAAACTTGTTATCTACTTGC | 2 | NC | NC | NC |
| 2384 | 3796 | ATAAACTTGTTATCTACTTG | 2 | NC | NC | NC |
| 2385 | 3798 | CAATAAACTTGTTATCTACT | 2 | NC | NC | NC |
| 2386 | 3799 | GCAATAAACTTGTTATCTAC | 2 | NC | NC | NC |
| 2387 | 3800 | GGCAATAAACTTGTTATCTA | 2 | NC | NC | NC |
| 2388 | 3801 | AGGCAATAAACTTGTTATCT | 2 | NC | NC | NC |
| 2389 | 3802 | CAGGCAATAAACTTGTTATC | 1 | NC | NC | NC |
| 2390 | 3803 | ACAGGCAATAAACTTGTTAT | 2 | NC | NC | NC |
| 2391 | 3804 | AACAGGCAATAAACTTGTTA | 2 | NC | NC | NC |
| 2392 | 3805 | AAACAGGCAATAAACTTGTT | 2 | NC | NC | NC |
| 2393 | 3806 | CAAACAGGCAATAAACTTGT | 1 | NC | NC | NC |
| 2394 | 3807 | TCAAACAGGCAATAAACTTG | 2 | 2 | NC | NC |
| 2395 | 3808 | ATCAAACAGGCAATAAACTT | 2 | 2 | NC | NC |
| 2396 | 3809 | CATCAAACAGGCAATAAACT | 1 | 1 | NC | NC |
| 2397 | 3810 | TCATCAAACAGGCAATAAAC | 2 | 2 | NC | NC |
| 2398 | 3811 | CTCATCAAACAGGCAATAAA | 2 | 2 | NC | NC |
| 2399 | 3812 | GCTCATCAAACAGGCAATAA | 2 | 2 | NC | NC |
| 2400 | 3813 | TGCTCATCAAACAGGCAATA | 2 | 2 | NC | NC |
| 2401 | 3814 | GTGCTCATCAAACAGGCAAT | 2 | 2 | NC | NC |
| 2402 | 3815 | AGTGCTCATCAAACAGGCAA | 2 | 2 | NC | NC |
| 2403 | 3816 | TAGTGCTCATCAAACAGGCA | 2 | 3 | NC | NC |
| 2404 | 3817 | TTAGTGCTCATCAAACAGGC | 2 | 3 | NC | NC |
| 2405 | 3818 | CTTAGTGCTCATCAAACAGG | 2 | 2 | NC | NC |
| 2406 | 3819 | TCTTAGTGCTCATCAAACAG | 2 | 2 | NC | NC |
| 2407 | 3820 | GTCTTAGTGCTCATCAAACA | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2408 | 3821 | AGTCTTAGTGCTCATCAAAC | 2 | 2 | NC | NC |
| 2409 | 3822 | CAGTCTTAGTGCTCATCAAA | 2 | 2 | NC | NC |
| 2410 | 3823 | TCAGTCTTAGTGCTCATCAA | 2 | 2 | NC | NC |
| 2411 | 3824 | TTCAGTCTTAGTGCTCATCA | 2 | 2 | NC | NC |
| 2412 | 3825 | CTTCAGTCTTAGTGCTCATC | 2 | 2 | NC | NC |
| 2413 | 3826 | TCTTCAGTCTTAGTGCTCAT | 2 | 2 | NC | NC |
| 2414 | 3827 | CTCTTCAGTCTTAGTGCTCA | 2 | 2 | NC | NC |
| 2415 | 3828 | TCTCTTCAGTCTTAGTGCTC | 2 | 2 | NC | NC |
| 2416 | 3829 | TTCTCTTCAGTCTTAGTGCT | 2 | 2 | NC | NC |
| 2417 | 3830 | ATTCTCTTCAGTCTTAGTGC | 2 | 2 | NC | NC |
| 2418 | 3831 | CATTCTCTTCAGTCTTAGTG | 2 | 2 | NC | NC |
| 2419 | 3832 | CCATTCTCTTCAGTCTTAGT | 2 | 2 | NC | NC |
| 2420 | 3833 | GCCATTCTCTTCAGTCTTAG | 2 | 2 | NC | NC |
| 2421 | 3834 | CGCCATTCTCTTCAGTCTTA | 2 | 2 | NC | NC |
| 2422 | 3835 | TCGCCATTCTCTTCAGTCTT | 2 | 2 | NC | NC |
| 2423 | 3836 | CTCGCCATTCTCTTCAGTCT | 2 | 2 | NC | NC |
| 2424 | 3837 | CCTCGCCATTCTCTTCAGTC | 2 | 2 | NC | NC |
| 2425 | 3838 | GCCTCGCCATTCTCTTCAGT | 2 | 2 | NC | NC |
| 2426 | 3839 | TGCCTCGCCATTCTCTTCAG | 2 | 2 | NC | NC |
| 2427 | 3840 | CTGCCTCGCCATTCTCTTCA | 2 | 1 | NC | NC |
| 2428 | 3842 | ACCTGCCTCGCCATTCTCTT | 1 | 2 | NC | NC |
| 2429 | 3904 | AGCTGCTCCAGACGTATACG | 3 | NC | NC | NC |
| 2430 | 3905 | AAGCTGCTCCAGACGTATAC | 3 | NC | NC | NC |
| 2431 | 3906 | TAAGCTGCTCCAGACGTATA | 3 | NC | NC | NC |
| 2432 | 3907 | ATAAGCTGCTCCAGACGTAT | 3 | NC | NC | NC |
| 2433 | 3908 | GATAAGCTGCTCCAGACGTA | 3 | NC | NC | NC |
| 2434 | 3909 | TGATAAGCTGCTCCAGACGT | 2 | NC | NC | NC |
| 2435 | 3910 | ATGATAAGCTGCTCCAGACG | 2 | 3 | NC | NC |
| 2436 | 3911 | AATGATAAGCTGCTCCAGAC | 2 | 2 | NC | NC |
| 2437 | 3912 | CAATGATAAGCTGCTCCAGA | 2 | 2 | NC | NC |
| 2438 | 3913 | TCAATGATAAGCTGCTCCAG | 1 | 2 | NC | NC |
| 2439 | 3914 | ATCAATGATAAGCTGCTCCA | 1 | 2 | NC | NC |
| 2440 | 3915 | AATCAATGATAAGCTGCTCC | 2 | 2 | NC | NC |
| 2441 | 3916 | GAATCAATGATAAGCTGCTC | 2 | 3 | NC | NC |
| 2442 | 3917 | GGAATCAATGATAAGCTGCT | 2 | 2 | NC | NC |
| 2443 | 3918 | AGGAATCAATGATAAGCTGC | 2 | 2 | NC | NC |
| 2444 | 3919 | TAGGAATCAATGATAAGCTG | 2 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2445 | 3920 | GTAGGAATCAATGATAAGCT | 3 | NC | NC | NC |
| 2446 | 3921 | CGTAGGAATCAATGATAAGC | 3 | NC | NC | NC |
| 2447 | 3922 | TCGTAGGAATCAATGATAAG | 2 | NC | NC | NC |
| 2448 | 3923 | CTCGTAGGAATCAATGATAA | 2 | NC | NC | NC |
| 2449 | 3924 | TCTCGTAGGAATCAATGATA | 2 | NC | NC | NC |
| 2450 | 3925 | TTCTCGTAGGAATCAATGAT | 2 | NC | NC | NC |
| 2451 | 3926 | CTTCTCGTAGGAATCAATGA | 2 | NC | NC | NC |
| 2452 | 3927 | GCTTCTCGTAGGAATCAATG | 2 | NC | NC | NC |
| 2453 | 3928 | TGCTTCTCGTAGGAATCAAT | 2 | NC | NC | NC |
| 2454 | 3929 | TTGCTTCTCGTAGGAATCAA | 2 | NC | NC | NC |
| 2455 | 3930 | GTTGCTTCTCGTAGGAATCA | 2 | NC | NC | NC |
| 2456 | 3931 | TGTTGCTTCTCGTAGGAATC | 2 | NC | NC | NC |
| 2457 | 3932 | CTGTTGCTTCTCGTAGGAAT | 2 | NC | NC | NC |
| 2458 | 3933 | CCTGTTGCTTCTCGTAGGAA | 2 | NC | NC | NC |
| 2459 | 3934 | GCCTGTTGCTTCTCGTAGGA | 3 | NC | NC | NC |
| 2460 | 3953 | TTTCCGACCAGAGCCTTGTG | 2 | 3 | NC | NC |
| 2461 | 3954 | TTTTCCGACCAGAGCCTTGT | 2 | 3 | NC | NC |
| 2462 | 3955 | TTTTTCCGACCAGAGCCTTG | 2 | 2 | NC | NC |
| 2463 | 3971 | AGTAGAAGACAGTAATTTTT | 1 | 2 | NC | NC |
| 2464 | 3972 | GAGTAGAAGACAGTAATTTT | 2 | 2 | NC | NC |
| 2465 | 3973 | AGAGTAGAAGACAGTAATTT | 1 | 1 | NC | NC |
| 2466 | 3974 | TAGAGTAGAAGACAGTAATT | 2 | 2 | NC | NC |
| 2467 | 3975 | TTAGAGTAGAAGACAGTAAT | 2 | 2 | NC | NC |
| 2468 | 3976 | ATTAGAGTAGAAGACAGTAA | 2 | 2 | NC | NC |
| 2469 | 3977 | AATTAGAGTAGAAGACAGTA | 1 | 2 | NC | NC |
| 2470 | 3978 | GAATTAGAGTAGAAGACAGT | 2 | 2 | NC | NC |
| 2471 | 3979 | GGAATTAGAGTAGAAGACAG | 1 | 1 | NC | NC |
| 2472 | 3980 | AGGAATTAGAGTAGAAGACA | 1 | 1 | NC | NC |
| 2473 | 3981 | GAGGAATTAGAGTAGAAGAC | 2 | 2 | NC | NC |
| 2474 | 3982 | GGAGGAATTAGAGTAGAAGA | 1 | 2 | NC | NC |
| 2475 | 3983 | CGGAGGAATTAGAGTAGAAG | 2 | NC | NC | NC |
| 2476 | 3984 | GCGGAGGAATTAGAGTAGAA | 2 | NC | NC | NC |
| 2477 | 3985 | AGCGGAGGAATTAGAGTAGA | 2 | NC | NC | NC |
| 2478 | 3986 | TAGCGGAGGAATTAGAGTAG | 3 | NC | NC | NC |
| 2479 | 3987 | CTAGCGGAGGAATTAGAGTA | 2 | NC | NC | NC |
| 2480 | 3988 | TCTAGCGGAGGAATTAGAGT | 3 | NC | NC | NC |
| 2481 | 3999 | TCACTGTTATCTCTAGCGGA | 3 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2482 | 4000 | GTCACTGTTATCTCTAGCGG | 3 | NC | NC | NC |
| 2483 | 4001 | TGTCACTGTTATCTCTAGCG | 3 | NC | NC | NC |
| 2484 | 4002 | CTGTCACTGTTATCTCTAGC | 2 | NC | NC | NC |
| 2485 | 4003 | TCTGTCACTGTTATCTCTAG | 1 | 2 | NC | NC |
| 2486 | 4004 | CTCTGTCACTGTTATCTCTA | 1 | 1 | NC | NC |
| 2487 | 4005 | CCTCTGTCACTGTTATCTCT | 1 | 2 | NC | NC |
| 2488 | 4006 | TCCTCTGTCACTGTTATCTC | 1 | 1 | NC | NC |
| 2489 | 4007 | TTCCTCTGTCACTGTTATCT | 2 | 2 | NC | NC |
| 2490 | 4008 | GTTCCTCTGTCACTGTTATC | 2 | 2 | NC | NC |
| 2491 | 4009 | TGTTCCTCTGTCACTGTTAT | 2 | 2 | NC | NC |
| 2492 | 4010 | TTGTTCCTCTGTCACTGTTA | 2 | 2 | NC | NC |
| 2493 | 4011 | TTTGTTCCTCTGTCACTGTT | 1 | 1 | NC | NC |
| 2494 | 4012 | CTTTGTTCCTCTGTCACTGT | 1 | 1 | NC | NC |
| 2495 | 4013 | CCTTTGTTCCTCTGTCACTG | 2 | 2 | NC | NC |
| 2496 | 4014 | TCCTTTGTTCCTCTGTCACT | 1 | 1 | NC | NC |
| 2497 | 4015 | CTCCTTTGTTCCTCTGTCAC | 2 | 2 | NC | NC |
| 2498 | 4016 | TCTCCTTTGTTCCTCTGTCA | 2 | 2 | NC | NC |
| 2499 | 4017 | GTCTCCTTTGTTCCTCTGTC | 2 | 1 | NC | NC |
| 2500 | 4018 | AGTCTCCTTTGTTCCTCTGT | 2 | 2 | NC | NC |
| 2501 | 4019 | GAGTCTCCTTTGTTCCTCTG | 1 | NC | NC | NC |
| 2502 | 4020 | AGAGTCTCCTTTGTTCCTCT | 2 | NC | NC | NC |
| 2503 | 4021 | AAGAGTCTCCTTTGTTCCTC | 1 | NC | NC | NC |
| 2504 | 4022 | TAAGAGTCTCCTTTGTTCCT | 2 | NC | NC | NC |
| 2505 | 4023 | ATAAGAGTCTCCTTTGTTCC | 1 | NC | NC | NC |
| 2506 | 4024 | CATAAGAGTCTCCTTTGTTC | 1 | NC | NC | NC |
| 2507 | 4025 | CCATAAGAGTCTCCTTTGTT | 1 | NC | NC | NC |
| 2508 | 4026 | ACCATAAGAGTCTCCTTTGT | 2 | NC | NC | NC |
| 2509 | 4027 | CACCATAAGAGTCTCCTTTG | 2 | NC | NC | NC |
| 2510 | 4028 | ACACCATAAGAGTCTCCTTT | 2 | NC | NC | NC |
| 2511 | 4029 | AACACCATAAGAGTCTCCTT | 2 | NC | NC | NC |
| 2512 | 4030 | TAACACCATAAGAGTCTCCT | 3 | NC | NC | NC |
| 2513 | 4031 | GTAACACCATAAGAGTCTCC | 3 | NC | NC | NC |
| 2514 | 4032 | GGTAACACCATAAGAGTCTC | 3 | NC | NC | NC |
| 2515 | 4046 | TTCCAGATTTTTGTGGTAAC | 2 | 2 | NC | NC |
| 2516 | 4047 | CTTCCAGATTTTTGTGGTAA | 2 | 2 | NC | NC |
| 2517 | 4048 | TCTTCCAGATTTTTGTGGTA | 1 | 2 | NC | NC |
| 2518 | 4049 | ATCTTCCAGATTTTTGTGGT | 2 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2519 | 4050 | GATCTTCCAGATTTTTGTGG | 2 | 2 | NC | NC |
| 2520 | 4051 | AGATCTTCCAGATTTTTGTG | 2 | 1 | NC | NC |
| 2521 | 4052 | CAGATCTTCCAGATTTTTGT | 2 | 1 | NC | NC |
| 2522 | 4053 | CCAGATCTTCCAGATTTTTG | 2 | 1 | NC | NC |
| 2523 | 4054 | CCCAGATCTTCCAGATTTTT | 1 | 1 | NC | NC |
| 2524 | 4055 | GCCCAGATCTTCCAGATTTT | 2 | 2 | NC | NC |
| 2525 | 4056 | GGCCCAGATCTTCCAGATTT | 2 | 3 | NC | NC |
| 2526 | 4057 | AGGCCCAGATCTTCCAGATT | 2 | 2 | NC | NC |
| 2527 | 4058 | AAGGCCCAGATCTTCCAGAT | 2 | 1 | NC | NC |
| 2528 | 4059 | CAAGGCCCAGATCTTCCAGA | 2 | 2 | NC | NC |
| 2529 | 4060 | TCAAGGCCCAGATCTTCCAG | 2 | 2 | NC | NC |
| 2530 | 4061 | TTCAAGGCCCAGATCTTCCA | 2 | 2 | NC | NC |
| 2531 | 4062 | ATTCAAGGCCCAGATCTTCC | 2 | NC | NC | NC |
| 2532 | 4063 | AATTCAAGGCCCAGATCTTC | 2 | NC | NC | NC |
| 2533 | 4064 | AAATTCAAGGCCCAGATCTT | 1 | NC | NC | NC |
| 2534 | 4065 | CAAATTCAAGGCCCAGATCT | 1 | NC | NC | NC |
| 2535 | 4066 | ACAAATTCAAGGCCCAGATC | 0 | NC | NC | NC |
| 2536 | 4067 | TACAAATTCAAGGCCCAGAT | 1 | NC | NC | NC |
| 2537 | 4068 | ATACAAATTCAAGGCCCAGA | 2 | NC | NC | NC |
| 2538 | 4069 | AATACAAATTCAAGGCCCAG | 2 | NC | NC | NC |
| 2539 | 4070 | AAATACAAATTCAAGGCCCA | 2 | NC | NC | NC |
| 2540 | 4071 | GAAATACAAATTCAAGGCCC | 1 | NC | NC | NC |
| 2541 | 4072 | GGAAATACAAATTCAAGGCC | 2 | NC | NC | NC |
| 2542 | 4073 | TGGAAATACAAATTCAAGGC | 1 | NC | NC | NC |
| 2543 | 4074 | CTGGAAATACAAATTCAAGG | 1 | NC | NC | NC |
| 2544 | 4075 | TCTGGAAATACAAATTCAAG | 1 | NC | NC | NC |
| 2545 | 4076 | GTCTGGAAATACAAATTCAA | 1 | NC | NC | NC |
| 2546 | 4077 | TGTCTGGAAATACAAATTCA | 1 | NC | NC | NC |
| 2547 | 4078 | GTGTCTGGAAATACAAATTC | 2 | NC | NC | NC |
| 2548 | 4079 | AGTGTCTGGAAATACAAATT | 2 | NC | NC | NC |
| 2549 | 4080 | TAGTGTCTGGAAATACAAAT | 2 | NC | NC | NC |
| 2550 | 4081 | CTAGTGTCTGGAAATACAAA | 2 | NC | NC | NC |
| 2551 | 4082 | ACTAGTGTCTGGAAATACAA | 2 | 2 | NC | NC |
| 2552 | 4083 | CACTAGTGTCTGGAAATACA | 2 | 2 | NC | NC |
| 2553 | 4084 | TCACTAGTGTCTGGAAATAC | 2 | 2 | NC | NC |
| 2554 | 4085 | ATCACTAGTGTCTGGAAATA | 2 | 2 | NC | NC |
| 2555 | 4086 | AATCACTAGTGTCTGGAAAT | 1 | 2 | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2556 | 4087 | GAATCACTAGTGTCTGGAAA | 2 | 2 | NC | NC |
| 2557 | 4088 | AGAATCACTAGTGTCTGGAA | 2 | 2 | NC | NC |
| 2558 | 4089 | GAGAATCACTAGTGTCTGGA | 2 | 2 | NC | NC |
| 2559 | 4090 | AGAGAATCACTAGTGTCTGG | 2 | 2 | NC | NC |
| 2560 | 4091 | CAGAGAATCACTAGTGTCTG | 2 | 2 | NC | NC |
| 2561 | 4092 | CCAGAGAATCACTAGTGTCT | 2 | 2 | NC | NC |
| 2562 | 4093 | ACCAGAGAATCACTAGTGTC | 2 | 2 | NC | NC |
| 2563 | 4094 | GACCAGAGAATCACTAGTGT | 2 | NC | NC | NC |
| 2564 | 4095 | GGACCAGAGAATCACTAGTG | 2 | NC | NC | NC |
| 2565 | 4096 | AGGACCAGAGAATCACTAGT | 2 | NC | NC | NC |
| 2566 | 4097 | AAGGACCAGAGAATCACTAG | 2 | NC | NC | NC |
| 2567 | 4098 | CAAGGACCAGAGAATCACTA | 2 | NC | NC | NC |
| 2568 | 4099 | ACAAGGACCAGAGAATCACT | 2 | NC | NC | NC |
| 2569 | 4100 | CACAAGGACCAGAGAATCAC | 2 | NC | NC | NC |
| 2570 | 4101 | CCACAAGGACCAGAGAATCA | 2 | NC | NC | NC |
| 2571 | 4102 | CCCACAAGGACCAGAGAATC | 2 | NC | NC | NC |
| 2572 | 4118 | ACATAGTGGTACTTTTCCCA | 2 | NC | NC | NC |
| 2573 | 4119 | AACATAGTGGTACTTTTCCC | 2 | NC | NC | NC |
| 2574 | 4120 | AAACATAGTGGTACTTTTCC | 1 | NC | NC | NC |
| 2575 | 4121 | AAAACATAGTGGTACTTTTC | 2 | NC | NC | NC |
| 2576 | 4122 | CAAAACATAGTGGTACTTTT | 2 | NC | NC | NC |
| 2577 | 4123 | ACAAAACATAGTGGTACTTT | 2 | NC | NC | NC |
| 2578 | 4124 | CACAAAACATAGTGGTACTT | 2 | NC | NC | NC |
| 2579 | 4130 | TCTTTCCACAAAACATAGTG | 1 | NC | NC | NC |
| 2580 | 4131 | CTCTTTCCACAAAACATAGT | 1 | NC | NC | NC |
| 2581 | 4132 | TCTCTTTCCACAAAACATAG | 1 | NC | NC | NC |
| 2582 | 4133 | TTCTCTTTCCACAAAACATA | 1 | NC | NC | NC |
| 2583 | 4134 | CTTCTCTTTCCACAAAACAT | 1 | NC | NC | NC |
| 2584 | 4135 | GCTTCTCTTTCCACAAAACA | 2 | 2 | NC | NC |
| 2585 | 4136 | GGCTTCTCTTTCCACAAAAC | 2 | 2 | NC | NC |
| 2586 | 4137 | TGGCTTCTCTTTCCACAAAA | 1 | 1 | NC | NC |
| 2587 | 4138 | TTGGCTTCTCTTTCCACAAA | 1 | 1 | NC | NC |
| 2588 | 4139 | ATTGGCTTCTCTTTCCACAA | 1 | 1 | NC | NC |
| 2589 | 4140 | CATTGGCTTCTCTTTCCACA | 1 | 1 | NC | NC |
| 2590 | 4141 | TCATTGGCTTCTCTTTCCAC | 1 | 1 | NC | NC |
| 2591 | 4142 | TTCATTGGCTTCTCTTTCCA | 2 | 1 | NC | NC |
| 2592 | 4143 | GTTCATTGGCTTCTCTTTCC | 2 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2593 | 4144 | AGTTCATTGGCTTCTCTTTC | 2 | 2 | NC | NC |
| 2594 | 4145 | AAGTTCATTGGCTTCTCTTT | 2 | 2 | NC | NC |
| 2595 | 4146 | GAAGTTCATTGGCTTCTCTT | 2 | 2 | NC | NC |
| 2596 | 4151 | TCTCCGAAGTTCATTGGCTT | 2 | 2 | NC | NC |
| 2597 | 4152 | CTCTCCGAAGTTCATTGGCT | 1 | 2 | NC | NC |
| 2598 | 4153 | CCTCTCCGAAGTTCATTGGC | 3 | 2 | NC | NC |
| 2599 | 4154 | TCCTCTCCGAAGTTCATTGG | 3 | 2 | NC | NC |
| 2600 | 4155 | TTCCTCTCCGAAGTTCATTG | 2 | 2 | NC | NC |
| 2601 | 4156 | CTTCCTCTCCGAAGTTCATT | 2 | 2 | NC | NC |
| 2602 | 4163 | AGTAGATCTTCCTCTCCGAA | 2 | 3 | NC | NC |
| 2603 | 4164 | CAGTAGATCTTCCTCTCCGA | 2 | 2 | NC | NC |
| 2604 | 4165 | ACAGTAGATCTTCCTCTCCG | 3 | 2 | NC | NC |
| 2605 | 4166 | CACAGTAGATCTTCCTCTCC | 2 | 2 | NC | NC |
| 2606 | 4167 | TCACAGTAGATCTTCCTCTC | 2 | 2 | NC | NC |
| 2607 | 4168 | GTCACAGTAGATCTTCCTCT | 2 | 2 | NC | NC |
| 2608 | 4169 | GGTCACAGTAGATCTTCCTC | 2 | 2 | NC | NC |
| 2609 | 4170 | TGGTCACAGTAGATCTTCCT | 2 | 2 | NC | NC |
| 2610 | 4171 | TTGGTCACAGTAGATCTTCC | 2 | 2 | NC | NC |
| 2611 | 4172 | CTTGGTCACAGTAGATCTTC | 2 | 2 | NC | NC |
| 2612 | 4173 | TCTTGGTCACAGTAGATCTT | 2 | 2 | NC | NC |
| 2613 | 4174 | CTCTTGGTCACAGTAGATCT | 2 | 2 | NC | NC |
| 2614 | 4175 | ACTCTTGGTCACAGTAGATC | 2 | 2 | NC | NC |
| 2615 | 4176 | TACTCTTGGTCACAGTAGAT | 2 | 2 | NC | NC |
| 2616 | 4177 | ATACTCTTGGTCACAGTAGA | 2 | 2 | NC | NC |
| 2617 | 4178 | AATACTCTTGGTCACAGTAG | 2 | NC | NC | NC |
| 2618 | 4179 | CAATACTCTTGGTCACAGTA | 2 | NC | NC | NC |
| 2619 | 4180 | ACAATACTCTTGGTCACAGT | 2 | NC | NC | NC |
| 2620 | 4181 | CACAATACTCTTGGTCACAG | 3 | NC | NC | NC |
| 2621 | 4182 | CCACAATACTCTTGGTCACA | 2 | NC | NC | NC |
| 2622 | 4183 | TCCACAATACTCTTGGTCAC | 2 | NC | NC | NC |
| 2623 | 4184 | CTCCACAATACTCTTGGTCA | 2 | NC | NC | NC |
| 2624 | 4185 | CCTCCACAATACTCTTGGTC | 2 | NC | NC | NC |
| 2625 | 4186 | TCCTCCACAATACTCTTGGT | 2 | NC | NC | NC |
| 2626 | 4187 | TTCCTCCACAATACTCTTGG | 2 | NC | NC | NC |
| 2627 | 4188 | ATTCCTCCACAATACTCTTG | 2 | NC | NC | NC |
| 2628 | 4189 | AATTCCTCCACAATACTCTT | 1 | NC | NC | NC |
| 2629 | 4190 | AAATTCCTCCACAATACTCT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2630 | 4191 | TAAATTCCTCCACAATACTC | 1 | NC | NC | NC |
| 2631 | 4192 | ATAAATTCCTCCACAATACT | 1 | NC | NC | NC |
| 2632 | 4193 | GATAAATTCCTCCACAATAC | 1 | NC | NC | NC |
| 2633 | 4204 | AGTTGTTCTCGGATAAATTC | 2 | NC | NC | NC |
| 2634 | 4205 | CAGTTGTTCTCGGATAAATT | 2 | NC | NC | NC |
| 2635 | 4206 | CCAGTTGTTCTCGGATAAAT | 2 | NC | NC | NC |
| 2636 | 4207 | TCCAGTTGTTCTCGGATAAA | 3 | NC | NC | NC |
| 2637 | 4208 | CTCCAGTTGTTCTCGGATAA | 3 | NC | NC | NC |
| 2638 | 4209 | GCTCCAGTTGTTCTCGGATA | 3 | NC | NC | NC |
| 2639 | 4210 | AGCTCCAGTTGTTCTCGGAT | 2 | NC | NC | NC |
| 2640 | 4211 | TAGCTCCAGTTGTTCTCGGA | 2 | NC | NC | NC |
| 2641 | 4212 | GTAGCTCCAGTTGTTCTCGG | 1 | NC | NC | NC |
| 2642 | 4213 | AGTAGCTCCAGTTGTTCTCG | 2 | NC | NC | NC |
| 2643 | 4214 | GAGTAGCTCCAGTTGTTCTC | 2 | NC | NC | NC |
| 2644 | 4244 | CAATGTCCCTTGGATGCCTC | 2 | 2 | NC | NC |
| 2645 | 4245 | GCAATGTCCCTTGGATGCCT | 2 | 2 | NC | NC |
| 2646 | 4247 | TGGCAATGTCCCTTGGATGC | 2 | 2 | NC | NC |
| 2647 | 4248 | GTGGCAATGTCCCTTGGATG | 2 | 1 | NC | NC |
| 2648 | 4249 | AGTGGCAATGTCCCTTGGAT | 3 | 2 | NC | NC |
| 2649 | 4250 | CAGTGGCAATGTCCCTTGGA | 2 | 1 | NC | NC |
| 2650 | 4251 | TCAGTGGCAATGTCCCTTGG | 2 | 2 | NC | NC |
| 2651 | 4252 | GTCAGTGGCAATGTCCCTTG | 2 | 2 | NC | NC |
| 2652 | 4253 | AGTCAGTGGCAATGTCCCTT | 1 | 2 | NC | NC |
| 2653 | 4254 | CAGTCAGTGGCAATGTCCCT | 2 | 2 | NC | NC |
| 2654 | 4255 | ACAGTCAGTGGCAATGTCCC | 2 | 2 | NC | NC |
| 2655 | 4256 | GACAGTCAGTGGCAATGTCC | 2 | 2 | NC | NC |
| 2656 | 4257 | GGACAGTCAGTGGCAATGTC | 2 | 2 | NC | NC |
| 2657 | 4258 | TGGACAGTCAGTGGCAATGT | 1 | 2 | NC | NC |
| 2658 | 4259 | CTGGACAGTCAGTGGCAATG | 2 | 2 | NC | NC |
| 2659 | 4260 | TCTGGACAGTCAGTGGCAAT | 1 | 2 | NC | NC |
| 2660 | 4261 | TTCTGGACAGTCAGTGGCAA | 1 | 1 | NC | NC |
| 2661 | 4262 | CTTCTGGACAGTCAGTGGCA | 2 | 2 | 2 | NC |
| 2662 | 4264 | ACCTTCTGGACAGTCAGTGG | 2 | 3 | 2 | NC |
| 2663 | 4265 | CACCTTCTGGACAGTCAGTG | 2 | 2 | 1 | NC |
| 2664 | 4266 | ACACCTTCTGGACAGTCAGT | 2 | 2 | 2 | NC |
| 2665 | 4269 | CCAACACCTTCTGGACAGTC | 2 | 2 | 2 | 2 |
| 2666 | 4270 | GCCAACACCTTCTGGACAGT | 2 | 3 | 2 | 2 |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2667 | 4271 | TGCCAACACCTTCTGGACAG | 2 | 2 | NC | NC |
| 2668 | 4272 | ATGCCAACACCTTCTGGACA | 2 | 2 | NC | NC |
| 2669 | 4273 | GATGCCAACACCTTCTGGAC | 2 | 3 | NC | NC |
| 2670 | 4274 | GGATGCCAACACCTTCTGGA | 2 | 2 | NC | NC |
| 2671 | 4276 | TGGGATGCCAACACCTTCTG | 2 | 2 | NC | NC |
| 2672 | 4277 | TTGGGATGCCAACACCTTCT | 3 | 2 | NC | NC |
| 2673 | 4278 | CTTGGGATGCCAACACCTTC | 2 | 2 | NC | NC |
| 2674 | 4279 | GCTTGGGATGCCAACACCTT | 2 | 2 | NC | NC |
| 2675 | 4302 | TAAACTTAATGGCCCCATGG | 3 | 2 | NC | NC |
| 2676 | 4303 | TTAAACTTAATGGCCCCATG | 2 | 2 | NC | NC |
| 2677 | 4312 | AGGCCATCATTAAACTTAAT | 2 | 2 | NC | NC |
| 2678 | 4313 | CAGGCCATCATTAAACTTAA | 2 | 2 | NC | NC |
| 2679 | 4314 | TCAGGCCATCATTAAACTTA | 1 | 2 | NC | NC |
| 2680 | 4315 | CTCAGGCCATCATTAAACTT | 1 | 2 | NC | NC |
| 2681 | 4316 | GCTCAGGCCATCATTAAACT | 1 | 2 | NC | NC |
| 2682 | 4330 | CAACTTTCCTGTAAGCTCAG | 1 | 2 | NC | NC |
| 2683 | 4331 | GCAACTTTCCTGTAAGCTCA | 2 | 1 | NC | NC |
| 2684 | 4332 | GGCAACTTTCCTGTAAGCTC | 2 | 2 | NC | NC |
| 2685 | 4333 | CGGCAACTTTCCTGTAAGCT | 2 | 2 | NC | NC |
| 2686 | 4334 | GCGGCAACTTTCCTGTAAGC | 2 | 2 | NC | NC |
| 2687 | 4335 | GGCGGCAACTTTCCTGTAAG | 2 | 3 | NC | NC |
| 2688 | 4336 | AGGCGGCAACTTTCCTGTAA | 2 | 3 | NC | NC |
| 2689 | 4337 | AAGGCGGCAACTTTCCTGTA | 2 | 3 | NC | NC |
| 2690 | 4338 | TAAGGCGGCAACTTTCCTGT | 3 | 2 | NC | NC |
| 2691 | 4339 | ATAAGGCGGCAACTTTCCTG | 3 | 3 | NC | NC |
| 2692 | 4340 | AATAAGGCGGCAACTTTCCT | 2 | 2 | NC | NC |
| 2693 | 4341 | CAATAAGGCGGCAACTTTCC | 2 | 2 | NC | NC |
| 2694 | 4342 | TCAATAAGGCGGCAACTTTC | 2 | 2 | NC | NC |
| 2695 | 4343 | TTCAATAAGGCGGCAACTTT | 2 | 2 | NC | NC |
| 2696 | 4344 | CTTCAATAAGGCGGCAACTT | 3 | NC | NC | NC |
| 2697 | 4345 | GCTTCAATAAGGCGGCAACT | 2 | NC | NC | NC |
| 2698 | 4346 | AGCTTCAATAAGGCGGCAAC | 3 | NC | NC | NC |
| 2699 | 4347 | GAGCTTCAATAAGGCGGCAA | 3 | NC | NC | NC |
| 2700 | 4348 | AGAGCTTCAATAAGGCGGCA | 3 | NC | NC | NC |
| 2701 | 4349 | CAGAGCTTCAATAAGGCGGC | 3 | NC | NC | NC |
| 2702 | 4350 | ACAGAGCTTCAATAAGGCGG | 2 | NC | NC | NC |
| 2703 | 4351 | GACAGAGCTTCAATAAGGCG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2704 | 4352 | GGACAGAGCTTCAATAAGGC | 2 | NC | NC | NC |
| 2705 | 4353 | AGGACAGAGCTTCAATAAGG | 2 | NC | NC | NC |
| 2706 | 4354 | GAGGACAGAGCTTCAATAAG | 2 | NC | NC | NC |
| 2707 | 4355 | TGAGGACAGAGCTTCAATAA | 2 | NC | NC | NC |
| 2708 | 4356 | ATGAGGACAGAGCTTCAATA | 2 | NC | NC | NC |
| 2709 | 4357 | CATGAGGACAGAGCTTCAAT | 1 | NC | NC | NC |
| 2710 | 4358 | GCATGAGGACAGAGCTTCAA | 2 | NC | NC | NC |
| 2711 | 4359 | GGCATGAGGACAGAGCTTCA | 2 | NC | NC | NC |
| 2712 | 4360 | TGGCATGAGGACAGAGCTTC | 2 | NC | NC | NC |
| 2713 | 4379 | AGCACACTGGAATGGCAGCT | 2 | 2 | NC | NC |
| 2714 | 4381 | TGAGCACACTGGAATGGCAG | 1 | 1 | NC | NC |
| 2715 | 4398 | GCATAGAAGGTCTCCCGTGA | 3 | 2 | NC | NC |
| 2716 | 4399 | AGCATAGAAGGTCTCCCGTG | 2 | 2 | NC | NC |
| 2717 | 4400 | CAGCATAGAAGGTCTCCCGT | 3 | 2 | NC | NC |
| 2718 | 4404 | ACGGCAGCATAGAAGGTCTC | 2 | NC | NC | NC |
| 2719 | 4405 | AACGGCAGCATAGAAGGTCT | 2 | NC | NC | NC |
| 2720 | 4406 | TAACGGCAGCATAGAAGGTC | 2 | NC | NC | NC |
| 2721 | 4407 | CTAACGGCAGCATAGAAGGT | 2 | NC | NC | NC |
| 2722 | 4420 | TGGTCTATGTCAGCTAACGG | 2 | NC | NC | NC |
| 2723 | 4421 | GTGGTCTATGTCAGCTAACG | 3 | NC | NC | NC |
| 2724 | 4422 | AGTGGTCTATGTCAGCTAAC | 2 | NC | NC | NC |
| 2725 | 4423 | AAGTGGTCTATGTCAGCTAA | 2 | 3 | NC | NC |
| 2726 | 4424 | CAAGTGGTCTATGTCAGCTA | 3 | 3 | NC | NC |
| 2727 | 4425 | CCAAGTGGTCTATGTCAGCT | 2 | 2 | NC | NC |
| 2728 | 4426 | TCCAAGTGGTCTATGTCAGC | 2 | 2 | NC | NC |
| 2729 | 4427 | TTCCAAGTGGTCTATGTCAG | 2 | NC | NC | NC |
| 2730 | 4428 | GTTCCAAGTGGTCTATGTCA | 2 | NC | NC | NC |
| 2731 | 4429 | TGTTCCAAGTGGTCTATGTC | 2 | NC | NC | NC |
| 2732 | 4430 | CTGTTCCAAGTGGTCTATGT | 1 | NC | NC | NC |
| 2733 | 4431 | CCTGTTCCAAGTGGTCTATG | 2 | NC | NC | NC |
| 2734 | 4432 | TCCTGTTCCAAGTGGTCTAT | 2 | NC | NC | NC |
| 2735 | 4433 | TTCCTGTTCCAAGTGGTCTA | 2 | NC | NC | NC |
| 2736 | 4434 | TTTCCTGTTCCAAGTGGTCT | 2 | NC | NC | NC |
| 2737 | 4435 | TTTTCCTGTTCCAAGTGGTC | 1 | NC | NC | NC |
| 2738 | 4436 | TTTTTCCTGTTCCAAGTGGT | 2 | NC | NC | NC |
| 2739 | 4437 | GTTTTTCCTGTTCCAAGTGG | 1 | NC | NC | NC |
| 2740 | 4438 | TGTTTTTCCTGTTCCAAGTG | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2741 | 4439 | CTGTTTTTCCTGTTCCAAGT | 2 | NC | NC | NC |
| 2742 | 4440 | TCTGTTTTTCCTGTTCCAAG | 2 | NC | NC | NC |
| 2743 | 4441 | ATCTGTTTTTCCTGTTCCAA | 1 | NC | NC | NC |
| 2744 | 4442 | AATCTGTTTTTCCTGTTCCA | 1 | NC | NC | NC |
| 2745 | 4443 | TAATCTGTTTTTCCTGTTCC | 2 | NC | NC | NC |
| 2746 | 4444 | TTAATCTGTTTTTCCTGTTC | 1 | NC | NC | NC |
| 2747 | 4445 | TTTAATCTGTTTTTCCTGTT | 1 | NC | NC | NC |
| 2748 | 4446 | GTTTAATCTGTTTTTCCTGT | 1 | NC | NC | NC |
| 2749 | 4447 | GGTTTAATCTGTTTTTCCTG | 0 | 0 | NC | NC |
| 2750 | 4448 | GGGTTTAATCTGTTTTTCCT | 1 | 1 | NC | NC |
| 2751 | 4449 | TGGGTTTAATCTGTTTTTCC | 1 | 1 | NC | NC |
| 2752 | 4450 | TTGGGTTTAATCTGTTTTTC | 1 | 0 | NC | NC |
| 2753 | 4451 | GTTGGGTTTAATCTGTTTTT | 1 | NC | NC | NC |
| 2754 | 4452 | GGTTGGGTTTAATCTGTTTT | 1 | NC | NC | NC |
| 2755 | 4453 | AGGTTGGGTTTAATCTGTTT | 2 | NC | NC | NC |
| 2756 | 4454 | GAGGTTGGGTTTAATCTGTT | 2 | NC | NC | NC |
| 2757 | 4455 | TGAGGTTGGGTTTAATCTGT | 2 | NC | NC | NC |
| 2758 | 4456 | GTGAGGTTGGGTTTAATCTG | 2 | NC | NC | NC |
| 2759 | 4457 | AGTGAGGTTGGGTTTAATCT | 2 | NC | NC | NC |
| 2760 | 4458 | TAGTGAGGTTGGGTTTAATC | 2 | NC | NC | NC |
| 2761 | 4459 | TTAGTGAGGTTGGGTTTAAT | 1 | NC | NC | NC |
| 2762 | 4460 | TTTAGTGAGGTTGGGTTTAA | 2 | NC | NC | NC |
| 2763 | 4461 | GTTTAGTGAGGTTGGGTTTA | 2 | NC | NC | NC |
| 2764 | 4462 | AGTTTAGTGAGGTTGGGTTT | 2 | NC | NC | NC |
| 2765 | 4463 | AAGTTTAGTGAGGTTGGGTT | 1 | NC | NC | NC |
| 2766 | 4464 | GAAGTTTAGTGAGGTTGGGT | 2 | NC | NC | NC |
| 2767 | 4465 | CGAAGTTTAGTGAGGTTGGG | 2 | NC | NC | NC |
| 2768 | 4466 | GCGAAGTTTAGTGAGGTTGG | 3 | NC | NC | NC |
| 2769 | 4467 | TGCGAAGTTTAGTGAGGTTG | 3 | NC | NC | NC |
| 2770 | 4468 | TTGCGAAGTTTAGTGAGGTT | 2 | NC | NC | NC |
| 2771 | 4469 | TTTGCGAAGTTTAGTGAGGT | 3 | NC | NC | NC |
| 2772 | 4470 | TTTTGCGAAGTTTAGTGAGG | 2 | NC | NC | NC |
| 2773 | 4471 | ATTTTGCGAAGTTTAGTGAG | 3 | NC | NC | NC |
| 2774 | 4472 | CATTTTGCGAAGTTTAGTGA | 2 | NC | NC | NC |
| 2775 | 4473 | CCATTTTGCGAAGTTTAGTG | 3 | NC | NC | NC |
| 2776 | 4474 | GCCATTTTGCGAAGTTTAGT | 2 | NC | NC | NC |
| 2777 | 4475 | GGCCATTTTGCGAAGTTTAG | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2778 | 4476 | GGGCCATTTTGCGAAGTTTA | 3 | 3 | NC | NC |
| 2779 | 4477 | TGGGCCATTTTGCGAAGTTT | 2 | 3 | NC | NC |
| 2780 | 4478 | CTGGGCCATTTTGCGAAGTT | 2 | 3 | NC | NC |
| 2781 | 4479 | CCTGGGCCATTTTGCGAAGT | 2 | 3 | NC | NC |
| 2782 | 4498 | TTTCCAAAGAGACGCCAGGC | 2 | 2 | NC | NC |
| 2783 | 4499 | TTTTCCAAAGAGACGCCAGG | 2 | 2 | NC | NC |
| 2784 | 4500 | CTTTTCCAAAGAGACGCCAG | 2 | 2 | NC | NC |
| 2785 | 4501 | GCTTTTCCAAAGAGACGCCA | 2 | 2 | NC | NC |
| 2786 | 4502 | TGCTTTTCCAAAGAGACGCC | 1 | 1 | NC | NC |
| 2787 | 4503 | CTGCTTTTCCAAAGAGACGC | 1 | 1 | NC | NC |
| 2788 | 4504 | TCTGCTTTTCCAAAGAGACG | 1 | 1 | NC | NC |
| 2789 | 4505 | CTCTGCTTTTCCAAAGAGAC | 2 | 2 | NC | NC |
| 2790 | 4506 | ACTCTGCTTTTCCAAAGAGA | 1 | 1 | NC | NC |
| 2791 | 4508 | ACACTCTGCTTTTCCAAAGA | 2 | 2 | NC | NC |
| 2792 | 4509 | CACACTCTGCTTTTCCAAAG | 2 | 2 | NC | NC |
| 2793 | 4510 | TCACACTCTGCTTTTCCAAA | 1 | 2 | NC | NC |
| 2794 | 4511 | ATCACACTCTGCTTTTCCAA | 2 | 1 | NC | NC |
| 2795 | 4512 | TATCACACTCTGCTTTTCCA | 2 | 2 | NC | NC |
| 2796 | 4513 | GTATCACACTCTGCTTTTCC | 1 | 2 | NC | NC |
| 2797 | 4514 | TGTATCACACTCTGCTTTTC | 2 | 2 | NC | NC |
| 2798 | 4515 | TTGTATCACACTCTGCTTTT | 1 | 1 | NC | NC |
| 2799 | 4516 | CTTGTATCACACTCTGCTTT | 1 | NC | NC | NC |
| 2800 | 4517 | CCTTGTATCACACTCTGCTT | 1 | NC | NC | NC |
| 2801 | 4518 | GCCTTGTATCACACTCTGCT | 2 | NC | NC | NC |
| 2802 | 4519 | TGCCTTGTATCACACTCTGC | 2 | NC | NC | NC |
| 2803 | 4520 | CTGCCTTGTATCACACTCTG | 2 | NC | NC | NC |
| 2804 | 4521 | TCTGCCTTGTATCACACTCT | 1 | NC | NC | NC |
| 2805 | 4522 | CTCTGCCTTGTATCACACTC | 2 | NC | NC | NC |
| 2806 | 4523 | GCTCTGCCTTGTATCACACT | 2 | NC | NC | NC |
| 2807 | 4549 | TCACAGGGAGGCATGGATTG | 2 | 2 | NC | NC |
| 2808 | 4562 | TTCTCATGGTGGCTCACAGG | 2 | 2 | NC | NC |
| 2809 | 4563 | GTTCTCATGGTGGCTCACAG | 2 | 2 | NC | NC |
| 2810 | 4564 | TGTTCTCATGGTGGCTCACA | 2 | 2 | NC | NC |
| 2811 | 4565 | CTGTTCTCATGGTGGCTCAC | 2 | 2 | NC | NC |
| 2812 | 4566 | TCTGTTCTCATGGTGGCTCA | 1 | 2 | NC | NC |
| 2813 | 4567 | TTCTGTTCTCATGGTGGCTC | 2 | 2 | NC | NC |
| 2814 | 4568 | ATTCTGTTCTCATGGTGGCT | 2 | 2 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2815 | 4569 | GATTCTGTTCTCATGGTGGC | 2 | 2 | NC | NC |
| 2816 | 4570 | TGATTCTGTTCTCATGGTGG | 2 | 2 | NC | NC |
| 2817 | 4571 | GTGATTCTGTTCTCATGGTG | 2 | 2 | NC | NC |
| 2818 | 4572 | AGTGATTCTGTTCTCATGGT | 2 | 2 | NC | NC |
| 2819 | 4577 | AGACCAGTGATTCTGTTCTC | 2 | 2 | NC | NC |
| 2820 | 4583 | CCTTTTAGACCAGTGATTCT | 1 | NC | NC | NC |
| 2821 | 4584 | TCCTTTTAGACCAGTGATTC | 1 | NC | NC | NC |
| 2822 | 4585 | TTCCTTTTAGACCAGTGATT | 2 | NC | NC | NC |
| 2823 | 4586 | GTTCCTTTTAGACCAGTGAT | 2 | NC | NC | NC |
| 2824 | 4587 | TGTTCCTTTTAGACCAGTGA | 2 | NC | NC | NC |
| 2825 | 4588 | TTGTTCCTTTTAGACCAGTG | 2 | NC | NC | NC |
| 2826 | 4589 | TTTGTTCCTTTTAGACCAGT | 1 | NC | NC | NC |
| 2827 | 4590 | CTTTGTTCCTTTTAGACCAG | 2 | NC | NC | NC |
| 2828 | 4591 | CCTTTGTTCCTTTTAGACCA | 2 | NC | NC | NC |
| 2829 | 4592 | CCCTTTGTTCCTTTTAGACC | 2 | NC | NC | NC |
| 2830 | 4593 | TCCCTTTGTTCCTTTTAGAC | 2 | NC | NC | NC |
| 2831 | 4594 | ATCCCTTTGTTCCTTTTAGA | 2 | NC | NC | NC |
| 2832 | 4595 | CATCCCTTTGTTCCTTTTAG | 2 | NC | NC | NC |
| 2833 | 4596 | ACATCCCTTTGTTCCTTTTA | 2 | NC | NC | NC |
| 2834 | 4597 | AACATCCCTTTGTTCCTTTT | 2 | NC | NC | NC |
| 2835 | 4604 | TACAGTGAACATCCCTTTGT | 2 | NC | NC | NC |
| 2836 | 4605 | ATACAGTGAACATCCCTTTG | 2 | NC | NC | NC |
| 2837 | 4606 | CATACAGTGAACATCCCTTT | 2 | NC | NC | NC |
| 2838 | 4607 | GCATACAGTGAACATCCCTT | 2 | NC | NC | NC |
| 2839 | 4608 | GGCATACAGTGAACATCCCT | 2 | NC | NC | NC |
| 2840 | 4609 | AGGCATACAGTGAACATCCC | 2 | NC | NC | NC |
| 2841 | 4610 | GAGGCATACAGTGAACATCC | 2 | NC | NC | NC |
| 2842 | 4611 | AGAGGCATACAGTGAACATC | 1 | NC | NC | NC |
| 2843 | 4612 | CAGAGGCATACAGTGAACAT | 2 | NC | NC | NC |
| 2844 | 4613 | TCAGAGGCATACAGTGAACA | 2 | NC | NC | NC |
| 2845 | 4614 | CTCAGAGGCATACAGTGAAC | 1 | NC | NC | NC |
| 2846 | 4615 | GCTCAGAGGCATACAGTGAA | 1 | 2 | NC | NC |
| 2847 | 4616 | TGCTCAGAGGCATACAGTGA | 1 | 2 | NC | NC |
| 2848 | 4672 | AGGGACACTGGGCTGATTCA | 2 | 2 | NC | NC |
| 2849 | 4683 | CTAAGCTGCTCAGGGACACT | 2 | 2 | NC | NC |
| 2850 | 4684 | TCTAAGCTGCTCAGGGACAC | 2 | 2 | NC | NC |
| 2851 | 4685 | GTCTAAGCTGCTCAGGGACA | 2 | 1 | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2852 | 4686 | TGTCTAAGCTGCTCAGGGAC | 2 | 2 | NC | NC |
| 2853 | 4687 | CTGTCTAAGCTGCTCAGGGA | 2 | NC | NC | NC |
| 2854 | 4704 | TGATACAGAGAGCCCTGCTG | 2 | NC | NC | NC |
| 2855 | 4705 | CTGATACAGAGAGCCCTGCT | 2 | NC | NC | NC |
| 2856 | 4706 | ACTGATACAGAGAGCCCTGC | 2 | NC | NC | NC |
| 2857 | 4708 | AGACTGATACAGAGAGCCCT | 2 | NC | NC | NC |
| 2858 | 4709 | AAGACTGATACAGAGAGCCC | 2 | NC | NC | NC |
| 2859 | 4710 | AAAGACTGATACAGAGAGCC | 2 | NC | NC | NC |
| 2860 | 4711 | GAAAGACTGATACAGAGAGC | 1 | NC | NC | NC |
| 2861 | 4712 | AGAAAGACTGATACAGAGAG | 1 | NC | NC | NC |
| 2862 | 4713 | AAGAAAGACTGATACAGAGA | 2 | NC | NC | NC |
| 2863 | 4714 | CAAGAAAGACTGATACAGAG | 2 | NC | NC | NC |
| 2864 | 4715 | TCAAGAAAGACTGATACAGA | 2 | NC | NC | NC |
| 2865 | 4717 | GCTCAAGAAAGACTGATACA | 2 | NC | NC | NC |
| 2866 | 4718 | TGCTCAAGAAAGACTGATAC | 2 | NC | NC | NC |
| 2867 | 4719 | CTGCTCAAGAAAGACTGATA | 2 | NC | NC | NC |
| 2868 | 4720 | TCTGCTCAAGAAAGACTGAT | 2 | NC | NC | NC |
| 2869 | 4721 | ATCTGCTCAAGAAAGACTGA | 2 | NC | NC | NC |
| 2870 | 4722 | CATCTGCTCAAGAAAGACTG | 2 | NC | NC | NC |
| 2871 | 4723 | TCATCTGCTCAAGAAAGACT | 2 | NC | NC | NC |
| 2872 | 4724 | ATCATCTGCTCAAGAAAGAC | 2 | NC | NC | NC |
| 2873 | 4725 | AATCATCTGCTCAAGAAAGA | 2 | NC | NC | NC |
| 2874 | 4726 | GAATCATCTGCTCAAGAAAG | 2 | NC | NC | NC |
| 2875 | 4727 | GGAATCATCTGCTCAAGAAA | 2 | 2 | NC | NC |
| 2876 | 4728 | GGGAATCATCTGCTCAAGAA | 2 | NC | NC | NC |
| 2877 | 4746 | ATCTGGCTACTCAACTAGGG | 2 | NC | NC | NC |
| 2878 | 4747 | CATCTGGCTACTCAACTAGG | 2 | NC | NC | NC |
| 2879 | 4748 | TCATCTGGCTACTCAACTAG | 2 | NC | NC | NC |
| 2880 | 4749 | TTCATCTGGCTACTCAACTA | 2 | NC | NC | NC |
| 2881 | 4750 | TTTCATCTGGCTACTCAACT | 2 | NC | NC | NC |
| 2882 | 4751 | ATTTCATCTGGCTACTCAAC | 2 | NC | NC | NC |
| 2883 | 4752 | AATTTCATCTGGCTACTCAA | 2 | NC | NC | NC |
| 2884 | 4753 | GAATTTCATCTGGCTACTCA | 2 | NC | NC | NC |
| 2885 | 4754 | TGAATTTCATCTGGCTACTC | 2 | NC | NC | NC |
| 2886 | 4755 | TTGAATTTCATCTGGCTACT | 2 | NC | NC | NC |
| 2887 | 4756 | CTTGAATTTCATCTGGCTAC | 2 | NC | NC | NC |
| 2888 | 4757 | GCTTGAATTTCATCTGGCTA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2889 | 4758 | GGCTTGAATTTCATCTGGCT | 2 | NC | NC | NC |
| 2890 | 4759 | AGGCTTGAATTTCATCTGGC | 2 | NC | NC | NC |
| 2891 | 4760 | TAGGCTTGAATTTCATCTGG | 2 | NC | NC | NC |
| 2892 | 4761 | TTAGGCTTGAATTTCATCTG | 3 | NC | NC | NC |
| 2893 | 4762 | TTTAGGCTTGAATTTCATCT | 2 | NC | NC | NC |
| 2894 | 4763 | CTTTAGGCTTGAATTTCATC | 2 | NC | NC | NC |
| 2895 | 4764 | TCTTTAGGCTTGAATTTCAT | 2 | NC | NC | NC |
| 2896 | 4765 | GTCTTTAGGCTTGAATTTCA | 2 | NC | NC | NC |
| 2897 | 4766 | TGTCTTTAGGCTTGAATTTC | 2 | NC | NC | NC |
| 2898 | 4767 | TTGTCTTTAGGCTTGAATTT | 2 | NC | NC | NC |
| 2899 | 4768 | ATTGTCTTTAGGCTTGAATT | 2 | NC | NC | NC |
| 2900 | 4769 | AATTGTCTTTAGGCTTGAAT | 2 | NC | NC | NC |
| 2901 | 4770 | GAATTGTCTTTAGGCTTGAA | 2 | NC | NC | NC |
| 2902 | 4771 | TGAATTGTCTTTAGGCTTGA | 2 | NC | NC | NC |
| 2903 | 4772 | ATGAATTGTCTTTAGGCTTG | 2 | NC | NC | NC |
| 2904 | 4773 | AATGAATTGTCTTTAGGCTT | 2 | NC | NC | NC |
| 2905 | 4774 | GAATGAATTGTCTTTAGGCT | 2 | NC | NC | NC |
| 2906 | 4775 | TGAATGAATTGTCTTTAGGC | 1 | NC | NC | NC |
| 2907 | 4776 | ATGAATGAATTGTCTTTAGG | 2 | NC | NC | NC |
| 2908 | 4777 | AATGAATGAATTGTCTTTAG | 1 | NC | NC | NC |
| 2909 | 4779 | CAAATGAATGAATTGTCTTT | 1 | NC | NC | NC |
| 2910 | 4780 | GCAAATGAATGAATTGTCTT | 2 | NC | NC | NC |
| 2911 | 4781 | TGCAAATGAATGAATTGTCT | 2 | NC | NC | NC |
| 2912 | 4782 | ATGCAAATGAATGAATTGTC | 2 | NC | NC | NC |
| 2913 | 4783 | GATGCAAATGAATGAATTGT | 2 | NC | NC | NC |
| 2914 | 4784 | GGATGCAAATGAATGAATTG | 2 | NC | NC | NC |
| 2915 | 4785 | TGGATGCAAATGAATGAATT | 2 | NC | NC | NC |
| 2916 | 4786 | ATGGATGCAAATGAATGAAT | 2 | NC | NC | NC |
| 2917 | 4787 | CATGGATGCAAATGAATGAA | 2 | 2 | NC | NC |
| 2918 | 4788 | CCATGGATGCAAATGAATGA | 2 | 2 | NC | NC |
| 2919 | 4789 | CCCATGGATGCAAATGAATG | 2 | NC | NC | NC |
| 2920 | 4790 | GCCCATGGATGCAAATGAAT | 2 | NC | NC | NC |
| 2921 | 4791 | TGCCCATGGATGCAAATGAA | 2 | NC | NC | NC |
| 2922 | 4797 | CTTCTGTGCCCATGGATGCA | 2 | NC | NC | NC |
| 2923 | 4799 | ACCTTCTGTGCCCATGGATG | 2 | NC | NC | NC |
| 2924 | 4800 | AACCTTCTGTGCCCATGGAT | 1 | NC | NC | NC |
| 2925 | 4801 | CAACCTTCTGTGCCCATGGA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 2926 | 4803 | AGCAACCTTCTGTGCCCATG | 2 | NC | NC | NC |
| 2927 | 4804 | TAGCAACCTTCTGTGCCCAT | 2 | NC | NC | NC |
| 2928 | 4805 | ATAGCAACCTTCTGTGCCCA | 3 | NC | NC | NC |
| 2929 | 4806 | TATAGCAACCTTCTGTGCCC | 2 | NC | NC | NC |
| 2930 | 4807 | ATATAGCAACCTTCTGTGCC | 2 | NC | NC | NC |
| 2931 | 4808 | TATATAGCAACCTTCTGTGC | 1 | NC | NC | NC |
| 2932 | 4809 | CTATATAGCAACCTTCTGTG | 2 | NC | NC | NC |
| 2933 | 4810 | ACTATATAGCAACCTTCTGT | 2 | NC | NC | NC |
| 2934 | 4811 | TACTATATAGCAACCTTCTG | 2 | NC | NC | NC |
| 2935 | 4812 | ATACTATATAGCAACCTTCT | 2 | NC | NC | NC |
| 2936 | 4813 | GATACTATATAGCAACCTTC | 2 | NC | NC | NC |
| 2937 | 4814 | AGATACTATATAGCAACCTT | 2 | NC | NC | NC |
| 2938 | 4815 | TAGATACTATATAGCAACCT | 1 | NC | NC | NC |
| 2939 | 4816 | GTAGATACTATATAGCAACC | 2 | NC | NC | NC |
| 2940 | 4817 | GGTAGATACTATATAGCAAC | 3 | NC | NC | NC |
| 2941 | 4818 | AGGTAGATACTATATAGCAA | 2 | NC | NC | NC |
| 2942 | 4819 | AAGGTAGATACTATATAGCA | 2 | NC | NC | NC |
| 2943 | 4820 | AAAGGTAGATACTATATAGC | 2 | NC | NC | NC |
| 2944 | 4821 | AAAAGGTAGATACTATATAG | 2 | NC | NC | NC |
| 2945 | 4822 | CAAAAGGTAGATACTATATA | 1 | NC | NC | NC |
| 2946 | 4823 | GCAAAAGGTAGATACTATAT | 2 | 2 | NC | NC |
| 2947 | 4824 | AGCAAAAGGTAGATACTATA | 1 | 1 | NC | NC |
| 2948 | 4825 | TAGCAAAAGGTAGATACTAT | 1 | 1 | NC | NC |
| 2949 | 4826 | GTAGCAAAAGGTAGATACTA | 2 | 2 | NC | NC |
| 2950 | 4827 | AGTAGCAAAAGGTAGATACT | 2 | 2 | NC | NC |
| 2951 | 4828 | AAGTAGCAAAAGGTAGATAC | 2 | 2 | NC | NC |
| 2952 | 4829 | TAAGTAGCAAAAGGTAGATA | 1 | 1 | NC | NC |
| 2953 | 4830 | ATAAGTAGCAAAAGGTAGAT | 1 | 2 | NC | NC |
| 2954 | 4831 | AATAAGTAGCAAAAGGTAGA | 1 | 2 | NC | NC |
| 2955 | 4832 | AAATAAGTAGCAAAAGGTAG | 1 | 1 | NC | NC |
| 2956 | 4833 | TAAATAAGTAGCAAAAGGTA | 1 | 2 | NC | NC |
| 2957 | 4834 | TTAAATAAGTAGCAAAAGGT | 1 | 2 | NC | NC |
| 2958 | 4835 | ATTAAATAAGTAGCAAAAGG | 1 | 1 | NC | NC |
| 2959 | 4836 | CATTAAATAAGTAGCAAAAG | 0 | 2 | NC | NC |
| 2960 | 4861 | CAATCAAACTGTCATTAAAT | 2 | NC | NC | NC |
| 2961 | 4862 | CCAATCAAACTGTCATTAAA | 2 | NC | NC | NC |
| 2962 | 4863 | ACCAATCAAACTGTCATTAA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 2963 | 4864 | AACCAATCAAACTGTCATTA | 2 | NC | NC | NC |
| 2964 | 4865 | CAACCAATCAAACTGTCATT | 2 | NC | NC | NC |
| 2965 | 4866 | GCAACCAATCAAACTGTCAT | 1 | NC | NC | NC |
| 2966 | 4867 | AGCAACCAATCAAACTGTCA | 1 | NC | NC | NC |
| 2967 | 4868 | AAGCAACCAATCAAACTGTC | 2 | NC | NC | NC |
| 2968 | 4869 | CAAGCAACCAATCAAACTGT | 2 | NC | NC | NC |
| 2969 | 4870 | CCAAGCAACCAATCAAACTG | 2 | NC | NC | NC |
| 2970 | 4871 | ACCAAGCAACCAATCAAACT | 2 | NC | NC | NC |
| 2971 | 4872 | AACCAAGCAACCAATCAAAC | 1 | NC | NC | NC |
| 2972 | 4873 | AAACCAAGCAACCAATCAAA | 1 | NC | NC | NC |
| 2973 | 4874 | CAAACCAAGCAACCAATCAA | 1 | NC | NC | NC |
| 2974 | 4875 | ACAAACCAAGCAACCAATCA | 1 | NC | NC | NC |
| 2975 | 4876 | AACAAACCAAGCAACCAATC | 1 | NC | NC | NC |
| 2976 | 4877 | TAACAAACCAAGCAACCAAT | 2 | NC | NC | NC |
| 2977 | 4878 | ATAACAAACCAAGCAACCAA | 1 | NC | NC | NC |
| 2978 | 4879 | AATAACAAACCAAGCAACCA | 2 | NC | NC | NC |
| 2979 | 4880 | AAATAACAAACCAAGCAACC | 1 | NC | NC | NC |
| 2980 | 4881 | CAAATAACAAACCAAGCAAC | 1 | NC | NC | NC |
| 2981 | 4882 | TCAAATAACAAACCAAGCAA | 2 | NC | NC | NC |
| 2982 | 4883 | TTCAAATAACAAACCAAGCA | 2 | NC | NC | NC |
| 2983 | 4884 | CTTCAAATAACAAACCAAGC | 2 | NC | NC | NC |
| 2984 | 4885 | CCTTCAAATAACAAACCAAG | 2 | NC | NC | NC |
| 2985 | 4886 | CCCTTCAAATAACAAACCAA | 2 | NC | NC | NC |
| 2986 | 4887 | ACCCTTCAAATAACAAACCA | 2 | NC | NC | NC |
| 2987 | 4888 | CACCCTTCAAATAACAAACC | 2 | NC | NC | NC |
| 2988 | 4889 | ACACCCTTCAAATAACAAAC | 2 | NC | NC | NC |
| 2989 | 4890 | CACACCCTTCAAATAACAAA | 2 | NC | NC | NC |
| 2990 | 4891 | TCACACCCTTCAAATAACAA | 2 | NC | NC | NC |
| 2991 | 4892 | ATCACACCCTTCAAATAACA | 2 | NC | NC | NC |
| 2992 | 4893 | AATCACACCCTTCAAATAAC | 2 | NC | NC | NC |
| 2993 | 4894 | AAATCACACCCTTCAAATAA | 2 | NC | NC | NC |
| 2994 | 4895 | AAAATCACACCCTTCAAATA | 2 | NC | NC | NC |
| 2995 | 4896 | AAAAATCACACCCTTCAAAT | 1 | NC | NC | NC |
| 2996 | 4897 | CAAAAATCACACCCTTCAAA | 1 | NC | NC | NC |
| 2997 | 4898 | ACAAAAATCACACCCTTCAA | 1 | NC | NC | NC |
| 2998 | 4899 | AACAAAAATCACACCCTTCA | 2 | NC | NC | NC |
| 2999 | 4900 | AAACAAAAATCACACCCTTC | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3000 | 4901 | AAAACAAAAATCACACCCTT | 1 | NC | NC | NC |
| 3001 | 4902 | AAAAACAAAAATCACACCCT | 0 | NC | NC | NC |
| 3002 | 4903 | CAAAAACAAAAATCACACCC | 0 | NC | NC | NC |
| 3003 | 4904 | ACAAAAACAAAAATCACACC | 0 | NC | NC | NC |
| 3004 | 4905 | TACAAAAACAAAAATCACAC | 1 | NC | NC | NC |
| 3005 | 4906 | GTACAAAAACAAAAATCACA | 1 | NC | NC | NC |
| 3006 | 4907 | TGTACAAAAACAAAAATCAC | 1 | NC | NC | NC |
| 3007 | 4908 | CTGTACAAAAACAAAAATCA | 1 | NC | NC | NC |
| 3008 | 4909 | ACTGTACAAAAACAAAAATC | 1 | NC | NC | NC |
| 3009 | 4931 | CAAATGTGAAGCTTGAAAAA | 2 | NC | NC | NC |
| 3010 | 4932 | GCAAATGTGAAGCTTGAAAA | 2 | NC | NC | NC |
| 3011 | 4933 | CGCAAATGTGAAGCTTGAAA | 2 | NC | NC | NC |
| 3012 | 4934 | ACGCAAATGTGAAGCTTGAA | 2 | NC | NC | NC |
| 3013 | 4944 | AATTAGATACACGCAAATGT | 2 | NC | NC | NC |
| 3014 | 4945 | GAATTAGATACACGCAAATG | 3 | NC | NC | NC |
| 3015 | 4946 | TGAATTAGATACACGCAAAT | 3 | NC | NC | NC |
| 3016 | 4947 | CTGAATTAGATACACGCAAA | 3 | NC | NC | NC |
| 3017 | 4948 | GCTGAATTAGATACACGCAA | 2 | NC | NC | NC |
| 3018 | 4949 | AGCTGAATTAGATACACGCA | 2 | NC | NC | NC |
| 3019 | 4950 | CAGCTGAATTAGATACACGC | 2 | NC | NC | NC |
| 3020 | 4951 | TCAGCTGAATTAGATACACG | 2 | NC | NC | NC |
| 3021 | 4952 | ATCAGCTGAATTAGATACAC | 1 | NC | NC | NC |
| 3022 | 4953 | CATCAGCTGAATTAGATACA | 2 | NC | NC | NC |
| 3023 | 4969 | ACCCCTTGGACTTGAGCATC | 2 | NC | NC | NC |
| 3024 | 4970 | TACCCCTTGGACTTGAGCAT | 1 | NC | NC | NC |
| 3025 | 4971 | CTACCCCTTGGACTTGAGCA | 2 | NC | NC | NC |
| 3026 | 4972 | ACTACCCCTTGGACTTGAGC | 2 | NC | NC | NC |
| 3027 | 4973 | GACTACCCCTTGGACTTGAG | 2 | NC | NC | NC |
| 3028 | 4974 | AGACTACCCCTTGGACTTGA | 2 | NC | NC | NC |
| 3029 | 4975 | CAGACTACCCCTTGGACTTG | 2 | NC | NC | NC |
| 3030 | 4976 | GCAGACTACCCCTTGGACTT | 3 | NC | NC | NC |
| 3031 | 4979 | AAGGCAGACTACCCCTTGGA | 2 | NC | NC | NC |
| 3032 | 5031 | AGACTGAAGGGAAAAGAGGG | 2 | NC | NC | NC |
| 3033 | 5032 | AAGACTGAAGGGAAAAGAGG | 1 | NC | NC | NC |
| 3034 | 5033 | GAAGACTGAAGGGAAAAGAG | 1 | NC | NC | NC |
| 3035 | 5034 | AGAAGACTGAAGGGAAAAGA | 2 | NC | NC | NC |
| 3036 | 5035 | AAGAAGACTGAAGGGAAAAG | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3037 | 5036 | GAAGAAGACTGAAGGGAAAA | 1 | NC | NC | NC |
| 3038 | 5037 | TGAAGAAGACTGAAGGGAAA | 1 | NC | NC | NC |
| 3039 | 5038 | GTGAAGAAGACTGAAGGGAA | 1 | NC | NC | NC |
| 3040 | 5039 | AGTGAAGAAGACTGAAGGGA | 1 | NC | NC | NC |
| 3041 | 5040 | AAGTGAAGAAGACTGAAGGG | 1 | NC | NC | NC |
| 3042 | 5041 | GAAGTGAAGAAGACTGAAGG | 2 | NC | NC | NC |
| 3043 | 5042 | GGAAGTGAAGAAGACTGAAG | 2 | NC | NC | NC |
| 3044 | 5043 | GGGAAGTGAAGAAGACTGAA | 1 | NC | NC | NC |
| 3045 | 5044 | AGGGAAGTGAAGAAGACTGA | 2 | NC | NC | NC |
| 3046 | 5045 | TAGGGAAGTGAAGAAGACTG | 2 | NC | NC | NC |
| 3047 | 5046 | ATAGGGAAGTGAAGAAGACT | 2 | NC | NC | NC |
| 3048 | 5047 | CATAGGGAAGTGAAGAAGAC | 2 | NC | NC | NC |
| 3049 | 5048 | GCATAGGGAAGTGAAGAAGA | 2 | NC | NC | NC |
| 3050 | 5049 | AGCATAGGGAAGTGAAGAAG | 2 | NC | NC | NC |
| 3051 | 5050 | CAGCATAGGGAAGTGAAGAA | 1 | NC | NC | NC |
| 3052 | 5051 | GCAGCATAGGGAAGTGAAGA | 2 | NC | NC | NC |
| 3053 | 5052 | AGCAGCATAGGGAAGTGAAG | 2 | NC | NC | NC |
| 3054 | 5053 | CAGCAGCATAGGGAAGTGAA | 2 | NC | NC | NC |
| 3055 | 5067 | TGTAGCACATGAAGCAGCAG | 2 | NC | NC | NC |
| 3056 | 5068 | ATGTAGCACATGAAGCAGCA | 2 | NC | NC | NC |
| 3057 | 5069 | GATGTAGCACATGAAGCAGC | 2 | NC | NC | NC |
| 3058 | 5070 | AGATGTAGCACATGAAGCAG | 2 | NC | NC | NC |
| 3059 | 5071 | GAGATGTAGCACATGAAGCA | 2 | NC | NC | NC |
| 3060 | 5072 | TGAGATGTAGCACATGAAGC | 2 | NC | NC | NC |
| 3061 | 5073 | CTGAGATGTAGCACATGAAG | 2 | NC | NC | NC |
| 3062 | 5074 | TCTGAGATGTAGCACATGAA | 2 | NC | NC | NC |
| 3063 | 5075 | GTCTGAGATGTAGCACATGA | 2 | NC | NC | NC |
| 3064 | 5076 | AGTCTGAGATGTAGCACATG | 2 | NC | NC | NC |
| 3065 | 5078 | TAAGTCTGAGATGTAGCACA | 2 | NC | NC | NC |
| 3066 | 5079 | TTAAGTCTGAGATGTAGCAC | 2 | NC | NC | NC |
| 3067 | 5080 | TTTAAGTCTGAGATGTAGCA | 2 | NC | NC | NC |
| 3068 | 5081 | CTTTAAGTCTGAGATGTAGC | 2 | NC | NC | NC |
| 3069 | 5082 | TCTTTAAGTCTGAGATGTAG | 2 | NC | NC | NC |
| 3070 | 5083 | CTCTTTAAGTCTGAGATGTA | 2 | NC | NC | NC |
| 3071 | 5084 | ACTCTTTAAGTCTGAGATGT | 1 | NC | NC | NC |
| 3072 | 5085 | AACTCTTTAAGTCTGAGATG | 2 | NC | NC | NC |
| 3073 | 5086 | AAACTCTTTAAGTCTGAGAT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3074 | 5087 | GAAACTCTTTAAGTCTGAGA | 2 | NC | NC | NC |
| 3075 | 5088 | AGAAACTCTTTAAGTCTGAG | 1 | NC | NC | NC |
| 3076 | 5089 | GAGAAACTCTTTAAGTCTGA | 2 | NC | NC | NC |
| 3077 | 5090 | AGAGAAACTCTTTAAGTCTG | 2 | NC | NC | NC |
| 3078 | 5100 | TCACTGTAGTAGAGAAACTC | 2 | NC | NC | NC |
| 3079 | 5101 | TTCACTGTAGTAGAGAAACT | 2 | NC | NC | NC |
| 3080 | 5102 | TTTCACTGTAGTAGAGAAAC | 1 | NC | NC | NC |
| 3081 | 5104 | GTTTTCACTGTAGTAGAGAA | 1 | NC | NC | NC |
| 3082 | 5105 | TGTTTTCACTGTAGTAGAGA | 1 | NC | NC | NC |
| 3083 | 5106 | ATGTTTTCACTGTAGTAGAG | 1 | NC | NC | NC |
| 3084 | 5107 | AATGTTTTCACTGTAGTAGA | 1 | NC | NC | NC |
| 3085 | 5108 | GAATGTTTTCACTGTAGTAG | 2 | NC | NC | NC |
| 3086 | 5109 | AGAATGTTTTCACTGTAGTA | 2 | NC | NC | NC |
| 3087 | 5110 | GAGAATGTTTTCACTGTAGT | 2 | NC | NC | NC |
| 3088 | 5111 | AGAGAATGTTTTCACTGTAG | 2 | NC | NC | NC |
| 3089 | 5112 | TAGAGAATGTTTTCACTGTA | 2 | NC | NC | NC |
| 3090 | 5113 | CTAGAGAATGTTTTCACTGT | 2 | NC | NC | NC |
| 3091 | 5114 | CCTAGAGAATGTTTTCACTG | 2 | NC | NC | NC |
| 3092 | 5115 | CCCTAGAGAATGTTTTCACT | 2 | NC | NC | NC |
| 3093 | 5116 | ACCCTAGAGAATGTTTTCAC | 2 | NC | NC | NC |
| 3094 | 5117 | GACCCTAGAGAATGTTTTCA | 2 | NC | NC | NC |
| 3095 | 5118 | AGACCCTAGAGAATGTTTTC | 2 | NC | NC | NC |
| 3096 | 5119 | AAGACCCTAGAGAATGTTTT | 2 | NC | NC | NC |
| 3097 | 5120 | AAAGACCCTAGAGAATGTTT | 2 | NC | NC | NC |
| 3098 | 5121 | GAAAGACCCTAGAGAATGTT | 1 | NC | NC | NC |
| 3099 | 5122 | TGAAAGACCCTAGAGAATGT | 2 | NC | NC | NC |
| 3100 | 5123 | ATGAAAGACCCTAGAGAATG | 1 | NC | NC | NC |
| 3101 | 5124 | GATGAAAGACCCTAGAGAAT | 2 | NC | NC | NC |
| 3102 | 5125 | TGATGAAAGACCCTAGAGAA | 2 | NC | NC | NC |
| 3103 | 5126 | CTGATGAAAGACCCTAGAGA | 1 | NC | NC | NC |
| 3104 | 5127 | CCTGATGAAAGACCCTAGAG | 1 | NC | NC | NC |
| 3105 | 5128 | GCCTGATGAAAGACCCTAGA | 2 | NC | NC | NC |
| 3106 | 5129 | GGCCTGATGAAAGACCCTAG | 2 | NC | NC | NC |
| 3107 | 5130 | AGGCCTGATGAAAGACCCTA | 2 | NC | NC | NC |
| 3108 | 5131 | AAGGCCTGATGAAAGACCCT | 2 | NC | NC | NC |
| 3109 | 5132 | AAAGGCCTGATGAAAGACCC | 2 | NC | NC | NC |
| 3110 | 5133 | TAAAGGCCTGATGAAAGACC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3111 | 5134 | CTAAAGGCCTGATGAAAGAC | 2 | NC | NC | NC |
| 3112 | 5135 | ACTAAAGGCCTGATGAAAGA | 2 | NC | NC | NC |
| 3113 | 5136 | AACTAAAGGCCTGATGAAAG | 2 | NC | NC | NC |
| 3114 | 5137 | TAACTAAAGGCCTGATGAAA | 2 | NC | NC | NC |
| 3115 | 5138 | ATAACTAAAGGCCTGATGAA | 2 | NC | NC | NC |
| 3116 | 5139 | AATAACTAAAGGCCTGATGA | 2 | NC | NC | NC |
| 3117 | 5140 | AAATAACTAAAGGCCTGATG | 2 | NC | NC | NC |
| 3118 | 5141 | AAAATAACTAAAGGCCTGAT | 2 | NC | NC | NC |
| 3119 | 5142 | TAAAATAACTAAAGGCCTGA | 2 | NC | NC | NC |
| 3120 | 5143 | CTAAAATAACTAAAGGCCTG | 2 | NC | NC | NC |
| 3121 | 5144 | CCTAAAATAACTAAAGGCCT | 1 | NC | NC | NC |
| 3122 | 5145 | CCCTAAAATAACTAAAGGCC | 2 | NC | NC | NC |
| 3123 | 5146 | TCCCTAAAATAACTAAAGGC | 2 | NC | NC | NC |
| 3124 | 5147 | ATCCCTAAAATAACTAAAGG | 2 | NC | NC | NC |
| 3125 | 5148 | TATCCCTAAAATAACTAAAG | 1 | NC | NC | NC |
| 3126 | 5153 | GTTTTTATCCCTAAAATAAC | 2 | NC | NC | NC |
| 3127 | 5158 | CAATAGTTTTTATCCCTAAA | 2 | NC | NC | NC |
| 3128 | 5159 | TCAATAGTTTTTATCCCTAA | 1 | NC | NC | NC |
| 3129 | 5160 | ATCAATAGTTTTTATCCCTA | 2 | NC | NC | NC |
| 3130 | 5161 | TATCAATAGTTTTTATCCCT | 1 | NC | NC | NC |
| 3131 | 5162 | TTATCAATAGTTTTTATCCC | 1 | NC | NC | NC |
| 3132 | 5169 | GTCCTTTTTATCAATAGTTT | 2 | NC | NC | NC |
| 3133 | 5170 | TGTCCTTTTTATCAATAGTT | 2 | NC | NC | NC |
| 3134 | 5171 | TTGTCCTTTTTATCAATAGT | 2 | NC | NC | NC |
| 3135 | 5172 | CTTGTCCTTTTTATCAATAG | 2 | NC | NC | NC |
| 3136 | 5173 | CCTTGTCCTTTTTATCAATA | 2 | NC | NC | NC |
| 3137 | 5174 | TCCTTGTCCTTTTTATCAAT | 2 | NC | NC | NC |
| 3138 | 5175 | ATCCTTGTCCTTTTTATCAA | 2 | NC | NC | NC |
| 3139 | 5176 | TATCCTTGTCCTTTTTATCA | 2 | NC | NC | NC |
| 3140 | 5177 | CTATCCTTGTCCTTTTTATC | 2 | NC | NC | NC |
| 3141 | 5178 | TCTATCCTTGTCCTTTTTAT | 2 | NC | NC | NC |
| 3142 | 5179 | TTCTATCCTTGTCCTTTTTA | 2 | NC | NC | NC |
| 3143 | 5180 | GTTCTATCCTTGTCCTTTTT | 2 | NC | NC | NC |
| 3144 | 5181 | TGTTCTATCCTTGTCCTTTT | 2 | NC | NC | NC |
| 3145 | 5182 | CTGTTCTATCCTTGTCCTTT | 2 | NC | NC | NC |
| 3146 | 5183 | TCTGTTCTATCCTTGTCCTT | 2 | NC | NC | NC |
| 3147 | 5184 | CTCTGTTCTATCCTTGTCCT | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3148 | 5185 | TCTCTGTTCTATCCTTGTCC | 2 | NC | NC | NC |
| 3149 | 5186 | TTCTCTGTTCTATCCTTGTC | 1 | NC | NC | NC |
| 3150 | 5187 | TTTCTCTGTTCTATCCTTGT | 2 | NC | NC | NC |
| 3151 | 5188 | TTTTCTCTGTTCTATCCTTG | 1 | NC | NC | NC |
| 3152 | 5189 | ATTTTCTCTGTTCTATCCTT | 1 | NC | NC | NC |
| 3153 | 5190 | AATTTTCTCTGTTCTATCCT | 1 | NC | NC | NC |
| 3154 | 5191 | AAATTTTCTCTGTTCTATCC | 1 | NC | NC | NC |
| 3155 | 5192 | TAAATTTTCTCTGTTCTATC | 1 | NC | NC | NC |
| 3156 | 5195 | CTTTAAATTTTCTCTGTTCT | 1 | NC | NC | NC |
| 3157 | 5196 | ACTTTAAATTTTCTCTGTTC | 1 | NC | NC | NC |
| 3158 | 5197 | GACTTTAAATTTTCTCTGTT | 1 | NC | NC | NC |
| 3159 | 5198 | GGACTTTAAATTTTCTCTGT | 2 | NC | NC | NC |
| 3160 | 5199 | AGGACTTTAAATTTTCTCTG | 2 | NC | NC | NC |
| 3161 | 5200 | CAGGACTTTAAATTTTCTCT | 2 | NC | NC | NC |
| 3162 | 5201 | ACAGGACTTTAAATTTTCTC | 2 | NC | NC | NC |
| 3163 | 5202 | AACAGGACTTTAAATTTTCT | 1 | NC | NC | NC |
| 3164 | 5203 | GAACAGGACTTTAAATTTTC | 2 | NC | NC | NC |
| 3165 | 5204 | GGAACAGGACTTTAAATTTT | 2 | NC | NC | NC |
| 3166 | 5205 | CGGAACAGGACTTTAAATTT | 2 | NC | NC | NC |
| 3167 | 5206 | CCGGAACAGGACTTTAAATT | 1 | NC | NC | NC |
| 3168 | 5207 | CCCGGAACAGGACTTTAAAT | 1 | NC | NC | NC |
| 3169 | 5208 | ACCCGGAACAGGACTTTAAA | 1 | NC | NC | NC |
| 3170 | 5209 | AACCCGGAACAGGACTTTAA | 2 | NC | NC | NC |
| 3171 | 5210 | AAACCCGGAACAGGACTTTA | 2 | NC | NC | NC |
| 3172 | 5211 | AAAACCCGGAACAGGACTTT | 2 | NC | NC | NC |
| 3173 | 5212 | AAAAACCCGGAACAGGACTT | 2 | NC | NC | NC |
| 3174 | 5239 | CTCTGAGTTTTTAAAGAAAA | 1 | NC | NC | NC |
| 3175 | 5240 | TCTCTGAGTTTTTAAAGAAA | 1 | NC | NC | NC |
| 3176 | 5241 | GTCTCTGAGTTTTTAAAGAA | 2 | NC | NC | NC |
| 3177 | 5242 | AGTCTCTGAGTTTTTAAAGA | 1 | NC | NC | NC |
| 3178 | 5243 | CAGTCTCTGAGTTTTTAAAG | 2 | NC | NC | NC |
| 3179 | 5244 | TCAGTCTCTGAGTTTTTAAA | 2 | NC | NC | NC |
| 3180 | 5254 | ATATTGAACATCAGTCTCTG | 1 | NC | NC | NC |
| 3181 | 5255 | GATATTGAACATCAGTCTCT | 1 | NC | NC | NC |
| 3182 | 5256 | GGATATTGAACATCAGTCTC | 2 | NC | NC | NC |
| 3183 | 5257 | GGGATATTGAACATCAGTCT | 1 | NC | NC | NC |
| 3184 | 5258 | TGGGATATTGAACATCAGTC | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3185 | 5259 | TTGGGATATTGAACATCAGT | 2 | NC | NC | NC |
| 3186 | 5260 | TTTGGGATATTGAACATCAG | 2 | NC | NC | NC |
| 3187 | 5261 | GTTTGGGATATTGAACATCA | 2 | NC | NC | NC |
| 3188 | 5262 | GGTTTGGGATATTGAACATC | 2 | NC | NC | NC |
| 3189 | 5263 | TGGTTTGGGATATTGAACAT | 2 | NC | NC | NC |
| 3190 | 5264 | CTGGTTTGGGATATTGAACA | 2 | NC | NC | NC |
| 3191 | 5265 | ACTGGTTTGGGATATTGAAC | 2 | NC | NC | NC |
| 3192 | 5266 | TACTGGTTTGGGATATTGAA | 2 | NC | NC | NC |
| 3193 | 5267 | TTACTGGTTTGGGATATTGA | 2 | NC | NC | NC |
| 3194 | 5268 | TTTACTGGTTTGGGATATTG | 1 | NC | NC | NC |
| 3195 | 5269 | TTTTACTGGTTTGGGATATT | 2 | NC | NC | NC |
| 3196 | 5270 | ATTTTACTGGTTTGGGATAT | 1 | NC | NC | NC |
| 3197 | 5271 | CATTTTACTGGTTTGGGATA | 1 | NC | NC | NC |
| 3198 | 5272 | CCATTTTACTGGTTTGGGAT | 1 | NC | NC | NC |
| 3199 | 5281 | GTATTTTCACCATTTTACTG | 1 | NC | NC | NC |
| 3200 | 5282 | AGTATTTTCACCATTTTACT | 1 | NC | NC | NC |
| 3201 | 5283 | TAGTATTTTCACCATTTTAC | 1 | NC | NC | NC |
| 3202 | 5285 | CATAGTATTTTCACCATTTT | 1 | NC | NC | NC |
| 3203 | 5286 | TCATAGTATTTTCACCATTT | 1 | NC | NC | NC |
| 3204 | 5287 | CTCATAGTATTTTCACCATT | 2 | NC | NC | NC |
| 3205 | 5288 | GCTCATAGTATTTTCACCAT | 2 | NC | NC | NC |
| 3206 | 5289 | AGCTCATAGTATTTTCACCA | 2 | NC | NC | NC |
| 3207 | 5290 | AAGCTCATAGTATTTTCACC | 2 | NC | NC | NC |
| 3208 | 5291 | CAAGCTCATAGTATTTTCAC | 2 | NC | NC | NC |
| 3209 | 5292 | ACAAGCTCATAGTATTTTCA | 1 | NC | NC | NC |
| 3210 | 5293 | AACAAGCTCATAGTATTTTC | 2 | NC | NC | NC |
| 3211 | 5294 | AAACAAGCTCATAGTATTTT | 2 | NC | NC | NC |
| 3212 | 5295 | AAAACAAGCTCATAGTATTT | 2 | NC | NC | NC |
| 3213 | 5296 | AAAAACAAGCTCATAGTATT | 2 | NC | NC | NC |
| 3214 | 5346 | CTTTCACATAAAGAGATACT | 2 | NC | NC | NC |
| 3215 | 5347 | GCTTTCACATAAAGAGATAC | 2 | NC | NC | NC |
| 3216 | 5348 | TGCTTTCACATAAAGAGATA | 2 | NC | NC | NC |
| 3217 | 5349 | TTGCTTTCACATAAAGAGAT | 2 | NC | NC | NC |
| 3218 | 5350 | ATTGCTTTCACATAAAGAGA | 2 | NC | NC | NC |
| 3219 | 5351 | AATTGCTTTCACATAAAGAG | 2 | NC | NC | NC |
| 3220 | 5352 | CAATTGCTTTCACATAAAGA | 2 | NC | NC | NC |
| 3221 | 5353 | ACAATTGCTTTCACATAAAG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3222 | 5354 | GACAATTGCTTTCACATAAA | 2 | NC | NC | NC |
| 3223 | 5355 | TGACAATTGCTTTCACATAA | 2 | NC | NC | NC |
| 3224 | 5356 | ATGACAATTGCTTTCACATA | 2 | NC | NC | NC |
| 3225 | 5357 | TATGACAATTGCTTTCACAT | 2 | NC | NC | NC |
| 3226 | 5358 | ATATGACAATTGCTTTCACA | 2 | NC | NC | NC |
| 3227 | 5359 | GATATGACAATTGCTTTCAC | 2 | NC | NC | NC |
| 3228 | 5360 | TGATATGACAATTGCTTTCA | 2 | NC | NC | NC |
| 3229 | 5361 | TTGATATGACAATTGCTTTC | 2 | NC | NC | NC |
| 3230 | 5362 | TTTGATATGACAATTGCTTT | 2 | NC | NC | NC |
| 3231 | 5363 | TTTTGATATGACAATTGCTT | 2 | NC | NC | NC |
| 3232 | 5364 | GTTTTGATATGACAATTGCT | 2 | NC | NC | NC |
| 3233 | 5365 | TGTTTTGATATGACAATTGC | 2 | NC | NC | NC |
| 3234 | 5366 | GTGTTTTGATATGACAATTG | 2 | NC | NC | NC |
| 3235 | 5367 | TGTGTTTTGATATGACAATT | 2 | NC | NC | NC |
| 3236 | 5368 | CTGTGTTTTGATATGACAAT | 2 | NC | NC | NC |
| 3237 | 5369 | GCTGTGTTTTGATATGACAA | 2 | NC | NC | NC |
| 3238 | 5370 | TGCTGTGTTTTGATATGACA | 2 | NC | NC | NC |
| 3239 | 5371 | ATGCTGTGTTTTGATATGAC | 2 | NC | NC | NC |
| 3240 | 5372 | TATGCTGTGTTTTGATATGA | 1 | NC | NC | NC |
| 3241 | 5373 | GTATGCTGTGTTTTGATATG | 2 | NC | NC | NC |
| 3242 | 5374 | TGTATGCTGTGTTTTGATAT | 1 | NC | NC | NC |
| 3243 | 5375 | ATGTATGCTGTGTTTTGATA | 1 | NC | NC | NC |
| 3244 | 5376 | TATGTATGCTGTGTTTTGAT | 1 | NC | NC | NC |
| 3245 | 5377 | GTATGTATGCTGTGTTTTGA | 2 | NC | NC | NC |
| 3246 | 5378 | CGTATGTATGCTGTGTTTTG | 2 | NC | NC | NC |
| 3247 | 5379 | ACGTATGTATGCTGTGTTTT | 2 | NC | NC | NC |
| 3248 | 5380 | AACGTATGTATGCTGTGTTT | 2 | NC | NC | NC |
| 3249 | 5381 | GAACGTATGTATGCTGTGTT | 2 | NC | NC | NC |
| 3250 | 5382 | TGAACGTATGTATGCTGTGT | 2 | NC | NC | NC |
| 3251 | 5383 | TTGAACGTATGTATGCTGTG | 3 | NC | NC | NC |
| 3252 | 5384 | GTTGAACGTATGTATGCTGT | 3 | NC | NC | NC |
| 3253 | 5385 | GGTTGAACGTATGTATGCTG | 3 | NC | NC | NC |
| 3254 | 5386 | AGGTTGAACGTATGTATGCT | 2 | NC | NC | NC |
| 3255 | 5387 | TAGGTTGAACGTATGTATGC | 1 | NC | NC | NC |
| 3256 | 5388 | TTAGGTTGAACGTATGTATG | 2 | NC | NC | NC |
| 3257 | 5389 | GTTAGGTTGAACGTATGTAT | 2 | NC | NC | NC |
| 3258 | 5390 | GGTTAGGTTGAACGTATGTA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3259 | 5391 | TGGTTAGGTTGAACGTATGT | 2 | NC | NC | NC |
| 3260 | 5392 | TTGGTTAGGTTGAACGTATG | 2 | NC | NC | NC |
| 3261 | 5393 | TTTGGTTAGGTTGAACGTAT | 2 | NC | NC | NC |
| 3262 | 5394 | ATTTGGTTAGGTTGAACGTA | 2 | NC | NC | NC |
| 3263 | 5395 | TATTTGGTTAGGTTGAACGT | 2 | NC | NC | NC |
| 3264 | 5396 | ATATTTGGTTAGGTTGAACG | 3 | NC | NC | NC |
| 3265 | 5397 | GATATTTGGTTAGGTTGAAC | 2 | NC | NC | NC |
| 3266 | 5398 | AGATATTTGGTTAGGTTGAA | 1 | NC | NC | NC |
| 3267 | 5399 | AAGATATTTGGTTAGGTTGA | 1 | NC | NC | NC |
| 3268 | 5400 | AAAGATATTTGGTTAGGTTG | 2 | NC | NC | NC |
| 3269 | 5401 | TAAAGATATTTGGTTAGGTT | 2 | NC | NC | NC |
| 3270 | 5402 | GTAAAGATATTTGGTTAGGT | 2 | NC | NC | NC |
| 3271 | 5403 | TGTAAAGATATTTGGTTAGG | 2 | NC | NC | NC |
| 3272 | 5404 | GTGTAAAGATATTTGGTTAG | 2 | NC | NC | NC |
| 3273 | 5405 | AGTGTAAAGATATTTGGTTA | 2 | NC | NC | NC |
| 3274 | 5406 | AAGTGTAAAGATATTTGGTT | 2 | NC | NC | NC |
| 3275 | 5407 | AAAGTGTAAAGATATTTGGT | 2 | NC | NC | NC |
| 3276 | 5408 | AAAAGTGTAAAGATATTTGG | 2 | NC | NC | NC |
| 3277 | 5414 | GAAAGAAAAAGTGTAAAGAT | 0 | NC | NC | NC |
| 3278 | 5415 | TGAAAGAAAAAGTGTAAAGA | 1 | NC | NC | NC |
| 3279 | 5416 | CTGAAAGAAAAAGTGTAAAG | 1 | NC | NC | NC |
| 3280 | 5417 | CCTGAAAGAAAAAGTGTAAA | 1 | NC | NC | NC |
| 3281 | 5418 | TCCTGAAAGAAAAAGTGTAA | 2 | NC | NC | NC |
| 3282 | 5419 | CTCCTGAAAGAAAAAGTGTA | 2 | NC | NC | NC |
| 3283 | 5420 | TCTCCTGAAAGAAAAAGTGT | 2 | NC | NC | NC |
| 3284 | 5421 | GTCTCCTGAAAGAAAAAGTG | 1 | NC | NC | NC |
| 3285 | 5422 | TGTCTCCTGAAAGAAAAAGT | 2 | NC | NC | NC |
| 3286 | 5423 | TTGTCTCCTGAAAGAAAAAG | 2 | NC | NC | NC |
| 3287 | 5424 | CTTGTCTCCTGAAAGAAAAA | 1 | NC | NC | NC |
| 3288 | 5425 | CCTTGTCTCCTGAAAGAAAA | 1 | NC | NC | NC |
| 3289 | 5426 | CCCTTGTCTCCTGAAAGAAA | 1 | NC | NC | NC |
| 3290 | 5427 | ACCCTTGTCTCCTGAAAGAA | 2 | NC | NC | NC |
| 3291 | 5428 | AACCCTTGTCTCCTGAAAGA | 2 | NC | NC | NC |
| 3292 | 5429 | GAACCCTTGTCTCCTGAAAG | 2 | NC | NC | NC |
| 3293 | 5430 | AGAACCCTTGTCTCCTGAAA | 2 | NC | NC | NC |
| 3294 | 5431 | AAGAACCCTTGTCTCCTGAA | 2 | NC | NC | NC |
| 3295 | 5432 | AAAGAACCCTTGTCTCCTGA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3296 | 5433 | CAAAGAACCCTTGTCTCCTG | 2 | NC | NC | NC |
| 3297 | 5434 | CCAAAGAACCCTTGTCTCCT | 2 | NC | NC | NC |
| 3298 | 5435 | CCCAAAGAACCCTTGTCTCC | 2 | NC | NC | NC |
| 3299 | 5436 | ACCCAAAGAACCCTTGTCTC | 2 | NC | NC | NC |
| 3300 | 5437 | GACCCAAAGAACCCTTGTCT | 2 | NC | NC | NC |
| 3301 | 5438 | GGACCCAAAGAACCCTTGTC | 2 | NC | NC | NC |
| 3302 | 5444 | TGAAAGGGACCCAAAGAACC | 2 | NC | NC | NC |
| 3303 | 5445 | TTGAAAGGGACCCAAAGAAC | 2 | NC | NC | NC |
| 3304 | 5446 | TTTGAAAGGGACCCAAAGAA | 2 | NC | NC | NC |
| 3305 | 5447 | GTTTGAAAGGGACCCAAAGA | 2 | NC | NC | NC |
| 3306 | 5448 | CGTTTGAAAGGGACCCAAAG | 2 | NC | NC | NC |
| 3307 | 5457 | CCAAGATACCGTTTGAAAGG | 3 | NC | NC | NC |
| 3308 | 5458 | ACCAAGATACCGTTTGAAAG | 3 | NC | NC | NC |
| 3309 | 5459 | CACCAAGATACCGTTTGAAA | 2 | NC | NC | NC |
| 3310 | 5460 | ACACCAAGATACCGTTTGAA | 2 | NC | NC | NC |
| 3311 | 5461 | AACACCAAGATACCGTTTGA | 2 | NC | NC | NC |
| 3312 | 5462 | TAACACCAAGATACCGTTTG | 3 | NC | NC | NC |
| 3313 | 5463 | ATAACACCAAGATACCGTTT | 2 | NC | NC | NC |
| 3314 | 5464 | AATAACACCAAGATACCGTT | 2 | NC | NC | NC |
| 3315 | 5465 | TAATAACACCAAGATACCGT | 2 | NC | NC | NC |
| 3316 | 5466 | GTAATAACACCAAGATACCG | 2 | NC | NC | NC |
| 3317 | 5467 | TGTAATAACACCAAGATACC | 2 | NC | NC | NC |
| 3318 | 5468 | ATGTAATAACACCAAGATAC | 2 | NC | NC | NC |
| 3319 | 5469 | AATGTAATAACACCAAGATA | 1 | NC | NC | NC |
| 3320 | 5470 | TAATGTAATAACACCAAGAT | 2 | NC | NC | NC |
| 3321 | 5471 | ATAATGTAATAACACCAAGA | 2 | NC | NC | NC |
| 3322 | 5472 | CATAATGTAATAACACCAAG | 2 | NC | NC | NC |
| 3323 | 5473 | GCATAATGTAATAACACCAA | 2 | NC | NC | NC |
| 3324 | 5474 | GGCATAATGTAATAACACCA | 2 | NC | NC | NC |
| 3325 | 5475 | AGGCATAATGTAATAACACC | 2 | NC | NC | NC |
| 3326 | 5476 | TAGGCATAATGTAATAACAC | 2 | NC | NC | NC |
| 3327 | 5478 | GATAGGCATAATGTAATAAC | 2 | NC | NC | NC |
| 3328 | 5479 | AGATAGGCATAATGTAATAA | 2 | NC | NC | NC |
| 3329 | 5480 | TAGATAGGCATAATGTAATA | 1 | NC | NC | NC |
| 3330 | 5481 | ATAGATAGGCATAATGTAAT | 1 | NC | NC | NC |
| 3331 | 5482 | AATAGATAGGCATAATGTAA | 2 | NC | NC | NC |
| 3332 | 5483 | CAATAGATAGGCATAATGTA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3333 | 5484 | GCAATAGATAGGCATAATGT | 2 | NC | NC | NC |
| 3334 | 5485 | GGCAATAGATAGGCATAATG | 2 | NC | NC | NC |
| 3335 | 5486 | GGGCAATAGATAGGCATAAT | 2 | NC | NC | NC |
| 3336 | 5487 | AGGGCAATAGATAGGCATAA | 2 | NC | NC | NC |
| 3337 | 5488 | AAGGGCAATAGATAGGCATA | 2 | NC | NC | NC |
| 3338 | 5489 | TAAGGGCAATAGATAGGCAT | 2 | NC | NC | NC |
| 3339 | 5490 | ATAAGGGCAATAGATAGGCA | 2 | NC | NC | NC |
| 3340 | 5491 | TATAAGGGCAATAGATAGGC | 2 | NC | NC | NC |
| 3341 | 5492 | TTATAAGGGCAATAGATAGG | 2 | NC | NC | NC |
| 3342 | 5493 | ATTATAAGGGCAATAGATAG | 2 | NC | NC | NC |
| 3343 | 5494 | TATTATAAGGGCAATAGATA | 2 | NC | NC | NC |
| 3344 | 5495 | ATATTATAAGGGCAATAGAT | 2 | NC | NC | NC |
| 3345 | 5496 | GATATTATAAGGGCAATAGA | 2 | NC | NC | NC |
| 3346 | 5497 | TGATATTATAAGGGCAATAG | 2 | NC | NC | NC |
| 3347 | 5498 | GTGATATTATAAGGGCAATA | 2 | NC | NC | NC |
| 3348 | 5499 | AGTGATATTATAAGGGCAAT | 2 | NC | NC | NC |
| 3349 | 5500 | AAGTGATATTATAAGGGCAA | 2 | NC | NC | NC |
| 3350 | 5501 | CAAGTGATATTATAAGGGCA | 2 | NC | NC | NC |
| 3351 | 5502 | CCAAGTGATATTATAAGGGC | 2 | NC | NC | NC |
| 3352 | 5503 | CCCAAGTGATATTATAAGGG | 3 | NC | NC | NC |
| 3353 | 5504 | TCCCAAGTGATATTATAAGG | 1 | NC | NC | NC |
| 3354 | 5505 | GTCCCAAGTGATATTATAAG | 2 | NC | NC | NC |
| 3355 | 5506 | GGTCCCAAGTGATATTATAA | 2 | NC | NC | NC |
| 3356 | 5507 | TGGTCCCAAGTGATATTATA | 2 | NC | NC | NC |
| 3357 | 5508 | CTGGTCCCAAGTGATATTAT | 2 | NC | NC | NC |
| 3358 | 5509 | CCTGGTCCCAAGTGATATTA | 2 | NC | NC | NC |
| 3359 | 5510 | TCCTGGTCCCAAGTGATATT | 1 | NC | NC | NC |
| 3360 | 5511 | GTCCTGGTCCCAAGTGATAT | 2 | NC | NC | NC |
| 3361 | 5512 | AGTCCTGGTCCCAAGTGATA | 2 | NC | NC | NC |
| 3362 | 5513 | CAGTCCTGGTCCCAAGTGAT | 1 | NC | NC | NC |
| 3363 | 5514 | TCAGTCCTGGTCCCAAGTGA | 1 | NC | NC | NC |
| 3364 | 5515 | ATCAGTCCTGGTCCCAAGTG | 2 | NC | NC | NC |
| 3365 | 5516 | GATCAGTCCTGGTCCCAAGT | 1 | NC | NC | NC |
| 3366 | 5518 | ACGATCAGTCCTGGTCCCAA | 2 | NC | NC | NC |
| 3367 | 5519 | AACGATCAGTCCTGGTCCCA | 3 | NC | NC | NC |
| 3368 | 5521 | AGAACGATCAGTCCTGGTCC | 2 | NC | NC | NC |
| 3369 | 5522 | CAGAACGATCAGTCCTGGTC | 3 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3370 | 5523 | GCAGAACGATCAGTCCTGGT | 3 | NC | NC | NC |
| 3371 | 5524 | TGCAGAACGATCAGTCCTGG | 3 | NC | NC | NC |
| 3372 | 5525 | TTGCAGAACGATCAGTCCTG | 3 | NC | NC | NC |
| 3373 | 5526 | TTTGCAGAACGATCAGTCCT | 3 | NC | NC | NC |
| 3374 | 5527 | ATTTGCAGAACGATCAGTCC | 2 | NC | NC | NC |
| 3375 | 5528 | CATTTGCAGAACGATCAGTC | 2 | NC | NC | NC |
| 3376 | 5541 | ATGGCATAACAAGCATTTGC | 2 | NC | NC | NC |
| 3377 | 5543 | GAATGGCATAACAAGCATTT | 2 | NC | NC | NC |
| 3378 | 5544 | AGAATGGCATAACAAGCATT | 2 | NC | NC | NC |
| 3379 | 5545 | GAGAATGGCATAACAAGCAT | 2 | NC | NC | NC |
| 3380 | 5546 | TGAGAATGGCATAACAAGCA | 1 | NC | NC | NC |
| 3381 | 5547 | TTGAGAATGGCATAACAAGC | 1 | NC | NC | NC |
| 3382 | 5548 | ATTGAGAATGGCATAACAAG | 1 | NC | NC | NC |
| 3383 | 5549 | GATTGAGAATGGCATAACAA | 2 | NC | NC | NC |
| 3384 | 5550 | AGATTGAGAATGGCATAACA | 2 | NC | NC | NC |
| 3385 | 5551 | TAGATTGAGAATGGCATAAC | 2 | NC | NC | NC |
| 3386 | 5552 | ATAGATTGAGAATGGCATAA | 2 | NC | NC | NC |
| 3387 | 5553 | AATAGATTGAGAATGGCATA | 2 | NC | NC | NC |
| 3388 | 5554 | AAATAGATTGAGAATGGCAT | 2 | NC | NC | NC |
| 3389 | 5555 | AAAATAGATTGAGAATGGCA | 2 | NC | NC | NC |
| 3390 | 5556 | AAAAATAGATTGAGAATGGC | 2 | NC | NC | NC |
| 3391 | 5557 | GAAAAATAGATTGAGAATGG | 2 | NC | NC | NC |
| 3392 | 5558 | GGAAAAATAGATTGAGAATG | 1 | NC | NC | NC |
| 3393 | 5559 | GGGAAAAATAGATTGAGAAT | 1 | NC | NC | NC |
| 3394 | 5560 | CGGGAAAAATAGATTGAGAA | 2 | NC | NC | NC |
| 3395 | 5561 | GCGGGAAAAATAGATTGAGA | 2 | NC | NC | NC |
| 3396 | 5562 | TGCGGGAAAAATAGATTGAG | 3 | NC | NC | NC |
| 3397 | 5563 | GTGCGGGAAAAATAGATTGA | 2 | NC | NC | NC |
| 3398 | 5564 | GGTGCGGGAAAAATAGATTG | 2 | NC | NC | NC |
| 3399 | 5565 | AGGTGCGGGAAAAATAGATT | 2 | NC | NC | NC |
| 3400 | 5566 | AAGGTGCGGGAAAAATAGAT | 2 | NC | NC | NC |
| 3401 | 5567 | AAAGGTGCGGGAAAAATAGA | 2 | NC | NC | NC |
| 3402 | 5568 | AAAAGGTGCGGGAAAAATAG | 2 | NC | NC | NC |
| 3403 | 5569 | GAAAAGGTGCGGGAAAAATA | 2 | NC | NC | NC |
| 3404 | 5570 | TGAAAAGGTGCGGGAAAAAT | 2 | NC | NC | NC |
| 3405 | 5571 | GTGAAAAGGTGCGGGAAAAA | 2 | NC | NC | NC |
| 3406 | 5572 | TGTGAAAAGGTGCGGGAAAA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3407 | 5573 | ATGTGAAAAGGTGCGGGAAA | 2 | NC | NC | NC |
| 3408 | 5574 | CATGTGAAAAGGTGCGGGAA | 2 | NC | NC | NC |
| 3409 | 5575 | TCATGTGAAAAGGTGCGGGA | 3 | NC | NC | NC |
| 3410 | 5576 | ATCATGTGAAAAGGTGCGGG | 3 | NC | NC | NC |
| 3411 | 5577 | AATCATGTGAAAAGGTGCGG | 3 | NC | NC | NC |
| 3412 | 5578 | AAATCATGTGAAAAGGTGCG | 2 | NC | NC | NC |
| 3413 | 5579 | CAAATCATGTGAAAAGGTGC | 2 | NC | NC | NC |
| 3414 | 5590 | CCTATTAACCACAAATCATG | 2 | NC | NC | NC |
| 3415 | 5591 | TCCTATTAACCACAAATCAT | 2 | NC | NC | NC |
| 3416 | 5592 | GTCCTATTAACCACAAATCA | 2 | NC | NC | NC |
| 3417 | 5593 | AGTCCTATTAACCACAAATC | 3 | NC | NC | NC |
| 3418 | 5594 | GAGTCCTATTAACCACAAAT | 3 | NC | NC | NC |
| 3419 | 5595 | TGAGTCCTATTAACCACAAA | 2 | NC | NC | NC |
| 3420 | 5596 | TTGAGTCCTATTAACCACAA | 2 | NC | NC | NC |
| 3421 | 5597 | GTTGAGTCCTATTAACCACA | 2 | NC | NC | NC |
| 3422 | 5598 | TGTTGAGTCCTATTAACCAC | 2 | NC | NC | NC |
| 3423 | 5599 | CTGTTGAGTCCTATTAACCA | 2 | NC | NC | NC |
| 3424 | 5600 | TCTGTTGAGTCCTATTAACC | 2 | NC | NC | NC |
| 3425 | 5601 | GTCTGTTGAGTCCTATTAAC | 2 | NC | NC | NC |
| 3426 | 5602 | AGTCTGTTGAGTCCTATTAA | 2 | NC | NC | NC |
| 3427 | 5603 | TAGTCTGTTGAGTCCTATTA | 2 | NC | NC | NC |
| 3428 | 5604 | TTAGTCTGTTGAGTCCTATT | 2 | NC | NC | NC |
| 3429 | 5605 | TTTAGTCTGTTGAGTCCTAT | 3 | NC | NC | NC |
| 3430 | 5606 | TTTTAGTCTGTTGAGTCCTA | 2 | NC | NC | NC |
| 3431 | 5607 | ATTTTAGTCTGTTGAGTCCT | 2 | NC | NC | NC |
| 3432 | 5608 | AATTTTAGTCTGTTGAGTCC | 2 | NC | NC | NC |
| 3433 | 5609 | CAATTTTAGTCTGTTGAGTC | 2 | NC | NC | NC |
| 3434 | 5610 | GCAATTTTAGTCTGTTGAGT | 2 | NC | NC | NC |
| 3435 | 5611 | TGCAATTTTAGTCTGTTGAG | 2 | NC | NC | NC |
| 3436 | 5612 | ATGCAATTTTAGTCTGTTGA | 2 | NC | NC | NC |
| 3437 | 5613 | TATGCAATTTTAGTCTGTTG | 2 | NC | NC | NC |
| 3438 | 5614 | CTATGCAATTTTAGTCTGTT | 2 | NC | NC | NC |
| 3439 | 5615 | ACTATGCAATTTTAGTCTGT | 2 | NC | NC | NC |
| 3440 | 5616 | TACTATGCAATTTTAGTCTG | 2 | NC | NC | NC |
| 3441 | 5617 | CTACTATGCAATTTTAGTCT | 2 | NC | NC | NC |
| 3442 | 5618 | TCTACTATGCAATTTTAGTC | 2 | NC | NC | NC |
| 3443 | 5619 | TTCTACTATGCAATTTTAGT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3444 | 5620 | TTTCTACTATGCAATTTTAG | 2 | NC | NC | NC |
| 3445 | 5655 | GCAATAAACATTACCAGCTG | 2 | NC | NC | NC |
| 3446 | 5656 | TGCAATAAACATTACCAGCT | 2 | NC | NC | NC |
| 3447 | 5657 | TTGCAATAAACATTACCAGC | 2 | NC | NC | NC |
| 3448 | 5658 | GTTGCAATAAACATTACCAG | 2 | NC | NC | NC |
| 3449 | 5659 | AGTTGCAATAAACATTACCA | 2 | NC | NC | NC |
| 3450 | 5660 | CAGTTGCAATAAACATTACC | 2 | NC | NC | NC |
| 3451 | 5661 | CCAGTTGCAATAAACATTAC | 2 | NC | NC | NC |
| 3452 | 5662 | CCCAGTTGCAATAAACATTA | 2 | NC | NC | NC |
| 3453 | 5663 | CCCCAGTTGCAATAAACATT | 2 | NC | NC | NC |
| 3454 | 5664 | ACCCCAGTTGCAATAAACAT | 2 | NC | NC | NC |
| 3455 | 5665 | CACCCCAGTTGCAATAAACA | 2 | NC | NC | NC |
| 3456 | 5666 | GCACCCCAGTTGCAATAAAC | 2 | NC | NC | NC |
| 3457 | 5667 | AGCACCCCAGTTGCAATAAA | 2 | NC | NC | NC |
| 3458 | 5668 | TAGCACCCCAGTTGCAATAA | 2 | NC | NC | NC |
| 3459 | 5669 | ATAGCACCCCAGTTGCAATA | 2 | NC | NC | NC |
| 3460 | 5670 | TATAGCACCCCAGTTGCAAT | 2 | NC | NC | NC |
| 3461 | 5671 | GTATAGCACCCCAGTTGCAA | 3 | NC | NC | NC |
| 3462 | 5672 | TGTATAGCACCCCAGTTGCA | 2 | NC | NC | NC |
| 3463 | 5673 | TTGTATAGCACCCCAGTTGC | 3 | NC | NC | NC |
| 3464 | 5674 | ATTGTATAGCACCCCAGTTG | 2 | NC | NC | NC |
| 3465 | 5675 | AATTGTATAGCACCCCAGTT | 2 | NC | NC | NC |
| 3466 | 5676 | TAATTGTATAGCACCCCAGT | 2 | NC | NC | NC |
| 3467 | 5677 | CTAATTGTATAGCACCCCAG | 2 | NC | NC | NC |
| 3468 | 5678 | ACTAATTGTATAGCACCCCA | 3 | NC | NC | NC |
| 3469 | 5679 | TACTAATTGTATAGCACCCC | 2 | NC | NC | NC |
| 3470 | 5680 | TTACTAATTGTATAGCACCC | 2 | NC | NC | NC |
| 3471 | 5681 | CTTACTAATTGTATAGCACC | 2 | NC | NC | NC |
| 3472 | 5682 | TCTTACTAATTGTATAGCAC | 2 | NC | NC | NC |
| 3473 | 5683 | ATCTTACTAATTGTATAGCA | 2 | NC | NC | NC |
| 3474 | 5684 | CATCTTACTAATTGTATAGC | 2 | NC | NC | NC |
| 3475 | 5685 | TCATCTTACTAATTGTATAG | 2 | NC | NC | NC |
| 3476 | 5687 | CATCATCTTACTAATTGTAT | 1 | NC | NC | NC |
| 3477 | 5688 | GCATCATCTTACTAATTGTA | 2 | NC | NC | NC |
| 3478 | 5689 | TGCATCATCTTACTAATTGT | 2 | NC | NC | NC |
| 3479 | 5690 | TTGCATCATCTTACTAATTG | 2 | NC | NC | NC |
| 3480 | 5691 | ATTGCATCATCTTACTAATT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3481 | 5692 | CATTGCATCATCTTACTAAT | 2 | NC | NC | NC |
| 3482 | 5693 | TCATTGCATCATCTTACTAA | 2 | NC | NC | NC |
| 3483 | 5694 | CTCATTGCATCATCTTACTA | 2 | NC | NC | NC |
| 3484 | 5695 | TCTCATTGCATCATCTTACT | 1 | NC | NC | NC |
| 3485 | 5696 | TTCTCATTGCATCATCTTAC | 2 | NC | NC | NC |
| 3486 | 5697 | ATTCTCATTGCATCATCTTA | 2 | NC | NC | NC |
| 3487 | 5698 | AATTCTCATTGCATCATCTT | 1 | NC | NC | NC |
| 3488 | 5699 | AAATTCTCATTGCATCATCT | 2 | NC | NC | NC |
| 3489 | 5700 | GAAATTCTCATTGCATCATC | 2 | NC | NC | NC |
| 3490 | 5701 | AGAAATTCTCATTGCATCAT | 2 | NC | NC | NC |
| 3491 | 5702 | TAGAAATTCTCATTGCATCA | 1 | NC | NC | NC |
| 3492 | 5703 | GTAGAAATTCTCATTGCATC | 1 | NC | NC | NC |
| 3493 | 5704 | AGTAGAAATTCTCATTGCAT | 1 | NC | NC | NC |
| 3494 | 5705 | AAGTAGAAATTCTCATTGCA | 2 | NC | NC | NC |
| 3495 | 5706 | AAAGTAGAAATTCTCATTGC | 2 | NC | NC | NC |
| 3496 | 5707 | AAAAGTAGAAATTCTCATTG | 1 | NC | NC | NC |
| 3497 | 5708 | CAAAAGTAGAAATTCTCATT | 2 | NC | NC | NC |
| 3498 | 5709 | ACAAAAGTAGAAATTCTCAT | 2 | NC | NC | NC |
| 3499 | 5710 | TACAAAAGTAGAAATTCTCA | 2 | NC | NC | NC |
| 3500 | 5711 | ATACAAAAGTAGAAATTCTC | 2 | NC | NC | NC |
| 3501 | 5715 | GGAAATACAAAAGTAGAAAT | 1 | NC | NC | NC |
| 3502 | 5716 | AGGAAATACAAAAGTAGAAA | 1 | NC | NC | NC |
| 3503 | 5717 | CAGGAAATACAAAAGTAGAA | 1 | NC | NC | NC |
| 3504 | 5718 | TCAGGAAATACAAAAGTAGA | 1 | NC | NC | NC |
| 3505 | 5719 | GTCAGGAAATACAAAAGTAG | 1 | NC | NC | NC |
| 3506 | 5720 | GGTCAGGAAATACAAAAGTA | 2 | NC | NC | NC |
| 3507 | 5721 | TGGTCAGGAAATACAAAAGT | 2 | NC | NC | NC |
| 3508 | 5722 | CTGGTCAGGAAATACAAAAG | 2 | NC | NC | NC |
| 3509 | 5723 | GCTGGTCAGGAAATACAAAA | 1 | NC | NC | NC |
| 3510 | 5724 | GGCTGGTCAGGAAATACAAA | 1 | NC | NC | NC |
| 3511 | 5725 | AGGCTGGTCAGGAAATACAA | 2 | NC | NC | NC |
| 3512 | 5726 | CAGGCTGGTCAGGAAATACA | 2 | NC | NC | NC |
| 3513 | 5727 | GCAGGCTGGTCAGGAAATAC | 2 | NC | NC | NC |
| 3514 | 5728 | AGCAGGCTGGTCAGGAAATA | 2 | NC | NC | NC |
| 3515 | 5742 | TAAAAGCCACTTTGAGCAGG | 2 | NC | NC | NC |
| 3516 | 5743 | ATAAAAGCCACTTTGAGCAG | 2 | NC | NC | NC |
| 3517 | 5744 | TATAAAAGCCACTTTGAGCA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3518 | 5745 | ATATAAAAGCCACTTTGAGC | 2 | NC | NC | NC |
| 3519 | 5746 | GATATAAAAGCCACTTTGAG | 2 | NC | NC | NC |
| 3520 | 5747 | TGATATAAAAGCCACTTTGA | 2 | NC | NC | NC |
| 3521 | 5748 | TTGATATAAAAGCCACTTTG | 2 | NC | NC | NC |
| 3522 | 5749 | ATTGATATAAAAGCCACTTT | 2 | NC | NC | NC |
| 3523 | 5750 | AATTGATATAAAAGCCACTT | 2 | NC | NC | NC |
| 3524 | 5751 | CAATTGATATAAAAGCCACT | 2 | NC | NC | NC |
| 3525 | 5752 | TCAATTGATATAAAAGCCAC | 2 | NC | NC | NC |
| 3526 | 5753 | TTCAATTGATATAAAAGCCA | 2 | NC | NC | NC |
| 3527 | 5754 | ATTCAATTGATATAAAAGCC | 2 | NC | NC | NC |
| 3528 | 5755 | CATTCAATTGATATAAAAGC | 2 | NC | NC | NC |
| 3529 | 5762 | GGAAAATCATTCAATTGATA | 1 | NC | NC | NC |
| 3530 | 5763 | AGGAAAATCATTCAATTGAT | 1 | NC | NC | NC |
| 3531 | 5764 | GAGGAAAATCATTCAATTGA | 1 | NC | NC | NC |
| 3532 | 5765 | TGAGGAAAATCATTCAATTG | 2 | NC | NC | NC |
| 3533 | 5766 | ATGAGGAAAATCATTCAATT | 1 | NC | NC | NC |
| 3534 | 5786 | TTGGTTTCCTGTATTAAAAA | 2 | NC | NC | NC |
| 3535 | 5787 | ATTGGTTTCCTGTATTAAAA | 1 | NC | NC | NC |
| 3536 | 5788 | AATTGGTTTCCTGTATTAAA | 2 | NC | NC | NC |
| 3537 | 5789 | GAATTGGTTTCCTGTATTAA | 2 | NC | NC | NC |
| 3538 | 5790 | CGAATTGGTTTCCTGTATTA | 3 | NC | NC | NC |
| 3539 | 5791 | ACGAATTGGTTTCCTGTATT | 2 | NC | NC | NC |
| 3540 | 5792 | CACGAATTGGTTTCCTGTAT | 1 | NC | NC | NC |
| 3541 | 5793 | GCACGAATTGGTTTCCTGTA | 2 | NC | NC | NC |
| 3542 | 5794 | AGCACGAATTGGTTTCCTGT | 3 | NC | NC | NC |
| 3543 | 5795 | GAGCACGAATTGGTTTCCTG | 2 | NC | NC | NC |
| 3544 | 5796 | TGAGCACGAATTGGTTTCCT | 2 | NC | NC | NC |
| 3545 | 5797 | ATGAGCACGAATTGGTTTCC | 2 | NC | NC | NC |
| 3546 | 5798 | CATGAGCACGAATTGGTTTC | 3 | NC | NC | NC |
| 3547 | 5799 | CCATGAGCACGAATTGGTTT | 2 | NC | NC | NC |
| 3548 | 5800 | TCCATGAGCACGAATTGGTT | 2 | NC | NC | NC |
| 3549 | 5802 | CTTCCATGAGCACGAATTGG | 3 | NC | NC | NC |
| 3550 | 5803 | TCTTCCATGAGCACGAATTG | 3 | NC | NC | NC |
| 3551 | 5804 | TTCTTCCATGAGCACGAATT | 2 | NC | NC | NC |
| 3552 | 5805 | TTTCTTCCATGAGCACGAAT | 2 | NC | NC | NC |
| 3553 | 5806 | TTTTCTTCCATGAGCACGAA | 2 | NC | NC | NC |
| 3554 | 5807 | CTTTTCTTCCATGAGCACGA | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3555 | 5808 | ACTTTTCTTCCATGAGCACG | 2 | NC | NC | NC |
| 3556 | 5809 | AACTTTTCTTCCATGAGCAC | 2 | NC | NC | NC |
| 3557 | 5810 | GAACTTTTCTTCCATGAGCA | 2 | NC | NC | NC |
| 3558 | 5835 | ATTCACTTCAAGGCTGCTGG | 2 | NC | NC | NC |
| 3559 | 5836 | GATTCACTTCAAGGCTGCTG | 2 | NC | NC | NC |
| 3560 | 5837 | AGATTCACTTCAAGGCTGCT | 2 | NC | NC | NC |
| 3561 | 5838 | AAGATTCACTTCAAGGCTGC | 2 | NC | NC | NC |
| 3562 | 5848 | TTGCTCCTGTAAGATTCACT | 2 | NC | NC | NC |
| 3563 | 5849 | ATTGCTCCTGTAAGATTCAC | 2 | NC | NC | NC |
| 3564 | 5850 | CATTGCTCCTGTAAGATTCA | 3 | NC | NC | NC |
| 3565 | 5851 | TCATTGCTCCTGTAAGATTC | 2 | NC | NC | NC |
| 3566 | 5852 | TTCATTGCTCCTGTAAGATT | 1 | NC | NC | NC |
| 3567 | 5853 | TTTCATTGCTCCTGTAAGAT | 1 | NC | NC | NC |
| 3568 | 5854 | CTTTCATTGCTCCTGTAAGA | 2 | NC | NC | NC |
| 3569 | 5855 | ACTTTCATTGCTCCTGTAAG | 2 | NC | NC | NC |
| 3570 | 5856 | TACTTTCATTGCTCCTGTAA | 2 | NC | NC | NC |
| 3571 | 5857 | ATACTTTCATTGCTCCTGTA | 2 | NC | NC | NC |
| 3572 | 5858 | AATACTTTCATTGCTCCTGT | 2 | NC | NC | NC |
| 3573 | 5859 | CAATACTTTCATTGCTCCTG | 2 | NC | NC | NC |
| 3574 | 5865 | TGAATGCAATACTTTCATTG | 2 | NC | NC | NC |
| 3575 | 5869 | CTAATGAATGCAATACTTTC | 0 | NC | NC | NC |
| 3576 | 5870 | GCTAATGAATGCAATACTTT | 1 | NC | NC | NC |
| 3577 | 5871 | CGCTAATGAATGCAATACTT | 1 | NC | NC | NC |
| 3578 | 5872 | ACGCTAATGAATGCAATACT | 1 | NC | NC | NC |
| 3579 | 5873 | GACGCTAATGAATGCAATAC | 2 | NC | NC | NC |
| 3580 | 5874 | AGACGCTAATGAATGCAATA | 2 | NC | NC | NC |
| 3581 | 5875 | CAGACGCTAATGAATGCAAT | 2 | NC | NC | NC |
| 3582 | 5876 | GCAGACGCTAATGAATGCAA | 2 | NC | NC | NC |
| 3583 | 5896 | TTCTCTGAACCTTCTCTGGG | 1 | NC | NC | NC |
| 3584 | 5897 | TTTCTCTGAACCTTCTCTGG | 1 | NC | NC | NC |
| 3585 | 5898 | TTTTCTCTGAACCTTCTCTG | 1 | NC | NC | NC |
| 3586 | 5899 | GTTTTCTCTGAACCTTCTCT | 1 | NC | NC | NC |
| 3587 | 5906 | AGTGAAGGTTTTCTCTGAAC | 2 | NC | NC | NC |
| 3588 | 5907 | AAGTGAAGGTTTTCTCTGAA | 1 | NC | NC | NC |
| 3589 | 5908 | CAAGTGAAGGTTTTCTCTGA | 1 | NC | NC | NC |
| 3590 | 5909 | ACAAGTGAAGGTTTTCTCTG | 1 | NC | NC | NC |
| 3591 | 5910 | AACAAGTGAAGGTTTTCTCT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3592 | 5911 | AAACAAGTGAAGGTTTTCTC | 2 | NC | NC | NC |
| 3593 | 5916 | CTTGAAAACAAGTGAAGGTT | 2 | NC | NC | NC |
| 3594 | 5917 | CCTTGAAAACAAGTGAAGGT | 2 | NC | NC | NC |
| 3595 | 5918 | CCCTTGAAAACAAGTGAAGG | 2 | NC | NC | NC |
| 3596 | 5919 | CCCCTTGAAAACAAGTGAAG | 2 | NC | NC | NC |
| 3597 | 5920 | TCCCCTTGAAAACAAGTGAA | 2 | NC | NC | NC |
| 3598 | 5921 | ATCCCCTTGAAAACAAGTGA | 2 | NC | NC | NC |
| 3599 | 5922 | GATCCCCTTGAAAACAAGTG | 2 | NC | NC | NC |
| 3600 | 5923 | GGATCCCCTTGAAAACAAGT | 2 | NC | NC | NC |
| 3601 | 5935 | GTAAATCTACAAGGATCCCC | 3 | NC | NC | NC |
| 3602 | 5936 | CGTAAATCTACAAGGATCCC | 2 | NC | NC | NC |
| 3603 | 5937 | ACGTAAATCTACAAGGATCC | 2 | NC | NC | NC |
| 3604 | 5938 | TACGTAAATCTACAAGGATC | 2 | NC | NC | NC |
| 3605 | 5939 | TTACGTAAATCTACAAGGAT | 2 | NC | NC | NC |
| 3606 | 5940 | ATTACGTAAATCTACAAGGA | 2 | NC | NC | NC |
| 3607 | 5941 | AATTACGTAAATCTACAAGG | 2 | NC | NC | NC |
| 3608 | 5942 | CAATTACGTAAATCTACAAG | 2 | NC | NC | NC |
| 3609 | 5943 | CCAATTACGTAAATCTACAA | 2 | NC | NC | NC |
| 3610 | 5944 | TCCAATTACGTAAATCTACA | 2 | NC | NC | NC |
| 3611 | 5945 | TTCCAATTACGTAAATCTAC | 2 | NC | NC | NC |
| 3612 | 5946 | ATTCCAATTACGTAAATCTA | 2 | NC | NC | NC |
| 3613 | 5947 | GATTCCAATTACGTAAATCT | 2 | NC | NC | NC |
| 3614 | 5948 | GGATTCCAATTACGTAAATC | 1 | NC | NC | NC |
| 3615 | 5949 | AGGATTCCAATTACGTAAAT | 1 | NC | NC | NC |
| 3616 | 5950 | CAGGATTCCAATTACGTAAA | 2 | NC | NC | NC |
| 3617 | 5951 | TCAGGATTCCAATTACGTAA | 2 | NC | NC | NC |
| 3618 | 5952 | TTCAGGATTCCAATTACGTA | 2 | NC | NC | NC |
| 3619 | 5953 | CTTCAGGATTCCAATTACGT | 2 | NC | NC | NC |
| 3620 | 5954 | TCTTCAGGATTCCAATTACG | 1 | NC | NC | NC |
| 3621 | 5955 | TTCTTCAGGATTCCAATTAC | 0 | NC | NC | NC |
| 3622 | 5956 | GTTCTTCAGGATTCCAATTA | 0 | NC | NC | NC |
| 3623 | 5957 | TGTTCTTCAGGATTCCAATT | 1 | NC | NC | NC |
| 3624 | 5993 | TAGAAGAATAAAAGCCATTT | 2 | NC | NC | NC |
| 3625 | 5994 | TTAGAAGAATAAAAGCCATT | 1 | NC | NC | NC |
| 3626 | 5995 | TTTAGAAGAATAAAAGCCAT | 1 | NC | NC | NC |
| 3627 | 5996 | ATTTAGAAGAATAAAAGCCA | 1 | NC | NC | NC |
| 3628 | 5997 | TATTTAGAAGAATAAAAGCC | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3629 | 5998 | GTATTTAGAAGAATAAAAGC | 2 | NC | NC | NC |
| 3630 | 6007 | CGTTTATATGTATTTAGAAG | 2 | NC | NC | NC |
| 3631 | 6008 | CCGTTTATATGTATTTAGAA | 2 | NC | NC | NC |
| 3632 | 6009 | TCCGTTTATATGTATTTAGA | 2 | NC | NC | NC |
| 3633 | 6010 | ATCCGTTTATATGTATTTAG | 2 | NC | NC | NC |
| 3634 | 6011 | CATCCGTTTATATGTATTTA | 2 | NC | NC | NC |
| 3635 | 6012 | ACATCCGTTTATATGTATTT | 2 | NC | NC | NC |
| 3636 | 6013 | AACATCCGTTTATATGTATT | 2 | NC | NC | NC |
| 3637 | 6023 | CCATCTATAAAACATCCGTT | 2 | NC | NC | NC |
| 3638 | 6024 | CCCATCTATAAAACATCCGT | 2 | NC | NC | NC |
| 3639 | 6025 | TCCCATCTATAAAACATCCG | 3 | NC | NC | NC |
| 3640 | 6026 | TTCCCATCTATAAAACATCC | 2 | NC | NC | NC |
| 3641 | 6027 | CTTCCCATCTATAAAACATC | 2 | NC | NC | NC |
| 3642 | 6028 | TCTTCCCATCTATAAAACAT | 1 | NC | NC | NC |
| 3643 | 6029 | GTCTTCCCATCTATAAAACA | 1 | NC | NC | NC |
| 3644 | 6030 | TGTCTTCCCATCTATAAAAC | 1 | NC | NC | NC |
| 3645 | 6031 | ATGTCTTCCCATCTATAAAA | 1 | NC | NC | NC |
| 3646 | 6032 | CATGTCTTCCCATCTATAAA | 1 | NC | NC | NC |
| 3647 | 6033 | TCATGTCTTCCCATCTATAA | 2 | NC | NC | NC |
| 3648 | 6034 | GTCATGTCTTCCCATCTATA | 2 | NC | NC | NC |
| 3649 | 6035 | GGTCATGTCTTCCCATCTAT | 1 | NC | NC | NC |
| 3650 | 6036 | AGGTCATGTCTTCCCATCTA | 1 | NC | NC | NC |
| 3651 | 6037 | AAGGTCATGTCTTCCCATCT | 2 | NC | NC | NC |
| 3652 | 6038 | TAAGGTCATGTCTTCCCATC | 2 | NC | NC | NC |
| 3653 | 6039 | CTAAGGTCATGTCTTCCCAT | 2 | NC | NC | NC |
| 3654 | 6040 | TCTAAGGTCATGTCTTCCCA | 2 | NC | NC | NC |
| 3655 | 6041 | TTCTAAGGTCATGTCTTCCC | 2 | NC | NC | NC |
| 3656 | 6042 | TTTCTAAGGTCATGTCTTCC | 2 | NC | NC | NC |
| 3657 | 6043 | CTTTCTAAGGTCATGTCTTC | 2 | NC | NC | NC |
| 3658 | 6054 | AAAACTCTCTCCTTTCTAAG | 1 | NC | NC | NC |
| 3659 | 6055 | GAAAACTCTCTCCTTTCTAA | 1 | NC | NC | NC |
| 3660 | 6056 | TGAAAACTCTCTCCTTTCTA | 2 | NC | NC | NC |
| 3661 | 6057 | CTGAAAACTCTCTCCTTTCT | 1 | NC | NC | NC |
| 3662 | 6058 | TCTGAAAACTCTCTCCTTTC | 1 | NC | NC | NC |
| 3663 | 6059 | CTCTGAAAACTCTCTCCTTT | 1 | NC | NC | NC |
| 3664 | 6060 | CCTCTGAAAACTCTCTCCTT | 1 | NC | NC | NC |
| 3665 | 6061 | TCCTCTGAAAACTCTCTCCT | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3666 | 6062 | ATCCTCTGAAAACTCTCTCC | 1 | NC | NC | NC |
| 3667 | 6063 | AATCCTCTGAAAACTCTCTC | 1 | NC | NC | NC |
| 3668 | 6064 | AAATCCTCTGAAAACTCTCT | 1 | NC | NC | NC |
| 3669 | 6065 | CAAATCCTCTGAAAACTCTC | 2 | NC | NC | NC |
| 3670 | 6066 | GCAAATCCTCTGAAAACTCT | 2 | NC | NC | NC |
| 3671 | 6067 | GGCAAATCCTCTGAAAACTC | 2 | NC | NC | NC |
| 3672 | 6068 | TGGCAAATCCTCTGAAAACT | 1 | NC | NC | NC |
| 3673 | 6069 | CTGGCAAATCCTCTGAAAAC | 2 | NC | NC | NC |
| 3674 | 6070 | CCTGGCAAATCCTCTGAAAA | 1 | NC | NC | NC |
| 3675 | 6071 | GCCTGGCAAATCCTCTGAAA | 1 | NC | NC | NC |
| 3676 | 6072 | AGCCTGGCAAATCCTCTGAA | 1 | NC | NC | NC |
| 3677 | 6073 | CAGCCTGGCAAATCCTCTGA | 1 | NC | NC | NC |
| 3678 | 6074 | ACAGCCTGGCAAATCCTCTG | 2 | NC | NC | NC |
| 3679 | 6075 | GACAGCCTGGCAAATCCTCT | 1 | NC | NC | NC |
| 3680 | 6076 | TGACAGCCTGGCAAATCCTC | 2 | NC | NC | NC |
| 3681 | 6077 | CTGACAGCCTGGCAAATCCT | 2 | NC | NC | NC |
| 3682 | 6174 | TTACAACTCCCAGGACAGTT | 2 | NC | NC | NC |
| 3683 | 6175 | TTTACAACTCCCAGGACAGT | 1 | NC | NC | NC |
| 3684 | 6176 | TTTTACAACTCCCAGGACAG | 2 | NC | NC | NC |
| 3685 | 6177 | TTTTTACAACTCCCAGGACA | 2 | NC | NC | NC |
| 3686 | 6178 | ATTTTTACAACTCCCAGGAC | 2 | NC | NC | NC |
| 3687 | 6179 | GATTTTTACAACTCCCAGGA | 2 | NC | NC | NC |
| 3688 | 6180 | AGATTTTTACAACTCCCAGG | 2 | NC | NC | NC |
| 3689 | 6181 | AAGATTTTTACAACTCCCAG | 2 | NC | NC | NC |
| 3690 | 6182 | AAAGATTTTTACAACTCCCA | 2 | NC | NC | NC |
| 3691 | 6183 | AAAAGATTTTTACAACTCCC | 2 | NC | NC | NC |
| 3692 | 6184 | TAAAAGATTTTTACAACTCC | 2 | NC | NC | NC |
| 3693 | 6187 | CCTTAAAAGATTTTTACAAC | 2 | NC | NC | NC |
| 3694 | 6188 | GCCTTAAAAGATTTTTACAA | 1 | NC | NC | NC |
| 3695 | 6189 | GGCCTTAAAAGATTTTTACA | 2 | NC | NC | NC |
| 3696 | 6190 | TGGCCTTAAAAGATTTTTAC | 2 | NC | NC | NC |
| 3697 | 6191 | CTGGCCTTAAAAGATTTTTA | 1 | NC | NC | NC |
| 3698 | 6192 | TCTGGCCTTAAAAGATTTTT | 1 | NC | NC | NC |
| 3699 | 6193 | GTCTGGCCTTAAAAGATTTT | 2 | NC | NC | NC |
| 3700 | 6194 | GGTCTGGCCTTAAAAGATTT | 2 | NC | NC | NC |
| 3701 | 6206 | ATCCCTCAAATTGGTCTGGC | 2 | NC | NC | NC |
| 3702 | 6207 | AATCCCTCAAATTGGTCTGG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3703 | 6208 | AAATCCCTCAAATTGGTCTG | 2 | NC | NC | NC |
| 3704 | 6209 | AAAATCCCTCAAATTGGTCT | 2 | NC | NC | NC |
| 3705 | 6210 | TAAAATCCCTCAAATTGGTC | 2 | NC | NC | NC |
| 3706 | 6211 | TTAAAATCCCTCAAATTGGT | 2 | NC | NC | NC |
| 3707 | 6212 | TTTAAAATCCCTCAAATTGG | 1 | NC | NC | NC |
| 3708 | 6213 | TTTTAAAATCCCTCAAATTG | 2 | NC | NC | NC |
| 3709 | 6215 | CTTTTTAAAATCCCTCAAAT | 1 | NC | NC | NC |
| 3710 | 6216 | ACTTTTTAAAATCCCTCAAA | 1 | NC | NC | NC |
| 3711 | 6217 | CACTTTTTAAAATCCCTCAA | 2 | NC | NC | NC |
| 3712 | 6218 | ACACTTTTTAAAATCCCTCA | 1 | NC | NC | NC |
| 3713 | 6219 | GACACTTTTTAAAATCCCTC | 1 | NC | NC | NC |
| 3714 | 6220 | AGACACTTTTTAAAATCCCT | 1 | NC | NC | NC |
| 3715 | 6221 | GAGACACTTTTTAAAATCCC | 2 | NC | NC | NC |
| 3716 | 6222 | TGAGACACTTTTTAAAATCC | 1 | NC | NC | NC |
| 3717 | 6223 | CTGAGACACTTTTTAAAATC | 1 | NC | NC | NC |
| 3718 | 6224 | ACTGAGACACTTTTTAAAAT | 1 | NC | NC | NC |
| 3719 | 6225 | CACTGAGACACTTTTTAAAA | 1 | NC | NC | NC |
| 3720 | 6226 | GCACTGAGACACTTTTTAAA | 2 | NC | NC | NC |
| 3721 | 6227 | GGCACTGAGACACTTTTTAA | 2 | NC | NC | NC |
| 3722 | 6228 | AGGCACTGAGACACTTTTTA | 2 | NC | NC | NC |
| 3723 | 6242 | TCTGAAATCATAAGAGGCAC | 1 | NC | NC | NC |
| 3724 | 6243 | TTCTGAAATCATAAGAGGCA | 2 | NC | NC | NC |
| 3725 | 6244 | CTTCTGAAATCATAAGAGGC | 2 | NC | NC | NC |
| 3726 | 6245 | CCTTCTGAAATCATAAGAGG | 2 | NC | NC | NC |
| 3727 | 6246 | ACCTTCTGAAATCATAAGAG | 2 | NC | NC | NC |
| 3728 | 6247 | AACCTTCTGAAATCATAAGA | 2 | NC | NC | NC |
| 3729 | 6248 | AAACCTTCTGAAATCATAAG | 2 | NC | NC | NC |
| 3730 | 6249 | AAAACCTTCTGAAATCATAA | 2 | NC | NC | NC |
| 3731 | 6250 | CAAAACCTTCTGAAATCATA | 2 | NC | NC | NC |
| 3732 | 6251 | GCAAAACCTTCTGAAATCAT | 2 | NC | NC | NC |
| 3733 | 6252 | AGCAAAACCTTCTGAAATCA | 1 | NC | NC | NC |
| 3734 | 6253 | TAGCAAAACCTTCTGAAATC | 2 | NC | NC | NC |
| 3735 | 6254 | ATAGCAAAACCTTCTGAAAT | 1 | NC | NC | NC |
| 3736 | 6255 | TATAGCAAAACCTTCTGAAA | 2 | NC | NC | NC |
| 3737 | 6256 | ATATAGCAAAACCTTCTGAA | 2 | NC | NC | NC |
| 3738 | 6257 | CATATAGCAAAACCTTCTGA | 2 | NC | NC | NC |
| 3739 | 6258 | ACATATAGCAAAACCTTCTG | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3740 | 6259 | TACATATAGCAAAACCTTCT | 2 | NC | NC | NC |
| 3741 | 6260 | TTACATATAGCAAAACCTTC | 2 | NC | NC | NC |
| 3742 | 6261 | ATTACATATAGCAAAACCTT | 2 | NC | NC | NC |
| 3743 | 6262 | GATTACATATAGCAAAACCT | 2 | NC | NC | NC |
| 3744 | 6263 | GGATTACATATAGCAAAACC | 2 | NC | NC | NC |
| 3745 | 6264 | GGGATTACATATAGCAAAAC | 2 | NC | NC | NC |
| 3746 | 6265 | TGGGATTACATATAGCAAAA | 2 | NC | NC | NC |
| 3747 | 6266 | TTGGGATTACATATAGCAAA | 2 | NC | NC | NC |
| 3748 | 6267 | GTTGGGATTACATATAGCAA | 2 | NC | NC | NC |
| 3749 | 6268 | AGTTGGGATTACATATAGCA | 2 | NC | NC | NC |
| 3750 | 6269 | TAGTTGGGATTACATATAGC | 2 | NC | NC | NC |
| 3751 | 6270 | GTAGTTGGGATTACATATAG | 2 | NC | NC | NC |
| 3752 | 6271 | AGTAGTTGGGATTACATATA | 1 | NC | NC | NC |
| 3753 | 6272 | CAGTAGTTGGGATTACATAT | 1 | NC | NC | NC |
| 3754 | 6273 | ACAGTAGTTGGGATTACATA | 1 | NC | NC | NC |
| 3755 | 6274 | AACAGTAGTTGGGATTACAT | 1 | NC | NC | NC |
| 3756 | 6275 | AAACAGTAGTTGGGATTACA | 2 | NC | NC | NC |
| 3757 | 6276 | AAAACAGTAGTTGGGATTAC | 2 | NC | NC | NC |
| 3758 | 6277 | GAAAACAGTAGTTGGGATTA | 2 | NC | NC | NC |
| 3759 | 6278 | AGAAAACAGTAGTTGGGATT | 1 | NC | NC | NC |
| 3760 | 6279 | AAGAAAACAGTAGTTGGGAT | 1 | NC | NC | NC |
| 3761 | 6280 | CAAGAAAACAGTAGTTGGGA | 2 | NC | NC | NC |
| 3762 | 6281 | TCAAGAAAACAGTAGTTGGG | 2 | NC | NC | NC |
| 3763 | 6282 | CTCAAGAAAACAGTAGTTGG | 2 | NC | NC | NC |
| 3764 | 6283 | TCTCAAGAAAACAGTAGTTG | 2 | NC | NC | NC |
| 3765 | 6285 | ACTCTCAAGAAAACAGTAGT | 2 | NC | NC | NC |
| 3766 | 6286 | TACTCTCAAGAAAACAGTAG | 2 | NC | NC | NC |
| 3767 | 6287 | CTACTCTCAAGAAAACAGTA | 2 | NC | NC | NC |
| 3768 | 6288 | GCTACTCTCAAGAAAACAGT | 2 | NC | NC | NC |
| 3769 | 6289 | TGCTACTCTCAAGAAAACAG | 2 | NC | NC | NC |
| 3770 | 6290 | CTGCTACTCTCAAGAAAACA | 2 | NC | NC | NC |
| 3771 | 6291 | TCTGCTACTCTCAAGAAAAC | 2 | NC | NC | NC |
| 3772 | 6292 | CTCTGCTACTCTCAAGAAAA | 2 | NC | NC | NC |
| 3773 | 6293 | CCTCTGCTACTCTCAAGAAA | 2 | NC | NC | NC |
| 3774 | 6294 | TCCTCTGCTACTCTCAAGAA | 2 | NC | NC | NC |
| 3775 | 6295 | ATCCTCTGCTACTCTCAAGA | 2 | NC | NC | NC |
| 3776 | 6296 | AATCCTCTGCTACTCTCAAG | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3777 | 6297 | TAATCCTCTGCTACTCTCAA | 2 | NC | NC | NC |
| 3778 | 6298 | CTAATCCTCTGCTACTCTCA | 2 | NC | NC | NC |
| 3779 | 6299 | TCTAATCCTCTGCTACTCTC | 2 | NC | NC | NC |
| 3780 | 6300 | TTCTAATCCTCTGCTACTCT | 1 | NC | NC | NC |
| 3781 | 6301 | TTTCTAATCCTCTGCTACTC | 1 | NC | NC | NC |
| 3782 | 6302 | TTTTCTAATCCTCTGCTACT | 2 | NC | NC | NC |
| 3783 | 6303 | TTTTTCTAATCCTCTGCTAC | 2 | NC | NC | NC |
| 3784 | 6304 | CTTTTTCTAATCCTCTGCTA | 1 | NC | NC | NC |
| 3785 | 6305 | ACTTTTTCTAATCCTCTGCT | 1 | NC | NC | NC |
| 3786 | 6306 | GACTTTTTCTAATCCTCTGC | 1 | NC | NC | NC |
| 3787 | 6307 | GGACTTTTTCTAATCCTCTG | 2 | NC | NC | NC |
| 3788 | 6308 | AGGACTTTTTCTAATCCTCT | 2 | NC | NC | NC |
| 3789 | 6311 | TGGAGGACTTTTTCTAATCC | 1 | NC | NC | NC |
| 3790 | 6312 | ATGGAGGACTTTTTCTAATC | 1 | NC | NC | NC |
| 3791 | 6313 | TATGGAGGACTTTTTCTAAT | 1 | NC | NC | NC |
| 3792 | 6314 | TTATGGAGGACTTTTTCTAA | 2 | NC | NC | NC |
| 3793 | 6315 | TTTATGGAGGACTTTTTCTA | 2 | NC | NC | NC |
| 3794 | 6316 | ATTTATGGAGGACTTTTTCT | 2 | NC | NC | NC |
| 3795 | 6317 | AATTTATGGAGGACTTTTTC | 2 | NC | NC | NC |
| 3796 | 6318 | TAATTTATGGAGGACTTTTT | 2 | NC | NC | NC |
| 3797 | 6319 | ATAATTTATGGAGGACTTTT | 2 | NC | NC | NC |
| 3798 | 6320 | CATAATTTATGGAGGACTTT | 2 | NC | NC | NC |
| 3799 | 6330 | AGGCCGGTTACATAATTTAT | 2 | NC | NC | NC |
| 3800 | 6331 | AAGGCCGGTTACATAATTTA | 2 | NC | NC | NC |
| 3801 | 6332 | GAAGGCCGGTTACATAATTT | 2 | NC | NC | NC |
| 3802 | 6333 | GGAAGGCCGGTTACATAATT | 2 | NC | NC | NC |
| 3803 | 6347 | AGTCAGGCTAGTCAGGAAGG | 2 | NC | NC | NC |
| 3804 | 6348 | GAGTCAGGCTAGTCAGGAAG | 2 | NC | NC | NC |
| 3805 | 6349 | TGAGTCAGGCTAGTCAGGAA | 2 | NC | NC | NC |
| 3806 | 6350 | TTGAGTCAGGCTAGTCAGGA | 2 | NC | NC | NC |
| 3807 | 6351 | CTTGAGTCAGGCTAGTCAGG | 2 | NC | NC | NC |
| 3808 | 6352 | GCTTGAGTCAGGCTAGTCAG | 2 | NC | NC | NC |
| 3809 | 6353 | TGCTTGAGTCAGGCTAGTCA | 2 | NC | NC | NC |
| 3810 | 6354 | TTGCTTGAGTCAGGCTAGTC | 3 | NC | NC | NC |
| 3811 | 6355 | ATTGCTTGAGTCAGGCTAGT | 2 | NC | NC | NC |
| 3812 | 6356 | CATTGCTTGAGTCAGGCTAG | 2 | NC | NC | NC |
| 3813 | 6357 | ACATTGCTTGAGTCAGGCTA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3814 | 6358 | TACATTGCTTGAGTCAGGCT | 2 | NC | NC | NC |
| 3815 | 6359 | TTACATTGCTTGAGTCAGGC | 2 | NC | NC | NC |
| 3816 | 6360 | CTTACATTGCTTGAGTCAGG | 2 | NC | NC | NC |
| 3817 | 6361 | TCTTACATTGCTTGAGTCAG | 2 | NC | NC | NC |
| 3818 | 6362 | CTCTTACATTGCTTGAGTCA | 2 | NC | NC | NC |
| 3819 | 6363 | TCTCTTACATTGCTTGAGTC | 2 | NC | NC | NC |
| 3820 | 6364 | ATCTCTTACATTGCTTGAGT | 2 | NC | NC | NC |
| 3821 | 6365 | TATCTCTTACATTGCTTGAG | 2 | NC | NC | NC |
| 3822 | 6366 | TTATCTCTTACATTGCTTGA | 2 | NC | NC | NC |
| 3823 | 6367 | ATTATCTCTTACATTGCTTG | 2 | NC | NC | NC |
| 3824 | 6368 | AATTATCTCTTACATTGCTT | 2 | NC | NC | NC |
| 3825 | 6369 | TAATTATCTCTTACATTGCT | 2 | NC | NC | NC |
| 3826 | 6370 | ATAATTATCTCTTACATTGC | 2 | NC | NC | NC |
| 3827 | 6374 | CAGAATAATTATCTCTTACA | 1 | NC | NC | NC |
| 3828 | 6375 | ACAGAATAATTATCTCTTAC | 2 | NC | NC | NC |
| 3829 | 6379 | GAAAACAGAATAATTATCTC | 1 | NC | NC | NC |
| 3830 | 6396 | CCACACTTATAAATTATGAA | 2 | NC | NC | NC |
| 3831 | 6397 | CCCACACTTATAAATTATGA | 2 | NC | NC | NC |
| 3832 | 6398 | CCCCACACTTATAAATTATG | 2 | NC | NC | NC |
| 3833 | 6399 | CCCCCACACTTATAAATTAT | 2 | NC | NC | NC |
| 3834 | 6400 | GCCCCCACACTTATAAATTA | 2 | NC | NC | NC |
| 3835 | 6401 | TGCCCCCACACTTATAAATT | 2 | NC | NC | NC |
| 3836 | 6402 | ATGCCCCCACACTTATAAAT | 2 | NC | NC | NC |
| 3837 | 6403 | CATGCCCCCACACTTATAAA | 2 | NC | NC | NC |
| 3838 | 6404 | GCATGCCCCCACACTTATAA | 3 | NC | NC | NC |
| 3839 | 6405 | GGCATGCCCCCACACTTATA | 3 | NC | NC | NC |
| 3840 | 6423 | AGGTTGTTTTTATGCTGAGG | 2 | NC | NC | NC |
| 3841 | 6424 | TAGGTTGTTTTTATGCTGAG | 2 | NC | NC | NC |
| 3842 | 6425 | ATAGGTTGTTTTTATGCTGA | 1 | NC | NC | NC |
| 3843 | 6426 | AATAGGTTGTTTTTATGCTG | 1 | NC | NC | NC |
| 3844 | 6427 | TAATAGGTTGTTTTTATGCT | 2 | NC | NC | NC |
| 3845 | 6428 | CTAATAGGTTGTTTTTATGC | 2 | NC | NC | NC |
| 3846 | 6429 | CCTAATAGGTTGTTTTTATG | 2 | NC | NC | NC |
| 3847 | 6430 | CCCTAATAGGTTGTTTTTAT | 2 | NC | NC | NC |
| 3848 | 6431 | TCCCTAATAGGTTGTTTTTA | 2 | NC | NC | NC |
| 3849 | 6432 | TTCCCTAATAGGTTGTTTTT | 2 | NC | NC | NC |
| 3850 | 6433 | TTTCCCTAATAGGTTGTTTT | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3851 | 6434 | TTTTCCCTAATAGGTTGTTT | 1 | NC | NC | NC |
| 3852 | 6435 | TTTTTCCCTAATAGGTTGTT | 1 | NC | NC | NC |
| 3853 | 6436 | ATTTTTCCCTAATAGGTTGT | 1 | NC | NC | NC |
| 3854 | 6437 | TATTTTTCCCTAATAGGTTG | 2 | NC | NC | NC |
| 3855 | 6438 | ATATTTTTCCCTAATAGGTT | 2 | NC | NC | NC |
| 3856 | 6439 | GATATTTTTCCCTAATAGGT | 1 | NC | NC | NC |
| 3857 | 6440 | AGATATTTTTCCCTAATAGG | 1 | NC | NC | NC |
| 3858 | 6441 | TAGATATTTTTCCCTAATAG | 1 | NC | NC | NC |
| 3859 | 6445 | CTATTAGATATTTTTCCCTA | 1 | NC | NC | NC |
| 3860 | 6446 | TCTATTAGATATTTTTCCCT | 1 | NC | NC | NC |
| 3861 | 6447 | ATCTATTAGATATTTTTCCC | 1 | NC | NC | NC |
| 3862 | 6457 | GATAAAGGTAATCTATTAGA | 2 | NC | NC | NC |
| 3863 | 6458 | CGATAAAGGTAATCTATTAG | 3 | NC | NC | NC |
| 3864 | 6459 | GCGATAAAGGTAATCTATTA | 3 | NC | NC | NC |
| 3865 | 6460 | GGCGATAAAGGTAATCTATT | 3 | NC | NC | NC |
| 3866 | 6461 | AGGCGATAAAGGTAATCTAT | 2 | NC | NC | NC |
| 3867 | 6462 | CAGGCGATAAAGGTAATCTA | 2 | NC | NC | NC |
| 3868 | 6463 | ACAGGCGATAAAGGTAATCT | 3 | NC | NC | NC |
| 3869 | 6464 | AACAGGCGATAAAGGTAATC | 2 | NC | NC | NC |
| 3870 | 6465 | TAACAGGCGATAAAGGTAAT | 2 | NC | NC | NC |
| 3871 | 6466 | CTAACAGGCGATAAAGGTAA | 2 | NC | NC | NC |
| 3872 | 6467 | CCTAACAGGCGATAAAGGTA | 2 | NC | NC | NC |
| 3873 | 6468 | CCCTAACAGGCGATAAAGGT | 3 | NC | NC | NC |
| 3874 | 6469 | ACCCTAACAGGCGATAAAGG | 3 | NC | NC | NC |
| 3875 | 6470 | AACCCTAACAGGCGATAAAG | 3 | NC | NC | NC |
| 3876 | 6471 | AAACCCTAACAGGCGATAAA | 2 | NC | NC | NC |
| 3877 | 6472 | AAAACCCTAACAGGCGATAA | 2 | NC | NC | NC |
| 3878 | 6473 | TAAAACCCTAACAGGCGATA | 2 | NC | NC | NC |
| 3879 | 6474 | ATAAAACCCTAACAGGCGAT | 2 | NC | NC | NC |
| 3880 | 6475 | CATAAAACCCTAACAGGCGA | 3 | NC | NC | NC |
| 3881 | 6476 | ACATAAAACCCTAACAGGCG | 3 | NC | NC | NC |
| 3882 | 6477 | AACATAAAACCCTAACAGGC | 2 | NC | NC | NC |
| 3883 | 6478 | CAACATAAAACCCTAACAGG | 1 | NC | NC | NC |
| 3884 | 6479 | ACAACATAAAACCCTAACAG | 1 | NC | NC | NC |
| 3885 | 6480 | AACAACATAAAACCCTAACA | 1 | NC | NC | NC |
| 3886 | 6481 | AAACAACATAAAACCCTAAC | 2 | NC | NC | NC |
| 3887 | 6482 | AAAACAACATAAAACCCTAA | 1 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 3888 | 6483 | AAAAACAACATAAAACCCTA | 1 | NC | NC | NC |
| 3889 | 6484 | TAAAAACAACATAAAACCCT | 1 | NC | NC | NC |
| 3890 | 6485 | TTAAAAACAACATAAAACCC | 1 | NC | NC | NC |
| 3891 | 6486 | GTTAAAAACAACATAAAACC | 2 | NC | NC | NC |
| 3892 | 6490 | CTGAGTTAAAAACAACATAA | 1 | NC | NC | NC |
| 3893 | 6491 | TCTGAGTTAAAAACAACATA | 2 | NC | NC | NC |
| 3894 | 6492 | ATCTGAGTTAAAAACAACAT | 2 | NC | NC | NC |
| 3895 | 6493 | CATCTGAGTTAAAAACAACA | 1 | NC | NC | NC |
| 3896 | 6494 | GCATCTGAGTTAAAAACAAC | 2 | NC | NC | NC |
| 3897 | 6495 | GGCATCTGAGTTAAAAACAA | 2 | NC | NC | NC |
| 3898 | 6496 | TGGCATCTGAGTTAAAAACA | 2 | NC | NC | NC |
| 3899 | 6497 | ATGGCATCTGAGTTAAAAAC | 1 | NC | NC | NC |
| 3900 | 6498 | TATGGCATCTGAGTTAAAAA | 2 | NC | NC | NC |
| 3901 | 6499 | TTATGGCATCTGAGTTAAAA | 2 | NC | NC | NC |
| 3902 | 6500 | CTTATGGCATCTGAGTTAAA | 2 | NC | NC | NC |
| 3903 | 6501 | TCTTATGGCATCTGAGTTAA | 2 | NC | NC | NC |
| 3904 | 6502 | TTCTTATGGCATCTGAGTTA | 2 | NC | NC | NC |
| 3905 | 6503 | GTTCTTATGGCATCTGAGTT | 2 | NC | NC | NC |
| 3906 | 6504 | TGTTCTTATGGCATCTGAGT | 2 | NC | NC | NC |
| 3907 | 6505 | TTGTTCTTATGGCATCTGAG | 2 | NC | NC | NC |
| 3908 | 6506 | TTTGTTCTTATGGCATCTGA | 2 | NC | NC | NC |
| 3909 | 6507 | CTTTGTTCTTATGGCATCTG | 1 | NC | NC | NC |
| 3910 | 6508 | TCTTTGTTCTTATGGCATCT | 1 | NC | NC | NC |
| 3911 | 6509 | ATCTTTGTTCTTATGGCATC | 1 | NC | NC | NC |
| 3912 | 6510 | TATCTTTGTTCTTATGGCAT | 0 | NC | NC | NC |
| 3913 | 6511 | GTATCTTTGTTCTTATGGCA | 1 | NC | NC | NC |
| 3914 | 6512 | TGTATCTTTGTTCTTATGGC | 1 | NC | NC | NC |
| 3915 | 6513 | ATGTATCTTTGTTCTTATGG | 1 | NC | NC | NC |
| 3916 | 6514 | CATGTATCTTTGTTCTTATG | 2 | NC | NC | NC |
| 3917 | 6515 | ACATGTATCTTTGTTCTTAT | 2 | NC | NC | NC |
| 3918 | 6516 | TACATGTATCTTTGTTCTTA | 1 | NC | NC | NC |
| 3919 | 6517 | TTACATGTATCTTTGTTCTT | 2 | NC | NC | NC |
| 3920 | 6518 | ATTACATGTATCTTTGTTCT | 2 | NC | NC | NC |
| 3921 | 6519 | AATTACATGTATCTTTGTTC | 2 | NC | NC | NC |
| 3922 | 6550 | CACAATATAGGTATTAATGA | 2 | NC | NC | NC |
| 3923 | 6551 | GCACAATATAGGTATTAATG | 1 | NC | NC | NC |
| 3924 | 6552 | AGCACAATATAGGTATTAAT | 1 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3925 | 6553 | AAGCACAATATAGGTATTAA | 2 | NC | NC | NC |
| 3926 | 6554 | AAAGCACAATATAGGTATTA | 2 | NC | NC | NC |
| 3927 | 6555 | TAAAGCACAATATAGGTATT | 1 | NC | NC | NC |
| 3928 | 6556 | TTAAAGCACAATATAGGTAT | 1 | NC | NC | NC |
| 3929 | 6557 | CTTAAAGCACAATATAGGTA | 2 | NC | NC | NC |
| 3930 | 6558 | CCTTAAAGCACAATATAGGT | 2 | NC | NC | NC |
| 3931 | 6559 | ACCTTAAAGCACAATATAGG | 2 | NC | NC | NC |
| 3932 | 6560 | AACCTTAAAGCACAATATAG | 2 | NC | NC | NC |
| 3933 | 6561 | AAACCTTAAAGCACAATATA | 2 | NC | NC | NC |
| 3934 | 6562 | TAAACCTTAAAGCACAATAT | 1 | NC | NC | NC |
| 3935 | 6563 | GTAAACCTTAAAGCACAATA | 1 | NC | NC | NC |
| 3936 | 6564 | TGTAAACCTTAAAGCACAAT | 1 | NC | NC | NC |
| 3937 | 6565 | TTGTAAACCTTAAAGCACAA | 1 | NC | NC | NC |
| 3938 | 6566 | TTTGTAAACCTTAAAGCACA | 1 | NC | NC | NC |
| 3939 | 6567 | TTTTGTAAACCTTAAAGCAC | 1 | NC | NC | NC |
| 3940 | 6568 | ATTTTGTAAACCTTAAAGCA | 1 | NC | NC | NC |
| 3941 | 6569 | TATTTTGTAAACCTTAAAGC | 1 | NC | NC | NC |
| 3942 | 6592 | CTAAGATAAAGTATGAGAAA | 2 | NC | NC | NC |
| 3943 | 6593 | ACTAAGATAAAGTATGAGAA | 1 | NC | NC | NC |
| 3944 | 6594 | AACTAAGATAAAGTATGAGA | 1 | NC | NC | NC |
| 3945 | 6595 | AAACTAAGATAAAGTATGAG | 2 | NC | NC | NC |
| 3946 | 6597 | CTAAACTAAGATAAAGTATG | 2 | NC | NC | NC |
| 3947 | 6601 | GAAACTAAACTAAGATAAAG | 1 | NC | NC | NC |
| 3948 | 6604 | CAAGAAACTAAACTAAGATA | 1 | NC | NC | NC |
| 3949 | 6605 | TCAAGAAACTAAACTAAGAT | 1 | NC | NC | NC |
| 3950 | 6606 | GTCAAGAAACTAAACTAAGA | 1 | NC | NC | NC |
| 3951 | 6607 | TGTCAAGAAACTAAACTAAG | 2 | NC | NC | NC |
| 3952 | 6608 | CTGTCAAGAAACTAAACTAA | 2 | NC | NC | NC |
| 3953 | 6609 | ACTGTCAAGAAACTAAACTA | 2 | NC | NC | NC |
| 3954 | 6610 | GACTGTCAAGAAACTAAACT | 2 | NC | NC | NC |
| 3955 | 6611 | GGACTGTCAAGAAACTAAAC | 2 | NC | NC | NC |
| 3956 | 6612 | TGGACTGTCAAGAAACTAAA | 1 | NC | NC | NC |
| 3957 | 6613 | ATGGACTGTCAAGAAACTAA | 1 | NC | NC | NC |
| 3958 | 6614 | CATGGACTGTCAAGAAACTA | 2 | NC | NC | NC |
| 3959 | 6615 | TCATGGACTGTCAAGAAACT | 2 | NC | NC | NC |
| 3960 | 6616 | CTCATGGACTGTCAAGAAAC | 2 | NC | NC | NC |
| 3961 | 6617 | CCTCATGGACTGTCAAGAAA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3962 | 6625 | CCACCTTACCTCATGGACTG | 1 | NC | NC | NC |
| 3963 | 6626 | ACCACCTTACCTCATGGACT | 2 | NC | NC | NC |
| 3964 | 6627 | TACCACCTTACCTCATGGAC | 2 | NC | NC | NC |
| 3965 | 6628 | CTACCACCTTACCTCATGGA | 2 | NC | NC | NC |
| 3966 | 6630 | AGCTACCACCTTACCTCATG | 2 | NC | NC | NC |
| 3967 | 6631 | AAGCTACCACCTTACCTCAT | 2 | NC | NC | NC |
| 3968 | 6632 | AAAGCTACCACCTTACCTCA | 2 | NC | NC | NC |
| 3969 | 6633 | TAAAGCTACCACCTTACCTC | 2 | NC | NC | NC |
| 3970 | 6634 | ATAAAGCTACCACCTTACCT | 2 | NC | NC | NC |
| 3971 | 6635 | GATAAAGCTACCACCTTACC | 2 | NC | NC | NC |
| 3972 | 6636 | TGATAAAGCTACCACCTTAC | 2 | NC | NC | NC |
| 3973 | 6637 | GTGATAAAGCTACCACCTTA | 2 | NC | NC | NC |
| 3974 | 6643 | AAAATGGTGATAAAGCTACC | 1 | NC | NC | NC |
| 3975 | 6644 | TAAAATGGTGATAAAGCTAC | 1 | NC | NC | NC |
| 3976 | 6645 | GTAAAATGGTGATAAAGCTA | 1 | NC | NC | NC |
| 3977 | 6646 | TGTAAAATGGTGATAAAGCT | 2 | NC | NC | NC |
| 3978 | 6647 | TTGTAAAATGGTGATAAAGC | 2 | NC | NC | NC |
| 3979 | 6648 | TTTGTAAAATGGTGATAAAG | 1 | NC | NC | NC |
| 3980 | 6649 | CTTTGTAAAATGGTGATAAA | 1 | NC | NC | NC |
| 3981 | 6650 | ACTTTGTAAAATGGTGATAA | 1 | NC | NC | NC |
| 3982 | 6651 | CACTTTGTAAAATGGTGATA | 1 | NC | NC | NC |
| 3983 | 6652 | CCACTTTGTAAAATGGTGAT | 1 | NC | NC | NC |
| 3984 | 6653 | CCCACTTTGTAAAATGGTGA | 1 | NC | NC | NC |
| 3985 | 6654 | TCCCACTTTGTAAAATGGTG | 1 | NC | NC | NC |
| 3986 | 6655 | TTCCCACTTTGTAAAATGGT | 1 | NC | NC | NC |
| 3987 | 6656 | TTTCCCACTTTGTAAAATGG | 1 | NC | NC | NC |
| 3988 | 6657 | GTTTCCCACTTTGTAAAATG | 1 | NC | NC | NC |
| 3989 | 6658 | CGTTTCCCACTTTGTAAAAT | 2 | NC | NC | NC |
| 3990 | 6659 | TCGTTTCCCACTTTGTAAAA | 2 | NC | NC | NC |
| 3991 | 6660 | TTCGTTTCCCACTTTGTAAA | 1 | NC | NC | NC |
| 3992 | 6661 | CTTCGTTTCCCACTTTGTAA | 2 | NC | NC | NC |
| 3993 | 6662 | CCTTCGTTTCCCACTTTGTA | 2 | NC | NC | NC |
| 3994 | 6663 | ACCTTCGTTTCCCACTTTGT | 2 | NC | NC | NC |
| 3995 | 6664 | AACCTTCGTTTCCCACTTTG | 2 | NC | NC | NC |
| 3996 | 6665 | GAACCTTCGTTTCCCACTTT | 2 | NC | NC | NC |
| 3997 | 6666 | GGAACCTTCGTTTCCCACTT | 2 | NC | NC | NC |
| 3998 | 6667 | AGGAACCTTCGTTTCCCACT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 3999 | 6668 | GAGGAACCTTCGTTTCCCAC | 2 | NC | NC | NC |
| 4000 | 6669 | AGAGGAACCTTCGTTTCCCA | 2 | NC | NC | NC |
| 4001 | 6670 | AAGAGGAACCTTCGTTTCCC | 2 | NC | NC | NC |
| 4002 | 6671 | TAAGAGGAACCTTCGTTTCC | 2 | NC | NC | NC |
| 4003 | 6672 | CTAAGAGGAACCTTCGTTTC | 2 | NC | NC | NC |
| 4004 | 6673 | CCTAAGAGGAACCTTCGTTT | 2 | NC | NC | NC |
| 4005 | 6684 | ACAACTAGGTTCCTAAGAGG | 1 | NC | NC | NC |
| 4006 | 6685 | GACAACTAGGTTCCTAAGAG | 2 | NC | NC | NC |
| 4007 | 6686 | TGACAACTAGGTTCCTAAGA | 2 | NC | NC | NC |
| 4008 | 6687 | GTGACAACTAGGTTCCTAAG | 2 | NC | NC | NC |
| 4009 | 6688 | GGTGACAACTAGGTTCCTAA | 2 | NC | NC | NC |
| 4010 | 6689 | AGGTGACAACTAGGTTCCTA | 2 | NC | NC | NC |
| 4011 | 6690 | AAGGTGACAACTAGGTTCCT | 2 | NC | NC | NC |
| 4012 | 6691 | AAAGGTGACAACTAGGTTCC | 2 | NC | NC | NC |
| 4013 | 6692 | CAAAGGTGACAACTAGGTTC | 2 | NC | NC | NC |
| 4014 | 6693 | ACAAAGGTGACAACTAGGTT | 2 | NC | NC | NC |
| 4015 | 6694 | TACAAAGGTGACAACTAGGT | 2 | NC | NC | NC |
| 4016 | 6695 | ATACAAAGGTGACAACTAGG | 2 | NC | NC | NC |
| 4017 | 6696 | TATACAAAGGTGACAACTAG | 2 | NC | NC | NC |
| 4018 | 6697 | TTATACAAAGGTGACAACTA | 2 | NC | NC | NC |
| 4019 | 6698 | ATTATACAAAGGTGACAACT | 2 | NC | NC | NC |
| 4020 | 6699 | TATTATACAAAGGTGACAAC | 2 | NC | NC | NC |
| 4021 | 6700 | TTATTATACAAAGGTGACAA | 2 | NC | NC | NC |
| 4022 | 6701 | TTTATTATACAAAGGTGACA | 2 | NC | NC | NC |
| 4023 | 6702 | TTTTATTATACAAAGGTGAC | 2 | NC | NC | NC |
| 4024 | 6703 | GTTTTATTATACAAAGGTGA | 2 | NC | NC | NC |
| 4025 | 6704 | AGTTTTATTATACAAAGGTG | 2 | NC | NC | NC |
| 4026 | 6706 | GAAGTTTTATTATACAAAGG | 2 | NC | NC | NC |
| 4027 | 6707 | CGAAGTTTTATTATACAAAG | 2 | NC | NC | NC |
| 4028 | 6710 | CTTCGAAGTTTTATTATACA | 2 | NC | NC | NC |
| 4029 | 6711 | GCTTCGAAGTTTTATTATAC | 2 | NC | NC | NC |
| 4030 | 6712 | AGCTTCGAAGTTTTATTATA | 2 | NC | NC | NC |
| 4031 | 6713 | GAGCTTCGAAGTTTTATTAT | 2 | NC | NC | NC |
| 4032 | 6730 | AACCAGTTAACAGCTCCGAG | 2 | NC | NC | NC |
| 4033 | 6731 | AAACCAGTTAACAGCTCCGA | 2 | NC | NC | NC |
| 4034 | 6732 | CAAACCAGTTAACAGCTCCG | 2 | NC | NC | NC |
| 4035 | 6733 | GCAAACCAGTTAACAGCTCC | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4036 | 6734 | AGCAAACCAGTTAACAGCTC | 2 | NC | NC | NC |
| 4037 | 6735 | CAGCAAACCAGTTAACAGCT | 2 | NC | NC | NC |
| 4038 | 6736 | TCAGCAAACCAGTTAACAGC | 2 | NC | NC | NC |
| 4039 | 6737 | TTCAGCAAACCAGTTAACAG | 1 | NC | NC | NC |
| 4040 | 6738 | CTTCAGCAAACCAGTTAACA | 2 | NC | NC | NC |
| 4041 | 6739 | CCTTCAGCAAACCAGTTAAC | 2 | NC | NC | NC |
| 4042 | 6752 | TCTTACAGCTAAGCCTTCAG | 1 | NC | NC | NC |
| 4043 | 6753 | CTCTTACAGCTAAGCCTTCA | 1 | NC | NC | NC |
| 4044 | 6765 | TCTGAATTCTGGCTCTTACA | 1 | NC | NC | NC |
| 4045 | 6766 | GTCTGAATTCTGGCTCTTAC | 1 | NC | NC | NC |
| 4046 | 6767 | GGTCTGAATTCTGGCTCTTA | 1 | NC | NC | NC |
| 4047 | 6768 | GGGTCTGAATTCTGGCTCTT | 1 | NC | NC | NC |
| 4048 | 6769 | TGGGTCTGAATTCTGGCTCT | 0 | NC | NC | NC |
| 4049 | 6770 | CTGGGTCTGAATTCTGGCTC | 0 | NC | NC | NC |
| 4050 | 6771 | CCTGGGTCTGAATTCTGGCT | 0 | NC | NC | NC |
| 4051 | 6772 | ACCTGGGTCTGAATTCTGGC | 1 | NC | NC | NC |
| 4052 | 6791 | GCAGTTTGAAGTCACTCAGA | 2 | NC | NC | NC |
| 4053 | 6792 | TGCAGTTTGAAGTCACTCAG | 2 | NC | NC | NC |
| 4054 | 6793 | GTGCAGTTTGAAGTCACTCA | 2 | NC | NC | NC |
| 4055 | 6794 | TGTGCAGTTTGAAGTCACTC | 2 | NC | NC | NC |
| 4056 | 6795 | CTGTGCAGTTTGAAGTCACT | 2 | NC | NC | NC |
| 4057 | 6796 | ACTGTGCAGTTTGAAGTCAC | 2 | NC | NC | NC |
| 4058 | 6807 | TAATGGGAAGGACTGTGCAG | 2 | NC | NC | NC |
| 4059 | 6808 | ATAATGGGAAGGACTGTGCA | 2 | NC | NC | NC |
| 4060 | 6809 | AATAATGGGAAGGACTGTGC | 1 | NC | NC | NC |
| 4061 | 6810 | TAATAATGGGAAGGACTGTG | 2 | NC | NC | NC |
| 4062 | 6811 | GTAATAATGGGAAGGACTGT | 1 | NC | NC | NC |
| 4063 | 6812 | GGTAATAATGGGAAGGACTG | 1 | NC | NC | NC |
| 4064 | 6813 | GGGTAATAATGGGAAGGACT | 1 | NC | NC | NC |
| 4065 | 6814 | TGGGTAATAATGGGAAGGAC | 2 | NC | NC | NC |
| 4066 | 6815 | ATGGGTAATAATGGGAAGGA | 2 | NC | NC | NC |
| 4067 | 6816 | TATGGGTAATAATGGGAAGG | 2 | NC | NC | NC |
| 4068 | 6817 | ATATGGGTAATAATGGGAAG | 2 | NC | NC | NC |
| 4069 | 6818 | CATATGGGTAATAATGGGAA | 2 | NC | NC | NC |
| 4070 | 6819 | GCATATGGGTAATAATGGGA | 2 | NC | NC | NC |
| 4071 | 6820 | AGCATATGGGTAATAATGGG | 2 | NC | NC | NC |
| 4072 | 6821 | TAGCATATGGGTAATAATGG | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 4073 | 6822 | ATAGCATATGGGTAATAATG | 2 | NC | NC | NC |
| 4074 | 6823 | GATAGCATATGGGTAATAAT | 2 | NC | NC | NC |
| 4075 | 6824 | GGATAGCATATGGGTAATAA | 3 | NC | NC | NC |
| 4076 | 6825 | GGGATAGCATATGGGTAATA | 2 | NC | NC | NC |
| 4077 | 6826 | AGGGATAGCATATGGGTAAT | 3 | NC | NC | NC |
| 4078 | 6827 | AAGGGATAGCATATGGGTAA | 2 | NC | NC | NC |
| 4079 | 6828 | TAAGGGATAGCATATGGGTA | 2 | NC | NC | NC |
| 4080 | 6829 | ATAAGGGATAGCATATGGGT | 3 | NC | NC | NC |
| 4081 | 6830 | TATAAGGGATAGCATATGGG | 2 | NC | NC | NC |
| 4082 | 6831 | ATATAAGGGATAGCATATGG | 2 | NC | NC | NC |
| 4083 | 6832 | AATATAAGGGATAGCATATG | 2 | NC | NC | NC |
| 4084 | 6833 | AAATATAAGGGATAGCATAT | 2 | NC | NC | NC |
| 4085 | 6834 | AAAATATAAGGGATAGCATA | 2 | NC | NC | NC |
| 4086 | 6835 | AAAAATATAAGGGATAGCAT | 1 | NC | NC | NC |
| 4087 | 6836 | TAAAAATATAAGGGATAGCA | 2 | NC | NC | NC |
| 4088 | 6837 | TTAAAAATATAAGGGATAGC | 1 | NC | NC | NC |
| 4089 | 6869 | CCAAGTTTATAAATGAATGA | 1 | NC | NC | NC |
| 4090 | 6870 | ACCAAGTTTATAAATGAATG | 1 | NC | NC | NC |
| 4091 | 6871 | CACCAAGTTTATAAATGAAT | 1 | NC | NC | NC |
| 4092 | 6872 | TCACCAAGTTTATAAATGAA | 1 | NC | NC | NC |
| 4093 | 6873 | ATCACCAAGTTTATAAATGA | 2 | NC | NC | NC |
| 4094 | 6874 | AATCACCAAGTTTATAAATG | 1 | NC | NC | NC |
| 4095 | 6875 | GAATCACCAAGTTTATAAAT | 1 | NC | NC | NC |
| 4096 | 6876 | TGAATCACCAAGTTTATAAA | 1 | NC | NC | NC |
| 4097 | 6877 | GTGAATCACCAAGTTTATAA | 2 | NC | NC | NC |
| 4098 | 6888 | ATCTAATAAAGGTGAATCAC | 2 | NC | NC | NC |
| 4099 | 6889 | AATCTAATAAAGGTGAATCA | 2 | NC | NC | NC |
| 4100 | 6890 | GAATCTAATAAAGGTGAATC | 2 | NC | NC | NC |
| 4101 | 6891 | AGAATCTAATAAAGGTGAAT | 2 | NC | NC | NC |
| 4102 | 6892 | CAGAATCTAATAAAGGTGAA | 1 | NC | NC | NC |
| 4103 | 6893 | CCAGAATCTAATAAAGGTGA | 2 | NC | NC | NC |
| 4104 | 6894 | ACCAGAATCTAATAAAGGTG | 2 | NC | NC | NC |
| 4105 | 6895 | GACCAGAATCTAATAAAGGT | 2 | NC | NC | NC |
| 4106 | 6896 | CGACCAGAATCTAATAAAGG | 2 | NC | NC | NC |
| 4107 | 6897 | GCGACCAGAATCTAATAAAG | 2 | NC | NC | NC |
| 4108 | 6898 | AGCGACCAGAATCTAATAAA | 3 | NC | NC | NC |
| 4109 | 6899 | CAGCGACCAGAATCTAATAA | 3 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4110 | 6900 | TCAGCGACCAGAATCTAATA | 2 | NC | NC | NC |
| 4111 | 6901 | TTCAGCGACCAGAATCTAAT | 2 | NC | NC | NC |
| 4112 | 6902 | CTTCAGCGACCAGAATCTAA | 2 | NC | NC | NC |
| 4113 | 6903 | CCTTCAGCGACCAGAATCTA | 1 | NC | NC | NC |
| 4114 | 6904 | GCCTTCAGCGACCAGAATCT | 2 | NC | NC | NC |
| 4115 | 6916 | GAAGTTACTAAAGCCTTCAG | 1 | NC | NC | NC |
| 4116 | 6918 | CTGAAGTTACTAAAGCCTTC | 2 | NC | NC | NC |
| 4117 | 6919 | TCTGAAGTTACTAAAGCCTT | 2 | NC | NC | NC |
| 4118 | 6920 | CTCTGAAGTTACTAAAGCCT | 2 | NC | NC | NC |
| 4119 | 6921 | ACTCTGAAGTTACTAAAGCC | 2 | NC | NC | NC |
| 4120 | 6922 | TACTCTGAAGTTACTAAAGC | 2 | NC | NC | NC |
| 4121 | 6923 | TTACTCTGAAGTTACTAAAG | 1 | NC | NC | NC |
| 4122 | 6924 | TTTACTCTGAAGTTACTAAA | 1 | NC | NC | NC |
| 4123 | 6925 | TTTTACTCTGAAGTTACTAA | 1 | NC | NC | NC |
| 4124 | 6926 | GTTTTACTCTGAAGTTACTA | 2 | NC | NC | NC |
| 4125 | 6927 | AGTTTTACTCTGAAGTTACT | 2 | NC | NC | NC |
| 4126 | 6928 | AAGTTTTACTCTGAAGTTAC | 2 | NC | NC | NC |
| 4127 | 6929 | CAAGTTTTACTCTGAAGTTA | 2 | NC | NC | NC |
| 4128 | 6930 | TCAAGTTTTACTCTGAAGTT | 2 | NC | NC | NC |
| 4129 | 6932 | TCTCAAGTTTTACTCTGAAG | 1 | NC | NC | NC |
| 4130 | 6933 | CTCTCAAGTTTTACTCTGAA | 2 | NC | NC | NC |
| 4131 | 6934 | TCTCTCAAGTTTTACTCTGA | 2 | NC | NC | NC |
| 4132 | 6935 | ATCTCTCAAGTTTTACTCTG | 1 | NC | NC | NC |
| 4133 | 6936 | CATCTCTCAAGTTTTACTCT | 2 | NC | NC | NC |
| 4134 | 6937 | TCATCTCTCAAGTTTTACTC | 2 | NC | NC | NC |
| 4135 | 6938 | CTCATCTCTCAAGTTTTACT | 2 | NC | NC | NC |
| 4136 | 6939 | TCTCATCTCTCAAGTTTTAC | 2 | NC | NC | NC |
| 4137 | 6940 | ATCTCATCTCTCAAGTTTTA | 2 | NC | NC | NC |
| 4138 | 6941 | CATCTCATCTCTCAAGTTTT | 1 | NC | NC | NC |
| 4139 | 6942 | ACATCTCATCTCTCAAGTTT | 2 | NC | NC | NC |
| 4140 | 6943 | TACATCTCATCTCTCAAGTT | 2 | NC | NC | NC |
| 4141 | 6944 | TTACATCTCATCTCTCAAGT | 1 | NC | NC | NC |
| 4142 | 6945 | TTTACATCTCATCTCTCAAG | 1 | NC | NC | NC |
| 4143 | 6946 | TTTTACATCTCATCTCTCAA | 2 | NC | NC | NC |
| 4144 | 6947 | ATTTTACATCTCATCTCTCA | 1 | NC | NC | NC |
| 4145 | 6948 | CATTTTACATCTCATCTCTC | 1 | NC | NC | NC |
| 4146 | 6949 | GCATTTTACATCTCATCTCT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4147 | 6950 | TGCATTTTACATCTCATCTC | 1 | NC | NC | NC |
| 4148 | 6951 | CTGCATTTTACATCTCATCT | 2 | NC | NC | NC |
| 4149 | 6952 | GCTGCATTTTACATCTCATC | 2 | NC | NC | NC |
| 4150 | 6953 | GGCTGCATTTTACATCTCAT | 2 | NC | NC | NC |
| 4151 | 6954 | TGGCTGCATTTTACATCTCA | 2 | NC | NC | NC |
| 4152 | 6955 | ATGGCTGCATTTTACATCTC | 2 | NC | NC | NC |
| 4153 | 6956 | AATGGCTGCATTTTACATCT | 2 | NC | NC | NC |
| 4154 | 6957 | GAATGGCTGCATTTTACATC | 2 | NC | NC | NC |
| 4155 | 6958 | AGAATGGCTGCATTTTACAT | 2 | NC | NC | NC |
| 4156 | 6959 | AAGAATGGCTGCATTTTACA | 1 | NC | NC | NC |
| 4157 | 6960 | CAAGAATGGCTGCATTTTAC | 2 | NC | NC | NC |
| 4158 | 6961 | TCAAGAATGGCTGCATTTTA | 1 | NC | NC | NC |
| 4159 | 6962 | CTCAAGAATGGCTGCATTTT | 1 | NC | NC | NC |
| 4160 | 6963 | TCTCAAGAATGGCTGCATTT | 2 | NC | NC | NC |
| 4161 | 6964 | CTCTCAAGAATGGCTGCATT | 2 | NC | NC | NC |
| 4162 | 6965 | ACTCTCAAGAATGGCTGCAT | 2 | NC | NC | NC |
| 4163 | 6966 | AACTCTCAAGAATGGCTGCA | 1 | NC | NC | NC |
| 4164 | 6967 | GAACTCTCAAGAATGGCTGC | 2 | NC | NC | NC |
| 4165 | 6968 | GGAACTCTCAAGAATGGCTG | 2 | NC | NC | NC |
| 4166 | 6969 | AGGAACTCTCAAGAATGGCT | 2 | NC | NC | NC |
| 4167 | 6970 | AAGGAACTCTCAAGAATGGC | 2 | NC | NC | NC |
| 4168 | 6971 | AAAGGAACTCTCAAGAATGG | 2 | NC | NC | NC |
| 4169 | 6972 | AAAAGGAACTCTCAAGAATG | 2 | NC | NC | NC |
| 4170 | 6973 | AAAAAGGAACTCTCAAGAAT | 2 | NC | NC | NC |
| 4171 | 6974 | GAAAAAGGAACTCTCAAGAA | 2 | NC | NC | NC |
| 4172 | 6975 | AGAAAAAGGAACTCTCAAGA | 2 | NC | NC | NC |
| 4173 | 6976 | CAGAAAAAGGAACTCTCAAG | 1 | NC | NC | NC |
| 4174 | 6977 | ACAGAAAAAGGAACTCTCAA | 1 | NC | NC | NC |
| 4175 | 6978 | TACAGAAAAAGGAACTCTCA | 1 | NC | NC | NC |
| 4176 | 6979 | TTACAGAAAAAGGAACTCTC | 2 | NC | NC | NC |
| 4177 | 6980 | GTTACAGAAAAAGGAACTCT | 1 | NC | NC | NC |
| 4178 | 6981 | TGTTACAGAAAAAGGAACTC | 2 | NC | NC | NC |
| 4179 | 6983 | AATGTTACAGAAAAAGGAAC | 1 | NC | NC | NC |
| 4180 | 6984 | GAATGTTACAGAAAAAGGAA | 1 | NC | NC | NC |
| 4181 | 6985 | TGAATGTTACAGAAAAAGGA | 1 | NC | NC | NC |
| 4182 | 6986 | ATGAATGTTACAGAAAAAGG | 2 | NC | NC | NC |
| 4183 | 6987 | GATGAATGTTACAGAAAAAG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4184 | 6988 | TGATGAATGTTACAGAAAAA | 1 | NC | NC | NC |
| 4185 | 6989 | TTGATGAATGTTACAGAAAA | 1 | NC | NC | NC |
| 4186 | 6990 | GTTGATGAATGTTACAGAAA | 1 | NC | NC | NC |
| 4187 | 6991 | TGTTGATGAATGTTACAGAA | 1 | NC | NC | NC |
| 4188 | 6992 | GTGTTGATGAATGTTACAGA | 2 | NC | NC | NC |
| 4189 | 6993 | AGTGTTGATGAATGTTACAG | 2 | NC | NC | NC |
| 4190 | 6994 | AAGTGTTGATGAATGTTACA | 2 | NC | NC | NC |
| 4191 | 6995 | GAAGTGTTGATGAATGTTAC | 2 | NC | NC | NC |
| 4192 | 6996 | TGAAGTGTTGATGAATGTTA | 2 | NC | NC | NC |
| 4193 | 6997 | ATGAAGTGTTGATGAATGTT | 1 | NC | NC | NC |
| 4194 | 6998 | AATGAAGTGTTGATGAATGT | 1 | NC | NC | NC |
| 4195 | 6999 | CAATGAAGTGTTGATGAATG | 1 | NC | NC | NC |
| 4196 | 7000 | TCAATGAAGTGTTGATGAAT | 1 | NC | NC | NC |
| 4197 | 7001 | CTCAATGAAGTGTTGATGAA | 1 | NC | NC | NC |
| 4198 | 7002 | TCTCAATGAAGTGTTGATGA | 2 | NC | NC | NC |
| 4199 | 7003 | TTCTCAATGAAGTGTTGATG | 2 | NC | NC | NC |
| 4200 | 7012 | AACCTTCACTTCTCAATGAA | 2 | NC | NC | NC |
| 4201 | 7013 | GAACCTTCACTTCTCAATGA | 2 | NC | NC | NC |
| 4202 | 7014 | GGAACCTTCACTTCTCAATG | 2 | NC | NC | NC |
| 4203 | 7015 | AGGAACCTTCACTTCTCAAT | 2 | NC | NC | NC |
| 4204 | 7016 | TAGGAACCTTCACTTCTCAA | 2 | NC | NC | NC |
| 4205 | 7017 | ATAGGAACCTTCACTTCTCA | 2 | NC | NC | NC |
| 4206 | 7018 | CATAGGAACCTTCACTTCTC | 2 | NC | NC | NC |
| 4207 | 7019 | CCATAGGAACCTTCACTTCT | 2 | NC | NC | NC |
| 4208 | 7020 | GCCATAGGAACCTTCACTTC | 2 | NC | NC | NC |
| 4209 | 7021 | AGCCATAGGAACCTTCACTT | 2 | NC | NC | NC |
| 4210 | 7022 | CAGCCATAGGAACCTTCACT | 2 | NC | NC | NC |
| 4211 | 7023 | ACAGCCATAGGAACCTTCAC | 2 | NC | NC | NC |
| 4212 | 7024 | GACAGCCATAGGAACCTTCA | 3 | NC | NC | NC |
| 4213 | 7025 | AGACAGCCATAGGAACCTTC | 2 | NC | NC | NC |
| 4214 | 7026 | GAGACAGCCATAGGAACCTT | 2 | NC | NC | NC |
| 4215 | 7027 | AGAGACAGCCATAGGAACCT | 2 | NC | NC | NC |
| 4216 | 7028 | TAGAGACAGCCATAGGAACC | 2 | NC | NC | NC |
| 4217 | 7029 | GTAGAGACAGCCATAGGAAC | 2 | NC | NC | NC |
| 4218 | 7030 | GGTAGAGACAGCCATAGGAA | 1 | NC | NC | NC |
| 4219 | 7031 | AGGTAGAGACAGCCATAGGA | 2 | NC | NC | NC |
| 4220 | 7032 | AAGGTAGAGACAGCCATAGG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4221 | 7033 | GAAGGTAGAGACAGCCATAG | 1 | NC | NC | NC |
| 4222 | 7034 | TGAAGGTAGAGACAGCCATA | 2 | NC | NC | NC |
| 4223 | 7035 | TTGAAGGTAGAGACAGCCAT | 2 | NC | NC | NC |
| 4224 | 7036 | CTTGAAGGTAGAGACAGCCA | 2 | NC | NC | NC |
| 4225 | 7037 | TCTTGAAGGTAGAGACAGCC | 2 | NC | NC | NC |
| 4226 | 7049 | TAAAGCTAAGCCTCTTGAAG | 1 | NC | NC | NC |
| 4227 | 7050 | CTAAAGCTAAGCCTCTTGAA | 0 | NC | NC | NC |
| 4228 | 7051 | ACTAAAGCTAAGCCTCTTGA | 1 | NC | NC | NC |
| 4229 | 7052 | GACTAAAGCTAAGCCTCTTG | 2 | NC | NC | NC |
| 4230 | 7053 | TGACTAAAGCTAAGCCTCTT | 2 | NC | NC | NC |
| 4231 | 7054 | GTGACTAAAGCTAAGCCTCT | 2 | NC | NC | NC |
| 4232 | 7055 | AGTGACTAAAGCTAAGCCTC | 2 | NC | NC | NC |
| 4233 | 7056 | CAGTGACTAAAGCTAAGCCT | 1 | NC | NC | NC |
| 4234 | 7057 | TCAGTGACTAAAGCTAAGCC | 2 | NC | NC | NC |
| 4235 | 7058 | CTCAGTGACTAAAGCTAAGC | 1 | NC | NC | NC |
| 4236 | 7059 | TCTCAGTGACTAAAGCTAAG | 1 | NC | NC | NC |
| 4237 | 7060 | TTCTCAGTGACTAAAGCTAA | 2 | NC | NC | NC |
| 4238 | 7061 | TTTCTCAGTGACTAAAGCTA | 1 | NC | NC | NC |
| 4239 | 7062 | CTTTCTCAGTGACTAAAGCT | 2 | NC | NC | NC |
| 4240 | 7063 | TCTTTCTCAGTGACTAAAGC | 2 | NC | NC | NC |
| 4241 | 7064 | GTCTTTCTCAGTGACTAAAG | 2 | NC | NC | NC |
| 4242 | 7065 | TGTCTTTCTCAGTGACTAAA | 2 | NC | NC | NC |
| 4243 | 7066 | TTGTCTTTCTCAGTGACTAA | 2 | NC | NC | NC |
| 4244 | 7067 | CTTGTCTTTCTCAGTGACTA | 1 | NC | NC | NC |
| 4245 | 7068 | CCTTGTCTTTCTCAGTGACT | 2 | NC | NC | NC |
| 4246 | 7069 | TCCTTGTCTTTCTCAGTGAC | 2 | NC | NC | NC |
| 4247 | 7070 | TTCCTTGTCTTTCTCAGTGA | 2 | NC | NC | NC |
| 4248 | 7071 | TTTCCTTGTCTTTCTCAGTG | 2 | NC | NC | NC |
| 4249 | 7072 | GTTTCCTTGTCTTTCTCAGT | 1 | NC | NC | NC |
| 4250 | 7073 | AGTTTCCTTGTCTTTCTCAG | 1 | NC | NC | NC |
| 4251 | 7074 | TAGTTTCCTTGTCTTTCTCA | 1 | NC | NC | NC |
| 4252 | 7075 | TTAGTTTCCTTGTCTTTCTC | 1 | NC | NC | NC |
| 4253 | 7076 | ATTAGTTTCCTTGTCTTTCT | 1 | NC | NC | NC |
| 4254 | 7077 | CATTAGTTTCCTTGTCTTTC | 1 | NC | NC | NC |
| 4255 | 7078 | TCATTAGTTTCCTTGTCTTT | 1 | NC | NC | NC |
| 4256 | 7079 | ATCATTAGTTTCCTTGTCTT | 2 | NC | NC | NC |
| 4257 | 7080 | TATCATTAGTTTCCTTGTCT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4258 | 7081 | CTATCATTAGTTTCCTTGTC | 2 | NC | NC | NC |
| 4259 | 7082 | TCTATCATTAGTTTCCTTGT | 2 | NC | NC | NC |
| 4260 | 7083 | TTCTATCATTAGTTTCCTTG | 2 | NC | NC | NC |
| 4261 | 7084 | ATTCTATCATTAGTTTCCTT | 1 | NC | NC | NC |
| 4262 | 7085 | TATTCTATCATTAGTTTCCT | 2 | NC | NC | NC |
| 4263 | 7086 | ATATTCTATCATTAGTTTCC | 2 | NC | NC | NC |
| 4264 | 7091 | CTACTATATTCTATCATTAG | 2 | NC | NC | NC |
| 4265 | 7092 | GCTACTATATTCTATCATTA | 2 | NC | NC | NC |
| 4266 | 7093 | AGCTACTATATTCTATCATT | 1 | NC | NC | NC |
| 4267 | 7094 | AAGCTACTATATTCTATCAT | 1 | NC | NC | NC |
| 4268 | 7095 | GAAGCTACTATATTCTATCA | 2 | NC | NC | NC |
| 4269 | 7096 | AGAAGCTACTATATTCTATC | 2 | NC | NC | NC |
| 4270 | 7097 | AAGAAGCTACTATATTCTAT | 2 | NC | NC | NC |
| 4271 | 7098 | GAAGAAGCTACTATATTCTA | 2 | NC | NC | NC |
| 4272 | 7099 | AGAAGAAGCTACTATATTCT | 2 | NC | NC | NC |
| 4273 | 7100 | CAGAAGAAGCTACTATATTC | 1 | NC | NC | NC |
| 4274 | 7101 | CCAGAAGAAGCTACTATATT | 1 | NC | NC | NC |
| 4275 | 7102 | GCCAGAAGAAGCTACTATAT | 2 | NC | NC | NC |
| 4276 | 7103 | CGCCAGAAGAAGCTACTATA | 1 | NC | NC | NC |
| 4277 | 7104 | ACGCCAGAAGAAGCTACTAT | 2 | NC | NC | NC |
| 4278 | 7105 | AACGCCAGAAGAAGCTACTA | 3 | NC | NC | NC |
| 4279 | 7106 | TAACGCCAGAAGAAGCTACT | 2 | NC | NC | NC |
| 4280 | 7107 | CTAACGCCAGAAGAAGCTAC | 2 | NC | NC | NC |
| 4281 | 7108 | CCTAACGCCAGAAGAAGCTA | 3 | NC | NC | NC |
| 4282 | 7109 | ACCTAACGCCAGAAGAAGCT | 2 | NC | NC | NC |
| 4283 | 7110 | TACCTAACGCCAGAAGAAGC | 3 | NC | NC | NC |
| 4284 | 7111 | ATACCTAACGCCAGAAGAAG | 2 | NC | NC | NC |
| 4285 | 7112 | GATACCTAACGCCAGAAGAA | 3 | NC | NC | NC |
| 4286 | 7113 | TGATACCTAACGCCAGAAGA | 2 | NC | NC | NC |
| 4287 | 7114 | GTGATACCTAACGCCAGAAG | 3 | NC | NC | NC |
| 4288 | 7115 | TGTGATACCTAACGCCAGAA | 2 | NC | NC | NC |
| 4289 | 7116 | CTGTGATACCTAACGCCAGA | 2 | NC | NC | NC |
| 4290 | 7117 | TCTGTGATACCTAACGCCAG | 3 | NC | NC | NC |
| 4291 | 7118 | CTCTGTGATACCTAACGCCA | 2 | NC | NC | NC |
| 4292 | 7119 | ACTCTGTGATACCTAACGCC | 2 | NC | NC | NC |
| 4293 | 7120 | GACTCTGTGATACCTAACGC | 2 | NC | NC | NC |
| 4294 | 7121 | TGACTCTGTGATACCTAACG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4295 | 7122 | GTGACTCTGTGATACCTAAC | 2 | NC | NC | NC |
| 4296 | 7123 | TGTGACTCTGTGATACCTAA | 2 | NC | NC | NC |
| 4297 | 7124 | CTGTGACTCTGTGATACCTA | 2 | NC | NC | NC |
| 4298 | 7125 | GCTGTGACTCTGTGATACCT | 2 | NC | NC | NC |
| 4299 | 7126 | AGCTGTGACTCTGTGATACC | 2 | NC | NC | NC |
| 4300 | 7127 | TAGCTGTGACTCTGTGATAC | 2 | NC | NC | NC |
| 4301 | 7128 | CTAGCTGTGACTCTGTGATA | 2 | NC | NC | NC |
| 4302 | 7129 | ACTAGCTGTGACTCTGTGAT | 1 | NC | NC | NC |
| 4303 | 7130 | AACTAGCTGTGACTCTGTGA | 2 | NC | NC | NC |
| 4304 | 7131 | TAACTAGCTGTGACTCTGTG | 2 | NC | NC | NC |
| 4305 | 7132 | GTAACTAGCTGTGACTCTGT | 2 | NC | NC | NC |
| 4306 | 7133 | TGTAACTAGCTGTGACTCTG | 2 | NC | NC | NC |
| 4307 | 7134 | CTGTAACTAGCTGTGACTCT | 2 | NC | NC | NC |
| 4308 | 7145 | TAAAGGGCTAGCTGTAACTA | 3 | NC | NC | NC |
| 4309 | 7146 | ATAAAGGGCTAGCTGTAACT | 2 | NC | NC | NC |
| 4310 | 7147 | AATAAAGGGCTAGCTGTAAC | 3 | NC | NC | NC |
| 4311 | 7148 | TAATAAAGGGCTAGCTGTAA | 2 | NC | NC | NC |
| 4312 | 7149 | ATAATAAAGGGCTAGCTGTA | 2 | NC | NC | NC |
| 4313 | 7150 | AATAATAAAGGGCTAGCTGT | 2 | NC | NC | NC |
| 4314 | 7151 | CAATAATAAAGGGCTAGCTG | 2 | NC | NC | NC |
| 4315 | 7152 | TCAATAATAAAGGGCTAGCT | 1 | NC | NC | NC |
| 4316 | 7153 | TTCAATAATAAAGGGCTAGC | 1 | NC | NC | NC |
| 4317 | 7154 | TTTCAATAATAAAGGGCTAG | 1 | NC | NC | NC |
| 4318 | 7155 | CTTTCAATAATAAAGGGCTA | 2 | NC | NC | NC |
| 4319 | 7156 | TCTTTCAATAATAAAGGGCT | 2 | NC | NC | NC |
| 4320 | 7157 | TTCTTTCAATAATAAAGGGC | 1 | NC | NC | NC |
| 4321 | 7158 | CTTCTTTCAATAATAAAGGG | 2 | NC | NC | NC |
| 4322 | 7159 | TCTTCTTTCAATAATAAAGG | 1 | NC | NC | NC |
| 4323 | 7160 | CTCTTCTTTCAATAATAAAG | 2 | NC | NC | NC |
| 4324 | 7161 | CCTCTTCTTTCAATAATAAA | 2 | NC | NC | NC |
| 4325 | 7162 | TCCTCTTCTTTCAATAATAA | 2 | NC | NC | NC |
| 4326 | 7163 | CTCCTCTTCTTTCAATAATA | 1 | NC | NC | NC |
| 4327 | 7164 | GCTCCTCTTCTTTCAATAAT | 2 | NC | NC | NC |
| 4328 | 7165 | AGCTCCTCTTCTTTCAATAA | 2 | NC | NC | NC |
| 4329 | 7166 | TAGCTCCTCTTCTTTCAATA | 2 | NC | NC | NC |
| 4330 | 7167 | CTAGCTCCTCTTCTTTCAAT | 2 | NC | NC | NC |
| 4331 | 7168 | GCTAGCTCCTCTTCTTTCAA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4332 | 7169 | TGCTAGCTCCTCTTCTTTCA | 2 | NC | NC | NC |
| 4333 | 7170 | CTGCTAGCTCCTCTTCTTTC | 1 | NC | NC | NC |
| 4334 | 7171 | ACTGCTAGCTCCTCTTCTTT | 1 | NC | NC | NC |
| 4335 | 7172 | GACTGCTAGCTCCTCTTCTT | 2 | NC | NC | NC |
| 4336 | 7173 | GGACTGCTAGCTCCTCTTCT | 2 | NC | NC | NC |
| 4337 | 7175 | TGGGACTGCTAGCTCCTCTT | 2 | NC | NC | NC |
| 4338 | 7178 | TAGTGGGACTGCTAGCTCCT | 2 | NC | NC | NC |
| 4339 | 7179 | ATAGTGGGACTGCTAGCTCC | 2 | NC | NC | NC |
| 4340 | 7180 | GATAGTGGGACTGCTAGCTC | 3 | NC | NC | NC |
| 4341 | 7181 | TGATAGTGGGACTGCTAGCT | 2 | NC | NC | NC |
| 4342 | 7182 | CTGATAGTGGGACTGCTAGC | 2 | NC | NC | NC |
| 4343 | 7183 | TCTGATAGTGGGACTGCTAG | 2 | NC | NC | NC |
| 4344 | 7184 | TTCTGATAGTGGGACTGCTA | 3 | NC | NC | NC |
| 4345 | 7185 | ATTCTGATAGTGGGACTGCT | 2 | NC | NC | NC |
| 4346 | 7186 | AATTCTGATAGTGGGACTGC | 2 | NC | NC | NC |
| 4347 | 7187 | TAATTCTGATAGTGGGACTG | 2 | NC | NC | NC |
| 4348 | 7188 | TTAATTCTGATAGTGGGACT | 3 | NC | NC | NC |
| 4349 | 7189 | CTTAATTCTGATAGTGGGAC | 3 | NC | NC | NC |
| 4350 | 7190 | TCTTAATTCTGATAGTGGGA | 2 | NC | NC | NC |
| 4351 | 7191 | GTCTTAATTCTGATAGTGGG | 2 | NC | NC | NC |
| 4352 | 7192 | AGTCTTAATTCTGATAGTGG | 1 | NC | NC | NC |
| 4353 | 7193 | TAGTCTTAATTCTGATAGTG | 1 | NC | NC | NC |
| 4354 | 7194 | CTAGTCTTAATTCTGATAGT | 2 | NC | NC | NC |
| 4355 | 7195 | TCTAGTCTTAATTCTGATAG | 2 | NC | NC | NC |
| 4356 | 7196 | CTCTAGTCTTAATTCTGATA | 2 | NC | NC | NC |
| 4357 | 7197 | TCTCTAGTCTTAATTCTGAT | 2 | NC | NC | NC |
| 4358 | 7198 | ATCTCTAGTCTTAATTCTGA | 2 | NC | NC | NC |
| 4359 | 7199 | CATCTCTAGTCTTAATTCTG | 2 | NC | NC | NC |
| 4360 | 7200 | CCATCTCTAGTCTTAATTCT | 2 | NC | NC | NC |
| 4361 | 7201 | ACCATCTCTAGTCTTAATTC | 2 | NC | NC | NC |
| 4362 | 7202 | TACCATCTCTAGTCTTAATT | 2 | NC | NC | NC |
| 4363 | 7203 | TTACCATCTCTAGTCTTAAT | 2 | NC | NC | NC |
| 4364 | 7204 | ATTACCATCTCTAGTCTTAA | 1 | NC | NC | NC |
| 4365 | 7205 | TATTACCATCTCTAGTCTTA | 1 | NC | NC | NC |
| 4366 | 7206 | CTATTACCATCTCTAGTCTT | 1 | NC | NC | NC |
| 4367 | 7207 | CCTATTACCATCTCTAGTCT | 2 | NC | NC | NC |
| 4368 | 7208 | TCCTATTACCATCTCTAGTC | 2 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 4369 | 7209 | CTCCTATTACCATCTCTAGT | 2 | NC | NC | NC |
| 4370 | 7210 | GCTCCTATTACCATCTCTAG | 2 | NC | NC | NC |
| 4371 | 7211 | AGCTCCTATTACCATCTCTA | 2 | NC | NC | NC |
| 4372 | 7212 | TAGCTCCTATTACCATCTCT | 1 | NC | NC | NC |
| 4373 | 7213 | CTAGCTCCTATTACCATCTC | 2 | NC | NC | NC |
| 4374 | 7214 | ACTAGCTCCTATTACCATCT | 2 | NC | NC | NC |
| 4375 | 7215 | TACTAGCTCCTATTACCATC | 2 | NC | NC | NC |
| 4376 | 7216 | ATACTAGCTCCTATTACCAT | 2 | NC | NC | NC |
| 4377 | 7217 | GATACTAGCTCCTATTACCA | 2 | NC | NC | NC |
| 4378 | 7218 | TGATACTAGCTCCTATTACC | 2 | NC | NC | NC |
| 4379 | 7219 | CTGATACTAGCTCCTATTAC | 2 | NC | NC | NC |
| 4380 | 7220 | TCTGATACTAGCTCCTATTA | 2 | NC | NC | NC |
| 4381 | 7221 | TTCTGATACTAGCTCCTATT | 1 | NC | NC | NC |
| 4382 | 7222 | TTTCTGATACTAGCTCCTAT | 2 | NC | NC | NC |
| 4383 | 7223 | TTTTCTGATACTAGCTCCTA | 2 | NC | NC | NC |
| 4384 | 7224 | CTTTTCTGATACTAGCTCCT | 2 | NC | NC | NC |
| 4385 | 7225 | GCTTTTCTGATACTAGCTCC | 2 | NC | NC | NC |
| 4386 | 7226 | AGCTTTTCTGATACTAGCTC | 2 | NC | NC | NC |
| 4387 | 7228 | TAAGCTTTTCTGATACTAGC | 2 | NC | NC | NC |
| 4388 | 7229 | TTAAGCTTTTCTGATACTAG | 1 | NC | NC | NC |
| 4389 | 7230 | CTTAAGCTTTTCTGATACTA | 1 | NC | NC | NC |
| 4390 | 7231 | CCTTAAGCTTTTCTGATACT | 2 | NC | NC | NC |
| 4391 | 7244 | ACTTTATGCTTTGCCTTAAG | 2 | NC | NC | NC |
| 4392 | 7245 | CACTTTATGCTTTGCCTTAA | 1 | NC | NC | NC |
| 4393 | 7246 | ACACTTTATGCTTTGCCTTA | 1 | NC | NC | NC |
| 4394 | 7247 | TACACTTTATGCTTTGCCTT | 2 | NC | NC | NC |
| 4395 | 7248 | CTACACTTTATGCTTTGCCT | 2 | NC | NC | NC |
| 4396 | 7249 | CCTACACTTTATGCTTTGCC | 2 | NC | NC | NC |
| 4397 | 7250 | GCCTACACTTTATGCTTTGC | 2 | NC | NC | NC |
| 4398 | 7251 | AGCCTACACTTTATGCTTTG | 2 | NC | NC | NC |
| 4399 | 7252 | TAGCCTACACTTTATGCTTT | 2 | NC | NC | NC |
| 4400 | 7253 | CTAGCCTACACTTTATGCTT | 3 | NC | NC | NC |
| 4401 | 7254 | TCTAGCCTACACTTTATGCT | 3 | NC | NC | NC |
| 4402 | 7255 | TTCTAGCCTACACTTTATGC | 2 | NC | NC | NC |
| 4403 | 7256 | ATTCTAGCCTACACTTTATG | 2 | NC | NC | NC |
| 4404 | 7257 | CATTCTAGCCTACACTTTAT | 2 | NC | NC | NC |
| 4405 | 7258 | TCATTCTAGCCTACACTTTA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4406 | 7259 | TTCATTCTAGCCTACACTTT | 2 | NC | NC | NC |
| 4407 | 7260 | CTTCATTCTAGCCTACACTT | 2 | NC | NC | NC |
| 4408 | 7261 | GCTTCATTCTAGCCTACACT | 2 | NC | NC | NC |
| 4409 | 7269 | ATTCTCCAGCTTCATTCTAG | 1 | NC | NC | NC |
| 4410 | 7270 | CATTCTCCAGCTTCATTCTA | 1 | NC | NC | NC |
| 4411 | 7271 | CCATTCTCCAGCTTCATTCT | 1 | NC | NC | NC |
| 4412 | 7272 | CCCATTCTCCAGCTTCATTC | 1 | NC | NC | NC |
| 4413 | 7273 | CCCCATTCTCCAGCTTCATT | 1 | NC | NC | NC |
| 4414 | 7274 | TCCCCATTCTCCAGCTTCAT | 1 | NC | NC | NC |
| 4415 | 7275 | CTCCCCATTCTCCAGCTTCA | 1 | NC | NC | NC |
| 4416 | 7296 | TCTGGATGTTACCCAAGCCC | 2 | NC | NC | NC |
| 4417 | 7297 | TTCTGGATGTTACCCAAGCC | 2 | NC | NC | NC |
| 4418 | 7298 | GTTCTGGATGTTACCCAAGC | 2 | NC | NC | NC |
| 4419 | 7299 | GGTTCTGGATGTTACCCAAG | 2 | NC | NC | NC |
| 4420 | 7300 | AGGTTCTGGATGTTACCCAA | 2 | NC | NC | NC |
| 4421 | 7301 | CAGGTTCTGGATGTTACCCA | 2 | NC | NC | NC |
| 4422 | 7322 | ATGTAGTTCCAGGTCCCCAG | 1 | NC | NC | NC |
| 4423 | 7323 | CATGTAGTTCCAGGTCCCCA | 2 | NC | NC | NC |
| 4424 | 7324 | TCATGTAGTTCCAGGTCCCC | 2 | NC | NC | NC |
| 4425 | 7325 | CTCATGTAGTTCCAGGTCCC | 2 | NC | NC | NC |
| 4426 | 7326 | TCTCATGTAGTTCCAGGTCC | 3 | NC | NC | NC |
| 4427 | 7327 | ATCTCATGTAGTTCCAGGTC | 2 | NC | NC | NC |
| 4428 | 7328 | CATCTCATGTAGTTCCAGGT | 2 | NC | NC | NC |
| 4429 | 7339 | CTCCATTCTTACATCTCATG | 2 | NC | NC | NC |
| 4430 | 7340 | TCTCCATTCTTACATCTCAT | 1 | NC | NC | NC |
| 4431 | 7341 | CTCTCCATTCTTACATCTCA | 1 | NC | NC | NC |
| 4432 | 7342 | CCTCTCCATTCTTACATCTC | 1 | NC | NC | NC |
| 4433 | 7343 | ACCTCTCCATTCTTACATCT | 1 | NC | NC | NC |
| 4434 | 7344 | AACCTCTCCATTCTTACATC | 1 | NC | NC | NC |
| 4435 | 7345 | GAACCTCTCCATTCTTACAT | 0 | NC | NC | NC |
| 4436 | 7346 | AGAACCTCTCCATTCTTACA | 0 | NC | NC | NC |
| 4437 | 7347 | TAGAACCTCTCCATTCTTAC | 1 | NC | NC | NC |
| 4438 | 7348 | CTAGAACCTCTCCATTCTTA | 1 | NC | NC | NC |
| 4439 | 7349 | GCTAGAACCTCTCCATTCTT | 1 | NC | NC | NC |
| 4440 | 7351 | CTGCTAGAACCTCTCCATTC | 2 | NC | NC | NC |
| 4441 | 7352 | ACTGCTAGAACCTCTCCATT | 2 | NC | NC | NC |
| 4442 | 7353 | GACTGCTAGAACCTCTCCAT | 3 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4443 | 7354 | TGACTGCTAGAACCTCTCCA | 2 | NC | NC | NC |
| 4444 | 7355 | CTGACTGCTAGAACCTCTCC | 2 | NC | NC | NC |
| 4445 | 7356 | TCTGACTGCTAGAACCTCTC | 2 | NC | NC | NC |
| 4446 | 7357 | CTCTGACTGCTAGAACCTCT | 2 | NC | NC | NC |
| 4447 | 7358 | CCTCTGACTGCTAGAACCTC | 2 | NC | NC | NC |
| 4448 | 7359 | ACCTCTGACTGCTAGAACCT | 2 | NC | NC | NC |
| 4449 | 7360 | GACCTCTGACTGCTAGAACC | 2 | NC | NC | NC |
| 4450 | 7361 | TGACCTCTGACTGCTAGAAC | 2 | NC | NC | NC |
| 4451 | 7362 | CTGACCTCTGACTGCTAGAA | 1 | NC | NC | NC |
| 4452 | 7363 | CCTGACCTCTGACTGCTAGA | 2 | NC | NC | NC |
| 4453 | 7364 | ACCTGACCTCTGACTGCTAG | 1 | NC | NC | NC |
| 4454 | 7365 | TACCTGACCTCTGACTGCTA | 2 | NC | NC | NC |
| 4455 | 7366 | GTACCTGACCTCTGACTGCT | 2 | NC | NC | NC |
| 4456 | 7367 | TGTACCTGACCTCTGACTGC | 2 | NC | NC | NC |
| 4457 | 7368 | TTGTACCTGACCTCTGACTG | 3 | NC | NC | NC |
| 4458 | 7369 | TTTGTACCTGACCTCTGACT | 2 | NC | NC | NC |
| 4459 | 7370 | ATTTGTACCTGACCTCTGAC | 2 | NC | NC | NC |
| 4460 | 7371 | CATTTGTACCTGACCTCTGA | 2 | NC | NC | NC |
| 4461 | 7372 | TCATTTGTACCTGACCTCTG | 1 | NC | NC | NC |
| 4462 | 7373 | TTCATTTGTACCTGACCTCT | 2 | NC | NC | NC |
| 4463 | 7374 | GTTCATTTGTACCTGACCTC | 2 | NC | NC | NC |
| 4464 | 7375 | TGTTCATTTGTACCTGACCT | 2 | NC | NC | NC |
| 4465 | 7376 | CTGTTCATTTGTACCTGACC | 2 | NC | NC | NC |
| 4466 | 7377 | GCTGTTCATTTGTACCTGAC | 2 | NC | NC | NC |
| 4467 | 7378 | AGCTGTTCATTTGTACCTGA | 2 | NC | NC | NC |
| 4468 | 7379 | CAGCTGTTCATTTGTACCTG | 2 | NC | NC | NC |
| 4469 | 7380 | CCAGCTGTTCATTTGTACCT | 1 | NC | NC | NC |
| 4470 | 7381 | CCCAGCTGTTCATTTGTACC | 1 | NC | NC | NC |
| 4471 | 7382 | TCCCAGCTGTTCATTTGTAC | 1 | NC | NC | NC |
| 4472 | 7383 | ATCCCAGCTGTTCATTTGTA | 1 | NC | NC | NC |
| 4473 | 7384 | GATCCCAGCTGTTCATTTGT | 2 | NC | NC | NC |
| 4474 | 7385 | AGATCCCAGCTGTTCATTTG | 2 | NC | NC | NC |
| 4475 | 7386 | CAGATCCCAGCTGTTCATTT | 2 | NC | NC | NC |
| 4476 | 7387 | GCAGATCCCAGCTGTTCATT | 2 | NC | NC | NC |
| 4477 | 7388 | CGCAGATCCCAGCTGTTCAT | 2 | NC | NC | NC |
| 4478 | 7391 | ATGCGCAGATCCCAGCTGTT | 2 | NC | NC | NC |
| 4479 | 7406 | TTTTCACTGTCTGCCATGCG | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4480 | 7407 | TTTTTCACTGTCTGCCATGC | 1 | NC | NC | NC |
| 4481 | 7423 | TTTTGCTTGCCTGGGTTTTT | 1 | NC | NC | NC |
| 4482 | 7424 | ATTTTGCTTGCCTGGGTTTT | 1 | NC | NC | NC |
| 4483 | 7425 | CATTTTGCTTGCCTGGGTTT | 2 | NC | NC | NC |
| 4484 | 7426 | CCATTTTGCTTGCCTGGGTT | 2 | NC | NC | NC |
| 4485 | 7427 | ACCATTTTGCTTGCCTGGGT | 2 | NC | NC | NC |
| 4486 | 7428 | GACCATTTTGCTTGCCTGGG | 2 | NC | NC | NC |
| 4487 | 7429 | TGACCATTTTGCTTGCCTGG | 1 | NC | NC | NC |
| 4488 | 7430 | CTGACCATTTTGCTTGCCTG | 2 | NC | NC | NC |
| 4489 | 7431 | TCTGACCATTTTGCTTGCCT | 1 | NC | NC | NC |
| 4490 | 7432 | CTCTGACCATTTTGCTTGCC | 1 | NC | NC | NC |
| 4491 | 7433 | GCTCTGACCATTTTGCTTGC | 2 | NC | NC | NC |
| 4492 | 7434 | TGCTCTGACCATTTTGCTTG | 2 | NC | NC | NC |
| 4493 | 7435 | CTGCTCTGACCATTTTGCTT | 2 | NC | NC | NC |
| 4494 | 7436 | TCTGCTCTGACCATTTTGCT | 2 | NC | NC | NC |
| 4495 | 7437 | TTCTGCTCTGACCATTTTGC | 2 | NC | NC | NC |
| 4496 | 7438 | TTTCTGCTCTGACCATTTTG | 2 | NC | NC | NC |
| 4497 | 7439 | CTTTCTGCTCTGACCATTTT | 2 | NC | NC | NC |
| 4498 | 7440 | CCTTTCTGCTCTGACCATTT | 2 | NC | NC | NC |
| 4499 | 7441 | CCCTTTCTGCTCTGACCATT | 2 | NC | NC | NC |
| 4500 | 7442 | CCCCTTTCTGCTCTGACCAT | 2 | NC | NC | NC |
| 4501 | 7465 | CATCTCAAGAACGTGGCCTT | 1 | NC | NC | NC |
| 4502 | 7466 | ACATCTCAAGAACGTGGCCT | 2 | NC | NC | NC |
| 4503 | 7467 | CACATCTCAAGAACGTGGCC | 3 | NC | NC | NC |
| 4504 | 7470 | CTCCACATCTCAAGAACGTG | 2 | NC | NC | NC |
| 4505 | 7471 | CCTCCACATCTCAAGAACGT | 2 | NC | NC | NC |
| 4506 | 7472 | CCCTCCACATCTCAAGAACG | 1 | NC | NC | NC |
| 4507 | 7473 | CCCCTCCACATCTCAAGAAC | 2 | NC | NC | NC |
| 4508 | 7474 | CCCCCTCCACATCTCAAGAA | 1 | NC | NC | NC |
| 4509 | 7495 | TACTTGGCGTGGCTTCCTCA | 2 | NC | NC | NC |
| 4510 | 7496 | TTACTTGGCGTGGCTTCCTC | 2 | NC | NC | NC |
| 4511 | 7497 | CTTACTTGGCGTGGCTTCCT | 2 | NC | NC | NC |
| 4512 | 7499 | TCCTTACTTGGCGTGGCTTC | 3 | NC | NC | NC |
| 4513 | 7500 | GTCCTTACTTGGCGTGGCTT | 3 | NC | NC | NC |
| 4514 | 7501 | TGTCCTTACTTGGCGTGGCT | 2 | NC | NC | NC |
| 4515 | 7503 | TCTGTCCTTACTTGGCGTGG | 2 | NC | NC | NC |
| 4516 | 7504 | ATCTGTCCTTACTTGGCGTG | 3 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4517 | 7505 | CATCTGTCCTTACTTGGCGT | 3 | NC | NC | NC |
| 4518 | 7506 | GCATCTGTCCTTACTTGGCG | 2 | NC | NC | NC |
| 4519 | 7507 | TGCATCTGTCCTTACTTGGC | 2 | NC | NC | NC |
| 4520 | 7508 | CTGCATCTGTCCTTACTTGG | 2 | NC | NC | NC |
| 4521 | 7509 | GCTGCATCTGTCCTTACTTG | 2 | NC | NC | NC |
| 4522 | 7510 | AGCTGCATCTGTCCTTACTT | 2 | NC | NC | NC |
| 4523 | 7511 | GAGCTGCATCTGTCCTTACT | 1 | NC | NC | NC |
| 4524 | 7512 | TGAGCTGCATCTGTCCTTAC | 2 | NC | NC | NC |
| 4525 | 7513 | CTGAGCTGCATCTGTCCTTA | 2 | NC | NC | NC |
| 4526 | 7514 | GCTGAGCTGCATCTGTCCTT | 2 | NC | NC | NC |
| 4527 | 7515 | TGCTGAGCTGCATCTGTCCT | 1 | NC | NC | NC |
| 4528 | 7536 | TTGTCAGGGCTCGCTAGGAA | 3 | NC | NC | NC |
| 4529 | 7586 | ACTCCACTGTGCCATGACTG | 2 | NC | NC | NC |
| 4530 | 7587 | CACTCCACTGTGCCATGACT | 2 | NC | NC | NC |
| 4531 | 7588 | TCACTCCACTGTGCCATGAC | 2 | NC | NC | NC |
| 4532 | 7589 | TTCACTCCACTGTGCCATGA | 2 | NC | NC | NC |
| 4533 | 7590 | CTTCACTCCACTGTGCCATG | 2 | NC | NC | NC |
| 4534 | 7591 | CCTTCACTCCACTGTGCCAT | 1 | NC | NC | NC |
| 4535 | 7592 | TCCTTCACTCCACTGTGCCA | 1 | NC | NC | NC |
| 4536 | 7593 | TTCCTTCACTCCACTGTGCC | 1 | NC | NC | NC |
| 4537 | 7594 | CTTCCTTCACTCCACTGTGC | 2 | NC | NC | NC |
| 4538 | 7596 | CTCTTCCTTCACTCCACTGT | 1 | NC | NC | NC |
| 4539 | 7597 | GCTCTTCCTTCACTCCACTG | 2 | NC | NC | NC |
| 4540 | 7598 | TGCTCTTCCTTCACTCCACT | 1 | NC | NC | NC |
| 4541 | 7599 | CTGCTCTTCCTTCACTCCAC | 1 | NC | NC | NC |
| 4542 | 7600 | ACTGCTCTTCCTTCACTCCA | 1 | NC | NC | NC |
| 4543 | 7601 | AACTGCTCTTCCTTCACTCC | 2 | NC | NC | NC |
| 4544 | 7602 | AAACTGCTCTTCCTTCACTC | 1 | NC | NC | NC |
| 4545 | 7603 | GAAACTGCTCTTCCTTCACT | 2 | NC | NC | NC |
| 4546 | 7604 | TGAAACTGCTCTTCCTTCAC | 2 | NC | NC | NC |
| 4547 | 7605 | CTGAAACTGCTCTTCCTTCA | 1 | NC | NC | NC |
| 4548 | 7606 | CCTGAAACTGCTCTTCCTTC | 1 | NC | NC | NC |
| 4549 | 7607 | GCCTGAAACTGCTCTTCCTT | 0 | NC | NC | NC |
| 4550 | 7608 | TGCCTGAAACTGCTCTTCCT | 0 | NC | NC | NC |
| 4551 | 7609 | GTGCCTGAAACTGCTCTTCC | 0 | NC | NC | NC |
| 4552 | 7610 | GGTGCCTGAAACTGCTCTTC | 1 | NC | NC | NC |
| 4553 | 7611 | GGGTGCCTGAAACTGCTCTT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4554 | 7612 | TGGGTGCCTGAAACTGCTCT | 2 | NC | NC | NC |
| 4555 | 7613 | TTGGGTGCCTGAAACTGCTC | 2 | NC | NC | NC |
| 4556 | 7614 | TTTGGGTGCCTGAAACTGCT | 2 | NC | NC | NC |
| 4557 | 7615 | TTTTGGGTGCCTGAAACTGC | 2 | NC | NC | NC |
| 4558 | 7616 | GTTTTGGGTGCCTGAAACTG | 2 | NC | NC | NC |
| 4559 | 7617 | GGTTTTGGGTGCCTGAAACT | 2 | NC | NC | NC |
| 4560 | 7618 | AGGTTTTGGGTGCCTGAAAC | 2 | NC | NC | NC |
| 4561 | 7643 | AGGTGGAAAACAGGTCGTGG | 2 | NC | NC | NC |
| 4562 | 7644 | CAGGTGGAAAACAGGTCGTG | 2 | NC | NC | NC |
| 4563 | 7645 | TCAGGTGGAAAACAGGTCGT | 2 | NC | NC | NC |
| 4564 | 7646 | TTCAGGTGGAAAACAGGTCG | 2 | NC | NC | NC |
| 4565 | 7647 | CTTCAGGTGGAAAACAGGTC | 2 | NC | NC | NC |
| 4566 | 7648 | TCTTCAGGTGGAAAACAGGT | 2 | NC | NC | NC |
| 4567 | 7649 | CTCTTCAGGTGGAAAACAGG | 2 | NC | NC | NC |
| 4568 | 7650 | GCTCTTCAGGTGGAAAACAG | 2 | NC | NC | NC |
| 4569 | 7651 | GGCTCTTCAGGTGGAAAACA | 2 | NC | NC | NC |
| 4570 | 7652 | TGGCTCTTCAGGTGGAAAAC | 2 | NC | NC | NC |
| 4571 | 7653 | GTGGCTCTTCAGGTGGAAAA | 2 | NC | NC | NC |
| 4572 | 7654 | GGTGGCTCTTCAGGTGGAAA | 2 | NC | NC | NC |
| 4573 | 7658 | AATGGGTGGCTCTTCAGGTG | 2 | NC | NC | NC |
| 4574 | 7659 | GAATGGGTGGCTCTTCAGGT | 2 | NC | NC | NC |
| 4575 | 7661 | TGGAATGGGTGGCTCTTCAG | 2 | NC | NC | NC |
| 4576 | 7662 | ATGGAATGGGTGGCTCTTCA | 2 | NC | NC | NC |
| 4577 | 7663 | GATGGAATGGGTGGCTCTTC | 2 | NC | NC | NC |
| 4578 | 7664 | GGATGGAATGGGTGGCTCTT | 2 | NC | NC | NC |
| 4579 | 7665 | TGGATGGAATGGGTGGCTCT | 2 | NC | NC | NC |
| 4580 | 7666 | TTGGATGGAATGGGTGGCTC | 2 | NC | NC | NC |
| 4581 | 7667 | TTTGGATGGAATGGGTGGCT | 1 | NC | NC | NC |
| 4582 | 7668 | GTTTGGATGGAATGGGTGGC | 1 | NC | NC | NC |
| 4583 | 7669 | GGTTTGGATGGAATGGGTGG | 2 | NC | NC | NC |
| 4584 | 7670 | GGGTTTGGATGGAATGGGTG | 2 | NC | NC | NC |
| 4585 | 7671 | AGGGTTTGGATGGAATGGGT | 2 | NC | NC | NC |
| 4586 | 7672 | AAGGGTTTGGATGGAATGGG | 2 | NC | NC | NC |
| 4587 | 7673 | CAAGGGTTTGGATGGAATGG | 2 | NC | NC | NC |
| 4588 | 7683 | AGACTTTTGCCAAGGGTTTG | 2 | NC | NC | NC |
| 4589 | 7684 | CAGACTTTTGCCAAGGGTTT | 2 | NC | NC | NC |
| 4590 | 7685 | GCAGACTTTTGCCAAGGGTT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4591 | 7702 | GCCGGTTCTCTCTGTTAGCA | 2 | NC | NC | NC |
| 4592 | 7704 | TGGCCGGTTCTCTCTGTTAG | 2 | NC | NC | NC |
| 4593 | 7705 | CTGGCCGGTTCTCTCTGTTA | 2 | NC | NC | NC |
| 4594 | 7706 | ACTGGCCGGTTCTCTCTGTT | 1 | NC | NC | NC |
| 4595 | 7707 | TACTGGCCGGTTCTCTCTGT | 2 | NC | NC | NC |
| 4596 | 7708 | ATACTGGCCGGTTCTCTCTG | 1 | NC | NC | NC |
| 4597 | 7709 | CATACTGGCCGGTTCTCTCT | 1 | NC | NC | NC |
| 4598 | 7711 | AGCATACTGGCCGGTTCTCT | 2 | NC | NC | NC |
| 4599 | 7735 | AGACAGGCATGATCGCGACT | 3 | NC | NC | NC |
| 4600 | 7736 | AAGACAGGCATGATCGCGAC | 3 | NC | NC | NC |
| 4601 | 7737 | AAAGACAGGCATGATCGCGA | 2 | NC | NC | NC |
| 4602 | 7738 | TAAAGACAGGCATGATCGCG | 2 | NC | NC | NC |
| 4603 | 7739 | GTAAAGACAGGCATGATCGC | 2 | NC | NC | NC |
| 4604 | 7740 | GGTAAAGACAGGCATGATCG | 2 | NC | NC | NC |
| 4605 | 7741 | GGGTAAAGACAGGCATGATC | 2 | NC | NC | NC |
| 4606 | 7742 | AGGGTAAAGACAGGCATGAT | 2 | NC | NC | NC |
| 4607 | 7743 | GAGGGTAAAGACAGGCATGA | 1 | NC | NC | NC |
| 4608 | 7744 | AGAGGGTAAAGACAGGCATG | 1 | NC | NC | NC |
| 4609 | 7745 | TAGAGGGTAAAGACAGGCAT | 1 | NC | NC | NC |
| 4610 | 7746 | TTAGAGGGTAAAGACAGGCA | 1 | NC | NC | NC |
| 4611 | 7747 | CTTAGAGGGTAAAGACAGGC | 2 | NC | NC | NC |
| 4612 | 7748 | GCTTAGAGGGTAAAGACAGG | 2 | NC | NC | NC |
| 4613 | 7749 | AGCTTAGAGGGTAAAGACAG | 2 | NC | NC | NC |
| 4614 | 7750 | CAGCTTAGAGGGTAAAGACA | 2 | NC | NC | NC |
| 4615 | 7751 | TCAGCTTAGAGGGTAAAGAC | 2 | NC | NC | NC |
| 4616 | 7752 | TTCAGCTTAGAGGGTAAAGA | 2 | NC | NC | NC |
| 4617 | 7753 | CTTCAGCTTAGAGGGTAAAG | 1 | NC | NC | NC |
| 4618 | 7767 | CCGTTGATGAGCAGCTTCAG | 2 | NC | NC | NC |
| 4619 | 7768 | ACCGTTGATGAGCAGCTTCA | 2 | NC | NC | NC |
| 4620 | 7769 | CACCGTTGATGAGCAGCTTC | 2 | NC | NC | NC |
| 4621 | 7770 | TCACCGTTGATGAGCAGCTT | 2 | NC | NC | NC |
| 4622 | 7771 | CTCACCGTTGATGAGCAGCT | 2 | NC | NC | NC |
| 4623 | 7779 | TTTGCCATCTCACCGTTGAT | 2 | NC | NC | NC |
| 4624 | 7780 | TTTTGCCATCTCACCGTTGA | 3 | NC | NC | NC |
| 4625 | 7781 | TTTTTGCCATCTCACCGTTG | 3 | NC | NC | NC |
| 4626 | 7782 | CTTTTTGCCATCTCACCGTT | 2 | NC | NC | NC |
| 4627 | 7783 | CCTTTTTGCCATCTCACCGT | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4628 | 7784 | ACCTTTTTGCCATCTCACCG | 2 | NC | NC | NC |
| 4629 | 7785 | CACCTTTTTGCCATCTCACC | 1 | NC | NC | NC |
| 4630 | 7786 | CCACCTTTTTGCCATCTCAC | 2 | NC | NC | NC |
| 4631 | 7787 | CCCACCTTTTTGCCATCTCA | 2 | NC | NC | NC |
| 4632 | 7788 | ACCCACCTTTTTGCCATCTC | 2 | NC | NC | NC |
| 4633 | 7789 | GACCCACCTTTTTGCCATCT | 2 | NC | NC | NC |
| 4634 | 7790 | GGACCCACCTTTTTGCCATC | 3 | NC | NC | NC |
| 4635 | 7803 | TTTCCCCTCTTCTGGACCCA | 1 | NC | NC | NC |
| 4636 | 7804 | TTTTCCCCTCTTCTGGACCC | 1 | NC | NC | NC |
| 4637 | 7805 | CTTTTCCCCTCTTCTGGACC | 1 | NC | NC | NC |
| 4638 | 7806 | TCTTTTCCCCTCTTCTGGAC | 1 | NC | NC | NC |
| 4639 | 7807 | TTCTTTTCCCCTCTTCTGGA | 1 | NC | NC | NC |
| 4640 | 7808 | CTTCTTTTCCCCTCTTCTGG | 1 | NC | NC | NC |
| 4641 | 7809 | CCTTCTTTTCCCCTCTTCTG | 1 | NC | NC | NC |
| 4642 | 7810 | CCCTTCTTTTCCCCTCTTCT | 1 | NC | NC | NC |
| 4643 | 7811 | TCCCTTCTTTTCCCCTCTTC | 1 | NC | NC | NC |
| 4644 | 7812 | CTCCCTTCTTTTCCCCTCTT | 1 | NC | NC | NC |
| 4645 | 7813 | ACTCCCTTCTTTTCCCCTCT | 1 | NC | NC | NC |
| 4646 | 7814 | GACTCCCTTCTTTTCCCCTC | 1 | NC | NC | NC |
| 4647 | 7815 | AGACTCCCTTCTTTTCCCCT | 1 | NC | NC | NC |
| 4648 | 7816 | CAGACTCCCTTCTTTTCCCC | 1 | NC | NC | NC |
| 4649 | 7817 | ACAGACTCCCTTCTTTTCCC | 2 | NC | NC | NC |
| 4650 | 7818 | CACAGACTCCCTTCTTTTCC | 2 | NC | NC | NC |
| 4651 | 7819 | TCACAGACTCCCTTCTTTTC | 2 | NC | NC | NC |
| 4652 | 7820 | TTCACAGACTCCCTTCTTTT | 2 | NC | NC | NC |
| 4653 | 7821 | TTTCACAGACTCCCTTCTTT | 2 | NC | NC | NC |
| 4654 | 7822 | TTTTCACAGACTCCCTTCTT | 2 | NC | NC | NC |
| 4655 | 7823 | GTTTTCACAGACTCCCTTCT | 2 | NC | NC | NC |
| 4656 | 7824 | TGTTTTCACAGACTCCCTTC | 2 | NC | NC | NC |
| 4657 | 7825 | TTGTTTTCACAGACTCCCTT | 1 | NC | NC | NC |
| 4658 | 7826 | TTTGTTTTCACAGACTCCCT | 2 | NC | NC | NC |
| 4659 | 7827 | TTTTGTTTTCACAGACTCCC | 1 | NC | NC | NC |
| 4660 | 7828 | ATTTTGTTTTCACAGACTCC | 1 | NC | NC | NC |
| 4661 | 7829 | CATTTTGTTTTCACAGACTC | 1 | NC | NC | NC |
| 4662 | 7830 | GCATTTTGTTTTCACAGACT | 2 | NC | NC | NC |
| 4663 | 7831 | AGCATTTTGTTTTCACAGAC | 2 | NC | NC | NC |
| 4664 | 7832 | CAGCATTTTGTTTTCACAGA | 2 | NC | NC | NC |

TABLE 2-continued

Exemplary Oligonucleotides

| SEQ ID NO | Position | Sequence | Off-target Score Human | Cyno | Mouse | Rat |
|---|---|---|---|---|---|---|
| 4665 | 7833 | TCAGCATTTTGTTTTCACAG | 2 | NC | NC | NC |
| 4666 | 7834 | TTCAGCATTTTGTTTTCACA | 1 | NC | NC | NC |
| 4667 | 7835 | CTTCAGCATTTTGTTTTCAC | 1 | NC | NC | NC |
| 4668 | 7836 | TCTTCAGCATTTTGTTTTCA | 1 | NC | NC | NC |
| 4669 | 7837 | TTCTTCAGCATTTTGTTTTC | 1 | NC | NC | NC |
| 4670 | 7838 | ATTCTTCAGCATTTTGTTTT | 1 | NC | NC | NC |
| 4671 | 7839 | GATTCTTCAGCATTTTGTTT | 1 | NC | NC | NC |
| 4672 | 7840 | AGATTCTTCAGCATTTTGTT | 1 | NC | NC | NC |
| 4673 | 7841 | CAGATTCTTCAGCATTTTGT | 1 | NC | NC | NC |
| 4674 | 7842 | GCAGATTCTTCAGCATTTTG | 2 | NC | NC | NC |
| 4675 | 7843 | TGCAGATTCTTCAGCATTTT | 1 | NC | NC | NC |
| 4676 | 7848 | TTTGATGCAGATTCTTCAGC | 2 | NC | NC | NC |
| 4677 | 7849 | ATTTGATGCAGATTCTTCAG | 2 | NC | NC | NC |
| 4678 | 7850 | TATTTGATGCAGATTCTTCA | 1 | NC | NC | NC |
| 4679 | 7851 | TTATTTGATGCAGATTCTTC | 1 | NC | NC | NC |
| 4680 | 7852 | TTTATTTGATGCAGATTCTT | 1 | NC | NC | NC |
| 4681 | 7853 | GTTTATTTGATGCAGATTCT | 2 | NC | NC | NC |
| 4682 | 7854 | GGTTTATTTGATGCAGATTC | 2 | NC | NC | NC |
| 4683 | 7855 | GGGTTTATTTGATGCAGATT | 2 | NC | NC | NC |
| 4684 | 7856 | AGGGTTTATTTGATGCAGAT | 2 | NC | NC | NC |
| 4685 | 7857 | AAGGGTTTATTTGATGCAGA | 1 | NC | NC | NC |
| 4686 | 7858 | GAAGGGTTTATTTGATGCAG | 2 | NC | NC | NC |
| 4687 | 7859 | GGAAGGGTTTATTTGATGCA | 2 | NC | NC | NC |
| 4688 | 7860 | AGGAAGGGTTTATTTGATGC | 2 | NC | NC | NC |
| 4689 | 7861 | AAGGAAGGGTTTATTTGATG | 2 | NC | NC | NC |
| 4690 | 7862 | GAAGGAAGGGTTTATTTGAT | 2 | NC | NC | NC |
| 4691 | 7863 | GGAAGGAAGGGTTTATTTGA | 2 | NC | NC | NC |
| 4692 | 7864 | AGGAAGGAAGGGTTTATTTG | 2 | NC | NC | NC |
| 4693 | 7865 | AAGGAAGGAAGGGTTTATTT | 1 | NC | NC | NC |
| 4694 | 7866 | GAAGGAAGGAAGGGTTTATT | 1 | NC | NC | NC |
| 4695 | 7867 | GGAAGGAAGGAAGGGTTTAT | 1 | NC | NC | NC |
| 4696 | 7868 | AGGAAGGAAGGAAGGGTTTA | 0 | NC | NC | NC |
| 4697 | 7869 | AAGGAAGGAAGGAAGGGTTT | 0 | NC | NC | NC |
| 4698 | 7870 | AAAGGAAGGAAGGAAGGGTT | 1 | NC | NC | NC |
| 4699 | 7871 | AAAAGGAAGGAAGGAAGGGT | 0 | NC | NC | NC |
| 4700 | 7872 | AAAAAGGAAGGAAGGAAGGG | 0 | NC | NC | NC |
| 4701 | 7873 | GAAAAAGGAAGGAAGGAAGG | 0 | NC | NC | NC |

TABLE 2-continued

| Exemplary Oligonucleotides | | | | | | |
|---|---|---|---|---|---|---|
| SEQ | | | Off-target Score | | | |
| ID NO | Position | Sequence | Human | Cyno | Mouse | Rat |
| 4702 | 7874 | GGAAAAAGGAAGGAAGGAAG | 0 | NC | NC | NC |
| 4703 | 7875 | AGGAAAAAGGAAGGAAGGAA | 0 | NC | NC | NC |
| 4704 | 7876 | AAGGAAAAAGGAAGGAAGGA | 0 | NC | NC | NC |
| 4705 | 7877 | GAAGGAAAAAGGAAGGAAGG | 0 | NC | NC | NC |
| 4706 | 7878 | TGAAGGAAAAAGGAAGGAAG | 1 | NC | NC | NC |
| 4707 | 7879 | TTGAAGGAAAAAGGAAGGAA | 1 | NC | NC | NC |
| 4708 | 7880 | TTTGAAGGAAAAAGGAAGGA | 1 | NC | NC | NC |
| 4709 | 7881 | TTTTGAAGGAAAAAGGAAGG | 1 | NC | NC | NC |
| 4710 | 7882 | TTTTTGAAGGAAAAAGGAAG | 1 | NC | NC | NC |

Example 2. Antisense Inhibition of MLH3

Inhibition or knockdown of MLH3 can be demonstrated using a cell-based assay. For example. HEK293. NIH3T3, or Hela or another available mammalian cell line with oligonucleotides targeting MLH3 identified above in Example 1 using at least five different dose levels, using transfection reagents such as LIPOFECTAMINE™ 2000 (Invitrogen) following the manufacturer's instructions. Cells are harvested at multiple time points up to 7 days post transfection for either mRNA or protein analyses. Knockdown of mRNA and protein are determined by RT-gPCR or western blot analyses respectively, using standard molecular biology techniques as previously described (see, for example, as described in Drouet et al., 2014, PLOS One 9(6): e99341). The relative levels of the MLH3 mRNA and protein at the different oligonucleotide levels are compared with a mock oligonucleotide control. The most potent oligonucleotides (for example, those which are capable of at least 90%, at least 95%, at least 97%, at least 98%, or at least 99% or more, reduction in protein levels when compared with controls) are selected for subsequent studies, for example, as described in the examples below.

Human cell lines

HeLa cells were obtained from ATCC (ATCC in partnership with LGC Standards, Wesel, Germany, cat. #ATCC-CRM-CCL-2) and cultured in HAM's F12 (#FG0815, Biochrom, Berlin, Germany), supplemented to contain 10% fetal calf serum (1248D, Biochrom GmbH, Berlin, Germany), and 100 U/ml Penicillin/100 μg/ml Streptomycin (A2213, Biochrom GmbH, Berlin, Germany) at 37° C. in an atmosphere with 5% $CO_2$ in a humidified incubator. For transfection of HeLa cells with ASOs, cells were seeded at a density of 15,000 cells/well into 96-well tissue culture plates (#655180, GBO, Germany).

Transfections

In HeLa cells, transfection of ASOs was carried out with LIPOFECTAMINE™ 2000 (Invitrogen/Life Technologies, Karlsruhe, Germany) according to manufacturer's instructions for reverse transfection with 0.25 μL LIPOFECTAMINE$^{T}$" 2000 per well.

The dual dose screen was performed with ASOs in quadruplicates at 20 nM and 2 nM respectively, with two ASOs targeting AHSA1 (one MOE-ASO and one 2'oMe-ASO) as unspecific controls and a mock transfection Dose-response experiments were done with ASOs in 5 concentrations transfected in quadruplicates, starting at 20 nM in 5-6-fold dilutions steps down to ~15-32 pM. Mock transfected cells served as control in dose-response curve (DRC) experiments.

Analysis and Quantitation

After 24 h of incubation with ASOs, medium was removed and cells were lysed in 150 μl Medium-Lysis Mixture (1 volume lysis mixture, 2 volumes cell culture medium) and then incubated at 53° C. for 30 minutes, bDNA assay was performed according to manufacturer's instructions. Luminescence was read using 1420 Luminescence Counter (WALLAC VICTOR Light, Perkin Elmer, Rodgau-Jügesheim, Germany) following 30 minutes incubation at RT in the dark.

The two Ahsa1-ASOs (one 2'-OMe and one MOE-modified) served at the same time as unspecific controls for respective target mRNA expression and as a positive control to analyze transfection efficiency with regards to Ahsa1 mRNA level. By hybridization with an Ahsa1 probeset, the mock transfected wells served as controls for Ahsa1 mRNA level. Transfection efficiency for each 96-well plate and both doses in the dual dose screen were calculated by relating Ahsa1-level with Ahsa1-ASO (normalized to GapDH) to Ahsa1-level obtained with mock controls.

For each well, the target mRNA level was normalized to the respective GAPDH mRNA level. The activity of a given ASO was expressed as percent mRNA concentration of the respective target (normalized to GAPDH mRNA) in treated cells, relative to the target mRNA concentration (normalized to GAPDH mRNA) averaged across control wells.

The results of the dual-dose screen of ~480 ASOs targeting MLH3, as well as $IC_{20}$, $IC_{50}$ and $IC_{80}$ values of approximately 48 positive ASOs from the dual dose screen, are shown in Table 3.

TABLE 3

| Positive ASOs | | | | | | | | | | | | | |
|---|---|---|---|---|---|---|---|---|---|---|---|---|---|
| SEQ ID NO | Position | Sequence | Off-target Score | | | | mean % mRNA remaining | | SD % mRNA remaining | | IC20 (nM) | IC50 (nM) | IC80 (nM) |
| | | | Human | Cyno | Mouse | Rat | 2 nM | 20 nM | 2 nM | 20 nM | | | |
| 89 | 224 | TACTTCAACTGACAAGCACT | 2 | 2 | NC | NC | 74.75 | 16.41 | 5.11 | 1.90 | NA | NA | NA |
| 90 | 225 | GTACTTCAACTGACAAGCAC | 2 | 2 | NC | NC | 77.73 | 52.54 | 2.17 | 2.02 | NA | NA | NA |
| 92 | 227 | TTGTACTTCAACTGACAAGC | 2 | 2 | NC | NC | 75.57 | 30.32 | 5.23 | 1.51 | NA | NA | NA |
| 101 | 237 | GCAATTTGGCTTGTACTTCA | 2 | 2 | NC | NC | 77.37 | 64.88 | 5.04 | 9.95 | NA | NA | NA |
| 102 | 238 | CGCAATTTGGCTTGTACTTC | 2 | 3 | NC | NC | 71.59 | 15.63 | 3.42 | 1.01 | NA | NA | NA |
| 103 | 239 | ACGCAATTTGGCTTGTACTT | 2 | 3 | NC | NC | 72.11 | 60.32 | 3.42 | 7.53 | NA | NA | NA |
| 106 | 242 | AGAACGCAATTTGGCTTGTA | 2 | 2 | NC | NC | 71.44 | 71.53 | 4.33 | 37.95 | NA | NA | NA |
| 107 | 243 | CAGAACGCAATTTGGCTTGT | 3 | 2 | NC | NC | 66.80 | 36.49 | 5.84 | 5.28 | NA | NA | NA |
| 108 | 244 | CCAGAACGCAATTTGGCTTG | 3 | 3 | NC | NC | 62.90 | 37.68 | 3.87 | 4.83 | NA | NA | NA |
| 109 | 245 | ACCAGAACGCAATTTGGCTT | 3 | 2 | NC | NC | 66.82 | 98.40 | 2.36 | 16.21 | NA | NA | NA |
| 110 | 246 | AACCAGAACGCAATTTGGCT | 2 | 2 | NC | NC | 60.40 | 44.74 | 15.63 | 2.25 | NA | NA | NA |
| 111 | 247 | AAACCAGAACGCAATTTGGC | 2 | 2 | NC | NC | 70.74 | 28.71 | 1.63 | 2.76 | NA | NA | NA |
| 115 | 270 | ATTGGCCCAAGGAGCTTATG | 2 | 2 | NC | NC | 78.95 | 45.99 | 2.10 | 2.57 | NA | NA | NA |
| 116 | 271 | CATTGGCCCAAGGAGCTTAT | 2 | 3 | NC | NC | 76.12 | 28.26 | 10.83 | 1.81 | NA | NA | NA |
| 117 | 272 | ACATTGGCCCAAGGAGCTTA | 2 | 3 | NC | NC | 75.06 | 53.28 | 2.48 | 2.00 | NA | NA | NA |
| 133 | 288 | GGGCAAGTTCCTCAACACAT | 2 | 2 | NC | NC | 69.85 | 94.09 | 0.43 | 11.41 | NA | NA | NA |
| 134 | 289 | AGGGCAAGTTCCTCAACACA | 2 | 2 | NC | NC | 74.03 | 69.07 | 3.53 | 5.32 | NA | NA | NA |
| 135 | 296 | ACTGTTGAGGGCAAGTTCCT | 2 | 2 | NC | NC | 79.51 | 65.67 | 4.25 | 5.62 | NA | NA | NA |
| 150 | 324 | CAGCCACACATTTTGCTTCA | 2 | 2 | NC | NC | 66.83 | 25.32 | 2.76 | 2.23 | NA | NA | NA |
| 151 | 325 | ACAGCCACACATTTTGCTTC | 2 | 2 | NC | NC | 69.96 | 72.78 | 4.30 | 4.32 | NA | NA | NA |
| 152 | 326 | GACAGCCACACATTTTGCTT | 2 | 2 | NC | NC | 80.79 | 113.47 | 16.94 | 5.71 | NA | NA | NA |
| 154 | 328 | CTGACAGCCACACATTTTGC | 2 | 2 | NC | NC | 79.02 | 26.85 | 2.20 | 3.00 | NA | NA | NA |
| 160 | 334 | TTCACCCTGACAGCCACACA | 2 | 1 | NC | NC | 92.28 | 10.93 | 2.00 | 2.21 | NA | NA | NA |
| 161 | 335 | ATTCACCCTGACAGCCACAC | 2 | 2 | NC | NC | 83.55 | 10.33 | 5.21 | 1.56 | NA | NA | NA |
| 163 | 337 | ATATTCACCCTGACAGCCAC | 2 | 2 | NC | NC | 87.05 | 9.72 | 2.44 | 0.70 | NA | NA | NA |
| 164 | 338 | CATATTCACCCTGACAGCCA | 2 | 2 | NC | NC | 81.52 | 8.96 | 1.50 | 1.61 | 0.31 | 1.06 | 4.15 |
| 166 | 340 | TCCATATTCACCCTGACAGC | 2 | 2 | NC | NC | 87.79 | 9.93 | 13.96 | 0.77 | NA | NA | NA |
| 168 | 342 | TTTCCATATTCACCCTGACA | 2 | 2 | NC | NC | 77.41 | 15.50 | 4.02 | 2.31 | NA | NA | NA |
| 170 | 344 | GGTTTCCATATTCACCCTGA | 2 | 2 | NC | NC | 65.76 | 79.24 | 1.84 | 6.95 | NA | NA | NA |
| 174 | 358 | ACTTGAACTTGGAAGGTTTC | 2 | 2 | 2 | 2 | 82.04 | 114.15 | 4.85 | 4.63 | NA | NA | NA |
| 175 | 359 | CACTTGAACTTGGAAGGTTT | 2 | 2 | 2 | 1 | 83.32 | 25.76 | 16.25 | 2.93 | NA | NA | NA |
| 176 | 360 | TCACTTGAACTTGGAAGGTT | 1 | 1 | 1 | 2 | 75.49 | 22.95 | 3.67 | 3.55 | NA | NA | NA |
| 178 | 362 | TATCACTTGAACTTGGAAGG | 1 | 1 | 2 | 3 | 95.08 | 17.86 | 19.33 | 1.20 | NA | NA | NA |
| 180 | 364 | TCTATCACTTGAACTTGGAA | 2 | 1 | 1 | 2 | 79.06 | 19.79 | 4.78 | 1.89 | NA | NA | NA |
| 181 | 365 | GTCTATCACTTGAACTTGGA | 2 | 1 | 1 | 2 | 77.01 | 50.90 | 0.99 | 4.78 | NA | NA | NA |
| 182 | 366 | TGTCTATCACTTGAACTTGG | 2 | 2 | 1 | 1 | 75.65 | 39.52 | 1.01 | 6.03 | NA | NA | NA |

TABLE 3-continued

Positive ASOs

| SEQ ID NO | Position | Sequence | Off-target Score Human | Off-target Score Cyno | Off-target Score Mouse | Off-target Score Rat | mean % mRNA remaining 2 nM | mean % mRNA remaining 20 nM | SD % mRNA remaining 2 nM | SD % mRNA remaining 20 nM | IC20 (nM) | IC50 (nM) | IC80 (nM) |
|---|---|---|---|---|---|---|---|---|---|---|---|---|---|
| 183 | 367 | TTGTCTATCACTTGAACTTG | 2 | 2 | 2 | 2 | 88.34 | 20.10 | 5.86 | 3.29 | NA | NA | NA |
| 184 | 368 | ATTGTCTATCACTTGAACTT | 2 | 2 | 2 | NC | 84.20 | 54.98 | 1.73 | 3.67 | NA | NA | NA |
| 185 | 369 | CATTGTCTATCACTTGAACT | 2 | 2 | 2 | NC | 95.44 | 25.25 | 17.34 | 2.84 | NA | NA | NA |
| 186 | 370 | CCATTGTCTATCACTTGAAC | 2 | 2 | 2 | NC | 75.20 | 15.87 | 2.35 | 0.58 | 0.25 | 0.92 | 4.36 |
| 187 | 371 | TCCATTGTCTATCACTTGAA | 2 | 2 | 2 | NC | 70.21 | 17.69 | 1.89 | 1.61 | 0.36 | 1.21 | 8.86 |
| 188 | 372 | ATCCATTGTCTATCACTTGA | 2 | 2 | NC | NC | 73.77 | 22.51 | 1.88 | 5.13 | NA | NA | NA |
| 189 | 373 | AATCCATTGTCTATCACTTG | 2 | 2 | NC | NC | 77.83 | 26.73 | 3.24 | 1.26 | NA | NA | NA |
| 201 | 386 | ACTCCCCATCCCAAATCCAT | 2 | 2 | NC | NC | 80.75 | 22.43 | 3.52 | 1.83 | NA | NA | NA |
| 211 | 396 | CTACATCATCACTCCCCATC | 2 | 2 | NC | NC | 77.20 | 12.74 | 2.53 | 1.37 | NA | NA | NA |
| 212 | 397 | TCTACATCATCACTCCCCAT | 2 | 2 | NC | NC | 74.42 | 12.19 | 2.00 | 0.49 | 3.10 | 11.27 | ND |
| 229 | 414 | AACGATTTCCCACTTTCTCT | 2 | 2 | NC | NC | 72.64 | 22.78 | 3.19 | 1.16 | NA | NA | NA |
| 230 | 415 | TAACGATTTCCCACTTTCTC | 2 | 2 | NC | NC | 79.03 | 11.66 | 5.33 | 1.49 | NA | NA | NA |
| 231 | 416 | ATAACGATTTCCCACTTTCT | 2 | 2 | NC | NC | 78.95 | 14.41 | 4.83 | 4.50 | NA | NA | NA |
| 234 | 426 | TACTGGTGAAATAACGATTT | 2 | 3 | NC | NC | 80.89 | 30.57 | 2.84 | 0.46 | NA | NA | NA |
| 235 | 427 | TTACTGGTGAAATAACGATT | 2 | 2 | NC | NC | 65.31 | 19.49 | 5.20 | 0.84 | 0.48 | 1.36 | 4.89 |
| 236 | 428 | TTTACTGGTGAAATAACGAT | 2 | 2 | NC | NC | 87.08 | 21.12 | 7.01 | 2.19 | NA | NA | NA |
| 237 | 429 | ATTTACTGGTGAAATAACGA | 2 | 2 | NC | NC | 85.92 | 41.52 | 3.99 | 1.99 | NA | NA | NA |
| 238 | 430 | CATTTACTGGTGAAATAACG | 2 | 2 | NC | NC | 90.43 | 20.60 | 14.34 | 1.10 | NA | NA | NA |
| 241 | 433 | TGGCATTTACTGGTGAAATA | 2 | 2 | NC | NC | 75.60 | 27.06 | 6.23 | 2.19 | NA | NA | NA |
| 242 | 434 | GTGGCATTTACTGGTGAAAT | 2 | 1 | NC | NC | 74.62 | 65.91 | 5.68 | 4.88 | NA | NA | NA |
| 248 | 452 | CTCCAAGTCCTGTACCGAGT | 3 | 3 | NC | NC | 66.48 | 35.79 | 2.84 | 6.63 | NA | NA | NA |
| 249 | 453 | TCTCCAAGTCCTGTACCGAG | 3 | 3 | NC | NC | 69.72 | 35.31 | 5.64 | 2.28 | NA | NA | NA |
| 250 | 454 | TTCTCCAAGTCCTGTACCGA | 2 | 3 | NC | NC | 80.09 | 15.49 | 5.44 | 1.27 | NA | NA | NA |
| 254 | 468 | CATAAAACCTTGGATTCTCC | 2 | 1 | NC | NC | 72.14 | 15.86 | 27.20 | 0.86 | NA | NA | NA |
| 265 | 480 | CTCCTCGGAAACCATAAAAC | 2 | 2 | NC | NC | 81.92 | 20.89 | 5.26 | 2.21 | NA | NA | NA |
| 266 | 481 | TCTCCTCGGAAACCATAAAA | 2 | 2 | NC | NC | 84.83 | 18.78 | 3.51 | 2.57 | NA | NA | NA |
| 267 | 482 | CTCTCCTCGGAAACCATAAA | 2 | 2 | NC | NC | 86.89 | 12.64 | 2.43 | 1.22 | NA | NA | NA |
| 268 | 483 | CCTCTCCTCGGAAACCATAA | 2 | 2 | NC | NC | 81.76 | 11.71 | 7.00 | 1.87 | NA | NA | NA |
| 269 | 484 | GCCTCTCCTCGGAAACCATA | 2 | 1 | NC | NC | 80.11 | 25.50 | 4.59 | 1.33 | NA | NA | NA |
| 282 | 537 | TTTTCTTGGACGAAATTTCC | 2 | 2 | NC | NC | 86.51 | 14.81 | 2.17 | 2.33 | NA | NA | NA |
| 283 | 538 | TTTTTCTTGGACGAAATTTC | 2 | 1 | NC | NC | 92.35 | 17.43 | 9.00 | 1.47 | NA | NA | NA |
| 284 | 539 | GTTTTTCTTGGACGAAATTT | 2 | 2 | NC | NC | 85.97 | 63.49 | 5.37 | 2.09 | NA | NA | NA |
| 285 | 540 | TGTTTTTCTTGGACGAAATT | 2 | 2 | NC | NC | 91.72 | 30.14 | 6.86 | 5.01 | NA | NA | NA |
| 286 | 541 | CTGTTTTTCTTGGACGAAAT | 2 | 2 | NC | NC | 78.31 | 16.19 | 11.18 | 2.23 | NA | NA | NA |
| 287 | 542 | CCTGTTTTTCTTGGACGAAA | 3 | 1 | NC | NC | 72.73 | 19.56 | 4.99 | 2.01 | NA | NA | NA |
| 288 | 543 | TCCTGTTTTTCTTGGACGAA | 2 | 2 | NC | NC | 78.70 | 23.15 | 4.59 | 1.40 | NA | NA | NA |

TABLE 3-continued

| Positive ASOs | | | | | | | | | | | | | |
|---|---|---|---|---|---|---|---|---|---|---|---|---|---|
| SEQ ID NO | Position | Sequence | Off-target Score | | | | mean % mRNA remaining | | SD % mRNA remaining | | IC20 (nM) | IC50 (nM) | IC80 (nM) |
| | | | Human | Cyno | Mouse | Rat | 2 nM | 20 nM | 2 nM | 20 nM | | | |
| 294 | 552 | TTTTCATTGTCCTGTTTTTC | 2 | 1 | NC | NC | 88.62 | 13.49 | 2.05 | 3.75 | NA | NA | NA |
| 296 | 554 | AGTTTTCATTGTCCTGTTTT | 2 | 1 | NC | NC | 85.86 | 26.44 | 6.19 | 2.68 | NA | NA | NA |
| 309 | 567 | ACAGTTTCACAAAAGTTTTC | 2 | 2 | NC | NC | 89.08 | 82.86 | 5.13 | 4.37 | NA | NA | NA |
| 316 | 584 | GGCTTTTCCACTCTGAAACA | 2 | 1 | NC | NC | 79.87 | 105.73 | 3.27 | 5.14 | NA | NA | NA |
| 317 | 585 | GGGCTTTTCCACTCTGAAAC | 2 | 2 | NC | NC | 75.58 | 156.14 | 5.08 | 9.80 | NA | NA | NA |
| 318 | 586 | AGGGCTTTTCCACTCTGAAA | 2 | 2 | NC | NC | 66.99 | 95.25 | 5.64 | 11.62 | NA | NA | NA |
| 319 | 587 | CAGGGCTTTTCCACTCTGAA | 2 | 2 | NC | NC | 64.01 | 27.51 | 4.07 | 0.76 | NA | NA | NA |
| 320 | 588 | TCAGGGCTTTTCCACTCTGA | 2 | 2 | NC | NC | 61.84 | 36.06 | 14.35 | 2.59 | NA | NA | NA |
| 321 | 589 | TTCAGGGCTTTTCCACTCTG | 2 | 2 | NC | NC | 56.27 | 43.83 | 9.73 | 4.59 | NA | NA | NA |
| 322 | 590 | TTTCAGGGCTTTTCCACTCT | 2 | 1 | NC | NC | 69.47 | 12.11 | 2.21 | 2.43 | 0.23 | 0.99 | 4.72 |
| 328 | 613 | CTAGTCACATCAGCTTCACA | 3 | 3 | NC | NC | 74.37 | 15.78 | 6.09 | 6.37 | NA | NA | NA |
| 329 | 614 | TCTAGTCACATCAGCTTCAC | 2 | 2 | NC | NC | 64.74 | 30.36 | 2.06 | 3.30 | NA | NA | NA |
| 366 | 684 | CCATGCATTTCCTCCTTACA | 2 | 2 | NC | NC | 82.11 | 9.26 | 14.94 | 1.38 | NA | NA | NA |
| 367 | 685 | TCCATGCATTTCCTCCTTAC | 2 | 2 | NC | NC | 67.01 | 8.69 | 3.44 | 1.52 | 0.21 | 0.73 | 3.24 |
| 368 | 686 | GTCCATGCATTTCCTCCTTA | 2 | 2 | NC | NC | 72.03 | 17.51 | 4.65 | 2.55 | 0.13 | 0.42 | 3.75 |
| 370 | 688 | GGGTCCATGCATTTCCTCCT | 2 | 2 | NC | NC | 55.45 | 95.20 | 4.57 | 3.51 | NA | NA | NA |
| 376 | 694 | AGTCTAGGGTCCATGCATTT | 2 | 2 | NC | NC | 68.73 | 71.63 | 4.31 | 5.94 | NA | NA | NA |
| 377 | 695 | CAGTCTAGGGTCCATGCATT | 2 | 3 | NC | NC | 65.93 | 29.22 | 2.48 | 1.68 | NA | NA | NA |
| 378 | 696 | CCAGTCTAGGGTCCATGCAT | 2 | 2 | NC | NC | 68.89 | 43.82 | 12.06 | 2.01 | NA | NA | NA |
| 379 | 697 | TCCAGTCTAGGGTCCATGCA | 2 | 2 | NC | NC | 69.40 | 17.13 | 6.12 | 4.20 | 0.04 | 0.14 | 0.69 |
| 381 | 700 | AACTCCAGTCTAGGGTCCAT | 2 | 2 | NC | NC | 70.96 | 25.76 | 2.51 | 2.83 | NA | NA | NA |
| 382 | 701 | AAACTCCAGTCTAGGGTCCA | 2 | 2 | NC | NC | 65.58 | 25.73 | 2.58 | 2.89 | NA | NA | NA |
| 383 | 702 | CAAACTCCAGTCTAGGGTCC | 2 | 2 | NC | NC | 67.74 | 20.58 | 1.66 | 3.61 | NA | NA | NA |
| 384 | 703 | TCAAACTCCAGTCTAGGGTC | 2 | 2 | NC | NC | 68.97 | 17.75 | 1.89 | 5.81 | 0.04 | 0.16 | 0.89 |
| 385 | 704 | CTCAAACTCCAGTCTAGGGT | 2 | 2 | NC | NC | 64.06 | 17.11 | 0.68 | 4.06 | 0.01 | 0.06 | 0.44 |
| 386 | 705 | TCTCAAACTCCAGTCTAGGG | 2 | 2 | NC | NC | 59.61 | 27.43 | 2.42 | 1.28 | NA | NA | NA |
| 387 | 706 | TTCTCAAACTCCAGTCTAGG | 2 | 2 | NC | NC | 69.04 | 20.37 | 4.66 | 1.93 | NA | NA | NA |
| 388 | 707 | CTTCTCAAACTCCAGTCTAG | 2 | 2 | NC | NC | 62.05 | 16.91 | 6.78 | 1.92 | 0.39 | 1.16 | 8.90 |
| 389 | 708 | CCTTCTCAAACTCCAGTCTA | 2 | 2 | NC | NC | 71.55 | 15.14 | 2.65 | 3.37 | 0.34 | 1.31 | 6.20 |
| 390 | 709 | ACCTTCTCAAACTCCAGTCT | 2 | 2 | NC | NC | 71.92 | 25.78 | 4.24 | 1.45 | NA | NA | NA |
| 391 | 710 | AACCTTCTCAAACTCCAGTC | 2 | 2 | NC | NC | 71.82 | 13.89 | 1.28 | 2.30 | 0.07 | 0.31 | 3.27 |
| 392 | 711 | TAACCTTCTCAAACTCCAGT | 2 | 1 | NC | NC | 74.03 | 11.74 | 5.34 | 1.85 | 0.15 | 0.84 | 5.10 |
| 393 | 712 | CTAACCTTCTCAAACTCCAG | 2 | 2 | NC | NC | 79.92 | 11.57 | 3.50 | 1.51 | NA | NA | NA |
| 394 | 713 | CCTAACCTTCTCAAACTCCA | 2 | 1 | NC | NC | 79.57 | 11.43 | 4.85 | 2.23 | NA | NA | NA |
| 395 | 714 | GCCTAACCTTCTCAAACTCC | 2 | 2 | NC | NC | 64.28 | 20.03 | 15.77 | 3.63 | 0.12 | 0.45 | 3.27 |
| 396 | 715 | TGCCTAACCTTCTCAAACTC | 2 | 2 | NC | NC | 96.06 | 22.74 | 15.84 | 1.57 | NA | NA | NA |

TABLE 3-continued

Positive ASOs

| SEQ ID NO | Position | Sequence | Off-target Score Human | Off-target Score Cyno | Off-target Score Mouse | Off-target Score Rat | mean % mRNA remaining 2 nM | mean % mRNA remaining 20 nM | SD % mRNA remaining 2 nM | SD % mRNA remaining 20 nM | IC20 (nM) | IC50 (nM) | IC80 (nM) |
|---|---|---|---|---|---|---|---|---|---|---|---|---|---|
| 397 | 716 | CTGCCTAACC TTCTCAAACT | 2 | 1 | NC | NC | 85.17 | 21.36 | 4.27 | 3.49 | NA | NA | NA |
| 398 | 717 | TCTGCCTAAC CTTCTCAAAC | 2 | 1 | NC | NC | 88.59 | 27.39 | 1.59 | 4.98 | NA | NA | NA |
| 399 | 718 | CTCTGCCTAA CCTTCTCAAA | 2 | 2 | NC | NC | 78.68 | 14.58 | 9.47 | 4.65 | NA | NA | NA |
| 487 | 821 | ACATACGTCTT TGGTTTTAG | 2 | 2 | NC | NC | 70.72 | 35.34 | 6.48 | 2.24 | NA | NA | NA |
| 488 | 822 | AACATACGTC TTTGGTTTTA | 2 | 2 | NC | NC | 83.56 | 35.11 | 2.57 | 4.54 | NA | NA | NA |
| 489 | 823 | GAACATACGT CTTTGGTTTT | 2 | 2 | NC | NC | 81.77 | 57.14 | 4.53 | 10.08 | NA | NA | NA |
| 511 | 845 | TCCATAAATTT GACAAAATC | 2 | 1 | NC | NC | 96.45 | 23.33 | 3.53 | 3.81 | NA | NA | NA |
| 514 | 850 | CCCAATCCAT AAATTTGACA | 2 | 2 | NC | NC | 86.56 | 11.43 | 6.66 | 2.22 | NA | NA | NA |
| 515 | 851 | TCCCAATCCA TAAATTTGAC | 2 | 2 | NC | NC | 60.68 | 12.61 | 14.38 | 1.93 | 0.25 | 0.95 | 4.36 |
| 516 | 852 | TTCCCAATCC ATAAATTTGA | 2 | 1 | NC | NC | 75.59 | 15.97 | 2.48 | 1.98 | NA | NA | NA |
| 517 | 853 | TTTCCCAATCC ATAAATTTG | 2 | 1 | NC | NC | 87.53 | 18.38 | 2.99 | 4.84 | NA | NA | NA |
| 520 | 856 | GACTTTCCCA ATCCATAAAT | 2 | 2 | NC | NC | 80.81 | 39.33 | 2.85 | 2.22 | NA | NA | NA |
| 521 | 857 | GGACTTTCCC AATCCATAAA | 2 | 2 | NC | NC | 71.46 | 112.84 | 8.75 | 11.34 | NA | NA | NA |
| 566 | 955 | AACAAAAACT GCATATTCTT | 1 | 2 | 1 | 2 | 91.61 | 33.40 | 4.65 | 2.33 | NA | NA | NA |
| 567 | 956 | AAACAAAAACT GCATATTCT | 1 | 1 | 1 | 2 | 94.58 | 27.27 | 4.20 | 1.24 | NA | NA | NA |
| 568 | 957 | CAAACAAAAA CTGCATATTC | 2 | 2 | 2 | 1 | 89.77 | 24.51 | 3.48 | 2.37 | NA | NA | NA |
| 569 | 958 | ACAAACAAAA ACTGCATATT | 1 | 1 | 1 | 2 | 99.32 | 53.98 | 6.18 | 3.61 | NA | NA | NA |
| 573 | 962 | GTTCACAAAC AAAAACTGCA | 1 | 2 | 1 | 2 | 68.74 | 37.94 | 5.84 | 2.62 | NA | NA | NA |
| 591 | 991 | TGTAGCTTTGT CCTTAAAAC | 2 | 2 | NC | NC | 71.77 | 21.72 | 4.41 | 2.37 | NA | NA | NA |
| 593 | 993 | TATGTAGCTTT GTCCTTAAA | 2 | 2 | NC | NC | 74.13 | 15.76 | 5.06 | 5.42 | NA | NA | NA |
| 594 | 994 | TTATGTAGCTT TGTCCTTAA | 2 | 2 | NC | NC | 74.46 | 11.80 | 4.57 | 6.26 | 0.14 | 0.49 | 2.69 |
| 596 | 996 | GTTTATGTAG CTTTGTCCTT | 2 | 2 | NC | NC | 80.57 | 93.92 | 9.82 | 4.48 | NA | NA | NA |
| 598 | 998 | GAGTTTATGTA GCTTTGTCC | 2 | 2 | NC | NC | 71.72 | 57.48 | 4.63 | 6.60 | NA | NA | NA |
| 599 | 999 | TGAGTTTATGT AGCTTTGTC | 2 | 2 | NC | NC | 74.89 | 27.84 | 3.23 | 1.82 | NA | NA | NA |
| 600 | 1000 | ATGAGTTTATG TAGCTTTGT | 2 | 1 | NC | NC | 78.20 | 51.14 | 3.45 | 1.92 | NA | NA | NA |
| 602 | 1002 | CAATGAGTTTA TGTAGCTTT | 2 | 2 | NC | NC | 75.22 | 13.63 | 4.08 | 0.86 | NA | NA | NA |
| 666 | 1132 | CACTGCACAT TAATTACATA | 2 | 2 | NC | NC | 86.38 | 19.28 | 5.73 | 2.62 | NA | NA | NA |
| 667 | 1133 | GCACTGCACA TTAATTACAT | 2 | 1 | NC | NC | 83.35 | 96.52 | 4.00 | 4.57 | NA | NA | NA |
| 669 | 1135 | TGGCACTGCA CATTAATTAC | 2 | 2 | NC | NC | 88.48 | 15.35 | 20.54 | 2.58 | NA | NA | NA |
| 670 | 1136 | TTGGCACTGC ACATTAATTA | 2 | 2 | NC | NC | 80.34 | 19.46 | 4.68 | 0.91 | NA | NA | NA |
| 671 | 1137 | ATTGGCACTG CACATTAATT | 2 | 2 | NC | NC | 86.17 | 51.51 | 4.80 | 2.16 | NA | NA | NA |
| 701 | 1180 | ATCAGAGTTTT GGCTGGCTC | 2 | 2 | 2 | 2 | 69.02 | 35.95 | 2.06 | 3.49 | NA | NA | NA |
| 702 | 1181 | AATCAGAGTTT TGGCTGGCT | 2 | 2 | 2 | 2 | 63.90 | 39.92 | 1.63 | 4.52 | NA | NA | NA |
| 703 | 1182 | CAATCAGAGT TTTGGCTGGC | 2 | 2 | 2 | 2 | 65.26 | 26.28 | 2.95 | 3.50 | 0.07 | 0.23 | ND |
| 704 | 1183 | TCAATCAGAG TTTTGGCTGG | 2 | 2 | 2 | 2 | 71.61 | 34.85 | 3.07 | 2.52 | NA | NA | NA |
| 719 | 1204 | AGAGTGTCCC AGTTCTGAAA | 2 | 2 | NC | NC | 64.55 | 148.30 | 1.97 | 6.08 | NA | NA | NA |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 720 | 1205 | GAGAGTGTCC CAGTTCTGAA | 2 | 2 | NC | NC | 66.32 | 98.81 | 6.09 | 5.02 | NA | NA | NA |
| 721 | 1206 | AGAGAGTGTC CCAGTTCTGA | 2 | 2 | NC | NC | 62.41 | 75.95 | 1.14 | 25.39 | NA | NA | NA |
| 728 | 1213 | CAAAACAAGA GAGTGTCCCA | 2 | 1 | NC | NC | 76.06 | 13.81 | 12.21 | 1.67 | NA | NA | NA |
| 749 | 1234 | ATTTTCACTCC TTCCTGAAT | 2 | 1 | NC | NC | 81.05 | 40.09 | 3.41 | 4.01 | NA | NA | NA |
| 750 | 1235 | CATTTTCACTC CTTCCTGAA | 2 | 2 | NC | NC | 76.24 | 14.95 | 6.33 | 3.38 | NA | NA | NA |
| 751 | 1236 | ACATTTTCACT CCTTCCTGA | 2 | 2 | NC | NC | 69.48 | 15.51 | 9.75 | 1.75 | 0.39 | 1.41 | ND |
| 752 | 1237 | AACATTTTCAC TCCTTCCTG | 2 | 2 | NC | NC | 70.68 | 13.87 | 2.65 | 1.57 | 0.39 | 1.07 | 8.02 |
| 753 | 1238 | AAACATTTTCA CTCCTTCCT | 2 | 2 | NC | NC | 75.55 | 11.15 | 3.73 | 1.12 | 0.57 | 1.84 | 7.69 |
| 755 | 1240 | AAAAACATTTT CACTCCTTC | 2 | 1 | NC | NC | 79.25 | 13.25 | 6.99 | 1.87 | NA | NA | NA |
| 757 | 1242 | TTAAAAACATT TTCACTCCT | 2 | 1 | NC | NC | 82.65 | 17.72 | 6.24 | 2.56 | NA | NA | NA |
| 784 | 1290 | ATTCCTTAATA TCCTCACCT | 2 | 2 | NC | NC | 78.04 | 15.48 | 5.23 | 0.95 | NA | NA | NA |
| 786 | 1292 | AAATTCCTTAA TATCCTCAC | 2 | 2 | NC | NC | 81.35 | 17.87 | 5.88 | 2.23 | NA | NA | NA |
| 787 | 1293 | TAAATTCCTTA ATATCCTCA | 2 | 2 | NC | NC | 83.49 | 23.29 | 3.85 | 4.04 | NA | NA | NA |
| 788 | 1294 | CTAAATTCCTT AATATCCTC | 2 | 2 | NC | NC | 77.48 | 26.26 | 3.28 | 2.35 | NA | NA | NA |
| 790 | 1296 | CACTAAATTCC TTAATATCC | 2 | 2 | NC | NC | 82.57 | 31.46 | 2.87 | 2.53 | NA | NA | NA |
| 828 | 1354 | TCATCGGAAG TCACACGCTT | 2 | 3 | NC | NC | 67.51 | 11.20 | 3.20 | 1.82 | 0.22 | 0.77 | 4.29 |
| 829 | 1355 | CTCATCGGAA GTCACACGCT | 2 | 2 | NC | NC | 68.94 | 15.81 | 3.19 | 1.49 | 0.19 | 0.67 | 3.18 |
| 830 | 1356 | TCTCATCGGA AGTCACACGC | 2 | 2 | NC | NC | 73.66 | 14.18 | 2.63 | 3.48 | 0.17 | 0.69 | 3.43 |
| 959 | 1539 | GACCACCTGA TTCATAAATG | 2 | 2 | NC | NC | 69.12 | 47.95 | 6.78 | 11.48 | NA | NA | NA |
| 960 | 1540 | GGACCACCTG ATTCATAAAT | 2 | 2 | NC | NC | 79.02 | 206.94 | 4.65 | 56.26 | NA | NA | NA |
| 961 | 1542 | CTGGACCACC TGATTCATAA | 2 | 2 | NC | NC | 79.65 | 55.49 | 7.13 | 4.02 | NA | NA | NA |
| 964 | 1563 | GCTCTGTCAT TTTGCTATGG | 2 | 2 | NC | NC | 77.42 | 70.22 | 1.40 | 2.14 | NA | NA | NA |
| 965 | 1564 | GGCTCTGTCA TTTTGCTATG | 2 | 2 | NC | NC | 78.46 | 81.64 | 2.58 | 1.06 | NA | NA | NA |
| 967 | 1566 | ATGGCTCTGT CATTTTGCTA | 2 | 2 | NC | NC | 77.47 | 50.42 | 1.09 | 1.68 | NA | NA | NA |
| 968 | 1567 | GATGGCTCTG TCATTTTGCT | 2 | 2 | NC | NC | 75.71 | 104.49 | 3.59 | 15.27 | NA | NA | NA |
| 971 | 1570 | AAAGATGGCT CTGTCATTTT | 2 | 2 | NC | NC | 85.42 | 51.21 | 4.94 | 0.57 | NA | NA | NA |
| 972 | 1571 | TAAAGATGGC TCTGTCATTT | 2 | 2 | NC | NC | 71.44 | 16.26 | 18.64 | 2.69 | NA | NA | NA |
| 973 | 1572 | GTAAAGATGG CTCTGTCATT | 2 | 2 | NC | NC | 85.49 | 84.58 | 2.18 | 10.18 | NA | NA | NA |
| 974 | 1573 | TGTAAAGATG GCTCTGTCAT | 2 | 2 | NC | NC | 87.95 | 17.81 | 3.14 | 1.82 | NA | NA | NA |
| 975 | 1574 | TTGTAAAGAT GGCTCTGTCA | 2 | 2 | NC | NC | 88.69 | 14.78 | 0.99 | 1.26 | NA | NA | NA |
| 976 | 1575 | TTTGTAAAGAT GGCTCTGTC | 2 | 2 | NC | NC | 86.84 | 14.94 | 1.99 | 2.71 | NA | NA | NA |
| 977 | 1576 | TTTTGTAAAGA TGGCTCTGT | 2 | 2 | NC | NC | 90.05 | 17.51 | 1.81 | 3.62 | NA | NA | NA |
| 986 | 1588 | GAGCTGTCTT TGTTTTGTAA | 2 | 2 | NC | NC | 80.81 | 130.73 | 2.60 | 8.33 | NA | NA | NA |
| 987 | 1589 | AGAGCTGTCT TTGTTTTGTA | 2 | 2 | NC | NC | 78.87 | 83.79 | 2.43 | 6.83 | NA | NA | NA |
| 1002 | 1626 | CAATTGTCTCT TGTTCTAAC | 2 | 2 | NC | NC | 77.84 | 12.02 | 5.97 | 2.15 | NA | NA | NA |
| 1003 | 1627 | ACAATTGTCTC TTGTTCTAA | 2 | 1 | NC | NC | 86.71 | 66.67 | 3.79 | 3.42 | NA | NA | NA |

TABLE 3-continued

Positive ASOs

| SEQ ID NO | Posi-tion | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 1004 | 1628 | TACAATTGTCT CTTGTTCTA | 2 | 2 | NC | NC | 77.06 | 24.92 | 4.21 | 2.75 | NA | NA | NA |
| 1005 | 1629 | CTACAATTGTC TCTTGTTCT | 2 | 2 | NC | NC | 71.10 | 17.61 | 3.81 | 3.54 | 0.14 | 0.48 | 2.52 |
| 1006 | 1630 | GCTACAATTG TCTCTTGTTC | 2 | 2 | NC | NC | 75.21 | 164.15 | 3.53 | 7.38 | NA | NA | NA |
| 1007 | 1631 | TGCTACAATT GTCTCTTGTT | 2 | 2 | NC | NC | 68.01 | 43.68 | 5.57 | 3.18 | NA | NA | NA |
| 1008 | 1633 | GATGCTACAA TTGTCTCTTG | 2 | 2 | NC | NC | 76.75 | 157.84 | 4.28 | 14.35 | NA | NA | NA |
| 1009 | 1634 | TGATGCTACA ATTGTCTCTT | 2 | 2 | NC | NC | 93.24 | 19.27 | 32.66 | 1.18 | NA | NA | NA |
| 1010 | 1635 | CTGATGCTAC AATTGTCTCT | 2 | 2 | NC | NC | 79.27 | 34.33 | 2.33 | 1.43 | NA | NA | NA |
| 1011 | 1636 | TCTGATGCTA CAATTGTCTC | 2 | 1 | NC | NC | 74.33 | 26.98 | 3.75 | 2.56 | NA | NA | NA |
| 1012 | 1637 | TTCTGATGCTA CAATTGTCT | 2 | 1 | NC | NC | 74.47 | 19.62 | 3.96 | 6.13 | NA | NA | NA |
| 1013 | 1638 | CTTCTGATGC TACAATTGTC | 2 | 2 | NC | NC | 76.90 | 39.77 | 1.15 | 4.56 | NA | NA | NA |
| 1014 | 1639 | GCTTCTGATG CTACAATTGT | 2 | 2 | NC | NC | 72.48 | 113.69 | 5.55 | 8.85 | NA | NA | NA |
| 1086 | 1742 | TGGTGTCTGA AAAGGGCTTA | 2 | 2 | NC | NC | 75.01 | 41.17 | 4.46 | 5.94 | NA | NA | NA |
| 1110 | 1785 | CTTTCCATATT TCTAGATCC | 2 | 2 | NC | NC | 85.18 | 26.06 | 2.72 | 2.17 | NA | NA | NA |
| 1111 | 1786 | TCTTTCCATAT TTCTAGATC | 2 | 2 | NC | NC | 78.80 | 27.68 | 3.78 | 2.79 | NA | NA | NA |
| 1121 | 1796 | AGTAGTACTTT CTTTCCATA | 2 | 2 | NC | NC | 80.48 | 64.18 | 2.34 | 2.76 | NA | NA | NA |
| 1126 | 1801 | TTAACAGTAGT ACTTTCTTT | 2 | 2 | NC | NC | 84.35 | 22.72 | 2.03 | 2.88 | NA | NA | NA |
| 1127 | 1802 | ATTAACAGTA GTACTTTCTT | 2 | 2 | NC | NC | 55.07 | 79.59 | 34.67 | 5.19 | NA | NA | NA |
| 1147 | 1848 | GTTGATTCTG AATTCTATTA | 2 | 2 | NC | NC | 69.33 | 128.16 | 3.03 | 3.50 | NA | NA | NA |
| 1148 | 1849 | GGTTGATTCT GAATTCTATT | 2 | 2 | NC | NC | 65.93 | 188.28 | 4.48 | 11.46 | NA | NA | NA |
| 1149 | 1850 | TGGTTGATTCT GAATTCTAT | 2 | 2 | NC | NC | 69.18 | 44.46 | 4.72 | 7.24 | NA | NA | NA |
| 1172 | 1873 | TCAGTAGCAT CTTTAAATCT | 2 | 1 | NC | NC | 74.20 | 20.17 | 5.52 | 2.86 | NA | NA | NA |
| 1175 | 1876 | ACTTCAGTAG CATCTTTAAA | 2 | 2 | NC | NC | 78.49 | 123.59 | 4.03 | 9.36 | NA | NA | NA |
| 1176 | 1877 | CACTTCAGTA GCATCTTTAA | 2 | 1 | NC | NC | 75.25 | 11.77 | 5.40 | 1.32 | 0.69 | 2.09 | 8.02 |
| 1177 | 1878 | CCACTTCAGT AGCATCTTTA | 2 | 2 | NC | NC | 68.95 | 8.07 | 4.38 | 0.39 | 0.14 | 0.58 | 3.80 |
| 1178 | 1879 | CCCACTTCAG TAGCATCTTT | 2 | 2 | NC | NC | 65.87 | 8.11 | 2.09 | 1.80 | 0.10 | 0.39 | 1.99 |
| 1179 | 1880 | TCCCACTTCA GTAGCATCTT | 2 | 2 | NC | NC | 67.23 | 10.92 | 2.21 | 3.12 | 0.15 | 0.54 | 2.51 |
| 1180 | 1881 | ATCCCACTTC AGTAGCATCT | 2 | 2 | NC | NC | 67.00 | 18.94 | 2.11 | 2.86 | 0.04 | 0.28 | 2.14 |
| 1181 | 1882 | CATCCCACTT CAGTAGCATC | 2 | 2 | NC | NC | 71.78 | 20.23 | 2.13 | 1.55 | NA | NA | NA |
| 1182 | 1883 | GCATCCCACT TCAGTAGCAT | 2 | 2 | NC | NC | 68.68 | 114.92 | 2.54 | 10.08 | NA | NA | NA |
| 1183 | 1884 | GGCATCCCAC TTCAGTAGCA | 2 | 2 | NC | NC | 72.93 | 113.70 | 11.52 | 21.89 | NA | NA | NA |
| 1184 | 1885 | TGGCATCCCA CTTCAGTAGC | 2 | 2 | NC | NC | 69.63 | 69.40 | 4.84 | 3.66 | NA | NA | NA |
| 1185 | 1886 | CTGGCATCCC ACTTCAGTAG | 2 | 2 | NC | NC | 72.14 | 45.78 | 4.09 | 2.59 | NA | NA | NA |
| 1186 | 1887 | GCTGGCATCC CACTTCAGTA | 2 | 2 | NC | NC | 69.71 | 65.90 | 4.70 | 2.86 | NA | NA | NA |
| 1260 | 2029 | TGAGTTATAAA GCCAGTGGA | 2 | 1 | 2 | NC | 68.42 | 47.42 | 4.50 | 2.18 | NA | NA | NA |
| 1261 | 2030 | ATGAGTTATAA AGCCAGTGG | 2 | 2 | 2 | NC | 72.80 | 57.12 | 0.99 | 3.07 | NA | NA | NA |
| 1270 | 2065 | GTTTCAGTTG ATTTAGTTTT | 2 | 2 | NC | NC | 78.59 | 106.70 | 2.25 | 29.03 | NA | NA | NA |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 1271 | 2066 | TGTTTCAGTTGATTTAGTTT | 2 | 1 | NC | NC | 82.53 | 32.40 | 3.39 | 4.98 | NA | NA | NA |
| 1272 | 2067 | CTGTTTCAGTTGATTTAGTT | 2 | 2 | NC | NC | 76.30 | 24.47 | 2.77 | 5.14 | NA | NA | NA |
| 1273 | 2068 | TCTGTTTCAGTTGATTTAGT | 2 | 2 | NC | NC | 68.38 | 27.94 | 14.27 | 2.36 | NA | NA | NA |
| 1274 | 2069 | TTCTGTTTCAGTTGATTTAG | 2 | 1 | 2 | NC | 76.46 | 12.90 | 6.14 | 0.77 | 0.38 | 1.13 | 4.72 |
| 1275 | 2070 | GTTCTGTTTCAGTTGATTTA | 2 | 2 | 2 | NC | 66.45 | 118.07 | 4.03 | 5.40 | NA | NA | NA |
| 1276 | 2071 | TGTTCTGTTTCAGTTGATTT | 1 | 1 | 1 | NC | 65.68 | 30.63 | 2.73 | 0.37 | NA | NA | NA |
| 1277 | 2072 | ATGTTCTGTTTCAGTTGATT | 1 | 1 | 2 | NC | 65.66 | 34.51 | 2.06 | 1.78 | NA | NA | NA |
| 1297 | 2118 | TTTCTTGGGCACGTGTGGGA | 2 | 1 | NC | NC | 61.03 | 18.52 | 6.51 | 2.34 | 0.05 | 0.31 | 2.96 |
| 1300 | 2122 | AATGTTTCTTGGGCACGTGT | 2 | 2 | NC | NC | 60.38 | 53.85 | 2.71 | 9.00 | NA | NA | NA |
| 1302 | 2124 | CAAATGTTTCTTGGGCACGT | 2 | 2 | NC | NC | 50.98 | 16.06 | 15.03 | 2.05 | 0.14 | 0.41 | 2.23 |
| 1310 | 2138 | ACGTGTTCTATTTCCAAATG | 2 | 2 | NC | NC | 73.53 | 79.81 | 8.72 | 2.83 | NA | NA | NA |
| 1387 | 2259 | TAGGTTCATTCTCTAGCCCA | 2 | 2 | NC | NC | 63.57 | 12.33 | 1.67 | 1.91 | 0.03 | 0.14 | 1.04 |
| 1388 | 2260 | GTAGGTTCATTCTCTAGCCC | 2 | 2 | NC | NC | 69.80 | 48.38 | 3.08 | 0.78 | NA | NA | NA |
| 1389 | 2261 | TGTAGGTTCATTCTCTAGCC | 2 | 2 | NC | NC | 69.61 | 45.78 | 2.74 | 9.52 | NA | NA | NA |
| 1390 | 2262 | CTGTAGGTTCATTCTCTAGC | 2 | 2 | NC | NC | 71.89 | 31.39 | 7.34 | 2.62 | NA | NA | NA |
| 1391 | 2263 | GCTGTAGGTTCATTCTCTAG | 2 | 2 | NC | NC | 73.44 | 130.40 | 5.21 | 13.47 | NA | NA | NA |
| 1392 | 2264 | TGCTGTAGGTTCATTCTCTA | 2 | 2 | NC | NC | 68.83 | 29.39 | 10.26 | 1.58 | NA | NA | NA |
| 1393 | 2265 | TTGCTGTAGGTTCATTCTCT | 2 | 2 | NC | NC | 64.56 | 18.57 | 5.04 | 1.50 | 0.05 | 0.23 | 2.96 |
| 1394 | 2266 | GTTGCTGTAGGTTCATTCTC | 2 | 2 | NC | NC | 70.73 | 117.81 | 5.81 | 15.37 | NA | NA | NA |
| 1395 | 2267 | AGTTGCTGTAGGTTCATTCT | 2 | 2 | NC | NC | 70.69 | 95.10 | 3.97 | 10.79 | NA | NA | NA |
| 1396 | 2268 | AAGTTGCTGTAGGTTCATTC | 2 | 2 | NC | NC | 69.93 | 42.84 | 2.50 | 9.05 | NA | NA | NA |
| 1461 | 2390 | ATCTGTTTTCCTACTATCAT | 2 | 2 | NC | NC | 78.96 | 23.24 | 5.39 | 2.08 | NA | NA | NA |
| 1462 | 2391 | TATCTGTTTTCCTACTATCA | 2 | 2 | NC | NC | 73.74 | 13.91 | 4.95 | 2.57 | NA | NA | NA |
| 1463 | 2392 | TTATCTGTTTTCCTACTATC | 2 | 2 | NC | NC | 61.32 | 12.11 | 19.41 | 2.41 | 0.54 | 1.28 | 3.42 |
| 1473 | 2424 | TACGGACGATTGGTTTGGAG | 2 | 3 | NC | NC | 64.86 | 42.49 | 2.84 | 8.14 | NA | NA | NA |
| 1474 | 2425 | TTACGGACGATTGGTTTGGA | 3 | 3 | NC | NC | 74.71 | 28.87 | 4.48 | 1.96 | NA | NA | NA |
| 1482 | 2433 | TTAGCTTCTTACGGACGATT | 2 | 2 | NC | NC | 73.20 | 16.43 | 1.80 | 2.24 | NA | NA | NA |
| 1485 | 2436 | AGCTTAGCTTCTTACGGACG | 2 | 3 | NC | NC | 67.08 | 81.14 | 3.07 | 4.19 | NA | NA | NA |
| 1486 | 2448 | GCTGTGAACTCAAGCTTAGC | 3 | 3 | NC | NC | 68.69 | 128.36 | 1.70 | 2.50 | NA | NA | NA |
| 1487 | 2449 | AGCTGTGAACTCAAGCTTAG | 2 | 2 | NC | NC | 70.69 | 62.48 | 4.99 | 4.34 | NA | NA | NA |
| 1490 | 2453 | TCCTAGCTGTGAACTCAAGC | 2 | 2 | NC | NC | 70.82 | 39.13 | 4.00 | 3.11 | NA | NA | NA |
| 1491 | 2454 | ATCCTAGCTGTGAACTCAAG | 2 | 2 | NC | NC | 73.02 | 39.97 | 2.91 | 6.24 | NA | NA | NA |
| 1492 | 2455 | GATCCTAGCTGTGAACTCAA | 2 | 2 | NC | NC | 70.55 | 60.81 | 1.82 | 6.58 | NA | NA | NA |
| 1493 | 2456 | AGATCCTAGCTGTGAACTCA | 2 | 2 | NC | NC | 71.35 | 60.70 | 3.51 | 5.37 | NA | NA | NA |
| 1494 | 2457 | AAGATCCTAGCTGTGAACTC | 2 | 2 | NC | NC | 72.72 | 51.80 | 3.01 | 3.51 | NA | NA | NA |
| 1495 | 2458 | AAAGATCCTAGCTGTGAACT | 2 | 2 | NC | NC | 79.93 | 49.47 | 2.18 | 1.51 | NA | NA | NA |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 1498 | 2461 | TCTAAAGATCCTAGCTGTGA | 2 | 2 | NC | NC | 74.47 | 23.80 | 5.24 | 0.46 | NA | NA | NA |
| 1499 | 2462 | CTCTAAAGATCCTAGCTGTG | 2 | 2 | NC | NC | 69.91 | 27.63 | 6.82 | 2.73 | NA | NA | NA |
| 1500 | 2463 | TCTCTAAAGATCCTAGCTGT | 2 | 2 | NC | NC | 75.81 | 26.67 | 2.37 | 1.97 | NA | NA | NA |
| 1501 | 2464 | TTCTCTAAAGATCCTAGCTG | 2 | 2 | NC | NC | 78.09 | 38.79 | 2.41 | 3.40 | NA | NA | NA |
| 1502 | 2465 | CTTCTCTAAAGATCCTAGCT | 2 | 2 | NC | NC | 68.81 | 22.90 | 6.78 | 1.92 | NA | NA | NA |
| 1505 | 2468 | AAACTTCTCTAAAGATCCTA | 2 | 2 | NC | NC | 86.60 | 24.26 | 4.80 | 1.82 | NA | NA | NA |
| 1508 | 2471 | CTTAAACTTCTCTAAAGATC | 2 | 2 | NC | NC | 84.65 | 17.74 | 3.17 | 2.47 | NA | NA | NA |
| 1510 | 2473 | CTCTTAAACTTCTCTAAAGA | 2 | 1 | 1 | 2 | 87.47 | 13.20 | 6.48 | 0.80 | NA | NA | NA |
| 1511 | 2474 | CCTCTTAAACTTCTCTAAAG | 1 | 1 | 2 | 2 | 73.37 | 15.35 | 5.97 | 2.14 | 0.16 | 0.81 | 4.45 |
| 1512 | 2475 | GCCTCTTAAACTTCTCTAAA | 2 | 1 | 2 | 2 | 72.85 | 31.27 | 2.89 | 1.55 | NA | NA | NA |
| 1513 | 2476 | TGCCTCTTAAACTTCTCTAA | 2 | 1 | 1 | 2 | 79.53 | 42.74 | 13.31 | 3.65 | NA | NA | NA |
| 1514 | 2477 | TTGCCTCTTAAACTTCTCTA | 2 | 1 | NC | NC | 73.71 | 11.85 | 2.24 | 1.40 | 0.02 | 0.38 | 5.13 |
| 1516 | 2479 | TATTGCCTCTTAAACTTCTC | 2 | 2 | NC | NC | 79.30 | 16.65 | 3.72 | 3.94 | NA | NA | NA |
| 1517 | 2480 | ATATTGCCTCTTAAACTTCT | 2 | 2 | NC | NC | 76.59 | 29.78 | 5.84 | 1.81 | NA | NA | NA |
| 1518 | 2481 | CATATTGCCTCTTAAACTTC | 2 | 2 | NC | NC | 86.67 | 17.75 | 3.02 | 3.06 | NA | NA | NA |
| 1525 | 2488 | ACCTTCCCATATTGCCTCTT | 2 | 2 | NC | NC | 72.28 | 28.62 | 1.91 | 3.82 | NA | NA | NA |
| 1526 | 2489 | AACCTTCCCATATTGCCTCT | 2 | 2 | NC | NC | 70.59 | 19.06 | 1.32 | 7.43 | NA | NA | NA |
| 1529 | 2492 | TTCAACCTTCCCATATTGCC | 2 | 2 | NC | NC | 74.01 | 13.77 | 5.21 | 2.28 | NA | NA | NA |
| 1530 | 2493 | TTTCAACCTTCCCATATTGC | 2 | 2 | NC | NC | 81.55 | 13.64 | 6.64 | 1.18 | NA | NA | NA |
| 1546 | 2519 | TTCCTCTACTTCTGTATCCA | 2 | 2 | NC | NC | 84.26 | 19.50 | 4.19 | 5.90 | NA | NA | NA |
| 1547 | 2520 | TTTCCTCTACTTCTGTATCC | 2 | 2 | NC | NC | 85.00 | 20.32 | 5.40 | 3.25 | NA | NA | NA |
| 1572 | 2545 | CTGAGATTGGTAGTGACTCC | 2 | 3 | NC | NC | 68.27 | 28.46 | 7.17 | 0.96 | NA | NA | NA |
| 1573 | 2546 | ACTGAGATTGGTAGTGACTC | 2 | 3 | NC | NC | 69.11 | 52.86 | 6.10 | 3.94 | NA | NA | NA |
| 1574 | 2547 | GACTGAGATTGGTAGTGACT | 2 | 2 | NC | NC | 78.60 | 50.74 | 8.80 | 2.24 | NA | NA | NA |
| 1595 | 2568 | GAATGTCAGGTTCAACTTGA | 2 | 2 | NC | NC | 78.06 | 56.47 | 5.71 | 10.65 | NA | NA | NA |
| 1596 | 2569 | AGAATGTCAGGTTCAACTTG | 2 | 2 | NC | NC | 77.01 | 48.82 | 4.77 | 4.06 | NA | NA | NA |
| 1597 | 2570 | CAGAATGTCAGGTTCAACTT | 2 | 2 | NC | NC | 74.20 | 17.39 | 4.52 | 1.90 | NA | NA | NA |
| 1721 | 2730 | TAGGCATCTGTTGTTCTAAA | 2 | 2 | NC | NC | 73.06 | 21.72 | 4.85 | 2.93 | NA | NA | NA |
| 1722 | 2731 | CTAGGCATCTGTTGTTCTAA | 2 | 2 | NC | NC | 68.46 | 20.27 | 3.55 | 1.95 | NA | NA | NA |
| 1723 | 2732 | ACTAGGCATCTGTTGTTCTA | 2 | 3 | NC | NC | 75.00 | 69.45 | 1.93 | 7.25 | NA | NA | NA |
| 1724 | 2733 | AACTAGGCATCTGTTGTTCT | 2 | 2 | NC | NC | 76.27 | 33.88 | 5.64 | 1.90 | NA | NA | NA |
| 1725 | 2734 | AAACTAGGCATCTGTTGTTC | 2 | 2 | NC | NC | 70.43 | 26.81 | 24.22 | 2.05 | NA | NA | NA |
| 1726 | 2735 | CAAACTAGGCATCTGTTGTT | 2 | 1 | NC | NC | 77.29 | 14.21 | 1.87 | 1.23 | NA | NA | NA |
| 1727 | 2736 | TCAAACTAGGCATCTGTTGT | 2 | 2 | NC | NC | 80.67 | 14.87 | 3.79 | 1.40 | NA | NA | NA |
| 1744 | 2764 | AACTCCTTCAGGGTCATAGG | 2 | 2 | NC | NC | 66.84 | 32.00 | 3.65 | 2.80 | NA | NA | NA |
| 1745 | 2765 | TAACTCCTTCAGGGTCATAG | 2 | 2 | NC | NC | 74.04 | 9.12 | 3.74 | 1.45 | 0.34 | 1.20 | 4.67 |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 1746 | 2766 | ATAACTCCTTC AGGGTCATA | 2 | 2 | NC | NC | 86.21 | 14.10 | 4.66 | 3.64 | NA | NA | NA |
| 1747 | 2767 | GATAACTCCTT CAGGGTCAT | 2 | 2 | NC | NC | 73.17 | 71.61 | 4.49 | 4.91 | NA | NA | NA |
| 1748 | 2768 | AGATAACTCC TTCAGGGTCA | 2 | 2 | NC | NC | 76.10 | 58.88 | 4.53 | 4.26 | NA | NA | NA |
| 1786 | 2818 | GCTAGTGATT CAGATGACTT | 2 | 2 | NC | NC | 77.18 | 61.81 | 6.95 | 4.16 | NA | NA | NA |
| 1797 | 2829 | ATAATTTAGAG GCTAGTGAT | 2 | 2 | NC | NC | 94.05 | 34.62 | 8.58 | 2.35 | NA | NA | NA |
| 1799 | 2831 | GGATAATTTA GAGGCTAGTG | 2 | 2 | NC | NC | 75.22 | 65.82 | 7.97 | 3.21 | NA | NA | NA |
| 1800 | 2832 | TGGATAATTTA GAGGCTAGT | 3 | 3 | NC | NC | 79.60 | 28.73 | 5.81 | 2.69 | NA | NA | NA |
| 1801 | 2833 | CTGGATAATTT AGAGGCTAG | 2 | 2 | NC | NC | 77.03 | 22.93 | 6.10 | 1.34 | NA | NA | NA |
| 1802 | 2834 | TCTGGATAATT TAGAGGCTA | 2 | 2 | NC | NC | 78.17 | 49.18 | 6.44 | 2.39 | NA | NA | NA |
| 1824 | 2856 | TTTCTCTTTCG GAACCCTTC | 3 | 2 | NC | NC | 79.87 | 5.65 | 7.71 | 0.67 | 0.43 | 1.29 | 4.72 |
| 1825 | 2857 | GTTTCTCTTTC GGAACCCTT | 2 | 2 | NC | NC | 75.83 | 33.27 | 3.68 | 1.25 | NA | NA | NA |
| 1826 | 2858 | AGTTTCTCTTT CGGAACCCT | 2 | 2 | NC | NC | 76.81 | 34.76 | 5.54 | 3.44 | NA | NA | NA |
| 1831 | 2863 | GTTTGAGTTTC TCTTTCGGA | 2 | 2 | NC | NC | 67.51 | 72.93 | 1.34 | 4.78 | NA | NA | NA |
| 1832 | 2864 | TGTTTGAGTTT CTCTTTCGG | 2 | 2 | NC | NC | 66.75 | 29.27 | 2.81 | 1.55 | NA | NA | NA |
| 1835 | 2867 | CATTGTTTGA GTTTCTCTTT | 2 | 2 | NC | NC | 75.22 | 20.20 | 5.27 | 3.46 | NA | NA | NA |
| 1836 | 2868 | CCATTGTTTGA GTTTCTCTT | 2 | 2 | NC | NC | 71.49 | 16.43 | 3.31 | 0.78 | NA | NA | NA |
| 1859 | 2891 | TTCATTAAAAC GACTCATCA | 2 | 2 | NC | NC | 91.66 | 16.04 | 2.16 | 1.84 | NA | NA | NA |
| 1860 | 2892 | GTTCATTAAAA CGACTCATC | 2 | 2 | NC | NC | 77.55 | 62.84 | 1.74 | 4.67 | NA | NA | NA |
| 1861 | 2893 | AGTTCATTAAA ACGACTCAT | 2 | 2 | NC | NC | 69.23 | 66.80 | 27.11 | 3.31 | NA | NA | NA |
| 1862 | 2894 | AAGTTCATTAA AACGACTCA | 2 | 2 | NC | NC | 84.65 | 51.64 | 7.39 | 1.43 | NA | NA | NA |
| 1865 | 2897 | TGGAAGTTCA TTAAAACGAC | 3 | 3 | NC | NC | 88.69 | 46.47 | 35.27 | 8.33 | NA | NA | NA |
| 1866 | 2898 | TTGGAAGTTC ATTAAAACGA | 2 | 2 | NC | NC | 71.25 | 26.95 | 4.16 | 3.49 | NA | NA | NA |
| 1869 | 2902 | GAATTTGGAA GTTCATTAAA | 2 | 2 | NC | NC | 86.52 | 58.00 | 3.96 | 4.41 | NA | NA | NA |
| 1870 | 2903 | TGAATTTGGA AGTTCATTAA | 2 | 2 | NC | NC | 90.65 | 27.21 | 4.10 | 5.36 | NA | NA | NA |
| 1871 | 2904 | CTGAATTTGG AAGTTCATTA | 2 | 2 | NC | NC | 75.35 | 14.63 | 1.81 | 2.65 | NA | NA | NA |
| 1872 | 2905 | TCTGAATTTG GAAGTTCATT | 2 | 1 | NC | NC | 84.12 | 14.91 | 23.88 | 3.23 | NA | NA | NA |
| 1873 | 2906 | ATCTGAATTTG GAAGTTCAT | 2 | 2 | NC | NC | 71.15 | 36.46 | 4.06 | 2.57 | NA | NA | NA |
| 1875 | 2908 | GAATCTGAATT TGGAAGTTC | 2 | 2 | NC | NC | 70.90 | 45.27 | 2.36 | 2.44 | NA | NA | NA |
| 1878 | 2911 | CTGGAATCTG AATTTGGAAG | 2 | 2 | NC | NC | 68.83 | 25.87 | 1.50 | 1.22 | NA | NA | NA |
| 1879 | 2912 | ACTGGAATCT GAATTTGGAA | 2 | 2 | NC | NC | 62.97 | 111.52 | 22.17 | 6.89 | NA | NA | NA |
| 1880 | 2913 | TACTGGAATC TGAATTTGGA | 2 | 2 | NC | NC | 67.96 | 25.92 | 4.97 | 1.56 | NA | NA | NA |
| 1881 | 2914 | CTACTGGAAT CTGAATTTGG | 2 | 2 | NC | NC | 68.54 | 17.06 | 2.52 | 1.28 | 0.22 | 0.86 | 4.29 |
| 1882 | 2915 | CCTACTGGAA TCTGAATTTG | 2 | 2 | NC | NC | 73.57 | 27.67 | 6.55 | 1.77 | NA | NA | NA |
| 1892 | 2957 | ACAAAAATCTT GTGTTAACA | 2 | 2 | NC | NC | 89.43 | 78.75 | 5.59 | 1.97 | NA | NA | NA |
| 1906 | 3003 | GGATGACACC ATTCTCTGTT | 2 | 3 | NC | NC | 70.86 | 222.24 | 1.88 | 14.27 | NA | NA | NA |
| 1907 | 3004 | GGGATGACAC CATTCTCTGT | 2 | 2 | NC | NC | 76.49 | 280.50 | 3.49 | 7.46 | NA | NA | NA |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 1908 | 3005 | TGGGATGACACCATTCTCTG | 2 | 2 | NC | NC | 68.03 | 76.92 | 5.51 | 2.43 | NA | NA | NA |
| 1910 | 3007 | GTTGGGATGACACCATTCTC | 2 | 2 | NC | NC | 73.32 | 93.25 | 5.01 | 10.64 | NA | NA | NA |
| 1911 | 3008 | TGTTGGGATGACACCATTCT | 2 | 2 | NC | NC | 76.23 | 48.47 | 6.77 | 1.44 | NA | NA | NA |
| 1912 | 3009 | ATGTTGGGATGACACCATTC | 2 | 2 | NC | NC | 72.48 | 66.65 | 3.78 | 1.22 | NA | NA | NA |
| 1913 | 3010 | GATGTTGGGATGACACCATT | 2 | 3 | NC | NC | 72.20 | 97.94 | 3.79 | 9.05 | NA | NA | NA |
| 1914 | 3011 | TGATGTTGGGATGACACCAT | 2 | 2 | NC | NC | 69.42 | 43.57 | 2.16 | 3.03 | NA | NA | NA |
| 1915 | 3012 | CTGATGTTGGGATGACACCA | 2 | 2 | NC | NC | 72.15 | 33.77 | 5.50 | 1.85 | NA | NA | NA |
| 1916 | 3013 | TCTGATGTTGGGATGACACC | 2 | 2 | NC | NC | 77.50 | 27.52 | 2.90 | 2.27 | NA | NA | NA |
| 1917 | 3014 | ATCTGATGTTGGGATGACAC | 2 | 2 | NC | NC | 78.06 | 35.90 | 1.79 | 3.12 | NA | NA | NA |
| 1918 | 3015 | AATCTGATGTTGGGATGACA | 2 | 2 | NC | NC | 79.81 | 45.61 | 4.85 | 2.12 | NA | NA | NA |
| 1922 | 3019 | GCAGAATCTGATGTTGGGAT | 2 | 2 | NC | NC | 80.19 | 72.76 | 4.80 | 2.76 | NA | NA | NA |
| 1923 | 3020 | GGCAGAATCTGATGTTGGGA | 2 | 2 | NC | NC | 75.56 | 82.00 | 4.49 | 7.01 | NA | NA | NA |
| 1924 | 3021 | TGGCAGAATCTGATGTTGGG | 2 | 1 | NC | NC | 76.53 | 27.81 | 6.51 | 4.41 | NA | NA | NA |
| 1925 | 3022 | GTGGCAGAATCTGATGTTGG | 2 | 2 | NC | NC | 77.58 | 69.65 | 6.65 | 4.52 | NA | NA | NA |
| 1927 | 3024 | GTGTGGCAGAATCTGATGTT | 2 | 2 | NC | NC | 83.41 | 99.90 | 7.50 | 4.41 | NA | NA | NA |
| 1945 | 3081 | TCTCTGTTGTATTGCTGTTA | 2 | 2 | NC | NC | 64.35 | 37.03 | 23.98 | 2.00 | NA | NA | NA |
| 1946 | 3082 | TTCTCTGTTGTATTGCTGTT | 2 | 2 | NC | NC | 64.62 | 23.18 | 11.74 | 2.00 | NA | NA | NA |
| 1947 | 3083 | GTTCTCTGTTGTATTGCTGT | 2 | 2 | NC | NC | 71.29 | 64.40 | 5.04 | 6.83 | NA | NA | NA |
| 1948 | 3084 | AGTTCTCTGTTGTATTGCTG | 2 | 1 | NC | NC | 79.95 | 65.34 | 5.20 | 4.98 | NA | NA | NA |
| 1949 | 3085 | CAGTTCTCTGTTGTATTGCT | 2 | 2 | NC | NC | 77.26 | 28.90 | 9.66 | 3.12 | NA | NA | NA |
| 1968 | 3114 | GCAATACCAAAGGAGTTTCT | 2 | 2 | NC | NC | 85.36 | 75.14 | 6.44 | 5.22 | NA | NA | NA |
| 2000 | 3162 | TGATAAGAACATCTGAATCT | 1 | 2 | 2 | 1 | 88.43 | 21.05 | 2.07 | 0.62 | NA | NA | NA |
| 2001 | 3163 | CTGATAAGAACATCTGAATC | 2 | 2 | 1 | 2 | 89.58 | 25.29 | 2.86 | 7.13 | NA | NA | NA |
| 2035 | 3217 | TTCATTAACATTCCACTGGG | 2 | 2 | NC | NC | 80.45 | 36.25 | 1.53 | 9.09 | NA | NA | NA |
| 2064 | 3247 | TTTTGGTCACCTGTGGCATC | 2 | 2 | NC | NC | 67.98 | 35.11 | 2.77 | 8.18 | NA | NA | NA |
| 2065 | 3248 | ATTTTGGTCACCTGTGGCAT | 2 | 2 | NC | NC | 69.79 | 51.93 | 3.01 | 3.52 | NA | NA | NA |
| 2066 | 3249 | CATTTTGGTCACCTGTGGCA | 2 | 2 | NC | NC | 76.12 | 28.42 | 5.63 | 2.67 | NA | NA | NA |
| 2067 | 3250 | CCATTTTGGTCACCTGTGGC | 2 | 3 | NC | NC | 68.04 | 33.46 | 20.39 | 2.51 | NA | NA | NA |
| 2090 | 3285 | CTCTTGCTTTAGATTCCTCA | 2 | 1 | NC | NC | 83.53 | 9.18 | 1.81 | 2.58 | NA | NA | NA |
| 2091 | 3286 | GCTCTTGCTTTAGATTCCTC | 2 | 2 | NC | NC | 71.84 | 47.28 | 4.04 | 12.13 | NA | NA | NA |
| 2163 | 3429 | AAGCAGCCTGAATGTCCTCA | 2 | 2 | NC | NC | 87.95 | 25.49 | 4.25 | 1.13 | NA | NA | NA |
| 2165 | 3431 | ACAAGCAGCCTGAATGTCCT | 2 | 2 | NC | NC | 99.44 | 110.40 | 3.74 | 5.44 | NA | NA | NA |
| 2166 | 3432 | TACAAGCAGCCTGAATGTCC | 2 | 1 | NC | NC | 97.23 | 31.29 | 6.00 | 0.83 | NA | NA | NA |
| 2167 | 3433 | GTACAAGCAGCCTGAATGTC | 2 | 2 | NC | NC | 90.96 | 76.47 | 4.29 | 17.69 | NA | NA | NA |
| 2168 | 3434 | AGTACAAGCAGCCTGAATGT | 2 | 2 | NC | NC | 102.95 | 74.55 | 23.06 | 9.33 | NA | NA | NA |
| 2169 | 3435 | TAGTACAAGCAGCCTGAATG | 3 | 2 | NC | NC | 93.15 | 26.83 | 2.25 | 2.87 | NA | NA | NA |

TABLE 3-continued

Positive ASOs

| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 2170 | 3436 | TTAGTACAAGCAGCCTGAAT | 2 | 2 | NC | NC | 83.07 | 20.20 | 4.86 | 2.24 | NA | NA | NA |
| 2171 | 3437 | TTTAGTACAAGCAGCCTGAA | 2 | 2 | NC | NC | 81.15 | 25.05 | 3.20 | 3.65 | NA | NA | NA |
| 2172 | 3438 | CTTTAGTACAAGCAGCCTGA | 2 | 3 | NC | NC | 75.61 | 30.14 | 1.47 | 2.07 | NA | NA | NA |
| 2173 | 3439 | TCTTTAGTACAAGCAGCCTG | 2 | 2 | NC | NC | 75.65 | 50.49 | 3.75 | 1.41 | NA | NA | NA |
| 2174 | 3440 | GTCTTTAGTACAAGCAGCCT | 2 | 2 | NC | NC | 83.92 | 81.72 | 2.88 | 2.28 | NA | NA | NA |
| 2175 | 3441 | GGTCTTTAGTACAAGCAGCC | 3 | 2 | NC | NC | 69.59 | 105.72 | 17.55 | 8.17 | NA | NA | NA |
| 2176 | 3442 | AGGTCTTTAGTACAAGCAGC | 3 | 2 | NC | NC | 82.11 | 68.72 | 3.70 | 3.29 | NA | NA | NA |
| 2178 | 3444 | TCAGGTCTTTAGTACAAGCA | 3 | 2 | NC | NC | 79.56 | 25.17 | 2.17 | 1.26 | NA | NA | NA |
| 2179 | 3445 | GTCAGGTCTTTAGTACAAGC | 2 | 2 | NC | NC | 75.74 | 78.33 | 4.46 | 3.66 | NA | NA | NA |
| 2181 | 3447 | TTGTCAGGTCTTTAGTACAA | 2 | 2 | NC | NC | 77.68 | 27.60 | 2.41 | 3.45 | NA | NA | NA |
| 2183 | 3449 | AGTTGTCAGGTCTTTAGTAC | 2 | 3 | NC | NC | 87.32 | 62.47 | 8.57 | 5.19 | NA | NA | NA |
| 2184 | 3450 | CAGTTGTCAGGTCTTTAGTA | 2 | 2 | NC | NC | 90.24 | 31.68 | 10.33 | 4.92 | NA | NA | NA |
| 2185 | 3451 | ACAGTTGTCAGGTCTTTAGT | 2 | 2 | NC | NC | 84.62 | 57.48 | 2.93 | 4.81 | NA | NA | NA |
| 2186 | 3452 | CACAGTTGTCAGGTCTTTAG | 2 | 2 | NC | NC | 81.04 | 24.63 | 3.98 | 1.43 | NA | NA | NA |
| 2188 | 3454 | GCCACAGTTGTCAGGTCTTT | 2 | 2 | NC | NC | 77.28 | 59.83 | 4.56 | 6.54 | NA | NA | NA |
| 2189 | 3455 | AGCCACAGTTGTCAGGTCTT | 2 | 2 | NC | NC | 80.32 | 54.89 | 1.38 | 5.77 | NA | NA | NA |
| 2194 | 3461 | ATCCACAGCCACAGTTGTCA | 2 | 1 | 1 | NC | 93.62 | 32.21 | 3.07 | 2.37 | NA | NA | NA |
| 2196 | 3463 | ACATCCACAGCCACAGTTGT | 2 | 2 | 1 | NC | 97.71 | 100.75 | 2.65 | 3.98 | NA | NA | NA |
| 2231 | 3517 | ACAAGGTCGCTTCTAAAAGG | 3 | 3 | NC | NC | 96.15 | 99.00 | 3.83 | 6.99 | NA | NA | NA |
| 2232 | 3518 | AACAAGGTCGCTTCTAAAAG | 2 | 2 | NC | NC | 96.10 | 50.39 | 6.27 | 3.96 | NA | NA | NA |
| 2255 | 3564 | GTCTCATCACAGTCCTCTCT | 2 | 2 | NC | NC | 69.15 | 21.87 | 4.29 | 1.53 | NA | NA | NA |
| 2256 | 3565 | TGTCTCATCACAGTCCTCTC | 2 | 2 | NC | NC | 74.55 | 12.10 | 3.74 | 3.37 | 0.51 | 1.60 | 6.81 |
| 2305 | 3643 | ACTGGATTGTCCCATTCTGA | 2 | 2 | NC | NC | 76.91 | 78.44 | 5.14 | 4.97 | NA | NA | NA |
| 2307 | 3645 | ATACTGGATTGTCCCATTCT | 2 | 2 | NC | NC | 83.27 | 18.42 | 4.00 | 3.26 | NA | NA | NA |
| 2308 | 3646 | AATACTGGATTGTCCCATTC | 2 | 2 | NC | NC | 89.74 | 54.56 | 3.68 | 2.13 | NA | NA | NA |
| 2312 | 3650 | GGCAAATACTGGATTGTCCC | 2 | 2 | NC | NC | 67.99 | 53.63 | 9.93 | 3.74 | NA | NA | NA |
| 2319 | 3658 | GGATAACGGGCAAATACTGG | 3 | 3 | NC | NC | 84.10 | 57.31 | 13.98 | 0.63 | NA | NA | NA |
| 2321 | 3660 | CTGGATAACGGGCAAATACT | 3 | 2 | NC | NC | 80.58 | 19.76 | 1.26 | 1.57 | NA | NA | NA |
| 2333 | 3685 | CCACTGCTTACATCAACAGC | 2 | 2 | NC | NC | 73.32 | 20.40 | 11.92 | 4.24 | NA | NA | NA |
| 2343 | 3718 | TTGTGAATTTTAACTGCTAA | 2 | 1 | NC | NC | 78.23 | 30.28 | 13.06 | 3.81 | NA | NA | NA |
| 2344 | 3719 | GTTGTGAATTTTAACTGCTA | 2 | 2 | NC | NC | 66.42 | 75.05 | 2.06 | 1.87 | NA | NA | NA |
| 2345 | 3720 | TGTTGTGAATTTTAACTGCT | 2 | 1 | NC | NC | 67.78 | 31.64 | 3.07 | 1.50 | NA | NA | NA |
| 2346 | 3721 | ATGTTGTGAATTTTAACTGC | 2 | 2 | NC | NC | 74.39 | 45.73 | 5.60 | 1.64 | NA | NA | NA |
| 2347 | 3722 | GATGTTGTGAATTTTAACTG | 2 | 2 | NC | NC | 69.84 | 80.44 | 3.44 | 4.12 | NA | NA | NA |
| 2348 | 3723 | AGATGTTGTGAATTTTAACT | 2 | 1 | NC | NC | 73.52 | 56.41 | 4.60 | 2.09 | NA | NA | NA |
| 2349 | 3724 | AAGATGTTGTGAATTTTAAC | 2 | 1 | NC | NC | 85.86 | 61.92 | 1.65 | 2.53 | NA | NA | NA |

TABLE 3-continued

Positive ASOs

| SEQ ID NO | Posi-tion | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
|---|---|---|---|---|---|---|---|---|---|---|---|---|---|
| 2353 | 3745 | TTGGTGAAAC GATAGGGATA | 3 | 2 | NC | NC | 86.80 | 31.94 | 2.61 | 2.18 | NA | NA | NA |
| 2354 | 3746 | TTTGGTGAAA CGATAGGGAT | 3 | 2 | NC | NC | 87.43 | 48.40 | 2.51 | 2.09 | NA | NA | NA |
| 2355 | 3747 | CTTTGGTGAA ACGATAGGGA | 3 | 2 | NC | NC | 79.57 | 41.96 | 2.83 | 9.43 | NA | NA | NA |
| 2394 | 3807 | TCAAACAGGC AATAAACTTG | 2 | 2 | NC | NC | 85.98 | 17.77 | 3.56 | 0.98 | NA | NA | NA |
| 2395 | 3808 | ATCAAACAGG CAATAAACTT | 2 | 2 | NC | NC | 77.20 | 34.29 | 3.93 | 5.96 | NA | NA | NA |
| 2402 | 3815 | AGTGCTCATC AAACAGGCAA | 2 | 2 | NC | NC | 71.00 | 59.57 | 3.50 | 2.67 | NA | NA | NA |
| 2403 | 3816 | TAGTGCTCAT CAAACAGGCA | 2 | 3 | NC | NC | 73.32 | 22.08 | 4.57 | 1.81 | NA | NA | NA |
| 2404 | 3817 | TTAGTGCTCAT CAAACAGGC | 2 | 3 | NC | NC | 67.42 | 18.47 | 3.66 | 3.11 | 0.11 | 0.52 | 4.24 |
| 2460 | 3953 | TTTCCGACCA GAGCCTTGTG | 2 | 3 | NC | NC | 68.68 | 26.50 | 3.08 | 2.92 | NA | NA | NA |
| 2461 | 3954 | TTTTCCGACC AGAGCCTTGT | 2 | 3 | NC | NC | 72.55 | 21.26 | 8.32 | 1.45 | NA | NA | NA |
| 2462 | 3955 | TTTTTCCGACC AGAGCCTTG | 2 | 2 | NC | NC | 80.37 | 21.01 | 7.60 | 0.85 | NA | NA | NA |
| 2489 | 4007 | TTCCTCTGTCA CTGTTATCT | 2 | 2 | NC | NC | 70.56 | 20.33 | 4.00 | 2.58 | NA | NA | NA |
| 2490 | 4008 | GTTCCTCTGT CACTGTTATC | 2 | 2 | NC | NC | 57.22 | 45.09 | 3.16 | 4.14 | NA | NA | NA |
| 2491 | 4009 | TGTTCCTCTGT CACTGTTAT | 2 | 2 | NC | NC | 46.82 | 19.73 | 5.54 | 1.38 | 0.81 | 2.08 | 8.70 |
| 2492 | 4010 | TTGTTCCTCTG TCACTGTTA | 2 | 2 | NC | NC | 80.76 | 17.70 | 5.97 | 2.11 | NA | NA | NA |
| 2495 | 4013 | CCTTTGTTCCT CTGTCACTG | 2 | 2 | NC | NC | 76.11 | 27.57 | 3.18 | 1.96 | NA | NA | NA |
| 2499 | 4017 | GTCTCCTTTGT TCCTCTGTC | 2 | 1 | NC | NC | 74.25 | 27.62 | 5.34 | 2.50 | NA | NA | NA |
| 2500 | 4018 | AGTCTCCTTT GTTCCTCTGT | 2 | 2 | NC | NC | 77.94 | 41.70 | 4.52 | 3.15 | NA | NA | NA |
| 2524 | 4055 | GCCCAGATCT TCCAGATTTT | 2 | 2 | NC | NC | 76.59 | 23.44 | 6.97 | 5.81 | NA | NA | NA |
| 2525 | 4056 | GGCCCAGATC TTCCAGATTT | 2 | 3 | NC | NC | 79.60 | 24.75 | 7.75 | 4.87 | NA | NA | NA |
| 2526 | 4057 | AGGCCCAGAT CTTCCAGATT | 2 | 2 | NC | NC | 87.17 | 42.54 | 6.66 | 2.40 | NA | NA | NA |
| 2527 | 4058 | AAGGCCCAGA TCTTCCAGAT | 2 | 1 | NC | NC | 74.99 | 24.17 | 4.99 | 1.25 | NA | NA | NA |
| 2528 | 4059 | CAAGGCCCAG ATCTTCCAGA | 2 | 2 | NC | NC | 69.53 | 12.61 | 6.77 | 1.96 | 0.19 | 0.78 | 3.63 |
| 2529 | 4060 | TCAAGGCCCA GATCTTCCAG | 2 | 2 | NC | NC | 79.06 | 11.16 | 6.66 | 1.99 | NA | NA | NA |
| 2530 | 4061 | TTCAAGGCCC AGATCTTCCA | 2 | 2 | NC | NC | 71.09 | 10.79 | 15.83 | 1.14 | 0.67 | 2.40 | 8.30 |
| 2561 | 4092 | CCAGAGAATC ACTAGTGTCT | 2 | 2 | NC | NC | 75.02 | 18.73 | 1.75 | 3.89 | NA | NA | NA |
| 2562 | 4093 | ACCAGAGAAT CACTAGTGTC | 2 | 2 | NC | NC | 83.46 | 32.29 | 4.66 | 2.17 | NA | NA | NA |
| 2591 | 4142 | TTCATTGGCTT CTCTTTCCA | 2 | 1 | NC | NC | 100.38 | 16.31 | 8.53 | 1.96 | NA | NA | NA |
| 2595 | 4146 | GAAGTTCATT GGCTTCTCTT | 2 | 2 | NC | NC | 80.58 | 38.80 | 10.34 | 1.73 | NA | NA | NA |
| 2616 | 4177 | ATACTCTTGGT CACAGTAGA | 2 | 2 | NC | NC | 106.26 | 20.10 | 17.09 | 2.60 | NA | NA | NA |
| 2644 | 4244 | CAATGTCCCT TGGATGCCTC | 2 | 2 | NC | NC | 77.84 | 12.14 | 15.18 | 0.55 | NA | NA | NA |
| 2645 | 4245 | GCAATGTCCC TTGGATGCCT | 2 | 2 | NC | NC | 60.68 | 31.07 | 16.38 | 3.72 | NA | NA | NA |
| 2646 | 4247 | TGGCAATGTC CCTTGGATGC | 2 | 2 | NC | NC | 70.78 | 15.47 | 2.39 | 2.28 | 0.07 | 0.30 | 1.71 |
| 2647 | 4248 | GTGGCAATGT CCCTTGGATG | 2 | 1 | NC | NC | 69.26 | 31.74 | 1.13 | 3.38 | NA | NA | NA |
| 2648 | 4249 | AGTGGCAATG TCCCTTGGAT | 3 | 2 | NC | NC | 90.27 | 38.94 | 11.22 | 2.21 | NA | NA | NA |
| 2649 | 4250 | CAGTGGCAAT GTCCCTTGGA | 2 | 1 | NC | NC | 77.65 | 23.04 | 6.54 | 2.25 | NA | NA | NA |

TABLE 3-continued

| Positive ASOs | | | | | | | | | | | | | |
|---|---|---|---|---|---|---|---|---|---|---|---|---|---|
| SEQ ID NO | Position | Sequence | Off-target Score | | | | mean % mRNA remaining | | SD % mRNA remaining | | IC20 | IC50 | IC80 |
| | | | Human | Cyno | Mouse | Rat | 2 nM | 20 nM | 2 nM | 20 nM | (nM) | (nM) | (nM) |
| 2650 | 4251 | TCAGTGGCAA TGTCCCTTGG | 2 | 2 | NC | NC | 85.94 | 20.36 | 8.42 | 1.96 | NA | NA | NA |
| 2651 | 4252 | GTCAGTGGCA ATGTCCCTTG | 2 | 2 | NC | NC | 85.16 | 27.43 | 7.37 | 2.02 | NA | NA | NA |
| 2653 | 4254 | CAGTCAGTGG CAATGTCCCT | 2 | 2 | NC | NC | 93.15 | 17.75 | 10.65 | 4.43 | NA | NA | NA |
| 2654 | 4255 | ACAGTCAGTG GCAATGTCCC | 2 | 2 | NC | NC | 96.92 | 27.17 | 5.79 | 3.70 | NA | NA | NA |
| 2661 | 4262 | CTTCTGGACA GTCAGTGGCA | 2 | 2 | 2 | NC | 88.73 | 25.80 | 4.68 | 2.02 | NA | NA | NA |
| 2662 | 4264 | ACCTTCTGGA CAGTCAGTGG | 2 | 3 | 2 | NC | 80.03 | 24.32 | 11.32 | 1.04 | NA | NA | NA |
| 2663 | 4265 | CACCTTCTGG ACAGTCAGTG | 2 | 2 | 1 | NC | 84.78 | 19.26 | 5.85 | 0.82 | NA | NA | NA |
| 2664 | 4266 | ACACCTTCTG GACAGTCAGT | 2 | 2 | 2 | NC | 88.41 | 20.19 | 9.00 | 1.26 | NA | NA | NA |
| 2666 | 4270 | GCCAACACCT TCTGGACAGT | 2 | 3 | 2 | 2 | 70.57 | 59.95 | 5.04 | 11.62 | NA | NA | NA |
| 2674 | 4279 | GCTTGGGATG CCAACACCTT | 2 | 2 | NC | NC | 60.17 | 36.14 | 1.75 | 4.07 | NA | NA | NA |
| 2683 | 4331 | GCAACTTTCC TGTAAGCTCA | 2 | 1 | NC | NC | 73.18 | 40.51 | 1.94 | 4.45 | NA | NA | NA |
| 2684 | 4332 | GGCAACTTTC CTGTAAGCTC | 2 | 2 | NC | NC | 73.71 | 24.96 | 1.41 | 4.04 | NA | NA | NA |
| 2685 | 4333 | CGGCAACTTT CCTGTAAGCT | 2 | 2 | NC | NC | 72.28 | 42.00 | 3.03 | 4.43 | NA | NA | NA |
| 2686 | 4334 | GCGGCAACTT TCCTGTAAGC | 2 | 2 | NC | NC | 73.11 | 53.99 | 4.51 | 5.22 | NA | NA | NA |
| 2687 | 4335 | GGCGGCAACT TTCCTGTAAG | 2 | 3 | NC | NC | 71.34 | 43.45 | 2.25 | 2.01 | NA | NA | NA |
| 2688 | 4336 | AGGCGGCAAC TTTCCTGTAA | 2 | 3 | NC | NC | 69.70 | 64.52 | 3.46 | 4.27 | NA | NA | NA |
| 2689 | 4337 | AAGGCGGCAA CTTTCCTGTA | 2 | 3 | NC | NC | 71.47 | 58.98 | 2.65 | 5.60 | NA | NA | NA |
| 2690 | 4338 | TAAGGCGGCA ACTTTCCTGT | 3 | 2 | NC | NC | 74.69 | 43.99 | 7.35 | 10.52 | NA | NA | NA |
| 2691 | 4339 | ATAAGGCGGC AACTTTCCTG | 3 | 3 | NC | NC | 78.56 | 42.65 | 5.65 | 5.21 | NA | NA | NA |
| 2692 | 4340 | AATAAGGCGG CAACTTTCCT | 2 | 2 | NC | NC | 89.94 | 64.68 | 2.17 | 4.62 | NA | NA | NA |
| 2693 | 4341 | CAATAAGGCG GCAACTTTCC | 2 | 2 | NC | NC | 94.34 | 21.32 | 2.79 | 0.66 | NA | NA | NA |
| 2694 | 4342 | TCAATAAGGC GGCAACTTTC | 2 | 2 | NC | NC | 90.44 | 18.79 | 5.41 | 2.47 | NA | NA | NA |
| 2695 | 4343 | TTCAATAAGG CGGCAACTTT | 2 | 2 | NC | NC | 96.91 | 21.42 | 6.53 | 3.19 | NA | NA | NA |
| 2725 | 4423 | AAGTGGTCTA TGTCAGCTAA | 2 | 3 | NC | NC | 103.47 | 34.92 | 18.44 | 5.10 | NA | NA | NA |
| 2726 | 4424 | CAAGTGGTCT ATGTCAGCTA | 3 | 3 | NC | NC | 89.60 | 27.45 | 11.00 | 6.09 | NA | NA | NA |
| 2727 | 4425 | CCAAGTGGTC TATGTCAGCT | 2 | 2 | NC | NC | 81.51 | 20.32 | 8.29 | 3.05 | NA | NA | NA |
| 2728 | 4426 | TCCAAGTGGT CTATGTCAGC | 2 | 2 | NC | NC | 92.66 | 17.90 | 18.04 | 1.23 | NA | NA | NA |
| 2777 | 4475 | GGCCATTTTG CGAAGTTTAG | 2 | 2 | NC | NC | 78.11 | 21.08 | 3.67 | 2.43 | NA | NA | NA |
| 2778 | 4476 | GGGCCATTTT GCGAAGTTTA | 3 | 3 | NC | NC | 73.18 | 17.87 | 4.11 | 1.66 | NA | NA | NA |
| 2779 | 4477 | TGGGCCATTT TGCGAAGTTT | 2 | 3 | NC | NC | 76.21 | 21.60 | 5.41 | 3.30 | NA | NA | NA |
| 2780 | 4478 | CTGGGCCATT TTGCGAAGTT | 2 | 3 | NC | NC | 78.35 | 23.66 | 5.34 | 2.29 | NA | NA | NA |
| 2781 | 4479 | CCTGGGCCAT TTTGCGAAGT | 2 | 3 | NC | NC | 77.45 | 30.09 | 4.91 | 2.39 | NA | NA | NA |
| 2782 | 4498 | TTTCCAAAGA GACGCCAGGC | 2 | 2 | NC | NC | 84.94 | 25.18 | 4.09 | 2.62 | NA | NA | NA |
| 2784 | 4500 | CTTTTCCAAAG AGACGCCAG | 2 | 2 | NC | NC | 88.49 | 23.15 | 2.79 | 2.49 | NA | NA | NA |
| 2785 | 4501 | GCTTTTCCAAA GAGACGCCA | 2 | 2 | NC | NC | 82.32 | 26.63 | 4.10 | 2.04 | NA | NA | NA |
| 2789 | 4505 | CTCTGCTTTTC CAAAGAGAC | 2 | 2 | NC | NC | 83.50 | 37.28 | 7.11 | 8.40 | NA | NA | NA |

TABLE 3-continued

| Positive ASOs | | | | | | | | | | | | | |
|---|---|---|---|---|---|---|---|---|---|---|---|---|---|
| SEQ ID NO | Position | Sequence | Off-target Score Human | Cyno | Mouse | Rat | mean % mRNA remaining 2 nM | 20 nM | SD % mRNA remaining 2 nM | 20 nM | IC20 (nM) | IC50 (nM) | IC80 (nM) |
| 2791 | 4508 | ACACTCTGCT TTTCCAAAGA | 2 | 2 | NC | NC | 73.84 | 20.07 | 19.34 | 2.81 | NA | NA | NA |
| 2792 | 4509 | CACACTCTGC TTTTCCAAAG | 2 | 2 | NC | NC | 79.18 | 14.66 | 2.80 | 0.76 | NA | NA | NA |
| 2794 | 4511 | ATCACACTCT GCTTTTCCAA | 2 | 1 | NC | NC | 78.29 | 17.01 | 3.86 | 3.71 | NA | NA | NA |
| 2795 | 4512 | TATCACACTCT GCTTTTCCA | 2 | 2 | NC | NC | 93.31 | 19.05 | 0.79 | 2.98 | NA | NA | NA |
| 2797 | 4514 | TGTATCACACT CTGCTTTTC | 2 | 2 | NC | NC | 97.20 | 16.90 | 2.92 | 0.94 | NA | NA | NA |
| 2848 | 4672 | AGGGACACTG GGCTGATTCA | 2 | 2 | NC | NC | 94.48 | 45.86 | 2.48 | 0.73 | NA | NA | NA |
| 2849 | 4683 | CTAAGCTGCT CAGGGACACT | 2 | 2 | NC | NC | 81.53 | 19.47 | 9.03 | 2.11 | NA | NA | NA |
| 2850 | 4684 | TCTAAGCTGC TCAGGGACAC | 2 | 2 | NC | NC | 81.17 | 21.06 | 7.52 | 1.31 | NA | NA | NA |
| 2851 | 4685 | GTCTAAGCTG CTCAGGGACA | 2 | 1 | NC | NC | 76.71 | 30.35 | 7.66 | 6.99 | NA | NA | NA |
| 2852 | 4686 | TGTCTAAGCT GCTCAGGGAC | 2 | 2 | NC | NC | 87.76 | 29.98 | 8.64 | 2.25 | NA | NA | NA |
| 2917 | 4787 | CATGGATGCA AATGAATGAA | 2 | 2 | NC | NC | 80.58 | 21.83 | 5.14 | 6.54 | NA | NA | NA |
| 2918 | 4788 | CCATGGATGC AAATGAATGA | 2 | 2 | NC | NC | 73.11 | 25.80 | 8.72 | 2.66 | NA | NA | NA |

Example 3. In Vitro Screen for Reduced Expansion

Expansion of DNA triplet repeats can be replicated in vitro using patient-derived cells lines and DNA-damaging agents Human fibroblasts from Huntington's (GM04281, GM04687 and GM04212) or Friedreich's Ataxia patients (GM03816 and GM02153) or Myotonic Dystrophyl (GM04602, GM03987 and GM03989) are purchased from Coriell Cell Repositories and are maintained in medium following the manufacturer's instructions (Kovtum et al., 2007 Nature, 447(7143). 447-452; Li et al., 2016 Biopreservation and Btobanking 14(4):324-29; Zhang et al., 2013 Mol Ther 22(2): 312-320). To induce CAG-repeat expansion in vitro, fibroblast cells are treated with oxidizing agents such as hydrogen peroxide (H2O2) potassium chromate (K2CrO4) or potassium bromate (KBrOa) for up to 2 hrs (Kovtum et al., ibid). Cells are washed, and medium replace to allow cells to recover for 3 days. The treatment is repeated up to twice more before cells are harvested and DNA isolated. CAG repeat length is determined using methods described below.

Expansion of DNA triplet repeats can be replicated in vitro using patient-derived cell lines. Induced pluripotent stem cells (iPSC) derived from Human fibroblasts from Huntington's Patients (CSO9iHD-109n1) are purchased from Cedars-Sinai RMI Induced Pluripotent Stem Cell Core and are maintained following the manufacturer's recommendations (httos://www cedars-sinai.org/content/dam/cedars-sinai/research/documents/biomanufacturina/recommended-guidelines-for-handlina-ioscsvl.Ddf). The CAG repeat from an iPSC line with 109 CAGs shows an increase in CAG repeat size overtime, with an average expansion of 4 CAG repeats over 70 days in dividing iPS cells (Goold et al., 2019 Human Molecular Genetics February 15, 28(4): 650-661).

CSO9iHD-109n1 iPSC are treated with ASO for continuous knockdown of target mRNA and CAG repeat expansion is determined by DNA fragment analysis described below. ASOs are added to cells in varying concentrations every 3 to 15 days and knockdown of mRNA is determined by RT-qPCR using standard molecular biology techniques. DNA and mRNA are isolated from cells according to standard techniques at t=0.14 days, 28 days, 42 days, 56 days and 80 days. The differences in expansion between treatment and control are compared according to a linear repeated-measures model, and at each time point according to Tukey's post-hoc tests.

Example 4

Genomic DNA Extraction and Quantitation of CAG Repeat Length by Small Pool-PCR (sp-PCR) Analyses Genomic DNA is purified using standard Proteinase K digestions and extracted using DNAzol (Invitrogen) following the manufacturer's instructions. CAG repeat length is determined by small pool-PCR analyses as previously described (Mario Gomes-Pereira and Darren Monckton, 2017, Front Cell Neuro 11:153). In brief, DNA is digested with Hindlll, diluted to a final concentration between 1-6 pg/μl and approximately 10 μg was used in subsequent PCR reactions. Primer flaking Exon 1 of the human HTT are used to amplify the CAG alleles and the PCR product is resolved by electrophoresis. Subsequently, Southern blot hybridization is performed, and the CAG alleles are observed by autoradiography OR visualized with ethidium bromide staining. CAG length can be measured directly by sequencing on a MiSeQ or appropriate machine. The change in CAG repeat number in various treatment groups in comparison with controls is calculated using simple descriptive statistics (e.g. mean±standard deviation).

Genomic DNA Extraction and Quantitation of CAG Repeat Length by DNA Fragment Analyses Genomic DNA is purified using DNAeasy Blood and Tissue Kit (Qiagen) following the manufacturers instructions. DNA is quantified by Qubit dsDNA assay (Themo- Scientific) and CAG repeat length is determined by fragment analysis by Laragen (Culver City, CA)

Example 5. Mouse Studies

Natural History Studies in HD Mouse Models:

The HD mouse R6/2 line is transgenic for the 5' end of the human HD gene (HTT) carrying approximately 120 CAG repeat expansions. HTT is ubiquitously expressed. Transgenic mice exhibit a progressive neurological phenotype that mimics many of the pathological features of HD, including choreiform-like movements, involuntary stereotypic movements, tremor, and epileptic seizures, as well as nonmovement disorder components, including unusual vocalization. They urinate frequently and exhibit loss of body weight and muscle bulk through the course of the disease Neurologically these mice develop Neuronal Intranuclear Inclusions (Nil) which contain both the huntingtin and ubiquitin proteins. Previously unknown, these NIl have subsequently been identified in HD patients. The age of onset for development of HD symptoms in R6/2 mice has been reported to occur between 9 and 11 weeks (Mangiarini et al., 1996 Cell 87: 493-506).

Figure 2:
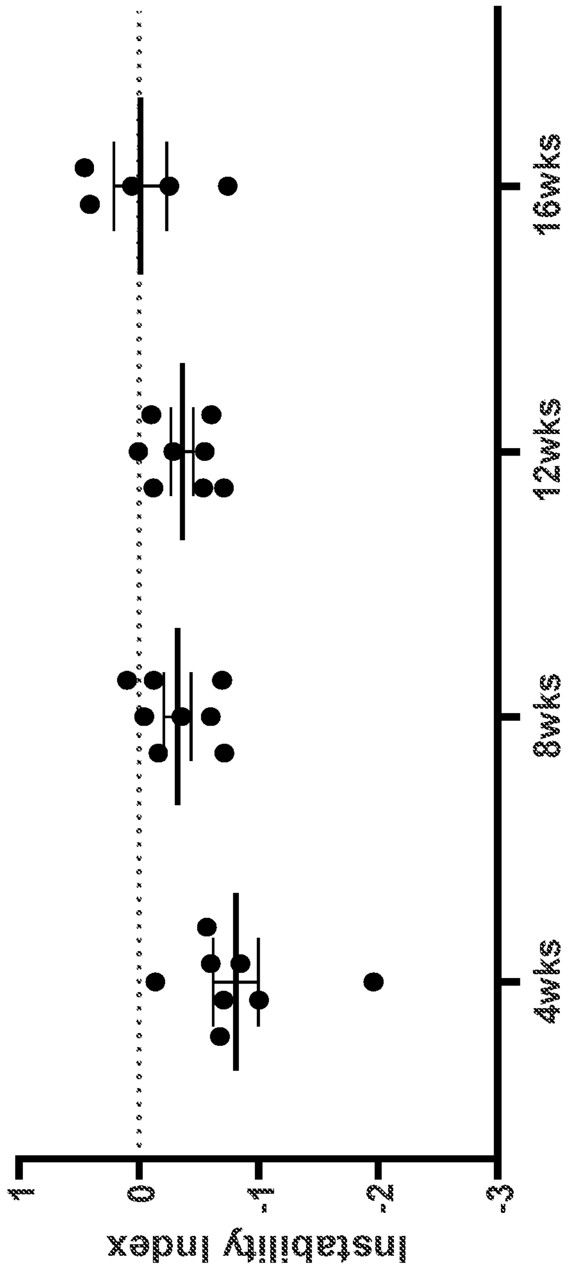
FIG. 2 is a distribution plot showing the somatic expansion of a human HTT transgene in the cerebellum as measured by the instability index in R6/2 mice at 4, 8, 12, and 16 weeks of age (4 male and 4 female per age group).

Somatic expansions were reported in R6/2 mice striatum, cortex and liver. Somatic instability increased with higher constitutive length (Larson et al, Neurobiology of Disease 76 (2015) 98-111). A natural history study in R6/2 mice with 120 CAG repeats was performed. Their genotype and length of CAG expansion was determined. R6/2 mice at 4, 8, 12 and 16 weeks of age (4 male and 4 female mice per age group) were sacrificed. Striatum, cerebellum, cortex, liver, kidney, heart, spleen, lung, duodenum, colon, quadricep, CSF and plasma were collected and snap frozen in liquid nitrogen. Genomic DNA was extracted, the length of CAG repeats measured, and the instability index was calculated from striatum, cerebellum, cortex, liver and kidney according to Lee et al. BMC Systems Biology 2010, 4:29). At 12 and 16 weeks of age, the striatum showed a significant increase of somatic expansion as measured by the instability index (**$p<0.0001$, One-way ANOVA) (FIG. 1). No changes in somatic expansion were observed across all ages in the R6/2 mouse cerebellum (FIG. 2**).

Mouse models recapitulating many of the features of trinucleotide repeat expansion diseases including, HD, FA and DM1, are readily available from commercial venders and academic institutions (Polyglutamine Disorders, Advances in Experimental Medicine and Biology, Vol 1049, 2018: Editors Clevio Nobrega and Lois Pereira de Almeida, Springer). All mouse experiments are conducted in accordance with local IACUC guidelines. Three examples of different diseased mouse models and how they could be used to investigate the usefulness of pharmacological intervention against MLH3 for somatic expansion are included below.

In Huntington's research, several transgenic and knock-in mouse models were generated to investigate the underlying pathological mechanisms involved in the disease. For example, the R6/2 transgenic mouse contains a transgene of ~1.9 kb of human HTT containing 144 copies of the CAG repeat (Mangiarini et al., 1996 Cell 87: 493-506) while the HdhQ111 model was generated by replacing the mouse HTT exon 1 with a human exon1 containing 111 copies of the CAG repeat (Wheeler et al., 2000 *Hum Mol Genet* 9:503-513). Both the R6/2 and HdhQ111 models replicate many of the features of human HD including motor and behavioral dysfunctions, neuronal loss, as well as the expansion of CAG repeats in the striatum (Pouladi et al., 2013, *Nature Reviews Neuroscience* 14: 708-721; Mangiarini et al., 1997 *Nature Genet* 15: 197-200; Wheeler et al., *Hum Mol Genet* 8: 115-122).

R6/2 mice are genotyped using DNA derived from tail snips at weaning and the CAG repeat size is determined. Mice are randomized into groups (n=12/group) at weaning at 4 wks old and dosed with monthly (week 4 and 8) ICV injection of either PBS (control) or up to a 500 μg dose of oligos targeting MLH3. A series of oligos targeting different regions of MLH3 can be tested to identify the most efficacious oligo sequence in vivo. At 12 weeks of age, mice are euthanized, and tissues extracted for analyses. The list of tissues includes, but not restricted to, striatum, cortex, cerebellum, and liver. Genomic DNA is extracted and the length of CAG repeats measured as described below. CSF and plasma are collected for biomarker analysis. Additional pertinent mouse models of HD can be considered.

In Friedreich Ataxia, the YG8 FRDA transgenic mouse model is commonly used to understand the pathology (Al-Mahdawi et al., 2006 Genomics 88(5)580-590; Bourn et al., 2012 PLOS One 7(10); e47085). This model was generated through the insertion of a human YAC transgenic containing in the background of a null FRDA mouse. The YG8 model demonstrates somatic expansion of the GAA triplet repeat expansion in neuronal tissues with only mild motor defects. YG8 FRDA mice are genotyped using DNA derived from tail snips at weaning and the CAG repeat size is determined using methods. To determine if MLH3 μlays a role in somatic expansion of the disease allele, hemizygous YG8 FRDA animals are administered ICV with oligos targeting knockdown of MLH3 identified above.

Approximately 2 months later, animals are euthanized and tissues collected for molecular analyses. Suitable tissues are heart, quadriceps, dorsal root ganglia (DRG's), cerebellum, kidney, and liver. Genomic DNA is extracted, and the length of CAG repeats measured as described above in Example 4.

In Myotonic Dystrophy, the DM300-328 transgenic mouse model is suitable for investigating the pathology behind DM1. This mouse model has a large human genomic sequence (~45 kb) containing over 300 CTG repeats and displays both the somatic expansion and degenerative muscle changes observed in human DM1 (Seznec et al., 2000; Tome et al., 2009 PLOS Genetics 5(5): e1000482; Pandey et al., 2015 *J Pharmacol Exp Ther* 355:329-340). DM300-328 mice are genotyped using DNA derived from tail snips at weaning and the CAG repeat size is determined. To determine if MLH3 μlays a role in somatic expansion of the disease allele in myotonic dystrophy, DM300-328 transgenic animals are administered ASOs targeting knockdown of MLH3 by either subcutaneous injections (sc), intraperitoneal (ip) or intravenous tail injections (iv). Mice are administered ASOs up to 2×/week for maximum 8 weeks of treatment. Animals are euthanized at multiple time points and tissues collected for molecular analyses. Suitable tissues are quadriceps, heart, diaphragm, cortex, cerebellum, sperm, kidney, and liver. Genomic DNA is extracted and the length of CAG repeats measured and compared with parallel controls.

The $Hdh^{Q111}$ mouse model for Huntington Disease is a heterozygous knock-in line, in which the majority of exon 1 and part of intron 1 on one allele of the huntingtin gene (i.e., HTT or Huntington Disease gene) are replaced with human DNA containing ~111 CAG repeats. In this example, ASOs to knock down MLH3 activity or levels is administered. After a treatment period, brain tissue from treated or untreated mice is isolated (e.g., striatum tissue) and analyzed using qRT-PCR as previously described to determine RNA levels of MLH3. Huntingtin gene repeat analysis is performed using mouse tissues (e.g., striatum tissue) after a treatment period using a human-specific PCR assay that amplifies the HTT CAG repeat from the knock-in allele but does not amplify the mouse sequence (i e., the wild type allele). In this protocol, the forward primer is fluorescently labeled (e.g., with 6-FAM as described previously, for example Pinto RM, Dragileva E, Kirby A, et al. Mismatch repair genes MLH1 and MLH3 modify CAG instability in Huntington's disease mice: genome-wide and candidate approaches. PLoS Genet. 2013; 9(10):e1003930.), and products can be resolved using an analyzer with comparison against an internal size standard to generate CAG repeat size distribution traces. Repeat size is determined from the peak with the greatest intensity from a control tissue (e.g., tail tissue in a mouse) and from an affected tissue (e.g., brain striatum tissue or brain cortex tissue). Immunohistochemistry is carried out with polyclonal anti-huntingtin antibody (e.g., EM48) on paraffin-embedded or otherwise prepared sections of brain tissue and can be quantified using a standardized staining index to capture both nuclear staining intensity and number of stained nuclei. A decrease in repeat size in affected tissue indicates that the agent that reduces the level and/or activity of MLH3 is capable of decreasing the repeat which are responsible for the toxic and/or defective gene products in Huntington's disease.

Other Aspects

All publications, patents, and patent applications mentioned in this specification are incorporated herein by reference in their entirety to the same extent as if each individual publication, patent, or patent application was specifically and individually indicated to be incorporated by reference in its entirety. Where a term in the present application is found to be defined differently in a document incorporated herein by reference, the definition provided herein is to serve as the definition for the term.

While the invention has been described in connection with specific aspects thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and can be applied to the essential features hereinbefore set forth, and follows in the scope of the claimed.

In addition to the various aspects described herein, the present disclosure includes the following aspects numbered E1 through E90. This list of aspects is presented as an exemplary list and the application is not limited to these aspects.

E1. A single-stranded oligonucleotide of 10-30 linked nucleosides in length, wherein the oligonucleotide comprises a region of at least 10 contiguous nucleobases having at least 80% complementarity to an MLH3 gene.

E2. The oligonucleotide of E1, wherein the oligonucleotide comprises: (a) a DNA core sequence comprising linked deoxyribonucleosides, (b) a 5' flanking sequence comprising linked nucleosides; and (c) a 3' flanking sequence comprising linked nucleosides; wherein the DNA core comprises a region of at least 10 contiguous nucleobases having at least 80% complementarity to an MLH3 gene and is positioned between the 5' flanking sequence and the 3'flanking sequence; wherein the 5' flanking sequence and the 3' flanking sequence each comprises at least two linked nucleosides; and wherein at least one nucleoside of each flanking sequence comprises an alternative nucleoside.

E3. A single-stranded oligonucleotide of 10-30 linked nucleosides in length for inhibiting expression of a human MLH3 gene in a cell, wherein the oligonucleotide comprises a region of at least 10 contiguous nucleobases having at least 80% complementarity to an MLH3 gene E4. The oligonucleotide of E3, wherein the oligonucleotide comprises: (a) a DNA core comprising linked deoxyribonucleosides; (b) a 5' flanking sequence comprising linked nucleosides; and (c) a 3' flanking sequence comprising linked nucleosides; wherein the DNA core comprises a region of at least 10 contiguous nucleobases having at least 80% complementarity to an MLH3 gene and is positioned between the 5' flanking sequence and the 3' flanking sequence, wherein the 5' flanking sequence and the 3' flanking sequence each comprises at least two linked nucleosides; and wherein at least one nucleoside of each flanking sequence comprises an alternative nucleoside.

E5. The oligonucleotide of any one of E1-E4, wherein the region of at least 10 nucleobases has at least 90% complementary to an MLH3 gene.

E6. The oligonucleotide of any one of E1-E5, wherein the region of at least 10 nucleobases has at least 95% complementary to an MLH3 gene.

E7. The oligonucleotide of any one of E1-E6, wherein the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1536-1598, 1623-1660, 1739-1764, 1782-1823, 1847-1908, 2026-2051, 2063-2094, 2115-2146, 2256-2290, 2387-2414, 2421-2592, 2727-2788, 2826-2937, 3005-3043, 3078-3107, 3159-3185, 3214-3239, 3244-3272, 3282-3308, 3426-3483, 3561-3587, 3642-3769, 3804-3839, 3950-3977, 4004-4040, 4052-4115, 4139-4199, 4241-4301, 4328-4365, 4420-4448, 4472-4536, 4669-4708, or 4784-4810 of the MLH3 gene E8. The oligonucleotide of any one of E1-E6, wherein the region of at least 10 nucleobases is complementary to an MLH3 gene corresponding to a sequence of reference mRNA NM_001040108.1 at one or more of positions 221-293, 321-506, 534-576, 584-636, 681-740, 818-878, 952-1024, 1129-1158, 1177-1264, 1287-1318, 1351-1378, 1568-1598, 1623-1660, 1782-1823, 1870-1904, 2063-2094, 2115-2146, 2256-2287, 2387-2414, 2422-2592, 2727-2788, 2826-2937, 3009-3043, 3078-3107, 3159-3185, 3214-3272, 3282-3307, 3426-3483, 3561-3587, 3642-3767, 3804-3839, 3950-3977, 4004-4039, 4052-4115, 4139-4199, 4241-4301, 4329-4365, 4420-4448, 4472-4536, 4680-4708, or 4784-4810 of the MLH3 gene.

E9. The oligonucleotide of any one of E1-E6, wherein the region of at least 10 nucleobases is complementary to an MLH3 gene corresponding to a sequence of reference mRNA NM_001040108.1 at one or more of positions 221-293, 321-506, 534-635, 681-740, 842-875, 953-1024, 1129-1158, 1179-1264, 1287-1316, 1351-1378, 1568-1598, 1623-1659, 1782-1823, 1870-1904, 2064-2091, 2115-2146, 2256-2287, 2387-2414, 2422-2592, 2727-2788,2829-2937, 3010-3043, 3079-3107, 3159-3185, 3246-3271, 3282-3307, 3426-3474, 3561-3587, 3642-3707, 3804-3839, 3950-3977, 4004-4039, 4052-4114, 4139-4164, 4174-4199, 4241-4288, 4329-4365, 4421-4448, 4472-4536, 4680-4708, or 4784-4810 of the MLH3 gene.

E10. The oligonucleotide of any one of E1-E6, wherein the region of at least 10 nucleobases is complementary to an MLH3 gene corresponding to a sequence of reference mRNA NM_001040108.1 at one or more of positions 331-362, 393-438, 479-505, 534-574, 587-612, 681-740, 847-873, 991-1024, 1210-1262, 1351-1378, 1571-1597, 1623-1648, 1874-1902, 2066-2091, 2256-2281, 2388-2414, 2470-2515, 2732-2788, 2853-2878, 2901-2927, 3282-3307, 3562-3587, 4056-4083, 42414266, or 4506-4531 of the MLH3 gene.

E11. The oligonucleotide of any one of E1-E6, wherein the region of at least 10 nucleobases is complementary to an MLH3 gene corresponding to a sequence of reference mRNA NM_001040108.1 at one or more of positions 335-449, 587-612, 682-736, 848-873, 991-1016, 1179-1204, 1233-1260, 1351-1378, 1626-1651, 1874-1903, 2066-2091, 2115-2146, 2256-2287, 2389-2414, 2471-2499, 2762-2787, 2853-2878, 2911-2936, 3562-3587, 3814-3839, 4006-4031, 4056-4083, or 4244-4269 of the MLH3 gene.

E12 The oligonucleotide of any one of E1-E6, wherein the region of at least 10 nucleobases is complementary to an MLH3 gene corresponding to a sequence of reference mRNA NM_001040108.1 at one or more of positions 355-393, 952-984, 1177-1205, 2026-2052, 2066-2094, 2470-2498, 3159-3185, 3458-3485, or 4259-4292 of the MLH3 gene.

E13. The oligonucleotide of any one of E1-E6, wherein the oligonucleotide comprises the nucleobase sequence of any one of SEQ ID NOs. 6-4710.

E14. The oligonucleotide of any one of E1-E6, wherein the oligonucleotide comprises the nucleobase sequence of any one of SEQ ID NOs: 89, 92, 102, 107-108, 110-111, 115-116, 150, 154, 160-161, 163-164, 166, 168, 175-176, 178, 180, 182-183, 185-189, 201, 211-212, 229-231, 234-238, 241, 248-250, 254, 265-269, 282-283, 285-288, 294, 296, 319-322, 328-329, 366-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086,1110-1111, 1126,1149, 1172, 1176-1181, 1185,1260, 1271-1274, 1276-1277,1297, 1302, 1387-1390, 1392-1393, 1396, 1461-1463, 1473-1474, 1482, 1490-1491, 1495, 1498-1502, 1505, 1508, 1510-1514, 1516-1518, 1525-1526, 1529-1530, 1546-1547, 1572, 1596-1597, 1721-1722, 1724-1727, 1744-1746, 1797, 1800-1802, 1824-1826, 1832,1835-1836,1859,1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-2785, 2789, 2791-2792, 2794-2795, 2797, 2848-2852, or 2917-2918.

E15. The oligonucleotide of any one of E1-E6, wherein the oligonucleotide comprises the nucleobase sequence of any one of SEQ ID NOs: 89, 92, 102, 107-108, 111, 116, 150, 154, 160-161, 163-164, 166, 168, 175-176, 178, 180, 182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-1111, 1126,1172,1176-1181, 1271-1274, 1276-1277, 1297, 1302, 1387,1390,1392-1393,1461-1463, 1474, 1482, 1490-1491, 1498-1502, 1505, 1508, 1510-1512, 1514, 1516-1518, 1525-1526, 1529-1530, 1546-1547, 1572, 1597, 1721-1722, 1724-1727, 1744-1746, 1797, 1800-1801, 1824-1826, 1832, 1835-1836, 1859, 1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, or 2917-2918.

E16. The oligonucleotide of any one of E1-E6, wherein the oligonucleotide comprises the nucleobase sequence of any one of SEQ ID NOs: 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368. 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, or 2917-2918.

E17. The oligonucleotide of any one of E1-E6, the oligonucleotide comprises the nucleobase sequence of any one of SEQ ID NOs: 160-161, 163-164, 166, 211-212, 230-231, 267-268, 282, 294, 322, 366-367, 391-394, 399, 514-515, 594, 602, 728, 750, 752-753, 755, 828, 830, 975-976, 1002, 1176-1179,1274, 1387,1462-1463,1510,1514, 1529-1530, 1726-1727, 1745-1746, 1824, 1871-1872, 2090, 2256, 2528-2530, 2644, or 2792.

E18. The oligonucleotide of any one of E1-E6, the oligonucleotide comprises the nucleobase sequence of any one of SEQ ID NOs: 164, 186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, or 2646

E19. The oligonucleotide of any one of E1-E6, the oligonucleotide comprises the nucleobase sequence of any one of SEQ ID NOs: 174-176, 178, 180-187, 566-569, 573, 701-704, 1260-1261, 1274-1277, 1510-1513, 2000-2001, 2194, 2196, 2661-2664, or 2666.

E20. The oligonucleotide of any one of E1-E6, wherein the nucleobase sequence of the oligonucleotide consists of any one of SEQ ID NOs: 6-4710.

E21. The oligonucleotide of any one of E1-E6, wherein the oligonucleotide consists of the nucleobase sequence of any one of SEQ ID NOs. 89, 92, 102, 107-108, 110-111, 115-116, 150, 154, 160-161, 163-164, 166, 168, 175-176, 178, 180, 182-183, 185-189, 201, 211-212, 229-231, 234-238, 241, 248-250, 254, 265-269, 282-283, 285-288, 294, 296, 319-322, 328-329, 366-367-368, 377-379, 381-399, 487-488, 511, 514-517, 520, 566-568, 573, 591, 593-594, 599, 602, 666, 669-670, 701-704, 728, 749-753, 755, 757, 784, 786-788, 790, 828-830, 959, 972, 974-977, 1002, 1004-1005, 1007, 1009-1013, 1086, 1110-1111, 1126, 1149, 1172, 1176-1181, 1185, 1260, 1271-1274, 1276-1277, 1297, 1302, 1387-1390, 1392-1393, 1396, 1461-1463, 1473-1474, 1482, 1490-1491, 1495, 1498-1502, 1505,1508,1510-1514, 1516-1518,1525-1526, 1529-1530,1546-1547, 1572, 1596-1597, 1721-1722, 1724-1725-1726-1727, 1744-1746, 1797, 1800-1802, 1824-1826, 1832, 1835-1836, 1859, 1865-1866, 1870-1873, 1875, 1878, 1880-1882, 1911, 1914-1918, 1924, 1945-1946, 1949, 2000-2001, 2035, 2064, 2066-2067, 2090-2091, 2163, 2166, 2169-2172, 2178, 2181, 2184, 2186, 2194, 2255-2256, 2307, 2321, 2333, 2343, 2345-2346, 2353-2355, 2394-2395, 2403-2404, 2460-2462, 2489-2492, 2495, 2499-2500, 2524-2530, 2561-2562, 2591, 2595, 2616, 2644-2651, 2653-2654, 2661-2664, 2674, 2683-2685, 2687, 2690-2691, 2693-2695, 2725-2728, 2777-2782, 2784-2785, 2789, 2791-2792, 2794-2795, 2797, 2848-2852, or 2917-2918.

E22 The oligonucleotide of any one of E1-E6, wherein the oligonucleotide consists of the nucleobase sequence of any one of SEQ ID NOs: 89, 92, 102, 107-108, 111, 116, 150, 154, 160-161, 163-164, 166, 168, 175-176, 178, 180, 182-183, 185-189, 201, 211-212, 229-231, 234-236, 238, 241, 248-250, 254, 265-269, 282-283, 285-288, 294, 296, 319-320, 322, 328-329, 366-368, 377, 379, 381-399, 487-488, 511, 514-517, 520, 566-568, 573, 591, 593-594, 599, 602, 666, 669-670, 701-704, 728, 750-753, 755, 757, 784, 786-788, 790, 828-830, 972, 974-977, 1002, 1004-1005, 1009-1013, 1110-1111, 1126,1172, 1176-1181, 1271-1274, 1276-1277, 1297, 1302, 1387, 1390, 1392-1393, 1461-1462-1463, 1474, 1482, 1490-1491, 1498-1502, 1505, 1508, 1510-1512, 1514, 1516-1518, 1525-1526, 1529-1530, 1546-1547, 1572, 1597, 1721-1722, 1724-1727, 1744-1746, 1797, 1800-1801, 1824-1826, 1832, 1835-1836, 1859,1866, 1870-1873, 1878, 1880-1882, 1915-1917, 1924, 1945-1946, 1949, 2000-2001, 2035, 2064, 2066-2067, 2090, 2163, 2166, 2169-2172, 2178, 2181, 2184, 2186, 2194, 2255-2256, 2307, 2321, 2333, 2343, 2345, 2353, 2394-2395, 2403-2404, 2460-2462, 2489, 2491-2492, 2495, 2499, 2524-2525, 2527-2530, 2561-2562, 2591, 2595, 2616, 2644-2651, 2653-2654, 2661-2664, 2674, 2684, 2693-2695, 2725-2728, 2777-2782, 2784-2785, 2789, 2791-2792, 2794-2795, 2797, 2849-2852, or 2917-2918.

E23. The oligonucleotide of any one of E1-E6, wherein the oligonucleotide consists of the nucleobase sequence of any one of SEQ ID NOs. 89, 102, 111, 116, 150, 154, 160-161, 163-164, 166, 168, 175-176, 178, 180, 183, 185-189, 201, 211-212, 229-231, 235-236, 238, 241, 250, 254, 265-269, 282-283, 286-288, 294, 296, 319, 322, 328, 366-368, 377, 379, 381-399, 511, 514-517, 567-568, 591, 593-594, 599, 602, 666, 669-670, 703, 728, 750-753, 755, 757, 784, 786-788, 828-830, 972, 974-977, 1002, 1004-1005, 1009, 1011-1012, 1110-1111, 1126, 1172, 1176-1181, 1272-1274, 1297, 1302, 1387, 1392-1393, 1461-1463, 1474, 1482, 1498-1500, 1502, 1505, 1508, 1510-1511, 1514, 1516-1518, 1525-1526, 1529-1530, 1546-1547, 1572, 1597, 1721-1722, 1725-1727, 1745-1746, 1800-1801, 1824, 1832, 1835-1836, 1859, 1866, 1870-1872, 1878, 1880-1882, 1916, 1924, 1946, 1949, 2000-2001, 2066, 2090, 2163, 2169-2171, 2178, 2181, 2186, 2255-2256, 2307, 2321, 2333, 2394, 2403-2404, 2460-2462, 2489, 2491-2492, 2495, 2499, 2524-2525, 2527-2530, 2561, 2591, 2616, 2644, 2646, 2649-2651, 2653-2654, 2661-2664, 2684, 2693-2695, 2726-2728, 2777-2780, 2782, 2784-2785, 2791-2792, 2794-2795, 2797, 2849-2850, 2852, or 2917-2918.

E24. The oligonucleotide of any one of E1-E6, wherein the oligonucleotide consists of the nucleobase sequence of any one of SEQ ID NOs: 160-161, 163-164,166, 211-212, 230-231, 267-268, 282, 294, 322, 366-367, 391-394, 399, 514-515, 594, 602, 728, 750, 752-753, 755, 828, 830, 975-976, 1002, 1176-1179, 1274, 1387, 1462-1463, 1510, 1514, 1529-1530, 1726-1727, 1745-1746, 1824, 1871-1872, 2090, 2256, 2528-2530, 2644, or 2792.

E25. The oligonucleotide of any one of E1-E6, wherein the oligonucleotide consists of the nucleobase sequence of any one of SEQ ID NOs: 164,186-187, 212, 235, 322, 367-368, 379, 384-385, 388-389, 391-392, 395, 515, 594, 703, 751-753, 828-830, 1005, 1176-1180, 1274, 1297, 1302, 1387, 1393, 1463, 1511, 1514, 1745, 1824, 1881, 2256, 2404, 2491, 2528, 2530, or 2646.

E26. The oligonucleotide of any one of E1-E6, wherein the oligonucleotide consists of the nucleobase sequence of any one of SEQ ID NOs: 174-176, 178, 180-187, 566-569, 573, 701-704, 1260-1261, 1274-1277, 1510-1513, 2000-2001, 2194, 2196, 2661-2664, or 2666.

E27. The oligonucleotide of any one of E1-E26, wherein the oligonucleotide exhibits at least 50% mRNA inhibition at a 20 nM oligonucleotide concentration when determined using a cell assay when compared with a control cell.

E28. The oligonucleotide of any one of E1-E26, wherein the oligonucleotide exhibits at least 60% mRNA inhibition at a 20 nM oligonucleotide concentration when determined using a cell assay when compared with a control cell.

E29. The oligonucleotide of any one of E1-E26, wherein the oligonucleotide exhibits at least 70% mRNA inhibition at a 20 nM oligonucleotide concentration when determined using a cell assay when compared with a control cell.

E30 The oligonucleotide of any one of E1-E26, wherein the oligonucleotide exhibits at least 85% mRNA inhibition at a 20 nM oligonucleotide concentration when determined using a cell assay when compared with a control cell.

E31. The oligonucleotide of any one of E1-E26, wherein the oligonucleotide exhibits at least 50% mRNA inhibition at a 2 nM oligonucleotide concentration when determined using a cell assay when compared with a control cell.

E32. The oligonucleotide of any one of E1-E26, wherein the oligonucleotide exhibits at least 60% mRNA inhibition at a 2 nM oligonucleotide concentration when determined using a cell assay when compared with a control cell.

E33 The oligonucleotide of any one of E1-E26, wherein the oligonucleotide exhibits at least 70% mRNA inhibition at a 2 nM oligonucleotide concentration when determined using a cell assay when compared with a control cell.

E34. The oligonucleotide of any one of E1-E26, wherein the oligonucleotide exhibits at least 85% mRNA inhibition at a 2 nM oligonucleotide concentration when determined using a cell assay when compared with a control cell.

E35. The oligonucleotide of any one of E1-E34, wherein the oligonucleotide comprises at least one alternative internucleoside linkage.

E36. The oligonucleotide of E35, wherein the at least one alternative internucleoside linkage is a phosphorothioate internucleoside linkage.

E37. The oligonucleotide of E35, wherein the at least one alternative internucleoside linkage is a 2'-alkoxy internucleoside linkage E38. The oligonucleotide of E35, wherein the at least one alternative internucleoside linkage is an alkyl phosphate internucleoside linkage.

E39. The oligonucleotide of any one of E1-E38, wherein the oligonucleotide comprises at least one alternative nucleobase.

E40. The oligonucleotide of E39, wherein the alternative nucleobase is 5-methylcytosine, pseudouridine, or 5-methoxyuridine.

E41 The oligonucleotide of any one of E1-E40, wherein the oligonucleotide comprises at least one alternative sugar moiety.

E42 The oligonucleotide of E41, wherein the alternative sugar moiety is 2'-OMe or a bicyclic nucleic acid.

E43. The oligonucleotide of any one of E1-E42, wherein the oligonucleotide further comprises a ligand conjugated to the 5' end or the 3' end of the oligonucleotide through a monovalent or branched bivalent or trivalent linker.

E44. The oligonucleotide of any one of E1-E43, wherein oligonucleotide comprises a region complementary to at least 17 contiguous nucleotides of a MLH3 gene.

E45 The oligonucleotide of any one of E1-E43, wherein oligonucleotide comprises a region complementary to at least 19 contiguous nucleotides of a MLH3 gene.

E46 The oligonucleotide of any one of E1-E43, wherein the oligonucleotide compnses a region complementary to 19 to 23 contiguous nucleotides of a MLH3 gene.

E47 The oligonucleotide of any one of E1-E43, wherein the oligonucleotide comprises a region complementary to 19 contiguous nucleotides of a MLH3 gene.

E48. The oligonucleotide of any one of E1-E43, wherein the oligonucleotide comprises a region complementary to 20 contiguous nucleotides of a MLH3 gene.

E49. The oligonucleotide of any one of E1-E43, wherein the oligonucleotide is from about 15 to 25 nucleosides in length.

E50. The oligonucleotide of any one of E1-E43, wherein the oligonucleotide is 20 nucleosides in length.

E51. A pharmaceutical composition comprising one or more of the oligonucleotides of any one of E1-E50 and a pharmaceutically acceptable carrier or excipient E52. A composition comprising one or more of the oligonucleotide of any one of E1-E50 and a lipid nanoparticle, a polyplex nanoparticle, a lipoplex nanoparticle, or a liposome.

E53. A method of inhibiting transcription of MLH3 in a cell, the method comprising contacting the cell with one or more of the oligonucleotides of any one of E1-E50, the pharmaceutical composition of E51, or the composition of E52 for a time sufficient to obtain degradation of an mRNA transcript of a MLH3 gene, inhibits expression of the MLH3 gene in the cell.

E54. A method of treating, preventing, or delaying the progression a trinucleotide repeat expansion disorder in a subject in need thereof, the method comprising administering to the subject one or more of the oligonucleotides of any one of E1-E50, the pharmaceutical composition of E51, or the composition of E52.

E55 A method of reducing the level and/or activity of MLH3 in a cell of a subject identified as having a trinucleotide repeat expansion disorder, the method comprising contacting the cell with one or more of the oligonucleotides of any one of E1-E50, the pharmaceutical composition of E51, or the composition of E52.

E56. A method for inhibiting expression of an MLH3 gene in a cell comprising contacting the cell with one or more of the oligonucleotides of any one of E1-E50, the pharmaceutical composition of E51, or the composition of E52 and maintaining the cell for a time sufficient to obtain degradation of a mRNA transcript of an MLH3 gene, thereby inhibiting expression of the MLH3 gene in the cell.

E57. A method of decreasing trinucleotide repeat expansion in a cell, the method comprising contacting the cell with one or more of the oligonucleotides of any one of E1-E50, the pharmaceutical composition of E51, or the composition of E52

E58. The method of E56 or E57, wherein the cell is in a subject.

E59. The method of any one of E54, E55, and E58, wherein the subject is a human.

E60. The method of any one of E54-E58, wherein the cell is a cell of the central nervous system or a muscle cell.

E61. The method of any one of E54, E55, and E58-A60, wherein the subject is identified as having a trinucleotide repeat expansion disorder.

E62. The method of any one of E54, E55, and E57-E61, wherein the trinucleotide repeat expansion disorder is a polyglutamine disease.

E63. The method of E62, wherein the polyglutamine disease is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, and Huntington's disease-like 2.

E64. The method of any one of E54-E61, wherein the trinucleotide repeat expansion disorder is a non-polyglutamine disease.

E65. The method of E64, wherein the non-polyglutamine disease is selected from the group consisting of fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy E66. One or more oligonucleotides of any one of E1-E50, the pharmaceutical composition of E51, or the composition of E52 for use in the prevention or treatment of a trinucleotide repeat expansion disorder.

E67. The oligonucleotide, pharmaceutical composition, or composition of E65, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E68. The oligonucleotide, pharmaceutical composition, or composition of E66 or E67, wherein the trinucleotide repeat expansion disorder is Huntington's disease.

E69. The oligonucleotide, pharmaceutical composition, or composition of E66 or E67, wherein the trinucleotide repeat expansion disorder is Friedreich's ataxia.

E70 The oligonucleotide, pharmaceutical composition, or composition of E66 or E67, wherein the trinucleotide repeat expansion disorder is myotonic dystrophy type 1.

E71 The oligonucleotide, pharmaceutical composition, or composition of any of E66-E70, wherein the oligonucleotide, pharmaceutical composition, or composition is administered intrathecally E72. The oligonucleotide, pharmaceutical composition, or composition of any of E66-E70, wherein the oligonucleotide, pharmaceutical composition, or composition is administered intraventricularly.

E73. The oligonucleotide, pharmaceutical composition, or composition of any of E66-E70, wherein the oligonucleotide, pharmaceutical composition, or composition is administered intramuscularly.

E74. A method of treating, preventing, or delaying the progression a disorder in a subject in need thereof wherein the subject is suffering from trinucleotide repeat expansion disorder, comprising administering to said subject one or more of the oligonucleotides of any one of E1-E50, the pharmaceutical composition of E51, or the composition of E52

E75. The method of E74, further comprising administering an additional therapeutic agent E76. The method of E75, wherein the additional therapeutic agent is another oligonucleotide that hybridizes to an mRNA encoding the Huntingtin gene.

E77. A method of preventing or delaying progression of a trinucleotide repeat expansion disorder in a subject, the method comprising administering to the subject one or more of the oligonucleotides of any one of E1-E50, the pharmaceutical composition of E51, or the composition of E52 in an amount effective to delay progression of a trinucleotide repeat expansion disorder of the subject.

E78 The method of E77, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E79. The method of E77 or E78, wherein the trinucleotide repeat expansion disorder is Huntington's disease E80. The method of E77 or E78, wherein the trinucleotide repeat expansion disorder is Friedrich's ataxia.

E81. The method of E77 or E78, wherein the trinucleotide repeat expansion disorder is myotonic Dystrophy type 1.

E82. The method of any of E77 or E78, further comprising administering an additional therapeutic agent.

E83. The method of E82, wherein the additional therapeutic agent is an oligonucleotide that hybridizes to an mRNA encoding the Huntingtin gene.

E84 The method of any of E77-E83, wherein progression of the trinucleotide repeat expansion disorder is delayed by at least 120 days, for example, at least 6 months, at least 12 months, at least 2 years, at least 3 years, at least 4 years, at least 5 years, at least 10 years or more, when compared with a predicted progression.

E85. One or more oligonucleotides of any one of E1-E50, the pharmaceutical composition of E51, or the composition of E52, for use in preventing or delaying the progression of a trinucleotide repeat expansion disorder in a subject.

E86. The oligonucleotide, pharmaceutical composition, or composition for the use of E85, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

E87. The oligonucleotide, pharmaceutical composition, or composition of E85 or E86, wherein the trinucleotide repeat expansion disorder is Huntington's disease.

E88. The oligonucleotide, pharmaceutical composition, or composition of E85 or E86, wherein the trinucleotide repeat expansion disorder is Friedrich's ataxia.

E89 The oligonucleotide, pharmaceutical composition, or composition of E85 or E85, wherein the trinucleotide repeat expansion disorder is myotonic Dystrophy type 1.

E90 The oligonucleotide, pharmaceutical composition, or composition for the use of any one of E85-E89, wherein progression of the trinucleotide repeat expansion disorder is delayed by at least 120 days, for example, at least 6 months, at least 12 months, at least 2 years, at least 3 years, at least 4 years, at least 5 years, at least 10 years or more, when compared with a predicted progression.

---

SEQUENCE LISTING

The patent contains a lengthy sequence listing. A copy of the sequence listing is available in electronic form from the USPTO web site (https://seqdata.uspto.gov/docdetail?docId=US12485136B2). An electronic copy of the sequence listing will also be available from the USPTO upon request and payment of the fee set forth in 37 CFR 1.19(b)(3).

---

The invention claimed is:

1. A single-stranded oligonucleotide of 20 linked nucleosides wherein the nucleobase sequence consists of SEQ ID NO: 515, 1302, or 2491, wherein all thymidines at positions 1-5 and 16-20 of the nucleobase sequence are substituted with 5-methyl-2'-O-methoxyethyl-uridine and all cytidines at positions 6-15 are substituted with 5-methyl-2'-O-methoxyethyl-cytidine, and wherein the backbone is fully phosphorothioate-modified.

2. The oligonucleotide of claim 1, further comprising a pseudouridine or 5-methoxyuridine.

3. The oligonucleotide of claim 1, further comprising an alternative sugar moiety, wherein the alternative sugar moiety is 2'-O-methyl or a bicyclic nucleic acid.

4. A pharmaceutical composition comprising the oligonucleotide of claim 1 and a pharmaceutically acceptable carrier or excipient.

5. A method of treating, preventing, or delaying the progression of a trinucleotide repeat expansion disorder in a subject in need thereof, the method comprising administering the oligonucleotide of claim 1 to the subject.

6. The method of claim 5, wherein the trinucleotide repeat expansion disorder is a polyglutamine disease.

7. The method of claim 5, wherein the trinucleotide repeat expansion disorder is a non-polyglutamine disease.

8. A method of preventing or delaying the progression of a trinucleotide repeat expansion disorder in a subject, the method comprising administering to the subject an oligonucleotide of claim 1 in an amount effective to delay progression of a trinucleotide repeat expansion disorder of the subject.

9. The method of claim 8, wherein the trinucleotide repeat expansion disorder is selected from the group consisting of dentatorubropallidoluysian atrophy, Huntington's disease, spinal and bulbar muscular atrophy, spinocerebellar ataxia type 1, spinocerebellar ataxia type 2, spinocerebellar ataxia type 3, spinocerebellar ataxia type 6, spinocerebellar ataxia type 7, spinocerebellar ataxia type 17, Huntington's disease-like 2, fragile X syndrome, fragile X-associated tremor/ataxia syndrome, fragile XE mental retardation, Friedreich's ataxia, myotonic dystrophy type 1, spinocerebellar ataxia type 8, spinocerebellar ataxia type 12, oculopharyngeal muscular dystrophy, Fragile X-associated premature ovarian failure, FRA2A syndrome, FRA7A syndrome, and early infantile epileptic encephalopathy.

* * * * *